US008163753B2

(12) United States Patent
Tsubouchi et al.

(10) Patent No.: US 8,163,753 B2
(45) Date of Patent: Apr. 24, 2012

(54) 2,3-DIHYDRO-6-NITROIMIDAZO (2,1-B) OXAZOLE COMPOUNDS FOR THE TREATMENT OF TUBERCULOSIS

(75) Inventors: Hidetsugu Tsubouchi, Tokushima (JP); Hirofumi Sasaki, Kitajima (JP); Motohiro Itotani, Tokushima (JP); Yoshikazu Haraguchi, Tokushima (JP); Shin Miyamura, Matsushige (JP); Makoto Matsumoto, Naruto (JP); Hiroyuki Hashizume, Naruto (JP); Tatsuo Tomishige, Tokushima (JP); Masanori Kawasaki, Ishii (JP); Kinue Ohguro, Tokushima (JP); Takumi Sumida, Tokushima (JP); Takeshi Hasegawa, Aizumi (JP); Kazuho Tanaka, Aizumi (JP); Isao Takemura, Naruto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1367 days.

(21) Appl. No.: 10/574,597

(22) PCT Filed: Oct. 29, 2004

(86) PCT No.: PCT/JP2004/016492

§ 371 (c)(1), (2), (4) Date: Apr. 27, 2007

(87) PCT Pub. No.: WO2005/042542

PCT Pub. Date: May 12, 2005

(65) Prior Publication Data

US 2008/0119478 A1 May 22, 2008

(30) Foreign Application Priority Data

Oct. 31, 2003 (JP) ................................ 2003-373206
Apr. 6, 2004 (JP) ................................ 2004-111720

(51) Int. Cl.

| | |
|---|---|
| *A61K 31/497* | (2006.01) |
| *A61K 31/47* | (2006.01) |
| *A61K 31/445* | (2006.01) |
| *A61K 31/42* | (2006.01) |
| *C07D 419/06* | (2006.01) |
| *C07D 215/04* | (2006.01) |
| *C07D 213/72* | (2006.01) |
| *C07D 498/04* | (2006.01) |

(52) U.S. Cl. .................. 514/252.16; 514/312; 514/323; 514/375; 544/368; 546/153; 546/304; 548/218

(58) Field of Classification Search ............ 514/252.16, 514/312, 323, 375; 544/368; 546/153, 304; 548/218

See application file for complete search history.

(56) References Cited

U.S. PATENT DOCUMENTS

| | | | | |
|---|---|---|---|---|
| 5,317,019 | A | 5/1994 | Bender et al. | |
| 5,668,127 | A | 9/1997 | Baker et al. | |
| 6,087,358 | A | 7/2000 | Baker et al. | |
| 2008/0119478 | A1 * | 5/2008 | Tsubouchi et al. ...... | 514/252.16 |
| 2010/0130508 | A1 * | 5/2010 | Kawasaki ................ | 514/254.02 |

FOREIGN PATENT DOCUMENTS

| | | | |
|---|---|---|---|
| EP | 0 164 830 | A2 | 12/1985 |
| EP | 0 294 176 | A1 | 12/1988 |
| EP | 1 508 355 | A1 | 2/2005 |
| JP | 10-238954 | | 9/1998 |
| JP | 2001-72472 | | 3/2001 |
| RU | 1383752 | A1 | 11/1993 |
| WO | WO 97/01562 | | 1/1997 |
| WO | WO-2004-033463 | A1 | 4/2004 |
| WO | WO-2004/035547 | A1 | 4/2004 |

OTHER PUBLICATIONS

Zakir Abdul Ghaffar Adil, Affidavit-in-Support of Notice of Opposition/Rejoinder in the matter of Pakistan Patent Application 860/2004(139907).

Zakir Abdul Ghaffar Adil, Affidavit-in-Support of Notice of Opposition/Rejoinder in the matter of Pakistan Patent Application 1225/2006(139912).

Office Action with English translation issued Jul. 1, 2009 in corresponding Belarusian application.

Melentieva G.A. et al., Pharmaceutical Chemistry, Moscow, Medicina, 1993, pp. 7-8.

(Continued)

*Primary Examiner* — James O Wilson
*Assistant Examiner* — Ebenezer O Sackey
(74) *Attorney, Agent, or Firm* — Finnegan, Henderson, Farabow, Garrett & Dunner, L.L.P.

(57) ABSTRACT

The present invention provides a 2,3-dihydro-6-nitroimidazo [2,1-b]oxazole compound represented by the following general formula: (1) in the above formula (1), R1 represents a hydrogen atom or C1-C6 alkyl group, n represents an integer of 0 to 6, R1 and —(CH2)nR2 may form a spiro ring represented by the formula (30) below, together with the adjacent carbon atom (in the formula below, RRR represents a piperidyl group which may have substituents on the piperidine ring), (30) and R2 represents a benzothiazolyloxy group, quinolyloxy group, pyridyloxy group or the like. The present compound has an excellent bactericidal action against *Mycobacterium tuberculosis*, multi-drug-resistant *Mycobacterium tuberculosis*, and atypical acid-fast bacteria.

(1)

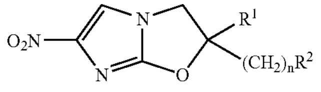

(30)

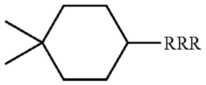

32 Claims, No Drawings

OTHER PUBLICATIONS

Nagarajan et al.; "Nitroimidazoles XXI 2,3-Dihydro-6-Nitroimidazo [2,1-*b*] Oxazoles With Antitubercular Activity"; Eur. J. Med. Chem., vol. 24, pp. 631-633, (1989).

Stover et al.; "A Small-Molecule Nitroimidazopyran Drug Candidate for the Treatment of Tuberculosis"; Nature, vol. 405, pp. 962-966, (2000).

Sehgal et al.; "Potential Radiosensitizing Agent. 2. Synthesis and Biological Activity of Derivatives of Dinitroimidazole With Oxiranes"; J. Med. Chem., vol. 24, pp. 601-604, (1981).

Ashtekar et al.; "In Vitro and in Vivo Activities of the Nitroimidazole CGI 17341 Against *Mycobacterium Tuberculosis*"; Antimicrobial Agents and Chemotherapy, vol. 37, No. 2, pp. 183-186, (1993).

* cited by examiner

2,3-DIHYDRO-6-NITROIMIDAZO (2,1-B) OXAZOLE COMPOUNDS FOR THE TREATMENT OF TUBERCULOSIS

TECHNICAL FIELD

The present invention relates to a 2,3-dihydroimidazo[2,1-b]oxazole compound.

BACKGROUND ART

From among acid-fast bacteria, human *Mycobacterium tuberculosis* has been widely known. It is said that the one-third of the human population is infected with this bacterium. In addition to the human *Mycobacterium tuberculosis, Mycobacterium africanum* and *Mycobacterium bovis* have also been known to belong to the *Mycobacterium tuberoculosis* group. These bacteria are known as *Mycobacteria* having a strong pathogenicity to humans.

Against these tuberculoses, treatment is carried out using three agents, rifampicin, isoniazid, and ethambutol (or streptomycin) that are regarded as first-line agents, or using four agents such as the above three agents and pyrazinamide.

However, since the treatment of tuberculosis requires extremely long-term administration of agents, it might result in poor compliance, and the treatment often ends in failure.

Moreover, in respect of the above agents, it has been reported that: rifampicin causes hepatopathy, flu syndrome, drug allergy, and its concomitant administration with other drugs is contraindicated due to P450-associated enzyme induction; that isoniazid causes peripheral nervous system disorder and induces serious hepatopathy when used in combination with rifampicin; that ethambutol brings on failure of eyesight due to optic nerve disorder; that streptomycin brings on diminution of the hearing faculty due to the 8th cranial nerve disorder; and that pyrazinamide causes adverse reactions such a hepatopathy, gouty attack associated with increase of uric acid level, vomiting (A Clinician's Guide To Tuberculosis, Michael D. Iseman 2000 by Lippincott Williams & Wilkins, printed in the USA, ISBN 0-7817-1749-3, Tuberculosis, 2nd edition, Fumiyuki Kuze and Takahide Izumi, Igaku-Shoin Ltd., 1992).

Actually, it has been reported that cases where the standard chemotherapy could not be carried out due to the adverse reactions to these agents made up 70% (approximately 23%, 52 cases) of the total cases where administration of the agents was discontinued (the total 228 hospitalized patients who were subject to the research) (Kekkaku, Vol. 74, 77-82, 1999).

In particular, hepatotoxicity, which is induced by rifampicin, isoniazid, and ethambutol out of the 5 agents used in combination for the aforementioned first-line treatment, is known as an adverse reaction that is developed most frequently. At the same time, *Mycobacterium tuberculosis* resistant to antitubercular agents, multi-drug-resistant *Mycobacterium tuberculosis*, and the like have been increasing, and the presence of these types of *Mycobacterium tuberculosis* makes the treatment more difficult.

According to the investigation made by WHO (1996 to 1999), the proportion of *Mycobacterium tuberculosis* that is resistant to any of the existing antitubercular agents to the total types of *Mycobacterium tuberculosis* that have been isolated over the world reaches 19%, and it has been published that the proportion of multi-drug-resistant *Mycobacterium tuberculosis* is 5.1%. The number of carriers infected with such multi-drug-resistant *Mycobacterium tuberculosis* is estimated to be 60,000,000, and concerns are still rising that multi-drug-resistant *Mycobacterium tuberculosis* will increase in the future (April 2001 as a supplement to the journal Tuberculosis, the "Scientific Blueprint for TB Drug Development.")

In addition, the major cause of death of AIDS patients is tuberculosis. It has been reported that the number of humans suffering from both tuberculosis and HIV reaches 10,1700,000 at the time of year 1997 (Global Alliance for TB drug development). Moreover, it is considered that the mixed infection of tuberculosis and HIV has an at least 30 times higher risk of developing tuberculosis than the ordinary circumstances.

Taking into consideration the aforementioned current situation, the profiles of the desired antitubercular agent is as follows: (1) an agent, which is effective even for multi-drug-resistant *Mycobacterium tuberculosis*, (2) an agent enabling a short-term chemotherapy, (3) an agent with fewer adverse reactions, (4) an agent showing an efficacy to latent infecting *Mycobacterium tuberculosis* (i.e., latent *Mycobacterium tuberculosis*), and (5) an orally administrable agent.

Examples of bacteria known to have a pathogenicity to humans include offending bacteria of recently increasing MAC infection (*Mycobacterium avium*-intracellulare complex infection) such as *Mycobacterium avium* and *Mycobacterium intracellulare*, and atypical acid-fast bacteria such as *Mycobacterium kansasii, Mycobacterium marinum, Mycobacterium simiae, Mycobacterium scrofulaceum, Mycobacterium szulgai, Mycobacterium xenopi, Mycobacterium malmoense, Mycobacterium haemophilum, Mycobacterium ulcerans, Mycobacterium shimoidei, Mycobacterium fortuitum, Mycobacterium chelonae, Mycobacterium smegmatis*, and *Mycobacterium aurum.*

Nowadays, there are few therapeutic agents effective for these atypical acid-fast bacterial infections. Under the presence circumstances, antitubercular agents such as rifampicin, isoniazid, ethambutol, streptomycin and kanamycin, a newquinolone agent that is a therapeutic agent for common bacterial infections, macrolide antibiotics, aminoglycoside antibiotics, and tetracycline antibiotics are used in combination.

However, when compared with the treatment of common bacterial infections, the treatment of atypical acid-fast bacterial infections requires a long-term administration of agents, and there have been reported cases where the infection is changed to an intractable one, finally leading to death. To break the aforementioned current situation, the development of an agent having a stronger efficacy is desired.

For example, National Publication of International Patent Application No. 11-508270 (WO97/01562) discloses that a 6-nitro-1,2,3,4-tetrahydro[2,1-b]-imidazopyran compound has a bactericidal action in vitro to *Mycobacterium tuberculosis* (H37Rv strain) and multi-drug-resistant *Mycobacterium tuberculosis*, and that the above compound has a therapeutic effect to a tuberculosis-infected animal model when it is orally administered and thus useful as antitubercular agent.

However, the compound described in the above publication differs from the compound of the present invention in terms of the basic skeleton, and it is considered to be a compound nonsimilar to the inventive compound.

Kuppsuwamy Nagarajan et al. have reported on European Journal of Medicinal Chemistry, 1989, Vol. 24, pp. 631-633 that compounds represented by the following general formula (1):

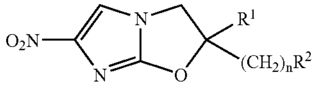

(I)

wherein $R^1$ represents a hydrogen atom or methyl group and $-(CH_2)_nR^2$ represents a chloromethyl group, C1-C7 alkyl group, isopropoxymethyl group, 3-propenyloxy-methyl group, or unsubstituted phenoxymethyl group, and compounds represented by the same above general formula (1), wherein $R^1$ and $-(CH_2)_nR^2$ bind to each other to form a cyclopentane or cyclohexane ring (16 types of compounds in total) have a bactericidal action to *Mycobacterium tuberculosis* (H37Rv strain).

However, the above publication describes that only the 4 types of compounds out of the above compounds are effective when they are orally administered. It also describes that the compound having the highest activity, that is, the compound (CGI-17341) represented by the above general formula (1) wherein $R^1$ represents a hydrogen atom and $-(CH_2)_nR^2$ represents ethyl, was found to have mutagenicity, and that accordingly, the development of these series of compounds as agents were abandoned.

In addition, Dilip R. Astekar et al. have reported on Antimicrobial Agents and Chemotherapy, February 1993, pp. 183-186 about the antimicrobial profile of the above compound CGI-17341. According to the report, the compound CGI-17341 has a bactericidal action to *Mycobacterium tuberculosis* (H37Rv strain) and multi-drug-resistant *Mycobacterium tuberculosis*, but it does not have the activity to atypical acid-fast bacteria, *M. avium, M. intracellulare*, and *M. fortuitum* when it is used at 250 μg/ml or less.

Moreover, Journal of Medicinal Chemistry, 1981, Vol. 24, pp. 601-604 discloses that 6-nitro-2,3-dihydroimidazo[2,1-b]oxazole compounds have a radiosensitizing ability for hypoxic mammalian cells.

DISCLOSURE OF THE INVENTION

It is an object of the present invention to provide a compound having an excellent bactericidal action to *Mycobacterium tuberculosis* and multi-drug-resistant *Mycobacterium tuberculosis.*

It is another object of the present invention to provide a compound having an excellent bactericidal action to atypical acid-fast bacteria.

As a result of intensive studies, the present inventors have succeeded in synthesizing a novel 2,3-dihydroimidazo[2,1-b]oxazole compound, which has an excellent bactericidal action to *Mycobacterium tuberculosis*, multi-drug-resistant *Mycobacterium tuberculosis*, and atypical acid-fast bacteria. The present invention have completed based on such findings.

The present invention provides a 2,3-dihydro-6-nitroimidazo[2,1-b]oxazole compound represented by the following general formula (1), optically active form thereof, or pharmaceutically acceptable salt thereof:

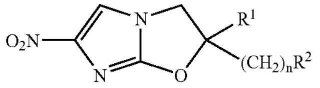

(1)

wherein $R^1$ represents a hydrogen atom or a C1-6 alkyl group, n represents an integer between 0 and 6, $R^1$ and $-(CH_2)_n R^2$ may bind to each other together with carbon atoms adjacent thereto, so as to form a spiro ring represented by general formula (30):

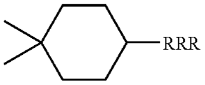

(30)

wherein RRR represents a piperidyl group [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], and $R^2$ represents a group described in any one of the following (a) to (y):

(a) a phenyl group (wherein, on the phenyl ring, at least one piperidyl group may be substituted [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]);

(b) a benzothiazolyloxy group (wherein, on the benzothiazole ring, at least one selected from the group consisting of the following (b-1) to (b-5) may be substituted:

(b-1) a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], (b-2) a piperazinyl group [wherein, on the piperazine ring, at least one selected from the group consisting of a phenyl C1-C6 alkyl group (wherein, on the phenyl group, at least one selected from the group consisting of a halogen atom, a halogen substituted or unsubstituted C1-C6 alkyl group, and a halogen substituted or unsubstituted C1-C6 alkoxy group, may be substituted), a phenyl C2-C6 alkenyl group (wherein, on the phenyl group, at least one selected from the group consisting of a halogen atom, a halogen substituted or unsubstituted C1-C6 alkyl group, and a halogen substituted or unsubstituted C1-C6 alkoxy group, may be substituted), and a phenyl group (wherein, on the phenyl group, at least one selected from the group consisting of a halogen atom, a halogen substituted or unsubstituted C1-C6 alkyl group, and a halogen substituted or unsubstituted C1-C6 alkoxy group, may be substituted), may be substituted], (b-3) a piperidyl group [wherein, on the piperidine ring, at least one selected from the group consisting of an amino group (wherein, on the amino group, at least one selected from the group consisting of a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted] and a C1-C6 alkyl group may be substituted), a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), may be substituted], (b-4) a pyrrolyl group [wherein, on the pyrrole ring, at least one selected from the group consisting of a C1-C6 alkyl group and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted], and (b-5) a phenylthio group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted));

(c) a quinolyloxy group (wherein, on the quinoline ring, at least one selected from the group consisting of the following (c-1) to (c-4) may be substituted:

(c-1) a halogen atom, (c-2) a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], (c-3) a piperazinyl group (wherein, on the piperazine ring, at least one selected from the group consisting of a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a phenyl group [wherein, on the phenyl ring, at least one group selected from the group consisting of a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a halogen atom, a halogen substituted or unsubstituted C1-C6 alkyl group, and a halogen substituted or unsubstituted C1-C6 alkoxy group, may be substituted], and a phenyl C2-C6 alkenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], may be substituted], and (c-4) a piperidyl group [wherein, on the piperidine ring, at least one selected from the following group may be substituted: an amino group (wherein, on the amino group, at least one selected from the group consisting of a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted] and a C1-C6 alkyl group may be substituted); a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a phenyl C1-C6 alkyl group (wherein, on the phenyl ring, at least one selected from the group consisting of a C1-C4 alkylenedioxy group, a halogen atom, a halogen substituted or unsubstituted C1-C6 alkyl group, and a halogen substituted or unsubstituted C1-C6 alkoxy group, may be substituted); a phenyl C1-C6 alkoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a naphthyl C1-C6 alkyl group; and a phenyl C1-C6 alkylidene group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]);

(d) a pyridyloxy group (wherein, on the pyridine ring, at least one selected from the group consisting of the following (d-1) and (d-2) may be substituted:

(d-1) a piperidyl group [wherein, on the piperidine ring, at least one selected from the group consisting of a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a phenyl C1-C6 alkoxy substituted C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a phenoxy C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), may be substituted]; and (d-2) a piperazinyl group [wherein, on the piperazine ring, at least one selected from the group consisting of a C1-C6 alkoxycarbonyl group, a furyl C1-C6 alkyl group [wherein, on the furan ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], a pyridyl C1-C6 alkyl group [wherein, on the pyridine ring, at 1-east one selected from the group consisting of a furyl group and a phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], a benzothienyl C1-C6 alkyl group (wherein, on the benzothiophene ring, at least one selected from the group consisting of a halogen atom, a halogen substituted or unsubstituted C1-C6 alkyl group, and a halogen substituted or unsubstituted C1-C6 alkoxy group, may be substituted), a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a benzofuryl C1-C6 alkyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted], a benzofuryl C2-C6 alkenyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted], a thiazolyl C1-C6 alkyl group [wherein, on the thiazole ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], a phenoxy C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), an indolyl C1-C6 alkyl group (wherein, on the indole ring, at least one selected from the group consisting of a halogen atom, a halogen substituted or unsubstituted C1-C6 alkyl group, and a halogen substituted or unsubstituted C1-C6 alkoxy group, may be substituted), and a phenyl C1-C6 alkyl group (wherein, on the phenyl ring, at least one selected from the group consisting of a benzofuryl group, a halogen atom, a halogen substituted or unsubstituted C1-C6 alkyl group, and a halogen substituted or unsubstituted C1-C6 alkoxy group, may be substituted) may be substituted]);

(e), a 1,2,3,4-tetrahydroquinolyloxy group (wherein, on the 1,2,3,4-tetrahydroquinoline ring, at least one selected from the group consisting of an oxo group, a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], and a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], may be substituted);

(f) a 1,2,3,4-tetrahydronaphthyloxy group (wherein, on the 1,2,3,4-tetrahydronaphthalene ring, at least one oxo group may be substituted);

(g) a 2H-chromenyoxyl group (wherein, on the 2H-chromene ring, at least one oxo group may be substituted);

(h) a naphthyloxy group (wherein, on the naphthalene ring, at least one piperidyl group may be substituted [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]);

(i) a 1,2,3,4-tetrahydroisoquinolyloxy group (wherein, on the 1,2,3,4-tetrahydroisoquinoline ring, at least one selected from the group consisting of a C1-C6 alkoxycarbonyl group, a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], and a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], may be substituted);

(j) a group —$NR^{22}R^{23}$ (wherein $R^{22}$ represents a hydrogen atom or C1-C6 alkyl group, and $R^{23}$ represents at least one selected from the following (j-1) to (j-5):

(j-1) a phenyl group [wherein, on the phenyl ring, at least one piperidyl group is substituted (wherein, on the piperidine ring, at least one phenoxy group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted])], (j-2) a phenyl C1-C6 alkyl group [wherein, on the phenyl ring, at least one group selected from the group consisting of a piperidyl group (wherein, on the piperidine ring, a phenoxy group is substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]) and a group —$NR^{24}R^{25}$ (wherein $R^{24}$ represents a hydrogen atom or C1-C6 alkyl group, and $R^{25}$ represents a phenyl C2-C6 alkenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]), is substituted], (j-3) a piperidyl C1-C6 alkyl group [wherein, on the piperidine ring, at least one phenyl group is substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], (j-4) a thiazolyl group [wherein, on the thiazole ring, at least one group selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a piperazinyl C1-C6 alkyl group (wherein, on the piperazine ring, at least one phenyl group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]), and a piperidyl C1-C6 alkyl group (wherein, on the piperidine ring, at least one phenoxy group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]), may be substituted], and (j-5) a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted));

(k) a benzoxazolyloxy group (wherein, on the benzoxazole ring, at least one selected from the group consisting of a piperazinyl group [wherein, on the piperazine ring, at least one selected from the group consisting of a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), and a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), may be substituted], a piperidyl group (wherein, on the piperidine ring, at least one selected from the group consisting of a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted] and an amino group [wherein, on the amino group, at least one selected from the group consisting of a C1-C6 alkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted] may be substituted), and a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], may be substituted);

(l) a benzoimidazolyloxy group (wherein, on the benzoimidazole ring, at least one selected from the group consisting of a C1-C6 alkyl group, a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], a piperidyl group [wherein, on the piperidine ring, at least one phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a piperazinyl group [wherein, on the piperazine ring, at least one phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] and a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], may be substituted);

(m) a 1,2,3,4-tetrahydroisoquinolyl group (wherein, on the 1,2,3,4-tetrahydroisoquinoline ring, at least one selected from the group consisting of the following (m-1) and (m-2) may be substituted:

(m-1) an amino group [wherein, on the amino group, at least one selected from the group consisting of a C1-C6 alkyl group, a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), may be substituted] and (m-2) a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

(n) a piperidyl group (wherein, on the piperidine ring, at least one selected from the group consisting of the following (n-1) to (n-4) may be substituted:

(n-1) a phenyl group [wherein, on the phenyl ring, at least one group —$NR^{26}R^{27}$ is substituted (wherein $R^{26}$ represents a hydrogen atom or C1-C6 alkyl group, and $R^{27}$ represents a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted])], (n-2) a group —$W_1NR^{28}R^{29}$ [wherein $W_1$ represents a C1-C6 alkylene group, $R^{28}$ represents a hydrogen atom or C1-C6 alkyl group, and $R^{29}$ represents a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], (n-3) a C1-C6 alkoxy group wherein two phenyl groups are substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], and (n-4) a phenyl C1-C6 alkyl group [wherein, on the phenyl group ring, at least one phenyl group is substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]);

(o) a piperazinyl group (wherein, on the piperazine ring, at least one selected from the following group is substituted: a C1-C6 alkyl group wherein two phenyl groups are substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], a phenyl C1-C6 alkyl group [wherein, on the phenyl ring, at least one phenoxy group is substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, is substituted)], a thiazolyl group (wherein, on the thiazole ring, at least one phenyl group may be substituted), a phenoxy C1-C6 alkyl group (wherein, on the phenyl ring, at least one selected from the group consisting of a phenyl group (wherein, on the phenyl ring, halogen atom, a halogen substituted or unsubstituted C1-C6 alkyl group, and a halogen substituted or unsubstituted C1-C6 alkoxy group, may be substituted), a halogen atom, a halogen substituted or unsubstituted C1-C6 alkyl group, and a halogen substituted or unsubstituted C1-C6 alkoxy group, may be substituted), a phenyl C2-C6 alkenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, is substituted], and an imidazolyl group [wherein, on the imidazole ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]);

(p) a thiazolyl C1-C6 alkoxy group (wherein, on the thiazole ring, at least one type selected from the group consisting of the following (p-1) to (p-5) may be substituted:

(p-1) a phenoxy C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], (p-2) an anilino C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], (p-3) a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], (p-4) a piperazinyl C1-C6 alkyl group [wherein, on the piperazine ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], and (p-5) a piperidyl C1-C6 alkyl group [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]);

(q) an 8-azabicyclo[3.2.1]octyl group (wherein, on the 8-azabicyclo[3,2,1]octane ring, at least one phenoxy group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

(r) a group represented by the following chemical formula (31):

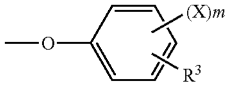

(31)

[wherein X represents a halogen atom, or an amino substituted C1-C6 alkyl group which may have a C1-C6 alkyl group as a substituent, m represents an integer between 0 and 3, and $R^3$ represents a group described in any one of the following (i) to (xxii):

(i) a group —(W)o—$NR^4R^5$ (wherein W represents a group —CO— or a C1-C6 alkylene group, o represents 0 or 1, $R^4$ represents a hydrogen atom, C1-C6 alkyl group, or phenylcarbamoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], and $R^5$ represents: a phenyl C1-C6 alkoxycarbonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C2-C6 alkenylcarbonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C2-C6 alkenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a piperidyl C1-C6 alkyl group [wherein, on the piperidine ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; a phenyl C1-C6 alkyl group (wherein, on the phenyl ring, at least one phenyl group is substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)); a benzofuryl C1-C6 alkyl group (wherein, on the benzofuran ring, at least one halogen substituted or unsubstituted C1-C6 alkyl group may be substituted); a piperidinylcarbonyl C1-C6 alkyl group [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); or a group represented by the following chemical formula (32):

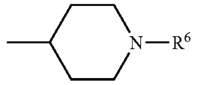

(32)

wherein $R^6$ represents: a C1-C6 alkyl group; a phenyl group (wherein, on the phenyl ring, at least one selected from the following group may be substituted: a C1-C4 alkylenedioxy group, a cyano group, a nitro group, an amino group that may have a C1-C6 alkyl group as a substituent, an amino substituted sulfonyl group that may have a C1-C6 alkyl group as a substituent, a C1-C6 alkoxycarbonyl group, a C1-C6 alkylthio group, a phenoxy group, a phenyl C1-C6 alkoxy group, a pyrrolidinyl group [wherein, on the pyrrolidine ring, at least one oxo group may be substituted], an imidazolyl group, an isoxazolyl group, an oxazolyl group, a phenyl C1-C6 alkyl group, a phenyl group, an amino C1-C6 alkyl group that may have a C1-C6 alkyl group as a substituent, a pyrrolidinyl C1-C6 alkoxy group, a halogen atom, a halogen substituted or unsubstituted C1-C6 alkyl group, and a halogen substituted or unsubstituted C1-C6 alkoxy group); a phenyl C1-C6 alkoxycarbonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a benzofuryl C1-C6 alkyl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted); a benzofuryl C2-C6 alkenyl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted); a phenoxy C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a thiazolyl C1-C6 alkyl group (wherein, on the thiazole ring, at least one phenyl group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]); a phenyl C1-C6 alkyl group [wherein, on the phenyl ring, at least one selected from the group consisting of a phenyl group (wherein, on the phenyl ring, a halogen atom, a halogen substituted or unsubstituted C1-C6 alkyl group, and a halogen substituted or unsubstituted C1-C6 alkoxy group, may be substituted), a halogen atom, a halogen substituted or unsubstituted C1-C6 alkyl group, and a halogen substituted or unsubstituted C1-C6 alkoxy group, may be substituted]; a pyridyl C1-C6 alkyl group. [wherein, on the pyridine ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; a C1-C6 alkoxycarbonyl group; a benzoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a phenylcarbamoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a benzothienyl C1-C6 alkyl group (wherein, on the benzothiophene ring, at least one halogen atom may be substituted); an indolyl C1-C6 alkyl group (wherein, on the indole ring, at least one selected from the group consisting of a halogen atom, a halogen substituted or unsubstituted C1-C6 alkyl group, and a halogen substituted or unsubstituted C1-C6 alkoxy group, may be substituted); a 4H-1,3-benzodioxinyl group (wherein, on the 4H-1,3-benzodioxine ring, at least one halogen atom may be substituted); benzothienyl group; a naphthyl group; a quinolyl group; a benzothiazolyl group (wherein, on the benzothiazole ring, at least one C1-C6 alkyl group may be substituted); a 2,3-dihydro-1H-indenyl group (wherein, on the 2,3-dihydro-1H-indan ring, at least one oxo group may be substituted); or a 9H-fluorenyl group or phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted));

(ii) a group represented by the following chemical formula (33):

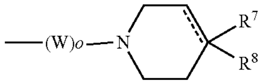

(33)

(wherein W and o are the same as above, a dotted line represents that the bond may be a double bond, and when the dotted line represents a double bond, it means that only $R^8$ is substituted; $R^7$ represents a hydrogen atom, hydroxyl group, C1-C6 alkoxy group, or phenyl group [wherein, on the phenyl ring, halogen may be substituted]; and $R^8$ represents a group described in any one of the following (1) to (63):

(1) a phenyl C1-C6 alkoxy substituted C1-C6 alkyl group (wherein, on the phenyl ring, at least one selected from the group consisting of a C1-C4 alkylenedioxy group, a halogen atom, a cyano group, a phenyl group, a phenyl C1-C6 alkoxy group, a phenyl C2-C6 alkenyl group, a phenoxy group, a C1-C6 alkylthio group, a halogen substituted or unsubstituted C1-C6 alkyl group, and a halogen substituted or unsubstituted C1-C6 alkoxy group, may be substituted);

(2) a phenyl C1-C6 alkoxy group (wherein, on the phenyl ring, at least one selected from the group consisting of a cyano group, a phenyl group, a C1-C6 alkoxycarbonyl group, a phenoxy group, a C1-C6 alkylthio group, a halogen atom, a halogen substituted or unsubstituted C1-C6 alkyl group, and a halogen substituted or unsubstituted C1-C6 alkoxy group, may be substituted);

(3) a phenyl C2-C6 alkenyloxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(4) a group —(W)o-$NR^9R^{10}$ (wherein W and o are the same as above, and $R^9$ and $R^{10}$ each identically or differently represent: a hydrogen atom; a C1-C6 alkyl group that may have a hydroxyl group as a substituent; a C1-C6 alkanoyl group; a C1-C6 alkoxycarbonyl group; a phenyl C1-C6 alkoxycarbonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl group [on the phenyl ring, at least one selected from the following group may be substituted as a substituent: a halogen atom, a halogen substituted or unsubstituted C1-C6 alkyl group, a halogen substituted or unsubstituted C1-C6 alkoxy group, an amino group that may have, as a substituent, a group selected from the group consisting of a C1-C6 alkanoyl group and a C1-C6 alkyl group, a C1-C6 alkoxycarbonyl group, a phenyl group, a phenoxy group (wherein, on the phenyl-ring, at least one selected from the group consisting of a halogen atom, a halogen substituted or unsubstituted C1-C6 alkyl group, and a halogen substituted or unsubstituted C1-C6 alkoxy group, may be substituted), an aminosulfonyl group, a 1,2,3,4-tetrahydroquinolyl group (wherein, on the 1,2,3,4-tetrahydroquinoline ring, at least one oxo group may be substituted as a substituent), a C1-C6 alkylsulfonyl group, a C3-C8 cycloalkyl group, a nitro group, a cyano group, a C1-C6 alkylthio group, a phenylsulfonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a hydroxyl group substituted C1-C6 alkyl group, and a group represented by the following chemical formula (34):

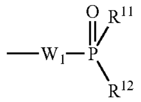

(34)

(wherein $W_1$ represents a C1-C6 alkylene group, and $R^{11}$ and $R^{12}$ each identically or differently represent a C1-C6 alkoxy group)]; a phenyl C1-C6 alkyl group [wherein, on the phenyl ring, at least one selected from the group consisting of a C1-C4 alkylenedioxy group, a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a group —$N(R^{11A})R^{12A}$ (wherein $R^{11A}$ and $R^{12A}$ each identically or differently represent a hydrogen atom, C1-C6 alkyl group, or phenyl group, and $R^{11A}$ and $R^{12A}$ may bind to each other together with nitrogen atoms adjacent thereto directly or through nitrogen, oxygen or sulfur atoms, so as to form a 5-7 membered saturated heterocyclic ring), a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a phenyl C1-C6 alkoxy group, an amino group substituted C1-C6 alkoxy group that may have a C1-C6 alkyl group as a substituent, a halogen atom, a halogen substituted or unsubstituted C1-C6 alkyl group, and a halogen substituted or unsubstituted C1-C10 alkoxy group, may be substituted as a substituent]; a benzofuryl C1-C6 alkyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted]; a phenylsulfonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, and a C1-C4 alkylenedioxy may be substituted]; a phenoxycarbonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C2-C6 alkenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], a C1-C6 alkoxy substituted C1-C6 alkyl group; a C2-C6 alkenyl group; a C1-C6 alkoxy substituted C2-C6 alkanoyl group; a C3-C8 cycloalkyl substituted C1-C6 alkyl group; a phenoxy C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a benzoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenylcarbamoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a pyridyl group; a pyridyl C1-C6 alkyl group; an imdazolyl C1-C6 alkyl group; a 1,2,3,4-tetrahydroquinolyl group [wherein, on the 1,2,3,4-tetrahydroquinoline ring, at least one selected from the group consisting of an oxo group and a C1-C6 alkyl group may be substituted as a substituent]; a quinolyl group; an indolyl group; an amino group that may have a C1-C6 alkyl group as a substituent; an indazolyl group; a naphthyl group; a C3-C8 cycloalkyl group; an amino substituted C1-C6 alkyl group that may have a C1-C6 alkyl group as a substituent; a cyano substituted C1-C6 alkyl group; a furyl substituted C1-C6 alkyl group; a group of the formula (35)

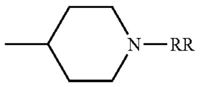

(35)

(wherein RR represents a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)); or a piperazinyl substituted C1-C6 alkyl group [wherein, on the piperazine ring, at least one phenyl group may be substituted as a substituent (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], further, $R^9$ and $R^{10}$ may bind to each other together with nitrogen atoms adjacent thereto directly or through nitrogen, oxygen or sulfur atoms, so as to form a 1,2,3,4-tetrahydroisoquinolyl group, isoindolyl group, or 5-7 membered saturated heterocyclic ring, wherein, on the heterocyclic ring, at least one selected from the following group may be substituted: a halogen atom, a halogen substituted or unsubstituted C1-C6 alkyl group, a halogen substituted or unsubstituted C1-C6 alkoxy group, a phenyl group [wherein, on the phenyl ring, at least one selected from the group consisting of a phenyl group, a halogen atom, a halogen-substituted or unsubstituted C1-C6 alkyl group, and a halogen substituted or unsubstituted C1-C6 alkoxy group, may be substituted], a benzoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], a pyridyl C1-C6 alkyl group, a C3-C8 cycloalkyl group, a phenyl C1-C6 alkyl group [wherein, on the phenyl ring, at least one selected from the group consisting of a C1-C4 alkylenedioxy group, a halogen atom, a halogen substituted or unsubstituted C1-C6 alkyl group, and a halogen substituted or unsubstituted C1-C6 alkoxy group, may be substituted], a piperidyl C1-C6 alkyl group, a piperidyl group, a phenyl C1-C6 alkoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], an amino group wherein at least one selected from the group consisting of a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], a C1-C6 alkyl group, and a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], may be substituted as a substituent, a benzoxazolyl group, a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), and a benzoimidazolyl group);

(5) a phenyl C1-C6 alkyl group (wherein, on the phenyl ring, at least one selected from the group consisting of a halogen atom, a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a halogen substituted or unsubstituted C1-C6 alkyl group, and a halogen substituted or unsubstituted C1-C6 alkoxy group, may be substituted);

(6) a carbamoyloxy group (wherein, on the amino group, at least one selected from the group consisting of a C1-C6 alkyl group and a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted] may be substituted);

(7) a carbamoyloxy substituted C1-C6 alkyl group (wherein, on the amino group, at least one selected from the group consisting of a C1-C6 alkyl group, a phenyl C1-C6 alkyl group, a C3-C8 cycloalkyl group, a naphthyl group, a 2,3-dihydro-1H-indenyl group, a 2,3-dihydrobenzofuryl group, and a phenyl group [wherein, on the phenyl ring, at least one selected from the group consisting of a C1-C4 alkylenedioxy group, a cyano group, a phenoxy group, a C1-C6 alkylthio group, a C1-C6 alkanoyl group, a phenyl group, a phenyl C1-C6 alkyl group, a halogen atom, a halogen substituted or unsubstituted C1-C10 alkyl group, and a halogen substituted or unsubstituted C1-C10 alkoxy group, may be substituted], may be substituted);

(8) a phenoxy C1-C6 alkyl group (wherein, on the phenyl ring, at least one selected from the following group may be substituted: a halogen atom; a C1-C4 alkylenedioxy group; a C1-C6 alkoxycarbonyl group; a phenyl group; a phenoxy group; a pyrrolyl group; a benzothiazolyl group; a 1,2,4-triazolyl group; an imidazolyl group; an isoxazolyl group; a benzoxazolyl group; a benzotriazolyl group; a cyano group; a nitro group; a C2-C6 alkenyl group; a C1-C6 alkanoyl group; a C1-C6 alkoxycarbonyl substituted C1-C6 alkyl group; a C1-C6 alkanoyl substituted C1-C6 alkyl group; a group —N($R^{11B}$)$R^{12B}$ (wherein $R^{11B}$ and $R^{12B}$ each identically or differently represent a hydrogen atom, C1-C6 alkyl group, C1-C6 alkanoyl group, or phenyl group, and $R^{11B}$ and $R^{12B}$ may bind to each other together with nitrogen atoms adjacent thereto directly or through nitrogen, oxygen or sulfur atoms, so as to form a 5-7 membered saturated heterocyclic ring, wherein, on the heterocyclic ring, at least one selected from the group consisting of a C1-C6 alkoxycarbonyl group and an amino group [wherein, on the amino group, at least one selected from a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted] may be substituted); a phenyl C1-C6 alkoxy group; a phenyl C1-C6 alkyl group; a C1-C6 alkylthio group; a C3-C8 cycloalkyl group; a halogen substituted or unsubstituted C1-C6 alkyl group; and a halogen substituted or unsubstituted C1-C10 alkoxy group);

(9) a tetrahydropyranyloxy C1-C6 alkyl group;

(10) a hydroxyl substituted C1-C6 alkyl group;

(11) a furyl C1-C6 alkoxy substituted C1-C6 alkyl group (wherein, on the furan ring, at least one C1-C6 alkoxycarbonyl group may be substituted);

(12) a tetrazolyl C1-C6 alkoxy substituted C1-C6 alkyl group (wherein, on the tetrazole ring, at least one selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a phenyl C1-C6 alkyl group, and a C3-C8 cycloalkyl C1-C6 alkyl group, may be substituted);

(13) an isoxazolyl C1-C6 alkoxy substituted C1-C6 alkyl group (wherein, on the isoxazole ring, at least one C1-C6 alkyl group may be substituted);

(14) a benzothienyl C1-C6 alkoxy substituted C1-C6 alkyl group (wherein, on the benzothiophene ring, at least one selected from the group consisting of a halogen atom, a halogen substituted or unsubstituted C1-C6 alkyl group, and a halogen substituted or unsubstituted C1-C6 alkoxy group, may be substituted);

(15) a 1,3,4-oxadiazolyl C1-C6 alkoxy substituted C1-C6 alkyl group (wherein, on the 1,3,4-oxadiazole ring, a phenyl group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

(16) a C2-C6 alkynyloxy substituted C1-C6 alkyl group;

(17) a naphthyl C1-C6 alkoxy substituted C1-C6 alkyl group;

(18) a 1,2,4-oxadiazolyl C1-C6 alkoxy substituted C1-C6 alkyl group [wherein, on the 1,2,4-oxadiazole ring, a phenyl group may be substituted];

(19) a pyridyl C1-C6 alkoxy substituted C1-C6 alkyl group [wherein, on the pyridine ring, at least one selected from the group consisting of a halogen atom, a halogen substituted or unsubstituted C1-C6 alkyl group, and a halogen substituted or unsubstituted C1-C6 alkoxy group, may be substituted];

(20) a thiazolyl C1-C6 alkoxy substituted C1-C6 alkyl group [wherein, on the thiazole ring, at least one selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted];

(21) a 1,2,3,4-tetrahydronaphthyl C1-C6 alkoxy substituted C1-C6 alkyl group [wherein, on the 1,2,3,4-tetrahydronaphthalene ring, at least one C1-C6 alkyl group may be substituted];

(22) a carbamoyl C1-C6 alkoxy substituted C1-C6 alkyl group [wherein, on the amino group, at least one selected from the group consisting of a C3-C8 cycloalkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted];

(23) a benzofuryl C1-C6 alkoxy substituted C1-C6 alkyl group [wherein, on the benzofuran ring, at least one cyano group may be substituted];

(24) a benzofuryl C1-C6 alkyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted];

(25) a phenoxy group [wherein, on the phenyl ring, at least one selected from the group consisting of a phenyl C1-C6 alkoxy group, a C3-C8 cycloalkyl group, a C7-C10 alkoxy group, and a phenoxy group, is substituted];

(26) a naphthyloxy group;

(27) a 2,3-dihydrobenzofuryloxy group [wherein, on the 2,3-dihydrobenzofuran ring, at least one oxo group may be substituted];

(28) a benzothiazolyloxy group [wherein, on the benzothiazole ring, at least one C1-C6 alkyl group may be substituted];

(29) a 1,2,3,4-tetrahydronaphthyloxy group [wherein, on the 1,2,3,4-tetrahydronaphthalene ring, at least one oxo group may be substituted];

(30) a dibenzofuryloxy group;

(31) a quinolyloxy group;

(32) a furyl C1-C6 alkoxy group [wherein, on the furan ring, at least one C1-C6 alkoxycarbonyl group may be substituted];

(33) a tetrazolyl C1-C6 alkoxy group [wherein, on the tetrazole ring, at least one selected from the group consisting of a phenyl C1-C6 alkyl group and a C3-C8 cycloalkyl C1-C6 alkyl group may be substituted];

(34) a 1,2,4-oxadiazolyl C1-C6 alkoxy group [wherein, on the 1,2,4-oxadiazole ring, a phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)];

(35) a benzothienyl C1-C6 alkoxy group [wherein, on the benzothiophene ring, at least one halogen atom may be substituted];

(36) an isoxazolyl C1-C6 alkoxy group [wherein, on the isoxazole ring, at least one C1-C6 alkyl group may be substituted];

(37) a 1,3,4-oxadiazolyl C1-C6 alkoxy group [wherein, on the 1,3,4-oxadiazole ring, at least one phenyl group may be substituted (wherein, on the phenyl ring, at least one C1-C6 alkyl group may be substituted)];

(38) a naphthyl C1-C6 alkoxy group;

(39) a pyridyl C1-C6 alkoxy group (wherein, on the pyridine ring, at least one halogen substituted or unsubstituted C1-C6 alkyl group may be substituted);

(40) a thiazolyl C1-C6 alkoxy group [wherein, on the thiazole ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)];

(41) a 1,2,3,4-tetrahydronaphthyl C1-C6 alkoxy group (wherein, on the 1,2,3,4-tetrahydronaphthalene ring, at least one C1-C6 alkyl group may be substituted);

(42) a phenoxy C1-C6 alkoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(43) a carbamoyl C1-C6 alkoxy group [wherein, on the amino group, at least one selected from the group consisting of a C3-C8 cycloalkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted];

(44) a benzofuryl C1-C6 alkoxy group (wherein, on the benzofuran ring, at least one cyano group may be substituted);

(45) a naphthyloxy C1-C6 alkyl group (wherein, on the naphthalene ring, at least one C1-C6 alkoxy group may be substituted);

(46) a benzothiazolyloxy C1-C6 alkyl group (wherein, on the benzothiazole ring, at least one C1-C6 alkyl group may be substituted);

(47) a quinolyloxy C1-C6 alkyl group (wherein, on the quinoline ring, at least one C1-C6 alkyl group may be substituted);

(48) a 2,3-dihydrobenzofuryloxy C1-C6 alkyl group (wherein, on the 2,3-dihydrobenzofuran ring, at least one selected from the group consisting of a C1-C6 alkyl group and an oxo group may be substituted);

(49) a 1,2,3,4-tetrahydronaphthyloxy C1-C6 alkyl group (wherein, on the 1,2,3,4-tetrahydronaphthalene ring, at least one oxo group may be substituted);

(50) a 2,3-dihydro-1H-indenyloxy C1-C6 alkyl group (wherein, on the 2,3-dihydro-1H-indene ring, at least one oxo group may be substituted);

(51) a benzoxathiolanyloxy C1-C6 alkyl group (wherein, on the benzoxathiolane ring, at least one oxo group may be substituted);

(52) an isoquinolyloxy C1-C6 alkyl group;

(53) a pyridyloxy C1-C6 alkyl group;

(54) a dibenzofuryloxy C1-C6 alkyl group;

(55) a 2H-1-benzopyranyloxy C1-C6 alkyl group (wherein, on the 2H-1-benzopyran ring, at least one oxo group may be substituted);

(56) a benzoisoxazolyloxy C1-C6 alkyl group;

(57) a benzofurazanyloxy C1-C6 alkyl group;

(58) a quinoxalyloxy C1-C6 alkyl group;

(59) a C1-C6 alkoxy C1-C6 alkoxy substituted C1-C6 alkyl group;

(60) a thienyl C1-C6 alkoxy substituted C1-C6 alkyl group (wherein, on the thiophene ring, at least one halogen atom may be substituted);

(61) a phenyl C2-C6 alkenyloxy substituted C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(62) a quinolyl C1-C6 alkoxy substituted C1-C6 alkyl group; and

(63) a piperidylcarbonyl C1-C6 alkoxy substituted C1-C6 alkyl group, and further, $R^7$ and $R^8$ together may form a group $=C(R^{29})(R^{30})$, wherein $R^{29}$ and $R^{30}$ each identically or differently represent a hydrogen atom, C1-C6 alkyl group, or phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

(iii) a group represented by the following chemical formula (36):

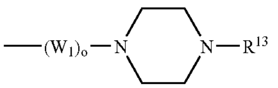

(36)

(wherein $W_1$ and o are the same as above, and $R^{13}$ represents: a 2,3-dihydro-1H-indenyl group; a benzothienyl group; a phenyl C2-C10 alkenyl group [wherein, on the phenyl ring, at least one selected from the group consisting of a halogen atom, a C1-C4 alkylenedioxy group, a C1-C6 alkylthio group, a benzoyl group, a cyano group, a nitro group, a C2-C6 alkanoyloxy group, an amino group that may have a C1-C6 alkyl group as a substituent, a hydroxyl group, a phenyl C1-C6 alkoxy group, a phenoxy group, a halogen substituted or unsubstituted C1-C6 alkyl group, and a halogen substituted or unsubstituted C1-C6 alkoxy group, may be substituted]; a naphthyl C2-C6 alkenyl group; a benzofuryl C1-C6 alkyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted]; a benzothienyl C2-C6 alkenyl group; a benzothiazolyl C2-C6 alkenyl group [wherein, on the benzothiazole ring, at least one C1-C6 alkyl group may be substituted]; a phenyl C1-C6 alkyl group [wherein, on the phenyl ring, at least one selected from the following group is substituted: a piperidinyl group (on the piperidine ring, at least one phenoxy group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]), a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, is substituted), and a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; a diphenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a benzoyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; an amino group wherein at least one selected from the following group may be substituted: a C1-C6 alkyl group, a C1-C6 alkoxycarbonyl group, and a phenyl C1-C6 alkyl group [wherein, on the phenyl ring, at least one selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a halogen atom, a halogen substituted or unsubstituted C1-C6 alkyl group, and a halogen substituted or unsubstituted C1-C6 alkoxy group, may be substituted]; an amino C1-C6 alkyl group wherein at least one selected from the group consisting of a C1-C6 alkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted; a benzofuryl C2-C6 alkenyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted]; a piperidyl group [wherein, on the piperidine ring, at least one phenyl C2-C6 alkenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; a ferrocene substituted C1-C6 alkyl group; an indolyl C1-C6 alkyl group (wherein, on the indole ring, at least one halogen atom may be substituted); a phenyl C2-C6 alkynyl group; a phenyl group [wherein, on the phenyl ring, at least one selected from the group consisting of a C1-C4 alkylenedioxy group, a phenyl group, a C1-C6 alkoxycarbonyl group, a hydroxyl group, and a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), is substituted]; a benzofuryl group [wherein, on the benzofuran ring, at least one selected from the group consisting of a halogen atom and a C1-C6 alkyl group may be substituted]; a benzohthiazolinyl group [wherein, on the benzothiazoline ring, at least one oxo group may be substituted]; a benzothienyl group [wherein, on the benzothiophene ring, at least one halogen atom may be substituted]; a naphthyl group; a 1,2,3,4-tetrahydroquinolyl group (wherein, on the 1,2,3,4-tetrahydroquinoline ring, at least one selected from the group consisting of an oxo group and a C1-C6 alkyl group may be substituted]; a benzoisoxazolyl group; a 2,3-dihydrobenzofuryl group; a 1,2-dihydroquinolyl group [wherein, on the 1,2-dihydroquinoline ring, at least one oxo group may be substituted]; a 1,2,3,4-tetrahydroquinazolinyl group [wherein, on the 1,2,3,4-tetrahydroquinazoline ring, at least one selected from the group consisting of an oxo group and a C1-C6 alkyl group may be substituted]; a benzocycloheptyl group; a phenoxy C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a benzothienyl substituted C1-C6 alkyl group (wherein, on the benzothiophene ring, at least one halogen atom may be substituted]; a naphthyl substituted C1-C6 alkyl group (wherein, on the naphthalene ring, at least one C1-C6 alkoxy group may be substituted); a pyridyl substituted C1-C6 alkyl group [wherein, on the pyridine ring, at least one halogen atom may be substituted]; a furyl substituted C1-C6 alkyl group [wherein, on the furan ring, at least one nitro group may be substituted]; a thienyl substituted C1-C6 alkyl group [wherein, on the thiophene ring, at least one halogen atom may be substituted]; a thiazolyl substituted C1-C6 alkyl group [wherein, on the thiazole ring, at least one selected from the group consisting of a C1-C6 alkyl group and a phenyl group (wherein, on the phenyl ring, at least one selected from the group consisting of a halogen atom and a halogen substituted or unsubstituted C1-C6 alkyl group may be substituted) may be substituted]; a tetrazolyl substituted C1-C6 alkyl group [wherein, on the tetrazole ring, at least one C1-C6 alkyl group may be substituted]; an isoxazolyl substituted C1-C6 alkyl group [wherein, on the isoxazole ring, at least one C1-C6 alkyl group may be substituted]; a 1,2,4-oxadiazolyl substituted C1-C6 alkyl group [wherein, on the 1,2,4-oxadiazole ring, at least one phenyl group may be substituted (wherein, on the phenyl ring, a C1-C6 alkyl group may be substituted)]; or a benzofurazanyl substituted C1-C6 alkyl group);

(iv) a group represented by the following chemical formula (37):

(37)

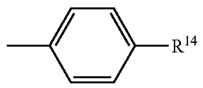

(wherein $R^{14}$ represents: a phenylamino group [wherein, at the N-position of the phenylamino group, a C1-C6 alkyl group may be substituted, and on the phenyl ring of the phenylamino group, at least one halogen substituted or unsubstituted C1-C6 alkoxy group may be substituted]; a piperidyl group [wherein, on the piperidine ring, at least one selected from the group consisting of a phenoxy group (wherein, on the phenyl ring, a halogen substituted or unsubstituted C1-C6 alkoxy group may be substituted) and an amino group (wherein, on the amino group, at least one selected from the group consisting of a C1-C6 alkyl group and a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted] may be substituted as a substituent) may be substituted]; a piperazinyl group [wherein, on the piperazine ring, at least one selected from the following group may be substituted: a C1-C6 alkoxycarbonyl group, a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), and a benzoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a homopiperazinyl group [wherein, on the homopiperazine ring, at least one selected from the group consisting of a C1-C6 alkoxycarbonyl group and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted]; or a phenoxy group [wherein, on the phenyl ring, at least one selected from the group consisting of a halogen substituted or unsubstituted C1-C6 alkoxy group and a phenoxy substituted phenyl group (wherein, on the phenyl ring, at least one halogen substituted or unsubstituted C1-C6 alkoxy group may be substituted), may be substituted]);

(v) a group represented by the following chemical formula (38):

(38)

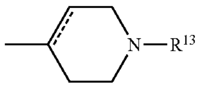

(wherein $R^{13}$ is the same as above, and a dotted line represents that the bond may be a double bond);

(vi) a homopiperazinyl group (wherein, on the homopiperazine ring, at least one selected from the following group may be substituted: a C1-C6 alkoxycarbonyl group; a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkoxycarbonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenylcarbamoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C2-C6 alkenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; and a benzoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

(vii) a group represented by the following chemical formula (39):

(39)

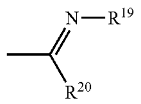

(wherein $R^{19}$ represents a C1-C6 alkoxy group, and $R^{20}$ represents a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

(viii) a group —$CHR^{20}R^{21}$ (wherein $R^{20}$ is the same as above, and $R^{21}$ represents an amino group that may have a C1-C6 alkyl group as a substituent);

(ix) a 1,2,3,4-tetrahydroisoquinolyl group (wherein, on the 1,2,3,4-tetrahydroisoquinoline ring, at least one amino group may be substituted [wherein, on the amino group, at least one selected from the group consisting of a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted]);

(x) an oxazolyl group (wherein, on the oxazole ring, at least one selected from the following group may be substituted: a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted], a C1-C6 alkyl group, and a piperidyl group [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]);

(xi) an isoindolinyl group (wherein, on the isoindoline ring, at least one selected from the group consisting of a halogen atom, a halogen substituted or unsubstituted C1-C6 alkyl group, and a halogen substituted or unsubstituted C1-C6 alkoxy group, may be substituted);

(xii) a thiazolyl group (wherein, on the thiazole ring, at least one selected from the following group may be substituted: a phenoxy C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]; a group —$(W_1)oNR^{31}R^{32}$ [wherein $W_1$ and o are the same as above, and $R^{31}$ and $R^{32}$ each identically or differently represent a hydrogen atom, C1-C6 alkyl group, phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), or phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; a piperazinyl group [wherein, on the piperazine ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; a piperidyl group [wherein, on the piperidine ring, at least one selected from the group consisting of a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and a phenyl C1-C6 alkyl group may be substituted]; and a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted]);

(xiii) a hydroxyl group substituted C1-C6 alkyl group;

(xiv) an oxazolyl C1-C6 alkyl group [wherein, on the oxazole ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)];

(xv) an isoxazolyl group [wherein, on the isoxazoline ring, at least one phenyl ring may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)];

(xvi) a benzoxazolyl group (wherein, on the benzoxazole ring, at least one halogen atom may be substituted);

(xvii) a phenylthio group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(xviii) a benzoimidazolyl group [wherein, on the benzoimidazole ring, at least one selected from the group consisting of a halogen atom and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted];

(xiv) a pyrrolidinyl group [wherein, on the pyrrolidine ring, at least one amino group is substituted (wherein, on the amino group, at least one selected from the group consisting of a C1-C6 alkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted)];

(xx) a phenylsulfonyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted);

(xxi) an imidazolyl group [wherein, on the imidazole ring, at least one phenyl group is substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)]; and (xxii) a phenylsulfinyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)];

(s) an imidazolyl group (wherein, on the imidazole ring, at least one selected from the group consisting of a halogen atom and a nitro group may be substituted);

(t) an isoindolinyloxy group [wherein, on the isoindoline ring, at least one selected from the following group may be substituted: a C1-C6 alkoxycarbonyl group, a phenyl C1-C6 alkyl group (wherein, on the phenyl ring, at least one selected from the group consisting of a benzofuryl group, a halogen atom, a halogen substituted or unsubstituted C1-C6 alkyl group, and a halogen substituted or unsubstituted C1-C6 alkoxy group, may be substituted), a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), a furyl C1-C6 alkyl group [wherein, on the furan ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], a pyridyl C1-C6 alkyl group [wherein, on the pyridine ring, at least one selected from the group consisting of a furyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted], a benzofuryl C1-C6 alkyl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted), a benzothienyl C1-C6 alkyl group (wherein, on the benzothiophene ring, at least one halogen atom may be substituted), a benzofuryl C2-C6 alkenyl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted), a thiazolyl group [wherein, on the thiazole ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], and a phenoxy C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)];

(u) a benzothiazolidinyloxy group [wherein, on the benzothiazolidine ring, at least one selected from the group consisting of an oxo group and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted), may be substituted];

(v) an indolyloxy group [wherein, on the indole ring, at least one phenyl C1-C6 alkyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)];

(w) a pyrrolidinyl group (wherein, on the pyrrolidine ring, at least one amino group is substituted (wherein, on the amino group, at least one selected from the group consisting of a C1-C6 alkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) may be substituted)];

(x) an indolinyl group (wherein, on the indoline ring, at least one halogen atom may be substituted); and (y) an indolinyloxy group [wherein, on the indoline ring, at least one selected from the group consisting of a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted) and an oxo group may be substituted].

The present invention provides 2,3-dihydro-6-nitroimidazo[2,1-b]oxazole compound, an optically active form thereof, or a pharmacologically acceptable salt thereof according to the above-mentioned general formula (1), wherein $R^2$ represents a group described in any one of (a) to (c), (e) to (h), (j) to (q), and (s) to (y).

The present invention provides 2,3-dihydro-6-nitroimidazo[2,1-b]oxazole compound, an optically active form thereof, or a pharmacologically acceptable salt thereof according to the above-mentioned general formula (1), wherein $R^2$ represents the group described in (d).

The present invention provides 2,3-dihydro-6-nitroimidazo[2,1-b]oxazole compound, an optically active form thereof, or a pharmacologically acceptable salt thereof according to the above-mentioned general formula (1), wherein $R^2$ represents the group described in (i).

The present invention provides 2,3-dihydro-6-nitroimidazo[2,1-b]oxazole compound, an optically active form thereof, or a pharmacologically acceptable salt thereof according to the above-mentioned general formula (1), wherein $R^2$ represents the group described in (r).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom.

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a C1-C6 alkyl group.

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ and $-(CH_2)_nR^2$ may bind to each other to form a spiro ring together with the carbon atom adjacent thereto, represented by the following formula (30):

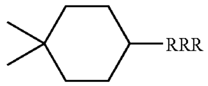

(30)

wherein RRR represents a piperidyl group [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)].

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (i).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (ii).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (iii).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (iv).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (v).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (vi).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (vii).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (viii).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (ix).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (x).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xi).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xii).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xiii).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xiv).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xv).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xvi).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xvii).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xviii).

The present invention provides 2,3-dihydro-6-nitroimidazo[2,1-b]oxazole compound, an optically active form thereof, or a pharmacologically acceptable salt thereof according to the above-mentioned general formula (1), wherein $R^3$ represents a hydrogen atom or a C1-C6 alkyl group and $R^3$ represents the group described in (xix).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xx).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xxi).

The present invention provides 2,3-dihydro-6-nitroimidazo[2,1-b]oxazole compound, an optically active form thereof, or a pharmacologically acceptable salt thereof according to the above-mentioned general formula (1), wherein $R^1$ represents a hydrogen atom or a C1-C6 alkyl group and $R^3$ represents the group described in (xxii).

In the compounds represented by the formula (1) of the present invention, particularly preferred are as follows:

2-methyl-6-nitro-2-{4-[4-(4-trifluoromethylbenzyloxymethyl)piperidin-1-yl]phenoxymethyl}-2,3-dihydroimidazo[2,1-b]oxazole, (R)-2-methyl-6-nitro-2-(4-[4-(4-trifluoromethylbenzyloxymethyl)piperidin-1-yl]phenoxymethy}-2,3-dihydroimidazo[2,1-b]oxazole, (S)-2-methyl-6-nitro-2-{4-[4-(4-trifluoromethylbenzyloxymethyl)piperidin-1-yl]phenoxymethyl}-2,3-dihydroimidazo[2,1-b]oxazole, 2-methyl-6-nitro-2-{4-[4-(4-chlorophenoxymethyl)piperidin-1-yl]phenoxymethyl}-2,3-dihydroimidazo[2,1-b]oxazole, (R)-2-methyl-6-nitro-2-{4-[4-(4-chlorophenoxymethyl)piperidin-1-yl]phenoxymethyl}-2,3-dihydroimidazo[2,1-b]oxazole, (S)-2-methyl-6-nitro-2-{4-[4-(4-chlorophenoxymethyl)piperidin-1-yl]phenoxymethyl}-2,3-dihydroimidazo[2,1-b]oxazole, 2-methyl-6-nitro-2-{4-[4-(4-trifluoromethylcinnamyl)piperazin-1-yl]phenoxymethyl}-2,3-dihydroimidazo[2,1-b]oxazole, (R)-2-methyl-6-nitro-2-{4-[4-(4-trifluoromethylcinnamyl)piperazin-1-yl]phenoxymethyl}-2,3-dihydroimidazo[2,1-b]oxazole, (S)-2-methyl-6-nitro-2-{4-[4-(4-trifluoromethylcinnamyl)piperazin-1-yl]phenoxymethyl}-2,3-dihydroimidazo[2,1-b]oxazole, 2-methyl-6-nitro-2-{4-[4-(4-trifluoromethoxycinnamyl)piperazin-1-yl]phenoxymethyl}-2,3-dihydroimidazo[2,1-b]oxazole, (R)-2-methyl-6-nitro-2-{4-[4-(4-trifluoromethoxycinnamyl)piperazin-1-yl]phenoxymethyl}-2,3-dihydroimidazo[2,1-b]oxazole, (S)-2-methyl-6-nitro-2-{4-[4-(4-trifluoromethoxycinnamyl)piperazin-1-yl]phenoxymethyl}-2,3-dihydroimidazo[2,1-b]oxazole, 2-methyl-6-nitro-2-{4-[4-(4-trifluoromethylphenoxymethyl)piperidin-1-yl]phenoxymethyl}-2,3-dihydroimidazo[2,1-b]oxazole, (R)-2-methyl-6-nitro-2-{4-[4-(4-trifluoromethylphenoxymethyl)piperidin-1-yl]phenoxymethyl}-2,3-dihydroimidazo[2,1-b]oxazole, (S)-2-methyl-6-nitro-2-{4-[4-(4-trifluoromethylphenoxymethyl)piperidin-1-yl]phenoxymethyl}-2,3-dihydroimidazo[2,1-b]oxazole, 6-nitro-2-{4-[4-(4-trifluoromethoxybenzyloxy)piperidin-1-yl]phenoxymethyl}-2,3-dihydroimidazo[2,1-b]oxazole, (R)-6-nitro-2-{4-[4-(4-trifluoromethoxybenzyloxy)piperidin-1-yl]phenoxymethyl}-2,3-dihydroimidazo[2,1-b]oxazole, (S)-6-nitro-2-{4-[4-(4-trifluoromethoxybenzyloxy)piperidin-1-yl]phenoxymethyl}-2,3-dihydroimidazo[2,1-b]oxazole, 6-nitro-2-{4-[4-(4-trifluoromethoxyphenoxymethyl)piperidin-1-yl]phenoxymethyl}-2,3-dihydroimidazo[2,1-b]oxazole, (R)-6-nitro-2-{4-[4-(4-trifluoromethoxyphenoxymethyl)piperidin-1-yl]phenoxymethyl}-2,3-dihydroimidazo[2,1-b]oxazole, (S)-6-nitro-2-{4-[4-(4-trifluoromethoxyphenoxymethyl)piperidin-1-yl]phenoxymethyl}-2,3-dihydroimidazo[2,1-b]oxazole, 6-nitro-2-{4-[4-(4-trifluoromethoxybenzyl)piperidin-1-yl]phenoxymethyl}-2,3-dihydroimidazo[2,1-b]oxazole, (R)-6-nitro-2-{4-[4-(4-trifluoromethoxybenzyl)piperidin-1-yl]phenoxymethyl}-2,3-dihydroimidazo[2,1-b]oxazole, (S)-6-nitro-2-{4-[4-(4-trifluoromethoxybenzyl)piperidin-1-yl]phenoxymethyl}-2,3-dihydroimidazo[2,1-b]oxazole, 2-methyl-6-nitro-2-{4-[4-(4-trifluoromethoxybenzyl)piperidin-1-yl]phenoxymethyl}-2,3-dihydroimidazo[2,1-b]oxazole, (R)-2-methyl-6-nitro-2-{4-[4-(4-trifluoromethoxybenzyl)piperidin-1-yl]phenoxymethyl}-2,3-dihydroimidazo[2,1-b]oxazole, (S)-2-methyl-6-nitro-2-{4-[4-(4-trifluoromethoxybenzyl)piperidin-1-yl]phenoxymethyl}-2,3-dihydroimidazo[2,1-b]oxazole, 2-methyl-6-nitro-2-[4-{4-[4-(4-trifluoromethylphenyl)piperazin-1-yl]piperidin-1-yl}phenoxymethyl]-2,3-dihydroimidazo[2,1-b]oxazole, (R)-2-methyl-6-nitro-2-[4-{4-[4-(4-trifluoromethylphenyl)piperazin-1-yl]piperidin-1-yl}phenoxymethyl]-2,3-dihydroimidazo[2,1-b]oxazole, (S)-2-methyl-6-nitro-2-[4-{4-[4-(4-trifluoromethylphenyl)piperazin-1-yl]piperidin-1-yl}phenoxymethyl]-2,3-dihydroimidazo[2,1-b]oxazole, 2-methyl-6-nitro-2-[4-{4-[4-(4-trifluoromethoxyphenoxy)benzyl]piperazin-1-yl}phenoxymethyl]-2,3-dihydroimidazo[2,1-b]oxazole, (R)-2-methyl-6-nitro-2-[4-{4-[4-(4-trifluoromethoxyphenoxy)benzyl]piperazin-1-yl}phenoxymethyl]-2,3-dihydroimidazo[2,1-b]oxazole, (S)-2-methyl-6-nitro-2-[4-{4-[4-(4-trifluoromethoxyphenoxy)benzyl]piperazin-1-yl}phenoxymethyl]-2,3-dihydroimidazo[2,1-b]oxazole, 6-nitro-2-[4-{4-[3-(4-trifluoromethoxyphenyl)propyl]piperidin-1-yl}phenoxymethyl]-2,3-dihydroimidazo[2,1-b]oxazole, (R)-6-nitro-2-[4-{4-[3-(4-trifluoromethoxyphenyl)propyl]piperidin-1-yl}phenoxymethyl]-2,3-dihydroimidazo[2,1-b]oxazole, (S)-6-nitro-2-[4-{4-[3-(4-trifluoromethoxyphenyl)propyl]piperidin-1-yl}phenoxymethyl]-2,3-dihydroimidazo[2,1-b]oxazole, 2-methyl-6-nitro-2-{4-[2-(4-trifluoromethoxyphenyl)oxazol-4-yl]phenoxymethyl}-2,3-dihydroimidazo[2,1-b]oxazole, (R)-2-methyl-6-nitro-2-{4-[2-(4-trifluoromethoxyphenyl)oxazol-4-yl]phenoxymethyl}-2,3-dihydroimidazo[2,1-b]oxazole, (S)-2-methyl-6-nitro-2-{4-[2-(4-trifluoromethoxyphenyl)oxazol-4-yl]phenoxymethyl}-2,3-dihydroimidazo[2,1-b]oxazole, 6-nitro-2-{4-[4-(4-chlorophenoxymethyl)piperidin-1-yl]phenoxymethyl}-2,3-dihydroimidazo[2,1-b]oxazole, (R)-6-nitro-2-{4-[4-(4-chlorophenoxymethyl)piperidin-1-yl]phenoxymethyl}-2,3-dihydroimidazo[2,1-b]oxazole, (S)-6-nitro-2-{4-[4-(4-chlorophenoxymethyl)piperidin-1-yl]phenoxymethyl}-2,3-dihydroimidazo[2,1-b]oxazole, 2-methyl-6-nitro-2-{4-[4-(5-trifluoromethylbenzofuran-2-yl)methylpiperidin-1-yl]phenoxymethyl}-2,3-dihydroimidazo[2,1-b]oxazole, (R)-2-methyl-6-nitro-2-{4-[4-(5-trifluoromethylbenzofuran-2-yl)methylpiperidin-1-yl]phenoxymethyl}-2,3-dihydroimidazo[2,1-b]oxazole, (S)-2-methyl-6-nitro-2-{4-[4-(5-trifluoromethylbenzofuran-2-yl)methylpiperidin-1-yl]phenoxymethyl}-2,3-dihydroimidazo[2,1-b]oxazole, 2-methyl-6-nitro-2-{4-[2-(4-chlorophenyl)oxazol-4-yl]phenoxymethyl}-2,3-dihydroimidazo[2,1-b]oxazole, (R)-2-methyl-6-nitro-2-{4-[2-(4-chlorophenyl)oxazol-4-yl]phenoxymethyl}-2,3-dihydroimidazo[2,1-b]oxazole, (S)-2-methyl-6-nitro-2-{4-[2-(4-chlorophenyl)oxazol-4-yl]phenoxymethyl}-2,3-dihydroimidazo[2,1-b]oxazole, 6-nitro-2-{4-[4-(4-trifluoromethylphenoxymethyl)piperidin-1-yl]phenoxymethyl}-2,3-dihydroimidazo[2,1-b]oxazole, (R)-6-nitro-2-{4-[4-(4-trifluoromethylphenoxymethyl)piperidin-1-yl]phenoxymethyl}-2,3-dihydroimidazo[2,1-b]oxazole, (S)-6-nitro-2-{4-[4-(4-trifluoromethylphenoxymethyl)piperidin-1-yl]phenoxymethyl}-2,3-dihydroimidazo[2,1-b]oxazole, 2-methyl-6-nitro-2-{4-[4-(4-bromocinnamyl)piperazin-1-yl]phenoxymethyl}-2,3-dihydroimidazo[2,1-b]oxazole, (R)-2-methyl-6-nitro-2-{4-[4-(4-bromocinnamyl)piperazin-1-yl]phenoxymethyl}-2,3-dihydroimidazo[2,1-b]oxazole, (S)-2-methyl-6-nitro-2-{4-[4-(4-bromocinnamyl)piperazin-1-yl]phenoxymethyl}-2,3-dihydroimidazo[2,1-b]oxazole, 2-methyl-6-nitro-2-[2-(4-trifluoromethoxyphenyl)-1,2,3,4-tetrahydroisoquinolin-6-yloxymethyl]-2,3-dihydroimidazo[2,1-b]oxazole, (R)-2-methyl-6-nitro-2-[2-(4-trifluoromethoxyphenyl)-1,2,3,4-tetrahydroisoquinolin-6-yloxymethyl]-2,3-dihydroimidazo[2,1-b]oxazole, and (S)-2-methyl-6-nitro-2-[2-(4-trifluoromethoxyphenyl)-1,2,3,4-tetrahydroisoquinolin-6-yloxymethyl]-2,3-dihydroimidazo[2,1-b]oxazole.

The present invention provides a pharmaceutical composition which is an antitubercular agent comprising, as an active ingredient, the 2,3-dihydro-6-nitroimidazo[2,1-b]oxazole compound, optically active form thereof, or pharmacologically acceptable salt thereof represented by general formula (1).

In particular, the present invention provides a pharmaceutical composition which is an antitubercular agent comprising, as an active ingredient, at least one compound selected from the 2,3-dihydro-6-nitroimidazo-[2,1-b]oxazole compounds that are preferred compound listed above.

The present invention provides a method for producing a compound represented by general formula (1):

(1)

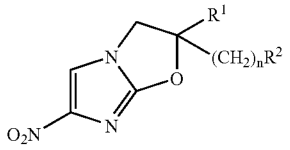

(wherein $R^1$, $R^2$, and n have the same definitions as described above), said method comprising:

a reaction of a 4-nitroimidazole compound represented by the following general formula (2):

(2)

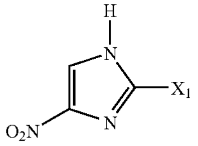

(wherein $X_1$ represents a halogen atom or a nitro group), with an epoxy compound represented by the following general formula (3a):

(3a)

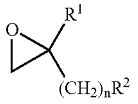

(wherein $R^1$, $R^2$ and n have the same definitions as described above), to obtain a compound represented by the following general formula (4a):

(4a)

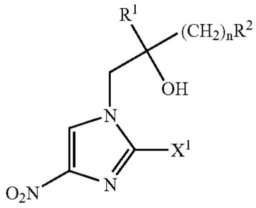

(wherein $R^1$, $R^2$ and n have the same definitions as described above, and $X^1$ represents a halogen atom or a nitro group); and a subsequent ring closure of the obtained compound represented by the above general formula (4a).

The present invention provides a method for producing a compound represented by the following general formula (1w):

(1w)

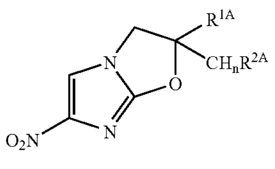

(wherein $R^{1A}$ represents a hydrogen atom, or a C1-C6 alkyl group, $R^{2A}$ represents a group described in any one of (a) to (y) as defined above, and n represents an integer between 0 and 6), said method comprising:

a reaction of a compound represented by the following general formula (3b):

(3b)

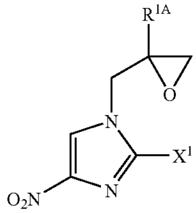

(wherein $R^{1A}$ is the same as described above, and $X^1$ represents a halogen atom or nitro group), with a compound $R^{2A}H(5)$ or a salt thereof (wherein $R^{2A}$ represents a group described in any one of (a) to (y) as defined above), to obtain a compound represented by the following general formula (4c):

(4c)

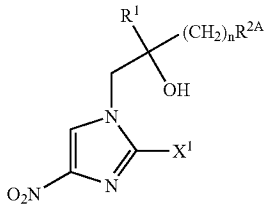

(wherein $R^1$ has the same definition as described above, $R^{2A}$ represents a group described in any one of (a) to (y) as defined above, and $X^1$ represents a halogen atom or a nitro group); and a subsequent ring closure of the obtained compound represented by the above general formula (4c).

The present invention provides a method for producing a compound represented by the following general formula (1w):

(1w)

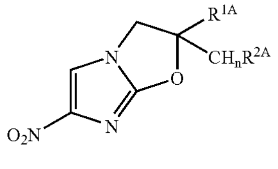

(wherein $R^{1A}$, $R^{2A}$, and n have the same definitions as described above), said method comprising:

a reaction of a compound represented by the following general formula (6):

(6)

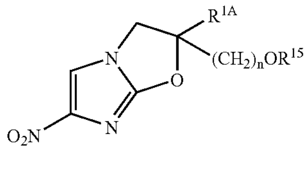

(wherein $R^{1A}$ and n have the same definitions as described above, and $R^{15}$ represents a C1-C6 alkylsulfonyl group or a benzenesulfonyl group wherein a C1-C6 alkyl group may be substituted), with a compound $R^{2A}H$(5) or a salt thereof (wherein $R^{2A}$ represents a group described in any one of (a) to (y) as defined above).

BEST MODE FOR CARRYING OUT THE INVENTION

In the compounds of the present invention, particularly preferred groups of $R^1$, $R^2$, $R^3$ are as follows. $R^1$ is preferably a hydrogen atom or C1-C6 alkyl group. $R^2$ is preferably a group (d), (i) or (r) as defined above. $R^3$ is preferably a group (ii), (iii) or (x) as defined above. $R^8$ is preferably a group (1), (2), (4), (5), (8), (24) or (25) as defined above. $R^{13}$ is preferably a phenyl C2-C10 alkenyl group [wherein, on the phenyl ring, at least one selected from the group consisting of a halogen atom, a C1-C4 alkylenedioxy group, a C1-C6 alkylthio group, a benzoyl group, a cyano group, a nitro group, a C2-C6 alkanoyloxy group, an amino group which may have C1-C6 alkyl group as substituent(s), a hydroxyl group, a phenyl C1-C6 alkoxy group, a phenoxy group, a halogen substituted or unsubstituted C1-C6 alkyl group and a halogen substituted or unsubstituted C1-C6 alkoxy group, may be substituted] or a phenyl C1-C6 alkyl group [wherein, on the phenyl ring, at least one selected from the group consisting of a piperidinyl group (wherein, on the piperidine ring, at least one phenoxy group may be substituted [wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted]), a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted) and a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted), may be substituted].

In this specification, each group represented by $R^1$, $R^2$, $R^3$ or the like is specifically as follows:

Examples of halogen atoms are fluorine atom, chlorine atom, bromine atom and iodine atom.

A C1-C6 alkyl group is a straight or branched alkyl group containing 1 to 6 carbon atoms, examples of which include a methyl group, ethyl group, n-propyl group, isopropyl group, n-butyl group, isobutyl group, tert-butyl group, sec-butyl group, n-pentyl group, neopentyl group, n-hexyl group, isohexyl group, 3-methylpentyl group or the like.

A C1-C6 alkoxy group is a group containing a C1-C6 alkyl group as defined above and an oxygen atom, examples of which include a methoxy group, ethoxy group, n-propoxy group, isopropoxy group, n-butoxy group, isobutoxy group, tert-butoxy group, sec-butoxy group, n-pentoxy group, neopentoxy group, n-hexyloxy group, isohexyloxy group, 3-methylpentoxy group or the like.

A halogen substituted or unsubstituted C1-C6 alkyl group is a straight or branched alkyl group containing 1 to 6 carbon atoms as defined above and optionally substituted by 1 to 7 halogen atoms, examples of which include a methyl group, ethyl group, n-propyl group, isopropyl group, n-butyl group, isobutyl group, tert-butyl group, sec-butyl group, n-pentyl group, neopentyl group, n-hexyl group, isohexyl group, 3-methylpentyl group, fluoromethyl group, difluoromethyl group, trifluoromethyl group, chloromethyl group, dichloromethyl group, trichloromethyl group, bromomethyl group, dibromomethyl group, dichlorofluoromethyl group, 2,2,2-trifluoroethyl group, pentafluoroethyl group, 2-chloroethyl group, 3,3,3-trifluoropropyl group, heptafluoropropyl group, heptafluoroisopropyl group, 3-chloropropyl group, 2-chloropropyl group, 3-bromopropyl group, 4,4,4-trifluorobutyl group, 4,4,4,3,3-pentafluorobutyl group, 4-chlorobutyl group, 4-bromobutyl group, 2-chlorobutyl group, 5,5,5-trifluoropentyl group, 5-chloropentyl group, 6,6,6-trifluorohexyl group, 6-chlorohexyl group or the like.

A halogen substituted or unsubstituted C1-C6 alkoxy group is a C1-C6 alkoxy group as defined above and an alkoxy group substituted by 1 to 7 halogen atoms, examples of which include a methoxy group, ethoxy group, n-propoxy group, isopropoxy group, n-butoxy group, isobutoxy group, tert-butoxy group, sec-butoxy group, n-pentoxy group, neopentoxy group, n-hexyloxy group, isohexyloxy group, 3-methylpentoxy group, fluoromethoxy group, difluoromethoxy group, trifluoromethoxy group, chloromethoxy group, dichloromethoxy group, trichloromethoxy group, bromomethoxy group, dibromomethoxy group, dichloro-fluoromethoxy group, 2,2,2-trifluoroethoxy group, pentafluoroethoxy group, 2-chloroethoxy group, 3,3,3-trifluoropropoxy group, heptafluoropropoxy group, heptafluoroisopropoxy group, 3-chloropropoxy group, 2-chloropropoxy group, 3-bromopropoxy group, 4,4,4-trifluorobutoxy group, 4,4,4,3,3-pentafluorobutoxy group, 4-chlorobutoxy group, 4-bromobutoxy group, 2-chlorobutoxy group, 5,5,5-trifluoropentoxy group, 5-chloropentoxy group, 6,6,6-trifluorohexyloxy group, 6-chlorohexyloxy group or the like.

A phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted) includes a phenoxy group (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted), for example, a phenoxy group, 2-fluorophenoxy group, 3-fluorophenoxy group, 4-fluorophenoxy group, 2-chlorophenoxy group, 3-chlorophenoxy group, 4-chlorophenoxy group, 2-bromophenoxy group, 3-bromophenoxy group, 4-bromophenoxy group, 2,3-dichlorophenoxy group, 3,4-dichlorophenoxy group, 2,4-dichlorophenoxy group, 3,4,5-trichlorophenoxy group, 2,4,6-trichlorophenoxy group, 2,3,4,5,6-pentafluorophenoxy group, 2-methylphenoxy group, 3-methylphenoxy group, 4-methylphenoxy group, 2-ethylphenoxy group, 3-ethylphenoxy group, 4-ethylphenoxy group, 4-n-propylphenoxy group, 4-tert-butylphenoxy group, 4-n-butylphenoxy group, 2-trifluoromethylphenoxy group, 3-trifluoromethylphenoxy group, 4-trifluoromethylphenoxy group, 2-pentafluoroethylphenoxy group, 3-pentafluoroethylphenoxy group, 2,3-dimethylphenoxy group, 3,4,5-trimethylphenoxy group, 4-n-pentylphenoxy group, 4-n-hexylphenoxy group, 2-methoxyphenoxy group, 3-methoxyphenoxy group, 4-methoxyphenoxy group, 2-ethoxyphenoxy group, 3-ethoxyphenoxy group, 4-ethoxyphenoxy group, 4-n-propoxyphenoxy group, 4-tert-butoxyphenoxy group, 4-n-butoxyphenoxy group, 2-trifluoromethoxyphenoxy group, 3-trifluoromethoxyphenoxy group, 4-trifluoromethoxyphenoxy group, 2-pentafluoroethoxyphenoxy group, 3-pentafluoroethoxyphenoxy group, 2,3-dimethoxyphenoxy group, 3,4,5-trimethoxyphenoxy group, 4-n-pentyloxyphenoxy group, 4-n-hexyloxyphenoxy group or the like.

A piperidyl group [wherein, on the piperidine ring, at least one phenoxy group may be substituted (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted)] includes a piperidyl group [wherein, on the piperidine ring, 1 to 3 phenoxy groups may be substituted (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted)], for example, a 1-piperidyl group, 2-piperidyl group, 3-piperidyl group, 4-piperidyl group, 4-phenoxy-1-piperidyl group, 2,4-diphenoxy-1-piperidyl group, 2,4,6-triphenoxy-1-piperidyl group, 2-(2-fluorophenoxy)-1-piperidyl group, 3-(3-fluorophenoxy)-2-piperidyl group, 4-(4-fluorophenoxy)-3-piperidyl group, 2-(2-chlorophenoxy)-4-piperidyl group, 3-(3-chlorophenoxy)-5-piperidyl group, 4-(4-chlorophenoxy)-2-piperidyl group, 5-(2-bromophenoxy)-2-piperidyl group, 6-(3-bromophenoxy)-3-piperidyl group, 4-(4-bromophenoxy)-1-piperidyl group, 3-(2,3-dichlorophenoxy)-2-piperidyl group, 4-(3,4-dichlorophenoxy)-3-piperidyl group, 3 (2,4-dichlorophenoxy)-4-piperidyl group, 2-(3,4,5-trichlorophenoxy)-3-piperidyl group, 6-(2,4,6-trichlorophenoxy)-2-piperidyl group, 3-(2,3,4,5,6-pentafluorophenoxy)-1-piperidyl group, 4-(2-methylphenoxy)-1-piperidyl group, 5-(3-methylphenoxy)-2-piperidyl group, 6-(4-methylphenoxy)-3-piperidyl group, 1-(2-ethylphenoxy)-4-piperidyl group, 2-(3-ethylphenoxy)-1-piperidyl group, 3-(4-ethylphenoxy)-2-piperidyl group, 4-(4-n-propylphenoxy)-3-piperidyl group, 3-(4-tert-butylphenoxy)-4-piperidyl group, 2-(4-n-butylphenoxy)-3-piperidyl group, 1-(2-trifluoromethylphenoxy)-2-piperidyl group, 2-(3-trifluoromethylphenoxy)-1-piperidyl group, 3-(4-trifluoromethylphenoxy)-1-piperidyl group, 1-(2-pentafluoroethylphenoxy)-4-piperidyl group, 1-(3-pentafluoroethylphenoxy)-4-piperidyl group, 4-(2,3-dimethylphenoxy)-1-piperidyl group, 1-(3,4,5-trimethylphenoxy)-4-piperidyl group, 1-(4-n-pentylphenoxy)-4-piperidyl group, 4-(4-n-hexylphenoxy)-1-piperidyl group, 4-(2-methoxyphenoxy)-1-piperidyl group, 1-(3-methoxyphenoxy)-4-piperidyl group, 1-(4-methoxyphenoxy)-4-piperidyl group, 2-(2-ethoxyphenoxy)-3-piperidyl group, 3-(3-ethoxyphenoxy)-4-piperidyl group, 4-(4-ethoxyphenoxy)-3-piperidyl group, 3-(4-n-propoxyphenoxy)-2-piperidyl group, 2-(4-tert-butoxyphenoxy)-1-piperidyl group, 1-(4-n-butoxyphenoxy)-2-piperidyl group, 2-(2-trifluoromethoxyphenoxy)-3-piperidyl group, 3-(3-trifluoromethoxyphenoxy)-4-piperidyl group, 4-(4-trifluoromethoxyphenoxy)-3-piperidyl group, 3-(2-pentafluoroethoxyphenoxy)-2-piperidyl group, 2-(4-pentafluoroethoxyphenoxy)-1-piperidyl group, 1-(2,3-dimethoxyphenoxy)-4-piperidyl group, 4-(3,4,5-trimethoxyphenoxy)-1-piperidyl group, 4-(4-n-pentyloxyphenoxy)-1-piperidyl group, 4-(4-n-hexyloxyphenoxy)-1-piperidyl group or the like.

A phenyl group (wherein, on the phenyl ring, at least one piperidyl group may be substituted [wherein, on the piperidine ring, at least one phenoxy group may be substituted (wherein, on the phenyl group, at least one selected from the group consisting of a halogen atom, a halogen substituted or unsubstituted C1-C6 alkyl group and a halogen substituted or unsubstituted C1-C6 alkoxy group, may be substituted)]) includes a phenyl group (wherein, on the phenyl ring, 1 to 3 piperidyl groups may be substituted [wherein, on the piperidine ring, 1 to 3 phenoxy groups may be substituted (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted)]), for example, a phenyl group, 4-(1-piperidyl)phenyl group, 2,4-di(1-piperidyl)phenyl group, 2,4,6-tri(1-piperidyl)phenyl group, 3-(4-piperidyl)phenyl group, 2-(2-piperidyl)phenyl group, 4-(3-piperidyl)phenyl group, 3-(4-phenoxy-1-piperidyl)phenyl group, 2-(2,4-diphenoxy-1-piperidyl)phenyl group, 4-(2,4,6-triphenoxy-1-piperidyl)phenyl group, 3-[2-(2-fluorophenoxy)-1-piperidyl]phenyl group, 2-[3-(3-fluorophenoxy)-2-piperidyl]phenyl group, 4-[4-(4-fluorophenoxy)-3-piperidyl]phenyl group, 3-[2-(2-chlorophenoxy)-4-piperidyl]phenyl group, 2-[3-(3-chlorophenoxy)-5-piperidyl]phenyl group, 4-[4-(4-chlorophenoxy)-2-piperidyl]phenyl group, 3-[5-(2-bromophenoxy)-2-piperidyl]phenyl group, 2-[6-(3-bromophenoxy)-3-piperidyl]phenyl group, 4-[4-(4-bromophenoxy)-1-piperidyl]phenyl group, 3-[3-(2,3-dichlorophenoxy)-2-piperidyl]phenyl group, 2-[4-(3,4-dichlorophenoxy)-3-piperidyl]phenyl group, 4-[3-(2,4-dichlorophenoxy)-4-piperidyl]phenyl group, 3-[2-(3,4,5-trichlorophenoxy)-3-piperidyl]phenyl group, 2-[6-(2,4,6-trichlorophenoxy)-2-piperidyl]phenyl group, 4-[3-(2,3,4,5,6-pentafluorophenoxy)-1-piperidyl]phenyl group, 3-[4-(2-methylphenoxy)-1-piperidyl]phenyl group, 2-[5-(3-methylphenoxy)-2-piperidyl]phenyl group, 4-[6-(4-methylphenoxy)-3-piperidyl]phenyl group, 3-[1-(2-ethylphenoxy)-4-piperidyl]phenyl group, 2-[2-(3-ethylphenoxy)-1-piperidyl]phenyl group, 4-[3-(4-ethylphenoxy)-2-piperidyl]phenyl group, 3-[4-(4-n-propylphenoxy)-3-piperidyl]phenyl group, 2-[3-(4-tert-butylphenoxy)-4-piperidyl]phenyl group, 4-[2-(4-n-butylphenoxy)-3-piperidyl]phenyl group, 3-[1-(2-trifluoromethylphenoxy)-2-piperidyl]phenyl group, 2-[2-(3-trifluoromethylphenoxy)-1-piperidyl]phenyl group, 4-[3-(4-trifluoromethylphenoxy)-1-piperidyl]phenyl group, 3-[1-(2-pentafluoroethylphenoxy)-4-piperidyl]phenyl group, 2-[1-(3-pentafluoroethylphenoxy)-4-piperidyl]phenyl group, 4-[4-(2,3-dimethylphenoxy)-1-piperidyl]phenyl group, 3-[1-(3,4,5-trimethylphenoxy)-4-piperidyl]phenyl group, 2-[1-(4-n-pentylphenoxy)-4-piperidyl]phenyl group, 4-[4-(4-n-hexylphenoxy)-1-piperidyl]phenyl group, 3-[4-(2-methoxyphenoxy)-1-piperidyl]phenyl group, 2-[1-(3-methoxyphenoxy)-4-piperidyl]phenyl group, 4-[1-(4-methoxyphenoxy)-4-piperidyl]phenyl group, 3-[2-(2-ethoxyphenoxy)-3-piperidyl]phenyl group, 2-[3-(3-ethoxyphenoxy)-4-piperidyl]phenyl group, 4-[4-(4-ethoxyphenoxy)-3-piperidyl]phenyl group, 3-[3-(4-n-propoxyphenoxy)-2-piperidyl]phenyl group, 2-[2-(4-tert-butoxyphenoxy)-1-piperidyl]phenyl group, 4-[1-(4-n-butoxyphenoxy)-2-piperidyl]phenyl group, 3-[2-(2-trifluoromethoxyphenoxy)-3-piperidyl]phenyl group, 2-[3-(3-trifluoromethoxyphenoxy)-4-piperidyl]phenyl group, 4-[4-(4-trifluoromethoxyphenoxy)-1-piperidyl]phenyl group, 3-[3-(2-pentafluoroethoxyphenoxy)-2-piperidyl]phenyl group, 2-[2-(4-pentafluoroethoxyphenoxy)-1-piperidyl]phenyl group, 4-[1-(2,3-dimethoxyphenoxy)-4-piperidyl]phenyl group, 3-[4-(3,4,5-trimethoxyphenoxy)-1-piperidyl]phenyl group, 2-[4-(4-n-pentyloxyphenoxy)-1-piperidyl]phenyl group, 4-[4-(4-n-hexyloxyphenoxy)-1-piperidyl]phenyl group or the like.

A phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted] includes a phenyl group unsubstituted or substituted by 1 to 5, preferably 1 to 3 substituents selected from the group consisting of a halogen atom, a halogen substituted or unsubstituted C1-C6 alkyl group and a halogen substituted or unsubstituted C1-C6 alkoxy group, as defined above, examples of which include a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-trichloro-phenyl group, 2,4,6-trifluorophenyl group, 2,4,6-trichlorophenyl group, 2-fluoro-4-bromophenyl group, 4-chloro-3-fluorophenyl group, 2,3,4-trichlorophenyl group, 2,3,4,5,6-pentafluorophenyl group, 2,4,6-trimethylphenyl group, 4-n-butylphenyl group, 2,4-dimethylphenyl group, 2,3-dimethylphenyl group, 2,6-dimethylphenyl group, 3,5-dimethylphenyl group, 2,5-dimethylphenyl group, 3,5-ditrifluoromethylphenyl group, 4-n-butoxyphenyl group, 2,4-dimethoxyphenyl group, 2,3-dimethoxyphenyl group, 2,6-dimethoxyphenyl group, 3,5-dimethoxyphenyl group, 2,5-dimethoxyphenyl group, 2,4,6-trimethoxyphenyl group, 3,5-ditrifluoromethoxyphenyl group, 3-chloro-4-methoxy-phenyl group, 2-chloro-4-trifluoromethoxyphenyl group, 3-methyl-4-fluorophenyl group, 4-bromo-3-trifluoro-methylphenyl group, 2-methylphenyl group, 3-methylphenyl group, 4-methylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoro-methylphenyl group, 4-trifluoromethylphenyl group, 2-pentafluoroethylphenyl group, 3-pentafluoroethylphenyl group, 4-pentafluoroethylphenyl group, 2-isopropyl-phenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoro-propylphenyl group, 4-pentylphenyl group, 4-hexylphenyl group, 2-methoxyphenyl group, 3-methoxyphenyl group, 4-methoxyphenyl group, 3-chloro-2-methoxyphenyl group, 2-fluoro-3-methoxyphenyl group, 2-fluoro-4-methoxyphenyl group, 2,3,4-trifluorophenyl group, 2-trifluoromethoxyphenyl group, 3-trifluoromethoxyphenyl group, 4-trifluoromethoxyphenyl group, 3-fluoro-2-trifluoromethoxyphenyl group, 2-fluoro-3-trifluoromethoxyphenyl group, 3-fluoro-4-trifluoromethoxyphenyl group, 3-chloro-2-trifluoromethoxyphenyl group, 2-chloro-3-trifluoromethoxyphenyl group, 3-chloro-4-trifluoro-methoxyphenyl group, 2-pentafluoroethoxyphenyl group, 3-pentafluoroethoxyphenyl group, 4-pentafluoroethoxy-phenyl group, 3-chloro-2-pentafluoroethoxyphenyl group, 2-chloro-3-pentafluoroethoxyphenyl group, 3-chloro-4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-n-pentoxyphenyl group, 4-n-hexyloxyphenyl group or the like.

Examples of a phenyl C1-C6 alkyl group include a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-methyl-3-phenylpropyl group, 1,1-dimethyl-2-phenylethyl group or the like.

A phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted) includes a phenyl C1-C6 alkyl group unsubstituted or substituted on the phenyl ring by 1 to 5, preferably 1 to 3 substituents selected from the group consisting of a halogen atom, a halogen substituted or unsubstituted C1-C6 alkyl group and a halogen substituted or unsubstituted C1-C6 alkoxy group, examples of which include a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,4-difluorobenzyl group, 2,6-difluorobenzyl group, 2,3-dichlorobenzyl group, 3,4-dichlorobenzyl group, 3,5-dichlorobenzyl group, 2,4-dichlorobenzyl group, 2,6-dichlorobenzyl group, 2-fluoro-4-bromobenzyl group, 4-chloro-3-fluorobenzyl group, 2,3,4-trichlorobenzyl group, 3,4,5-trifluorobenzyl group, 2,4,6-trichlorobenzyl group, 4-isopropylbenzyl group, 4-n-butylbenzyl group, 4-methylbenzyl group, 2-methylbenzyl group, 3-methylbenzyl group, 2,4-dimethylbenzyl group, 2,3-dimethylbenzyl group, 2,6-dimethylbenzyl group, 3,5-dimethylbenzyl group, 2,5-dimethylbenzyl group, 2,4, 6-trimethylbenzyl group, 3,5-ditrifluoromethylbenzyl group, 2,3, 4,5,6-pentafluorobenzyl group, 4-isopropoxybenzyl group, 4-n-butoxybenzyl group, 4-methoxybenzyl group, 2-methoxybenzyl group, 3-methoxybenzyl group, 2,4-dimethoxybenzyl group, 2,3-dimethoxybenzyl group, 2,6-dimethoxybenzyl group, 3,5-dimethoxybenzyl group, 2,5-dimethoxybenzyl group, 2,4,6-trimethoxybenzyl group, 3,5-ditrifluoromethoxybenzyl group, 2-isopropoxybenzyl group, 3-chloro-4-methoxybenzyl group, 2-chloro-4-trifluoromethoxybenzyl group, 3-methyl-4-fluorobenzyl group, 4-bromo-3-trifluoromethylbenzyl group, 2-trifluoromethylbenzyl group, 3-trifluoromethylbenzyl group, 4-trifluoromethylbenzyl group, 2-pentafluoro-ethylbenzyl group, 3-pentafluoroethylbenzyl group, 4-pentafluoroethylbenzyl group, 2-trifluoromethoxybenzyl group, 3-trifluoromethoxybenzyl group, 4-trifluoro-methoxybenzyl group, 2-pentafluoroethoxybenzyl group, 3-pentafluoroethoxybenzyl group, 4-pentafluoroethoxy-benzyl group, 2-(2-trifluoromethylphenyl) ethyl group, 2-(3-trifluoromethylphenyl)ethyl group, 2-(4-trifluoro-methylphenyl)ethyl group, 2-(2-trifluoromethoxyphenyl)-ethyl group, 2-(3-(trifluoromethoxyphenyl)ethyl group, 2-(4-trifluoromethoxyphenyl)ethyl group, 2-(2-pentafluoroethoxyphenyl)ethyl group, 2-(3-pentafluoroethoxyphenyl)ethyl group, 2-(4-pentafluoroethoxy-phenyl) ethyl group, 3-(2-trifluoromethylphenyl)propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 3-(3-pentafluoroethoxyphenyl)propyl group, 3-(4-pentafluoroethoxyphenyl)propyl group, 4-(3-pentafluoroethoxyphenyl)butyl group, 5-(4-trifluoromethylphenyl)-pentyl group, 4-(4-trifluoromethylphenyl)pentyl group, 4-(4-trifluoromethoxyphenyl)pentyl group, 6-(3- trifluoromethylphenyl)hexyl group, 6-(4-trifluoromethylphenyl)hexyl group, 6-(4-trifluoromethoxy-phenyl) hexyl group or the like.

A phenyl C1-C6 alkyl group [wherein, on the phenyl group, at least one selected from the group consisting of a halogen atom, a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted), a halogen substituted or unsubstituted C1-C6 alkyl group and a halogen substituted or unsubstituted C1-C6 alkoxy group, may be substituted] includes a phenyl alkyl group wherein the alkyl moiety is a straight or branched alkyl group containing 1 to 6 carbon atoms [wherein, on the phenyl group, 1 to 5, preferably 1 to 3 groups selected from the group consisting of a halogen atom, a phenyl group (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted), a halogen substituted or unsubstituted C1-C6 alkyl group and a halogen substituted or unsubstituted C1-C6 alkoxy group, may be substituted], examples of which include a 4-(4-trifluoromethylphenyl) benzyl group, 4-(4-trifluoromethoxyphenyl)benzyl group, 4-(4-chlorophenyl)benzyl group, 4-(4-trifluoromethylphenyl)-benzyl group, 4-phenylbenzyl group, 3-phenylbenzyl group, 3,4-diphenylbenzyl group, 3,4,5-triphenylbenzyl group, 4-nitro-3-trifluoromethylbenzyl group, 4-trifluoromethoxy-3-phenylbenzyl group or the like, in addition to the above-mentioned phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted).

A piperazinyl group [wherein, on the piperazine ring, at least one phenyl C1-C6 alkyl group may be substituted (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted)] includes a piperazinyl group [wherein, on the piperadine ring, 1 to 3 phenyl C1-C6 alkyl groups may be substituted (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted)], for example, 1-piperazinyl group, 2-piperazinyl group, 3,4-dibenzyl-1-piperazinyl group, 2,3,4-tribenzyl-1-piperazinyl group, 4-benzyl-1-piperazinyl group, 4-(2-phenetyl)-1-piperazinyl group, 4-(3-phenylpropyl)-1-piperazinyl group, 4-(4-phenylbutyl)-1-piperazinyl group, 4-(5-phenylpentyl)-1-piperazinyl group, 4-(6-phenylhexyl)-1-piperazinyl group, 4-(2-fluorobenzyl)-1-piperazinyl group, 4-(3-fluorobenzyl)-1-piperazinyl group, 4-(4-fluorobenzyl)-1-piperazinyl group, 4-(2-chlorobenzyl)-1-piperazinyl group, 4-(3-chlorobenzyl)-1-piperazinyl group, 4-(4-chlorobenzyl)-1-piperazinyl group, 4-(2,3-dichlorobenzyl)-1-piperazinyl group, 4-(2,4-dichlorobenzyl)-1-piperazinyl group, 4-(3,4-dicholorobenzyl)-1-piperazinyl group, 4-(3,5-dichlorobenzyl)-1-piperazinyl group, 4-(3,4,5-trichlorobenzyl)-1-piperazinyl group, 4-(2,3,4,5,6-pentafluorobenzyl)-1-piperazinyl group, 4-(2-trifluoromethylbenzyl)-1-piperazinyl group, 4-(3-trifluoromethylbenzyl)-1-piperazinyl group, 4-(4-trifluoromethylbenzyl)-1-piperazinyl group, 4-(4-methylbenzyl)-1-piperazinyl group, 4-(3,4-dimethylbenzyl)-1-piperazinyl group, 4-(2,4,6-trimethylbenzyl)-1-piperazinyl group, 4-(2-pentafluoroethylbenzyl)-1-piperazinyl group, 4-(3-pentafluoroethylbenzyl)-1-piperazinyl group, 4-(4-pentafluoroethylbenzyl)-1-piperazinyl group, 4-(2-trifluoromethoxybenzyl)-1-piperazinyl group, 4-(3-trifluoromethoxybenzyl)-1-piperazinyl group, 4-(4-trifluoromethoxybenzyl)-1-piperazinyl group, 4-(4-methoxybenzyl)-1-piperazinyl group, 4-(3,4-dimethoxybenzyl)-1-piperazinyl group, 4-(2,4,6-trimethoxybenzyl)-1-piperazinyl group, 4-(2-pentafluoroethoxybenzyl)-1-piperazinyl group, 4-(3-pentafluoroethoxybenzyl)-1-piperazinyl group, 4-(4-pentafluoroethoxybenzyl)-1-piperazinyl group, 4-[2-(4-trifluoromethoxyphenyl)ethyl]-1-piperazinyl group, 4-[3-(4-trifluoromethoxyphenyl)propyl]-1-piperazinyl group, 4-[4-(4-trifluoromethoxyphenyl)butyl]-1-piperazinyl group, 4-[5-(4-trifluoromethoxyphenyl)-pentyl]-1-piperazinyl group, 4-[6-(4-trifluoromethoxyphenyl)hexyl]-1-piperazinyl group, 4-[2-(4-trifluoromethylphenyl)ethyl]-1-piperazinyl group, 4-[3-(4-trifluoromethylphenyl)propyl]-1-piperazinyl group, 4-[4-(4-trifluoromethoxyphenyl)butyl]-1-piperazinyl group, 4-[5-(4-trifluoromethylphenyl)-pentyl]-1-piperazinyl group, 4-[6-(4-trifluoromethylphenyl)hexyl]-1-piperazinyl group or the like.

A piperidyl group [wherein, on the piperidine ring, at least one selected from the group consisting of an amino group (wherein, on the amino group, at least one selected from the group consisting of a phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted] and a C1-C6 alkyl group, may be substituted), a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group, may be substituted) and a phenyl C1-C6 alkyl group (wherein, on the phenyl ring, at least one group selected from the group consisting of a halogen atom, a halogen substituted or unsubstituted C1-C6 alkyl group and a halogen substituted or unsubstituted C1-C6 alkoxy group, may be substituted), may be substituted] includes a piperidyl group [wherein, on the piperidine ring, 1 to 3 substituents selected from the group consisting of an amino group (wherein, on the amino group, 1 or 2 substituents selected from the group consisting of a phenyl group [wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted] and a C1-C6 alkyl group, may be substituted), a phenoxy group (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted) and a phenyl C1-C6 alkyl group (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted), may be substituted), for example, a 1-piperidyl group, 2-piperidyl group, 3-piperidyl group, 4-piperidyl group, 2,4-diamino-1-piperidyl group, 2,4,6-triamino-1-piperidyl group, 2-amino-1-piperidyl group, 3-amino-1-piperidyl group, 4-amino-1-piperidyl group, 4-methylamino-1-piperidyl group, 4-ethylamino-1-piperidyl group, 4-n-propylamino-1-piperidyl group, 4-dimethylamino-1-piperidyl group, 4-diethylamino-1-piperidyl group, 4-di-n-propylamino-1-piperidyl group, 4-phenylamino-1-piperidyl group, 4-(N-phenyl-N-methylamino)-1-piperidyl group, 4-(2-fluorophenylamino)-1-piperidyl group, 4-(3-fluorophenylamino)-1-piperidyl group, 4-(4-fluorophenylamino)-1-piperidyl group, 4-(2-chlorophenylamino)-1-piperidyl group, 4-(3-chlorophenylamino)-1-piperidyl group, 4-(4-chlorophenylamino)-1-piperidyl group, 4-(2,3-dichlorophenylamino)-1-piperidyl group, 4-(2,4,6-trifluorophenylamino)-1-piperidyl group, 4-(2,4-dichlorophenylamino)-1-piperidyl group, 4-(3,4-dichlorophenylamino)-1-piperidyl group, 4-(3,5-dichlorophenylamino)-1-piperidyl group, 4-(2,3,4,5,6-pentafluorophenylamino)-1-piperidyl group, 4-(2-trifluoromethylphenylamino)-1-piperidyl group, 4-(2-methylphenylamino)-1-piperidyl group, 4-(2,3-dimethylphenylamino)-1-piperidyl group, 4-(2-trifluoromethylphenylamino)-1-piperidyl group, 4-(2,4,6-trimethylphenylamino)-1-piperidyl group, 4-(4-trifluoromethylphenylamino)-1-piperidyl group, 4-(2-pentafluoroethylphenylamino)-1-piperidyl group, 4-(3-pentafluoroethylphenylamino)-1-piperidyl group, 4-(4-pentafluoroethylphenylamino)-1-piperidyl group, 4-(2-trifluoromethoxyphenylamino)-1-piperidyl group, 4-(2-methoxyphenylamino)-1-piperidyl group, 4-(2,3-dimethoxyphenylamino)-1-piperidyl group, 4-(2,4,6-trimethoxyphenylamino)-1-piperidyl group, 4-[N-methyl-N-(2,4,6-trimethoxyphenylamino)]-1-piperidyl group, 4-[N-methyl-N-(3,4-dimethylphenylamino)]-1-piperidyl group, 4-(3-trifluoromethoxyphenylamino)-1-piperidyl group, 4-(4-trifluoromethoxyphenylamino)-1-piperidyl group, 4-(2-pentafluoroethoxyphenylamino)-1-piperidyl group, 4-(3-pentafluoroethoxyphenylamino)-1-piperidyl group, 4-(4-pentafluoroethoxyphenylamino)-1-piperidyl group, 4-phenoxy-1-piperidyl group, 2,4-diphenoxy-1-piperidyl group, 2,4,6-triphenoxy-1-piperidyl group, 2-(2-fluorophenoxy)-1-piperidyl group, 3-(3-fluorophenoxy)-2-piperidyl group, 4-(4-fluorophenoxy)-3-piperidyl group, 2-(2-chlorophenoxy)-4-piperidyl group, 3-(3-chlorophenoxy)-5-piperidyl group, 4-(4-chlorophenoxy)-2-piperidyl group, 5-(2-bromophenoxy)-2-piperidyl group, 6-(3-bromophenoxy)-3-piperidyl group, 4-(4-bromophenoxy)-1-piperidyl group, 3-(2,3-dichlorophenoxy)-2-piperidyl group, 4-(3,4-dichlorophenoxy)-3-piperidyl group, 3-(2,4-dichlorophenoxy)-4-piperidyl group, 2-(3,4,5-trichlorophenoxy)-3-piperidyl group, 6-(2,4,6-trichlorophenoxy)-2-piperidyl group, 3-(2,3,4,5,6-pentafluorophenoxy)-1-piperidyl group, 4-(2-methylphenoxy)-1-piperidyl group, 5-(3-methylphenoxy)-2-piperidyl group, 6-(4-methylphenoxy)-3-piperidyl group, 1-(2-ethylphenoxy)-4-piperidyl group, 2-(3-ethylphenoxy)-1-piperidyl group, 3-(4-ethylphenoxy)-2-piperidyl group, 4-(4-n-propylphenoxy)-3-piperidyl group, 3-(4-tert-butylphenoxy)-4-piperidyl group, 2-(4-n-butylphenoxy)-3-piperidyl group, 1-(2-trifluoromethylphenoxy)-2-piperidyl group, 2-(3-trifluoromethylphenoxy)-1-piperidyl group, 3-(4-trifluoromethylphenoxy)-1-piperidyl group, 1-(2-pentafluoroethylphenoxy)-4-piperidyl group, 1-(3-pentafluoroethylphenoxy)-4-piperidyl group, 4-(2,3-dimethylphenoxy)-1-piperidyl group, 1-(3,4,5-trimethylphenoxy)-4-piperidyl group, 1-(4-n-pentylphenoxy)-4-piperidyl group, 4-(4-n-hexylphenoxy)-1-piperidyl group, 4-(2-methoxyphenoxy)-1-piperidyl group, 1-(3-methoxyphenoxy)-4-piperidyl group, 1-(4-methoxyphenoxy)-4-piperidyl group, 2-(2-ethoxyphenoxy)-3-piperidyl group, 3-(3-ethoxyphenoxy)-4-piperidyl group, 4-(4-ethoxyphenoxy)-3-piperidyl group, 3-(4-n-propoxyphenoxy)-2-piperidyl group, 2-(4-tert-butoxyphenoxy)-1-piperidyl group, 1-(4-n-butoxyphenoxy)-2-piperidyl group, 2-(2-trifluoromethoxyphenoxy)-3-piperidyl group, 3-(3-trifluoromethoxyphenoxy)-4-piperidyl group, 4-(4-trifluoromethoxyphenoxy)-3-piperidyl group, 3-(2-pentafluoroethoxyphenoxy)-2-piperidyl group, 2-(4-pentafluoroethoxyphenoxy)-1-piperidyl group, 1-(2,3-dimethoxyphenoxy)-4-piperidyl group, 4-(3,4,5-trimethoxyphenoxy)-1-piperidyl group, 4-(4-n-pentyloxyphenoxy)-1-piperidyl group, 4-(4-n-hexyloxyphenoxy)-1-piperidyl group, 4-benzyl-1-piperidyl group, 2,4-dibenzyl-1-piperidyl group, 2,4,6-tribenzyl-1-piperidyl group, 2-(2-fluorobenzyl)-1-piperidyl group, 3-[2-(3-fluorophenyl)ethyl]-2-piperidyl group, 4-[1-(4-fluorophenyl)ethyl]-3-piperidyl group, 2-[3-(2-chlorophenyl)propyl]-4-piperidyl group, 3-[4-(3-chlorophenyl)butyl]-5-piperidyl group, 4-[5-(4-chlorophenyl)pentyl]-2-piperidyl group, 5-[6-(2-bromophenyl)hexyl]-2-piperidyl group, 6-(3-bromobenzyl)-3-piperidyl group, 4-(4-bromobenzyl)-1-piperidyl group, 3-(2,3-dichlorobenzyl)-2-piperidyl group, 4-(3,4-dichlorobenzyl)-3-piperidyl group, 3-(2,4-dichlorobenzyl)-4-piperidyl group, 2-(3,4,5-trichlorobenzyl)-3-piperidyl group, 6-(2,4,6-trichlorobenzyl)-2-piperidyl group, 3-(2,3,4,5,6-pentafluorobenzyl)-1-piperidyl group, 4-(2-methylbenzyl)-1-piperidyl group, 5-[2-(3-methylphenyl)ethyl]-2-piperidyl group, 6-[3-(4-methylphenyl)propyl]-3-piperidyl group, 1-[4-(2-ethylphenyl)butyl]-4-piperidyl group, 2-[5-(3-ethylphenyl)pentyl]-1-piperidyl group, 3-[6-(4-ethylphenyl)hexyl]-2-piperidyl group, 4-(4-n-propylbenzyl)-3-piperidyl group, 3-(4-tert-butylbenzyl)-4-piperidyl group, 2-(4-n-butylbenzyl)-3-piperidyl group, 1-(2-trifluoromethylbenzyl)-2-piperidyl group; 2-(3-trifluoromethylbenzyl)-1-piperidyl group, 3-(4-trifluoromethylbenzyl)-1-piperidyl group, 1-(2-pentafluoroethylbenzyl)-4-piperidyl group, 1-(3-pentafluoroethylbenzyl)-4-piperidyl group, 4-(2,3-dimethylbenzyl)-1-piperidyl group, 1-(3,4,5-trimethylbenzyl)-4-piperidyl group, 1-(4-n-pentylbenzyl)-4-piperidyl group, 4-(4-n-hexylbenzyl)-1-piperidyl group, 4-(2-methoxybenzyl)-1-piperidyl group, 1-[2-(3-methoxyphenyl)ethyl]-4-piperidyl group, 1-[1-(4-methoxyphenyl)ethyl]-4-piperidyl group, 2-[3-(2-ethoxylphenyl)propyl]-3-piperidyl group, 3-[4-(3-ethoxyphenyl)butyl]-4-piperidyl group, 4-[5-(4-ethoxyphenyl)pentyl]-3-piperidyl group, 3-[6-(4-n-propoxyphenyl)hexyl]-2-piperidyl group, 2-(4-tert-butoxybenzyl)-1-piperidyl group, 1-(4-n-butoxybenzyl)-2-piperidyl group, 2-(2-trifluoromethoxybenzyl)-3-piperidyl group, 3-(3-trifluoromethoxybenzyl)-4-piperidyl group, 4-(4-trifluoromethoxybenzyl)-3-piperidyl group, 3-(2-pentafluoroethoxybenzyl)-2-piperidyl group, 2-(4-pentafluoroethoxybenzyl)-1-piperidyl group, 1-(2,3-dimethoxybenzyl)-4-piperidyl group, 4-(3,4,5-trimethoxybenzyl)-1-piperidyl group, 4-(4-n-pentyloxybenzyl)-1-piperidyl group, 4-(4-n-hexyloxybenzyl)-1-piperidyl group, 4-benzyl-3-phenoxy-1-piperidyl group, 4-phenoxy-2-methylamino-1-piperidyl group or the like.

A C1-C6 alkoxy C1-C6 alkoxy substituted C1-C6 alkyl group includes an alkoxyalkoxyalkyl group having a straight or branched alkoxy group containing 1 to 6 carbon atoms on the alkoxy part and a straight or branched alkyl group containing 1 to 6 carbon atoms on the alkyl part, for example, a methoxymethoxymethyl group, 2-(methoxymethoxy)ethyl group, 1-(2-methoxyethoxy)ethyl group, 1-(methoxymethoxy)ethyl group, 2-(3-propoxy)propoxyethyl group, 3-(2-ethoxyisopropoxy)propyl group, 4-(4-butoxybutoxy) butyl group, 5-(5-penthyloxypentyloxy)pentyl group, 6-(6-hexyloxyhexyloxy)hexyl group, 1,1-dimethyl-2-(ethoxymethoxy)ethyl group, 2-methyl-3-(methoxyethoxy)-propyl or 3-(propoxymethoxy)propyl group or the like.

A thienyl C1-C6 alkoxy substituted C1-C6 alkyl group (wherein, on the thiophene ring, al least one halogen atom may be substituted) includes an thienylalkoxyalkyl group having a straight or branched alkoxy group containing 1 to 6 carbon atoms on the alkoxy part and a straight or branched alkyl group containing 1 to 6 carbon atoms on the alkyl part (wherein, on the thiophene ring, 1 to 3 halogen atoms may be substituted as a substituent group), for example, a 2-thienylmethoxymethyl group, 3-thienylmethoxymethyl group, 2-(2-(2-thienyl)ethoxy)ethyl group, 3-(3-(2-thienyl)propoxy)propyl group, 4-(4-(2-thienyl)butoxy)butyl group, 4-(4-(3-thienyl)butoxy)butyl group, 5-(5-(2-thienyl)pentyloxy)pentyl group, 5-(5-(3-thienyl)pentyloxy)pentyl group, 6-(6-(2-thienyl)hexyloxy)hexyl group, 6-(6-(3-thienyl)hexyloxy)hexyl group, (5-chloro-2-thienylmethoxy)methyl group, (5-chloro-3-thienyl methoxy)methyl group, 2-(2-(4-bromo-2-thienyl)ethoxy)ethyl group, 3-(3-(3-fluoro-2-thienyl)propoxy)propyl group, 4-(4-(5-iodo-2-thienyl)butoxy)butyl group, 4-(4-(4-chloro-3-thienyl)butoxy)butyl group, 5-(5-(3-chloro-2-thienyl)pentyloxy)pentyl group, 5-((2-chloro-3-thienyl)methoxy)pentyl group, 6-(2-(3-chloro-2-thienyl)ethoxy)hexyl group, 6-(6-(5-chloro-3-thienyl)hexyloxy)hexyl group, (2-(4,5-dichloro-2-thienyl)ethoxy)methyl group, ((2,4,5-trichloro-3-thienyl)methoxy)methyl or the like.

A phenyl C2-C6 alkenyloxy substituted C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is a group composed of a phenyl group unsubstituted or substituted by 1 to 5, preferably 1 to 3 substituents selected from the group consisting of a halogen atom, a halogen substituted or unsubstituted straight or branched alkyl group containing 1 to 6 halogen carbon atoms and a halogen substituted or unsubstituted straight or branched alkoxy group containing 1 to 6 carbon atoms and an alkenyl group containing 2 to 6 carbon atoms and having at least 1 to 3 double bonds. The phenyl C2-C6 alkenyloxy group includes both trans and cis forms. Such a phenyl C2-C6 alkenyloxy C1-C6 alkyl group includes a (2-phenylvinyloxy)methyl group, (3-phenyl-2-propenyloxy)methyl group, 2-(4-phenyl-2-butenyloxy)ethyl group, 1-(4-phenyl-3-butenyloxy)ethyl group, 3-(4-phenyl-1,3-butadienyloxy)propyl group, 4-(5-phenyl-1,3,5-hexatrienyloxy)butyl group, 5-(3-(2-fluorophenyl)-2-propenyloxy)pentyl group, 6-(3-(3-fluorophenyl)-2-propenyloxy)hexyl group, (3-(4-fluorophenyl)-2-propenyloxy)methyl group, 2-(3-(2,3-difluorophenyl)-2-propenyloxy)ethyl group, 3-(3-(2,3,4,5,6-pentafluorophenyl)-2-propenyloxy)propyl group, 4-(3-(2,4-difluorophenyl)-2-propenyloxy)butyl group, 5-(3-(3,4-difluorophenyl)-2-propenyloxy)pentyl group, 6-(3-(3,5-difluorophenyl)-2-propenyloxy)hexyl group, (3-(2-chlorophenyl)-2-propenyloxy)methyl group, 2-(3-(3-chlorophenyl)-2-propenyloxy)ethyl group, 3-(3-(4-chlorophenyl)-2-propenyloxy)propyl group, 4-(3-(2,3-dichlorophenyl)-2-propenyloxy)butyl group, 5-(3-(2,4-dichlorophenyl)-2-propenyloxy)pentyl group, 6-(3-(3,4-dichlorophenyl)-2-propenyloxy)hexyl group, (3-(3,5-dichlorophenyl)-2-propenyloxy)methyl group, 2-(3-(2-bromophenyl)-2-propenyloxy)ethyl group, 3-(3-(3-bromophenyl)-2-propenyloxy)propyl group, 4-(3-(4-bromophenyl)-2-propenyloxy)butyl group, 5-(3-(2-methylphenyl)-2-propenyloxy)pentyl group, 6-(3-(3-methylphenyl)-2-propenyloxy)hexyl group, (3-(4-methylphenyl)-2-propenyloxy)methyl group, 2-(3-(2-trifluoromethylphenyl)-2-propenyloxy)ethyl group, 3-(3-(2-fluoro-4-bromophenyl)-2-propenyloxy)propyl group, 4-(3-(4-chloro-3-fluorophenyl)-2-propenyloxy)butyl group, 5-(3-(2,3,4-trichlorophenyl)-2-propenyloxy)pentyl group, 6-(3-(2,4,6-trichlorophenyl)-2-propenyloxy)hexyl group, (3-(4-isopropylphenyl)-2-propenyloxy)methyl group, 2-(3((4-n-butylphenyl)-2-propenyloxy)ethyl group, 1-(3-(2,4-dimethylphenyl)-2-propenyloxy)ethyl group, 3-(3((2,3-dimethylphenyl)-2-propenyloxy)propyl group, ((2,6-dimethylphenyl)-2-propenyloxy)methyl group, 5-(3-(3,5-dimethylphenyl)-2-propenyloxy)pentyl group, 6-(3-(2,5-dimethylphenyl)-2-propenyloxy)hexyl group, (3-(2,4,6-trimethylphenyl)-2-propenyloxy)methyl group, (3-(3,5-ditrifluoromethylphenyl)-2-propenyloxy)methyl group, (3-(4-n-butoxyphenyl)-2-propenyloxy)methyl group, (3-(2,4-dimethoxyphenyl)-2-propenyloxy)methyl group, (3-(2,3-dimethoxyphenyl)-2-propenyloxy)methyl group, (3-(2,6-dimethoxyphenyl)-2-propenyloxy)methyl group, (3-(3,5-dimethoxyphenyl)-2-propenyloxy)methyl group, (3-(2,5-dimethoxyphenyl)-2-propenyloxy)methyl group, (3-(3,5-ditrifluoromethoxyphenyl)-2-propenyloxy)methyl group, (3-(3-chloro-4-methoxyphenyl)-2-propenyloxy)methyl group, (3-(2-chloro-4-trifluoromethoxyphenyl)-2-propenyloxy) methyl group, (3-(3-methyl-4-fluorophenyl)-2-propenyloxy) methyl group, (3-(4-bromo-3-trifluoromethylphenyl)-2-propenyloxy)methyl group, (3-(3-trifluoromethylphenyl)-2-propenyloxy)methyl group, (3-(4-trifluoromethylphenyl)-2-propenyloxy)methyl group, (3-(2-trifluoromethoxyphenyl)-2-propenyloxy)methyl group, (3-(3-trifluoromethoxyphenyl)-2-propenyloxy)methyl group, (3-(4-trifluoromethoxyphenyl)-2-propenyloxy)methyl group, (3-(2-methoxyphenyl)-2-propenyloxy)methyl group, (3-(3-methoxyphenyl)-2-propenyloxy)methyl group, (3-(4-methoxyphenyl)-2-propenyloxy)methyl group, (3-(3,4-dimethoxyphenyl)-2-propenyloxy)methyl group, (3-(3,5-dimethoxyphenyl)-2-propenyloxy)methyl group, (4-(4-chlorophenyl)-2-butenyloxy)methyl group, (4-(4-chlorophenyl)-3-butenyloxy)methyl group, (5-(4-chlorophenyl)-2-pentenyloxy)methyl group, (5-(4-chlorophenyl)-4-pentenyloxy)methyl group, (5-(4-chlorophenyl)-3-pentenyloxy)methyl group, (6-(4-chlorophenyl)-5-hexenyloxy)methyl group, (6-(4-chlorophenyl)-4-hexenyloxy)methyl group, (6-(4-chlorophenyl)-3-hexenyloxy)methyl group, (6-(4-chlorophenyl)-3-hexenyloxy)methyl group or the like.

A quinolyl C1-C6 alkoxy substituted C1-C6 alkyl group includes a quinolylalkoxyalkyl group having a straight or branched alkoxy group containing 1 to 6 carbon atoms on the alkoxy part and a straight or branched alkyl group containing 1 to 6 carbon atoms on the alkyl part, for example, a (2-, 3-, 4-, 5-, 6-, 7- or 8-)quinolylmethoxymethyl group, 2-(2-((2-, 3-, 4-, 5-, 6-, 7- or 8-)quinolyl)ethoxy)ethyl group, 3-(3-((2-, 3-, 4-, 5-, 6-, 7- or 8-)quinolyl)propoxy)propyl group, 4-(4-((2-, 3-, 4-, 5-, 6-, 7- or 8-)quinolyl)-butoxy)butyl group, 5-(5-((2-, 3-, 4-, 5-, 6-, 7- or 8-)quinolyl)pentyloxy)pentyl group, 6-(6-((2-, 3-, 4-, 5-, 6-, 7- or 8-)quinolyl)hexyloxy)hexyl group or the like.

A piperidylcarbonyl C1-C6 alkoxy substituted C1-C6 alkyl group includes a piperidylcarbonylalkoxyalkyl group having a straight or branched alkoxy group containing 1 to 6 carbon atoms on the alkoxy part and a straight or branched alkyl group containing 1 to 6 carbon atoms on the alkyl part, for example, (1-, 2- or 3-)piperidylcarbonylmethoxymethyl group, 2-(2-((1-, 2- or 3-)piperidylcarbonyl)-ethoxy)ethyl group, 3-(3-((1-, 2- or 3-)piperidyl-carbonyl)propoxy)propyl group, 4-(4-((1-, 2- or 3-)-piperidylcarbonyl)butoxy)butyl group, 5-(5-((1-, 2- or 3-)piperidylcarbonyl)pentyloxy)pentyl group, 6-(6-((1-, 2- or 3-)piperidylcarbonyl)hexyloxy)hexyl group or the like.

A phenyl C1-C6 alkyl group [wherein, on the phenyl ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group is substituted) is substituted] includes a phenylalkyl group having a straight or branched alkyl group containing 1 to 6 carbon atoms on the alkyl part [wherein, on the phenyl ring, 1 to 3 phenyl groups (wherein, on the phenyl ring, 1 to 5, preferably 1 to 3 substituents selected from the group consisting of a halogen atom, a halogen substituted or unsubstituted straight or branched C1-C6 alkyl group and a halogen substituted or unsubstituted straight or branched C1-C6 alkoxy group are substituted) are substituted], for example, a 2-(2-fluorophenyl)benzyl group, 3-(3-fluorophenyl)benzyl group, 4-(4-fluorophenyl)benzyl group, 2-(2-chlorophenyl) benzyl group, 3-(3-chlorophenyl)benzyl group, 4-(4-chlorophenyl)benzyl group, 2-(2-bromophenyl)benzyl group, 3-(3-bromophenylbenzyl group, 4-(4-bromophenyl)benzyl group, 2-(2-iodophenyl)benzyl group, 3-(3-iodophenyl)benzyl group, 4-(4-iodophenyl)benzyl group, 4-(2,3-difluorophenyl)benzyl group, 3-(3,4-difluorophenyl)benzyl group, 2-(3,5-dofluorophenyl)benzyl group, 4-(2,4-difluorophenyl) benzyl group, 3-(2,6-difluorophenyl)benzyl group, 2-(2,3-dichlorophenyl)benzyl group, 4-(3,4-dichlorophenyl)benzyl group, 3-(3,5-dichlorophenyl)benzyl group, 2-(2,4-dichlorophenyl)benzyl group, 4-(2,6-dichlorophenyl)benzyl group, 3-(2-fluoro-4-bromophenyl)benzyl group, 2-(4-chloro-3-fluorophenyl)benzyl group, 4-(2,3,4-trichlorophenyl)benzyl group, 3-(3,4,5-trifluorophenyl)benzyl group, 2-(2,4,6-trichlorophenyl)benzyl group, 4-(4-isopropylphenyl)benzyl group, 3-(4-n-butylphenyl)benzyl group, 2-(4-methylphenyl) benzyl group, 4-(2-methylphenyl)benzyl group, 3-(3-methylphenyl)benzyl group, 2-(2,4-dimethylphenyl)benzyl group, 4-(2,3-dimethylphenylbenzyl group, 3-(2,6-dimethylphenyl)benzyl group, 2-(3,5-dimethylphenyl)benzyl group, 4-(2,5-dimethylphenyl)benzyl group, 3-(2,4,6-trimethylphenyl)benzyl group, 2-(3,5-ditrifluoromethylphenyl) benzyl group, 4-(2,3,4,5,6-pentafluorophenyl)benzyl group, 3-(4-isopropoxyphenyl)benzyl group, 2-(4-n-butoxyphenyl) benzyl group, 4-(4-methoxyphenyl)benzyl group, 3-(2-methoxyphenyl)benzyl group, 2-(3-methoxyphenyl)benzyl group, 4-(2,4-dimethoxyphenyl)benzyl group, 3-(2,3-dimethoxyphenyl)benzyl group, 2-(2,6-dimethocyphenyl) benzyl group, 2-(3,5-dimethoxyphenyl)benzyl group, 4-(2,5-dimethoxyphenyl)benzyl group, 3-(2,4,6-trimethoxyphenyl) benzyl group, 2-(3,5-ditrifluoromethoxyphenyl)benzyl group, 4-(2-isopropoxyphenyl)benzyl group, 3-(3-chloro-4-methoxyphenyl)benzyl group, 2-(2-chloro-4-trifluoromethoxyphenyl)benzyl group, 4-(3-methyl-4-fluorophenyl)benzyl group, 3-(4-bromo-3-trifluoromethylphenyl) benzyl group, 4-(2-trifluoromethylphenyl)benzyl group, 3-(3-trifluoromethylphenyl)benzyl group, 4-(4-trifluoromethylphenyl)benzyl group, 2-(2-pentafluoroethylphenyl)benzyl group, 3-(3-pentafluoroethylphenyl)benzyl group, 2-(4-pentafluoroethylphenyl)benzyl group, 4-(2-trifluoromethoxyphenyl)benzyl group, 3-(3-trifluoromethoxyphenyl)benzyl group, 4-(4-trifluoromethoxyphenyl)benzyl group, 4-(2-pentafluoroethoxyphenyl)benzyl group, 3-(3-pentafluoroethoxyphenyl)benzyl group, 2-(4-pentafluoroethoxyphenyl)benzyl group, 2-(4-(2-trifluoromethylphenyl)phenyl)ethyl group, 2-(3-(3-trifluoromethylphenyl)phenyl)ethyl group, 2-(2-(4-trifluoromethylphenyl)phenyl)ethyl group, 2-(4-(2-trifluoromethoxyphenyl)phenyl)ethyl group, 2-(3-(3-trifluoromethoxyphenyl)phenyl)ethyl group, 2-(2-(4-trifluoromethoxyphenyl)phenyl)ethyl group, 2-(4-(2-pentafluoroethoxyphenyl)phenyl)ethyl group, 2-(3-(3-pentafluoroethoxyphenyl)phenyl)ethyl group, 2-(2-(4-pentafluoroethoxyphenyl)phenyl)ethyl group, 3-(4-(2-trifluoromethylphenyl)phenyl)propyl group, 3-(3-(3-trifluoromethylphenyl)phenyl)propyl group, 3-(2-(4-trifluoromethylphenyl)phenyl)propyl group, 3-(4-(2-trifluoromethoxyphenyl)phenyl)propyl group, 3-(3-(3-trifluoromethoxyphenyl)phenyl)propyl group, 3-(2-(4-trifluoromethoxyphenyl)phenyl)propyl group, 3-(4-(3-pentafluoroethoxyphenyl)phenyl)propyl group, 3-(3-(4-pentafluoroethoxyphenyl)phenyl)propyl group, 4-(2-(3-pentafluoroethoxyphenyl)phenyl)butyl group, 5-(4-(4-trifluoromethylphenyl)phenyl)pentyl group, 4-(3-(4-trifluoromethylphenyl)phenyl)pentyl group, 4-(2-(4-trifluoromethoxyphenyl)phenyl)pentyl group, 6-(4-(3-trifluoromethylphenyl)phenyl)hexyl group, 6-(3-(4-trifluoromethylphenyl)phenyl)hexyl group, 6-(2-(4-trifluoromethylphenyl)phenyl)hexyl group, 2,4-di(4-trifluoromethylphenyl)benzyl group, 2,4,6-tri(4-trifluoromethoxyphenyl)benzyl group or the like.

A benzoyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is a benzoyl C1-C6 alkyl group unsubstituted or substituted on the phenyl ring constituting the group by 1 to 5, preferably 1 to 3 substituents selected from the group consisting of a halogen atom, a halogen substituted or unsubstituted straight or branched C1-C6 alkyl group and a halogen substituted or unsubstituted straight or branched C1-C6 alkoxy group, examples of which include a benzoylmethyl group, 1-benzoylethyl group, 2-benzoylethyl group, 3-benzoylpropyl group, 2-benzoylpropyl group, 4-benzoylbutyl group, 5-benzoylpentyl group, 4-benzoylpentyl group, 6-benzoylhexyl group, 2-fluorobenzoylmethyl group, 3-fluorobenzoylmethyl group, 4-fluorobenzoylmethyl group, 2-chlorobenzoylmethyl group, 3-chlorobenzoylmethyl group, 4-chlorobenzoylmethyl group, 2-bromobenzoylmethyl group, 3-bromobenzoylmethyl group, 4-bromobenzoylmethyl group, 2-iodobenzoylmethyl group, 3-iodobenzoylmethyl group, 4-iodobenzoylmethyl group, 2,3-difluorobenzoylmethyl group, 3,4-difluorobenzoylmethyl group, 3,5-difluorobenzoylmethyl group, 2,4-difluorobenzylmethyl group, 2,6-difluorobenzoylmethyl group, 2,3-dichlorobenzoylmethyl group, 3,4-dichlorobenzoylmethyl group, 3,5-dichlorobenzoylmethyl group, 2,4-dichlorobenzoylmethyl group, 2,6-dichlorobenzoylmethyl group, 2-fluoro-4-bromobenzoylmethyl group, 4-chloro-3-fluorobenzoylmethyl group, 2,3,4-trichlorobenzoylmethyl group, 3,4,5-trifluorobenzoylmethyl group, 2,4,6-trichlorobenzoylmethyl group, 4-isopropylbenzoylmethyl group, 4-n-butylbenzoylmethyl group, 4-methylbenzoylmethyl group, 2-methylbenzoylmethyl group, 3-methylbenzoylmethyl group, 2,4-dimethylbenzoylmethyl group, 2,3-dimethylbenzoylmethyl group, 2,6-dimethylbenzoylmethyl group, 3,5-dimethylbenzoylmethyl group, 2,5-dimethylbenzoylmethyl group, 2,4,6-trimethylbenzoylmethyl group, 3,5-ditrifluoromethylbenzoylmethyl group, 2,3,4,5,6-pentafluorobenzoylmethyl group, 4-isopropoxybenzoylmethyl group, 4-n-butoxybenzoylmethyl group, 4-methoxybenzoylmethyl group, 2-methoxybenzoylmethyl group, 3-methoxybenzoylmethyl group, 2,4-dimethoxybenzoylmethyl group, 2,3-dimethoxybenzoylmethyl group, 2,6-dimethoxybenzoylmethyl group, 3,5-dimethoxybenzoylmethyl group, 2,5-dimethoxybenzoylmethyl group, 2,4,6-trimethoxybenzoylmethyl group, 3,5-ditrifluoromethoxybenzoylmethyl group, 2-isopropoxybenzoylmethyl group, 3-chloro-4-methoxybenzoylmethyl group, 2-chloro-4-trifluoromethoxybenzoylmethyl group, 3-methyl-4-fluorobenzoylmethyl group, 4-bromo-3-trifluoromethylbenzoylmethyl group, 2-trifluoromethylbenzoylmethyl group, 3-trifluoromethylbenzoylmethyl group, 4-trifluoromethylbenzoylmethyl group, 2-pentafluoroethylbenzoylmethyl group, 3-pentafluoroethylbenzoylmethyl group, 4-pentafluoroethylbenzoylmethyl group, 2-trifluoromethoxybenzoylmethyl group, 3-trifluoromethoxybenzoylmethyl group, 4-trifluoromethoxybenzoylmethyl group, 2-pentafluoroethoxybenzoylmethyl group, 3-pentafluoroethoxybenzoylmethyl group, 4-pentafluoroethoxybenzoylmethyl group, 2-(2-trifluoromethylbenzoyl)ethyl group, 2-(3-trifluoromethylbenzoyl)ethyl group, 2-(4-trifluoromethylbenzoyl)ethyl group, 2-(2-trifluoromethoxybenzoyl)ethyl group, 2-(3-trifluoromethoxybenzoyl)ethyl group, 2-(4-trifluoromethoxybenzoyl)ethyl group, 2-(2-pentafluoroethoxybenzoyl)ethyl group, 2-(3-pentafluoroethoxybenzoyl)ethyl group, 2-(4-pentafluoroethoxybenzoyl)ethyl group, 3-(2-trifluoromethylbenzoyl)propyl group, 3-(3-trifluoromethyl benzoyl)propyl group, 3-(4-trifluoromethylbenzoyl)propyl group, 3-(2-trifluoromethoxybenzoyl)propyl group, 3-(3-trifluoromethoxybenzoyl)propyl group, 3-(4-trifluoromethoxybenzoyl)propyl group, 3-(3-pentafluoroethoxybenzoyl)propyl group, 3-(4-pentafluoroethoxybenzoyl)propyl group, 4-(3-pentafluoroethoxybenzoyl)butyl group, 5-(4-trifluoromethylbenzoyl)pentyl group, 4-(4-trifluoromethylbenzoyl)pentyl group, 4-(4-trifluoromethoxybenzoyl)pentyl group, 6-(3-trifluoromethylbenzoyl)hexyl group, 6-(4-trifluoromethylbenzoyl)hexyl group, 6-(4-trifluoromethoxybenzoyl)hexyl group or the like.

An amino group which may be substituted by at least one selected from the group consisting of a C1-C6 alkyl group, a C1-C6 alkoxycarbonyl group and a phenyl C1-C6 alkyl group [wherein, on the phenyl ring, at least one selected from the group consisting of a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a halogen atom, a halogen substituted or unsubstituted C1-C6 alkyl group and a halogen substituted or unsubstituted C1-C6 alkoxy group may be substituted] includes an amino group which may be substituted by 1 or 2 substituents selected from the group consisting of a straight or branched alkyl group containing 1 to 6 carbon atoms as described above or later, a straight or branched alkoxycarbonyl group containing 1 to 6 carbon atoms, and a phenylalkyl group having a straight or branched alkyl group containing 1 to 6 carbon atoms on the alkyl part [wherein, on the phenyl ring, 1 to 5, preferably 1 to 3 substituents selected from the group consisting of a phenyl group (wherein, on the phenyl group, 1 to 5, preferably 1 to 3 substituents selected from the group consisting of a halogen atom, a halogen substituted or unsubstituted C1-C6 straight or branched alkyl group and a halogen substituted or unsubstituted C1-C6 straight or branched alkoxy group may be substituted), a halogen atom, a halogen substituted or unsubstituted C1-C6 straight or branched alkyl group and a halogen substituted or unsubstituted C1-C6 straight or branched alkoxy group may be substituted], for example, an amino group, tert-butoxycarbonylamino group, methylamino group, benzylamino group, (4-trifluoromethoxybenzyl)amino group, (4-trifluoromethylbenzyl)amino group, (4-chlorobenzyl)amino group, (4-(4-trifluoromethoxyphenyl)benzyl)amino group, (4-(4-trifluoromethylphenyl)benzyl)amino group, (4-(4-chlorophenyl)benzyl)amino group, N-methyl-N-benzylamino group, N-methyl-N-(4-trifluoromethoxybenzyl)amino group, N-methyl-N-(4-trifluoromethylbenzyl)amino group, N-methyl-N-(4-chlorobenzyl)amino group, N-methyl-N-(4-(4-trifluoromethoxyphenyl)benzyl)amino group, N-methyl-N-(4-(4-trifluoromethylphenyl)benzyl)amino group, N-methyl-N-(4-(4-chlorophenyl)benzyl)amino group, N-methoxycarbonyl-N-benzylamino group, N-ethoxycarbonyl-N-(4-trifluoromethoxybenzyl)amino group, N-propoxycarbonyl-N-(4-trifluoromethylbenzyl)amino group, N-n-butoxycarbonyl-N-(4-chlorobenzyl)amino group, N-n-pentyloxycarbonyl-N-(4-(4-trifluoromethoxyphenyl) benzyl)amino group, N-n-hexyloxycarbonyl-N-(4-(4-trifluoromethylphenyl)benzyl)amino group, N-ethoxycarbonyl-N-(4-(4-chlorophenyl)benzyl)amino group, N,N-dimethylamino group, N-methyl-N-ethylamino group or the like.

An amino C1-C6 alkyl group which may be substituted by at least one selected from the group consisting of a C1-C6 alkyl group and a phenyl group (wherein, on the phenyl ring, at least one selected from the group consisting of a halogen atom; a halogen substituted or unsubstituted C1-C6 alkyl group and a halogen substituted or unsubstituted C1-C6 alkoxy group may be substituted) includes an amino alkyl group having a straight or branched alkyl group containing 1 to 6 carbon atoms on the alkyl part, which may be substituted by 1 or 2 substituents selected from the group consisting of a straight or branched alkyl group containing 1 to 6 carbon atoms and a phenyl group (wherein, on the phenyl ring, 1 to 5, preferably 1 to 3 substituents selected from the group consisting of a halogen atom, a halogen substituted or unsubstituted C1-C6 straight or branched alkyl group and a halogen substituted or unsubstituted C1-C6 straight or branched alkoxy group may be substituted), for example, an aminomethyl group, 2-aminoethyl group, 1-aminoethyl group, 3-aminopropyl group, 4-aminobutyl group, 5-aminopentyl group, 6-aminohexyl group, 2-methyl-3-aminopropyl group, 1,1-dimethyl-2-aminoethyl group, ethylaminomethyl group, 1-(propylamino)ethyl group, 2-(methylamino)ethyl group, 3-(isopropylamino)propyl group, 4-(n-butylamino)butyl group, 5-(n-pentylamino)pentyl group, 6-(n-hexylamino) hexyl group, dimethylaminomethyl group, (N-ethyl-N-propylamino)methyl group, 2-(N-methyl-N-n-hexylamino) ethyl group, phenylaminomethyl group, 1-(phenylamino) ethyl group, 2-(4-chloroanilino)ethyl group, 2-(4-trifluoromethoxyanilino)ethyl group, 2-(4-trifluoromethylanilino)ethyl group, 3-(4-fluoroanilino) propyl group, 4-(3,4-difluoroanilino)butyl group, 5-(3,4,6-trifluoroanilino)pentyl group, 6-(4-methylanilino)hexyl group, (3-methoxyanilino)methyl group, (2,3,4-trimethoxyanilino)methyl group, (3,4-dimethylanilino)methyl group, (2,4,6-trimethylanilino)methyl group, (N-ethyl-N-(3,4-dimethoxyanilino))methyl group, 2-(N-methyl-n-(4-chloroanilino))ethyl group, 2-(N-methyl-N-(4-trifluoromethoxyanilino))ethyl group, 2-(N-methyl-N-(4-trifluoromethylanilino))ethyl group or the like.

A benzofuryl C2-C6 alkenyl group [wherein, on the benzofuran ring, at least one selected from the group consisting of a halogen atom, a halogen substituted or unsubstituted C1-C6 alkyl group and a halogen substituted or unsubstituted C1-C6 alkoxy group may be substituted] includes a benzofurylalkenyl group having a straight or branched alkenyl group containing 2 to 6 carbon atoms on the alkenyl part and having 1 to 3 double bonds and including both trans and cis forms [wherein, on the benzofuran ring, 1 to 3 substituents selected from the group consisting of a halogen atom, a halogen substituted or unsubstituted C1-C6 straight or branched alkyl group and a halogen substituted or unsubstituted C1-C6 straight or branched alkoxy group may be substituted], for example, a 2-((2-, 3-, 4-, 5-, 6- or 7-)benzofuryl)vinyl group, 3-((2-, 3-, 4-, 5-, 6- or 7-)benzofuryl)-2-2-propenyl group, 3-((2-, 3-, 4-, 5-, 6- or 7-)benzofuryl)-2-methyl-2-propenyl group, 4-((2-, 3-, 4-, 5-, 6- or 7-)benzofuryl)-2-butenyl group, 4-((2-, 3-, 4-, 5-, 6- or 7-)benzofuryl-3-butenyl group, 4-((2-, 3-, 4-, 5-, 6- or 7-)benzofuryl)-1,3-butadienyl group, 5-((2-, 3-, 4-, 5-, 6- or 7-)-benzofuryl)-1,3,5-hexatrienyl group, 5-((2-, 3-, 4-, 5-, 6- or 7-)benzofuryl)-2,4-hexadienyl group, 5-((2-, 3-, 4-, 5-, 6- or 7-)benzofuryl)-3-pentenyl group, 3-(5-trifluoromethyl-(2-, 3-, 4-, 6- or 7-)benzofuryl)-2-propenyl group, 3-(6-trifluoromethoxy-(2-, 3-, 4-, 5- or 7-)benzofuryl) 2-propenyl group, 3-(6-trifluorormethyl-(2-, 3-, 4-, 5- or 7-)benzofuryl)-2-propenyl group, 3-(4-chloro-(2-, 3-, 5-, 6-, or 7-)benzofuryl)-2-propenyl group, 3-(4,5-dimethoxy-(2-, 3-, 6- or 7-)benzofuryl)-2-propenyl group, 3-(3,4,5-trimethyl-(2-, 6- or 7-)benzofuryl)-2-propenyl group, 3-(3-methyl-5-methoxy-(2-, 4-, 6- or 7-)benzofuryl)-2-propenyl or the like, which includes a benzofurylalkenyl group (wherein, on the benzofuran ring, 1 to 3 substituents selected from the group consisting of a halogen atom, a halogen substituted or unsubstituted C1-C6 straight or branched alkyl group and a halogen substituted or unsubstituted C1-C6 straight or branched alkoxy group may be substituted] including both trans or cis forms.

A piperidyl group [wherein, on the piperidine ring, at least one phenyl C2-C6 alkenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a piperidyl group [wherein, on the piperidine ring, 1 to 3 phenylalkenyl groups having a straight or branched alkenyl group containing 2 to 6 carbon atoms on the alkenyl part as described above and having 1 to 3 double bonds and including both trans and cis forms (wherein, on the phenyl ring, 1 to 5, preferably 1 to 3 substituents selected from the group consisting of a halogen atom, a halogen substituted or unsubstituted C1-C6 straight or branched alkyl group and a halogen substituted or unsubstituted C1-C6 straight or branched alkoxy group may be substituted) may be substituted], for example, a (1-, 2-, 3- or 4-)piperidyl group, 1-(3-phenyl-2-propenyl)-(2-, 3- or 4-)piperidyl group, 1,3-di(3-phenyl-2-propenyl)-(2-, 4-, 5- or 6-)piperidyl group, 1,2,4-tri(3-phenyl-2-propenyl)-(3-, 5- or 6-)-piperidyl group, 1-(3-(4-trifluoromethoxyphenyl)-2-propenyl)-(2-, 3- or 4-)piperidyl group, 1-(3-(4-trifluoromethylphenyl)-2-propenyl)-(2-, 3- or 4-)-piperidyl group, 1-(3-(4-chlorophenyl)-2-propenyl)-(2-, 3- or 4-)piperidyl group, 1-(3-(3,4-dimethoxyphenyl)-2-propenyl)-(2-, 3- or 4-)piperidyl group, 1-(3-(2,4,6-trimethylphenyl)-2-propenyl)-2(2-, 3- or 4-)piperidyl group or the like.

A ferrocene substituted C1-C6 alkyl group includes a ferrocenealkyl group having a straight or branched alkyl group containing 1 to 6 carbon atoms on the alkyl part, for example, a ferrocenemethyl group, 1-ferroceneethyl group, 2-ferroceneethyl group, 3-ferrocenepropyl group, 2-ferrocenepropyl group, 4-ferrocenebutyl group, 5-ferrocenepentyl group, 4-ferrocenepentyl group, 6-ferrocenehexyl group, 1,1-dimethyl-2-ferroceneethyl group, 2-methyl-3-ferrocenepropyl group or the like.

An indolyl C1-C6 alkyl group (wherein, on the indole ring, at least one halogen atom may be substituted) includes an indolylalkyl group having a straight or branched alkyl group containing 1 to 6 carbon atoms on the alkyl part (wherein, on the indole ring, 1 to 3 halogen atoms may be substituted), for example, ((1-, 2-, 3-, 4-, 5-, 6- or 7-)indolyl)methyl group, 1-((1-, 2-, 3-, 4-, 5-, 6- or 7-)indolyl)ethyl group, 2-((1-, 2-, 3-, 4-, 5-, 6- or 7-)indolyl)ethyl group, 3-((1-, 2-, 3-, 4-, 5-, 6- or 7-)indolyl)propyl group, 2-((1-, 2-, 3-, 4-, 5-, 6- or 7-)indolyl) propyl group, 4-((1-, 2-, 3-, 4-, 5-, 6- or 7-)indolyl)butyl group, 5-((1-, 2-, 3-, 4-, 5-, 6- or 7-)indolyl)pentyl group, 4-((1-, 2-, 3-, 4-, 5-, 6- or 7-)indolyl)pentyl group, 6-((1-, 2-, 3-, 4-, 5-, 6- or 7-)indolyl)hexyl group, 1,1-dimethyl-2-((1-, 2-, 3-, 4-, 5-, 6- or 7-)-indolyl)ethyl group, 2-methyl-3-((1-, 2-, 3-, 4-, 5-, 6- or 7-)indolyl)propyl group, (5-chloro-(1-, 2-, 3-, 4-, 6- or 7-)indolyl)methyl group, (5,6-difluoro-(1-, 2-, 3-, 4- or 7-)indolyl)methyl group, (3,5,6-tribromo-(1-, 2-, 4- or 7-)indolyl)methyl group or the like.

A phenyl C2-C6 alkynyl group includes a phenylalkenyl group having a straight or branched alkynyl group containing 2 to 6 carbon atoms on the alkynyl part, for example, a 2-phenylethynyl group, 3-phenyl-2-propynyl group, 3-phenyl-1-methyl-2-propynyl group, 4-phenyl-2-butynyl group, 4-phenyl-3-butynyl group, 4-phenyl-1-butynyl group, 5-phenyl-2-pentynyl group, 6-phenyl-2-hexynyl group or the like.

A naphthyl substituted C1-C6 alkyl group (wherein, on the naphthalene ring, at least one C1-C6 alkoxy group may be substituted) includes a naphthyl substituted alkyl group having a straight or branched alkyl group containing 1 to 6 carbon atoms on the alkyl part (wherein, on the naphthalene ring, 1 to 3 straight or branched alkoxy groups containing 1 to 6 carbon atoms as described above may be substituted), for example, (1- or 2-)naphthyl)methyl group, 1-((1- or 2-)naphthyl)ethyl group, 2-((1- or 2-)naphthyl)ethyl group, 3-((1- or 2-)naphthyl)propyl group, 2-((1- or 2-)naphthyl)propyl group, 4-((1- or 2-)naphthyl)butyl group, 5-((1- or 2-)naphthyl)pentyl group, 4-((1- or 2-)naphthyl)pentyl group, 6-((1- or 2-)naphthyl)hexyl group, 1,1-dimethyl-2-((1- or 2-)naphthyl)ethyl group, 2-methyl-3-((1- or 2-)naphthyl)propyl group, (6-methoxy-(1-, 2-, 3-, 4-, 5-, 7- or 8-)naphthyl)methyl group, (5,6-dimethoxy-(1-, 2-, 3-, 4-, 7- or 8-)-naphthyl)methyl group, (5,6,7-trimethoxy-(1-, 2-, 3-, 4- or 8-)naphthyl)methyl group or the like.

A benzothiazolyloxy group (wherein, on the benzothiazole ring, at least one selected from the group consisting of a (b-1)phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted], a (b-2)piperadinyl group [wherein, on the piperidine ring, at least one selected from the group consisting of a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl C2-C6 alkenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) and a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], (b-3)piperidyl group [wherein, on the piperidine ring, at least one selected from the group consisting of an amino group (wherein, on the amino group, at least one selected from the group consisting of a phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] and a C1-C6 alkyl group may be substituted), a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a (b-4)pyrrolyl group [wherein, on the pyrrole ring, at least one selected from the group consisting of a C1-C6 alkyl group and a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] and a (b-5)phenylthio group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted) includes a benzothiazolyloxy group (wherein, on the benzothiazole ring, 1 to 3 substituents selected from the group consisting of a (b-1)phenyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a (b-2)piperadinyl group [wherein, on the piperidine ring, 1 to 3 substituents selected from the group consisting of a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a phenyl C2-C6 alkenyl group having a straight or branched alkenyl group containing 2 to 6 carbon atoms on the alkenyl part and having 1 to 3 double bonds as described later and including both trans and cis forms (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a (b-3)piperidyl group [wherein, on the piperidine ring, 1 to 3 substituents selected from the group consisting of an amino group (wherein, on the amino group, 1 or 2 groups selected from the group consisting of a phenyl group [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] and 1 or 2 groups selected from the group consisting of C1-C6 alkyl groups may be substituted), a phenoxy group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be constituted], a (b-4)pyrrolyl group as described later [wherein, on the pyrrole ring, 1 to 3 substituents selected from the group consisting of a C1-C6 alkyl group and a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] and a (b-5)phenylthio group as described later (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted), for example, a 2-benzothiazolyloxy group, 4-benzothiazolyloxy group, 5-benzothiazolyloxy group, 6-benzothiazolyloxy group, 7-benzothiazolyloxy group, 2-(1-piperadinyl)-4-benzothiazolyloxy group, 2-(4-benzyl-1-piperadinyl)-4-benzothiazolyloxy group, 2-(3,4-dibenzyl-1-piperadinyl)-4-benzothiazolyloxy group, 5-(2,3,4-tribenzyl-1-piperadinyl)-2-benzothiazolyloxy group, 4-(4-(2-phenethyl)-1-piperadinyl)-2-benzothiazolyloxy group, 4-(4-(3-phenylpropyl)-1-piperadinyl)-5-benzothiazolyloxy group, 4-(4-(4-phenylbutyl)-1-piperadinyl)-6-benzothiazolyloxy group, 4-(4-(5-phenylpentyl)-1-piperadinyl)-7-benzothiazolyloxy group, 2-(4-(6-phenylhexyl)-1-piperadinyl)-4-benzothiazolyloxy group, 4-(4-(2-fluorobenzyl)-1-piperadinyl)-2-benzothiazolyloxy group, 2-(4-(3-fluorobenzyl)-1-piperadimyl)-4-benzothiazolyloxy group, 2-(4-(4-fluorobenzyl)-1-piperadinyl)-5-benzothiazolyloxy group, 2-(4-(2-chlorobenzyl)-1-piperadinyl)-6-benzothiazolyloxy group, 2-(4-(3-chlorobenzyl)-1-piperazinyl)-7-benzothiazolyloxy group, 5-(4-(4-chlorobenzyl)-1-piperadinyl)-4-benzothiazolyloxy group, 6-(4-(2,3-dichlorobenzyl)-1-piperadinyl)-4-benzothiazolyloxy group, 7-(4-(2,4-dichlorobenzyl)-1-piperadinyl)-4-benzothiazolyloxy group, 2-(4-(3,4-dichlorobenzyl)-1-piperadimyl)-4-benzothiazolyloxy group, 4-(4-(3,5-dichlorobenzyl)-1-piperadinyl)-2-benzothiazolyloxy group, 4-(4-(3,4,5-trichlorobenzyl)-1-piperadinyl)-5-benzothiazolyloxy group, 4-(4-(2,3,4,5,6-pentafluorobenzyl)-1-piperadinyl)-2-benzothiazolyloxy group, 4-(4-(2-trifluoromethylbenzyl)-1-piperadinyl)-6-benzothiazolyloxy group, 4-(4-(3-trifluoromethylbenzyl)-1-piperadinyl)-7-benzothiazolyloxy group, 2-(4-(4-trifluoromethylbenzyl)-1-piperadinyl)-4-benzothiazolyloxy group, 5-(4-(4-methylbenzyl)-1-piperadinyl)-4-benzothiazolyloxy group, 6-(4-(3,4-dimethylbenzyl)-1-piperadinyl)-4-benzothiazolyloxy group, 7-(4-(2,4,6-trimethylbenzyl)-1-piperadinyl)-4-benzothiazolyloxy group, 4-(4-(2-pentafluoroethylbenzyl)-1-piperadinyl)-2-benzothiazolyloxy group, 4-(4-(3-pentafluoroethylbenzyl)-1-piperadinyl)-5-benzothiazolyloxy group, 4-(4-(4-pentafluoroethylbenzyl)-1-piperadinyl)-6-benzothiazolyloxy group, 4-(4-(2-trifluoromethoxybenzyl)-1-piperadinyl)-7-benzothiazolyloxy group, 5-(4-(3-trifluoromethoxybenzyl)-1-piperadinyl)-4-benzothiazolyloxy group, 6-(4-(4-trifluoromethoxybenzyl)-1-piperadinyl)-5-benzothiazolyloxy group, 7-(4-(4-methoxybenzyl)-1-piperadinyl)-5-benzothiazolyloxy group, 6-(4-(3,4-dimethoxybenzyl)-1-piperadinyl)-4-benzothiazolyloxy group, 7-(4-(2,4,6-trimethoxybenzyl)-1-piperadinyl)-4-benzothiazolyloxy group, 5-(4-(2-pentafluoroethoxybenzyl)-1-piperadinyl)-4-benzothiazolyloxy group, 4-(4-(3-pentafluoroethoxybenzyl)-1-piperadinyl)-2-benzothiazolyloxy group, 6-(4-(4-pentafluoroethoxybenzyl)-1-piperadinyl)-4- benzothiazolyloxy group, 4-(4-(2-(4-trifluoromethoxyphenyl)ethyl)-1-piperadinyl)-2-benzothiazolyloxy group, 4-(4-(3-(4-trifluoromethoxyphenyl)propyl)-1-piperadinyl)-2-benzothiazolyloxy group, 4-(4-(4-(4-trifluoromethoxyphenyl)butyl)-1-piperadinyl)-2-benzothiazolyloxy group, 4-(4-(5-(4-trifluoromethoxyphenyl)pentyl)-1-piperadinyl)-2-benzothiazolyloxy group, 4-(4-(6-(4-trifluoromethoxyphenyl)hexyl)-1-piperadinyl)-2-benzothiazolyloxy group, 4-(4-(2-(4-trifluoromethylphenyl) ethyl)-1-piperadinyl)-2-benzothiazolyloxy group, 5-(4-(3-(4-trifluoromethylphenyl)propyl)-1-piperadinyl)-2-benzothiazolyloxy group, 6-(4-(4-(4-trifluoromethylphenyl) butyl)-1-piperadinyl)-2-benzothiazolyloxy group, 7-(4-(5-(4-trifluoromethylphenyl)pentyl)-1-piperadinyl)-2-benzothiazolyloxy group, 5-(4-(6-(4-trifluoromethylphenyl) hexyl)-1-piperadinyl)-2-benzothiazolyloxy group, 2-(4-(trifluoromethoxyphenoxy-1-piperidyl))-6-benzothiazolyloxy group, 2-(4-(trifluoromethoxybenzyl-1-piperidyl))-6-benzothiazolyloxy group, 2-(4-(N-ethyl-N-(4-chlororphenyl)amino)-1-piperidyl)-6-benzothiazolyloxy group, 2-phenyl-5-benzothiazolyloxy group, 2-(4-chlorophenyl)-5-benzothiazolyloxy group, 2-(4-trifluoromethoxyphenyl)-6-benzothiazolyloxy group, 2-(3-trifluoromethylphenyl)-5-benzothiazolyloxy group, 2-(1-piperidyl)-4-benzothiazolyloxy group, 2-(4-benzyl-1-piperidyl)-4-benzothiazolyloxy group, 2-(3,4-dibenzyl-1-piperidyl)-4-benzothiazolyloxy group, 5-(2,3,4-tribenzyl-1-piperidyl)-2-benzothiazolyloxy group, 4-(4-(2-phenethyl)-1-piperidyl)-2-benzothiazolyloxy group, 4-(4-(3-phenylpropyl)-1-piperidyl (-5-benzothiazolyloxy group, 4-(4-(4-phenylbutyl)-1-piperidyl)-6-benzothiazolyloxy group, 4-(4-(5-phenylpentyl)-1-piperidyl)-7-benzothiazolyloxy group, 2-(4-(6-phenylhexyl)-1-piperidyl)-4-benzothiazolyloxy group, 4-(4-(2-fluorobenzyl)-1-piperidyl)-2-benzothiazolyloxy group, 2-(4-(3-fluorobenzyl)-1-piperidyl)-4-benzothiazolyloxy group, 2-(4-(4-fluorobenzyl)-1-piperadinyl)-5-benzothiazolyloxy group, 2-(4-(2-chlorobenzyl)-1-piperidyl)-6-benzothiazolyloxy group, 2-(4-(3-chlorobenzyl)-1-piperidyl)-7-benzothiazolyloxy group, 5-(4-(4-chlorobenzyl)-1-piperidyl)-4-benzothiazolyloxy group, 6-(4-(2,3-dichlorobenzyl-1-piperidyl)-4-benzothiazolyloxy group, 7-(4-(2,4-dichlorobenzyl)-1-piperidyl)-4-benzothiazolyloxy group, 2-(4-(3,4-dichlorobenzyl)-1-piperidyl)-4-benzothiazolyloxy group, 4-(4-(3,5-dichlorobenzyl)-1-piperidyl)-2-benzothiazolyloxy group, 4-(4-(3,4,5-trichlorobenzyl)-1-piperidyl)-5-benzothiazolyloxy group, 4-(4-(2,3,4,5,6-pentafluorobenzyl)-1-piperidyl)-2-benzothiazolyloxy group, 4-(4-(2-trifluoromethylbenzyl)-1-piperizyl)-6-benzothiazolyloxy group, 4-(4-(3-trifluoromethylbenzyl)-1-piperidyl)-7-benzothiazolyloxy group, 2-(4-(4-trifluoromethylbenzyl)-1-piperidyl)-4-benzothiazolyloxy group, 5-(4-(4-methylbenzyl)-1-piperidyl)-4-benzothiazolyloxy group, 6-(4-(3,4-dimethylbenzyl)-1-piperidyl)-4-benzothiazolyloxy group, 7-(4-(2,4,6-trimethylbenzyl)-1-piperizyl)-4-benzothiazolyloxy group, 4-(4-(2-pentafluoroethylbenzyl)-1-piperidyl)-2-benzothiazolyloxy group, 4-(4-(3-pentafluoroethylbenzyl)-1-piperidyl)-5-benzothiazolyloxy group, 4-(4-(4-pentafluoroethylbenzyl)-1-piperidyl)-6-benzothiazolyloxy group, 4-(4-(2-trifluoromethoxybenzyl)-1-piperidyl)-7-benzothiazolyloxy group, 5-(4-(3-trifluoromethoxybenzyl)-1-piperidyl)-4-benzothiazolyloxy group, 6-(4-(4-trifluoromethoxybenzyl)-1-piperidyl)-5-benzothiazolyloxy group, 7-(4-(4-methoxybenzyl)-1-piperidyl)-5-benzothiazolyloxy group, 6-(4-(3,4-dimethoxybenzyl)-1-piperidyl)-4-benzothiazolyloxy group, 7-(4-(2,4,6-trimethoxybenzyl)-1-piperidyl)-4-benzothiazolyloxy group, 5-(4-(2-pentafluoroethoxybenzyl)-1-piperidyl)-4-benzothiazolyloxy group, 4-(4-(3-pentafluoroethoxybenzyl)-1-piperidyl)-2-benzothiazolyloxy group, 6-(4-(4-pentafluoroethoxybenzyl-1-piperidyl)-4-benzothiazolyloxy group, 4-(4-(2-(4-trifluoeomethoxyphenyl)ethyl)-1-piperidyl)-2-benzothiazolyloxy group, 4-(4-(3-(4-trifluoromethoxyphenyl)propyl)-1-piperidyl)-2-benzothiazolyloxy group, 4-(4-(4-(4-trifluoromethoxyphenyl)butyl)-1-piperidyl)-2-benzothiazolyloxy group, 4-(4-(5-(4-trifluoromethoxyphenyl)pentyl)-1-piperidyl)-2-benzothiazolyloxy group, 4-(4-(6-(4-trifluoromethoxyphenyl)hexyl)-1-piperidyl)-2-benzothiazolyloxy group, 4-(4-(2-(4-trifluoromethylphenyl) ethyl)-1-piperidyl)-2-benzothiazolyloxy group, 5-(4-(3-(4-trifluoromethylphenyl)propyl)-1-piperidyl)-2-benzothiazolyloxy group, 6-(4-(4-(4-trifluoromethylphenyl) butyl)-1-piperidyl)-2-benzothiazolyloxy group, 7-(4-(5-(4-trifluoromethylphenyl)pentyl)-1-piperidyl)-2-benzothiazolyloxy group, 5-(4-(6-(4-trifluoromethylphenyl) hexyl)-1-piperidyl)-2-benzothiazolyloxy group, 2-(4-phenoxy-1-piperidyl)-4-benzothiazolyloxy group, 2-(3,4-diphenoxy-1-piperidyl)-4-benzothiazolyloxy group, 5-(2,3,4-triphenoxy-1-piperidyl)-2-benzothiazolyloxy group, 4-(4-(2-fluorophenoxy)-1-piperidyl)-2-benzothiazolyloxy group, 2-(4-(3-fluorophenoxy)-1-piperizyl)-4-benzothiazolyloxy group, 2-(4-(4-fluorophenoxy)-1-piperadinyl)-5-benzothiazolyloxy group, 2-(4-(2-chlorophenoxy)-1-piperidyl)-6-benzothiazolyloxy group, 2-(4-(3-chlorophenoxy)-1-piperidyl)-7-benzothiazolyloxy group, 5-(4-(4-chlorophenoxy)-1-piperidyl)-4-benzothiazolyloxy group, 6-(4-(2,3-dichlorophenoxy)-1-piperidyl)-4-benzothiazolyloxy group, 7-(4-(2,4-dichlorophenoxy)-1-piperidyl)-4-benzothiazolyloxy group, 2-(4-(3,4-dichlorophenoxy)-1-piperidyl)-4-benzothiazolyloxy group, 4-(4-(3,5-dichlorophenoxy)-1-piperidyl)-2-benzothiazolyloxy group, 4-(4-(3,4,5-trichlorophenoxy)-1-piperidyl)-5-benzothiazolyloxy group, 4-(4-(2,3,4,5,6-pentafluorophenoxy)-1-piperidyl)-2-benzothiazolyloxy group, 4-(4-(2-trifluoromethylphenoxy)-1-piperidyl)-6-benzothiazolyloxy group, 4-(4-(3-trifluoromethylphenoxy)-1-piperidyl)-7-benzothiazolyloxy group, 2-(4-(4-trifluoromethylphenoxy)-1-piperidyl)-4-benzothiazolyloxy group, 5-(4-(4-methylphenoxy)-1-piperidyl)-4-benzothiazolyloxy group, 6-(4-(3,4-dimethylphenoxy)-1-piperidyl)-4-benzothiazolyloxy group, 7-(4-(2,4,6-trimethylphenoxy)-1-piperidyl)-4-benzothiazolyloxy group, 4-(4-(2-pentafluoroethylphenoxy)-1-piperidyl)-2-benzothiazolyloxy group, 4-(4-(3-pentafluoroethylphenoxy)-1-piperidyl)-5-benzothiazolyloxy group, 4-(4-(4-pentafluoroethylphenoxy)-1-piperidyl)-6-benzothiazolyloxy group, 4-(4-(2-trifluoromethoxyphenoxy)-1-piperidyl)-7-benzothiazolyloxy group, 5-(4-(3-trifluoromethoxyphenoxy)-1-piperidyl)-4-benzothiazolyloxy group, 6-(4-(4-trifluoromethoxyphenoxy)-1-piperidyl)-5-benzothiazolyloxy group, 7-(4-(4-methoxyphenoxy)-1-piperidyl)-5-benzothiazolyloxy group, 6-(4-(3,4-dimethoxyphenoxy)-1-piperidyl)-4-benzothiazolyloxy group, 7-(4-(2,4,6-trimethoxyphenoxy)-1-piperidyl)-4-benzothiazolyloxy group, 5-(4-(2-pentafluoroethoxyphenoxy)-1-piperidyl)-4-benzothiazolyloxy group, 4-(4-(3-pentafluoroethoxyphenoxy)-1-piperidyl)-2-benzothiazolyloxy group, 6-(4-(4-pentafluoroethoxyphenoxy)-1-piperidyl)-4-benzothiazolyloxy group, 2,5,6-triphenyl-7-benzothiazolyloxy group, 2-(4-amino-1-piperidyl)-6- benzothiazolyloxy group, 4-(2,4-diamino-1-piperidyl)-2-benzothiazolyloxy group, 5-(2,4,6-triamino-1-piperidyl)-4-benzothiazolyloxy group, 6-(2-amino-1-piperidyl)-5-benzothiazolyloxy group, 7-(3-amino-1-piperidyl)-6-benzothiazolyloxy group, 2-(4-methylamino-1-piperidyl)-4-benzothiazolyloxy group, 2-(4-ethylamino-1-piperidyl)-5-benzothiazolyloxy group, 2-(4-n-propylamino-1-piperidyl)-6-benzothiazolyloxy group, 2-(4-dimethylamino-1-piperidyl)-7-benzothiazolyloxy group, 2-(4-diethylamino-1-piperidyl)-4-benzothiazolyloxy group, 2-(4-di-n-propylamino-1-piperidyl)-5-benzothiazolyloxy group, 2-(4-phenylamino-1-piperidyl)-6-benzothiazolyloxy group, 2-(4-(N-phenyl-N-methylamino)-1-piperidyl)-7-benzothiazolyloxy group, 2-(4-(2-fluorophenylamino)-1-piperidyl)-4-benzothiazolyloxy group, 2-(4-(3-fluorophenylamino)-1-piperidyl)-5-benzothiazolyloxy group, 2-(4-(4-fluorophenylamino)-1-piperidyl)-6-benzothiazolyloxy group, 2-(4-(2-chlorophenylamino)-1-piperidyl)-7-benzothiazolyloxy group, 2-(4-(3-chlorophenylamino)-1-piperidyl)-4-benzothiazolyloxy group, 2-(4-(4-chlorophenylamino)-1-piperidyl)-5-benzothiazolyloxy group, 2-(4-(2,3-dichlorophenylamino)-1-piperidyl)-6-benzothiazolyloxy group, 2-(4-(2,4,6-trifluorophenylamino)-1-piperidyl)-7-benzothiazolyloxy group, 2-(4-(2,4-dichlorophenylamino)-1-piperidyl)-4-benzothiazolyloxy group, 2-(4-(3,4-dichlorophenylamino)-1-piperidyl)-6-benzothiazolyloxy group, 4-(3,5-dichlorophenylamino)-1-piperidyl)-5-benzothiazolyloxy group, 2-(4-(2,3,4,5,6-pentafluorophenylamino)-1-piperidyl)-6-benzothiazolyloxy group, 2-(4-(2-trifluoromethylphenylamino)-1-piperidyl)-7-benzothiazolyloxy group, 2-(4-(2-methylphenylamino)-1-piperidyl)-4-benzothiazolyloxy group, 2-(4-(2,3-dimethylphenylamino)-1-piperidyl)-5-benzothiazolyloxy group, 2-(4-(2-trifluoromethylphenylamino)-1-piperidyl)-6-benzothiazolyloxy group, 2-(4-(2,4,6-trimethylphenylamino)-1-piperidyl)-7-benzothiazolyloxy group, 2-(4-(4-trifluoromethylphenylamino)-1-piperidyl)-4-benzothiazolyloxy group, 2-(4-(2-pentafluoroethylphenylamino)-1-piperidyl)-5-benzothiazolyloxy group, 2-(4-(3-pentafluoroethylphenylamino)-1-piperidyl)-5-benzothiazolyloxy group, 2-(4-(4-pentafluoroethylphenylamino)-1-piperidyl)-6-benzothiazolyloxy group, 2-(4-(2-trifluoromethoxyphenylamino)-1-piperidyl)-7-benzothiazolyloxy group, 2-(4-(2-methoxyphenylamino)-1-piperidyl)-4-benzothiazolyloxy group, 2-(4-(2,3-dimethoxyphenylamino)-1-piperidyl)-5-benzothiazolyloxy group, 2-(4-(2,4,6-trimethoxyphenylamino)-1-piperidyl)-6-benzothiazolyloxy group, 2-(4-(N-methyl-N-(2,4,6-trimethoxyphenylamino))-1-piperidyl)-7-benzothiazolyloxy group, 2-(4-(N-methyl-N-(3,4-dimethylphenylamino))-1-piperidyl)-4-benzothiazolyloxy group, 2-(4-(3-trifluoromethoxyphenylamino)-1-piperidyl)-5-benzothiazolyloxy group, 2-(4-(4-trifluoromethoxyphenylamino)-1-piperidyl)-6-benzothiazolyloxy group, 2-(4-(2-pentafluoroethoxyphenylamino)-1-piperidyl)-7-benzothiazolyloxy group, 2-(4-(3-pentafluoroethoxyphenylamino)-1-piperidyl)-4-benzothiazolyloxy group, 2-(4-(4-pentafluoroethoxyphenylamino)-1-piperidyl)-5-benzothiazolyloxy group, 2-(4-(2-fluorophenylamino)-1-piperidyl)-5-benzothiazolyloxy group, 4-(3-fluorophenylamino)-1-piperidyl)-6-benzothiazolyloxy group, 2-(4-(4-fluorophenylamino)-1-piperidyl)-7-benzothiazolyloxy group, 2-phenyl-5-(4-phenoxy-1-piperidyl)-7-benzothiazolyloxy group, 2-(1-(4-trifluoromethoxyphenyl)-(2- or 3-)pyrrolyl)-(4-, 5-, 6-, or 7-)benzothiazolyloxy group, 2-(1-methyl-(2- or 3-)pyrrolyl)-(4-, 5-, 6- or 7-)benzothiazolyloxy group, 2-(4-(3-(4-trifluoromethylphenyl)-2-propenyl)-(1-, 2- or 3-)piperadinyl)-(4-, 5-, 6- or 7-)benzothiazolyloxy group, 2-(4-(4-trifluoromethoxyphenyl))-(1-, 2- or 3-)piperadinyl)-(4-, 5-, 6- or 7-)benzothiazolyloxy group, 2-(4-(4-trifluoromethylphenyl))-(1-, 2- or 3-)piperadinyl)-(4-, 5-, 6- or 7-)benzothiazolyloxy group, 2-(4-chlorophenylthio)-(4-, 5-, 6- or 7-)-benzothiazolyloxy group or the like.

A phenyl C1-C6 alkylidene group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) includes a phenyl C1-C6 alkylidene group (on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), for example, benzylidene group, 1-phenylethylidene group, 2-phenylethylidene group, 3-phenylpropylidene group, 2-phenylpropylidene group, 4-phenylbutylidene group, 5-phenylpentylidene group, 4-phenylpentylidene group, 6-phenylhexylidene group, 2-fluorobenzylidene group, 3-fluorobenzylidene group, 4-fluorobenzylidene group, 2-chlorobenzylidene group, 3-chlorobenzylidene group, 4-chlorobenzylidene group, 2-bromobenzylidene group, 3-bromobenzylidene group, 4-bromobenzylidene group, 2-iodobenzylidene group, 3-iodobenzylidene group, 4-iodobenzylidene group, 2,3-difluorobenzylidene group, 3,4-difluorobenzylidene group, 3,5-difluorobenzylidene group, 2,4-difluorobenzylidene group, 2,6-difluorobenzylidene group, 2,3-dichlorobenzylidene group, 3,4-dichlorobenzylidene group, 3,5-dichlorobenzylidene group, 2,4-dichlorobenzylidene group, 2,6-dichlorobenzylidene group, 2-fluoro-4-bromobenzylidene group, 4-chloro-3-fluorobenzylidene group, 2,3,4-trichlorobenzylidene group, 3,4,5-trifluorobenzylidene group, 2,4,6-trichlorobenzylidene group, 4-isopropylbenzylidene group, 4-n-butylbenzylidene group, 4-methylbenzylidene group, 2-methylbenzylidene group, 3-methylbenzylidene group, 2,4-dimethylbenzylidene group, 2,3-dimethylbenzylidene group, 2,6-dimethylbenzylidene group, 3,5-dimethylbenzylidene group, 2,5-dimethylbenzylidene group, 2,4,6-trimethylbenzylidene group, 3,5-ditrifluoromethylbenzylidene group, 2,3,4,5,6-pentafluorobenzylidene group, 4-isopropoxybenzylidene group, 4-n-butoxybenzylidene group, 4-methoxybenzylidene group, 2-methoxybenzylidene group, 3-methoxybenzylidene group, 2,4-dimethoxybenzylidene group, 2,3-dimethoxybenzylidene group, 2,6-dimethoxybenzylidene group, 3,5-dimethoxybenzylidene group, 2,5-dimethoxybenzylidene group, 2,4,6-trimethoxybenzylidene group, 3,5-ditrifluoromethoxybenzylidene group, 2-isopropoxybenzylidene group, 3-chloro-4-methoxybenzylidene group, 2-chloro-4-trifluoromethoxybenzylidene group, 3-methyl-4-fluorobenzylidene group, 4-bromo-3-trifluoromethylbenzylidene group, 2-trifluoromethylbenzylidene group, 3-trifluoromethylbenzylidene group, 4-trifluoromethylbenzylidene group, 2-pentafluoroethylbenzylidene group, 3-pentafluoroethylbenzylidene group, 4-pentafluoroethylbenzylidene group, 2-trifluoromethoxybenzylidene group, 3-trifluoromethoxybenzylidene group, 4-trifluoromethoxybenzylidene group, 2-pentafluoroethoxybenzylidene group, 3-pentafluoroethoxybenzylidene group, 4-pentafluoroethoxybenzylidene group, 2-(2-trifluoromethylphenyl)ethylidene group, 2-(3-trifluoromethylphenyl)ethylidene group, 2-(4-trifluoromethylphenyl)ethylidene group, 2-(2-trifluoromethoxyphenyl)ethylidene group, 2-(3-trifluoromethoxyphenyl)ethylidene group, 2-(4-trifluoromethoxyphenyl)ethylidene group, 2-(2-pentafluoroethoxyphenyl)ethylidene group, 2-(3-pentafluoroethoxyphenyl)ethylidene group, 2-(4-pentafluoroethoxyphenyl)ethylidene group, 3-(2-trifluoromethylphenyl)propylidene group, 3-(3-trifluoromethylphenyl)propylidene group, 3-(4-trifluoromethylphenyl)propylidene group, 3-(2-trifluoromethoxyphenyl)propylidene group, 3-(3-trifluoromethoxyphenyl)propylidene group, 3-(4-trifluoromethoxyphenyl)propylidene group, 3-(3-pentafluoroethoxyphenyl)propylidene group, 3-(4-pentafluoroethoxyphenyl)propylidene group, 4-(3-pentafluoroethoxyphenyl)butylidene group, 5-(4-trifluoromethylphenyl)pentylidene group, 4-(4-trifluoromethylphenyl)pentylidene group, 4-(4-trifluoromethoxyphenyl)pentylidene group, 6-(3-trifluoromethylphenyl)hexylidene group, 6-(4-trifluoromethylphenyl)hexylidene group, 6-(4-trifluoromethoxyphenyl)hexylidene group or the like.

A piperidyl group [wherein, on the piperidine ring, at least one selected from the group consisting of an amino group (wherein, on the amino group, at least one selected from the group consisting of a phenyl group [wherein, on the phenyl group, at least one selected from the group consisting of a halogen atom, a halogen substituted or unsubstituted C1-C6 alkyl group and a halogen substituted or unsubstituted C1-C6 alkoxy group may be substituted] and a C1-C6 alkyl group may be substituted); a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted); a phenyl C1-C6 alkyl group (wherein, on the phenyl ring, at least one selected from the group consisting of a C1-C4 alkylenedioxy group, a halogen atom, a halogen substituted or unsubstituted C1-C6 alkyl group and a halogen substituted or unsubstituted C1-C6 alkoxy group may be substituted); a phenyl C1-C6 alkoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted); a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted); a naphthyl C1-C6 alkyl group; and a phenyl C1-C6 alkylidene group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a piperidyl group [wherein, on the piperidine ring, 1 to 3 substituents selected from the group consisting of an amino group (wherein, on the amino group, 1 or 2 groups selected from the group consisting of a phenyl group [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] and a C1-C6 alkyl group may be substituted); a phenoxy group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted); a phenyl C1-C6 alkyl group (wherein, on the phenyl ring, 1 to 5, preferably 1 to 3 substituents selected from the group consisting of a straight or branched C1-C4 alkylenedioxy group containing 1 to 4 carbon atoms, a halogen atom, a halogen substituted or unsubstituted C1-C6 alkyl group and a halogen substituted or unsubstituted C1-C6 alkoxy group may be substituted); a phenyl C1-C6 alkoxy group as described later (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted); a phenyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted); a naphthyl C1-C6 alkyl group having a straight or branched alkyl group containing 1 to 6 carbon atoms on the alkyl part as described later; and a phenyl C1-C6 alkylidene group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a 1-piperidyl group, 2-piperidyl group, 3-piperidyl group, 4-piperidyl group, 2,4-diamino-1-piperidyl group, 2,4,6-triamino-1-piperidyl group, 2-amino-1-piperidyl group, 3-amino-1-piperidyl group, 4-amino-1-piperidyl group, 4-methylamino-1-piperidyl group, 4-ethylamino-1-piperidyl group, 4-n-propylamino-1-piperidyl group, 4-dimethylamino-1-piperidyl group, 4-diethylamino-1-piperidyl group, 4-di-n-propylamino-1-piperidyl group, 4-phenylamino-1-piperidyl group, 4-(N-phenyl-N-methylamino)-1-piperidyl group, 4-(2-fluorophenylamino)-1-piperidyl group, 4-(3-fluorophenylamino)-1-piperidyl group, 4-(4-fluorophenylamino)-1-piperidyl group, 4-(2-chlorophenylamino)-1-piperidyl group, 4-(3-chlorophenylamino)-1-piperidyl group, 4-(4-chlorophenylamino)-1-piperidyl group, 4-(2,3-dichlorophenylamino)-1-piperidyl group, 4-(2,4,6-trifluorophenylamino)-1-piperidyl group, 4-(2,4-dichlorophenylamino)-1-piperidyl group, 4-(3,4-dichlorophenylamino)-1-piperidyl group, 4-(3,5-dichlorophenylamino)-1-piperidyl group, 4-(2,3,4,5,6-pentafluorophenylamino)-1-piperidyl group, 4-(2-trifluoromethylphenylamino)-1-piperidyl group, 4-(2-methylphenylamino)-1-piperidyl group, 4-(2,3-dimethylphenylamino)-1-piperidyl group, 4-(3-trifluoromethylphenylamino)-1-piperidyl group, 4-(2,4,6-trimethylphenylamino)-1-piperidyl group, 4-(4-trifluoromethylphenylamino)-1-piperidyl group, 4-(2-pentafluoroethylphenylamino)-1-piperidyl group, 4-(3-pentafluoroethylphenylamino)-1-piperidyl group, 4-(4-pentafluoroethylphenylamino)-1-piperidyl group, 4-(2-trifluoromethoxyphenylamino)-1-piperidyl group, 4-(2-methoxyphenylamino)-1-piperidyl group, 4-(2,3-dimethoxyphenylamino)-1-piperidyl group, 4-(2,4,6-trimethoxyphenylamino)-1-piperidyl group, 4-(N-methyl-N-(2,4,6-trimethoxyphenylamino))-1-piperidyl group, 4-(N-methyl-N-(3,4-dimethylphenylamino))-1-piperidyl group, 4-(N-ethyl-N-(4-chlorophenylamino))-1-piperidyl group, 4-(3-trifluoromethoxyphenylamino)-1-piperidyl group, 4-(4-trifluoromethoxyphenylamino)-1-piperidyl group, 4-(2-pentafluoroethoxyphenylamino)-1-piperidyl group, 4-(3-pentafluoroethoxyphenylamino)-1-piperidyl group, 4-(4-pentafluoroethoxyphenylamino)-1-piperidyl group, 4-(N-methyl-N-(2-fluorophenyl)amino)-1-piperidyl group, 4-(N-methyl-N-(3-fluorophenyl)amino)-1-piperidyl group, 4-(N-methyl-N-(4-fluorophenyl)amino)-1-piperidyl group, 4-phenoxy-1-piperidyl group, 2,4-diphenoxy-1-piperidyl group, 2,4,6-triphenoxy-1-piperidyl group, 2-(2-fluorophenoxy)-1-piperidyl group, 3-(3-fluorophenoxy)-2-piperidyl group, 4-(4-fluorophenoxy)-3-piperidyl group, 2-(2-chlorophenoxy)-4-piperidyl group, 3-(3-chlorophenoxy)-5-piperidyl group, 4-(4-chlorophenoxy)-5-piperidyl group, 5-(2-bromophenoxy)-2-piperidyl group, 6-(3-bromophenoxy)-3-piperidyl group, 4-(4-bromophenoxy)-1-piperidyl group, 3-(2,3-dichlorophenoxy)-2-piperidyl group, 4-(3,4-dichlorophenoxy)-3-piperidyl group, 3-(2,4-dichlorophenoxy)-4-piperidyl group, 2-(3,4,5-trichlorophenoxy)-3-piperidyl group, 6-(2,4,6-trichlorophenoxy)-2-piperidyl group, 3-(2,3,4,5,6-pentafluorophenoxy)-1-piperidyl group, 4-(2-methylphenoxy)-1-piperidyl group, 5-(3-methylphenoxy)-2-piperidyl group, 6-(4-methylphenoxy)-3-piperidyl group, 4-(2-ethylphenoxy)-1-piperidyl group, 2-(3-ethylphenoxy)-1-piperidyl group, 3-(4-ethylphenoxy)-2-piperidyl group, 4-(4-n-propylphenoxy)-3-piperidyl group, 3-(4-tert-butylphenoxy)-4-piperidyl group, 2-(4-n-butylphenoxy)-3-piperidyl group, 1-(2-trifluoromethylphenoxy)-2-piperidyl group, 2-(3-trifluoromethylphenoxy)-1-piperidyl group, 4-(4-trifluoromethylphenoxy)-1-piperidyl group, 1-(2-pentafluoroethylphenoxy)-4-piperidyl group, 4-(3-pentafluoroethylphenoxy)-1-piperidyl group, 4-(2,3-dimethylphenoxy)-1-piperidyl group, 4-(3,4,5-trimethylphenoxy)-1-piperidyl group, 4-(4-n-pentylphenoxy)-1-piperidyl group, 4-(4-n-hexylphenoxy)-1-piperidyl group, 4-(2-methoxyphenoxy)-1-piperidyl group, 4-(3-methoxyphenoxy)-1-piperidyl group, 4-(4-methoxyphenoxy)-1-piperidyl group, 2-(2-ethoxyphenoxy)-3-piperidyl group, 3-(3-ethoxyphenoxy)-4-piperidyl group, 4-(4-ethoxyphenoxy)-3-piperidyl group, 3-(4-n-propoxyphenoxy)-2-piperidyl group, 2-(4-tert-butoxyphenoxy)-1-piperidyl group, 4-(4-n-butoxyphenoxy)-2-piperidyl group, 2-(2-trifluoromethoxyphenoxy)-3-piperidyl group, 3-(3-trifluoromethoxyphenoxy)-4-piperidyl group, 4-(4-trifluoromethoxyphenoxy)-3-piperidyl group, 3-(2-pentafluoroethoxyphenoxy)-2-piperidyl group, 2-(4-pentafluoroethoxyphenoxy)-1-piperidyl group, 4-(2,3-dimethoxyphenoxy)-14-piperidyl group, 4-(3,4,5-trimethoxyphenoxy)-1-piperidyl group, 4-(4-n-pentyloxyphenoxy)-1-piperidyl group, 4-(4-n-hexyloxyphenoxy)-1-piperidyl group, 4-benzyl-1-piperidyl group, 2,4-dibenzyl-1-piperidyl group, 2,4,6-tribenzyl-1-piperidyl group, 2-(2-fluorobenzyl)-1-piperidyl group, 3-(2-(3-fluorophenyl)ethyl)-2-piperidyl group, 4-(1-(4-fluorophenyl)ethyl)-3-piperidyl group, 2-(3-(2-chlorophenyl)propyl)-4-piperidyl group, 3-(4-(3-chlorophenyl)butyl)-5-piperidyl group, 4-(5-(4-chlorophenyl)pentyl)-2-piperidyl group, 5-(6-(2-bromophenyl)hexyl)-2-piperidyl group, 6-(3-bromobenzyl)-3-piperidyl group, 4-(4-bromobenzyl)-1-piperidyl group, 3-(2,3-dichlorobenzyl)-2-piperidyl group, 4-(3,4-dichlorobenzyl)-3-piperidyl group, 3-(2,4-dichlorobenzyl)-4-piperidyl group, 2-(3,4,5-trichlorobenzyl)-3-piperidyl group, 6-(2,4,6-trichlorobenzyl)-2-piperidyl group, 3-(2,3,4,5,6-pentafluorobenzyl)-1-piperidyl group, 4-(2-methylbenzyl)-1-piperidyl group, 5-(2-(3-methylphenyl)ethyl)-2-piperidyl group, 6-(3-(4-methylphenyl]propyl)-3-piperidyl group, 1-(4-(2-ethylphenyl)butyl)-4-piperidyl group, 2-(5-(3-ethylphenyl)pentyl)-1-piperidyl group, 3-(6-(4-ethylphenyl)hexyl)-2-piperidyl group, 4-(4-n-propylbenzyl)-3-piperidyl group, 3-(4-tert-butylbenzyl)-4-piperidyl group, 2-(4-n-butylbenzyl)-3-piperidyl group, 1-(2-trifluoromethylbenzyl)-2-piperidyl group, 2-(3-trifluoromethylbenzyl)-1-piperidyl group, 4-(4-trifluoromethylbenzyl)-1-piperidyl group, 1-(2-pentafluoroethylbenzyl)-4-piperidyl group, 1-(3-pentafluoroethylbenzyl)-4-piperidyl group, 4-(2,3-dimethylbenzyl)-1-piperidyl group, 1-(3,4,5-trimethylbenzyl)-4-piperidyl group, 1-(4-n-pentylbenzyl)-4-piperidyl group, 4-(4-n-hexylbenzyl)-1-piperidyl group, 4-(2-methoxybenzyl)-1-piperidyl group, 1-(2-(3-methoxyphenyl)ethyl)-4-piperidyl group, 1-(1-(4-methoxyphenyl)ethyl)-4-piperidyl group, 2 (3-(2-ethoxyphenyl)propyl)-3-piperidyl group, 3-(4-(3-ethoxyphenyl)butyl)-4-piperidyl group, 4-(5-(4-ethoxyphenyl)pentyl)-3-piperidyl group, 3-(6-(4-n-propoxyphenyl)hexyl)-2-piperidyl group, 2-(4-tert-butoxybenzyl)-1-piperidyl group, 1-(4-n-butoxybenzyl)-2-piperidyl group, 2-(2-trifluoromethoxybenzyl)-3-piperidyl group, 3-(3-trifluoromethoxybenzyl)-4-piperidyl group, 4-(4-trifluoromethoxybenzyl)-1-piperidyl group, 3-(2-pentafluoroethoxybenzyl)-2-piperidyl group, 2-(4-pentafluoroethoxybenzyl)-1-piperidyl group, 1-(2,3-dimethoxybenzyl)-4-piperidyl group, 4-(3,4,5-trimethoxybenzyl)-1-piperidyl group, 4-(4-n-pentyloxybenzyl)-1-piperidyl group, 4-(4-n-hexyloxybenzyl)-1-piperidyl group, 4-benzyl-3-phenoxy-1-piperidyl group, 4-phenoxy-2-methylamino-1-piperidyl group, 4-(4-trifluoromethoxybenzylidene)-1-piperidyl group, 4-(4-chlorobenzylidene)-1-piperidyl group, 4-(4-trifluorbmethylbenzylidene)-1-piperidyl group, 4-(3,4-dichlorobenzyloxy)-(1-, 2- or 3-)piperidyl group, 4-(4-methylbenzyloxy)-(1-, 2- or 3-)piperidyl group, 4-(4-trifluoromethoxybenzyloxy)-(1-, 2- or 3-)piperidyl group, 4-(4-methoxyphenyl)-(1-, 2- or 3-)piperidyl group, 4-(3,4-dichlorophenyl)-(1-, 2- or 3-)piperidyl group, 4-((1- or 2-)naphthylmethyl)-(1-, 2- or 3-)-piperidyl group, 4-(3,4-methylenedioxyphenyl)-(1-, 2- or 3-)piperidyl group, 4-(4-chlorobenzyloxy)-(1-, 2- or 3-)piperidyl group or the like.

A quinolyloxy group (wherein, on the quinoline ring, at least one selected from the group consisting of a (c-1)halogen atom, a (c-2)phenoxy group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted], a (c-3)piperadinyl group [wherein, on the piperadine ring, at least one selected from the group consisting of a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl group [wherein, on the phenyl ring, at least one selected from the group consisting of a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a halogen atom, a halogen substituted or unsubstituted C1-C6 alkyl group and a halogen substituted or unsubstituted C1-C6 alkoxy group may be substituted] and a phenyl C2-C6 alkenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted] and a (c-4)piperidyl group [wherein, on the piperidine ring, at least one selected from the group consisting of an amino group (wherein, on the amino group, at least one selected from the group consisting of a phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] and a C1-C6 alkyl group may be substituted); a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted); a phenyl C1-C6 alkyl group (wherein, on the phenyl ring, at least one selected from the group consisting of a C1-C4 alkylenedioxy group, a halogen atom, a halogen substituted or unsubstituted C1-C6 alkyl group and a halogen substituted or unsubstituted C1-C6 alkoxy group may be substituted); a phenyl C1-C6 alkoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted); a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted); a naphthyl C1-C6 alkyl group; and a phenyl C1-C6 alkylidene group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] may be substituted) includes an quinolyloxy group (wherein, on the quinoline ring, 1 to 3 substituents selected from the group consisting of a (c-1) halogen atom, a (c-2) phenoxy group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), (c-3) a piperadinyl group [wherein, on the piperadine ring, 1 to 5, preferably 1 to 3 groups selected from the group consisting of a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a phenyl group [wherein, on the phenyl ring, 1 to 5, preferably 1 to 3 groups selected from the group consisting of a phenoxy group (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted), a halogen atom, a halogen substituted or unsubstituted C1-C6 alkyl group and a halogen substituted or unsubstituted C1-C6 alkoxy group, may be substituted], and a phenylalkenyl group, containing a C2-C6 alkenyl group having at least 1 to 3 double bonds, wherein each double bond contains both of a trans-form and a cis-form (wherein, on the phenyl ring, at least one group selected from the group consisting of a halogen atom, a halogen substituted or unsubstituted C1-C6 alkyl group and a halogen substituted or unsubstituted C1-C6 alkoxy group, may be substituted) may be substituted] and a (C-4) piperidyl group [wherein, on the piperidine ring, 1 to 3 substituents selected from the group consisting of an amino group (wherein, on the amino group, 1 or 2 groups selected from the group consisting of a phenyl group [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] and a C1-C6 alkyl group may be substituted); a phenoxy group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted); a phenyl C1-C6 alkyl group (wherein, on the phenyl ring, 1 to 5, preferably 1 to 3 substituents selected from the group consisting of a straight or branched C1-C4 alkylenedioxy group, a halogen atom, a halogen substituted or unsubstituted C1-C6 alkyl group and a halogen substituted or unsubstituted C1-C6 alkoxy group may be substituted); a phenylalkoxy group in which the alkoxy moiety is a straight or branched C1-C6 alkoxy group (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted); a phenyl group (wherein, on the phenyl ring, 1 to 5, preferably 1 to 3 groups selected from the group consisting of a halogen atom, a halogen substituted or unsubstituted C1-C6 alkyl group and a halogen substituted or unsubstituted C1-C6 alkoxy group, may be substituted); a naphthylalkyl group in which the alkyl moiety is a straight or branched C1-C6 alkyl group; and a phenyl C1-C6 alkylidene group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted) may be substituted), for example, a 2-quinolyloxy group, 3-quinolyloxy group, 4-quinolyloxy group, 5-quinolyloxy group, 6-quinolyloxy group, 7-quinolyloxy group, 8-quinolyloxy group, 4-(1-piperadinyl)-2-quinolyloxy group, 3-(2-piperadinyl)-4-quinolyloxy group, 4-(1-piperadinyl)-3-quinolyloxy group, 5-(1-piperadinyl)-4-quinolyloxy group, 6-(3,4-dibenzyl-1-piperadinyl)-5-quinolyloxy group, 7-(2,3,4-tribenzyl-1-piperadinyl)-6-quinolyloxy group, 4-(4-benzyl-1-piperadinyl)-2-quinolyloxy group, 3-(4-(2-phenethyl)-1-piperadinyl)-2-quinolyloxy group, 4-(4-(3-phenylpropyl)-1-piperadinyl)-3-quinolyloxy group, 5-(4-(4-phenylbutyl)-1-piperadinyl)-4-quinolyloxy group, 6-(4-(5-phenylpentyl)-1-piperadinyl)-5-quinolyloxy group, 7-(4-(6-phenylhexyl)-1-piperadinyl)-6-quinolyloxy group, 8-(4-(2-fluorobenzyl)-1-piperadinyl)-7-quinolyloxy group, 2-(4-(3-fluorobenzyl)-1-piperadinyl)-8-quinolyloxy group, 3-(4-(4-fluorobenzyl)-1-piperadinyl)-2-quinolyloxy group, 4-(4-(2-chlorobenzyl)-1-piperadinyl)-3-quinolyloxy group, 5-(4-(3-chlorobenzyl)-1-piperadinyl)-4-quinolyloxy group, 2-(4-(4-chlorobenzyl)-1-piperadinyl)-6-quinolyloxy group, 7-(4-(2,3-dichlorobenzyl)-1-piperadinyl)-6-quinolyloxy group, 8-(4-(2,4-dichlorobenzyl)-1-piperadinyl)-7-quinolyloxy group, 2-(4-(3,4-dichlorobenzyl)-1-piperadinyl)-8-quinolyloxy group, 3-(4-(3,5-dichlorobenzyl)-1-piperadinyl)-2-quinolyloxy group, 4-(4-(3,4,5-trichlorobenzyl)-1-piperadinyl)-3-quinolyloxy group, 5-(4-(2,3,4,5,6-pentafluorobenzyl)-1-piperadinyl)-4-quinolyloxy group, 6-(4-(2-trifluoromethylbenzyl)-1-piperadinyl)-5-quinolyloxy group, 7-(4-(3-trifluoromethylbenzyl)-1-piperadinyl)-6-quinolyloxy group, 2-(4-(4-trifluoromethylbenzyl)-1-piperadinyl)-6-quinolyloxy group, 2-(4-(4-methylbenzyl)-1-piperadinyl)-8-quinolyloxy group, 3-(4-(3,4-dimethylbenzyl)-1-piperadinyl)-2-quinolyloxy group, 4-(4-(2,4,6-trimethylbenzyl)-1-piperadinyl)-3-quinolyloxy group, 5-(4-(2-pentafluoroethylbenzyl)-1-piperadinyl)-4-quinolyloxy group, 6-(4-(3-pentafluoroethylbenzyl)-1-piperadinyl)-5-quinolyloxy group, 7-(4-(4-pentafluoroethylbenzyl)-1-piperadinyl)-6-quinolyloxy group, 2-(4-(4-trifluoromethoxybenzyl)-1-piperadinyl)-6-quinolyloxy group, 2-(4-(3-trifluoromethoxybenzyl)-1-piperadinyl)-8-quinolyloxy group, 3-(4-(4-trifluoromethoxybenzyl)-1-piperadinyl)-2-quinolyloxy group, 4-(4-(4-methoxybenzyl)-1-piperadinyl)-3-quinolyloxy group, 5-(4-(3,4-dimethoxybenzyl)-1-piperadinyl)-4-quinolyloxy group, 6-(4-(2,4,6-trimethoxybenzyl)-1-piperadinyl)-5-quinolyloxy group, 7-(4-(2-pentafluoroethoxybenzyl)-1-piperadinyl)-6-quinolyloxy group, 8-(4-(3-pentafluoroethoxybenzyl)-1-piperadinyl)-2-quinolyloxy group, 3-(4-(4-pentafluoroethoxy-benzyl)-1-piperadinyl)-2-quinolyloxy group, 4-(4-(2-(4-trifluoromethoxyphenyl)ethyl)-1-piperadinyl)-3-quinolyloxy group, 5-(4-(3-(4-trifluoromethoxyphenyl) propyl)-1-piperadinyl)-4-quinolyloxy group, 6-(4-(4-(4-trifluoromethoxyphenyl)butyl)-1-piperadinyl)-5-quinolyloxy group, 7-(4-(5-(4-trifluoromethoxyphenyl) pentyl)-1-piperadinyl)-6-quinolyloxy group, 8-(4-(6-(4-trifluoromethoxyphenyl)hexyl)-1-piperadinyl)-7-quinolyloxy group, 2-(4-(2-(4-trifluoromethylphenyl)ethyl)-1-piperadinyl)-8-quinolyloxy group, 3-(4-(3-(4-trifluoromethylphenyl)propyl)-1-piperadinyl)-2-quinolyloxy group, 4-(4-(4-(4-trifluoromethylphenyl)butyl)-1-piperadinyl)-2-quinolyloxy group, 5-(4-(5-(4-trifluoromethylphenyl)pentyl)-1-piperadinyl)-2-quinolyloxy group, 6-(4-(6-(4-trifluoromethylphenyl)hexyl)-1-piperadinyl)-2-quinolyloxy group, 3-(2-piperidyl)-2-quinolyloxy group, 4-(3-piperidyl)-3-quinolyloxy group, 5-(4-piperidyl)-4-quinolyloxy group, 6-(2,4-diamino-1-piperidyl)-5-quinolyloxy group, 7-(2,4,6-triamino-1-piperidyl)-6-quinolyloxy group, 8-(4-amino-1-piperidyl)-7-quinolyloxy group, 2-(4-amino-1-piperidyl)-8-quinolyloxy group, 3-(4-amino-1-piperidyl)-2-quinolyloxy group, 4-(4-methylamino-1-piperidyl)-3-quinolyloxy group, 5-(4-ethylamino-1-piperidyl)-4-quinolyloxy group, 6-(4-n-propylamino-1-piperidyl)-5-quinolyloxy group, 7-(4-dimethylamino-1-piperidyl)-6-quinolyloxy group, 8-(4-diethylamino-1-piperidyl)-7-quinolyloxy group, 2-(4-di-n-propylamino-1-piperidyl)-8-quinolyloxy group, 3-(4-phenylamino-1-piperidyl)-2-quinolyloxy group, 4-(4-(N-phenyl-N-methylamino)-1-piperidyl)-3-quinolyloxy group, 5-(4-(2-fluorophenylamino)-1-piperidyl)-4-quinolyloxy group, 6-(4-(3-fluorophenylamino)-1-piperidyl)-5-quinolyloxy group, 7-(4-(4-fluorophenylamino)-1-piperidyl)-6-quinolyloxy group, 8-(4-(2-chlorophenylamino)-1-piperidyl)-7-quinolyloxy group, 2-(4-(3-chlorophenylamino)-1-piperidyl)-8-quinolyloxy group, 3-(4-(4-chlorophenylamino)-1-piperidyl)-2-quinolyloxy group, 4-(4-(2,3-dichlorophenylamino)-1-piperidyl)-3-quinolyloxy group, 5-(4-(2,4,6-trifluorophenylamino)-1-piperidyl)-4-quinolyloxy group, 6-(4-(2,4-dichlorophenylamino)-1-piperidyl)-5-quinolyloxy group, 7-(4-(3,4-dichlorophenylamino)-1-piperidyl)-6-quinolyloxy group, 8-(4-(3,5-dichlorophenylamino)-1-piperidyl)-7-quinolyloxy group, 2-(4-(2,3,4,5,6-pentafluorophenylamino)-1-piperidyl)-8-quinolyloxy group, 3-(4-(2-trifluoromethylphenylamino)-1-piperidyl)-2-quinolyloxy group, 4-(4-(2-methylphenylamino)-1-piperidyl)-3-quinolyloxy group, 5-(4-(2,3-dimethylphenylamino)-1-piperidyl)-4-quinolyloxy group, 6-(4-(2-trifluoromethylphenylamino)-1-piperidyl)-5-quinolyloxy group, 7-(4-(2,4,6-trimethylphenylamino)-1-piperidyl)-6-quinolyloxy group, 8-(4-(4-trifluoromethylphenylamino)-1-piperidyl)-7-quinolyloxy group, 2-(4-(2-pentafluoroethylphenylamino)-1-piperidyl)-8-quinolyloxy group, 3-(4-(3-pentafluoroethylphenylamino)-1-piperidyl)-2-quinolyloxy group, 4-(4-(4-pentafluoroethylphenylamino)-1-piperidyl)-3-quinolyloxy group, 5-(4-(2-trifluoromethoxyphenylamino)-1-piperidyl)-4-quinolyloxy group, 6-(4-(2-methoxyphenylamino)-1-piperidyl)-5-quinolyloxy group, 7-(4-(2,3-dimethoxyphenylamino)-1-piperidyl)-6-quinolyloxy group, 8-(4-(2,4,6-trimethoxyphenylamino)-1-piperidyl)-7-quinolyloxy group, 2-(4-(N-methyl-N-(2,4,6-trimethoxyphenylamino))-1-piperidyl)-8-quinolyloxy group, 3-(4-(N-methyl-N-(3,4-dimethylphenylamino))-1-piperidyl)-2-quinolyloxy group, 4-(4-(3-trifluoromethoxyphenylamino)-1-piperidyl)-2-quinolyloxy group, 5-(4-(4-trifluoromethoxyphenylamino)-1-piperidyl)-2-quinolyloxy group, 6-(4-(2-pentafluoroethoxyphenylamino)-1-piperidyl)-2-quinolyloxy group, 7-(4-(3-pentafluoroethoxyphenylamino)-1-piperidyl)-2-quinolyloxy group, 8-(4-(4-pentafluoroethoxyphenylamino)-1-piperidyl)-2-quinolyloxy group, 2-(4-(2-fluorophenylamino)-1-piperidyl)-3-quinolyloxy group, 3-(4-(3-fluorophenylamino)-1-piperidyl)-2-quinolyloxy group, 4-(4-(4-fluorophenylamino)-1-piperidyl)-2-quinolyloxy group, 2-(4-(N-ethyl-N-(4-chlorophenylamino))-1-piperidyl)-6-quinolyloxy group, 2,4-di(1-piperadinyl)-6-quinolyloxy group, 3-(1-piperidyl)-4-(1-piperadinyl)-2-quinolyloxy group, 2,4,6-tri(1-piperidinyl)-3-quinolyloxy group, 5-chloro-8-quinolyloxy group, 2-(4-trifluoromethoxyphenoxy)-6-quinolyloxy group, 2-(4-(4-trifluoromethoxybenzylidene)-1-piperidyl)-6-quinolyloxy group, 2-(4-(4-chlorobenzylidene)-1-piperidyl)-6-quinolyloxy group, 2-(4-(4-trifluoromethylbenzylidene)-1-piperidyl)-6-quinolyloxy group, 2-(4-benzyl-1-piperidyl)-4-quinolyloxy group, 2-(3,4-dibenzyl-1-piperidyl)-4-quinolyloxy group, 5-(2,3,4-tribenzyl-1-piperidyl)-2-quinolyloxy group, 4-(4-(2-phenethyl)-1-piperidyl)-2-quinolyloxy group, 4-(4-(3-phenylpropyl)-1-piperidyl)-5-quinolyloxy group, 4-(4-(4-phenylbutyl)-1-piperidyl)-6-quinolyloxy group, 4-(4-(5-phenylpentyl)-1-piperidyl)-7-quinolyloxy group, 2-(4-(6-phenylhexyl)-1-piperidyl)-4-quinolyloxy group, 4-(4-(2-fluorobenzyl)-1-piperidyl)-2-quinolyloxy group, 2-(4-(3-fluorobenzyl)-1-piperidyl)-4-quinolyloxy group, 2-(4-(4-fluorobenzyl)-1-piperidyl)-5-quinolyloxy group, 2-(4-(2-chlorobenzyl)-1-piperidyl)-6-quinolyloxy group, 2-(4-(3-chlorobenzyl)-1-piperidyl)-7-quinolyloxy group, 5-(4-(4-chlorobenzyl)-1-piperidyl)-4-quinolyloxy group, 6-(4-(2,3-dichlorobenzyl)-1-piperidyl)-4-quinolyloxy group, 7-(4-(2,4-dichlorobenzyl)-1-piperidyl)-8-quinolyloxy group, 2-(4-(3,4-dichlorobenzyl)-1-piperidyl)-8-quinolyloxy group, 4-(4-(3,5-dichlorobenzyl)-1-piperidyl)-2-quinolyloxy group, 4-(4-(3,4,5-trichlorobenzyl)-1-piperidyl)-5-quinolyloxy group, 4-(4-(2,3,4,5,6-pentafluorobenzyl)-1-piperidyl)-2-quinolyloxy group, 4-(4-(2-trifluoromethylbenzyl)-1-piperidyl)-6-quinolyloxy group, 4-(4-(3-trifluoromethylbenzyl)-1-piperidyl)-7-quinolyloxy group, 2-(4-(4-trifluoromethylbenzyl)-1-piperidyl)-8-quinolyloxy group, 5-(4-(4-methylbenzyl)-1-piperidyl)-4-quinolyloxy group, 6-(4-(3,4-dimethylbenzyl)-1-piperidyl)-4-quinolyloxy group, 8-(4-(2,4,6-trimethylbenzyl)-1-piperidyl)-4-quinolyloxy group, 3-(4-(2-pentafluoroethylbenzyl)-1-piperidyl)-2-quinolyloxy group, 8-(4-(3-pentafluoroethylbenzyl)-1-piperidyl)-5-quinolyloxy group, 4-(4-(4-pentafluoroethylbenzyl)-1-piperidyl)-6-quinolyloxy group, 4-(4-(2-trifluoromethoxybenzyl)-1-piperidyl)-7-quinolyloxy group, 5-(4-(3-trifluoromethoxybenzyl)-1-piperidyl)-4-quinolyloxy group, 6-(4-(4-trifluoromethoxybenzyl)-1-piperidyl)-5-quinolyloxy group, 7-(4-(4-methoxybenzyl)-1-piperidyl)-5-quinolyloxy group, 6-(4-(3,4-dimethoxybenzyl)-1-piperidyl)-4-quinolyloxy group, 1-(4-(2,4,6-trimethoxybenzyl)-1-piperidyl)-4-quinolyloxy group, 5-(4-(2-pentafluoroethoxybenzyl)-1-piperidyl)-4-quinolyloxy group, 4-(4-(3-pentafluoroethoxybenzyl)-1-piperidyl)-2-quinolyloxy group, 6-(4-(4-pentafluoroethoxybenzyl)-1-piperidyl)-4-quinolyloxy group, 4-(4-(2-(4-trifluoromethoxyphenyl)ethyl)-1-piperidyl)-2-quinolyloxy group, 4-(4-(3-(4-trifluoromethoxyphenyl)propyl)-1-piperidyl)-2-quinolyloxy group, 4-(4-(4-(4-trifluoromethoxyphenyl)butyl)-1-piperidyl)-2-quinolyloxy group, 4-(4-(5-(4-trifluoromethoxyphenyl)pentyl)-1-piperidyl)-3-quinolyloxy group, 4-(4-(6-(4-trifluoromethoxyphenyl) hexyl)-1-piperidyl)-3-quinolyloxy group, 4-(4-(2-(4-trifluoromethylphenyl)ethyl)-1-piperidyl)-2-quinolyloxy group, 5-(4-(3-(4-trifluoromethylphenyl)propyl)-1-piperidyl)-2-quinolyloxy group, 6-(4-(4-(4-trifluoromethylphenyl)butyl)-1-piperidyl)-2-quinolyloxy group, 7-(4-(5-(4-trifluoromethylphenyl)pentyl)-2-piperidyl)-2-quinolyloxy group, 5-(4-(6-(4-trifluoromethylphenyl)hexyl)-1-piperidyl)-2-quinolyloxy group, 2-(4-phenoxy-1-piperidyl)-4-quinolyloxy group, 2-(3,4-diphenoxy-1-piperidyl)-4-quinolyloxy group, 5-(2,3,4-triphenoxy-1-piperidyl)-2-quinolyloxy group, 4-(4-(2-fluorophenoxy)-1-piperidyl)-2-quinolyloxy group, 2-(4-(3-fluorophenoxy)-1-piperidyl)-4-quinolyloxy group, 2-(4-(4-fluorophenoxy)-1-piperidyl)-5-quinolyloxy group, 2-(4-(2-chlorophenoxy)-1-piperidyl)-6-quinolyloxy group, 2-(4-(3-chlorophenoxy)-1-piperidyl)-7-quinolyloxy group, 5-(4-(4-chlorophenoxy)-1-piperidyl)-4-quinolyloxy group, 6-(4-(2,3-dichlorophenoxy)-1-piperidyl)-4-quinolyloxy group, 7-(4-(2,4-dichlorophenoxy)-1-piperidyl)-4-quinolyloxy group, 2-(4-(3,4-dichlorophenoxy)-1-piperidyl)-8-quinolyloxy group, 4-(4-(3,5-dichlorophenoxy)-1-piperidyl)-2-quinolyloxy group, 4-(4-(3,4,5-trichlorophenoxy)-1-piperidyl)-5-quinolyloxy group, 4-(4-(2,3,4,5,6-pentafluorophenoxy)-1-piperidyl)-2-quinolyloxy group, 4-(4-(2-trifluoromethylphenoxy)-1-piperidyl)-6-quinolyloxy group, 4-(4-(3-trifluoromethylphenoxy)-1-piperidyl)-7-quinolyloxy group, 2-(4-(4-trifluoromethylphenoxy)-1-piperidyl)-4-quinolyloxy group, 5-(4-(4-methylphenoxy)-1-piperidyl)-4-quinolyloxy group, 6-(4-(3,4-dimethylphenoxy)-1-piperidyl)-4-quinolyloxy group, 7-(4-(2,4,6-trimethylphenoxy)-1-piperidyl)-4-quinolyloxy group, 4-(4-(2-pentafluoroethylphenoxy)-1-piperidyl)-2-quinolyloxy group, 4-(4-(3-pentafluoroethylphenoxy)-1-piperidyl)-5-quinolyloxy group, 4-(4-(4-pentafluoroethylphenoxy)-1-piperidyl)-6-quinolyloxy group, 4-(4-(2-trifluoromethoxyphenoxy)-1-piperidyl)-7-quinolyloxy group, 5-(4-(3-trifluoromethoxyphenoxy)-1-piperidyl)-4-quinolyloxy group, 6-(4-(4-trifluoromethoxyphenoxy)-1-piperidyl)-5-quinolyloxy group, 7-(4-(4-methoxyphenoxy)-1-piperidyl)-5-quinolyloxy group, 6-(4-(3,4-dimethoxyphenoxy)-1-piperidyl)-4-quinolyloxy group, 8-(4-(2,4,6-trimethoxyphenoxy)-1-piperidyl)-4-quinolyloxy group, 5-(4-(2-pentafluoroethoxyphenoxy)-1-piperidyl)-4-quinolyloxy group, 4-(4-(3-pentafluoroethoxyphenoxy)-1-piperidyl)-2-quinolyloxy group, 6-(4-(4-pentafluoroethoxyphenoxy)-1-piperidyl)-4-quinolyloxy group, 2,5,6-trifenoxy-7-quinolyloxy group, 4,5,6-trichloro-2-quinolyloxy group, 2-phenoxy-6-bromo-5-quinolyloxy group, 2-(2,3-dimethylphenoxy)-5-quinolyloxy group, 2-(3,4,5-trimethylphenoxy)-6-quinolyloxy group, 2-(2,3-dimethoxyphenoxy)-7-quinolyloxy group, 2-(3,4,5-trimethoxyphenoxy)-8-quinolyloxy group, 2-(2,3,4,5,6-pentafluorophenoxy)-6-quinolyloxy group, 2-(2-methylphenoxy)-4-quinolyloxy group, 2-(3-methylphenoxy)-3-quinolyloxy group, 3-(4-methylphenoxy)-2-quinolyloxy group, 4-(2-methoxyphenoxy)-3-quinolyloxy group, 5-(3-methoxyphenoxy)-4-quinolyloxy group, 6-(4-methoxyphenoxy)-5-quinolyloxy group, 7-(2-fluorophenoxy)-6-quinolyloxy group, 8-(3-fluorophenoxy)-7-quinolyloxy group, 2-(4-fluorophenoxy)-5-quinolyloxy group, 3-(2-chlorophenoxy)-2-quinolyloxy group, 4-(3-chlorophenoxy)-6-quinolyloxy group, 5-(4-chlorophenoxy)-2-quinolyloxy group, 6-(2-bromophenoxy)-3-quinolyloxy group, 7-(3-bromophenoxy)-4-quinolyloxy group, 8-(4-bromophenoxy)-2-quinolyloxy group, 2-(2,3-dichlorophenoxy)-6-quinolyloxy group, 3-(3,4-dichlorophenoxy)-7-quinolyloxy group, 4-(2,4-dichlorophenoxy)-5-quinolyloxy group, 2-(3,4,5-trichlorophenoxy)-6-quinolyloxy group, 2-(2,4,6-trichlorophenoxy)-5-quinolyloxy group, 2-(3-trifluoromethylphenoxy)-7-quinolyloxy group, 2-(4-(3-(4-trifluoromethylphenyl)-2-propenyl)-(1-, 2- or 3-)piperadinyl)-(3-, 4-, 5-, 6-, 7- or 8-)quinolyloxy group, 2-(4-(4-methoxyphenyl)-(1-, 2- or 3-)-piperadinyl)-(3-, 4-, 5-, 6-, 7- or 8-)quinolyloxy group, 2-(4-(3,4-dimethylphenyl)-(1-, 2- or 3-)-piperadinyl)-(3-, 4-, 5-, 6-, 7- or 8-)quinolyloxy group, 2-(4-(4-fluorophenyl)-(1-, 2- or 3-)-piperadinyl)-(3-, 4-, 5-, 6-, 7- or 8-)quinolyloxy group, 2-(4-(4-trifluoromethylphenyl)-(1-, 2- or 3-)-piperadinyl)-(3-, 4-, 5-, 6-, 7- or 8-)quinolyloxy group, 2-(4-(4-methylphenyl)-(1-, 2- or 3-)-piperadinyl)-(3-, 4-, 5-, 6-, 7- or 8-)quinolyloxy group, 2-(4-(3,4-dichlorophenyl)-(1-, 2- or 3-)-piperadinyl)-(3-, 4-, 5-, 6-, 7- or 8-)quinolyloxy group, 2-(4-(4-trifluoromethoxyphenyl)-(1-, 2- or 3-)-piperadinyl)-(3-, 4-, 5-, 6-, 7- or 8-)quinolyloxy group, 2-(4-(4-(4-chlorophenoxy)phenyl)-(1-, 2- or 3-)-piperadinyl)-(3-, 4-, 5-, 6-, 7- or 8-)quinolyloxy group, 2-(4-(3,4-dichlorobenzyloxy)-(1-, 2- or 3-)-piperadinyl)-(3-, 4-, 5-, 6-, 7- or 8-)quinolyloxy group, 2-(4-(4-methylbenzyloxy)-(1-, 2- or 3-)-piperadinyl)-(3-, 4-, 5-, 6-, 7- or 8-)quinolyloxy group, 2-(4-(4-trifluoromethoxybenzyloxy)-(1-, 2- or 3-)piperadinyl)-(3-, 4-, 5-, 6-, 7- or 8-)quinolyloxy group, 2-(4-(4-methoxyphenyl)-(1-, 2- or 3-)-piperadinyl)-(3-, 4-, 5-, 6-, 7- or 8-)quinolyloxy group, 2-(4-(3,4-dichlorophenyl)-(1-, 2- or 3-)-piperadinyl)-(3-, 4-, 5-, 6-, 7- or 8-)quinolyloxy, 2-(4-((1- or 2-)naphthylmethyl)-(1-, 2- or 3-)-piperadinyl)-(3-, 4-, 5-, 6-, 7- or 8-)quinolyloxy group, 2-(4-(3,4-methylenedioxyphenyl)-(1-, 2- or 3-)-piperadinyl)-(3-, 4-, 5-, 6-, 7- or 8-)quinolyloxy group, 2-(4-(4-chlorobenzyloxy)-(1-, 2- or 3-)-piperadinyl)-(3-, 4-, 5-, 6-, 7- or 8-)quinolyloxy group or the like.

A phenyl C1-C6 alkoxy substituted C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is a group composed of a phenyl C1-C6 alkoxy group and C1-C6 alkyl group which may be substituted by 1 to 5, preferably 1 to 3 substituents selected from the group consisting of a halogen atom, a halogen substituted or unsubstituted C1-C6 alkyl group and a halogen substituted or unsubstituted C1-C6 alkoxy group as defined above, examples of which include a benzyloxymethyl group, 2-phenylethoxymethyl group, 3-phenylpropoxymethyl group, 2-phenylpropoxymethyl group, 4-phenylbutoxymethyl group, 5-phenylpentoxymethyl group, 4-phenylpentoxymethyl group, 6-phenylhexyloxymethyl group, 2-fluorobenzyloxymethyl group, 4-fluorobenzyloxymethyl group, 4-chlorobenzyloxymethyl group, 3-chlorobenzyloxymethyl group, 2-chlorobenzyloxymethyl group, 3,5-dichlorobenzyloxymethyl group, 3,4-dichlorobenzyloxymethyl group, 2-(3-fluorobenzyloxy)ethyl group, 1-(4-fluorobenzyloxy)ethyl group, 3-(2-(2-fluorophenyl)ethoxy)propyl group, 4-(2-(3-fluorophenyl)ethoxy)butyl group, 5-(2-(4-fluorophenyl)ethoxy)pentyl group, 6-(2-chlorobenzyloxy)hexyl group, 3-chlorobenzyloxymethyl group, 2-(4-chlorobenzyloxy)ethyl group, 1-(2-fluoro-4-bromobenzyloxy)ethyl group, 3-(4-chloro-3-fluorobenzyloxy)propyl group, 4-(2,3,4-trichlorobenzyloxy)butyl group, 5-(3,4,5-trifluorobenzyloxy)pentyl group, 6-(2,3,4,5,6-pentafluorobenzyloxy)hexyl group, 2,4,6-trichlorobenzyloxymethyl group, 2-(4-isopropylbenzyloxy)ethyl group, 1-(4-n-butylbenzyloxy)ethyl group, 3-(4-methylbenzyloxy)propyl group, 4-(2-methylbenzyloxy)butyl group, 5-(3-methylbenzyloxy)pentyl group, 6-(2,4-dimethylpenzyloxy)hexyl group, 2,3-dimethylbenzyloxymethyl group, 4-methylbenzyloxymethyl group, 4-ethylbenzyloxymethyl group, 3,5-dimethylbenzyloxymethyl group, 4-isopropylbenzyloxymethyl group, 3-trifluoromethylbenzyloxymethyl group, 4-trifluoromethylbenzyloxymethyl group, 2-trifluoromethylbenzyloxymethyl group, 2-(2,6-dimethylbenzyloxy)ethyl group, 1-(3,5-dimethylbenzyloxy)ethyl group, 3-(2,5-dimethylbenzyloxy)propyl group, 4-(2,4,6-trimethylbenzyloxy)butyl group, 5-(3,5-ditrifluoromethylbenzyloxy)pentyl group, 6-(4-isopropoxybenzyloxy)hexyl group, 4-n-butoxybenzyloxymethyl group, 4-trifluoromethoxybenzyloxymethyl group, 2-trifluoromethoxybenzyloxymethyl group, 3-trifluoromethoxybenzyloxymethyl group, 3-methoxybenzyloxymethyl group, 2-(4-methoxybenzyloxy)ethyl group, 1-(2-methoxybenzyloxy)ethyl group, 3-(3-methoxybenzyloxy)propyl group, 4-(2,4-dimethoxybenzyloxy)butyl group, 5-(2,3-dimethoxybenzyloxy)pentyl group, 6-(2,6-dimethoxybenzyloxy)hexyl group, 3,5-dimethoxybenzyloxymethyl group, 2-(2,5-dimethoxybenzyloxy)ethyl group, 1-(2,4,6-trimethoxybenzyloxy)ethyl group, 3-(3,5-ditrifluoromethoxybenzyloxy) propyl group, 4-(2-isopropoxybenzyloxy)butyl group, 5-(3-chloro-4-methoxybenzyloxy)pentyl group, 6-(2-chloro-4-trifluoromethoxybenzyloxy)hexyl group, 3-methyl-4-fluorobenzyloxymethyl group, 2-(4-bromo-3-trifluoromethylbenzyloxy)ethyl group, 1-(2-(2-chlorophenyl)ethoxy)methyl group, 3-(2-(3-chlorophenyl) ethoxy)propyl group, 4-(2-(4-chlorophenyl)ethoxy)butyl group, 5-(2-trifluoromethylbenzyloxy)pentyl group, 6-(3-trifluoromethylbenzyloxy)hexyl group, 4-trifluoromethylbenzyloxymethyl group, 2-(2-trifluoromethoxybenzyloxy)ethyl group, 1-(3-trifluoromethoxybenzyloxy)ethyl group, 3-(4-trifluoromethoxybenzyloxy)propyl group, 4-(2-(2-trifluoromethylphenyl)ethoxy)butyl group, 5-(2-(3-trifluoromethylphenyl)ethoxy)pentyl group, 6-(2-(4-trifluoromethylphenyl)ethoxy)hexyl group, (2-(2-trifluoromethoxyphenyl)ethoxy)methyl group, 2-(2-(3-trifluoromethoxyphenyl)ethoxy)ethyl group, 1-(2-(4-trifluoromethoxyphenyl)ethoxy)ethyl group, 3-(3-(2-trifluoromethylphenyl)propoxy)propyl group, 4-(3-(3-trifluoromethylphenyl)propoxy)butyl group, 5-(3-(4-trifluoromethylphenyl)propoxy)pentyl group, 6-(3-(2-trifluoromethylphenyl)propoxy)pentyl group, (3-(3-trifluoromethoxyphenyl)propoxy)methyl group, 2-(3-(4-trifluoromethoxyphenyl)propoxy)ethyl group, 1-(4-(3-trifluoromethylphenyl)butoxy)ethyl group, 3-(5-(4-trifluoromethylphenyl)pentoxy)butyl group, 4-(4-(4-trifluoromethylphenyl)pentoxy)butyl group, 5-(4-(4-trifluoromethoxyphenyl)pentoxy)pentyl group, 6-(6-(3-trifluoromethylphenyl)hexyloxy)hexyl group, (6-(4-trifluoromethylphenyl)hexyloxy)methyl group, 2-(6-(4-trifluoromethoxyphenyl)hexyloxy)ethyl group or the like.

A piperidyl group [wherein, on the piperidine ring, at least one selected from the group consisting of a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl C1-C6 alkoxy substituted C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenoxy C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a piperidyl group [wherein, on the piperidine ring, 1 to 3 substituents selected from the group consisting of a phenoxy group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) a phenyl C1-C6 alkoxy substituted C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a phenoxy C1-C6 alkyl group having a straight or branched alkyl group containing 1 to 6 carbon atoms on the alkyl part described later (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a 1-piperidyl group, 4-piperidyl group, 2-piperidyl group, 3-piperidyl group, 4-phenoxy-1-piperidyl group, 2,4-diphenoxy-1-piperidyl group, 2,4,6-triphenoxy-1-piperidyl group, 2-(2-fluorophenoxy)-1-piperidyl group, 3-(3-fluorophenoxy)-2-piperidyl group, 4-(4-fluorophenoxy)-3-piperidyl group, 2-(2-chlorophenoxy)-4-piperidyl group, 3-(3-chlorophenoxy)-5-piperidyl group, 4-(4-chlorophenoxy)-2-piperidyl group, 5-(2-bromophenoxy)-2-piperidyl group, 6-(3-bromophenoxy)-3-piperidyl group, 4-(4-bromophenoxy)-1-piperidyl group, 3-(2,3-dichlorophenoxy)-2-piperidyl group, 4-(3,4-dichlorophenoxy)-3-piperidyl group, 3-(2,4-dichlorophenoxy)-4-piperidyl group, 2-(3,4,5-trichlorophenoxy)-3-piperidyl group, 6-(2,4,6-trichlorophenoxy)-2-piperidyl group, 3-(2,3,4,5,6-pentafluorophenoxy)-1-piperidyl group, 4-(2-methylphenoxy)-1-piperidyl group, 5-(3-methylphenoxy)-2-piperidyl group, 6-(4-methylphenoxy)-3-piperidyl group, 3-(2-ethylphenoxy)-4-piperidyl group, 2-(3-ethylphenoxy)-1-piperidyl group, 3-(4-ethylphenoxy)-2-piperidyl group, 4-(4-n-propylphenoxy)-3-piperidyl group, 3-(4-tert-butylphenoxy)-4-piperidyl group, 2-(4-n-butylphenoxy)-3-piperidyl group, 4-(2-trifluoromethylphenoxy)-2-piperidyl group, 2-(3-trifluoromethylphenoxy)-1-piperidyl group, 3-(4-trifluoromethylphenoxy)-1-piperidyl group, 1-(2-pentafluoroethylphenoxy)-4-piperidyl group, 1-(3-pentafluoroethylphenoxy)-4-piperidyl group, 4-(2,3-dimethylphenoxy)-1-piperidyl group, 3-(3,4,5-trimethylphenoxy)-4-piperidyl group, 1-(4-n-pentylphenoxy)-4-piperidyl group, 4-(4-n-hexylphenoxy)-1-piperidyl group, 4-(2-methoxyphenoxy)-1-piperidyl group, 1-(3-methoxyphenoxy)-4-piperidyl group, 3-(4-methoxyphenoxy)-4-piperidyl group, 2-(2-ethoxyphenoxy)-3-piperidyl group, 3-(3-ethoxyphenoxy)-4-piperidyl group, 4-(4-ethoxyphenoxy)-3-piperidyl group, 3-(4-n-propoxyphenoxy)-2-piperidyl group, 2-(4-tert-butoxyphenoxy)-2-piperidyl group, 4-(4-n-butoxyphenoxy)-2-piperidyl group, 2-(2-trifluoromethoxyphenoxy)-3-piperidyl group, 3-(3-trifluoromethoxyphenoxy)-4-piperidyl group, 4-(4-trifluoromethoxyphenoxy)-3-piperidyl group, 3-(2-pentafluoroethoxyphenoxy)-2-piperidyl group, 2-(4-pentafluoroethoxyphenoxy)-1-piperidyl group, 3-(2,3-dimethoxyphenoxy)-4-piperidyl group, 4-(3,4,5-trimethoxyphenoxy)-1-piperidyl group, 4-(4-n-pentyloxyphenoxy)-1-piperidyl group, 4-(4-n-hexyloxyphenoxy)-1-piperidyl group, 4-benzyl-1-piperidyl group, 2,4-dibenzyl-1-piperidyl group, 2,4,6-tribenzyl-1-piperidyl group, 2-(2-fluorobenzyl)-1-piperidyl group, 3-(2-(3-fluorophenyl)ethyl]-2-piperidyl group, 4-(1-(4-fluorophenyl)ethyl]-3-piperidyl group, 2-(3-(2-chlorophenyl)propyl]-4-piperidyl group, 3-(4-(3-chlorophenyl)butyl]-5-piperidyl group, 4-(5-(4-chlorophenyl)pentyl]-2-piperidyl group, 5-((6-(2-bromophenyl) hexyl]-2-piperidyl group, 6-(3-bromobenzyl)-3-piperidyl group, 4-(4-bromobenzyl)-1-piperidyl group, 3-(2,3-dichlorobenzyl)-2-piperidyl group, 4-(3,4-dichlorobenzyl)-3-piperidyl group, 3-(2,4-dichlorobenzyl)-4-piperidyl group, 2-(3,4,5-trichlorobenzyl)-3-piperidyl group, 6-(2,4,6-trichlorobenzyl)-2-piperidyl group, 3-(2,3,4,5,6-pentafluorobenzyl)-1-piperidyl group, 4-(2-methylbenzyl)-1-piperidyl group, 5-(2-(3-methylphenyl)ethyl]-2-piperidyl group, 6-(3-(4-methylphenyl)propyl]-3-piperidyl group, 1-(4-(2-ethylphenyl)butyl]-4-piperidyl group, 2-(5-(3-ethylphenyl)pentyl]-1-piperidyl group, 3-(6-(4-ethylphenyl) hexyl]-2-piperidyl group, 4-(4-n-propylbenzyl)-3-piperidyl group, 3-(4-tert-butylbenzyl)-4-piperidyl group, 2-(4-n-butylbenzyl)-3-piperidyl group, 1-(2-trifluoromethylbenzyl)-2-piperidyl group, 2-(3-trifluoromethylbenzyl)-1-piperidyl group, 4-(4-trifluoromethylbenzyl)-1-piperidyl group, 1-(2-pentafluoroethylbenzyl)-4-piperidyl group, 1-(3-pentafluoroethylbenzyl)-4-piperidyl group, 4-(2,3-dimethylbenzyl)-1-piperidyl group, 1-(3,4,5-trimethylbenzyl)-4-piperidyl group, 1-(4-n-pentylbenzyl)-4-piperidyl group, 4-(4-n-hexylbenzyl)-1-piperidyl group, 4-(2-methobenzyl)-1-piperidyl group, 1-(2-(3-methoxyphenyl)ethyl]-4-piperidyl group, 1(1-(4-methoxyphenyl)ethyl]-4-piperidyl group, 2-(3-(2-ethoxyphenyl)propyl]-3-piperidyl group, 3-(4-(3-ethoxyphenyl)butyl]-4-piperidyl group, 3-(4-(3-ethoxyphenyl)butyl]-4-piperidyl group, 4-(5-(4-ethoxyphenyl)pentyl]-3-piperidyl group, 3-(6-(4-n-propoxyphenyl)hexyl]-2-piperidyl group, 2-(4-tert-butoxybenzyl)-1-piperidyl group, 1-(4-n-butoxybenzyl)-2-piperidyl group, 2-(2-trifluoromethoxybenzyl)-3-piperidyl group, 3-(3-trifluoromethoxybenzyl)-4-piperidyl group, 4-(4-trifluoromethoxybenzyl)-1-piperidyl group, 3-(2-pentafluoroethoxybenzyl)-2-piperidyl group, 2-(4-pentafluoroethoxybenzyl)-1-piperidyl group, 1-(2,3-dimethoxybenzyl)-4-piperidyl group, 4-(3,4,5-trimethoxybenzyl)-1-piperidyl group, 4-(4-n-pentyloxybenzyl)-1-piperidyl group, 4-(4-n-hexyloxybenzyl)-1-piperidyl group, 4-benzyl-3-phenoxy-1-piperidyl group, 4-benzyloxymethyl-1-piperidyl group, 2,4-dibenzyloxymethyl-1-piperidyl group, 2,4,6-tribenzyloxymethyl-1-piperidyl group, 2-((2-fluorobenzyloxy)methyl]-1-piperidyl group, 3-(2-(2-(3-fluorophenyl)ethoxy]ethyl)-2-piperidyl group, 4-(1-(1-(4-fluorophenyl)ethyl]ethoxy)-3-piperidyl group, 2-(3-(3-(2-chlorophenyl)propoxy]propyl)-4-piperidyl group, 3-(4-(4-(3-chlorophenyl)butoxy]butyl)-5-piperidyl group, 4-(5-(5-(4-chlorophenyl)pentyloxy]pentyl)-2-piperidyl group, 5-(6-(6-(2-bromophenyl)hexyloxy]-2-piperidyl group, 6-(3-bromobenzyloxymethyl)-3-piperidyl group, 4-(4-bromobenzyloxymethyl)-1-piperidyl group, 3-(2,3-dichlorobenzyloxymethyl)-2-piperidyl group, 4-(3,4-dichlorobenzyloxymethyl)-3-piperidyl group, 3-(2,4-dichlorobenzyloxymethyl)-4-piperidyl group, 2-(3,4,5-trichlorobenzyloxymethyl)-3-piperidyl group, 6-(2,4,6-trichlorobenzyloxymethyl)-2-piperidyl group, 3-(2,3,4,5,6-pentafluorobenzyloxymethyl)-1-piperidyl group, 4-(2-methylbenzyloxymethyl)-1-piperidyl group, 5-(2-(2-(3-methylphenyl)ethoxy]ethyl)-2-piperidyl group, 6-(3-(3-(4-methylphenyl)propoxy)propyl)-3-piperidyl group, 1-(4-(4-(2-ethylphenyl)butoxy]butyl)-4-piperidyl group, 2-(5-(5-(3-ethylphenyl)pentyloxy]pentyl)-1-piperidyl group, 3-(6-(6-(4-ethylphenyl)hexyloxy]hexyl)-2-piperidyl group, 4-(4-n-propylbenzyloxymethyl)-3-piperidyl group, 3-(4-tert-butylbenzyloxymethyl)-4-piperidyl group, 2-(4-n-butylbenzyloxymethyl)-3-piperidyl group, 1-(2-trifluoromethylbenzyloxymethyl)-2-piperidyl group, 2-(3-trifluoromethylbenzyloxymethyl)-1-piperidyl group, 4-(4-trifluoromethylbenzyloxymethyl)-1-piperidyl group, 1-(2-pentafluoroethylbenzyloxymethyl)-4-piperidyl group, 1-(3-pentafluoroethylbenzyloxymethyl)-4-piperidyl group, 4-(2,3-dimethylbenzyloxymethyl)-1-piperidyl group, 1-(3,4,5-trimethylbenzyloxymethyl)-4-piperidyl group, 1-(4-n-pentylbenzyloxymethyl)-4-piperidyl group, 4-(4-n-hexylbenzyloxymethyl)-1-piperidyl group, 4-(2-methoxybenzyloxymethyl)-1-piperidyl group, 1-(2-(2-(3-methoxyphenyl)ethoxy]ethyl)-4-piperidyl group, 1-(1-(1-(4-methoxyphenyl)ethoxy]ethyl)-4-piperidyl group, 2-(3-(3-(2-ethoxyphenyl)propoxy]propyl)-3-piperidyl group, 3-(4-(4-(3-ethoxyphenyl)butoxy]butyl)-4-piperidyl group, 4-(5-(5-(4-ethoxyphenyl)pentyloxy]pentyl)-3-piperidyl group, 3-(6-(6-(4-n-propoxyphenyl)hexyloxy]hexyl)-2-piperidyl group, 2-(4-tert-butoxybenzyloxymethyl)-1-piperidyl group, 1-(4-n-butoxybenzyloxymethyl)-2-piperidyl group, 2-(2-trifluoromethoxybenzyloxymethyl)-3-piperidyl group, 3-(3-trifluoromethoxybenzyloxymethyl)-4-piperidyl group, 4-(4-trifluoromethoxybenzyloxymethyl)-1-piperidyl group, 3-(2-pentafluoroethoxybenzyloxymethyl)-2-piperidyl group, 2-(4-pentafluoroethoxybenzyloxymethyl)-1-piperidyl group, 1-(2,3-dimethoxybenzyloxymethyl)-4-piperidyl group, 4-(3,4,5-trimethoxybenzyloxymethyl)-1-piperidyl group, 4-(4-n-pentyloxybenzyloxymethyl)-1-piperidyl group, 4-(4-n-hexyloxybenzyloxymethyl)-1-piperidyl group, 4-benzyloxymethyl-3-phenoxy-1-piperidyl group, 4-benzyl-3-phenoxy-1-piperidyl group, 4-(4-chlorophenoxymethyl)-(1-, 2- or 3-)piperidyl group or the like.

A pyridyloxy group (wherein, on the pyridine ring, at least one selected from the group consisting of a (d-1) piperidyl group (wherein, on the piperidine ring, at least one selected from the group consisting of a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl C1-C6 alkoxy substituted C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenoxy C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] and a (d-2)piperadinyl group [wherein, on the piperadine ring, at least one selected from the group consisting of a C1-C6 alkoxycarbonyl group, a furyl C1-C6 alkyl group [wherein, on the furan ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a pyridyl C1-C6 alkyl group [wherein, on the pyridine ring, at least one selected from the group consisting of a furyl group and a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a benzothienyl C1-C6 alkyl group (wherein, on the benzothiophene ring, at least one selected from the group consisting of a halogen atom, a halogen substituted or unsubstituted C1-C6 alkyl group and a halogen substituted or unsubstituted C1-C6 alkoxy group may be substituted), a phenyl C2-C6 alkenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a benzofuryl C1-C6 alkyl group [wherein, on the benzofuran ring, at least one selected from the group consisting of a halogen atom, a halogen substituted or unsubstituted C1-C6 alkyl group and a halogen substituted or unsubstituted C1-C6 alkoxy group may be substituted], a benzofuryl C2-C6 alkenyl group [wherein, on the benzofuran ring, at least one selected from the group consisting of a halogen atom, a halogen substituted or unsubstituted C1-C6 alkyl group and a halogen substituted or unsubstituted C1-C6 alkoxy group may be substituted], a thiazolyl C1-C6 alkyl group [wherein, on the thiazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a phenoxy C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), an indolyl C1-C6 alkyl group (wherein, on the indole ring, at least one selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, at least one selected from the group consisting of a benzofuryl group, a halogen atom, a halogen substituted or unsubstituted C1-C6 alkyl group and a halogen substituted or unsubstituted C1-C6 alkoxy group may be substituted), may be substituted] may be substituted) includes a pyridyloxy group (wherein, on the pyridine ring, 1 to 3 substituents selected from the group consisting of a pyridyl group [wherein, on the piperidine ring, 1 to 5, preferably 1 to 3 substituents selected from the group consisting of a phenoxy group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a phenyl C1-C6 alkoxy substituted C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a phenoxy C1-C6 alkyl group having a straight or branched alkyl group containing 1 to 6 carbon atoms on the alkyl part as described later (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] and a (d-2)piperadinyl group [wherein, on the piperadine ring, 1 to 3 substituents selected from the group consisting of a C1-C6 alkoxycarbonyl group as described above, a furyl C1-C6 alkyl group having a straight or branched alkyl group containing 1 to 6 carbon atoms on the alkyl part as described later [wherein, on the furan ring, 1 to 3 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a pyridyl C1-C6 alkyl group having a straight or branched alkyl group containing 1 to 6 carbon atoms on the alkyl part as described later [wherein, on the pyridine ring, 1 to 3 substituents selected from the group consisting of a furyl group and a phenyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a benzothienyl C1-C6 alkyl group having a straight or branched alkyl group containing 1 to 6 carbon atoms on the alkyl part as described later (wherein, on the benzothiophene ring, 1 to 3 substituents selected from the group consisting of a halogen atom, a halogen substituted or unsubstituted C1-C6 alkyl group and a halogen substituted or unsubstituted C1-C6 alkoxy group may be substituted), a phenyl C2-C6 alkenyl group having a straight or branched alkenyl group containing 2 to 6 carbon atoms and having 1 to 3 double bonds, and including both trans and cis forms as described later (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a benzofuryl C1-C6 alkyl group having a straight or branched alkyl group containing 1 to 6 carbon atoms on the alkyl part as described later [wherein, on the benzofuran ring, 1 to 3 substituents selected from the group consisting of a halogen atom, a halogen substituted or unsubstituted C1-C6 alkyl group and a halogen substituted or unsubstituted C1-C6 alkoxy group may be substituted], a benzofuryl C2-C6 alkenyl group having a straight or branched alkenyl group containing 2 to 6 carbon atoms on the alkenyl part and having 1 to 3 double bonds, and including both trans and cis forms as described later (wherein, on the benzofuran ring, 1 to 3 substituents selected from the group consisting of a halogen atom, a halogen substituted or unsubstituted C1-C6 alkyl group and a halogen substituted or unsubstituted C1-C6 alkoxy group may be substituted), a thiazolyl C1-C6 alkyl group having a straight or branched alkyl group containing 1 to 6 carbon atoms on the alkyl part as described later [wherein, on the thiazole ring, 1 or 2 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a phenoxy C1-C6 alkyl group having a straight or branched alkyl group containing 1 to 6 carbon atoms on the alkyl part as described later (wherein, on the indole ring, 1 to 3 substituents selected from the group consisting of a halogen atom, a halogen substituted or unsubstituted C1-C6 alkyl group and a halogen substituted or unsubstituted C1-C6 alkoxy group may be substituted), an indolyl C1-C6 alkyl group having a straight or branched alkyl group containing 1 to 6 carbon atoms on the alkyl part as described later (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C1 to C6 alkyl group alkyl group (wherein, on the phenyl ring, 1 to 5, preferably 1 to 3 substituents selected from the group consisting of a benzofuryl group, a halogen atom, a halogen substituted or unsubstituted C1-C6 alkyl group and a halogen substituted or unsubstituted C1-C6 alkoxy group may be substituted) may be substituted] may be substituted, for example, a 2-pyridyloxy group, 3-pyridyloxy group, 4-pyridyloxy group, 3-(1-piperidyl)-2-pyridyloxy group, 2-(4-piperidyl)-3-pyridyloxy group, 4-(2-piperidyl)-3-pyridyloxy group, 5-(3-piperidyl)-2-pyridyloxy group, 2,4-di(1-piperidyl)-3-pyridyloxy group, 2-(1-piperidyl)-4-(2-(2-fluorophenoxy)-1-piperidyl]-3-pyridyloxy group, 2,4,6-tri(1-piperidyl)-3-pyridyloxy group, 2-(4-phenoxy-1-piperidyl)-3-pyridyloxy group, 2-(2,4-diphenoxy-1-piperidyl)-3-pyridyloxy group, 3-(2,4,6-triphenoxy-1-piperidyl)-4-pyridyloxy group, 4-(2-(2-fluorophenoxy)-1-piperidyl]-2-pyridyloxy group, 5-(3-(3-fluorophenoxy)-2-piperidyl]-3-pyridyloxy group, 6-(4-(4-fluorophenoxy)-3-piperidyl]-4-pyridyloxy group, 2-(2-(2-chlorophenoxy)-4-piperidyl]-3-pyridyloxy group, 3-(3-(3-chlorophenoxy)-5-piperidyl]-4-pyridyloxy group, 4-(4-(4-chlorophenoxy)-5-piperidyl]-4-pyridyloxy group, 5-(5-(2-bromophenoxy)-2-piperidyl]-3-pyridyloxy group, 2-(6-(3-bromophenoxy)-3-piperidyl]-4-pyridyloxy group, 2-(4-(4-bromophenoxy)-1-piperidyl]-2-pyridyloxy group, 3-(3-(2,3-dichlorophenoxy)-2-piperidyl]-4-pyridyloxy group, 3-(4-(3,4-dichlorophenoxy)-3-piperidyl]-4-pyridyloxy group, 4-(3-(2,4-dichlorophenoxy)-4-piperidyl]-2-pyridyloxy group, 5-(2-(3,4,5-trichlorophenoxy)-3-piperidyl]-2-pyridyloxy group, 6-(6-(2,4,6-trichlorophenoxy)-2-piperidyl]-3-pyridyloxy group, 2-(3-(2,3,4,5,6-pentafluorophenoxy)-1-piperidyl]-3-pyridyloxy group, 4-(4-(2-methylphenoxy)-1-piperidyl]-2-pyridyloxy group, 3-(5-(3-methylphenoxy)-2-piperidyl]-2-pyridyloxy group, 5-(6-(4-methylphenoxy)-3-piperidyl]-3-pyridyloxy group, 2-(1-(2-ethylphenoxy)-4-piperidyl]-4-pyridyloxy group, 2-(2-(3-ethylphenoxy)-1-piperidyl]-3-pyridyloxy group, 3-(3-(4-ethylphenoxy)-2-piperidyl]-4-pyridyloxy group, 4-(4-(4-n-propylphenoxy)-3-piperidyl]-2-pyridyloxy group, 5-(5-(4-tert-butylphenoxy)-4-piperidyl]-3-pyridyloxy group, 6-(2-(4-n-butylphenoxy)-3-piperidyl]-2-pyridyloxy group, 2-(1-(2-trifluoromethylphenoxy)-2-piperidyl]-4-pyridyloxy group, 3-(2-(3-trifluoromethylphenoxy)-1-piperidyl]-4-pyridyloxy group, 4-(3-(4-trifluoromethylphenoxy)-1-piperidyl]-2-pyridyloxy group, 5-(1-(2-pentafluoroethylphenoxy)-4-piperidyl]-3-pyridyloxy group, 6-(1-(3-pentafluoroethylphenoxy)-4-piperidyl]-2-pyridyloxy group, 2-(4-(2,3-dimethylphenoxy)-1-piperidyl]-3-pyridyloxy group, 3-(1-(3,4,5-trimethylphenoxy)-4-piperidyl]-2-pyridyloxy group, 4-(1-(4-n-pentylphenoxy)-4-piperidyl]-3-pyridyloxy group, 5-(4-(4-n-hexylphenoxy)-1-piperidyl]-2-pyridyloxy group, 6-(4-(2-methoxyphenoxy)-1-piperidyl]-2-pyridyloxy group, 2-(1-(3-methoxyphenoxy)-4-piperidyl]-4-pyridyloxy group, 3-(1-(4-methoxyphenoxy)-4-piperidyl]-2-pyridyloxy group, 4-(2-(2-ethoxyphenoxy)-3-piperidyl]-2-pyridyloxy group, 5-(3-(3-ethoxyphenoxy)-4-piperidyl]-3-pyridyloxy group, 2-(4-(4-ethoxyphenoxy)-5-piperidyl]-4-pyridyloxy group, 2-(3-(4-n-propoxyphenoxy)-2-piperidyl]-4-pyridyloxy group, 3-(2-(4-tert-butoxyphenoxy)-1-piperidyl]-4-pyridyloxy group, 4-(1-(4-n-butoxyphenoxy)-2-piperidyl]-2-pyridyloxy group, 5-(2-(2-trifluoromethoxyphenoxy)-3-piperidyl]-2-pyridyloxy group, 6-(3-(3-trifluoromethoxyphenoxy)-4-piperidyl]-2-pyridyloxy group, 6-(4-(4-trifluoromethoxyphenoxy)-3-piperidyl]-2-pyridyloxy group, 2-(3-(2-pentafluoroethoxyphenoxy)-2-piperidyl)-3-pyridyloxy group, 3-(4-(4-pentafluoroethoxyphenoxy)-1-piperidyl]-2-pyridyloxy group, 4-(1-(2,3-dimethoxyphenoxy)-4-piperidyl]-2-pyridyloxy group, 5-(4-(3,4,5-trimethoxyphenoxy)-1-piperidyl]-3-pyridyloxy group, 6-(4-(4-n-pentyloxyphenoxy)-1-piperidyl]-3-pyridyloxy group, 5-(4-(4-n-hexyloxyphenoxy)-1-piperidyl]-3-pyridyloxy group, 2-(4-(4-trifluoromethylbenzyloxymethyl)-1-piperidyl]-5-pyridyloxy group, 2-(4-trifluoromethoxybenzyl-1-piperidyl)-5-pyridyloxy group, 2-(4-(4-chlorobenzyl)-1-piperazinyl]-5-pyridyloxy group, 2-(4-(4-trifluoromethylbenzyl)-1-piperidyl]-5-pyridyloxy group, 2-(4-(4-chlorobenzyloxymethyl)-1-piperazinyl]-5-pyridyloxy group, 4-(4-fluorobenzyl-1-piperadinyl)-6-pyridyloxy group, 4-phenoxy-3-(4-(4-trifluoromethoxybenzyloxymethyl)-1-piperidyl]-2-pyridyloxy group, 2-(4-tert-butoxycarbonyl-(1-, 2- or 3-)piperadinyl]-(3-, 4-, 5- or 6-)pyridyloxy group, 2-(4-(4-((2-, 3-, 4-, 5-, 6- or 7-)benzofuryl]benzyl)-(1-, 2- or 3-)piperadinyl]-(3-, 4-, 5- or 6-)pyridyloxy group, 2-(4-(3-((2- or 3-)furyl]pyridylmethyl)-(1-, 2- or 3-)piperadinyl]-(3-, 4-, 5- or 6-)pyridyloxy group, 2-(4-(2-(4-trifluoromethoxyphenyl)pyridylmethyl]-(1-, 2- or 3-)piperadinyl)-(3-, 4-, 5- or 6-)pyridyloxy group, 2-(4-(2-(3-chloro-4-fluorophenyl)pyridylmethyl]-(1-, 2- or 3-)piperadinyl)-(3-, 4-, 5- or 6-)pyridyloxy group, 2-(4-(5-trifluoromethyl-(2-, 3-, 4-, 6- or 7-)-benzofurylmethyl]-(1-, 2- or 3-)piperadinyl)-(3-, 4-, 5- or 6-)pyridyloxy group, 2-(4-(6-trifluoromethyl-(2-, 3-, 4-, 5- or 7-)benzofurylmethyl]-(1-, 2- or 3-)-piperadinyl)-(3-, 4-, 5- or 6-)pyridyloxy group, 2-(4-(5-chloro-(2-, 3-, 4-, 6- or 7-)benzothienylmethyl]-(1-, 2- or 3-)piperadinyl)-(3-, 4-, 5- or 6-)pyridyloxy group, 2-(4-(6-chloro-(2-, 3-, 4-, 5- or 7-)-benzofurylmethyl]-(1-, 2- or 3-)piperadinyl)-(3-, 4-, 5- or 6-)pyridyloxy group, 2-(4-(5-trifluoromethoxy-(2-, 3-, 4-, 6- or 7-)benzofurylmethyl]-(1-, 2- or 3-)-piperadinyl)-(3-, 4-, 5- or 6-)pyridyloxy group, 2-(4-(3-(4-trifluoromethylphenyl)-2-propenyl]-(1-, 2- or 3-)piperadinyl)pyridyloxy group, 2-(4-(3-(3,4-dichlorophenyl)-2-propenyl]-(1-, 2- or 3-)piperadinyl)-pyridyloxy group, 2-(4-(3-(4-chlorophenyl)-2-propenyl]-(1-, 2- or 3-)piperadinyl)pyridyloxy group, 2-(4-(3-(6-trifluoromethyl-(2-, 3-, 4-, 5- or 7-)benzofuryl]-2-propenyl)-(1-, 2- or 3-)piperadinyl]pyridyloxy group, 2-(4-(3-(5-chloro-(2-, 3-, 4-, 5- or 7-)benzofuryl]-2-propenyl)-(1-, 2- or 3-)piperadinyl]pyridyloxy group, 2-(4-(5-chloro-(2-, 3-, 4-, 6- or 7-)benzofurylmethyl]-(1-, 2- or 3-)piperadinyl)-(3-, 4-, 5- or 6-)pyridyloxy group, 2-(4-(2-(4-trifluoromethylphenyl)-(4- or 5-)-thiazolylmethyl]-(1-, 2- or 3-)piperadinyl)pyridyloxy group, 2-(4-(2-(4-trifluoromethoxyphenoxy)ethyl]-(1-, 2- or 3-)piperadinyl)pyridyloxy group, 2-(4-(3-(4-trifluoromethoxyphenyl)-2-propenyl]-(1-, 2- or 3-)-piperadinyl)pyridyloxy group, 2-(4-(5-trifluoromethoxy-(1-, 2-, 3-, 4-, 6- or 7-)indolylmethyl]-(1-, 2- or 3-)piperadinyl) pyridyloxy group, 2-(4-(4-chlorophenoxymethyl)-(1-, 2- or 3-)piperidyl]-(3-, 4-, 5- or 6-)pyridyloxy group, 2-(4-(2-(4-chlorophenyl)-(3-, 4- or 5-)furylmethyl]-(1-, 2- or 3-)piperadinyl)-pyridyloxy group, 2-(4-(2-(2-chloro-5-trifluoromethylphenyl)-(3-, 4- or 5-)furylmethyl]-(1-, 2- or 3-)piperadinyl)pyridyloxy group or the like.

A 1,2,3,4-tetrahydroquinolyloxy group (wherein, on the 1,2,3,4-tetrahydroquinoline ring, at least one selected from the group consisting of an oxo group, a phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] and a phenyl C1-C6 alkyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted) includes a 1,2,3,4-tetrahydroquinolyloxy group [wherein, on the 1,2,3,4-tetrahydroquinoline ring, 1 to 3 substituents selected from the group consisting of an oxo group, a phenyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a 1,2,3,4-tetrahydro-(1-, 2-, 3-, 4-, 5-, 6-, 7- or 8-)quinolyloxy group, 1-(4-trifluoromethylbenzyl)-2-oxo-1,2,3,4-tetrahydro-6-quinolyloxy group, 1-(4-trifluoromethoxybenzyl)-2-oxo-1,2,3,4-tetrahydro-6-quinolyloxy group, 1-(4-chlorobenzyl)-2-oxo-1,2,3,4-tetrahydro-6-quinolyloxy group, 1-(4-trifluoromethylbenzyl)-1,2,3,4-tetrahydro-6-quinolyloxy group, 1-(4-trifluoromethoxybenzyl)-1,2,3,4-tetrahydro-6-quinolyloxy group, 1-(4-chlorobenzyl)-1,2,3,4-tetrahydro-6-quinolyloxy group, 1-(4-chlorophenyl)-1,2,3,4-tetrahydro-6-quinolyloxy group, 1-(4-trifluoromethoxyphenyl)-1,2,3,4-tetrahydro-6-quinolyloxy group, 1-(4-trifluoromethylphenyl)-1,2,3,4-tetrahydro-6-quinolyloxy group, 1-(3,4-dichlorobenzyl)-1,2,3,4-tetrahydro-6-quinolyloxy group, 1-(3,4-di(trifluoromethoxy)benzyl]-1,2,3,4-tetrahydro-6-quinolyloxy group, 1-(4-chlorophenyl)-1,2,3,4-tetrahydro-5-quinolyloxy group, 1-(4-trifluoromethoxyphenyl)-1,2,3,4-tetrahydro-5-quinolyloxy group, 1-(4-trifluoromethylphenyl)-1,2,3,4-tetrahydro-5-quinolyloxy group, 1-(4-chlorobenzyl)-1,2,3,4-tetrahydro-5-quinolyloxy group, 1-(4-trifluoromethoxybenzyl)-1,2,3,4-tetrahydro-5-quinolyloxy group, 1-(4-trifluoromethylbenzyl)-1,2,3,4-tetrahydro-5-quinolyloxy group, 1-(3,4,5-tri(trifluoromethyl)benzyl]-1,2,3,4-tetrahydro-6-quinolyloxy group, 1-benzyl-4-phenyl-1,2,3,4-tetrahydro-6-quinolyloxy group, 1-phenyl-4,6-dibenzyl-1,2,3,4-tetrahydro-5-quinolyloxy group, 4-phenyl-2-oxo-1,2,3,4-tetrahydro-1-quinolyloxy group or the like.

A 1,2,3,4-tetrahydronaphthyloxy group (wherein, on the 1,2,3,4-tetrahydronaphthalene ring, at least one oxo group may be substituted) includes a 1,2,3,4-tetrahydronaphthyloxy group (wherein, on the 1,2,3,4-tetrahydronaphthalene ring, 1 to 3 oxo groups may be substituted), for example, a (1-, 2-, 5- or 6-)1,2,3,4-tetrahydronaphthyloxy group, 4-oxo-7-1,2,3,4-tetrahydronaphthyloxy group, 1,4-dioxo-6-1,2,3,4-tetrahydronaphthyloxy group, 1,2,4-trioxo-5-1,2,3,4-tetrahydronaphthyloxy group or the like.

A 2H-chromenioxyl group (wherein, on the 2H-chromene ring, at least one oxo group may be substituted) includes a 2H-chromenioxyl group (wherein, on the 2H-chromene ring, at least one oxo group may be substituted), for example, a 2H-chromenioxyl group, 2-oxo-2H-chromenioxyl group or the like.

A naphthyloxy group (wherein, on the naphthalene ring, at least one piperidyl group [wherein, on the piperidyl ring, at least one phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] may be substituted) includes a naphthyloxy group (wherein, on the naphthalene ring, 1 to 3 piperidyl groups as described above [wherein, on the piperidine ring, 1 to 3 phenoxy groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] may be substituted), for example, a (1- or 2-)naphthyloxy group, 6-(4-(4-trifluoromethoxyphenoxy)-1-piperidyl]-2-naphthyloxy group, 5-(1-piperidyl)-2-naphthyloxy group, 2-(4-piperidyl)-3-naphthyloxy group, 4-(2-piperidyl)-1-naphthyloxy group, 5-(3-piperidyl)-2-naphthyloxy group, 5,6-di(1-piperidyl)-1-naphthyloxy group, 7-(1-piperidyl)-6-(2-(2-fluorophenoxy)-1-piperidyl]-1-naphthyloxy group, 5,6,7-tri(1-piperidyl)-2-naphthyloxy group, 6-(4-phenoxy-1-piperidyl)-3-naphthyloxy group, 2-(2,4-diphenoxy-1-piperidyl)-4-naphthyloxy group, 3-(2,4,6-triphenoxy-1-piperidyl)-5-naphthyloxy group, 4-(2-(2-fluorophenoxy)-1-piperidyl]-6-naphthyloxy group, 4-(3-(3-fluorophenoxy)-2-piperidyl]-2-naphthyloxy group, 3-(4-(4-fluorophenoxy)-3-piperidyl]-1-naphthyloxy group, 5-(2-(2-chlorophenoxy)-4-piperidyl]-2-naphthyloxy group, 6-(3-(3-chlorophenoxy)-5-piperidyl]-1-naphthyloxy group, 4-(4-(4-chlorophenoxy)-2-piperidyl]-2-naphthyloxy group, 5-(5-(2-bromophenoxy)-2-piperidyl]-3-naphthyloxy group, 6-(6-(3-bromophenoxy)-3-piperidyl]-4-naphthyloxy group, 6-(4-(4-bromophenoxy)-1-piperidyl]-2-naphthyloxy group, 3-(3-(2,3-dichlorophenoxy)-2-piperidyl]-4-naphthyloxy group, 6-(4-(3,4-dichlorophenoxy)-3-piperidyl]-1-naphthyloxy group, 4-(3-(2,4-dichlorophenoxy)-4-piperidyl]-2-naphthyloxy group, 5-(2-(3,4,5-trichlorophenoxy)-3-piperidyl]-2-naphthyloxy group, 6-(6-(2,4,6-trichlorophenoxy)-2-piperidyl]-3-naphthyloxy group, 2-(3-(2,3,4,5,6-pentafluorophenoxy)-1-piperidyl]-3-naphthyloxy group, 4-(4-(2-methylphenoxy)-1-piperidyl]-2-naphthyloxy group, 3-(5-(3-methylphenoxy)-2-piperidyl]-2-naphthyloxy group, 5-(6-(4-methylphenoxy)-3-piperidyl]-3-naphthyloxy group, 6-(1-(2-ethylphenoxy)-4-piperidyl]-4-naphthyloxy group, 2-(2-(3-ethylphenoxy)-1-piperidyl]-3-naphthyloxy group, 3-(3-(4-ethylphenoxy)-2-piperidyl]-4-naphthyloxy group, 4-(4-(4-n-propylphenoxy)-3-piperidyl]-2-naphthyloxy group, 5-(5-(4-tert-butylphenoxy)-4-piperidyl]-1-naphthyloxy group, 6-(2-(4-n-butylphenoxy)-3-piperidyl]-2-naphthyloxy group, 2-(1-(2-trifluoromethylphenoxy)-2-piperidyl]-4-naphthyloxy group, 3-(2-(3-trifluoromethylphenoxy)-1-piperidyl]-4-naphthyloxy group, 4-(3-(4-trifluoromethylphenoxy)-1-piperidyl]-2-naphthyloxy group, 5-(1-(2-pentafluoroethylphenoxy)-4-piperidyl]-3-naphthyloxy group, 6-(1-(3-pentafluoroethylphenoxy)-4-piperidyl]-2-naphthyloxy group, 2-(4-(2,3-dimethylphenoxy)-1-piperidyl)-1-naphthyloxy group, 3-(1-(3,4,5-trimethylphenoxy)-4-piperidyl]-2-naphthyloxy group, 4-(1-(4-n-pentylphenoxy)-4-piperidyl]-1-naphthyloxy group, 5-(4-(4-n-hexylphenoxy)-1-piperidyl]-2-naphthyloxy group, 6-(4-(2-methoxyphenoxy)-1-piperidyl]-2-naphthyloxy group, 2-(1-(3-methoxyphenoxy)-4-piperidyl]-4-naphthyloxy group, 3-(1-(4-methoxyphenoxy)-4-piperidyl]-2-naphthyloxy group, 4-(2-(2-ethoxyphenoxy)-3-piperidyl]-2-naphthyloxy group, 5-(3-(3-ethoxyphenoxy)-4-piperidyl]-1-naphthyloxy group, 6-(4-(4-ethoxyphenoxy)-5-piperidyl]-4-naphthyloxy group, 2-(3-(4-n-propoxyphenoxy)-2-piperidyl]-4-naphthyloxy group, 3-(2-(4-tert-butoxyphenoxy)-1-piperidyl]-4-naphthyloxy group, 4-(1-(4-n-butoxyphenoxy)-2-piperidyl]-2-naphthyloxy group, 5-(2-(2-trifluoromethoxyphenoxy)-3-piperidyl]-2-naphthyloxy group, 6-(3-(3-trifluoromethoxyphenoxy)-4-piperidyl]-2-naphthyloxy group, 6-(4-(4-trifluoromethoxyphenoxy)-3-piperidyl]-2- naphthyloxy group, 2-(3-(2-pentafluoroethoxyphenoxy)-2-piperidyl]-3-naphthyloxy group, 3-(4-(4-pentafluoroethoxyphenoxy)-1-piperidyl]-2-naphthyloxy group, 4-(1-(2,3-dimethoxyphenoxy)-4-piperidyl]-2-naphthyloxy group, 5-(4-(3,4,5-trimethoxyphenoxy)-1-piperidyl]-1-naphthyloxy group, 6-(4-(4-n-pentyloxyphenoxy)-1-piperidyl]-3-naphthyloxy group, 5-(4-(4-n-hexyloxyphenoxy)-1-piperidyl]-1-naphthyloxy group or the like.

A 1,2,3,4-tetrahydroisoquinolyloxy group (wherein, on the 1,2,3,4-tetrahydroisoquinoline ring, at least one selected from the group consisting of a C1-C6 alkoxycarbonyl group, a phenyl C1-C6 alkyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] and a phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted includes a 1,2,3,4-tetrahydroisoquinolyloxy group (wherein, on the 1,2,3,4-tetrahydroisoquinoline ring, 1 to 3 substituents selected from the group consisting of a C1-C6 alkoxycarbonyl group, a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl group as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted], for example, a 1,2,3,4-tetrahydroisoquinolyl (1-, 2-, 3-, 4-, 5-, 6-, 7- or 8-)quinolyloxy group, 2-tert-butoxycarbonyl-1,2,3,4-tetrahydro-6-isoquinolyloxy group, 2-(4-chlorobenzyl)-1,2,3,4-tetrahydro-6-isoquinolyloxy group, 2-(4-trifluoromethoxybenzyl)-1,2,3,4-tetrahydro-6-isoquinolyloxy group, 2-(4-trifluoromethylbenzyl)-1,2,3,4-tetrahydro-6-isoquinolyloxy group, 2-ethoxycarbonyl-4-benzyl-1,2,3,4-tetrahydro-7-isoquinolyloxy group, 1,4,6-tribenzyl-1,2,3,4-tetrahydro-8-isoquinolyloxy group, 1-(3,4-di(trifluoromethoxy)benzyl]-1,2,3,4-tetrahydro-6-isoquinolyloxy group, 1-(3,4,5-tri(trifluoromethyl)benzyl]-1,2,3,4-tetrahydro-6-isoquinolyloxy group, 2-(4-trifluoromethoxyphenyl)-(1-, 3-, 4-, 5-, 6-, 7- or 8-)isoquinolyloxy group or the like.

A phenyl group [wherein, on the phenyl ring, at least one piperidyl group (wherein, on the piperidine ring, at least one phenoxy group [wherein, on the phenyl group, at least one selected from the group consisting of a halogen atom, a halogen substituted or unsubstituted C1-C6 alkyl group and a halogen substituted or unsubstituted C1-C6 alkoxy group may be substituted] may be substituted) is substituted] includes, a phenyl group [wherein, on the phenyl ring, 1 to 3 piperidyl groups as described above (wherein, on the piperidine ring, 1 to 3 phenoxy groups [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] may be substituted) is substituted], for example, a 4-(1-piperidyl)phenyl group, 3-(2-piperidyl)phenyl group, 4-(4-(4-trifluoromethoxyphenoxy)-1-piperidyl]phenyl group, 4-(4-(4-trifluoromethylphenoxy)-1-piperidyl]phenyl group, 4-(4-(4-chlorophenoxy)-1-piperidyl]phenyl group, 4-(4-(3,4-di(trifluoromethoxy)phenoxy-1-piperidyl])phenyl group, 4-(4-(3,4,5-tri(trifluoromethyl)phenoxy-1-piperidyl])phenyl group, 4-(4-(2,4-dichlorophenoxy)-1-piperidyl]phenyl group, 4-(4-(2,4,6-trifluorophenoxy)-1-piperidyl]phenyl group, 2-(2,4,5-triphenoxy-1-piperidyl)phenyl group, 3-(1,2-diphenoxy-4-piperidyl)phenyl group, 2,4-di(4-piperidyl)phenyl group, 2,4,6-tri(3-piperidyl)phenyl group or the like.

A phenyl C1-C6 alkyl group [wherein, on the phenyl ring, at least one selected from the group consisting of at least one piperidyl group (wherein, on the piperidine ring, a phenoxy group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] is substituted) and a group-$NR^{24}R^{25}$ ($R^{24}$ represents a halogen atom or C1-C6 alkyl group. $R^{25}$ represents a phenyl C2-C6 alkenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted]) are substituted] includes a phenyl C1-C6 alkyl group as described above [wherein, on the phenyl ring, 1 to 3 substituents selected from the group consisting of 1 to 3 piperidyl groups as described above (wherein, on the piperidine ring, 1 to 3 phenoxy groups [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) are substituted) and a group—$NR^{24}R^{25}$ ($R^{24}$ represents a halogen atom or C1-C6 alkyl group. $R^{25}$ represents a phenyl C2-C6 alkenyl group as described later [a group composed of 1 or 2 phenyl groups unsubstituted or substituted by 1 to 5 preferably 1 to 3 substituents selected from the group consisting of a halogen atom, a halogen substituted or unsubstituted C1-C6 alkyl group and a halogen substituted or unsubstituted C1-C6 alkoxy group]) are substituted and an alkenyl group containing 2 to 6 carbon atoms and having 1 to 3 double bonds.], for example, a 4-(1-piperidyl)benzyl group, 2,4-di(4-piperidyl)benzyl group, 2,4,6-tri(2-piperidyl)benzyl group, 4-(4-(4-trifluoromethoxyphenoxy)-1-piperidyl]benzyl group, 4-(N-methyl-N-(4-trifluoromethoxycinnamyl)amino]benzyl group, 4-(N-(4-trifluoromethoxycinnamyl)amino]benzyl group, 4-(4-(4-trifluoromethylphenoxy)-1-piperidyl]benzyl group, 4-(4-(4-chlorophenoxy)-1-piperidyl]benzyl group, 4-(4-(3,4-di(trifluoromethoxy)phenoxy]-1-piperidyl)benzyl group, 4-(4-(2,4,6-tri(trifluoromethyl)phenoxy]-1-piperidyl)benzyl group, 4-(4-(2,4-dichlorophenoxy)-1-piperidyl]benzyl group, 4-(4-(2,4,6-trifluorophenoxy)-1-piperidyl]benzyl group, 3-(2,4-diphenoxy-3-piperidyl]benzyl group, 2-(1,2,3-triphenoxy-4-piperidyl]benzyl group, 4-(N-methyl-N-(4-trifluoromethoxycinnamy)amino]-3-(4-(4-trifluoromethoxyphenoxy)-1-piperodyl]benzyl group or the like.

A piperidyl C1-C6 alkyl group (wherein, on the piperidine ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is substituted) includes a piperidyl C1-C6 alkyl group (wherein, on the piperidine ring, 1 to 3 phenyl groups as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) are substituted), for example, a (4-phenyl-1-piperidyl)methyl group, 2-(3-phenyl-2-piperidyl)ethyl group, 3-(2-phenyl-3-piperidyl)propyl group; 4-(1-phenyl-4-piperidyl)butyl group, 5-(4-phenyl-1-piperidyl)pentyl group, 6-(1-phenyl-2-piperidyl)hexyl group, 1-(4-trifluoromethoxyphenyl)-4-piperidylmethyl group, 1-(4-trifluoromethylphenyl)-4-piperidylmethyl group, 1-(3-methoxyphenyl)-4-piperidylmethyl group, 1-(2-methylphenyl)-4-piperidylmethyl group, 1-(4-chlorophenyl)-4-piperidylmethyl group, 1-(3,4-di(trifluoromethoxy)phenyl]-4-piperidylmethyl group, 1-(2,4,6-tri(trifluoromethyl)phenyl]-4-piperidylmethyl group, 1-(3,4-dimethylphenyl)-4-piperidylmethyl group, 1-(2,4,6-trimethoxyphenyl)-4-piperidylmethyl group, 1-(3,4-dichlorophenyl)-4-piperidylmethyl group, 1-(2,4,6-tribromophenyl)-4-piperidylmethyl group, (1,2,6-triphenyl-4-piperidyl) methyl group, (2,4-diphenyl-1-piperidyl)methyl group or the like.

A piperadinyl C1-C6 alkyl group (wherein, on the piperadine ring, at least one phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted) includes a piperadinyl C1-C6 alkyl group (wherein, on the piperadine ring, 1 to 3 phenyl groups as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] may be substituted), for example, a 1-piperadinylmethyl group, 1-(2-piperadinyl) ethyl group, 2-(1-piperadinyl)ethyl group, 3-(1-piperadinyl) propyl group, 2-(1-piperadinyl)propyl group, 4-(2-piperadinyl)butyl group, 5-(2-piperadinyl)pentyl group, 4-(1-piperadinyl)pentyl group, 6-(1-piperadinyl)hexyl group, 2-methyl-3-(1-piperadinyl)propyl group, 1,1-dimethyl-2-(1-piperadinyl)ethyl group, (4-phenyl-1-piperadinyl)methyl group, (2,4-diphenyl-1-piperadinyl)methyl group, (2,4,5-triphenyl-1-piperadinyl)methyl group, (4-(4-trifluoromethoxyphenyl)-1-piperadinyl]methyl group, (4-(4-trifluoromethylphenyl)-1-piperadinyl]methyl group, (4-(4-chlorophenyl)-1-piperadinyl]methyl group, (4-(2,4-dichlorophenyl)-1-piperadinyl]methyl group, (4-(2,4,6-trifluorophenyl)-1-piperadinyl]methyl group, (2,4-di (trifluoromethyl)phenyl-1-piperadinyl]methyl group, (2,4,6-tri(trifluoromethoxy)phenyl-1-piperadinyl]methyl group or the like.

A piperidyl C1-C6 alkyl group (wherein, on the piperidine ring, at least one phenoxy group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted) includes a piperidyl C1-C6 alkyl group (wherein, on the piperidine ring, 1 to 3 phenoxy groups as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] may be substituted), for example, a 1-piperidylmethyl group, 2-(2-piperidyl)ethyl group, 3-(3-piperidyl)propyl group, 4-(4-piperidyl)butyl group, 5-(1-piperidyl)pentyl group, 6-(2-piperidyl)hexyl group, 1-(4-trifluoromethoxyphenoxy)-4-piperidylmethyl group, 1-(4-trifluoromethylphenoxy)-4-piperidylmethyl group, 2-methyl-3-(piperidine-1-yl)propyl group, 1,1-dimethyl-2-(piperidine-1-yl)ethyl group, 1-(4-chlorophenoxy)-4-piperidylmethyl group, 1-(3,4-di(trifluoromethoxy)phenoxy]-4-piperidylmethyl group, 1-(2,4,6-tri (trifluoromethoxy)phenoxy]-4-piperidylmethyl group, 1-(3,4-dichlorophenoxy)-4-piperidylmethyl group, 1-(2,4,6-tribromophenoxy)-4-piperidylmethyl group, (1,2,6-triphenoxy-4-piperidyl)methyl group, (2,4-diphenoxy-1-piperidyl)methyl group or the like.

A thiazolyl group [wherein, on the thiazole ring, at least one selected from the group consisting of a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a piperadinyl C1-C6 alkyl group (wherein, on the piperadine ring, at least one phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted) and a piperidyl C1-C6 alkyl group (wherein, on the piperidine ring, at least one phenoxy group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted) may be substituted] includes a thiazolyl group [wherein, on the thiazole ring, 1 or 2 substituents selected from the group consisting of a phenyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a piperadinyl C1-C6 alkyl group as described above (wherein, on the piperadine ring, 1 to 3 phenyl groups [wherein, on the phenyl group, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] may be substituted) and a piperidyl C1-C6 alkyl group as described above (wherein, on the piperidine ring, 1 to 3 phenoxy groups [wherein, on the phenyl group, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] may be substituted) may be substituted], for example, a (2-, 4- or 5-)thiazolyl group, 2-(4-trifluoromethoxyphenyl)-5-thiazolyl group, 2-(4-(4-trifluoromethoxyphenyl)-1-piperadinyl]methyl-5-thiazolyl group, 2-(4-(4-trifluoromethoxyphenoxy)-1-piperidyl]methyl-5-thiazolyl group, 2-(2,4-di(trifluoromethoxy)phenyl)-5-thiazolyl group, 2-(4-(2,4-di(trifluoromethoxy)phenyl)-1-piperadinyl)methyl-5-thiazolyl group, 2-(4-(2,4-di (trifluoromethoxy)phenoxy)-1-piperadinyl)methyl-5-thiazolyl group, 2-(4-trifluoromethylphenyl)-5-thiazolyl group, 2-(4-(4-trifluoromethylphenoxy)-1-piperidyl)methyl-5-thiazolyl group, 2-(4-(4-trifluorothylphenyl)-1-piperidyl) methyl-5-thiazolyl group, 2-(2,4,6-tri(trifluoromethyl)phenyl))-5-thiazolyl group, 2-(4-(2,4,6-tri(trifluoromethyl) phenyl)-1-piperadinyl)methyl-5-thiazolyl group, 2-(2-(2,4,6-tri(trifluoromethyl)phenoxy]-1-piperidyl)methyl-t-thiazolyl group, 2-(4-(2,4,6-tri(trifluoromethyl)phenoxy)-1-piperidyl)methyl-5-thiazol) 2-(4-chlorophenyl)-5-thiazolyl group, 2-(4-(4-chlorophenyl)-1-piperadinyl]methyl-5-thiazolyl group, 2-(4-(2-chlorophenoxy)-1-piperidyl]methyl-5-thiazolyl group, 2-(2,4-dichlorophenyl)-5-thiazolyl group, 2-(4-(2,4-dichlorophenyl)-1-piperadinyl)methyl-5-thizzolyl group, 2-(2-(2,4-dichlorophenyl)-1-piperadinyl]methyl-t-thiazolyl group, 2-(4-(2,4-dichlorophenoxy)-1-piperidyl] methyl-5-thiazolyl group, 2-(2,4,6-trifluorophenyl)-5-thiazolyl group, 2-(4-(2,4,6-trifluorophenyl)-1-piperadinyl] methyl-5-thiazolyl group, 2-(4-(2,4,6-trifluorophenoxy)-1-piperidyl]methyl-5-thiazolyl group, 2-(2,4-diphenoxy-1-piperidyl)methyl-5-thiazolyl group, 5-(2,4,5-triphenoxy-1-piperidyl)methyl-2-thiazolyl group, 5-(2,4-diphenyl-1-piperadinyl)methyl-2-thiazolyl group, 2-(2,4,5-triphenyl-1-piperadinyl)methyl-4-thiazolyl group, 4-(1-piperidyl)-2-(1-piperadinyl)-5-thiazolyl group or the like.

A benzooxazolyloxy group (wherein, on the benzooxazole ring, at least one selected from the group consisting of a piperazinyl group [wherein, on the piperadine ring, 1 to 3 groups selected from the group consisting of a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) and a phenyl C2-C6 alkenyl group having a straight or branched alkenyl group containing 2 to 6 carbon atoms on the alkenyl part and having 1 to 3 double bonds and including both trans and cis forms as described later (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a piperidyl group (wherein, on the piperidine ring, 1 to 3 substituents selected from the group consisting of a phenyl C1-C6 alkyl group as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] and an amino group [wherein, on the amino group, 1 or 2 substituents selected from the group consisting of a C1-C6 alkyl group as described above and a phenyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] may be substituted) and a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is substituted) includes a benzooxazolyloxy group (wherein, on the benzooxazole ring, 1 to 3 substituents selected from the group consisting of a piperadinyl group as described above [wherein, on the piperadine ring, at least one selected from the group consisting of a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C2-C6 alkenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a piperidyl group (wherein, on the piperidine ring, at least one selected from the group consisting of a phenyl C1-C6 alkyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] and an amino group [wherein, on the amino group, at least one selected from the group consisting of a C1-C6 alkyl group and a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] may be substituted) and a phenyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) are substituted), for example, a 2-(4((4-trifluoromethoxybenzyl)-1-piperadinyl]-6-benzooxazolyloxy group, 2-phenyl-5-benzooxazolyloxy group, 2-(4-chlorophenyl)-5-benzooxazolyloxy group, 2-(4-(4-trifluoromethylbenzyl)-1-piperadinyl]-6-benzooxazolyloxy group, 2-(4-(4-chlorobenzyl)-1-piperadinyl]-6-benzooxazolyloxy group, 2-(4-(2,4,6-tri(trifluoromethoxy) benzyl]-1-piperadinyl)-6-benzooxazolyloxy group, 2-(4-(2,4-di(trifluoromethyl)benzyl]-1-piperadinyl)-6-benzooxazolyloxy group, 2-(4-(2,4-dichlorobenzyl)-1-piperadinyl]-6-benzooxazolyloxy group, 2-(4-(2,4,6-trifluorobenzyl)-1-piperadinyl]-6-benzooxazolyloxy group, 2-(4-benzyl-1-piperadinyl)-4-benzooxazolyloxy group, 2-(2,4-dibenzyl-1-piperadinyl)-7-benzooxazolyloxy group, 2-(2,4,6-tribenzyl-1-piperadinyl)-6-benzooxazolyloxy group, 2-(4-trifluoromethoxyphenyl)-5-benzooxazolyloxy group, 2-(4-trifluoromethylphenyl)-5-benzooxazolyloxy group, 2-(2,4-dibromophenyl)-5-benzooxazolyloxy group, 2-(2,4,6-trichlorophenyl)-5-benzooxazolyloxy group, 2-(2,4,6-tri(trifluoromethoxy)phenyl]-5-benzooxazolyloxy group, 2-(2,4-di(trifluoromethyl)phenyl]-5-benzooxazolyloxy group, 4-phenyl-5-(1-piperadinyl)-2-benzooxazolyloxy group, 2,4,5-triphenyl-7-benzooxazolyloxy group, 2-(4-(4-trifluoromethoxybenzyl)-(1-, 2- or 3-)piperidyl]-(2-, 4-, 5-, 6- or 7-)benzooxazolyloxy group, 2-(4-(3-(4-trifluoromethylphenyl)-2-propenyl]-(1-, 2- or 3-)piperadinyl)-(2-, 4-, 5-, 6- or 7-)benzooxazolyloxy group, 4-(N-methyl-N-(4-chlorophenyl)amino]-(1-, 2- or 3-)piperidyl]-(2-, 4-, 5-, 6- or 7-)benzooxazolyloxy group or the like.

A benzoimidazolyloxy group (wherein, on the benzoimidazole ring, at least one selected from the group consisting of a C1-C6 alkyl group, a phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted], a piperidyl group [wherein, on the piperidine ring, at least one phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a piperadinyl group [wherein, on the piperadine ring, at least one phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] and a phenyl C1-C6 alkyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted) includes a benzoimidazolyloxy group (wherein, on the benzoimidazole ring, 1 to 3 substituents selected from the group consisting of a C1-C6 alkyl group, a phenyl group [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted], a piperidyl group as described above [wherein, on the piperidine ring, 1 to 3 phenoxy groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a piperadinyl group as described above [wherein, on the piperadine ring, 1 to 3 phenyl C1-C6 alkyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] and a phenyl C1-C6 alkyl group as described above [wherein, on the phenyl ring, 1 to 3 substituents selected from the group consisting of a halogen atom, a halogen substituted or unsubstituted C1-C6 alkyl group and a halogen substituted or unsubstituted C1-C6 alkoxy group may be substituted) may be substituted), for example, a (1-, 2-, 4-, 5-, 6- or 7-) benzoimidazolyloxy group, 2-phenyl-5-benzoimidazolyloxy group, 1-methyl-5-benzoimidazolyloxy group, 1-methyl-2-phenyl-5-benzoimidazolyloxy group, 2-(4-chlorophenyl)-5-benzoimidazolyloxy group, 1-methyl-2-(4-chlorophenyl)-5-benzoimidazolyloxy group, 1,2-diphenyl-5-benzoimidazolyloxy group, 1,4-dimethyl-5-benzoimidazolyloxy group, 1-methyl-2,6-diphenyl-5-benzoimidazolyloxy group, 2-(4-trifluoromethylphenyl)-5-benzoimidazolyloxy group, 1-methyl-2-(4-trifluoromethoxyphenyl)-5-benzoimidazolyloxy group, 1,2,7-triphenyl-5-benzoimidazolyloxy group, 1,2,4-trimethyl-5-benzoimidazolyloxy group, 1-ethyl-2,6-diphenyl-5-benzoimidazolyloxy group, 2-(2,4-di(trifluoromethyl) phenyl]-5-benzoimidazolyloxy group, 1-methyl-2-(2,4,6-tri (trifluoromethoxy)phenyl]-5-benzoimidazolyloxy group, 2-(2,4-dichlorophenyl)-5-benzoimidazolyloxy group, 2-(2,4,6-trifluorophenyl)-5-benzoimidazolyloxy group, 2-(3-bromophenyl)-5-benzoimidazolyloxy group, 2-(2-iodophenyl)-5-benzoimidazolyloxy group, 2-(4-trifluoromethoxyphenoxy-(1-, 2- or 3-)piperidyl-(1-, 4-, 5-, 6- or 7-)imidazolyloxy group, 1-benzyl-2-(4-trifluoromethoxybenzyl-(1-, 2- or 3-)piperadinyl]-(4-, 5-, 6- or -7)imidazolyloxy group, 1-(4-trifluoromethoxybenzyl)-(2-, 4-, 5-, 6- or 7-)imidazolyloxy group or the like.

A 1,2,3,4-tetrahydroisoquinolyl group (wherein, on the 1,2,3,4-tetrahydroisoquinoline ring, at least one selected from the group consisting of a (m-1) amino group [wherein, on the amino group, at least one selected from the group consisting of a C1-C6 alkyl group, a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be selected] and a (m-2) phenoxy group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted) includes a 1,2,3,4-tetrahydroisoquinolyl group (wherein, on the 1,2,3,4-tetrahydroisoquinoline ring, 1 to 3 substituents selected from the group consisting of an amino group as described later [wherein, on the amino group, 1 or 2 substituents selected from the group consisting of a C1-C6 alkyl group, a phenyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] and a phenoxy group as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] may be substituted), for example, a (1-, 2-, 3-, 4-, 5-, 6-, 7- or 8-)1,2,3,4-tetrahydroisoquinolyl group, 7-(N-methyl-N-(4-trifluoromethoxyphenyl)amino]-1,2,3,4-tetrahydro-2-isoquinolyl group, 7-(N-methyl-N-(4-trifluoromethoxybenzyl) amino]-1,2,3,4-tetrahydro-2-isoquinolyl group, 6-(4-trifluoromethoxyphenoxy)-1,2,3,4-tetrahydro-2-isoquinolyl group, 7-(N-methyl-N-(4-trifluoromethylphenyl)amino]-1,2,3,4-tetrahydro-2-isoquinolyl group, 7-(N-methyl-N-(4-trifluoromethylbenzyl)amino]-1,2,3,4-tetrahydro-2-isoquinolyl group, 6-(4-trifluoromethylphenoxy)-1,2,3,4-tetrahydro-2-isoquinolyl group, 7-(N-methyl-N-(4-chlorophenyl)amino]-1,2,3,4-tetrahydro-2-isoquinolyl group, 7-(N-(4-chlorophenyl)amino]-1,2,3,4-tetrahydro-2-isoquinolyl group, 7-(N-methyl-N-(4-chlorobenzyl)amino]-1,2,3,4-tetrahydro-2-isoquinolyl group, 7-(N-(4-chlorobenzyl)amino]-1,2,3,4-tetrahydro-2-isoquinolyl group, 6-(4-chlorophenoxy)-1,2,3,4-tetrahydro-2-isoquinolyl group, 7-(N-methyl-N-(2,4-di(trifluoromethoxy)phenyl]amino)-1,2,3,4-tetrahydro-2-isoquinolyl group, 7-(N-methyl-N-(2,4,6-tri(trifluoromethoxy)benzyl]amino)-1,2,3,4-tetrahydro-2-isoquinolyl group, 6-(2,4-di(trifluoromethoxy)phenoxy]-1,2,3,4-tetrahydro-2-isoquinolyl group, 7-(N-methyl-N-(2,4,6-tri(trifluoromethyl)phenyl]amino)-1,2,3,4-tetrahydro-2-isoquinolyl group, 7-(N-methyl-N-(2,4-di(trifluoromethyl) benzyl]amino)-1,2,3,4-tetrahydro-2-isoquinolyl group, 6-(2,4,6-tri(trifluoromethyl)-phenoxy]-1,2,3,4-tetrahydro-2-isoquinolyl group, 7-(N-methyl-N-(2,4-dibromophenyl) amino]-1,2,3,4-tetrahydro-2-isoquinolyl group, 7-(N-methyl-N-(2,3-diiodobenzyl)amino]-1,2,3,4-tetrahydro-2-isoquinolyl group, 6-(2,4,6-trifluorophenoxy)-1,2,3,4-tetrahydro-2-isoquinolyl group, 7-amino-6-phenoxy-1,2,3,4-tetrahydro-2-isoquinolyl group, 4,5,6-triphenoxy-1,2,3,4-tetrahydro-7-isoquinolyl group or the like.

A C1-C6 alkoxy group substituted by 2 phenyl groups [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] includes a C1-C6 alkoxy group substituted by 2 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), for example, a 1,1-diphenylmethoxy group, 1,2-diphenylethoxy group, 3,3-diphenylpropoxy group, 3,4-diphenylbutoxy group, 3,5-diphenylpentyloxy group, 4,6-diphenylhexyloxy group, 1,1-di(4-trifluoromethoxyphenyl)methoxy group, 1-(2-fluorophenyl)-1-(3-fluorophenyl)methoxy group, 1-(4-fluorophenyl)-1-(2-chlorophenyl)methoxy group, 1-(3-chlorophenyl)-1-(4-chlorophenyl)methoxy group, 1-(2- bromophenyl)-1-(3-bromophenyl)methoxy group, 1-(4-bromophenyl)-2-(2-iodophenyl)ethoxy group, 3-(3-iodophenyl)-3-(4-iodophenyl)propoxy group, 1-(2,3-difluorophenyl)-1-(3,4-difluorophenyl)methoxy group, 4-(3,5-difluorophenyl)-4-(2,4-difluorophenyl)butoxy group, 5-(2,6-difluorophenyl)-5(2,3-dichlorophenyl)pentyloxy group, 6-(3,4-dichlorophenyl)-6-(3,5-dichlorophenyl)hexyloxy group, 1-(2,4-dichlorophenyl)-1-(2,6-dichlorophenyl)methoxy group, 1-(3,4,5-trifluorophenyl)-1-(3,4,5-trichlorophenyl)methoxy group, 1-(2,3,4,5,6-pentafluorophenyl)-1-(2,4,6-trimethylphenyl)methoxy group, 1-(4-n-butylphenyl)-1-(2,4-dimethylphenyl)methoxy group, 1-(3,5-ditrifluoromethylphenyl)-1-(4-n-butoxyphenyl)methoxy group, 1-(2,4-dimethoxyphenyl)-1-(2,3-dimethoxyphenyl) methoxy group, 1-(2,4,6-trimethoxyphenyl)-1-(3,5-ditrifluoromethoxyphenyl)-methoxy group, 1-(3-chloro-4-methoxyphenyl)-1-(2-chloro-4-trifluoromethoxyphenyl)methoxy group, 1-(3-methyl-4-fluorophenyl)-1-(2-bromo-3-trifluoromethylphenyl)methoxy group, 1-(2-methylphenyl)-1-(3-methylphenyl)methoxy group, 1-(2-pentafluoroethylphenyl)-1-(3-pentafluoroethylphenyl)-methoxy group, 1-(2-isopropylphenyl)-1-(2-tert-butylphenyl)methoxy group, 1-(2-sec-butylphenyl)-1-(2-n-heptafluoropropylphenyl) methoxy group, 1-(4-pentylphenyl)-1-(4-hexylphenyl)methoxy group, 1-(2-methoxyphenyl)-1-(2,6-dimethoxyphenyl) methoxy group, 1-(2-pentafluoroethoxyphenyl)-1-(isopropoxyphenyl)methoxy group, 1-(2-tert-butoxyphenyl)-1-(2-sec-butoxyphenyl)methoxy group, 1-(2-n-heptafluoro-propoxyphenyl)-1-(4-n-pentoxyphenyl) methoxy group, 1,1-di(4-n-hexyloxyphenyl)methoxy or the like.

A piperidyl group (wherein, on the piperidine ring, at least one selected from the group consisting of (n-1) a phenyl group [wherein, on the phenyl ring, at least one group-$NR^{26}R^{27}$ ($R^{26}$ represents a hydrogen atom or C1-& alkyl group. $R^{27}$ represents a phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted]) is substituted], (n-2) a group-$W_1NR^{28}R^{29}$ [$W_1$ represents a C1-C6 alkylene group, $R^{28}$ represents a hydrogen atom or C1-C6 alkyl group and $R^{29}$ represents a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted)], (n-3) a C1-C6 alkoxy group substituted by 2 phenyl groups [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] and (n-4) a phenyl C1-C6 alkyl group [wherein, on the phenyl group ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is substituted] may be substituted) includes a piperidyl group (wherein, on the piperidine ring, 1 to 3 substituents selected from the group consisting of (n-1) a phenyl group [wherein, on the phenyl ring, 1 to 3 groups-$NRNR^{26}R^{27}$ ($R^{26}$ represents a hydrogen atom or C1-C6 alkyl group. $R^{27}$ represents a phenyl group as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted]) are substituted], (n-2) a group-$W_1NR^{28}R^{29}$ [$W_1$ represents C1-C6 alkylene group, $R^{28}$ represents a hydrogen atom or a C1-C6 alkyl group as described above and $R^{29}$ represents a phenyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted)], (n-3) a C1-C6 alkoxy group substituted by 2 phenyl groups as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] and (n-4) a phenyl C1-C6 alkyl group as described later [wherein, on the phenyl group ring, 1 to 3 phenyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) is substituted] may be substituted), for example, a (1-, 2-, 3- or 4-)piperidyl group, 4-(N-methyl-N-(4-trifluoromethoxyphenyl)amino]phenyl-1-piperidyl group, 4-(N-(4-trifluoromethoxyphenyl)-aminomethyl]-1-piperidyl group, 4-(N-methyl-N-(4-trifluoromethoxyphenyl)aminomethyl]-1-piperidyl group, 4-(N-ethyl-N-(4-trifluoromethoxyphenyl) aminomethyl]-1-piperidyl group, 4-(1,1-di(4-trifluoromethoxyphenyl)-methoxy]-1-piperidyl group, 4-(N-methyl-N-(4-trifluoromethylphenyl)amino]phenyl-1-piperidyl group, 4-(N-(4-trifluoromethylphenyl) aminomethyl]-1-piperidyl group, 4-(N-methyl-N-(2,4-di (trifluoromethyl)phenyl]-aminomethyl)-1-piperidyl group, 4-(N-ethyl-N-(2,4,6-tri(trifluoromethoxy)phenyl]aminomethyl)-1-piperidyl group, 4-(1,1-di(4-trifluoromethylphenyl) methoxy-1-piperidyl group, 4-(N-methyl-N-(4-chlorophenyl)amino]-phenyl-1-piperidyl group, 4-(N-(2,4-dibromophenyl)-aminomethyl]-1-piperidyl group, 4-(N-methyl-N-(2,4,6-trifluorophenyl)aminomethyl]-1-piperidyl group, 4-(N-ethyl-N-(4-chlorophenyl)aminomethyl]-1-piperidyl group, 4-(1,1-di(4-chlorophenyl)methoxy]-1-piperidyl group, 4-(N-methyl-N-(2,4-dibromophenyl)amino] phenyl-1-piperidyl group, 4-(1,1-di(2,4-dibromophenyl) methoxy]-1-piperidyl group, 4-(N-methyl-N-(2,4,6-trifluorophenyl)-amino]phenyl-1-piperidyl group, 4-(1,1-di (2,4,6-trifluorophenyl)methoxy]-1-piperidyl group, 4-(N-methyl-N-(2,4-di(trifluoromethyl)phenyl]amino)phenyl-1-piperidyl group, 4-(N-methyl-N-(2,4,6-tri(trifluoromethoxy) phenyl]amino)phenyl-1-piperidyl group, 4-(1-(2,4-di (trifluoromethyl)phenyl]-1-(2,4,6-tri(trifluoromethoxy) phenyl]methoxy)-1-piperidyl group, 4-(N-(4-trifluoromethoxyphenyl)aminomethyl]-3-(N-(4-trifluoromethylphenyl)aminomethyl]-1-piperidyl group, 3,4,6-tri(1,1-diphenylmethoxy)-1-piperidyl group, 4-(4-phenylbenzyl)-(1-, 2- or 3-)piperidinyl group or the like.

A C1-C6 alkyl group substituted by 2 phenyl groups [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] includes a C1-C6 alkyl group substituted by 2 phenyl groups [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted], for example, a 1,1-diphenylmethyl group, 1,2-diphenylethyl group, 3,3-diphenylpropyl group, 3,4-diphenylethyl group, 3,5-diphenylpentyl group, 4,6-diphenylhexyl group, 1,1-di(4-trifluoromethoxyphenyl)methyl group, 1,1-di(4-chlorophenyl)methyl group, 1-(2-fluorophenyl)-1-(3-fluorophenyl)methyl group, 1-(4-fluorophenyl)-1-(2-chlorophenyl)methyl group, 1-(3-chlorophenyl)-1-(4-chlorophenyl)methyl group, 1-(2-bromophenyl)-1-(3-bromophenyl)methyl group, 1-(4-bromophenyl)-2-(2-iodophenyl)ethyl group, 3-(3-iodophenyl)-3-(4-iodophenyl)propyl group, 1-(2,3-difluorophenyl)-1-(3,4-difluorophenyl)methyl group, 4-(3,5-difluorophenyl)-4-(2,4-difluorophenyl)butyl group, 5-(2,6-difluorophenyl)-5-(2,3-dichlorophenyl)pentyl group, 6-(3,4-dichlorophenyl)-6-(3,5-dichlorophenyl)hexyl group, 1-(2,4-dichlorophenyl)-1-(2,6-dichlorophenyl)methyl group, 1-(3,4,5-trifluorophenyl)-1-(3,4,5-trichlorophenyl)methyl group, 1-(2,3,4,5,6-pentafluorophenyl)-1-(2,4,6-trimethylphenyl)methyl group, 1-(4-n-butylphenyl)-1-(2,4-dimethylphenyl)methyl group, 1-(3,5-ditrifluoromethylphenyl)-[(4-n-butoxyphenyl)methyl group, 1-(2,4-dimethoxyphenyl)-1-(2,3-dimethoxyphenyl) methyl group, 1-(2,4,6-trimethoxyphenyl)-[(3,5-ditrifluoromethoxyphenyl)-methyl group, 1-(3-chloro-4-methoxyphenyl)-1-(2-chloro-4-trifluoromethoxyphenyl)methyl group, 1-(3-methyl-4-fluorophenyl)-1-(4-bromo-3-trifluoromethylphenyl)methyl group, 1-(2-methylphenyl)-1-(3-methylphenyl)methyl group, 1-(2-pentafluoroethylphenyl)-1-(3-pentafluoroethylphenyl)methyl group, 1-(2-isopropylphenyl)-1-(2-tert-butylphenyl)methyl group, 1-(2-sec-butylphenyl)-1-(2-n-heptafluoropropylphenyl)-methyl group, 1-(4-n-pentylphenyl)-1-(4-n-hexylphenyl)methyl group, 1-(2-methoxyphenyl)-1-(2,6-dimethoxyphenyl)methyl group, 1-(2-pentafluoro-ethoxyphenyl)-1-(isopropoxyphenyl)methyl group, 1-(2-tert-butoxyphenyl)-1-(2-sec-butoxyphenyl)methyl group, 1-(2-n-heptafluoropropoxyphenyl)-1-(4-n-pentoxyphenyl)methyl group, 1,1-di(4-n-hexyloxyphenyl)methyl group or the like.

A phenyl C2-C6 alkenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] is a group composed of 1 or 2 phenyl groups substituted by 1 to 5, preferably 1 to 3 substituents selected from the group consisting of a halogen atom, a halogen C1-C6 alkyl and a halogen substituted or unsubstituted C1-C6 alkoxy group and an alkenyl group containing 2 to 6 carbon atoms and 1 to 3 double bonds. The phenyl C2-C6 alkenyl group includes both trans and cis forms. Such a phenyl C2-C6 alkenyl group includes a 3-(2-fluorophenyl)-2-propenyl group, 3,3-di(2-fluorophenyl)-2-propenyl group, 3-(3-fluorophenyl)-2-propenyl group, 3-(4-fluorophenyl)-2-propenyl group, 3-(2,3-difluorophenyl)-2-propenyl group, 3-(2,3,4,5,6-pentafluorophenyl)-2-propenyl group, 3-(2,4-difluorophenyl)-2-propenyl group, 3-(3,4-difluorophenyl)-2-propenyl group, 3-(3,5-difluorophenyl)-2-propenyl group, 3-(2-chlorophenyl)-2-propenyl group, 3-(3-chlorophenyl)-2-propenyl group, 3-(4-chlorophenyl)-2-propenyl group, 3-(2,3-dichlorophenyl)-2-propenyl group, 3-(2,4-dichlorophenyl)-2-propenyl group, 3-(3,4-dichlorophenyl)-2-propenyl group, 3-(3,5-dichlorophenyl)-2-propenyl group, 3-(2-bromophenyl)-2-propenyl group, 3-(3-bromophenyl)-2-propenyl group, 3-(4-bromophenyl)-2-propenyl group, 3-(2-methylphenyl)-2-propenyl group, 3-(3-methylphenyl)-2-propenyl group, 3-(4-methylphenyl)-2-propenyl group, 3-(2-trifluoromethylphenyl)-2-propenyl group, 3-(2-fluoro-4-bromophenyl)-2-propenyl group, 3-(4-chloro-3-fluorophenyl)-2-propenyl group, 3-(2,3,4-trichlorophenyl)-2-propenyl group, 3-(2,4,6-trichlorophenyl)-2-propenyl group, 3-(4-isopropylphenyl)-2-propenyl group, 3-(4-n-butylphenyl)-2-propenyl group, 3-(2,4-dimethylphenyl)-2-propenyl group, 3-(2,3-dimethylphenyl)-2-propenyl group, 3-(2,6-dimethylphenyl)-2-propenyl group, 3-(3,5-dimethylphenyl)-2-propenyl group, 3-(2,5-dimethylphenyl)-2-propenyl group, 3-(2,4,6-trimethylphenyl)-2-propenyl group, 3-(3,5-ditrifluoromethylphenyl)-2-propenyl group, 3-(4-n-butoxyphenyl)-2-propenyl group, 3-(2,4-dimethoxyphenyl)-2-propenyl group, 3-(2,3-dimethoxyphenyl)-2-propenyl group, 3-(2,6-dimethoxyphenyl)-2-propenyl group, 3-(3,5-dimethoxyphenyl)-2-propenyl group, 3-(2,5-dimethoxyphenyl)-2-propenyl group, 3-(3,5-ditrifluoromethoxyphenyl)-2-propenyl group, 3-(3-chloro-4-methoxyphenyl-2-propenyl group, 3-(2-chloro-4-trifluoromethoxyphenyl-2-propenyl group, 3-(3-methyl-4-fluorophenyl)-2-propenyl group, 3-(4-bromo-3-trifluoromethylphenyl)-2-propenyl group, 3-(3-trifluoromethylphenyl)-2-propenyl group, 3-(4-trifluoromethylphenyl)-2-propenyl group, 3-(2-trifluoromethoxyphenyl)-2-propenyl group, 3-(3-trifluoromethoxyphenyl)-2-propenyl group, 3-(4-trifluoromethoxyphenyl)-2-propenyl group, 3-(2-methoxyphenyl)-2-propenyl group, 3-(3-methoxyphenyl)-2-propenyl group, 3-(4-methoxyphenyl)-2-propenyl group, 3-(3,4-dimethoxyphenyl)-2-propenyl group, 3-(3,5-dimethoxyphenyl)-2-propenyl group, 4-(4-chlorophenyl)-2-butenyl group, 4-(4-chlorophenyl)-3-butenyl group, 5-(4-chlorophenyl)-2-pentenyl group, 5-(4-chlorophenyl)-4-pentenyl group, 5-(4-chlorophenyl)-3-pentenyl group, 6-(4-chlorophenyl)-5-hexenyl group, 6-(4-chlorophenyl)-4-hexenyl group, 6-(4-chlorophenyl)-3-hexenyl group, 6-(4-chlorophenyl)-3-hexenyl group or the like.

An imidazolyl group [wherein, on the imidazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes an imidazolyl group [wherein, on the imidazole ring, 1 to 3 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a (1-, 2-, 4 or 5-)imidazolyl group, 1-phenyl-2-imidazolyl group, 2-(2-fluorophenyl)-1-imidazolyl group, 4-(3-fluorophenyl)-2-imidazolyl group, 5-(4-fluorophenyl)-3-imidazolyl group, 1-(2-chlorophenyl)-3-imidazolyl group, 2-(3-chlorophenyl)-5-imidazolyl group, 1-(4-chlorophenyl)-2-imidazolyl group, 4-(2-bromophenyl)-5-imidazolyl group, 5-(3-bromophenyl)-2-imidazolyl group, 1-(4-bromophenyl)-3-imidazolyl group, 2-(2-iodophenyl)-r-imidazolyl group, 4-(3-iodophenyl)-5-imidazolyl group, 5-(4-iodophenyl)-1-imidazolyl group, 1-(2,3-difluorophenyl)-2-imidazolyl group, 1-(3,4-difluorophenyl)-2-imidazolyl group, 1-(3,5-difluorophenyl)-2-imidazolyl group, 1-(2,4-difluorophenyl)-4-imidazolyl group, 1-(2,6-difluorophenyl)-5-imidazolyl group, 1-(2,3-dichlorophenyl)-2-imidazolyl group, 1-(3,4-dichlorophenyl)-4-imidazolyl group, 1-(3,5-dichlorophenyl)-5-imidazolyl group, 1-(2,4-dichlorophenyl)-2-imidazolyl group, 1-(2,6-dichlorophenyl)-4-imidazolyl group, 1-(3,4,5-trifluorophenyl)-5-imidazolyl group, 1-(3,4,5-trichlorophenyl)-2-imidazolyl group, 1-(2,4,6-trifluorophenyl)-4-imidazolyl group, 1-(2,4,6-trichlorophenyl)-5-imidazolyl group, 1-(2-fluoro-4-bromophenyl)-2-imidazolyl group, 1-(4-chloro-3-fluorophenyl)-4-imidazolyl group, 1-(2,3,4-trichlorophenyl)-5-imidazolyl group, 1-(2,3,4,5,6-pentafluorophenyl)-2-imidazolyl group, 1-(2,4,6-trimethylphenyl)-2-imidazolyl group, 2-(4-n-butylphenyl)-4-imidazolyl group, 4-(2,4-dimethylphenyl)-1-imidazolyl group, 5-(2,3-dimethylphenyl)-2-imidazolyl group, 1-(2,6-dimethylphenyl)-4-imidazolyl group, 2-(3,5-dimethylphenyl)-5-imidazolyl group, 4-(2,5-dimethylphenyl)-1-imidazolyl group, 5-(3,5-di-trifluoromethylphenyl)-2-imidazolyl group, 1-(4-n-butoxyphenyl)-2-imidazolyl group, 1-(2,4-dimethoxyphenyl)-2-imidazolyl group, 1-(2,3-dimethoxyphenyl)-2-imidazolyl group, 1-(2,6-dimethoxyphenyl)-2-imidazolyl group, 2-(3,5-dimethoxyphenyl)-4-imidazolyl group, 4-(2,5-dimethoxyphenyl)-1-imidazolyl group, 5-(2,4,6-triethoxyphenyl)-2-imidazolyl group, 1-(3,5-ditrifluoromethoxyphenyl)-2-imidazolyl group, 1-(3-chloro-4-methoxyphenyl)-2-imidazolyl group, 1-(2-chloro-4-trifluoromethoxyphenyl)-2-imidazolyl group, 1-(4-bromo-3-trifluoromethylphenyl)-2-imidazolyl group, 1-(2-methylphenyl)-2-imidazolyl group, 2-(3-methylphenyl)-4-imidazolyl group, 4-(4-methylphenyl)-5-imidazolyl group, 5-(2-methyl-3-chlorophenyl)-1-imidazolyl group, 1-(3-methyl-4-chlorophenyl)-2-imidazolyl group, 2-(2-chloro-4-methylphenyl)-4-imidazolyl group, 4-(2-methyl-3-fluorophenyl)-5-imidazolyl group, 5-(2-trifluoromethylphenyl)-1-imidazolyl group, 1-(3-trifluoromethylphenyl)-2-imidazolyl group, 2-(4-trifluoromethylphenyl)-4-imidazolyl group, 4-(2-pentafluoroethylphenyl)-5-imidazolyl group, 5-(3-pentafluoroethylphenyl)-1-imidazolyl group, 1-(4-pentafluoroethylphenyl)-2-imidazolyl group, 2-(2-isopropylphenyl)-4-imidazolyl group, 4-(3-isopropylphenyl)-5-imidazolyl group, 5-(4-isopropylphenyl)-1-imidazolyl group, 1-(2-tert-butylphenyl)-2-imidazolyl group, 2-(3-tert-butylphenyl)-4-imidazolyl group, 4-(4-tert-butylphenyl)-5-imidazolyl group, 5-(2-sec-butylphenyl)-1-imidazolyl group, 1-(3-sec-butylphenyl)-2-imidazolyl group, 2-(4-sec-butylphenyl)-4-imidazolyl group, 4-(2-n-heptafluoropropylphenyl)-5-imidazolyl group, 5-(3-n-heptafluoropropylphenyl)-1-imidazolyl group, 1-(4-n-heptafluoropropylphenyl)-2-imidazolyl group, 2-(4-pentylphenyl)-4-imidazolyl group, 4-(4-hexylphenyl)-5-imidazolyl group, 1-(2-methoxyphenyl)-2-imidazolyl group, 5-(3-methoxyphenyl)-1-imidazolyl group, 1-(4-methoxyphenyl)-2-imidazolyl group, 2-(3-chloro-2-methoxyphenyl)-4-imidazolyl group, 4-(2-fluoro-3-methoxyphenyl)-5-imidazolyl group, 5-(2-fluoro-4-methoxyphenyl)-1-imidazolyl group, 1-(2,6-dimethoxyphenyl)-2-imidazolyl group, 1-(2,3,4-trifluorophenyl)-2-imidazolyl group, 1-(2-trifluoromethoxyphenyl)-2-imidazolyl group, 2-(3-trifluoromethoxyphenyl)-4-imidazolyl group, 1-(4-trifluoromethoxyphenyl)-2-imidazolyl group, 1-(3-fluoro-2-trifluoromethoxyphenyl)-2-imidazolyl group, 1-(2-fluoro-3-trifluoromethoxyphenyl)-2-imidazolyl group, 1-(3-fluoro-4-trifluoromethoxyphenyl)-2-imidazolyl group, 1-(3-chloro-2-trifluoromethoxyphenyl)-2-imidazolyl group, 1-(2-chloro-3-trifluoromethoxyphenyl)-2-imidazolyl group, 1-(3-chloro-4-trifluoromethoxyphenyl)-2-imidazolyl group, 1-(2-pentafluoroethoxyphenyl)-2-imidazolyl group, 1-(3-pentafluoroethoxyphenyl)-2-imidazolyl group, 1-(4-pentafluoroethoxyphenyl)-2-imidazolyl group, 1-(3-chloro-2-pentafluoroethoxyphenyl)-2-imidazolyl group, 1-(2-chloro-3-pentafluoroethoxyphenyl)-2-imidazolyl group, 1-(3-chloro-4-pentafluoroethoxyphenyl)-2-imidazolyl group, 1-(2-isopropoxyphenyl)-2-imidazolyl group, 1-(3-isopropoxyphenyl)-2-imidazolyl group, 1-(4-isopropoxyphenyl)-2-imidazolyl group, 1-(2-tert-butoxyphenyl)-2-imidazolyl group, 1-(3-tert-butoxyphenyl)-2-imidazolyl group, 1-(4-tert-butoxyphenyl)-2-imidazolyl group, 1-(2-sec-butoxyphenyl)-2-imidazolyl group, 1-(3-sec-butoxyphenyl)-2-imidazolyl group, 1-(4-sec-butoxyphenyl)-2-imidazolyl group, 1-(2-n-heptafluoropropoxyphenyl)-2-imidazolyl group, 1-(3-n-heptafluoropropoxyphenyl)-2-imidazolyl group, 1-(4-n-heptafluoropropoxyphenyl)-2-imidazolyl group, 1-(4-n-pentoxyphenyl)-2-imidazolyl group, 1-(4-n-hexyloxyphenyl)-2-imidazolyl group, 1,4-diphenyl-2-imidazolyl group, 1,4,5-triphenyl-2-imidazolyl group or the like.

A piperadinyl group (wherein, on the piperadine ring, at least one selected from the group consisting of a C1-C6 alkyl group substituted by 2 phenyl groups [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted], a phenyl C1-C6 alkyl group [wherein, on the phenyl ring, at least one phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a thiazolyl group (wherein, on the thiazole ring, at least one phenyl group may be substituted), a phenoxy C1-C6 alkyl group (wherein, on the phenyl ring, at least one selected from the group consisting of a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a halogen atom, a halogen substituted or unsubstituted C1-C6 alkyl group and a halogen substituted or unsubstituted C1-C6 alkoxy group may be substituted), a phenyl C2-C6 alkenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] and a imidazolyl group [wherein, on the imidazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] is substituted) includes a piperadinyl group (wherein, on the piperadine ring, 1 to 3 substituents selected from the group consisting of a C1-C6 alkyl group substituted by 2 phenyl groups as described above [wherein, on the phenyl ring, 1 to 5, preferably 1 to 3 substitutes selected from the group consisting of a halogen atom, a halogen substituted or unsubstituted C1-C6 alkyl group and a halogen substituted or unsubstituted C1-C6 alkoxy group may be substituted], a phenyl C1-C6 alkyl group [wherein, on the phenyl ring, 1 to 3 phenoxy groups (wherein, on the phenyl ring, 1 to 5, preferably 1 to 3 substitutes selected from the group consisting of a halogen atom, a halogen substituted or unsubstituted C1-C6 alkyl group and a halogen substituted or unsubstituted C1-C6 alkoxy group may be substituted) are substituted], a thiazolyl group as described later (wherein, on the thiazole ring, 1 or 2 phenyl groups may be substituted), a phenoxy C1-C6 alkyl group as described later (wherein, on the phenyl ring, 1 to 5, preferably 1 to 3 substituents selected from the group consisting of a phenyl group as described above (wherein, on the phenyl ring, 1 to 5, preferably 1 to 3 substitutes selected from the group consisting of a halogen atom, a halogen substituted or unsubstituted C1-C6 alkyl group and a halogen substituted or unsubstituted C1-C6 alkoxy group may be substituted), a halogen atom, a halogen substituted or unsubstituted C1-C6 alkyl group and a halogen substituted or unsubstituted C1-C6 alkoxy group may be substituted), a phenyl C2-C6 alkenyl group [a group composed of a 1 or 2 phenyl groups substituted by 1 to 5, preferably 1 to 3 substituents selected from the group consisting of a halogen atom, a halogen substituted or unsubstituted C1-C6 alkyl group and a halogen substituted or unsubstituted C1-C6 alkoxy group and an alkenyl group containing 2 to 6 carbon atoms and having 1 to 3 double bonds] and an imidazolyl group [wherein, on the imidazole ring, 1 to 3 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] are substituted), for example, 4-(1,1-di(4-chlorophenyl)methyl]-1-piperadinyl group, 4-(1,1-di(4-trifluoromethoxyphenyl) methyl)-1-piperadinyl group, 4-(4-chlorocinnamyl)-1-piperadinyl group, 4-(4-trifluoromethoxycinnamyl)-1-piperadinyl group, 4-(1-(4-chlorophenyl)-2-imidazolyl]-1-piperadinyl group, 4-(1,1-di(2,4-dibromophenyl)methyl]-1-piperadinyl group, 4-(1,1-di(4-trifluoromethylphenyl)methyl]-1-piperadinyl group, 4-(2,4-dichlorocinnamyl)-1-piperadinyl group, 4-(4-trifluoromethylcinnamyl)-1-piperadinyl group, 4-(1-(2, 4-di(trifluoromethoxy)phenyl]-2-imidazolyl)-1-piperadinyl group, 4-(1,1-di(2,4,6-trifluorophenyl)methyl]-1-piperadinyl group, 4-(1,1-di(2,4-di(trifluoromethoxy)phenyl]methyl)-1-piperadinyl group, 4-(2,4,6-tri(trifluoromethoxy)cinnamyl]-1-piperadinyl group, 4-(2,4-di(trifluoromethoxy)-cinnamyl]-1-piperadinyl group, 4-(1-(4-trifluoromethylphenyl)-2-imidazolyl]-1-piperadinyl group, 4-(2,4,6-trifluorocinnamyl)-1-piperadinyl group, 4-(1-(2,4-dibromophenyl)-2-imidazolyl]-1-piperadinyl group, 4-(1,1-di(4-chlorophenyl)methyl]-3-(4-chlorocinnamyl)-1-1-piperadinyl group, 4-(4-trifluoromethoxycinnamyl)-2-(1-(4-chlorophenyl)-2-imidazolyl]-1-piperadinyl group, 4-(4-trifluoromethoxycinnamyl)-2-(1-(4-chlorophenyl)-2-imidazolyl]-6-(1-imidazolyl)-1-piperadinyl group, 4-(4-(4-trifluoromethoxyphenoxy)benzyl]-(1-, 2- or 3-)piperadinyl group, 4-(4-phenyl-(2- or 5-)thiazolyl]-(1-, 2- or 3-)piperadinyl group, 4-(2-(4-trifluoromethoxyphenoxy)ethyl]-(1-, 2- or 3-)piperadinyl group, 4-(2-(4-phenylphenoxy)ethyl]-(1-, 2- or 3-)piperadinyl group, 4-(2-(4-chlorophenoxy)ethyl]-(1-, 2- or 3-)piperadinyl group, 4-(2-(3,4-dichlorophenoxy) ethyl]-(1-, 2- or 3-)piperadinyl group, 4-(2-(4-trifluoromethylphenoxy)-ethyl]-(1-, 2- or 3-)piperadinyl group, 4-(2-(4-trifluoromethoxyphenoxy)ethyl]-(1-, 2- or 3-)piperadinyl or the like.

An anilino C1-C6 alkyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] includes a group composed of an anilino group which may be substituted by a C1-C6 alkyl group on the N position of the anilino group and is unsubstituted or substituted by 1 to 5, preferably 1 to 3 substituents selected from the group consisting of a halogen substituted or unsubstituted C1-C6 alkyl group as defined above, a halogen substituted or unsubstituted C1-C6 alkoxy group and a halogen, and a C1-C6 alkyl group, examples of which include an anilinomethyl group, N-methyl-N-anilinomethyl group, N-ethyl-N-anilinomethyl group, N-n-propyl-N-anilinomethyl group, N-n-butyl-N-anilinomethyl group, N-n-pentyl-N-anilinomethyl group, N-n-hexyl-N-anilinomethyl group, 2-anilinoethyl group, 3-anilinopropyl group, 4-anilinobutyl group, 5-anilinopentyl group, 6-anilinohexyl group, 4-fluoroanilinomethyl group, 2-fluoro-4-bromoanilinomethyl group, 4-chloro-3-fluoroanilinomethyl group, 2,3,4-trichloroanilinomethyl group, 3,4,5-trichloroanilinomethyl group, 2,4,6-trichloroanilinomethyl group, N-methyl-N-2,4,6-trichloroanilinomethyl group, 4-isopropylanilinomethyl group, 4-n-butylanilinomethyl group, 4-methylanilinomethyl group, 2-methylanilinomethyl group, 3-methylanilinomethyl group, 2,4-dimethylanilinomethyl group, 2,3-dimethylanilinomethyl group, 2,6-dimethylanilinomethyl group, 3,5-dimethylanilinomethyl group, 2,5-dimethylanilinomethyl group, N-methyl-N-2,5-dimethoxyanilinomethyl group, 2,4,6-trimethylanilinomethyl group, 3,5-ditrifluoromethylanilinomethyl group, 2,3,4,5,6-pentafluoroanilinomethyl group, 4-isopropoxyanilinomethyl group, 4-n-butoxyanilinomethyl group, 4-methoxyanilinomethyl group, 2-methoxyanilinomethyl group, 3-methoxyanilinomethyl group, N-methyl-N-3-methoxyanilinomethyl group, 2,4-dimethoxyanilinomethyl group, 2,3-dimethoxyanilinomethyl group, 2,6-dimethoxyanilinomethyl group, 3,5-dimethoxyanilinomethyl group, 2,5-dimethoxyanilinomethyl group, 2,4,6-trimethoxyanilinomethyl group, 3,5-ditrifluoromethoxyanilinomethyl group, 2-isopropoxyanilinomethyl group, 3-chloro-4-methoxyanilinomethyl group, 2-chloro-4-trifluoromethoxyanilinomethyl group, 3-methyl-4-fluoroanilinomethyl group, 4-bromo-3-trifluoromethylanilinomethyl group, 2-(4-fluoroanilino)ethyl group, 3-(4-fluoroanilino)propyl group, 4-(4-fluoroanilino) butyl group, 5-(4-fluoroanilino)pentyl group, 6-(4-fluoroanilino)hexyl group, 4-chloroanilinomethyl group, 2-(4-chloroanilino)ethyl group, 3-(4-chloroanilino)propyl group, 4-(4-chloroanilino)butyl group, 5-(4-chloroanilino)pentyl group, 6-(4-chloroanilino)hexyl group, 4-methylanilinomethyl group, 2-(4-methylanilino)ethyl group, 3-(4-methylanilino) propyl group, 4-(4-methylanilino)butyl group, 5-(4-methylanilino)pentyl group, 6-(4-methylanilino)hexyl group, 4-trifluoromethylanilinomethyl group, 2-(4-trifluoromethylanilino)ethyl group, 3-(4-trifluoromethylanilino)propyl group, 4-(4-trifluoromethylanilino)butyl group, N-methyl-N-(4-(4-trifluoromethylanilino)]butyl group, 5-(4-trifluoromethylanilino)pentyl group, 6-(4-trifluoromethylanilino)hexyl group, 4-trifluoromethoxyanilinomethyl group, N-methyl-N-4-trifluoromethoxyanilinomethyl group, 2-(4-trifluoromethoxyanilino)ethyl group, 3-(4-trifluoromethoxyanilino)propyl group, 4-(4-trifluoromethoxyanilino)butyl group, 5-(4-trifluoromethoxyanilino)pentyl group, 6-(4-trifluoromethoxyanilino)hexyl group, 4-methoxyanilinomethyl group, 2-(4-methoxyanilino)ethyl group, 3-(4-methoxyanilino)propyl group, 4-(4-methoxyanilino)butyl group, 5-(4-methoxyanilino)pentyl group, 6-(4-methoxyanilino)hexyl group or the like.

A thiazolyl C1-C6 alkoxy group (wherein, on the thiazole ring, at least one selected from the group consisting of a (p-1)phenoxy C1-C6 alkyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted], a (p-2)anilino C1-C6 alkyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted], a (p-3)phenyl C1-C6 alkyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted], a (p-4)piperadinyl group C1-C6 alkyl group [wherein, on the piperadine ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] and a (p-5)piperidyl C1-C6 alkyl group [wherein, on the piperidine ring, at least one phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] may be substituted) includes a thiazolyl C1-C6 alkoxy group (wherein, on the thiazole ring, 1 to 3 substituents selected from the group consisting of a phenoxy C1-C6 alkyl group as described later [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted], an anilino C1-C6 alkyl group as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted], a phenyl C1-C6 alkyl group as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted], a piperadinyl C1-C6 alkyl group as described above [wherein, on the piperadine ring, 1 to 3 phenyl groups (wherein, on the phenyl ring, 1 to 5, preferably. 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] and a piperidyl C1-C6 alkyl group as described above [wherein, on the piperidine ring, 1 to 3 phenoxy groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] may be substituted), for example, a (2-thiazolyl) methoxy group, 2-(4-thiazolyl)ethoxy group, 3-(5-thiazolyl) propoxy group, 4-(2-thiazolyl)butoxy group, 5-(4-thiazolyl) pentyloxy group, 6-(5-thiazolyl)hexyloxy group, (4-(4-(4-chlorophenoxy)-1-piperidylmethyl]-2-thiazolyl)methoxy group, (4-(4-(4-trifluoromethylphenoxy)-1-piperidylmethyl]-2-thiazolyl)methoxy group, 2-methyl-3-(2-thiazolyl) propoxy group, 1,1-dimethyl-2-(2-thiazolyl)ethoxy group, (4-(4-(4-trifluoromethoxyphenoxy)-1-piperidylmethyl]-2-thiazolyl)methoxy group, (4-(4-(2,4-di(trifluoromethoxy) phenoxy]-1-piperidylmethyl)-2-thiazolyl]methoxy group, (4-(4-(2,4,6-tri(trifluoromethyl)phenoxy]-1-piperidylmethyl)-2-thiazolyl]methoxy group, (4-(4-(2,4-dibromophenoxy)-1-piperidylmethyl]-2-thiazolyl)methoxy group, (4-(4-(2,4,6-trifluorophenoxy)-1-piperidylmethyl]-2-thiazolyl) methoxy group, (4-(4-(2,4-dibromophenoxy)-1-piperidylmethyl]-2-thiazolyl)methoxy group, (4-(4-(4-trifluoromethoxyphenyl)-1-piperadinylmethyl]-2-thiazolyl) methoxy group, (4-(4-(4-chlorophenyl)-1-piperadinylmethyl]-2-thiazolyl)methoxy group, (4-(4-(2,4-di(trifluoromethyl)phenyl]-1-piperadinylmethyl)-2-thiazolyl]methoxy group, (4-(4-(2,4,6-tri(trifluoromethoxy) phenyl]-1-piperadinylmethyl)-2-thiazolyl]methoxy group, (4-(4-(2,4-dibromophenyl)-1-piperadinylmethyl]-2-thiazolyl)methoxy group, (4-(4-(2,4,6-trifluorophenyl)-1-piperadinylmethyl]-2-thiazolyl)methoxy group, 4-(4-trifluoromethylphenoxymethyl)-2-thiazolyl group, (4-(4-trifluoromethoxyphenoxymethoxy)-2-thiazolyl]methoxy group, (4-(4-chlorophenoxymethyl)-2-thiazolyl]methoxy group, (4-(2,4-di(trifluoromethoxy)phenoxymethyl]-2-thiazolyl)methoxy group, (4-(2,4,6-tri(trifluoromethyl)phenoxymethyl]-2-thiazolyl)methoxy group, (4-(2,4-dibromophenoxymethyl)-2-thiazolyl]methoxy group, (4-(2,4,6-trifluorophenoxymethyl)-2-thiazolyl]methoxy group, (4-(4-trifluoromethylanilinomethyl)-2-thiazolyl]methoxy group, (4-(4-trifluoromethoxyanilinomethoxy)-2-thiazolyl]methoxy group, (4-(4-chloroanilinomethyl)-2-thiazolyl]methoxy group, (4-(2,4-di(trifluoromethoxy)anilinomethyl]-2-thiazolyl)methoxy group, (4-(2,4,6-tri(trifluoromethyl)anilinomethyl]-2-thiazolyl)methoxy group, (4-(2,4-dibromoanilinomethyl]-2-thiazolyl]methoxy group, (4-(2,4,6-trifluoroanilinomethyl)-2-thiazolyl]methoxy group, (4-(3-(4-trifluoromethoxyphenyl)propyl]-2-thiazolyl)methoxy group, (4-(3-(4-trifluoromethylphenyl)propyl]-2-thiazolyl) methoxy group, (4-(3-(4-chlorophenyl)propyl]-2-thiazolyl) methoxy group, (4-(2,4-diiodobenzyl)-2-thiazolyl]methoxy group, (4-(2,4,6-tribromobenzyl)-2-thiazolyl]methoxy group, (4-(2,4-di(trifluoromethoxy)benzyl]-2-thiazolyl) methoxy group, (4-(2,4,6-tri(trifluoromethyl)benzyl]-2-thiazolyl)methoxy group, (4,5-dibenzyl-2-thiazolyl)methoxy group, (2-phenoxymethyl-4-benzyl-5-thiazolyl)methoxy group, (2,5-dianilinomethyl-4-thiazolyl)methoxy group or the like.

An 8-azabicyclo[3.2.1]octyl group (wherein, on the 8-azabicyclo[3.2.1]octane ring, at least one phenoxy group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted) includes a 8-azabicyclo[3.2.1]octyl group (wherein, on the 8-azabicyclo[3.2.1]octane ring, 1 to 3 phenoxy groups as described above [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] may be substituted), for example, a 8-azabicyclo[3.2.1]octyl group, 3-(4-trifluoromethoxyphenoxy)-8-azabicyclo[3.2.1] octyl group, 3-(4-trifluoromethylphenoxy)-8-azabicyclo [3.2.1]octyl group, 3-(4-chlorophenoxy)-8-azabicyclo[3.2.1] octyl group, 3-(2,4-dichlorophenoxy)-8-azabicyclo[3.2.1] octyl group, 3-(2,4,6-trichlorophenoxy)-8-azabicyclo[3.2.1] octyl group, 3-(2-bromophenoxy)-8-azabicyclo[3.2.1]octyl group, 3-(3-fluorophenoxy)-8-azabicyclo[3.2.1]octyl group, 3-(2,4-di(trifluoromethoxy)phenoxy]-8-azabicyclo[3.2.1] octyl group, 3-(2,4,6-tri(trifluoromethoxy)phenoxy]-8-azabicyclo[3.2.1]octyl group, 3-(2,4-di(trifluoromethyl)phenoxy]-8-azabicyclo[3.2.1]octyl group, 3-(2,4,6-tri (trifluoromethyl)phenoxy]-8-azabicyclo[3.2.1]octyl group, 3,6-diphenoxy-8-azabicyclo[3.2.1]octyl group, 3,7,6-triphenoxy-8-azabicyclo[3.2.1]octyl group, 3-(4-methoxyphenoxy)-8-azabicyclo[3.2.1]octyl group, 3-(4-methylphenoxy)-8-azabicyclo[3.2.1]octyl group, 3-(2,4-dimethoxyphenoxy)-8-azabicyclo[3.2.1]octyl group, 3-(2,4,6-trimethoxyphenoxy)-8-azabicyclo[3.2.1]octyl group, 3-(2,4-dimethylphenoxy)-8-azabicyclo[3.2.1]octyl group, 3-(2,4,6-trimethylphenoxy)-8-azabicyclo[3.2.1]octyl group or the like.

An amino substituted C1-C6 alkyl group which may have a C1-C6 alkyl group as a substituent includes an amino-C1-C6 alkyl group which may have 1 or 2 C1-C6 alkyl groups as a substituent, for example, an aminomethyl group, 2-aminoethyl group, 1-aminoethyl group, 3-aminopropyl group, 4-aminobutyl group, 5-aminopentyl group, 6-aminohexyl group, 2-methyl-3-aminopropyl group, 1,1-dimethyl-2-aminoethyl group, ethylaminomethyl group, 1-(propylamino)

ethyl group, 2-(methylamino)ethyl group, 3-(isopropylamino)propyl group, 4-(n-butylamino)butyl group, 5-(n-pentylamino)pentyl group, 6-(n-hexylamino)hexyl group, dimethylamindmethyl group, (N-ethyl-N-propylamino)methyl group, 2-(N-methyl-N-hexylamino)ethyl group or the like.

A C1-C6 alkylene group includes a methylene group, ethylene group, trimethylene group, 2-methyltrimethylene group, 2,2-dimethyltrimethylene group, 1-methyltrimethylene group, methylmethylene group, ethylmethylene group, tetramethylene group, pentamethylene group, hexamethylene group or the like.

A phenyl C1-C6 alkoxycarbonyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] includes a group composed of a phenyl C1-C6 alkoxy group which may be substituted by 1 to 5, preferably 1 to 3 substituents selected from the group consisting of a halogen atom, a halogen substituted or unsubstituted C1-C6 alkyl group and a halogen substituted or unsubstituted C1-C6 alkoxy group as defined above and a carbonyl group, examples of which include a benzyloxycarbonyl group, 2-phenylethoxycarbonyl group, 3-phenylpropoxycarbonyl group, 2-phenylpropoxycarbonyl group, 4-phenylbutoxycarbonyl group, 5-phenylpentoxycarbonyl group, 4-phenylpentoxycarbonyl group, 6-phenylhexyloxycarbonyl group, 2-fluorobenzyloxycarbonyl group, 3-fluorobenzyloxycarbonyl group, 4-fluorobenzyloxycarbonyl group, 2-(2-fluorophenyl)ethoxycarbonyl group, 2-(3-fluorophenyl)ethoxycarbonyl group, 2-(4-fluorophenyl)ethoxycarbonyl group, 2-chlorobenzyloxycarbonyl group, 3-chlorobenzyloxycarbonyl group, 4-chlorobenzyloxycarbonyl group, 2-fluoro-4-bromobenzyloxycarbonyl group, 4-chloro-3-fluorobenzyloxycarbonyl group, 2,3,4-trichlorobenzyloxycarbonyl group, 3,4,5-trifluorobenzyloxycarbonyl group, 2,3,4,5,6-pentafluorobenzyloxycarbonyl group, 2,4,6-trichlorobenzyloxycarbonyl group, 4-isopropylbenzyloxycarbonyl group, 4-n-butylbenzyloxycarbonyl group, 4-methylbenzyloxycarbonyl group, 2-methylbenzyloxycarbonyl group, 3-methylbenzyloxycarbonyl group, 2,4-dimethylbenzyloxycarbonyl group, 2,3-dimethylbenzyloxycarbonyl group, 2,6-dimethylbenzyloxycarbonyl group, 3,5-dimethylbenzyloxycarbonyl group, 2,5-dimethylbenzyloxycarbonyl group, 2,4,6-trimethylbenzyloxycarbonyl group, 3,5-ditrifluoromethylbenzyloxycarbonyl group, 4-isopropoxybenzyloxycarbonyl group, 4-n-butoxybenzyloxycarbonyl group, 4-methoxybanzyloxycarbonyl group, 2-methoxybenzyloxycarbonyl group, 3-methoxybenzyloxycarbonyl group, 2,4-dimethoxybenzyloxycarbonyl group, 2,3-dimethoxybenzyloxycarbonyl group, 2,6-dimethoxybenzyloxycarbonyl group, 3,5-dimethoxybenzyloxycarbonyl group, 2,5-dimethoxybenzyloxycarbonyl group, 2,4,6-trimethoxybenzyloxycarbonyl group, 3,5-ditrifluoromethoxybenzyloxycarbonyl group, 2-isopropoxybenzyloxycarbonyl group, 3-chloro-4-methoxybenzyloxycarbonyl group, 2-chloro-4-trifluoromethoxybenzyloxycarbonyl group, 3-methyl-4-fluorobenzyloxycarbonyl group, 4-bromo-3-trifluoromethylbenzyloxycarbonyl group, 2-(2-chlorophenyl)ethoxycarbonyl group, 2-(3-chlorophenyl)ethoxycarbonyl group, 2-(4-chlorophenyl)ethoxycarbonyl group, 2-trifluoromethylbenzyloxycarbonyl group, 3-trifluoromethylbenzyloxycarbonyl group, 4-trifluoromethylbenzyloxycarbonyl group, 2-trifluoromethoxybenzyloxycarbonyl group, 3-trifluoromethoxybenzyloxycarbonyl group, 4-trifluoromethoxybenzyloxycarbonyl group, 2-(2-trifluoromethylphenyl)ethoxycarbonyl group, 2-(3-trifluoromethylphenyl)ethoxycarbonyl group, 2-(4-trifluoromethylphenyl)ethoxycarbonyl group, 2-(2-trifluoromethoxyphenyl)ethoxycarbonyl group, 2-(3-trifluoromethoxyphenyl)ethoxycarbonyl group, 2-(4-trifluoromethoxyphenyl)ethoxycarbonyl group, 3-(2-trifluoromethylphenyl)propoxycarbonyl group, 3-(3-trifluoromethylphenyl)propoxycarbonyl group, 3-(4-trifluoromethylphenyl)propoxycarbonyl group, 3-(2-trifluoromethylphenyl)propoxycarbonyl group, 3-(3-trifluoromethoxyphenyl)propoxycarbonyl group, 3-(4-trifluoromethoxyphenyl)propoxycarbonyl group, 4-(3-trifluoromethylphenyl)butoxycarbonyl group, 5-(4-trifluoromethylphenyl)pentoxycarbonyl group, 4-(4-trifluoromethylphenyl)pentoxycarbonyl group, 4-(4-trifluoromethoxyphenyl)pentoxycarbonyl group, 6-(3-trifluoromethylphenyl)hexyoxylcarbonyl group, 6-(4-trifluoromethylphenyl)hexyoxylcarbonyl group, 6-(4-trifluoromethoxyphenyl)hexyloxycarbonyl group or the like.

A phenyl C2-C6 alkenylcarbonyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] includes a group composed of a phenyl group substituted by 1 to 5, preferably 1 to 3 substituents selected from the group consisting of a halogen atom, a halogen substituted or unsubstituted C1-C6 alkyl group and a halogen substituted or unsubstituted C1-C6 alkoxy group and an alkenylcarbonyl group containing 2 to 6 carbon atoms and having 1 to 3 double bonds. The phenyl C2-C6 alkenylcarbonyl group includes both trans and cis forms. Such a phenyl C2-C6 alkenylcarbonyl group includes a 2-phenylvinylcarbonyl group, 3-phenyl-2-propenylcarbonyl group (common name: cinnamoyl), 4-phenyl-2-butenylcarbonyl group, 4-phenyl-3-butenylcarbonyl group, 4-phenyl-1,3-butadienylcarbonyl group, 5-phenyl-1,3,5-hexatrienylcarbonyl group, 3-(2-fluorophenyl)-2-propenylcarbonyl group, 3-(3-fluorophenyl)-2-propenylcarbonyl group, 3-(4-fluorophenyl)-2-propenylcarbonyl group, 3-(2,3-difluorophenyl)-2-propenylcarbonyl group, 3-(2,3,4,5,6-pentafluorophenyl)-2-propenylcarbonyl group, 3-(2,4-difluorophenyl)-2-propenylcarbonyl group, 3-(3,4-difluorophenyl)-2-propenylcarbonyl group, 3-(3,5-difluorophenyl)-2-propenylcarbonyl group, 3-(2-chlorophenyl)-2-propenylcarbonyl group, 3-(3-chlorophenyl)-2-propenylcarbonyl group, 3-(4-chlorophenyl)-2-propenylcarbonyl group, 3-(2,3-dichlorophenyl)-2-propenylcarbonyl group, 3-(2,4-dichlorophenyl)-2-propenylcarbonyl group, 3-(3,4-dichlorophenyl)-2-propenylcarbonyl group, 3-(3,5-dichlorophenyl)-2-propenylcarbonyl group, 3-(2-bromophenyl)-2-propenylcarbonyl group, 3-(3-bromophenyl)-2-propenylcarbonyl group, 3-(4-bromophenyl)-2-propenylcarbonyl group, 3-(2-methylphenyl)-2-propenylcarbonyl group, 3-(3-methylphenyl)-2-propenylcarbonyl group, 3-(4-methylphenyl)-2-propenylcarbonyl group, 3-(4-trifluoromethylphenyl)-2-propenylcarbonyl group, 3-(2-fluoro-4-bromophenyl)-2-propenylcarbonyl group, 3-(4-chloro-3-fluorophenyl)-2-propenylcarbonyl group, 3-(2,3,4-trichlorophenyl)-2-propenylcarbonyl group, 3-(2,4,6-trichlorophenyl)-2-propenylcarbonyl group, 3-(4-isopropylphenyl)-2-propenylcarbonyl group, 3-(4-n-butylphenyl)-2-propenylcarbonyl group, 3-(2,4-dimethylphenyl)-2-propenylcarbonyl group, 3-(2,3-dimethylphenyl)-2-propenylcarbonyl group, 3-(2,6-dimethylphenyl)-2-propenylcarbonyl group, 3-(3,5-dimethylphenyl-2- propenylcarbonyl group, 3-(2,5-dimethylphenyl)-2-propenylcarbonyl group, 3-(2,4,6-trimethylphenyl)-2-propenylcarbonyl group, 3-(3,5-ditrifluoromethylphenyl)-2-propenylcarbonyl group, 3-(4-n-butoxyphenyl)-2-propenylcarbonyl group, 3-(2,4-dimethoxyphenyl)-2-propenylcarbonyl group, 3-(2,3-dimethoxyphenyl)-2-propenylcarbonyl group, 3-(2,6-dimethoxyphenyl)-2-propenylcarbonyl group, 3-(3,5-dimethoxyphenyl)-2-propenylcarbonyl group, 3-(2,5-dimethoxyphenyl)-2-propenylcarbonyl group, 3-(3,5-ditrifluoromethoxyphenyl)-2-propenylcarbonyl group, 3-(3-chloro-4-methoxyphenyl)-2-propenylcarbonyl group, 3-(2-chloro-4-trifluoromethoxyphenyl)-2-propenylcarbonyl group, 3-(3-methyl-4-fluorophenyl)-2-propenylcarbonyl group, 3-(4-bromo-3-trifluoromethylphenyl)-2-propenylcarbonyl group, 3-(3-trifluoromethylphenyl)-2-propenylcarbonyl group, 3-(4-trifluoromethylphenyl)-2-propenylcarbonyl group, 3-(2-trifluoromethoxyphenyl)-2-propenylcarbonyl group, 3-(3-trifluoromethoxyphenyl)-2-propenylcarbonyl group, 3-(4-trifluoromethoxyphenyl)-2-propenylcarbonyl group, 3-(2-methoxyphenyl)-2-propenylcarbonyl group, 3-(3-methoxyphenyl)-2-propenylcarbonyl group, 3-(4-methoxyphenyl)-2-propenylcarbonyl group, 3-(3,4-dimethoxyphenyl)-2-propenylcarbonyl group, 3-(3,5-dimethoxyphenyl)-2-propenylcarbonyl group, 4-(4-chlorophenyl)-2-butenylcarbonyl group, 4-(4-chlorophenyl)-3-butenylcarbonyl group, 5-(4-chlorophenyl)-2-pentenylcarbonyl group, 5-(4-chlorophenyl)-4-pentenylcarbonyl group, 5-(4-chlorophenyl)-3-pentenylcarbonyl group, 6-(4-chlorophenyl)-5-hexenylcarbonyl group, 6-(4-chlorophenyl)-4-hexenylcarbonyl group, 6-(4-chlorophenyl)-3-hexenylcarbonyl group, 6-(4-chlorophenyl)-3-hexenylcarbonyl group or the like.

A C1-C4 alkylenedioxy group includes a methylenedioxy group, ethylenedioxy group, trimethylenedioxy group, tetramethylenedioxy group or the like.

An amino substituted sulfonyl group which may have a C1-C6 alkyl group as a substituent includes an aminosulfonyl group which may have 1 to 2 C1-C6 alkyl groups as substituent, for example an aminosulfonyl group, methylaminosulfonyl group, ethylaminosulfonyl group, propylaminosulfonyl group, isopropylaminosulfonyl group, butylaminosulfonyl group, tert-butylaminosulfonyl group, pentylaminosulfonyl group, hexylaminosulfonyl group, dimethylaminosulfonyl group, diethylaminosulfonyl group, dipropylaminosulfonyl group, dibutylaminosulfonyl group, dipentylaminosulfonyl group, dihexylaminosulfonyl group, N-methyl-N-ethylaminosulfonyl group, N-ethyl-N-propylaminosulfonyl group, N-methyl-N-butylaminosulfonyl group, N-methyl-N-hexylaminosulfonyl group or the like.

A phenyl C1-C6 alkoxy group includes a benzyloxy group, 2-phenylethoxy group, 1-phenylethoxy group, 3-phenylpropoxy group, 2-phenylpropoxy group, 4-phenylbutoxy group, 5-phenylpentoxy group, 4-phenylpentoxy group, 6-phenylhexyloxy group, 2-methyl-3-phenylpropoxy group, 1,1-dimethyl-2-phenylethoxy group or the like.

A pyrrolidinyl group [wherein, on the pyrrolidine ring, at least one oxo group may be substituted] includes a pyrrolidinyl group (wherein, on the pyrrolidine ring, 1 or 2 oxo groups may be substituted), for example, a pyrrolidinyl group, 2-oxopyrrolidinyl group, 2,5-dioxopyrrolidinyl group or the like.

A pyrrolidinyl C1-C6 alkoxy group includes a (1-pyrrolidinyl)methoxy group, 2-(1-pyrrolidinyl)-ethoxy group, 1-(2-pyrrolidinyl)ethoxy group, 3-(1-pyrrolidinyl)propoxy group, 2-(3-pyrrolidinyl)propoxy group, 4-(1-pyrrolidinyl)butoxy group, 5-(2-pyrrolidinyl)pentoxy group, 4-(3-pyrrolidinyl)pentoxy group, 6-(1-pyrrolidinyl)hexyloxy group, 2-methyl-3-(1-pyrrolidinyl)propoxy group, 1,1-dimethyl-2-(1-pyrrolidinyl)ethoxy group or the like.

A benzofuryl C1-C6 alkyl group (wherein, on the benzofuran ring, at least one halogen atom may be substituted as a substituent) includes a benzofuryl substituted C1-C6 alkyl group which may be substituted by 1 to 3 halogen atoms on the benzofuran ring, for example, a 2-benzofurylmethyl group, 1-(2-benzofuryl)ethyl group, 2-(4-benzofuryl)ethyl group, 3-(5-benzofuryl)propyl group, 4-(6-benzofuryl)butyl group, 5-(7-benzofurylpentyl group, 6-(2-benzofuryl)hexyl group, 4-fluoro-2-benzofurylmethyl group, 5-fluoro-2-benzofurylmethyl group, 6-fluoro-2-benzofurylmethyl group, 7-fluoro-2-benzofurylmethyl group, 4-chloro-2-benzofurylmethyl group, 5-chloro-2-benzofurylmethyl group, 6-chloro-2-benzofurylmethyl group, 7-chloro-2-benzofurylmethyl group, 4-bromo-2-benzofurylmethyl group, 5-bromo-2-benzofurylmethyl group, 6-bromo-2-benzofurylmethyl group, 7-bromo-2-benzofurylmethyl group, 4-iodo-2-benzofurylmethyl group, 5-iodo-2-benzofurylmethyl group, 6-iodo-2-benzofurylmethyl group, 7-iodo-2-benzofurylmethyl group, 4-fluoro-3-benzofurylmethyl group, 5-fluoro-3-benzofurylmethyl group, 6-fluoro-3-benzofurylmethyl group, 7-fluoro-3-benzofurylmethyl group, 4-chloro-3-benzofurylmethyl group, 5-chloro-3-benzofurylmethyl group, 6-chloro-3-benzofurylmethyl group, 7-chloro-3-benzofurylmethyl group, 4-bromo-3-benzofurylmethyl group, 5-bromo-3-benzofurylmethyl group, 6-bromo-3-benzofurylmethyl group, 7-bromo-3-benzofurylmethyl group, 4-iodo-3-benzofurylmethyl group, 5-iodo-3-benzofurylmethyl group, 6-iodo-3-benzofurylmethyl group, 7-iodo-3-benzofurylmethyl group, 2-(4-fluoro-2-benzofuryl)ethyl group, 2-(5-fluoro-2-benzofuryl)ethyl group, 2-(6-fluoro-2-benzofuryl)ethyl group, 2-(7-fluoro-2-benzofuryl)ethyl group, 2-(4-chloro-2-benzofuryl)ethyl group, 2-(5-chloro-2-benzofuryl)ethyl group, 2-(6-chloro-2-benzofuryl)ethyl group, 2-(7-chloro-2-benzofuryl)ethyl group, 2-(4-fluoro-3-benzofuryl)methyl group, 2-(5-fluoro-3-benzofuryl)methyl group, 2-(6-fluoro-3-benzofuryl)ethyl group, 2-(7-fluoro-3-benzofuryl)ethyl group, 2-(4-chloro-3-benzofuryl)ethyl group, 2-(5-chloro-3-benzofuryl)ethyl group, 2-(6-chloro-3-benzofuryl)ethyl group, 2-(7-chloro-3-benzofuryl)ethyl group, 2-(4-fluoro-2-benzofuryl)ethyl group, 6-(5-fluoro-2-benzofuryl)hexyl group, 6-(6-fluoro-2-benzofuryl)hexyl group, 6-(7-fluoro-2-benzofuryl)hexyl group, 6-(4-chloro-2-benzofuryl)hexyl group, 6-(5-chloro-2-benzofuryl)hexyl group, 6-(6-chloro-2-benzofuryl)hexyl group, 6-(7-chloro-2-benzofuryl)hexyl group, 6-(4-fluoro-3-benzofuryl)methyl group, 6-(5-fluoro-3-benzofuryl)hexyl group, 6-(6-fluoro-3-benzofuryl)hexyl group, 6-(7-fluoro-3-benzofuryl)hexyl group, 6-(4-chloro-3-benzofuryl)hexyl group, 6-(5-chloro-3-benzofuryl)hexyl group, 6-(6-chloro-3-benzofuryl)hexyl group, 6-(7-chloro-3-benzofuryl)hexyl group, (2,4-dibromo-3-benzofuryl)methyl group, (4,5,6-trichloro-3-benzofuryl)methyl or the like.

A phenoxy C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is a group composed of a phenoxy group unsubstituted or substituted by 1 to 5, preferably 1 to 3 substituents selected from a halogen substituted or unsubstituted C1-C6 alkyl group, a halogen substituted or unsubstituted C1-C6 alkoxy group and a halogen as defined above and a C1-C6 alkyl group, examples of which include a phenoxymethyl group, 2-phenoxyethyl group, 3-phenoxypropyl group, 4-phenoxybutyl group, 5-phenoxypentyl group, 6-phenoxyhexyl group, 4-fluoro-6-methylphenoxymethyl group, 2-fluoro-4-bromophenoxymethyl group, 2-fluoro-4-bromophenoxymethyl group, 4-chloro-3-fluorophenoxymethyl group, 2-chlorophenoxymethyl group, 3-chlorophenoxymethyl group, 4-chlorophenoxymethyl group, 3,4-dichlorophenoxymethyl group, 2,3,4-trichlorophenoxymethyl group, 3,4,5-trichlorophenoxymethyl group, 2,4,6-trichlorophenoxymethyl group, 2(2-chlorophenoxy)ethyl group, 2-(3-chlorophenoxy)ethyl group, 2-(4-chlorophenoxy)ethyl group, 2-(3,4-dichlorophenoxy)ethyl group, 2(4-fluorophenoxy)ethyl group, 4-isopropylphenoxymethyl group, 4-n-butylphenoxymethyl group, 4-methylphenoxymethyl group, 2-methylphenoxymethyl group, 3-methylphenoxymethyl group, 4-n-propylphenoxymethyl group, 4-isopropylphenoxymethyl group, 2,4-dimethylphenoxymethyl group, 2,3-dimethylphenoxymethyl group, 2,6-dimethylphenoxymethyl group, 3,5-dimethylphenoxymethyl group, 2,5-dimethylphenoxymethyl group, 2,4,6-trimethylphenoxymethyl group, 2,4,6-trimethylphenoxymethyl group, 4-hexylphenoxymethyl group, 2-(3-methylphenoxy)ethyl group, 2-(3,4-dimethylphenoxy)ethyl group, 3,5-ditrifluoromethylphenoxymethyl group, 2,3,4,5,6-pentafluorophenoxymethyl group, 4-isopropoxyphenoxymethyl group, 4-n-butoxyphenoxymethyl group, 4-methoxyphenoxymethyl group, 2-methoxyphenoxymethyl group, 3-methoxyphenoxymethyl group, 2-(3-methoxyphenoxy)ethyl group, 2-(4-methoxyphenoxy)ethyl group, 2-(3,4-dimethoxyphenoxy)ethyl group, 2,4-dimethoxyphenoxymethyl group, 2,3-dimethoxyphenoxymethyl group, 3,4-dimethoxyphenoxymethyl group, 2,6-dimethoxyphenoxymethyl group, 3,5-dimethoxyphenoxymethyl group, 2,5-dimethoxyphenoxymethyl group, 2,4,6-trimethoxyphenoxymethyl group, 3,4,5-trimethoxyphenoxymethyl group, 3,5-ditrifluoromethoxyphenoxymethyl group, 2-isopropoxyphenoxymethyl group, 3-chloro-4-methoxyphenoxymethyl group, 2-chloro-4-methoxyphenoxymethyl group, 2-chloro-4-trifluoromethoxyphenoxymethyl group, 3-methyl-4-fluorophenoxymethyl group, 4-bromo-3-trifluoromethylphenoxymethyl group, 2-(4-fluorophenoxy)ethyl group, 3-(4-fluorophenoxy)propyl group, 4-(4-fluorophenoxy)butyl group, 5-(4-fluorophenoxy)pentyl group, 6-(4-fluorophenoxy)hexyl group, 4-chlorophenoxymethyl group, 3-(4-chlorophenoxy)propyl group, 4-(4-chlorophenoxy)butyl group, 5-(4-chlorophenoxy)pentyl group, 6-(4-chlorophenoxy)hexyl group, 4-methylphenoxymethyl group, 2-(4-methylphenoxy)ethyl group, 2-(2-isopropylphenoxy)ethyl group, 2-(4-isopropylphenoxy)ethyl group, 2-(4-hexylphenoxy)ethyl group, 2-(2-fluoro-5-methylphenoxy)ethyl group, 2-(2-chloro-4-methoxyphenoxy)ethyl group, 2-(3-fluoro-4-chlorophenoxy)ethyl group, 2-(3,4,5-trimethylphenoxy)ethyl group, 3-(4-methylphenoxy)propyl group, 4-(4-methylphenoxy)butyl group, 5-(4-methylphenoxy)pentyl group, 6-(4-methylphenoxy) hexyl group, 4-trifluoromethylphenoxymethyl group, 2-trifluoromethylphenoxymethyl group, 3-trifluoromethylphenoxymethyl group, 2-(4-trifluoromethylphenoxy)ethyl group, 2-(2-trifluoromethylphenoxy)ethyl group, 2-(3-trifluoromethylphenoxy)ethyl group, 3-(4-trifluoromethylphenoxy)propyl group, 4-(4-trifluoromethylphenoxy)butyl group, 5-(4-trifluoromethylphenoxy)pentyl group, 6-(4-trifluoromethylphenoxy)hexyl group, 4-trifluoromethoxyphenoxymethyl group, 2-(4-trifluoromethoxyphenoxy)ethyl group, 2-(3-trifluoromethoxyphenoxy)ethyl group, 2-(2-trifluoromethoxyphenoxy)ethyl group, 3-(4-trifluoromethoxyphenoxy)propyl group, 4-(4-trifluoromethoxyphenoxy)butyl group, 5-(4-trifluoromethoxyphenoxy)pentyl group, 6-(4-trifluoromethoxyphenoxy)hexyl group, 4-methoxyphenoxymethyl group, 2-isopropoxyphenoxymethyl group, 2-(4-methoxyphenoxy)ethyl group, 3-(4-methoxyphenoxy)propyl group, 4-(4-methoxyphenoxy)butyl group, 5-(4-methoxyphenoxy)pentyl group, 6-(4-methoxyphenoxy)hexyl group or the like.

A thiazolyl C1-C6 alkyl group (wherein, on the thiazole ring, at least one phenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substitute) includes a thiazolyl C1-C6 alkyl group (wherein, on the thiazole ring, 1 or 2 phenyl groups [wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted] may be substitute), for example, a 2-thiazolylmethyl group, 4-thiazolylmethyl group, 5-thiazolylmethyl group, 5-phenyl-4-thiazolylmethyl group, 4-phenyl-5-thiazolylmethyl group, 2-phenyl-4-thiazolylmethyl group, 2-phenyl-5-thiazolylmethyl group, 2,5-diphenyl-4-thiazolylmethyl group, 2,4-diphenyl-5-thiazolylmethyl group, 5-(2-fluorophenyl)-4-thiazolylmethyl group, 4-(2-fluorophenyl)-5-thiazolylmethyl group, 2-(2-chlorophenyl)-4-thiazolylmethyl group, 2-(2-bromophenyl)-5-thiazolylmethyl group, 2-(2,3,4,5,6-pentafluorophenyl)-4-thiazolylmethyl group, 2-(2-bromophenyl)-5-thiazolylmethyl group, 5-(3-iodophenyl)-4-thiazolylmethyl group, 4-(3-fluorophenyl)-5-thiazolylmethyl group, 2-(2,3-difluorophenyl)-4-thiazolylmethyl group, 2-(3-bromophenyl)-5-thiazolylmethyl group, 2-(3,4,5-trifluorophenyl)-4-thiazolylmethyl group, 2-(3-fluorophenyl)-5-thiazolylmethyl group, 5-(2,4,6-trichlorophenyl)-4-thiazolylmethyl group, 4-(2,3,4,5,6-pentafluorophenyl)-5-thiazolylmethyl group, 2-(4-fluorophenyl)-4-thiazolylmethyl group, 4-(2-fluorophenyl)-5-thiazolylmethyl group, 2-(4-fluorophenyl)-5-thiazolylmethyl group, 5-(2-chlorophenyl)-4-thiazolylmethyl group, 4-(2-chlorophenyl)-5-thiazolylmethyl group, 2-(2-chlorophenyl)-5-thiazolylmethyl group, 5-(3-methylphenyl)-4-thiazolylmethyl group, 4-(3-ethylphenyl)-5-thiazolylmethyl group, 2-(3-propylphenyl)-4-thiazolylmethyl group, 2-(2-n-butylphenyl)-5-thiazolylmethyl group, 2-(3-n-pentylphenyl)-4-thiazolylmethyl group, 2-(3-n-hexylphenyl)-5-thiazolylmethyl group, 5-(3,4-dimethylphenyl)-4-thiazolylmethyl group, 4-(2,4,6-trimethylphenyl)-5-thiazolylmethyl group, 2-(4-methoxyphenyl)-4-thiazolylmethyl group, 2-(4-ethoxyphenyl)-5-thiazolylmethyl group, 2-(4-propoxyphenyl)-4-thiazolylmethyl group, 2-(4-n-butoxyphenyl)-5-thiazolylmethyl group, 2-(2-thiazolyl)ethyl group, 2-(4-thiazolyl)ethyl group, 2-(5-thiazolyl)ethyl group, 2-(5-(2-n-pentyloxyphenyl)-4-thiazolyl]ethyl group, 2-(2-(2-n-hexyloxyphenyl)-5-thiazolyl]ethyl group, 2-(2-(2,5-dimethoxyphenyl)-4-thiazolyl]ethyl group, 2-(2-(2,4,6-trimethoxyphenyl)-5-thiazolyl]ethyl group, 2-(2-trifluoromethylphenyl)-4-thiazolylmethyl group, 2,4-di(trifluoromethyl)phenyl-5-thiazolylmethyl group, 2-trifluoromethoxyphenyl-4-thiazolylmethyl group, 2,3-di(trifluoromethoxy)phenyl-5-thiazolylmethyl group, 2-(2-methyl-5-trifluoromethoxyphenyl-4-thiazolyl)ethyl group, 3-(2-thiazolyl)propyl group, 2-(4-thiazolyl)propyl group, 3-(5-thiazolyl)propyl group, 3-((2-methoxy-4-trifluoromethylphenyl)-4-thiazolyl]]propyl group, 4-(2-thiazolyl)butyl group, 4-(4-thiazolyl)butyl group, 3-(5-thiazolyl)butyl group, 4-(4-(2-chloro-4-methylphenyl)-2-thiazolyl]butyl group, 5-(2-thiazolyl)pentyl group, 5-(5-(2-fluoro-3-methoxyphenyl)-2-thiazolyl]pentyl group, 5-(4-thiazolyl)pentyl group, 5-(5-thiazolyl)pentyl group, 5-(2-thiazolyl)hexyl group, 5-(4-thiazolyl)hexyl group, 5-(5-thiazolyl)hexyl group or the like.

A C1-C6 alkoxycarbonyl group is a group composed of a C1-C6 alkoxy group as defined above and a carbonyl group, examples of which include a methoxycarbonyl group, ethoxycarbonyl group, propoxycarbonyl group, isopropoxycarbonyl group, n-butoxycarbonyl group, isobutoxycarbonyl group, tert-butoxycarbonyl group, sec-butoxycarbonyl group, n-pentoxycarbonyl group, neopentoxycarbonyl group, n-hexyloxycarbonyl group, isohexyloxycarbonyl group, 3-methylpentoxycarbonyl group or the like.

A benzoyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) includes a benzoyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), for example, a benzoyl group, 2-fluorobenzoyl group, 3-fluorobenzoyl group, 4-fluorobenzoyl group, 2,3-difluorobenzoyl group, 3,4-difluorobenzoyl group, 2-chlorobenzoyl group, 3-chlorobenzoyl group, 4-chlorobenzoyl group, 2,3-dichlorobenzoyl group, 3,4-dichlorobenzoyl group, 2,4,6-trichlorobenzoyl group, 4-iodobenzoyl group, 2,3,4,5,6-pentafluorobenzoyl group, 2-bromobenzoyl group, 3-bromobenzoyl group, 4-bromobenzoyl group, 2,3-dibromobenzoyl group, 3,4-dibromobenzoyl group, 2-methylbenzoyl group, 3-methylbenzoyl group, 4-methylbenzoyl group, 2,3-dimethylbenzoyl group, 3,4-dimethylbenzoyl group, 3,4,5-trimethylbenzoyl group, 2-trifluoromethylbenzoyl group, 3-trifluoromethylbenzoyl group, 4-trifluoromethylbenzoyl group, 2,3-ditrifluoromethylbenzoyl group, 3,4-ditrifluoromethylbenzoyl group, 2-methoxybenzoyl group, 3-methoxybenzoyl group, 4-methoxybenzoyl group, 3,4-dimethoxybenzoyl group, 2,4,6-trimethoxybenzoyl group, 2-trifluoromethoxybenzoyl group, 3-trifluoromethoxybenzoyl group, 4-trifluoromethoxybenzoyl group, 2-methoxy-3-fluorobenzoyl group, 3-methyl-4-chlorobenzoyl group, 3-trifluoromethoxy-4-methylbenzoyl group, 2-methoxy-4-trifluoromethylbenzoyl group or the like.

A phenylcarbamoyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is a group composed of an aniline which may be substituted on the phenyl ring by 1 to 5, preferably 1 to 3 substituents selected from the group consisting of a halogen atom, a halogen substituted or unsubstituted C1-C6 alkyl group and a halogen substituted or unsubstituted C1-C6 alkoxy group, an N—C1-C6 alkylaniline or an N-phenyl C1-C6 alkylaniline and a carbonyl group, examples of which include a phenylcarbamoyl group, 2-fluorophenylcarbamoyl group, 3-fluorophenylcarbamoyl group, 4-fluorophenylcarbamoyl group, 2-chlorophenylcarbamoyl group, 3-chlorophenylcarbamoyl group, 4-chlorophenylcarbamoyl group, 2-bromophenylcarbamoyl group, 3-bromophenylcarbamoyl group, 4-bromophenylcarbamoyl group, 2-iodophenylcarbamoyl group, 3-iodophenylcarbamoyl group, 4-iodophenylcarbamoyl group, 2,3-difluorophenylcarbamoyl group, 3,4-difluorophenylcarbamoyl group, 3,5-difluorophenylcarbamoyl group, 2,4-difluorophenylcarbamoyl group, 2,6-difluorophenylcarbamoyl group, 2,3-dichlorophenylcarbamoyl group, 3,4-dichlorophenylcarbamoyl group, 3,5-dichlorophenylcarbamoyl group, 2,4-dichlorophenylcarbamoyl group, 2,6-dichlorophenylcarbamoyl group, 3,4,5-trifluorophenylcarbamoyl group, 2,3,4,5,6-pentafluorophenylcarbamoyl group, 3,4,5-trichlorophenylcarbamoyl group, 2,4,6-trifluorophenylcarbamoyl group, 2,4,6-trichlorophenylcarbamoyl group, 2-methylphenylcarbamoyl group, 3-methylphenylcarbamoyl group, 4-methylphenylcarbamoyl group, 2-methyl-3-chlorophenylcarbamoyl group, 3-methyl-4-chlorophenylcarbamoyl group, 2-chloro-4-methylphenylcarbamoyl group, 2-methyl-3-fluorophenylcarbamoyl group, 2-trifluoromethylphenylcarbamoyl group, 3-trifluoromethylphenylcarbamoyl group, N-methyl-N-phenylcarbamoyl group, N-(2-fluorophenyl)-N-methylcarbamoyl group, N-(3-fluorophenyl)-N-methylcarbamoyl group, N-(4-fluorophenyl)-N-methylcarbamoyl group, N-(2-chlorophenyl)-N-methylcarbamoyl group, N-(3-chlorophenyl)-N-methylcarbamoyl group, N-(4-chlorophenyl)-N-methylcarbamoyl group, N-(4-bromophenyl)-N-methylcarbamoyl group, N-(2-iodophenyl)-N-methylcarbamoyl group, N-(3-iodophenyl)-N-methylcarbamoyl group, N-(4-iodophenyl)-N-methylcarbamoyl group, N-(2,3-difluorophenyl)-N-methylcarbamoyl group, N-(3,4-difluorophenyl)-N-methylcarbamoyl group, N-(3,5-difluorophenyl)-N-methylcarbamoyl group, N-(2,4-difluorophenyl)-N-methylcarbamoyl group, N-(2,6-difluorophenyl)-N-methylcarbamoyl group, N-(2,3-dichlorophenyl)-N-methylcarbamoyl group, N-(3,4-dichlorophenyl)-N-methylcarbamoyl group, N-(3,5-dichlorophenyl)-N-methylcarbamoyl group, N-(2,4-dichlorophenyl)-N-methylcarbamoyl group, N-(2,6-dichlorophenyl)-N-methylcarbamoyl group, N-(3,4,5-trifluorophenyl)-N-methylcarbamoyl group, N-(3,4,5-trichlorophenyl)-N-methylcarbamoyl group, N-(2,4,6-trifluorophenyl)-N-methylcarbamoyl group, N-(2,4,6-trichlorophenyl)-N-methylcarbamoyl group, N-(2-methylphenyl)-N-methylcarbamoyl group, N-(3-methylphenyl)-N-methylcarbamoyl group, N-(4-methylphenyl)-N-methylcarbamoyl group, N-(2-methyl-3-chlorophenyl)-N-methylcarbamoyl group, N-(3-methyl-4-chlorophenyl)-N-methylcarbamoyl group, N-(2-chloro-4-methylphenyl)-N-methylcarbamoyl group, N-(2-methyl-3-fluorophenyl)-N-methylcarbamoyl group, N-(2-trifluoromethylphenyl)-N-methylcarbamoyl group, N-(4-trifluoromethylphenyl)-N-methylcarbamoyl group, N-benzyl-N-phenylcarbamoyl group, N-benzyl-N-(2-fluorophenyl)carbamoyl group, N-benzyl-N-(3-fluorophenyl)carbamoyl group, N-benzyl-N-(4-fluorophenyl)carbamoyl group, N-benzyl-N-(2-chlorophenyl)carbamoyl group, N-benzyl-N-(3-chlorophenyl)carbamoyl group, N-benzyl-N-(4-chlorophenyl)carbamoyl group, N-benzyl-N-(2-bromophenyl)carbamoyl group, N-benzyl-N-(3-bromophenyl)carbamoyl group, N-benzyl-N-(4-bromophenyl)carbamoyl group, N-benzyl-N-(2-iodophenyl)carbamoyl group, N-benzyl-N-(3-iodophenyl)carbamoyl group, N-benzyl-N-(4-iodophenyl)carbamoyl group, N-benzyl-N-(2,3-difluorophenyl)carbamoyl group, N-benzyl-N-(3,4-difluorophenyl)carbamoyl group, N-benzyl-N-(3,5-difluorophenyl)carbamoyl group, N-benzyl-N-(2,4-difluorophenyl)carbamoyl group, N-benzyl-N-(2,6-difluorophenyl)carbamoyl group, N-benzyl-N-(2,3-dichlorophenyl)carbamoyl group, N-benzyl-N-(3,4-dichlorophenyl)carbamoyl group, N-benzyl-N-(3,5-dichlorophenyl)carbamoyl group, N-benzyl-N-(2,4-dichlorophenyl)carbamoyl group, N-benzyl-N-(2,6-dichlorophenyl)carbamoyl group, N-benzyl-N-(3,4,5-trifluorophenyl)carbamoyl group, N-benzyl-N-(3,4,5-trichlorophenyl)carbamoyl group, N-benzyl-N-(2,4,6- trifluorophenyl)carbamoyl group, N-benzyl-N-(2,4,6-trichilorophenyl)carbamoyl group, N-benzyl-N-(2-methylphenyl)carbamoyl group, N-benzyl-N-(3-methylphenyl)carbamoyl group, N-benzyl-N-(4-methylphenyl)carbamoyl group, N-benzyl-N-(2-methyl-3-chlorophenyl)carbamoyl group, N-benzyl-N-(3-methyl-4-chlorophenyl)carbamoyl group, N-benzyl-N-(2-chloro-4-methylphenyl)carbamoyl group, N-benzyl-N-(2-methyl-3-fluorophenyl)carbamoyl group, N-benzyl-N-(2-trifluoromethylphenyl)carbamoyl group, N-benzyl-N-(3-trifluoromethylphenyl)carbamoyl group, N-benzyl-N-(4-trifluoromethylphenyl)carbamoyl group, 2-pentafluoroethylphenylcarbamoyl group, 3-pentafluoroethylphenylcarbamoyl group, 4-pentafluoroethylphenylcarbamoyl group, 2-isopropylphenylcarbamoyl group, 3-isopropylphenylcarbamoyl group, 4-isopropylphenylcarbamoyl group, 2-tert-butylphenylcarbamoyl group, 3-tert-butylphenylcarbamoyl group, 4-tert-butylphenylcarbamoyl group, 2-sec-butylphenylcarbamoyl group, 3-sec-butylphenylcarbamoyl group, 4-sec-butylphenylcarbamoyl group, 2-n-heptafluoropropylphenylcarbamoyl group, 3-n-heptafluoropropylphenylcarbamoyl group, 4-n-heptafluoropropylphenylcarbamoyl group, 4-pentylphenylcarbamoyl group, 4-hexylphenylcarbamoyl group, 2,4-dimethylphenylcarbamoyl group, 2,4,6-trimethylphenylcarbamoyl group, 3,4-dimethoxyphenylcarbamoyl group, 3,4,5-trimethoxyphenylcarbamoyl group, 2-methoxyphenylcarbamoyl group, 3-methoxyphenylcarbamoyl group, 4-methoxyphenylcarbamoyl group, 2-methoxy-3-chlorophenylcarbamoyl group, 2-fluoro-3-methoxyphenylcarbamoyl group, 2-fluoro-4-methoxyphenylcarbamoyl group, 2,6-dimethoxyphenylcarbamoyl group, 2,3,4-trifluorophenylcarbamoyl group, 3,4,5-trifluorophenylcarbamoyl group, 2-trifluoromethoxyphenylcarbamoyl group, 3-trifluoromethoxyphenylcarbamoyl group, 4-trifluoromethoxyphenylcarbamoyl group, 2-pentafluoroethoxyphenylcarbamoyl group, 3-pentafluoroethoxyphenylcarbamoyl group, 4-pentafluoroethoxyphenylcarbamoyl group, 2-isopropoxyphenylcarbamoyl group, 3-isopropoxyphenylcarbamoyl group, 4-isopropoxyphenylcarbamoyl group, 2-tert-butoxyphenylcabamoyl group, 3-tert-butoxyphenylcabamoyl group, 4-tert-butoxyphenylcabamoyl group, 2-sec-butoxyphenylcabamoyl group, 3-sec-butoxyphenylcabamoyl group, 4-sec-butoxyphenylcabamoyl group, 2-n-heptafluoropropoxyphenylcarbamoyl group, 3-n-heptafluoropropoxyphenylcarbamoyl group, 4-n-heptafluoropropoxyphenylcarbamoyl group, 4-n-pentyloxyphenylcarbamoyl group, 4-n-hexyloxyphenylcarbamoyl group or the like.

A benzothiazolyl group (wherein, on the benzothiazole ring, 1 to 3 C1-C6 alkyl groups may be substituted) includes a benzothiazolyl group (wherein, on the benzothiazole ring, at least one C1-C6 alkyl group may be substituted), for example, a (2-, 4-, 5-, 6- or 7-) benzothiazolyl group, 2-methyl-5-benzothiazolyl group, 4-ethyl-6-benzothiazolyl group, 5-propyl-7-benzothiazolyl group, 6-tert-butyl-2-benzothiazolyl group, 7-pentyl-4-benzothiazolyl group, 2-hexyl-5-benzothiazolyl group, 2,4-dimethyl-5-benzothiazolyl group, 2,4,6-trimethyl-7-benzothiazolyl group or the like.

A 2,3-dihydro-1H-indenyl group (wherein, on the 2,3-dihydro-1H-indene ring, at least one oxo group may be substituted) includes a 2,3-dihydro-1H-indenyl group (wherein, on the 2,3-dihydro-1H-indene ring, 1 or 2 oxo groups may be substituted), for example, a 2,3-dihydro-1H-indenyl group, 1-oxo-2,3-dihydro-1H-indenyl group, 1,3-dioxo-2,3-dihydro-1H-indenyl group or the like.

A phenyl C2-C6 alkenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is a group composed of 1 or 2 phenyl groups unsubstituted or substituted by 1 to 5, preferably 1 to 3 substituents selected from the group consisting of a halogen atom, a halogen substituted or unsubstituted C1-C6 alkyl group and a halogen substituted or unsubstituted C1-C6 alkoxy group and an alkenyl group containing 2 to 6 carbon atoms and having 1 to 3 double bonds. The phenyl C2-C6 alkenyl group includes both trans and cis forms. Such a phenyl C2-C6 alkenyl group includes a 2-phenylvinyl group, 3-phenyl-2-propenyl group (common name: cinnamyl group), 3,3-diphenyl-2-propenyl group, 3-phenyl-2-methyl-2-propenyl group, 4-phenyl-2-butenyl group, 4,4-diphenyl-2-butenyl group, 4-phenyl-3-butenyl group, 4-phenyl-1,3-butadienyl group, 5-phenyl-1,3,5-hexatrienyl group, 5,5-diphenyl-3-pentenyl group, 6,6-diphenyl-2-hexenyl group, 6-phenyl-1,3-hexadienyl group, 3-(2-fluorophenyl)-2-propenyl group, 3-(3-fluorophenyl)-2-propenyl group, 3-(4-fluorophenyl)-2-propenyl group, 3-(2,3-difluorophenyl)-2-propenyl group, 3-(2,3,4,5,6-pentafluorophenyl)-2-propenyl group, 3-(2,4-difluorophenyl)-2-propenyl group, 3-(3,4-difluorophenyl)-2-propenyl group, 3-(3,5-difluorophenyl)-2-propenyl group, 3-(2-chlorophenyl)-2-propenyl group, 3-(3-chlorophenyl)-2-propenyl group, 3-(4-chlorophenyl)-2-propenyl group, 3-(2,3-dichlorophenyl)-2-propenyl group, 3-(2,4-dichlorophenyl)-2-propenyl group, 3-(3,4-dichlorophenyl)-2-propenyl group, 3-(3,5-dichlorophenyl)-2-propenyl group, 3-(2,6-dichlorophenyl)-2-propenyl group, 3-(3,6-dichlorophenyl)-2-propenyl group, 3-(3,5,6-trichlorophenyl)-2-propenyl group, 3-(2,4,5-trichlorophenyl)-2-propenyl group, 3-(2-bromophenyl)-2-propenyl group, 3-(3-bromophenyl)-2-propenyl group, 3-(4-bromophenyl)-2-propenyl group, 3-(2-methylphenyl)-2-propenyl group, 3-(3-methylphenyl)-2-propenyl group, 3-(4-methylphenyl)-2-propenyl group, 3-(2-trifluoromethylphenyl)-2-propenyl group, 3-(2-fluoro-4-bromophenyl)-2-propenyl group, 3-(4-chloro-3-fluorophenyl)-2-propenyl group, 3-(2,3,4-trichlorophenyl)-2-propenyl group, 3-(2,4,6-trichlorophenyl)-2-propenyl group, 3-(4-ethylphenyl)-2-propenyl group, 3-(4-n-hexylphenyl)-2-propenyl group, 3-(4-isopropylphenyl)-2-propenyl group, 3-(4-n-butylphenyl)-2-propenyl group, 3-(2,4-dimethylphenyl)-2-propenyl group, 3-(2,3-dimethylphenyl)-2-propenyl group, 3-(2,6-dimethylphenyl)-2-propenyl group, 3-(3,5-dimethylphenyl)-2-propenyl group, 3-(2,5-dimethylphenyl)-2-propenyl group, 3-(2,4,6-trimethylphenyl)-2-propenyl group, 3-(3,5-ditrifluoromethylphenyl)-2-propenyl group, 3-(4-n-butoxyphenyl)-2-propenyl group, 3-(2,4-dimethoxyphenyl)-2-propenyl group, 3-(2,3-dimethoxyphenyl)-2-propenyl group, 3-(2,6-dimethoxyphenyl)-2-propenyl group, 3-(3,5-dimethoxyphenyl)-2-propenyl group, 3-(2,5-dimethoxyphenyl)-2-propenyl group, 3-(3,5-ditrifluoromethoxyphenyl)-2-propenyl group, 3-(3-chloro-4-methoxyphenyl)-2-propenyl group, 3-(2-chloro-4-trifluoromethoxyphenyl)-2-propenyl group, 3-(3-methyl-4-fluorophenyl)-2-propenyl group, 3-(2-methyl-4-fluorophenyl)-2-propenyl group, 3-(3-trifluoromethyl-4-fluorophenyl)-2-propenyl group, 3-(3-trifluoromethyl-2-fluorophenyl)-2-propenyl group, 3-(4-bromo-3-trifluoromethylphenyl)-2-propenyl group, 3-(4-chloro-3-trifluoromethylphenyl)-2-propenyl group, 3-(3-trifluoromethylphenyl)-2-propenyl group, 3-(2-trifluoromethylphenyl)-2-propenyl group, 3-(4-trifluoromethylphenyl)-2-propenyl group, 3-(2- trifluoromethoxyphenyl)-2-propenyl group, 3-(3-trifluoromethoxyphenyl)-2-propenyl group, 3-(4-trifluoromethoxyphenyl)-2-propenyl group, 3-(2-methoxyphenyl)-2-propenyl group, 3-(3-methoxyphenyl)-2-propenyl group, 3-(4-methoxyphenyl)-2-propenyl group, 3-(4-n-hexyloxyphenyl)-2-propenyl group, 3-(3,4-dimethoxyphenyl)-2-propenyl group, 3-(3,5-dimethoxyphenyl)-2-propenyl group, 4-(4-chlorophenyl)-2-butenyl group, 4-(4-chlorophenyl)-3-butenyl group, 5-(4-chlorophenyl)-2-pentenyl group, 5-(4-chlorophenyl)-4-pentenyl group, 5-(4-chlorophenyl)-3-pentenyl group, 6-(4-chlorophenyl)-5-hexenyl group, 6-(4-chlorophenyl)-4-hexenyl group, 6-(4-chlorophenyl)-3-hexenyl group, 6-(4-chlorophenyl)-3-hexenyl group or the like.

A phenyl group (wherein, on the phenyl ring, at least one selected from the group consisting of a C1-C4 alkylenedioxy group, a cyano group, a nitro group, an amino group which may have a C1-C6 alkyl group as a substituent, an amino substituted sulfonyl group which may have a C1-C6 alkyl group as a substituent, a C1-C6 alkoxycarbonyl group, a C1-C6 alkylthio group, a phenoxy group, a phenyl C1-C6 alkoxy group, a pyrrolidinyl group (wherein, on the pyrrolidine ring, at least one oxo group may be substituted), an imidazolyl group, an isooxazolyl group, an oxazolyl group, a phenyl C1-C6 alkyl group, a phenyl group, an amino C1-C6 alkyl group which may have a C1-C6 alkyl group as a substituent, a pyrrolidinyl C1-C6 alkoxy group, a halogen atom, a halogen substituted or unsubstituted C1-C6 alkyl group and a halogen substituted or unsubstituted C1-C6 alkoxy group may be substituted) includes, in addition to a phenyl group as described above (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl group (wherein, on the phenyl ring, 1 to 5, preferably 1 to 3 substituents selected from the group consisting of a C1-C4 alkylenedioxy group as described above, a cyano group, a nitro group, an amino group which may have 1 or 2 C1-C6 alkyl groups as a substituent as described later, an amino substituted sulfonyl group which may have 1 or 2 C1-C6 alkyl groups as a substituent as described above, a C1-C6 alkoxycarbonyl group as described later, a C1-C6 alkylthio group as described later, a phenoxy group, a phenyl C1-C6 alkoxy group as described above, a pyrrolidinyl group as described above (wherein, on the pyrrolidine ring, at least one oxo group may be substituted), an imidazolyl group, an isooxazolyl group, an oxazolyl group, a phenyl C1-C6 alkyl group as described above, a phenyl group, an amino C1-C6 alkyl group which may have a C1-C6 alkyl group as a substituent as described later, a pyrrolidinyl C1-C6 alkoxy group as described above, a halogen atom, a halogen substituted or unsubstituted C1-C6 alkyl group and a halogen substituted or unsubstituted C1-C6 alkoxy group may be substituted), for example, a 4-cyanophenyl group, 3-cyanophenyl group, 2-cyanophenyl group, 3,4-dicyanophenyl group, 2,4,6-tricyanophenyl group, 4-nitrophenyl group, 3-nitrophenyl group, 2-nitrophenyl group, 3,4-dinitrophenyl group, 2,4,6-trinitrophenyl group, 4-dimethylaminophenyl group, 3-methylaminophenyl group, 2-N-ethyl-N-methylaminophenyl group, 2,4-di(methylamino)phenyl group, 2,4,6-tri(methylamino)phenyl group, 4-dimethylaminosulfonylphenyl group, 3-methylaminosulfonylphenyl group, 2-N-ethyl-N-methylaminosulfonylphenyl group, 2,4-di(methylaminosulfonyl)phenyl group, 2,4,6-tri(methylaminosulfonyl)phenyl group, 4-ethoxycarbonylphenyl group, 4-ethoxycarbonylphenyl group, 3-methoxycarbonylphenyl group, 2-propoxycarbonylphenyl group, 2,4-diethoxycarbonylphenyl group, 2,4,6-triethoxycarbonylphenyl group, 4-methylthiophenyl group, 3-ethylthiophenyl group, 2-methylthiophenyl group, 3,4-dimethylthiophenyl group, 2,4,6-trimethylthiophenyl group, 3,4-ethylenedioxyphenyl group, 3,4-methylenedioxyphenyl group, 4-diisopropylaminomethylphenyl group, 3-methylaminomethylphenyl group, 2-ethylaminomethylphenyl group, 2,4-dimethylaminomethylphenyl group, 2,4,6-triethylaminomethylphenyl group, 4-phenoxyphenyl group, 3-phenoxyphenyl group, 2-phenoxyphenyl group, 2,4-diphenoxyphenyl group, 3,4,5-triphenoxyphenyl group, 4-benzyloxyphenyl group, 3-benzyloxyphenyl group, 2-benzyloxyphenyl group, 2,4-dibenzyloxyphenyl group, 2,4,6-tribenzyloxyphenyl group, 4-(2-oxo-1-pyrrolidinyl)phenyl group, 4-(5-oxazolyl)phenyl group, 4-(5-isooxazolyl)phenyl group, 4-(1-imidazolyl)phenyl group, 4-benzylphenyl group, 3-benzylphenyl group, 2-benzylphenyl group, 3,4-dibenzylphenyl group, 2,4,6-tribenzylphenyl group, 4-biphenyl group, 3-biphenyl group, 2-biphenyl group, 2,4-diphenylphenyl group, 2,4,6-triphenylphenyl group, 2-(2-imidazolyl)-4-phenoxyphenyl group, 3-(2-oxazolyl)-4-benzyloxyphenyl group, 4-(3-isooxazolyl)-2-benzylphenyl or the like.

A phenyl group [wherein, on the phenyl ring, a halogen may be substituted] includes a phenyl group which may be substituted by 1 to 5 halogen atoms on the phenyl ring, for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-trichlorophenyl group, 2,4,6-trifluorophenyl group, 2,4,6-trichlorophenyl group, 2-fluoro-4-bromophenyl group, 4-chloro-3-fluorophenyl group, 2,3,4-trichlorophenyl group, 3,4,5-trifluorophenyl group, 2,4,6-tribromophenyl group, 2,3,4,5,6-pentafluorophenyl group or the like.

A phenyl C1-C6 alkoxy substituted C1-C6 alkyl group (wherein, on the phenyl ring, at least one selected from the group consisting of a C1-C4 alkylenedioxy group, a halogen atom, a cyano group, a phenyl group, a phenyl C1-C6 alkoxy group, a phenyl C2-C6 alkenyl group, a phenoxy group, a C1-C6 alkylthio group, a halogen substituted or unsubstituted C1-C6 alkyl group and a halogen substituted or unsubstituted C1-C6 alkoxy group may be substituted) includes, in addition to a phenyl C1-C6 alkoxy substituted C1-C6 alkyl group as described above (wherein, on the phenyl group, at least one selected from the group consisting of a halogen atom, a halogen substituted or unsubstituted C1-C6 alkyl group and a halogen substituted or unsubstituted C1-C6 alkoxy group may be substituted), a phenyl C1-C6 alkoxy substituted C1-C6 alkyl group (wherein, on the phenyl ring, 1 to 5, preferably 1 to 3 substituents (preferably 1 or 2 substituents if the substituent is a C1-C4 alkylenedioxy group) selected from the group consisting of a straight or branched alkylenedioxy group containing 1 to 4 carbon atoms on the alkyl part as described above or later, a halogen atom, a cyano group, a phenyl group, a phenylalkoxy group having a straight or branched alkoxy containing 1 to 6 carbon atoms on the alkoxy part, a phenylenealkenyl group which is composed of a alkenyl group containing 2 to 6 carbon atoms and having at least 1 to 3 double bonds and includes both trans and cis forms, a phenoxy group, a straight or branched C1-C6 alkylthio group containing 1 to 6 carbon atoms, a halogen substituted or unsubstituted straight or branched C1-C6 alkyl group containing 1 to 6 carbon atoms and a halogen substituted or unsubstituted straight or branched C1-C6 alkoxy group containing 1 to 6 carbon atoms may be substituted), for example, a 4-cyanophenylmethoxymethyl group, 3-cyanophenylmethoxymethyl group, 2-cyanophenylmethoxymethyl group, 2,4-dicyanophenylmethoxymethyl group, 2,4,6-tricyanophenylmethoxymethyl group, 4-biphenylmethoxymethyl group, 3-biphenylmethoxymethyl group, 2-biphenylmethoxymethyl group, 2,4-diphenylphenylmethoxymethyl, 2,4,6-triphenylphenylmethoxymethyl group, 4-phenoxyphenylmethoxymethyl group, 3-phenoxyphenylmethoxymethyl group, 2-phenoxyphenylmethoxymethyl group, 3,4-diphenoxyphenylmethoxymethyl group, 3,4,5-triphenoxyphenylmethoxymethyl group, 4-methylthiophenylmethoxymethyl group, 3-ethylthiophenylmethoxymethyl group, 2-methylthiophenylmethoxymethyl group, 2,4-dimethylthiophenylmethoxymethyl group, 2,4,6-trimethylthiophenylmethoxymethyl group, 4-cyano-2-phenylphenylmethoxymethyl group, 3-phenoxy-4-methylthiophenylmethoxymethyl group, 3-trifluoromethyl-4-methylthiophenylmethoxymethyl group, 3-trifluoromethoxy-2-phenoxyphenylmethoxymethyl group, 3,4-methylenedioxyphenylmethoxymethyl group, 4-benzyloxyphenylmethoxymethyl group, 3,4-dibenzyloxyphenylmethoxymethyl group, 2,4,6-tribenzyloxyphenylmethoxymethyl group, 3-benzyloxyphenylmethoxymethyl group, 2-benzyloxyphenylmethoxymethyl group, 4-styrylphenylmethoxymethyl group, 3-styrylphenylmethoxymethyl group, 2-styrylphenylmethoxymethyl group, 2,4-distyrylphenylmethoxymethyl group, 2,4,6-tristyrylphenylmethoxymethyl group or the like.

A phenyl C1-C6 alkoxy group (wherein, on the phenyl ring, at least one selected from the group consisting of a cyano group, a phenyl group, a C1-C6 alkoxycarbonyl group, a phenoxy group, a C1-C6 alkylthio group, a halogen atom, a halogen substituted or unsubstituted C1-C6 alkyl group and a halogen substituted or unsubstituted C1-C6 alkoxy group may be substituted) includes, in addition to a phenyl C1-C6 alkoxy group as described above (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a C1-C6 alkoxy group substituted by 1 or 2 phenyl groups (wherein, on the phenyl ring, 1 to 5, preferably 1 to 3 substituents selected from the group consisting of a cyano group, a phenyl group, a C1-C6 alkoxycarbonyl group as described above, a phenoxy group, a C1-C6 alkylthio group as described above, a halogen atom, a halogen substituted or unsubstituted C1-C6 alkyl group and a halogen substituted or unsubstituted C1-C6 alkoxy group may be substituted), for example, a 4-cyanophenylmethoxy group, 3-cyanobenzyloxy group, 2-cyanobenzyloxy group, 2,4-dicyanobenzyloxy group, 2,3,4-tricyanobenzyloxy group, 4-biphenylmethoxy group, 3-biphenylmethoxy group, 2-biphenylmethoxy group, 2,4-diphenylbenzyloxy group, 2,4,6-triphenylbenzyloxy group, 4-methoxycarbonylbenzyloxy group, 3-ethoxycarbonylbenzyloxy group, 2-methoxycarbonylbenzyloxy group, 3,4-diethoxycarbonylbenzyloxy group, 3,4,5-trimethoxycarbonylbenzyloxy group, 3-phenoxybenzyloxy group, 2-phenoxybenzyloxy group, 4-phenoxybenzyloxy group, 2,4-diphenoxybenzyloxy group, 2,4,6-triphenoxybenzyloxy group, 4-methylthiobenzyloxy group, 3-methylthiobenzyloxy group, 2-methylthiobenzyloxy group, 3,4-dimethylthiobenzyloxy group, 2,5,6-trimethylthiobenzyloxy group, 3-cyano-4-bibenzyloxy group, 4-ethoxycarbonyl-3-phenoxybenzyloxy group, 3-methylthio-4-ethylbenzyloxy group, di(4-trifluoromethoxyphenyl)methoxy group, di(4-trifluoromethylphenyl)methoxy group, di(4-chlorophenyl)methoxy group, di(3-methoxyphenyl)methoxy group, di(2-methylphenyl)methoxy group, di(2,4-dimethoxyphenyl)methoxy group, di(3,4-dimethylphenyl) methoxy group, di(2,4,6-trimethoxyphenyl)methoxy group, di(3,4,5-trifluoromethylphenyl)methoxy group, di(2,4,6-trifluorophenyl)methoxy group, 1-(4-trifluoromethoxyphenyl)-1-(2,4-dichlorophenyl)methoxy or the like.

A phenyl C2-C6 alkenyloxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) includes a group composed of a phenyl group unsubstituted or substituted by 1 to 5, preferably 1 to 3 substituents selected from the group consisting of a halogen atom, a halogen C1-C6 alkyl group and a halogen substituted or unsubstituted C1-C6 alkoxy group and an alkenyl group containing 2 to 6 carbon atoms and having at least 1 to 3 double bonds. The phenyl C2-C6 alkenyloxy group includes both trans and cis forms. Such a phenyl C2-C6 alkenyloxy group includes a 2-phenylvinyloxy group, 3-phenyl-2-propenyloxy group (common name: cinnamyloxy group), 4-phenyl-2-butenyloxy group, 4-phenyl-3-butenyloxy group, 4-phenyl-1,3-butadienyloxy group, 5-phenyl-1,3,5-hexatrienyloxy group, 3-(2-fluorophenyl)-2-propenyloxy group, 3-(3-fluorophenyl)-2-propenyloxy group, 3-(4-fluorophenyl)-2-propenyloxy group, 3-(2,3-difluorophenyl)-2-propenyloxy group, 3-(2,3,4,5,6-pentafluorophenyl)-2-propenyloxy group, 3-(2,4-difluorophenyl)-2-propenyloxy group, 3-(3,4-difluorophenyl)-2-propenyloxy group, 3-(3,5-difluorophenyl)-2-propenyloxy group, 3-(2-chlorophenyl)-2-propenyloxy group, 3-(3-chlorophenyl)-2-propenyloxy group, 3-(4-chlorophenyl)-2-propenyloxy group, 3-(2,3-dichlorophenyl)-2-propenyloxy group, 3-(2,4-dichlorophenyl)-2-propenyloxy group, 3-(3,4-dichlorophenyl)-2-propenyloxy group, 3-(3,5-dichlorophenyl)-2-propenyloxy group, 3-(2-bromophenyl)-2-propenyloxy group, 3-(3-bromophenyl)-2-propenyloxy group, 3-(4-bromophenyl)-2-propenyloxy group, 3-(2-methylphenyl)-2-propenyloxy group, 3-(3-methylphenyl)-2-propenyloxy group, 3-(4-methylphenyl)-2-propenyloxy group, 3-(2-trifluoromethylphenyl)-2-propenyloxy group, 3-(2-fluoro-4-bromophenyl)-2-propenyloxy group, 3-(4-chloro-3-fluorophenyl)-2-propenyloxy group, 3-(2,3,4-trichlorophenyl)-2-propenyloxy group, 3-(2,4,6-trichlorophenyl)-2-propenyloxy group, 3-(4-isopropylphenyl)-2-propenyloxy group, 3-(4-n-butylphenyl)-2-propenyloxy group, 3-(2,4-dimethylphenyl)-2-propenyloxy group, 3-(2,3-dimethylphenyl)-2-propenyloxy group, 3-(2,6-dimethylphenyl)-2-propenyloxy group, 3-(3,5-dimethylphenyl)-2-propenyloxy group, 3-(2,5-dimethylphenyl)-2-propenyloxy group, 3-(2,4,6-trimethylphenyl)-2-propenyloxy group, 3-(3,5-ditrifluoromethylphenyl)-2-propenyloxy group, 3-(4-n-butoxyphenyl)-2-propenyloxy group, 3-(2,4-dimethoxyphenyl)-2-propenyloxy group, 3-(2,3-dimethoxyphenyl)-2-propenyloxy group, 3-(2,6-dimethoxyphenyl)-2-propenyloxy group, 3-(3,5-dimethoxyphenyl)-2-propenyloxy group, 3-(2,5-dimethoxyphenyl)-2-propenyloxy group, 3-(3,5-ditrifluoromethoxyphenyl)-2-propenyloxy group, 3-(3-chloro-4-methoxyphenyl)-2-propenyloxy group, 3-(2-chloro-4-trifluoromethoxyphenyl)-2-propenyloxy group, 3-(3-methyl-4-fluorophenyl)-2-propenyloxy group, 3-(4-bromo-3-trifluoromethylphenyl)-2-propenyloxy group, 3-(3-trifluoromethylphenyl)-2-propenyloxy group, 3-(4-trifluoromethylphenyl)-2-propenyloxy group, 3-(2-trifluoromethoxyphenyl)-2- propenyloxy group, 3-(3-trifluoromethoxyphenyl)-2-propenyloxy group, 3-(4-trifluoromethoxyphenyl)-2-propenyloxy group, 3-(2-methoxyphenyl)-2-propenyloxy group, 3-(3-methoxyphenyl)-2-propenyloxy group, 3-(4-methoxyphenyl)-2-propenyloxy group, 3-(3,4-dimethoxyphenyl)-2-propenyloxy group, 3-(3,5-dimethoxyphenyl)-2-propenyloxy group, 4-(4-chlorophenyl)-2-butenyloxy group, 5-(4-chlorophenyl)-2-pentenyloxy group, 4-(4-chlorophenyl)-3-butenyloxy group, 5-(4-chlorophenyl)-4-pentenyloxy group, 5-(4-chlorophenyl)-3-pentenyloxy group, 6-(4-chlorophenyl)-5-hexenyloxy group, 6-(4-chlorophenyl)-4-hexenyloxy group, 6-(4-chlorophenyl)-3-hexenyloxy group, 6-(4-chlorophenyl)-3-hexenyloxy group or the like.

A C1-C6 alkyl group which may have a hydroxide group as a substituent includes, in addition to a C1-C6 alkyl group as described above, a C1-C6 straight or branched alkyl group which may have 1 to 3 hydroxide groups, for example, a hydroxymethyl group, 2-hydroxyethyl group, 1-hydroxyethyl group, 3-hydroxypropyl group, 2,3-dihydroxypropyl group, 4-hydroxybutyl group, 3,4-dihydroxybutyl group, 1,1-dimethyl-2-hydroxyethyl group, 5-hydroxypentyl group, 6-hydroxyhexyl group, 2-methyl-3-hydroxypropyl group, 2,3,4-trihydroxybutyl group or the like, A C1-C6 alkanoyl group includes a group derived from an aliphatic carboxylic acid containing 1 to 6 carbon atoms, examples of which include a formyl group, acetyl group, propionyl group, butyryl group, pentanoyl group, hexanoyl group or the like.

A phenyl C1-C6 alkoxycarbonyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] is a group composed of a phenyl C1-C6 alkoxy group which may be substituted by 1 to 5, preferably 1 to 3 substituents selected from the group consisting of a halogen atom, a halogen substituted or unsubstituted C1-C6 alkyl group and a halogen substituted or unsubstituted C1-C6 alkoxy group as defined above and a carbonyl group, examples of which include a benzyloxycarbonyl group, 2-phenylethoxycarbonyl group, 3-phenylpropoxycarbonyl group, 2-phenylpropoxycarbonyl group, 4-phenylbutoxycarbonyl group, 5-phenylpentoxycarbonyl group, 4-phenylpentoxycarbonyl group, 6-phenylhexyloxycarbonyl group, 2-fluorobenzyloxycarbonyl group, 3-fluorobenzyloxycarbonyl group, 4-fluorobenzyloxycarbonyl group, 2-(2-fluorophenyl)ethoxycarbonyl group, 2-(3-fluorophenyl)ethoxycarbonyl group, 2-(4-fluorophenyl)ethoxycarbonyl group, 2-chlorobenzyloxycarbonyl group, 3-chlorobenzyloxycarbonyl group, 4-chlorobenzyloxycarbonyl group, 2-fluoro-4-bromobenzyloxycarbonyl group, 4-chloro-3-fluorobenzyloxycarbonyl group, 2,3,4-trichlorobenzyloxycarbonyl group, 3,4,5-trifluorobenzyloxycarbonyl group, 2,3,4,5,6-pentafluorobenzyloxycarbonyl group, 2,4,6-trichlorobenzyloxycarbonyl group, 4-isopropylbenzyloxycarbonyl group, 4-n-butylbenzyloxycarbonyl group, 4-methylbenzyloxycarbonyl group, 2-methylbenzyloxycarbonyl group, 3-methylbenzyloxycarbonyl group, 2,4-dimethylbenzyloxycarbonyl group, 2,3-dimethylbenzyloxycarbonyl group, 2,6-dimethylbenzyloxycarbonyl group, 3,5-dimethylbenzyloxycarbonyl group, 2,5-dimethylbenzyloxycarbonyl group, 2,4,6-trimethylbenzyloxycarbonyl group, 3,5-ditrifluoromethylbenzyloxycarbonyl group, 4-isopropoxybenzyloxycarbonyl group, 4-n-butoxybenzyloxycarbonyl group, 4-methoxybenzyloxycarbonyl group, 2-methoxybenzyloxycarbonyl group, 3-methoxybenzyloxycarbonyl group, 2,4-dimethoxybenzyloxycarbonyl group, 2,3-dimethoxybenzyloxycarbonyl group, 2,6-dimethoxybenzyloxycarbonyl group, 3,5-dimethoxybenzyloxycarbonyl group, 2,5-dimethoxybenzyloxycarbonyl group, 2,4,6-trimethoxybenzyloxycarbonyl group, 3,5-ditrifluoromethoxybenzyloxycarbonyl group, 2-isopropoxybenzyloxycarbonyl group, 3-chloro-4-methoxybanzyloxycarbonyl group, 2-chloro-4-trifluoromethoxybenzyloxycarbonyl group, 3-methyl-4-fluorobenzyloxycarbonyl group, 4-bromo-3-trifluoromethylbenzyloxycarbonyl group, 2-(2-chlorophenyl)ethoxycarbonyl group, 2-(3-chlorophenyl)ethoxycarbonyl group, 2-(4-chlorophenyl)ethoxycarbonyl group, 2-trifluoromethylbenzyloxycarbonyl group, 3-trifluoromethylbenzyloxycarbonyl group, 4-trifluoromethylbenzyloxycarbonyl group, 2-trifluoromethoxybenzyloxycarbonyl group, 3-trifluoromethoxybenzyloxycarbonyl group, 4-trifluoromethoxybenzyloxycarbonyl group, 2-(2-trifluoromethylphenyl)ethoxycarbonyl group, 2-(3-trifluoromethylphenyl)ethoxycarbonyl group, 2-(4-trifluoromethylphenyl)ethoxycarbonyl group, 2-(2-trifluoromethoxyphenyl)ethoxycarbonyl group, 2-(3-trifluoromethoxyphenyl)ethoxycarbonyl group, 2-(4-trifluoromethoxyphenyl)ethoxycarbonyl group, 3-(2-trifluoromethylphenyl)propoxycarbonyl group, 3-(3-trifluoromethylphenyl)propoxycarbonyl group, 3-(4-trifluoromethylphenyl)propoxycarbonyl group, 3-(2-trifluoromethylphenyl)propoxycarbonyl group, 3-(3-trifluoromethoxuphenyl)propoxycarbonyl group, 3-(4-trifluoromethoxyphenyl)propoxycarbonyl group, 4-(3-trifluoromethylphenyl)butoxycarbonyl group, 5-(4-trifluoromethylphenyl)pentoxycarbonyl group, 4-(4-trifluoromethoxyphenyl)pentoxycarbonyl group, 6-(3-trifluoromethylphenylhexyloxycarbonyl group, 6-(4-trifluoromethylphenyl)hexyloxycarbonyl group, 6-(4-trifluoromethoxyphenyl)hexyloxycarbonyl group or the like.

An amino group which may have a group selected from the group consisting of a C1-C6 alkanoyl group and a C1-C6 alkyl group as a substituent includes an amino group which may have 1 or 2 groups selected from the group consisting of a C1-C6 alkanoyl group and a C1-C6 alkyl group as a substituent, for example, an amino group, methylamino group, ethylamino group, n-propylamino group, isopropylamino group, n-butylamino group, tert-butylamino group, n-pentylamino group, n-hexylamino group, dimethylamino group, diethylamino group, di-n-propylamino group, di-n-butylamino group, di-n-pentylamino group, di-n-hexylamino group, N-methyl-N-ethylamino group, N-ethyl-N-n-propylamino group, N-methyl-N-n-butylamino group, N-methyl-N-n-hexylamino group, N-methyl-N-acetylamino group, acetylamino group, formylamino group, n-propionylamino group, n-butyrylamino group, isobutyrylamino group, n-pentanoylamino group, n-hexanoylamino group, N-ethyl-N-acetylamino group or the like.

A 1,2,3,4-tetrahydroquinolyl group (wherein, on the 1,2,3,4-tetrahydroquinoline ring, at least one oxo group may be substituted as a substituent) includes a 1,2,3,4-tetrahydroquinolyl group (wherein, wherein, on the 1,2,3,4-tetrahydroquinoline ring, 1 or 2 oxo groups may be substituted as a substituent), for example, a 1,2,3,4-tetrahydro-1-quinolyl group, 1,2,3,4-tetrahydro-2-quinolyl group, 1,2,3,4-tetrahydro-3-quinolyl group, 1,2,3,4-tetrahydro-4-quinolyl group, 1,2,3,4-tetrahydro-5-quinolyl group, 1,2,3,4-tetrahydro-6-quinolyl group, 1,2,3,4-tetrahydro-7-quinolyl group, 1,2,3,4-tetrahydro-8-quinolyl group, 2-oxo-1,2,3,4-tetrahydro-1-quinolyl group, 4-oxo-1,2,3,4-tetrahydro-1-quinolyl group, 2,4-dioxo-1,2,3,4-tetrahydro-1-quinolyl group, 2-oxo-1,2,3,4-tetrahydro-6-quinolyl group, 2-oxo-1,2,3,4-tetrahydro-4-quinolyl group, 2-oxo-1,2,3,4-tetrahydro-7-quinolyl group, 2-oxo-1,2,3,4-tetrahydro-8-quinolyl group, 2-oxo-1,2,3,4-tetrahydro-5-quinolyl group, 2-oxo-1,2,3,4-tetrahydro-3-quinolyl group or the like.

A C1-C6 alkylsulfonyl group is a group composed of an alkyl group containing 1 to 6 carbon atoms and a sulfonyl group, examples of which include a methanesulfonyl group, ethanesulfonyl group, n-propanesulfonyl group and n-butanesulfonyl group, n-pentanesulfonyl group, n-hexanesulfonyl group or the like.

A C3-C8 cycloalkyl group is a three-membered, four-membered, five-membered, six-membered, seven-membered or eight-membered cyclic alkyl group containing 3 to 8 carbon atoms, examples of which include a cyclopropyl group, cyclobutyl group, cyclopentyl group, cyclohexyl group, cycloheptyl group, cyclooctyl group, 3,4-dimethylcyclopentyl group, 3,3-dimethylcyclohexyl group or the like.

A C1-C6 alkylthio group is a linear or branched alkylthio group containing 1 to 6 carbon atoms, examples of which include a methylthio group, ethylthio group, n-propylthio group, isopropylthio group, n-butylthio group, isobutylthio group, tert-butylthio group, sec-butylthio group, n-pentylthio group, neopentylthio group, n-hexylthio group, isohexylthio group, 3-methylpentylthio group or the like.

A phenylsulfonyl group (wherein, on the phenyl ring, at least one selected from the group consisting of a halogen atom, a halogen substituted or unsubstituted C1-C6 alkyl group, a halogen substituted or unsubstituted C1-C6 alkoxy group may be substituted) is a phenylsulfonyl group unsubstituted or having 1 to 5, preferably 1 to 3 substituents selected from the group consisting of a halogen atom, a halogen substituted or unsubstituted C1-C6 alkyl group, a halogen substituted or unsubstituted C1-C6 alkoxy group as defined above, examples of which include a phenylsulfonyl group, 2-fluorophenylsulfonyl group, 3-fluorophenylsulfonyl group, 4-fluorophenylsulfonyl group, 2-chlorophenylsulfonyl group, 3-chlorophenylsulfonyl group, 4-chlorophenylsulfonyl group, 2-bromophenylsulfonyl group, 3-bromophenylsulfonyl group, 4-bromophenylsulfonyl group, 2-iodophenylsulfonyl group, 3-iodophenylsulfonyl group, 4-iodophenylsulfonyl group, 2,3-difluorophenylsulfonyl group, 3,4-difluorophenylsulfonyl group, 3,5-difluorophenylsulfonyl group, 2,4-difluorophenylsulfonyl group, 2,6-difluorophenylsulfonyl group, 2,3-dichlorophenylsulfonyl group, 3,4-dichlorophenylsulfonyl group, 3,5-dichlorophenylsulfonyl group, 2,4-dichlorophenylsulfonyl group, 2,6-dichlorophenylsulfonyl group, 3,4,5-trifluorophenylsulfonyl group, 3,4,5-trichlorophenylsulfonyl group, 2,4,6-trifluorophenylsulfonyl group, 2,4,6-trichlorophenylsulfonyl group, 2-fluoro-4-bromophenylsulfonyl group, 4-chloro-3-fluorophenylsulfonyl group, 2,3,4-trichlorophenylsulfonyl group, 3,4,5-trifluorophenylsulfonyl group, 2,3,4,5,6-pentafluorophenylsulfonyl group, 2,4,6-trimethylphenylsulfonyl group, 4-n-butylphenylsulfonyl group, 2,4-dimethylphenylsulfonyl group, 2,3-dimethylphenylsulfonyl group, 2,6-dimethylphenylsulfonyl group, 3,5-dimethylphenylsulfonyl group, 2,5-dimethylphenylsulfonyl group, 3,5-ditrifluoromethylphenylsulfonyl group, 4-n-butoxyphenylsulfonyl group, 2,4-dimethoxyphenylsulfonyl group, 2,3-dimethoxyphenylsulfonyl group, 2,6-dimethoxyphenylsulfonyl group, 3,5-dimethoxyphenylsulfonyl group, 2,5-dimethoxyphenylsulfonyl group, 2,4,6-trimethoxyphenylsulfonyl group, 3,5-ditrifluoromethoxyphenylsulfonyl group, 3-chloro-4-methoxyphenylsulfonyl group, 2-chloro-4-trifluoromethoxyphenylsulfonyl group, 3-methyl-4-fluorophenylsulfonyl group, 4-bromo-3-trifluoromethylphenylsulfonyl group, 2-methylphenylsulfonyl group, 3-methylphenylsulfonyl group, 4-methylphenylsulfonyl group, 2-methyl-3-chlorophenylsulfonyl group, 3-methyl-4-chlorophenylsulfonyl group, 2-chloro-4-methylphenylsulfonyl group, 2-methyl-3-fluorophenylsulfonyl group, 2-trifluoromethylphenylsulfonyl group, 3-trifluoromethylphenylsulfonyl group, 4-trifluoromethylphenylsulfonyl group, 2-pentafluoroethylphenylsulfonyl group, 3-pentafluoroethylphenylsulfonyl group, 4-pentafluoroethylphenylsulfonyl group, 2-isopropylphenylsulfonyl group, 3-isopropylphenylsulfonyl group, 4-isopropylphenylsulfonyl group, 2-tert-butylphenylsulfonyl group, 3-tert-butylphenylsulfonyl group, 4-tert-butylphenylsulfonyl group, 2-sec-butylphenylsulfonyl group, 3-sec-butylphenylsulfonyl group, 4-sec-butylphenylsulfonyl group, 2-n-heptafluoropropylphenylsulfonyl group, 3-n-heptafluoropropylphenylsulfonyl group, 4-n-heptafluoropropylphenylsulfonyl group, 4-n-pentylphenylsulfonyl group, 4-n-hexylphenylsulfonyl group, 2-methoxyphenylsulfonyl group, 3-methoxyphenylsulfonyl group, 4-methoxyphenylsulfonyl group, 3-chloro-2-methoxyphenylsulfonyl group, 2-fluoro-3-methoxyphenylsulfonyl group, 2-fluoro-4-methoxyphenylsulfonyl group, 2,6-dimethoxyphenylsulfonyl group, 2,3,4-trifluoropheriylsulfonyl group, 2,4,6-trifluorophenylsulfonyl group, 2-trifluoromethoxyphenylsulfonyl group, 3-trifluoromethoxyphenylsulfonyl group, 4-trifluoromethoxyphenylsulfonyl group, 3-fluoro-2-trifluoromethoxyphenylsulfonyl group, 2-fluoro-3-trifluoromethoxyphenylsulfonyl group, 3-fluoro-4-trifluoromethoxyphenylsulfonyl group, 3-chloro-2-trifluoromethoxyphenylsulfonyl group, 2-chloro-3-trifluoromethoxyphenylsulfonyl group, 3-chloro-4-trifluoromethoxyphenylsulfonyl group, 2-pentafluoroethoxyphenylsulfonyl group, 3-pentafluoroethoxyphenylsulfonyl group, 4-pentafluoroethoxyphenylsulfonyl group, 3-chloro-2-pentafluoroethoxyphenylsulfonyl group, 2-chloro-3-pentafluoroethoxyphenylsulfonyl group, 3-Chloro-4-pentafluoroethoxyphenylsulfonyl group, 2-isopropoxyphenylsulfonyl group, 3-isopropoxyphenylsulfonyl group, 4-isopropoxyphenylsulfonyl group, 2-tert-butoxyphenylsulfonyl group, 3-tert-butoxyphenylsulfonyl group, 4-tert-butoxyphenylsulfonyl group, 2-sec-butoxyphenylsulfonyl group, 3-sec-butoxyphenylsulfonyl group, 4-sec-butoxyphenylsulfonyl group, 2-n-heptafluoropropoxyphenylsulfonyl group, 3-n-heptafluoropropoxyphenylsulfonyl group, 4-n-heptafluoropropoxyphenylsulfonyl group, 4-n-pentoxyphenylsulfonyl group, 4-n-hexyloxyphenylsulfonyl group or the like.

An amino substituted C1-C6 alkoxy group which may have C1-C6 alkyl group(s) as substituent includes an amino-C1-C6 alkoxy group which may have 1 or 2 C1-C6 alkyl groups as a substituent, for example, an aminomethoxy group, 2-aminoethoxy group, 1-aminoethoxy group, 3-aminopropoxy group, 4-aminobutoxy group, 5-aminopentyloxy group, 6-aminohexyloxy group, 2-methyl-3-aminopropoxy group, 1,1-dimethyl-2-aminoethoxy group, ethylaminoethoxy group, 1-(propylamino)ethoxy group, 2-(methylamino) ethoxy group, 3-(isopropylamino)propoxy group, 4-(n-butylamino)butoxy group, 5-(n-pentylamino)pentyloxy group, 6-(n-hexylamino)hexyloxy group, dimethylaminomethoxy group, 3-dimethylaminopropoxy group, (N-ethyl-N-propylamino)methoxy group, 2-(N-methyl-N-hexylamino)ethoxy group or the like.

A phenyl group [wherein, on the phenyl ring, at least one selected from the group consisting of a halogen atom, a halogen substituted or unsubstituted C1-C6 alkyl group, a halogen substituted or unsubstituted C1-C6 alkoxy group, an amino group which may have substituent(s) selected from the group consisting of a C1-C6 alkanoyl group and a C1-C6 alkyl group as substituent, a C1-C6 alkoxycarbonyl group, a phenyl group, a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), an aminosulfonyl group, a 1,2,3,4-tetrahydroquinolyl group (wherein, on the 1,2,3,4-tetrahydroquinoline ring, at least one oxo group may be substituted as a substituent), a C1-C6 alkylsulfonyl group, C3-C8 cycloalkyl group, a nitro group, a cyano group, a C1-C6 alkylthio group, a phenylsulfonyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a hydroxyl group substituted C1-C6 alkyl group and a group:

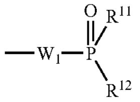

(wherein, $W_1$ represents a C1 to C6 alkylene group, and $R^{11}$ and $R^{12}$ are identical or different and each represent a C1-C6 alkoxy group) may be substituted as a substituent] includes a phenyl group which may be substituted at the 2 to 6 positions of the phenyl ring by 1 to 5, preferably 1 to 3 substituents selected from the group consisting of a halogen atom, a halogen substituted or unsubstituted C1-C6 alkyl group, a halogen substituted or unsubstituted C1-C6 alkoxy group, an amino group which may have 1 or 2 substituents selected from the group consisting of a C1-C6 alkanoyl group and a C1-C6 alkyl group as a substituent, a C1-C6 alkoxycarbonyl group, a phenyl group, a phenoxy group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), an aminosulfonyl group, a 1,2,3,4-tetrahydroquinolyl group (wherein, on the 1,2,3,4-tetrahydroquinoline ring, 1 to 2 oxo groups may be substituted as a substituent), a C1-C6 alkylsulfonyl group, C3-C8 cycloalkyl group, a nitro group, a cyano group, a C1-C6 alkylthio group, a phenylsulfonyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a hydroxyl group substituted C1-C6 alkyl group and a group:

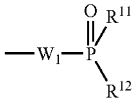

(wherein, $W_1$ represents a C1 to C6 alkylene group, and $R^{11}$ and $R^{12}$ are identical or different and each represent a C1-C6 alkoxy group) as described above.

A hydroxyl group substituted C1-C6 linear or branched alkyl group having 1 to 3 hydroxyl groups, for example, a hydroxymethyl group, 2-hydroxyethyl group, 1-hydroxyethyl group, 3-hydroxypropyl group, 2,3-dihydroxypropyl group, 4-hydroxybutyl group, 3,4-dihydroxybutyl group, 1,1-dimethyl-2-hydroxyethyl group, 5-hydroxypentyl group, 6-hydroxyhexyl group, 2-methyl-3-hydroxypropyl group, 2,3,4-trihydroxybutyl group or the like.

A halogen substituted or unsubstituted C1-C10 alkoxy group includes, in addition to a halogen substituted or unsubstituted C1-C6 alkoxy group as described above, a C1-C10 alkoxy group substituted by 1 to 7 C1-C10 alkoxy groups and halogen atoms, for example, a heptyloxy group, octyloxy group, nonyloxy group, decyloxy group, 7-fluoroheptyloxy group, 7,7,6-trifluoroheptyloxy group, 7,7,7,6,6,5,5-heptafluoroheptyloxy group, 8-chlorooctyloxy group, 8,8-dibromooctyloxy group, 6,7,8-trifluorooctyloxy group, 8,8,8,7,7,6,6-heptafluorooctyloxy group, 8,8,8,7,7-pentachlorooctyloxy group, 9-iodononyloxy group, 9,9-dibromononyloxy group, 9,9,9,8,8-pentachlorononyloxy group, 9,9,9,8,8,7,7-heptafluorononyloxy group, 10-chlorodecyloxy group, 10,10-dibromodecyloxy group, 10,10,10,9-tetrachlorodecyloxy group, 10,10,10,9,9,9,8,8-heptafluorodecyloxy group or the like.

A phenyl C1-C6 alkyl group (wherein, on the phenyl ring, at least one selected from the group consisting of a C1-C4 alkylenedioxy group, a phenyl group, a halogen atom, a halogen substituted or unsubstituted C1-C6 alkyl group and a halogen substituted or unsubstituted C1-C6 alkoxy group may be substituted as a substituent) is a phenyl C1-C6 alkyl group unsubstituted or substituted on the phenyl ring constituting the alkyl group by 1 to 5, preferably 1 to 3 substituents (preferably 1 or 2 substituents if the substituent is a C1-C4 alkylenedioxy group) selected from the group consisting of a C1-C4 alkylenedioxy group, a phenyl group, a halogen atom, a halogen substituted or unsubstituted C1-C6 alkyl group and a halogen substituted or unsubstituted C1-C6 alkoxy group, examples of which include a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2,3-methylenedioxybenzyl group, 3,4-methylenedioxybenzyl group, 3-phenylbenzyl group, 2-phenylbenzyl group, 4-phenylbenzyl group, 3,4-diphenylbenzyl group, 2,4,6-triphenylbenzyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,4-difluorobenzyl group, 2,6-difluorobenzyl group, 2,3-dichlorobenzyl group, 3,4-dichlorobenzyl group, 3,5-dichlorobenzyl group, 2,4-dichlorobenzyl group, 2,6-dichlorobenzyl group, 2-fluoro-4-bromobenzyl group, 4-chloro-3-fluorobenzyl group, 2,3,4-trichlorobenzyl group, 3,4,5-trifluorobenzyl group, 2,4,6-trichlorobenzyl group, 4-ethylbenzyl group, 4-sec-butylbenzyl group, 4-isopropylbenzyl group, 4-n-butylbenzyl group, 4-methylbenzyl group, 2-methylbenzyl group, 3-methylbenzyl group, 2,4-dimethylbenzyl group, 2,3-dimethylbenzyl group, 2,6-dimethylbenzyl group, 3,5-dimethylbenzyl group, 2,5-dimethylbenzyl group, 2,4,6-trimethylbenzyl group, 3,5-ditrifluoromethylbenzyl group, 2,3,4,5,6-pentafluorobenzyl group, 4-isopropoxybenzyl group, 4-n-butoxybenzyl group, 4-tert-butoxybenzyl group, 4-methoxybenzyl group, 2-methoxybenzyl group, 3-methoxybenzyl group, 2,4-dimethoxybenzyl group, 2,3-dimethoxybenzyl group, 2,6-dimethoxybenzyl group, 3,5-dimethoxybenzyl group, 2,5-dimethoxybenzyl group, 2,4,6-trimethoxybenzyl group, 3,5-ditrifluoromethoxybenzyl group, 2-isopropoxybenzyl group, 3-chloro-4-methoxybenzyl group, 2-chloro-4-trifluoromethoxybenzyl group, 3-methyl-4-fluorobenzyl group, 4-bromo-3-trifluoromethylbenzyl group, 2-trifluoromethylbenzyl group, 3-trifluoromethylbenzyl group, 4-trifluoromethylbenzyl group, 2-pentafluoroethylbenzyl group, 3-pentafluoroethylbenzyl group, 4-pentafluoroethylbenzyl group, 2-trifluoromethoxybenzyl group, 3-trifluoromethoxybenzyl group, 4-trifluoromethoxybenzyl group, 2-pentafluoroethoxybenzyl group, 3-pentafluoroethoxybenzyl group, 4-pentafluoroethoxybenzyl group, 2-(2-trifluoromethylphenyl)ethyl group, 2-(3-trifluoromethylphenyl)ethyl group, 2-(4-trifluoromethylphenyl)ethyl group, 2-(2-trifluoromethoxyphenyl)ethyl group, 1-(3-trifluoromethoxyphenyl)ethyl group, 2-(4-trifluoromethoxyphenyl)ethyl group, 2-(2-pentafluoroethoxyphenyl)ethyl group, 2-(3-pentafluoroethoxyphenyl)ethyl group, 2-(4-pentafluoroethoxyphenyl)ethyl group, 3-(2-trifluoromethylphenyl)propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 3-(3-pentafluoroethoxyphenyl)propyl group, 3-(4-pentafluoroethoxyphenyl)propyl group, 4-(3-pentafluoroethoxyphenyl)butyl group, 5-(4-trifluoromethylphenyl)pentyl group, 4-(4-trifluoromethylphenyl)pentyl group, 4-(4-trifluoromethoxyphenylpentyl group, 6-(3-trifluoromethylphenyl)hexyl group, 6-(4-trifluoromethylphenyl)hexyl group, 6-(4-trifluoromethoxyphenyl)hexyl group, 4-(4-chlorophenyl)butyl group or the like.

A phenyl C1-C6 alkyl group [wherein, on the phenyl ring, at least one selected from the group consisting of a C1-C4 alkylenedioxy group, a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a group-N($R^{11A}$)$R^{12A}$ (wherein $R^{11A}$ and $R^{12A}$ are identical or different, and each represent a hydrogen atom, C1-C6 alkyl group or phenyl group, and $R^{11A}$ and $R^{12A}$ may be bound to each other through or not through a nitrogen, oxygen or sulfur atom to form five to seven-membered saturated heterocyclic ring together with the nitrogen atom adjacent thereto), a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl C1-C6 alkoxy group, an amino group substituted C1-C6 alkoxy group which may have C1-C6 alkyl group(s) as a substituent, a halogen atom, a halogen substituted or unsubstituted C1-C6 alkyl group and a halogen substituted or unsubstituted C1-C10 alkoxy group may be substituted as a substituent] includes, in addition to a phenyl C1-C6 alkyl group as described above (wherein, on the phenyl ring, at least one selected from the group consisting of a C1-C4 alkylenedioxy group, a phenyl group, a halogen atom, a halogen substituted or unsubstituted C1-C6 alkyl group and a halogen substituted or unsubstituted C1-C6 alkoxy group may be substituted as a substituent), a phenyl C1-C6 alkyl group [wherein, on the phenyl ring, 1 to 5, preferably 1 to 3 substituents (preferably 1 or 2 substituents if the substituent is a C1-C4 alkylenedioxy group) selected from the group consisting of a C1-C4 alkylenedioxy group, a phenyl group as described above (wherein, on the phenyl ring, 1 to 5, preferably 1 to 3 substituents selected from the group consisting of a halogen atom, a halogen substituted or unsubstituted linear or branched alkyl group containing 1 to 6 carbon atoms, a halogen substituted or unsubstituted linear or branched alkoxy group containing 1 to 6 carbon atoms may be substituted), a group-N($R^{11A}$)$R^{12A}$ (wherein $R^{11A}$ and $R^{12A}$ are identical or different, and each represent a hydrogen atom, a C1-C6 alkyl group as described above or a phenyl group, and $R^{11A}$ and $R^{12A}$ as described later may be bound to each other through or not through a nitrogen, oxygen or sulfur atom to form five to seven-membered saturated heterocyclic ring together with the nitrogen atom adjacent thereto), a phenoxy group as described above (wherein, on the phenyl ring, 1 to 5, preferably 1 to 3 substituents selected from the group consisting of a halogen atom, a halogen substituted or unsubstituted linear or branched alkyl group containing 1 to 6 carbon atoms, a halogen substituted or unsubstituted linear or branched alkoxy group containing 1 to 6 carbon atoms may be substituted), a phenyl C1-C6 alkoxy group as described above, an amino group substituted C1-C6 alkoxy group which may have a C1-C6 alkyl group as a substituent as described above, a halogen atom as described above, a halogen substituted or unsubstituted C1-C6 alkyl group as described above and a halogen atom as described above, a halogen substituted or unsubstituted C1-C10 alkoxy group as described above may be substituted], for example, a 4-(4-trifluoromethylphenyl)benzyl group, 4-(4-trifluoromethoxyphenyl)benzyl group, 4-(4-chlorophenyl)benzyl group, 4-(4-trifluoromethylphenoxy)benzyl group, 4-(4-trifluoromethoxyphenoxy)benzyl group, 4-(4-chlorophenoxy)benzyl group, 4-phenoxybenzyl group, 3-phenoxybenzyl group, 2-phenoxybenzyl group, 2-4-diphenoxybenzyl group, 2,4,6-triphenoxybenzyl group, 4-benzyloxybenzyl group, 3-benzyloxybenzyl group, 2-benzyloxybenzyl group, 3,4-dibenzyloxybenzyl group, 3,4,5-tribenzyloxybenzyl group, 4-octyloxybenzyl group, 3-nonyloxybenzyl group, 2-decyloxybenzyl group, 4-heptyloxybenzyl group, 2,4-dioctyloxybenzyl group, 3,4,6-trioctyloxybenzyl group, 4-(8,8,8-trifluorooctyloxy)benzyl group, 4-dimethylaminobenzyl group, 4-diphenylaminobenzyl group, 4-(3-dimethylaminopropoxy)benzyl group, 4-di-n-butylaminobenzyl group, 3-(N-methyl-N-ethylamino)benzyl group, 2-(N-methyl-N-phenylamino)benzyl group, 2,4,6-methylaminobenzyl group, 3-(3-dimethylaminopropoxy)benzyl group, 2,4-di-n-butylaminobenzyl group, 4-(2-methylaminoethoxy)benzyl group, 2-(4-methylaminobutoxy)benzyl group, 4-(2-dimethylaminoethoxy)benzyl group, 2,3-diethylaminomethoxybenzyl group, 2,4,6-tri(2-dimethylaminoethoxy)benzyl group, 2-phenoxy-3-phenylbenzyl group, 4-octyloxy-3-trifluoromethoxybenzyl group, 4-benzyloxy-2-dimethylaminobenzyl group, 4-(1-pyrrolidinyl)benzyl group, 4-(1-piperidyl)benzyl group or the like.

A benzofuryl C1-C6 alkyl group [wherein, on the benzofuran ring, at least one selected from the group consisting of a halogen atom, a halogen substituted or unsubstituted C1-C6 alkyl group and a halogen substituted or unsubstituted C1-C6 alkoxy group may be substituted] includes a benzofuryl C1-C6 alkyl group [wherein, on the benzofuran ring, 1 to 3 substituents selected from the group consisting of a halogen atom as described above, a halogen substituted or unsubstituted C1-C6 alkyl group as described above and a halogen substituted or unsubstituted C1-C6 alkoxy group as described above may be substituted], for example, a (2-, 3-, 4-, 5-, 6- or 7-)benzofurylmethyl group, 1-(2-benzofuryl)ethyl group, 2-(3-benzofuryl)ethyl group, 3-(4-benzofuryl)propyl group, 2-(5-benzofuryl)propyl group, 2-(6-benzofuryl)propyl group, 4-(7-benzofuryl)butyl group, 5-(2-benzofuryl)pentyl group, 4-(3-benzofuryl)pentyl group, 6-(4-benzofuryl)hexyl group, 2-methyl-3-(5-benzofuryl)propyl group, 1,1-dimethyl-2-(6-benzofuryl)ethyl group, (5-chloro-2-benzofuryl)

methyl group, 2-(5-trifluoromethoxybenzofuryl)methyl group, 2-(5-trifluoromethylbenzofuryl)methyl group, (6-trifluoromethylbenzofuryl)methyl group, 2-(5-methylbenzofuryl)methyl group, 2-(5-methoxybenzofuryl)methyl group, (5,6-dibromo-2-benzofuryl)methyl group, (3,5,6-trifluoro-2-benzofuryl)methyl group, 2-(5,6-dimethylbenzofuryl)methyl group, 2-(5,7-dimethoxybenzofuryl)methyl group, 2-(5,6,7-trimethylbenzofuryl)methyl group, 2-(3,5,6-trimethoxybenzofuryl)methyl group, 2-(5-trifluoromethyl-6-chlorobenzofuryl)methyl group, 2-(5-trifluoromethoxy-6-methoxybenzofuryl)methyl group or the like.

A phenylsulfonyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] is a phenylsulfonyl group unsubstituted or having 1 to 5, preferably 1 to 3 substituents (preferably 1 or 2 substituents if the substituent is a C1-C4 alkylenedioxy group) selected from the group consisting of a halogen atom, a halogen substituted or unsubstituted C1-C6 alkyl group, a halogen substituted or unsubstituted C1-C6 alkoxy group and a C1-C4 alkylenedioxy group as defined above, for example, a phenylsulfonyl group, 2-fluorophenylsulfonyl group, 3-fluorophenylsulfonyl group, 4-fluorophenylsulfonyl group, 2-chlorophenylsulfonyl group, 3-chlorophenylsulfonyl group, 4-chlorophenylsulfonyl group, 2-bromophenylsulfonyl group, 3-bromophenylsulfonyl group, 4-bromophenylsulfonyl group, 2-iodophenylsulfonyl group, 3-iodophenylsulfonyl group, 4-iodophenylsulfonyl group, 2,3-difluorophenylsulfonyl group, 3,4-difluorophenylsulfonyl group, 3,5-difluorophenylsulfonyl group, 2,4-difluorophenylsulfonyl group, 2,6-difluorophenylsulfonyl group, 2,3-dichlorophenylsulfonyl group, 3,4-dichlorophenylsulfonyl group, 3,5-dichlorophenylsulfonyl group, 2,4-dichlorophenylsulfonyl group, 2,6-dichlorophenylsulfonyl group, 3,4,5-trifluorophenylsulfonyl group, 3,4,5-trichlorophenylsulfonyl group, 2,4,6-trifluorophenylsulfonyl group, 2,4,6-trichlorophenylsulfonyl group, 2-fluoro-4-bromophenylsulfonyl group, 4-chloro-3-fluorophenylsulfonyl group, 2,3,4-trichlorophenylsulfonyl group, 3,4,5-trifluorophenylsulfonyl group, 2,3,4,5,6-pentafluorophenylsulfonyl group, 2,4,6-trimethylphenylsulfonyl group, 4-n-butylphenylsulfonyl group, 2,4-dimethylphenylsulfonyl group, 2,3-dimethylphenylsulfonyl group, 2,6-dimethylphenylsulfonyl group, 3,5-dimethylphenylsulfonyl group, 2,5-dimethylphenylsulfonyl group, 3,5-ditrifluoromethylphenylsulfonyl group, 4-n-butoxyphenylsulfonyl group, 2,4-dimethoxyphenylsulfonyl group, 2,3-dimethoxyphenylsulfonyl group, 2,6-dimethoxyphenylsulfonyl group, 3,5-dimethoxyphenylsulfonyl group, 2,5-dimethoxyphenylsulfonyl group, 2,4,6-trimethoxyphenylsulfonyl group, 3,5-ditrifluoromethoxyphenylsulfonyl group, 3-chloro-4-methoxyphenylsulfonyl group, 2-chloro-4-trifluoromethoxyphenylsulfonyl group, 3-methyl-4-fluorophenylsulfonyl group, 4-bromo-3-trifluoromethylphenylsulfonyl group, 2-methylphenylsulfonyl group, 3-methylphenylsulfonyl group, 4-methylphenylsulfonyl group, 2-methyl-3-chlorophenylsulfonyl group, 3-methyl-4-chlorophenylsulfonyl group, 2-chloro-4-methylphenylsulfonyl group, 2-methyl-3-fluorophenylsulfonyl group, 2-trifluoromethylphenylsulfonyl group, 3-trifluoromethylphenylsulfonyl group, 4-trifluoromethylphenylsulfonyl group, 2-pentafluoroethylphenylsulfonyl group, 3-pentafluoroethylphenylsulfonyl group, 4-pentafluoroethylphenylsulfonyl group, 2-isopropylphenylsulfonyl group, 3-isopropylphenylsulfonyl group, 4-isopropylphenylsulfonyl group, 2-tert-butylphenylsulfonyl group, 3-tert-butylphenylsulfonyl group, 4-tert-butylphenylsulfonyl group, 2-sec-butylphenylsulfonyl group, 3-sec-butylphenylsulfonyl group, 4-sec-butylphenylsulfonyl group, 2-n-heptafluoropropylphenylsulfonyl group, 3-n-heptafluoropropylphenylsulfonyl group, 4-n-heptafluoropropylphenylsulfonyl group, 4-n-pentylphenylsulfonyl group, 4-n-hexylphenylsulfonyl group, 2-methoxyphenylsulfonyl group, 3-methoxyphenylsulfonyl group, 4-methoxyphenylsulfonyl group, 3-chloro-2-methoxyphenylsulfonyl group, 2-fluoro-3-methoxyphenylsulfonyl group, 2-fluoro-4-methoxyphenylsulfonyl group, 2,6-dimethoxyphenylsulfonyl group, 2,3,4-trifluorophenylsulfonyl group, 2,4,6-trifluorophenylsulfonyl group, 2-trifluoromethoxyphenylsulfonyl group, 3-trifluoromethoxyphenylsulfonyl group, 4-trifluoromethoxyphenylsulfonyl group, 3-fluoro-2-trifluoromethoxyphenylsulfonyl group, 2-fluoro-3-trifluoromethoxyphenylsulfonyl group, 3-fluoro-4-trifluoromethoxyphenylsulfonyl group, 3-chloro-2-trifluoromethoxyphenylsulfonyl group, 2-chloro-3-trifluoromethoxyphenylsulfonyl group, 3-chloro-4-trifluoromethoxyphenylsulfonyl group, 2-pentafluoroethoxyphenylsulfonyl group, 3-pentafluoroethoxyphenylsulfonyl group, 4-pentafluoroethoxyphenylsulfonyl group, 3-chloro-2-pentafluoroethoxyphenylsulfonyl group, 2-chloro-3-pentafluoroethoxyphenylsulfonyl group, 3-chloro-4-pentafluoroethoxyphenylsulfonyl group, 2-isopropoxyphenylsulfonyl group, 3-isopropoxyphenylsulfonyl group, 4-isopropoxyphenylsulfonyl group, 2-tert-butoxyphenylsulfonyl group, 3-tert-butoxyphenylsulfonyl group, 4-tert-butoxyphenylsulfonyl group, 2-sec-butoxyphenylsulfonyl group, 3-sec-butoxyphenylsulfonyl group, 4-sec-butoxyphenylsulfonyl group, 2-n-heptafluoropropoxyphenylsulfonyl group, 3-n-heptafluoropropoxyphenylsulfonyl group, 4-n-heptafluoropropoxyphenylsulfonyl group, 4-n-pentoxyphenylsolfonyl group, 4-n-hexyloxyphenylsulfonyl group, 2,3-methylenedioxyphenylsulfonyl group, 3,4-methylenedioxyphenylsulfonyl group or the like.

A phenoxycarbonyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] includes a phenoxycarbonyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), for example, a phenoxycarbonyl group, 2-fluorophenoxycarbonyl group, 3-fluorophenoxycarbonyl group, 2,3,4,5,6-pentafluorophenoxycarbonyl group, 4-fluorophenoxycarbonyl group, 2-chlorophenoxycarbonyl group, 3-chlorophenoxycarbonyl group, 4-chlorophenoxycarbonyl group, 2,3-dichlorophenoxycarbonyl group, 3,4-dichlorophenoxycarbonyl group, 3,5-dichlorophenoxycarbonyl group, 2-bromophenoxycarbonyl group, 3-bromophenoxycarbonyl group, 4-bromophenoxycarbonyl group, 2-methylphenoxycarbonyl group, 3-methylphenoxycarbonyl group, 4-methylphenoxycarbonyl group, 2-ethylphenoxycarbonyl group, 3-ethylphenoxycarbonyl group, 4-ethylphenoxycarbonyl group, 4-n-propylphenoxycarbonyl group, 4-tert-butylphenoxycarbonyl group, 4-n-butylphenoxycarbonyl group, 2,3-dimethylphenoxycarbonyl group, 3,4,5-trimethylphenoxycarbonyl group, 4-n-pentylphenoxycarbonyl group, 4-n-hexylphenoxycarbonyl group, 2-fluoro-4-bromophenoxycarbonyl group, 4-chloro-3-fluorophenoxycarbonyl group, 2,3,4-trichlorophenoxycarbonyl group, 2,4,6-trichlorophenoxycarbonyl group, 4-isopropylphenoxycarbonyl group, 4-n-butylphenoxycarbonyl group, 2,4-dimethylphenoxycarbonyl group, 2,3-dimethylphenoxycarbonyl group, 2,6-dimethylphenoxycarbonyl group, 3,5-dimethylphenoxycarbonyl group, 2,5-dimethylphenoxycarbonyl group, 2,4,6-trimethylphenoxycarbonyl group, 3,5-ditrifluoromethylphenoxycarbonyl group, 4-n-butoxyphenoxycarbonyl group, 2,4-dimethoxyphenoxycarbonyl group, 2,3-dimethoxyphenoxycarbonyl group, 2,6-dimethoxyphenoxycarbonyl group, 3,5-dimethoxyphenoxycarbonyl group, 2,5-dimethoxyphenoxycarbonyl group, 3,5-ditrifluoromethoxyphenoxycarbonyl group, 3-chloro-4-methoxyphenoxycarbonyl group, 2-chloro-4-trifluoromethoxyphenoxycarbonyl group, 3-methyl-4-fluorophenoxycarbonyl group, 4-bromo-3-trifluoromethylphenoxycarbonyl group, 2-trifluoromethylphenoxycarbonyl group, 3-trifluoromethylphenoxycarbonyl group, 4-trifluoromethylphenoxycarbonyl group, 2-pentafluoroethylphenoxycarbonyl group, 3-pentafluoroethylphenoxycarbonyl group, 4-pentafluoroethylphenoxycarbonyl group, 2-methoxyphenoxycarbonyl group, 3-methoxyphenoxycarbonyl group, 4-methoxyphenoxycarbonyl group, 2-ethoxyphenoxycarbonyl group, 3-ethoxyphenoxycarbonyl group, 4-ethoxyphenoxycarbonyl group, 4-n-propoxyphenoxycarbonyl group, 4-tert-butoxyphenoxycarbonyl group, 4-n-butoxyphenoxycarbonyl group, 2,3-dimethoxyphenoxycarbonyl group, 3,4,5-trimethoxyphenoxycarbonyl group, 4-n-pentoxyphenoxycarbonyl group, 4-n-hexyloxyphenoxycarbonyl group, 2-trifluoromethoxyphenoxycarbonyl group, 3-trifluoromethoxyphenoxycarbonyl group, 4-trifluoromethoxyphenoxycarbonyl group, 2-pentafluoroethoxyphenoxycarbonyl group, 3-pentafluoroethoxyphenoxycarbonyl group, 4-pentafluoroethoxyphenoxycarbonyl group or the like.

A C1-C6 alkoxy substituted C1-C6 alkyl group is a group consisting of a C1-C6 alkyl group and a C1-C6 alkoxy group, both as described above, examples of which include a methoxymethyl group, 2-methoxyethyl group, 3-methoxypropyl group, 4-methoxybutyl group, 5-methoxypentyl group, 6-methoxyhexyl group, ethoxymethyl group, 2-ethoxyethyl group, 3-ethoxypropyl group, 2-isopropoxyethyl group, tert-butoxymethyl group, pentyloxymethyl group, hexyloxymethyl group, 2-(tert-butoxy)ethyl group, 3-(tert-butoxy)propyl group, 6-(tert-butoxy)hexyl group, 4-(tert-butoxy)butyl group or the like.

A C2-C6 alkenyl group includes a vinyl group, 2-propenyl group, 3-butenyl group, 2-butenyl group, 4-pentenyl group, 3-pentenyl group, 5-hexenyl group, 4-hexenyl group, 3-hexenyl group or the like.

A C1-C6 alkoxy substituted C2-C6 alkanoyl group is a group consisting of a C1-C6 alkyl group and a C2-C6 alkanoyl group, both as described above, examples of which include a 2-methoxyacetyl group, 2-methoxypropionyl group, 3-methoxypropionyl group, 4-methoxybutylyl group, 5-methoxypentanoyl group, 6-methoxyhexanoyl group, 2-ethoxyacetyl group, 2-ethoxypropionyl group, 3-ethoxypropionyl group, 2-isopropoxypropionyl group, 2-(tert-butoxy)acetyl group, 2-pentyloxyacetyl group, 2-hexyloxyacetyl group, 2-(tert-butoxy)propionyl group, 3-(tert-butoxy) propionyl group, 6-(tert-butoxy)hexanoyl group, 4-(tert-butoxy)butylyl group or the like.

A C3-C8 cycloalkyl substituted C1-C6 alkyl group is a group consisting of a cyclic alkyl group containing 3 to 8 carbon atoms and an alkyl group containing 1 to 6 carbon atoms, examples of which a cyclopropylmethyl group, 2-cyclopropylethyl group, 3-cyclopropylpropyl group, 4-cyclopropylbutyl group, 5-cyclopropylpentyl group, 6-cyclopropylhexyl group, cyclobutylmethyl group, 2-cyclobutylethyl group, 3-cyclobutylpropyl group, 4-cyclobutylbutyl group, 5-cyclobutylpentyl group, 6-cyclobutylhexyl group, cyclopentylmethyl group, 2-cyclopentylethyl group, 3-cyclopentylpropyl group, 4-cyclopentylbutyl group, 5-cyclopentylpentyl group, 6-cyclopentylhexyl group, cyclohexylmethyl group, 2-cyclohexylethyl group, 3-cyclohexylpropyl group, 4-cyclohexylbutyl group, 5-cyclohexylpentyl group, 6-cyclohexylhexyl group, cycloheptylmethyl group, 2-cycloheptylethyl group, 3-cycloheptylpropyl group, 4-cycloheptylbutyl group, 5-cycloheptylpentyl group, 6-cycloheptylhexyl group, cyclooctylmethyl group, 2-cyclooctylethyl group, 3-cyclooctylpropyl group, 4-cyclooctylbutyl group, 5-cyclooctylpentyl group, 6-cyclooctylhexyl group or the like.

A pyridyl C1-C6 alkyl group includes a 2-pyridylmethyl group, 2-(3-pyridyl)ethyl group, 1-(4-pyridyl)ethyl group, 3-(2-pyridyl)propyl group, 4-(3-pyridyl)butyl, 5-(4-pyridyl) pentyl group, 6-(2-pyridyl)hexyl group, 2-methyl-3-(3-pyridyl)propyl group, 1,1-dimethyl-2-(2-pyridyl)ethyl group or the like.

An imidazolyl C1-C6 alkyl group (wherein, on the imidazole ring, a phenyl group may be substituted) includes an imidazolyl C1-C6 alkyl group (wherein, on the imidazole ring, 1 to 2 phenyl groups may be substituted), for example, a 4-imidazolylmethyl group, 2-(4-imidazolyl)ethyl group, 3-(2-imidazolyl)propyl group, 4-(1-imidazolyl)butyl group, 5-(5-imidazolyl)pentyl group, 6-(4-imidazolyl)hexyl group, 2,5-diphenyl-1-imidazolylmethyl group, 2-phenyl-4-imidazolylmethyl group, 2-(2-phenyl-4-imidazolyl)ethyl group, 3-(2-phenyl-4-imidazolyl)propyl group, 4-(2-phenyl-5-imidazolyl)butyl group, 5-(2-phenyl-4-imidazolyl)pentyl group, 6-(2-phenyl-4-imidazolyl)hexyl group or the like.

A 1,2,3,4-tetrahydroquinolyl group (wherein, on the 1,2,3,4-tetrahydroquinoline ring, at least one selected from the group consisting of an oxo group and a C1-C6 alkyl group may be substituted as a substituent) includes a 1,2,3,4-tetrahydroquinolyl group (wherein, on the 1,2,3,4-tetrahydroquinoline ring, 1 to 5 substituents selected from the group consisting of an oxo group and a C1-C6 alkyl group may be substituted), for example, a 1,2,3,4-tetrahydro-1-quinolyl group, 1,2,3,4-tetrahydro-2-quinolyl group, 1,2,3,4-tetrahydro-3-quinolyl group, 1,2,3,4-tetrahydro-4-quinolyl group, 1,2,3,4-tetrahydro-5-quinolyl group, 1,2,3,4-tetrahydro-6-quinolyl group, 1,2,3,4-tetrahydro-7-quinolyl group, 1,2,3,4-tetrahydro-8-quinolyl group, 2-oxo-1,2,3,4-tetrahydro-1-quinolyl group, 4-oxo-1,2,3,4-tetrahydro-1-quinolyl group, 2,4-dioxo-1,2,3,4-tetrahydro-1-quinolyl group, 2-oxo-1,2,3,4-tetrahydro-6-quinolyl group, 2-oxo-1,2,3,4-tetrahydro-4-quinolyl group, 2-oxo-1,2,3,4-tetrahydro-7-quinolyl group, 2-oxo-1,2,3,4-tetrahydro-8-quinolyl group, 2-oxo-1,2,3,4-tetrahydro-5-quinolyl group, 2-oxo-1,2,3,4-tetrahydro-3-quinolyl group, 2-methyl-1,2,3,4-tetrahydro-1-quinolyl group, 4-ethyl-1,2,3,4-tetrahydro-1-quinolyl group, 2,4-dimethyl-1,2,3,4-tetrahydro-1-quinolyl group, 1,5,6-trimethyl-1,2,3,4-tetrahydro-1-quinolyl group, 1,4,5,6-tetramethyl-2-oxo-1,2,3,4-tetrahydro-1-quinolyl group, 1-propyl-1,2,3,4-tetrahydro-6-quinolyl group, 5-n-pentyl-1,2,3,4-tetrahydro-4-quinolyl group, 6-n-hexyl-1,2,3,4-tetrahydro-7-quinolyl group, 7-tert-butyl-1,2,3,4-tetrahydro-8-quinolyl group, 8-n-pentyl-1,2,3,4-tetrahydro-8-quinolyl group, 1-n-hexyl-2-oxo-1,2,3,4-tetrahydro-8-quinolyl group, 1-methyl-2-oxo-1,2,3,4-tetrahydro-5-quinolyl group, 3-ethyl-2-oxo-1,2,3,4-tetrahydro-3-quinolyl group or the like.

An amino group which may have C1-C6 alkyl group(s) as substituent includes an amino group which may have 1 to 2 C1-C6 alkyl groups as substituent, for example, an amino group, methylamino group, ethylamino group, n-propylamino group, isopropylamino group, n-butylamino group, tert-butylamino group, n-pentylamino group, n-hexylamino group, dimethylamino group, diethylamino group, di-n-propylamino group, di-n-butylamino group, di-n-pentylamino group, di-n-hexylamino group, N-methyl-N-ethylamino group, N-ethyl-N-n-propylamino group, N-methyl-N-n-butylamino group, N-methyl-N-n-hexylamino group or the like.

A cyano substituted C1-C6 alkyl group includes a cyanomethyl group, 2-cyanoethyl group, 1-cyanoethyl group, 3-cyanopropyl group, 4-cyanobutyl group, 5-cyanopentyl group, 6-cyanohexyl group, 2-methyl-3-cyanopropyl group, 1,1-dimethyl-2-cyanoethyl group or the like.

A furyl substituted C1-C6 alkyl group includes a 2-furylmethyl group, 3-furylmethyl group, 2-(2-furyl)ethyl group, 1-(3-furyl)ethyl group, 3-(2-furyl)propyl group, 3-(3-furyl) propyl group, 4-(2-furyl)butyl group, 4-(3-furyl)butyl group, 5-(2-furyl)pentyl group, 5-(3-furyl)pentyl group, 6-(2-furyl) hexyl group, 6-(3-furyl)hexyl group or the like.

A piperazinyl substituted C1-C6 alkyl group [wherein, on the piperazine ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a piperazinyl substituted C1 to C6 alkyl group [wherein, on the piperazine ring, 1 to 3 phenyl groups as substituent (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a 1-piperazinylmethyl group, 2-(2-piperazinyl) ethyl group, 1-(1-piperazinyl)ethyl group, 3-(1-piperazinyl) propyl group, 4-(1-piperazinyl)butyl group, 5-(2-piperazinyl)pentyl group, 6-(1-piperazinyl)hexyl group, 2-(4-phenyl-1-piperazinyl)ethyl group, 3-(4-phenyl-1-piperazinyl)propyl group, 4-(4-phenyl-1-piperazinyl)butyl group, 5-(4-phenyl-1-piperazinyl)pentyl group, 6-(4-phenyl-1-piperazinyl)hexyl group, 2-(4-(2-fluorophenyl)-1-piperazinyl)ethyl group, 3-(4-(2-fluorophenyl)-1-piperazinyl)propyl group, 4-(4-(2,3-difluorophenyl)-1-piperazinyl)butyl group, 5-(4-(2-fluorophenyl)-1-piperazinyl)pentyl group, 6-(4-(4-fluorophenyl)-1-piperazinyl)hexyl group, 3-(4-(3-fluorophenyl)-1-piperazinyl)propyl group, 4-(4-(3-fluorophenyl)-1-piperazinyl)butyl group, 5-(4-(3-fluorophenyl)-1-piperazinyl)pentyl group, 3-(4-(4-fluorophenyl)-1-piperazinyl)propyl group, 4-(4-(fluorophenyl)-1-piperazinyl)butyl group, 5-(4-(4-fluorophenyl)-1-piperazinyl)pentyl group, 6-(4-(fluorophenyl)-1-piperazinyl) hexyl group, 2-(4-(2,3-dichlorophenyl)-1-piperazinyl)ethyl group, 3-(4-(2-chlorophenyl)-1-piperazinyl)propyl group, 4-(4-(2-chlorophenyl)-1-piperazinyl)butyl group, 5-(4-(2,4,6-trichlorophenyl)-1-piperazinyl)pentyl group, 6-(4-(2-chlorophenyl)-1-piperazinyl)hexyl group, 2-(4-(3-chlorophenyl)-1-piperazinyl)ethyl group, 3-(4-(3-chlorophenyl)-1-piperazinyl)propyl group, 4-(4-(3-chlorophenyl)-1-piperazinyl)butyl group, 5-(4-(2,3,4,5,6-pentafluorophenyl)-1-piperazinyl)pentyl group, 6-(4-(3-chloro-4-methylphenyl)-1-piperazinyl)hexyl group, 2-(4-(4-chlorophenyl)-1-piperazinyl)ethyl group, 3-(4-(4-chlorophenyl)-1-piperazinyl)propyl group, 4-(4-(4-chloro-3-methoxyphenyl)-1-piperazinyl)butyl group, 5-(4-(4-chlorophenyl)-1-piperazinyl)pentyl group, 6-(4-(4-chlorophenyl)-1-piperazinyl)hexyl group, 2-(4-(2-methylphenyl)-1-piperazinyl)methyl group, 2-(4-(2,4-dimethylphenyl)-1-piperazinyl)methyl group, 2-(4-(2,4,6-trimethylphenyl)-1-piperazinyl)methyl group, 2-(4-(2-trifluoromethylphenyl)-1-piperazinyl)ethyl group, 3-(4-(3,5-ditrifluoromethylphenyl)-1-piperazinyl)propyl group, 4-(4-(2-trifluoromethylphenyl)-1-piperazinyl)butyl group, 5-(4-(2-trifluoromethylphenyl)-1-piperazinyl)pentyl group, 6-(4-(2-trifluoromethylphenyl)-1-piperazinyl) hexyl group, 3-(4-(3-trifluoromethylphenyl)-1-piperazinyl)propyl group, 4-(4-(3-trifluoromethylphenyl)-1-piperazinyl)butyl group, 5-(4-(3-trifluoromethylphenyl)-1-piperazinyl)pentyl group, 3-(4-(4-trifluoromethylphenyl)-1-piperazinyl)propyl group, 4-(4-(4-trifluoromethylphenyl)-1-piperazinyl)butyl group, 5-(4-(4-trifluoromethylphenyl)-1-piperazinyl)pentyl group, 6-(4-(4-trifluoromethylphenyl)-1-piperazinyl)hexyl group, 2-(4-(3,5-ditrifluoromethoxyphenyl)-1-piperazinyl)ethyl group, 2-(4-(2-methoxyphenyl)-1-piperazinyl)methyl group, 2-(4-(2,4-dimethoxyphenyl)-1-piperazinyl)methyl group, 2-(4-(2,4,6-trimethoxyphenyl)-1-piperazinyl)methyl group, 3-(4-(2-trifluoromethoxyphenyl)-1-piperazinyl)propyl group, 4-(4-(2-trifluoromethoxyphenyl)-1-piperazinyl)butyl group, 5-(4-(2-trifluoromethoxyphenyl)-1-piperazinyl)pentyl group, 6-(4-(2-trifluoromethoxyphenyl)-1-piperazinyl)hexyl group, 3-(4-(3-trifluoromethoxyphenyl)-1-piperazinyl)propyl group, 4-(4-(3-trifluoromethoxyphenyl)-1-piperazinyl)butyl group, 5-(4-(3-trifluoromethoxyphenyl)-1-piperazinyl)pentyl group, 3-(4-(4-trifluoromethoxyphenyl)-1-piperazinyl) propyl group, 4-(4-(4-trifluoromethoxyphenyl)-1-piperazinyl)butyl group, 5-(4-(4-trifluoromethoxyphenyl)-1-piperazinyl)pentyl group, 6-(4-(4-trifluoromethoxyphenyl)-1-piperazinyl)hexyl group, 2,4-diphenyl-1-piperazinylmethyl group, (2,4,5-triphenyl-1-piperadiny) methyl group or the like.

$R^9$ and $R^{10}$, $R^{11A}$ and $R^{12A}$, or $R^{11B}$ and $R^{12B}$ may bind to each other directly or through a nitrogen, oxygen or sulfur atom, so as to form a 5-7 membered saturated heterocyclic ring group together with the nitrogen atom adjacent thereto. Examples of the 5-7 membered saturated heterocyclic ring group may include a pyrrolidinyl group, a piperazyl group, a piperidyl group, a morpholino group, a thiomorpholino group, and a homopiperazinyl group.

$R^9$ and $R^{10}$ may bind to each other directly or through a nitrogen, oxygen or sulfur atom, so as to form a 1,2,3,4-tetrahydroisoquinolyl group, an isoindolyl group, or the above described 5-7 membered saturated heterocyclic ring together with the nitrogen atom adjacent thereto. On the a group or ring, at least one selected from the group consisting of the following groups may be substituted: a halogen atom, a halogen substituted or unsubstituted C1-C6 alkyl group, a halogen substituted or unsubstituted C1-C6 alkoxy group, a phenyl group [wherein, on the phenyl ring, at least one selected from the group consisting of a phenyl group, a halogen atom, a halogen substituted or unsubstituted C1-C6 alkyl group, and a halogen substituted or unsubstituted C1-C6 alkoxy group may be substituted], a benzoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a pyridyl C1-C6 alkyl group, a C3-C8 cycloalkyl group, a phenyl C1-C6 alkyl group [wherein, on the phenyl ring, at least one selected from the group consisting of a C1-C4 alkylenedioxy group, a halogen atom, a halogen substituted or unsubstituted C1-C6 alkyl group, and a halogen substituted or unsubstituted C1-C6 alkoxy group may be substituted], a piperidyl C1-C6 alkyl group, a piperidyl group, a phenyl C1-C6 alkoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], an amino group wherein at least one selected from the group consisting of a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a C1-C6 alkyl group, and a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted] may be substituted as a substituent, a benzoxazolyl group, a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted), and a benzimidazolyl group. As such substituents, 1 to 3 groups selected from the following groups, each of which is described above or below, may be substituted: a halogen atom, a halogen substituted or unsubstituted C1-C6 alkyl group, a halogen substituted or unsubstituted C1-C6 alkoxy group, a phenyl group [wherein, on the phenyl ring, 1 to 5 groups, and preferably 1 to 3 groups selected from the group consisting of a phenyl group, a halogen atom, a halogen substituted or unsubstituted C1-C6 alkyl group, and a halogen substituted or unsubstituted C1-C6 alkoxy group may be substituted], a benzoyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], a pyridyl C1-C6 alkyl group, a C3-C8 cycloalkyl group, a phenyl C1-C6 alkyl group [wherein, on the phenyl ring, 1 to 5 groups, and preferably 1 to 3 groups selected from the group consisting of a C1-C4 alkylenedioxy group, a halogen atom, a halogen substituted or unsubstituted C1-C6 alkyl group, and a halogen substituted or unsubstituted C1-C6 alkoxy group may be substituted, and in a case where the substituent is a C1-C4 alkylenedioxy group, 1 or 2 groups are preferably substituted], a piperidyl C1-C6 alkyl group, a piperidyl group, a phenyl C1-C6 alkoxy group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], a phenoxy group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], an amino group wherein 1 or 2 groups selected from the group consisting of a phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], a C1-C6 alkyl group, and a phenyl C1-C6 alkyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted] may be substituted as a substituent, a benzoxazolyl group, a phenyl C2-C6 alkenyl group (wherein, on the phenyl ring, 1 to 5 groups, and preferably 1 to 3 groups selected from the group consisting of a halogen atom, a halogen substituted or unsubstituted linear or branched alkyl group containing 1 to 6 carbon atoms, and a halogen substituted or unsubstituted linear or branched alkoxy group containing 1 to 6 carbon atoms, may be substituted), and a benzimidazolyl group.

$R^{11B}$ and $R^{12B}$ may bind to each other directly or through a nitrogen, oxygen or sulfur atom, so as to form the above described 5-7 membered saturated heterocyclic ring together with the nitrogen atom adjacent thereto. On the a 5-7 membered saturated heterocyclic ring, at least one selected from the group consisting of a C1-C6 alkoxycarbonyl group and an amino group [wherein, on the amino group, at least one selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) and a C1-C6 alkyl group may be substituted] may be substituted. An example of the substituent may be a group selected from the group consisting of a C1-C6 alkoxycarbonyl group and an amino group [wherein, on the amino group, 1 or 2 groups selected from the group consisting of a phenyl group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted) and a C1-C6 alkyl group may be substituted], which are described above or below. Such 1 to 3 substituents may be substituted on the heterocyclic ring.

The term phenyl group [wherein, on the phenyl ring, at least one selected from the group consisting of a phenyl group, a halogen atom, a halogen substituted or unsubstituted C1-C6 alkyl group, and a halogen substituted or unsubstituted C1-C6 alkoxy group may be substituted] is used herein to mean an unsubstituted phenyl group or the above defined phenyl group, which comprises 1 to 5 substituents, and preferably 1 to 3 substituents selected from the group consisting of a phenyl group, a halogen atom, a halogen substituted or unsubstituted C1-C6 alkyl group, and a halogen substituted or unsubstituted C1-C6 alkoxy group. Examples of the phenyl group may include a phenyl group, a 2-phenylphenyl group, a 3-phenylphenyl group, a 4-phenylphenyl group, a 2,3-diphenylphenyl group, a 2,4,6-triphenylphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,3-difluorophenyl group, a 3,4-difluorophenyl group, a 3,5-difluorophenyl group, a 2,4-difluorophenyl group, a 2,6-difluorophenyl group, a 2,3-dichlorophenyl group, a 3,4-dichlorophenyl group, a 3,5-dichlorophenyl group, a 2,4-dichlorophenyl group, a 2,6-dichlorophenyl group, a 3,4,5-trifluorophenyl group, a 3,4,5-trichlorophenyl group, a 2,4,6-trifluorophenyl group, a 2,4,6-trichlorophenyl group, a 2-fluoro-4-bromophenyl group, a 4-chloro-3-fluorophenyl group, a 2,3,4-trichlorophenyl group, a 3,4,5-trifluorophenyl group, a 2,3,4,5,6-pentafluorophenyl group, a 2,4,6-trimethylphenyl group, a 4-n-butylphenyl group, a 2,4-dimethylphenyl group, a 2,3-dimethylphenyl group, a 2,6-dimethylphenyl group, a 3,5-dimethylphenyl group, a 2,5-dimethylphenyl group, a 3,5-ditrifluoromethylphenyl group, a 4-n-butoxyphenyl group, a 2,4-dimethoxyphenyl group, a 2,3-dimethoxyphenyl group, a 2,6-dimethoxyphenyl group, a 3,5-dimethoxyphenyl group, a 2,5-dimethoxyphenyl group, a 2,4,6-trimethoxyphenyl group, a 3,5-ditrifluoromethoxyphenyl group, a 3-chloro-4-methoxyphenyl group, a 2-chloro-4- trifluoromethoxyphenyl group, a 3-methyl-4-fluorophenyl group, a 4-bromo-3-trifluoromethylphenyl group, a 2-methylphenyl group, a 3-methylphenyl group, a 4-methylphenyl group, a 2-methyl-3-chlorophenyl group, a 3-methyl-4-chlorophenyl group, a 2-chloro-4-methylphenyl group, a 2-methyl-3-fluorophenyl group, a 2-trifluoromethylphenyl group, a 3-trifluoromethylphenyl group, a 4-trifluoromethylphenyl group, a 2-pentafluoroethylphenyl group, a 3-pentafluoroethylphenyl group, a 4-pentafluoroethylphenyl group, a 2-isopropylphenyl group, a 3-isopropylphenyl group, a 4-isopropylphenyl group, a 2-tert-butylphenyl group, a 3-tert-butylphenyl group, a 4-tert-butylphenyl group, a 2-sec-butylphenyl group, a 3-sec-butylphenyl group, a 4-sec-butylphenyl group, a 2-n-heptafluoropropylphenyl group, a 3-n-heptafluoropropylphenyl group, a 4-n-heptafluoropropylphenyl group, a 4-n-pentylphenyl group, a 4-n-hexylphenyl group, a 2-methoxyphenyl group, a 3-methoxyphenyl group, a 4-methoxyphenyl group, a 3-chloro-2-methoxyphenyl group, a 2-fluoro-3-methoxyphenyl group, a 2-fluoro-4-methoxyphenyl group, a 2,6-dimethoxyphenyl group, a 2,3,4-trifluorophenyl group, a 2,4,6-trifluorophenyl group, a 2-trifluoromethoxyphenyl group, a 3-trifluoromethoxyphenyl group, a 4-trifluoromethoxyphenyl group, a 3-fluoro-2-trifluoromethoxyphenyl group, a 2-fluoro-3-trifluoromethoxyphenyl group, a 3-fluoro-4-trifluoromethoxyphenyl group, a 3-chloro-2-trifluoromethoxyphenyl group, a 2-chloro-3-trifluoromethoxyphenyl group, a 3-chloro-4-trifluoromethoxyphenyl group, a 2-pentafluoroethoxyphenyl group, a 3-pentafluoroethoxyphenyl group, a 4-pentafluoroethoxyphenyl group, a 3-chloro-2-pentafluoroethoxyphenyl group, a 2-chloro-3-pentafluoroethoxyphenyl group, a 3-chloro-4-pentafluoroethoxyphenyl group, a 2-isopropoxyphenyl group, a 3-isopropoxyphenyl group, a 4-isopropoxyphenyl group, a 2-tert-butoxyphenyl group, a 3-tert-butoxyphenyl group, a 4-tert-butoxyphenyl group, a 2-sec-butoxyphenyl group, a 3-sec-butoxyphenyl group, a 4-sec-butoxyphenyl group, a 2-n-heptafluoropropoxyphenyl group, a 3-n-heptafluoropropoxyphenyl group, a 4-n-heptafluoropropoxyphenyl group, a 4-n-pentoxyphenyl group, and a 4-n-hexyloxyphenyl group.

The term phenyl C1-C6 alkoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted] is used herein to mean the above defined phenyl C1-C6 alkoxy group, wherein 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group, may be substituted. Examples of the phenyl C1-C6 alkoxy group may include a benzyloxy group, a 2-phenylethoxy group, a 3-phenylpropoxy group, a 2-phenylpropoxy group, a 4-phenylbutoxy group, a 5-phenylpentoxy group, a 4-phenylpentoxy group, a 6-phenylhexyloxy group, a 2-fluorobenzyloxy group, a 3-fluorobenzylxoy group, a 4-fluorobenzyloxy group, a 2-(2-fluorophenyl)ethoxy group, a 2-(3-fluorophenyl)ethoxy group, a 2-(4-fluorophenyl)ethoxy group, a 2-chlorobenzyloxy group, a 3-chlorobenzyloxy group, a 4-chlorobenzyloxy group, a 2-fluoro-4-bromobenzyloxy group, a 4-chloro-3-fluorobenzyloxy group, a 2-chloro-4-fluorobenzyloxy group, a 3,4-dichlorobenzyloxy group, a 3,5-dichlorobenzyloxy group, a 2,3-dichlorobenzyloxy group, a 2,5-dichlorobenzyloxy group, a 2,3,4-trichlorobenzyloxy group, a 3,4,5-trifluorobenzyloxy group, a 2,3,4,5,6-pentafluorobenzyloxy group, a 2,4,6-trichlorobenzyloxy group, a 4-isopropylbenzyloxy group, a 4-n-butylbenzyloxy group, a 4-methylbenzyloxy group, a 2-methylbenzyloxy group, a 3-methylbenzyloxy group, a 2,4-dimethylbenzyloxy group, a 2,3-dimethylbenzyloxy group, a 2,6-dimethylbenzyloxy group, a 3,5-dimethylbenzyloxy group, a 2,5-dimethylbenzyloxy group, a 2,4,6-trimethylbenzyloxy group, a 4-ethylbenzyloxy group, a 4-isopropylbenzyloxy group, a 3,5-ditrifluoromethylbenzyloxy group, a 4-isopropoxybenzyloxy group, a 4-n-butoxybenzyloxy group, a 4-methoxybenzyloxy group, a 2-methoxybenzyloxy group, a 3-methoxybenzyloxy group, a 2,4-dimethoxybenzyloxy group, a 2,3-dimethoxybenzyloxy group, a 2,6-dimethoxybenzyloxy group, a 3,5-dimethoxybenzyloxy group, a 2,5-dimethoxybenzyloxy group, a 2,4,6-trimethoxybenzyloxy group, a 3,5-ditrifluoromethoxybenzyloxy group, a 2-isopropoxybenzyloxy group, a 3-chloro-4-methoxybenzyloxy group, a 2-chloro-4-trifluoromethoxybenzyloxy group, a 3-methyl-4-fluorobenzyloxy group, a 4-bromo-3-trifluoromethylbenzyloxy group, a 2-(2-chlorophenyl)ethoxy group, a 2-(3-chlorophenyl)ethoxy group, a 2-(4-chlorophenyl)ethoxy group, a 2-trifluoromethylbenzyloxy group, a 3-trifluoromethylbenzyloxy group, a 4-trifluoromethylbenzyloxy group, a 2-trifluoromethoxybenzyloxy group, a 3-trifluoromethoxybenzyloxy group, a 4-trifluoromethoxybenzyloxy group, a 2-(2-trifluoromethylphenyl)ethoxy group, a 2-(3-trifluoromethylphenyl)ethoxy group, a 2-(4-trifluoromethylphenyl)ethoxy group, a 2-(2-trifluoromethoxyphenyl)ethoxy group, a 2-(3-trifluoromethoxyphenyl)ethoxy group, a 2-(4-trifluoromethoxyphenyl)ethoxy group, a 3-(2-trifluoromethylphenyl)propoxy group, a 3-(3-trifluoromethylphenyl)propoxy group, a 3-(4-trifluoromethylphenyl)propoxy group, a 3-(2-trifluoromethylphenyl)propoxy group, a 3-(3-trifluoromethoxyphenyl)propoxy group, a 3-(4-trifluoromethoxyphenyl)propoxy group, a 4-(3-trifluoromethylphenyl)butoxy group, a 5-(4-trifluoromethylphenyl)pentoxy group, a 4-(4-trifluoromethylphenyl)pentoxy group, a 4-(4-trifluoromethoxyphenyl)pentoxy group, a 6-(3-trifluoromethylphenyl)hexyloxy group, a 6-(4-trifluoromethylphenyl)hexyloxy group, and a 6-(4-trifluoromethoxyphenyl)hexyloxy group.

The term phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted] is used herein to mean an unsubstituted phenoxy group or the above defined phenoxy group, which comprises 1 to 5 substituents, and preferably 1 to 3 substituents selected from the group consisting of a halogen atom, a halogen substituted or unsubstituted C1-C6 alkyl group, and a halogen substituted or unsubstituted C1-C6 alkoxy group. Examples of the phenoxy group may include a phenoxy group, a 2-fluorophenoxy group, a 3-fluorophenoxy group, a 4-fluorophenoxy group, a 2-chlorophenoxy group, a 3-chlorophenoxy group, a 4-chlorophenoxy group, a 2-bromophenoxy group, a 3-bromophenoxy group, a 4-bromophenoxy group, a 2-iodophenoxy group, a 3-iodophenoxy group, a 4-iodophenoxy group, a 2,3-difluorophenoxy group, a 3,4-difluorophenoxy group, a 3,5-difluorophenoxy group, a 2,4-difluorophenoxy group, a 2,6-difluorophenoxy group, a 2,3-dichlorophenoxy group, a 3,4-dichlorophenoxy group, a 3,5-dichlorophenoxy group, a 2,4-dichlorophenoxy group, a 2,6-dichlorophenoxy group, a 3,4,5-trifluorophenoxy group, a 3,4,5-trichlorophenoxy group, a 2,4,6-trifluorophenoxy group, a 2,4,6-trichlorophenoxy group, a 2-fluoro-4-bromophenoxy group, a 4-chloro-3-fluorophenoxy group, a 2,3,4-trichlorophenoxy group, a 3,4,5-trifluorophenoxy group, a 2,3,4,5,6-pentafluorophenoxy group, a 2,4,6-trimethylphenoxy group, a 4-n-butylphenoxy group, a 2,4-dimethylphenoxy group, a 2,3-dimethylphenoxy group, a 2,6-dimethylphenoxy group, a 3,5-dimethylphenoxy group, a 2,5-dimethylphenoxy group, a 3,5-ditrifluoromethylphenoxy group, a 4-n-butoxyphenoxy group, a 2,4-dimethoxyphenoxy group, a 2,3-dimethoxyphenoxy group, a 2,6-dimethoxyphenoxy group, a 3,5-dimethoxyphenoxy group, a 2,5-dimethoxyphenoxy group, a 2,4,6-trimethoxyphenoxy group, a 3,5-ditrifluoromethoxyphenoxy group, a 3-chloro-4-methoxyphenoxy group, a 2-chloro-4-trifluoromethoxyphenoxy group, a 3-methyl-4-fluorophenoxy group, a 4-bromo-3-trifluoromethylphenoxy group, a 2-methylphenoxy group, a 3-methylphenoxy group, a 4-methylphenoxy group, a 2-methyl-3-chlorophenoxy group, a 3-methyl-4-chlorophenoxy group, a 2-chloro-4-methylphenoxy group, a 2-methyl-3-fluorophenoxy group, a 2-trifluoromethylphenoxy group, a 3-trifluoromethylphenoxy group, a 4-trifluoromethylphenoxy group, a 2-pentafluoroethylphenoxy group, a 3-pentafluoroethylphenoxy group, a 4-pentafluoroethylphenoxy group, a 2-isopropylphenoxy group, a 3-isopropylphenoxy group, a 4-isopropylphenoxy group, a 2-tert-butylphenoxy group, a 3-tert-butylphenoxy group, a 4-tert-butylphenoxy group, a 2-sec-butylphenoxy group, a 3-sec-butylphenoxy group, a 4-sec-butylphenoxy group, a 2-n-heptafluoropropylphenoxy group, a 3-n-heptafluoropropylphenoxy group, a 4-n-heptafluoropropylphenoxy group, a 4-n-pentylphenoxy group, a 4-n-hexylphenoxy group, a 2-methoxyphenoxy group, a 3-methoxyphenoxy group, a 4-methoxyphenoxy group, a 3-chloro-2-methoxyphenoxy group, a 2-fluoro-3-methoxyphenoxy group, a 2-fluoro-4-methoxyphenoxy group, a 2,6-dimethoxyphenoxy group, a 2,3,4-trifluorophenoxy group, a 2,4,6-trifluorophenoxy group, a 2-trifluoromethoxyphenoxy group, a 3-trifluoromethoxyphenoxy group, a 4-trifluoromethoxyphenoxy group, a 3-fluoro-2-trifluoromethoxyphenoxy group, a 2-fluoro-3-trifluoromethoxyphenoxy group, a 3-fluoro-4-trifluoromethoxyphenoxy group, a 3-chloro-2-trifluoromethoxyphenoxy group, a 2-chloro-3-trifluoromethoxyphenoxy group, a 3-chloro-4-trifluoromethoxyphenoxy group, a 2-pentafluoroethoxyphenoxy group, a 3-pentafluoroethoxyphenoxy group, a 4-pentafluoroethoxyphenoxy group, a 3-chloro-2-pentafluoroethoxyphenoxy group, a 2-chloro-3-pentafluoroethoxyphenoxy group, a 3-chloro-4-pentafluoroethoxyphenoxy group, a 2-isopropoxyphenoxy group, a 3-isopropoxyphenoxy group, a 4-isopropoxyphenoxy group, a 2-tert-butoxyphenoxy group, a 3-tert-butoxyphenoxy group, a 4-tert-butoxyphenoxy group, a 2-sec-butoxyphenoxy group, a 3-sec-butoxyphenoxy group, a 4-sec-butoxyphenoxy group, a 2-n-heptafluoropropoxyphenoxy group, a 3-n-heptafluoropropoxyphenoxy group, a 4-n-heptafluoropropoxyphenoxy group, a 4-n-pentoxyphenoxy group, and a 4-n-hexyloxyphenoxy group.

The term phenyl C1-C6 alkyl group [wherein, on the phenyl ring, at least one selected from the group consisting of a C1-C4 alkylenedioxy group, a halogen atom, a halogen substituted or unsubstituted C1-C6 alkyl group, and a halogen substituted or unsubstituted C1-C6 alkoxy group may be substituted] is used herein to mean an unsubstituted phenyl C1-C6 alkyl group, or a group wherein, on the phenyl ring constituting the group, 1 to 5 groups, and preferably 1 to 3 groups selected from the group consisting of a C1-C4 alkylenedioxy group, a halogen atom, a halogen substituted or unsubstituted C1-C6 alkyl group, and a halogen substituted or unsubstituted C1-C6 alkoxy group may be substituted, with the proviso that, when the substituent is a C1-C4 alkylenedioxy group, 1 to 2 substituents are preferably substituted). Examples of the phenyl C1-C6 alkyl group may include a benzyl group, a 1-phenethyl group, a 2-phenethyl group, a 3-phenylpropyl group, a 2-phenylpropyl group, a 4-phenylbutyl group, a 5-phenylpentyl group, a 4-phenylpentylgroup, a 6-phenylhexyl group, a 2,3-methylenedioxybenzyl group, a 3,4-methylenedioxybenzyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2,3-difluorobenzyl group, a 3,4-difluorobenzyl group, a 3,5-difluorobenzyl group, a 2,4-difluorobenzyl group, a 2,6-difluorobenzyl group, a 2,3-dichlorobenzyl group, a 3,4-dichlorobenzyl group, a 3,5-dichlorobenzyl group, a 2,4-dichlorobenzyl group, a 2,6-dichlorobenzyl group, a 2-fluoro-4-bromobenzyl group, a 4-chloro-3-fluorobenzyl group, a 2,3,4-trichlorobenzyl group, a 3,4,5-trifluorobenzyl group, a 2,4,6-trichlorobenzyl group, a 4-isopropylbenzyl group, a 4-n-butylbenzyl group, a 4-methylbenzyl group, a 2-methylbenzyl group, a 3-methylbenzyl group, a 2,4-dimethylbenzyl group, a 2,3-dimethylbenzyl group, a 2,6-dimethylbenzyl group, a 3,5-dimethylbenzyl group, a 2,5-dimethylbenzyl group, a 2,4,6-trimethylbenzyl group, a 3,5-ditrifluoromethylbenzyl group, a 2,3,4,5,6-pentafluorobenzyl group, a 4-isopropoxybenzyl group, a 4-n-butoxybenzyl group, a 4-methoxybenzyl group, a 2-methoxybenzyl group, a 3-methoxybenzyl group, a 2,4-dimethoxybenzyl group, a 2,3-dimethoxybenzyl group, a 2,6-dimethoxybenzyl group, a 3,5-dimethoxybenzyl group, a 2,5-dimethoxybenzyl group, a 2,4,6-trimethoxybenzyl group, a 3,5-ditrifluoromethoxybenzyl group, a 2-isopropoxybenzyl group, a 3-chloro-4-methoxybenzyl group, a 2-chloro-4-trifluoromethoxybenzyl group, a 3-methyl-4-fluorobenzyl group, a 4-bromo-3-trifluoromethylbenzyl group, a 2-trifluoromethylbenzyl group, a 3-trifluoromethylbenzyl group, a 4-trifluoromethylbenzyl group, a 2-pentafluoroethylbenzyl group, a 3-pentafluoroethylbenzyl group, a 4-pentafluoroethylbenzyl group, a 2-trifluoromethoxybenzyl group, a 3-trifluoromethoxybenzyl group, a 4-trifluoromethoxybenzyl group, a 2-pentafluoroethoxybenzyl group, a 3-pentafluoroethoxybenzyl group, a 4-pentafluoroethoxybenzyl group, a 2-(2-trifluoromethylphenyl)ethyl group, a 2-(3-trifluoromethylphenyl)ethyl group, a 2-(4-trifluoromethylphenyl)ethyl group, 2-(2-trifluoromethoxyphenyl)ethyl group, a 2-(3-trifluoromethoxyphenyl)ethyl group, a 2-(4-trifluoromethoxyphenyl)ethyl group, a 2-(2-pentafluoroethoxyphenyl)ethyl group, a 2-(3-pentafluoroethoxyphenyl)ethyl group, a 2-(4-pentafluoroethoxyphenyl)ethyl group, a 3-(2-trifluoromethylphenyl)propyl group, a 3-(3-trifluoromethylphenyl)propyl group, a 3-(4-trifluoromethylphenyl)propyl group, a 3-(2-trifluoromethoxyphenyl)propyl group, a 3-(3-trifluoromethoxyphenyl)propyl group, a 3-(4-trifluoromethylphenyl)propyl group, a 3-(3-pentafluoroethoxyphenyl)propyl group, a 3-(4-pentafluoroethoxyphenyl)propyl group, a 4-(3-pentafluoroethoxyphenyl)butyl group, a 5-(4-trifluoromethylphenyl)pentyl group, a 4-(4-trifluoromethylphenyl)pentyl group, a 4-(4-trifluoromethoxyphenyl)pentyl group, a 6-(3-trifluoromethylphenyl)hexyl group, a 6-(4-trifluoromethylphenyl)hexyl group, and a 6-(4-trifluoromethoxyphenyl)hexyl group.

Examples of the piperidyl C1-C6 alkyl group may include a piperidin-1-ylmethyl group, a piperidin-2-ylethyl group, a piperidin-3-ylpropyl group, a piperidin-4-ylbutyl group, a piperidin-1-ylpentyl group, and a piperidin-2-ylhexyl group.

An amino group, wherein at least one selected from the group consisting of a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a C1-C6 alkyl group, and a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], may be substituted as a substituent, may be an amino group wherein 1 or 2 groups selected from the group consisting of a phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], a C1-C6 alkyl group, and a phenyl C1-C6 alkyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], may be substituted as substituents. Examples of the amino group may include an amino group, a methylamino group, a dimethylamino group, an ethylamino group, a diethylamino group, an n-propylamino group, an n-butylamino group, an n-pentylamino group, an n-hexylamino group, a phenylamino group, a (4-chlorophenyl)amino group, a (4-bromophenyl)amino group, a (2,4-dichlorophenyl)amino group, a (2,4,6-trichlorophenyl)amino group, a (2,3,4,5,6-pentafluorophenyl)amino group, a (4-fluorophenyl)amino group, a (4-iodophenyl)amino group, a (4-chlorophenyl)amino group, a (3-methylphenyl)amino group, a (2-trifluoromethylphenyl) amino group, a (3-trifluoromethylphenyl)amino group, a (4-trifluoromethylphenyl)amino group, a (3,4-dimethylphenyl)amino group, a (3,4,5-trimethylphenyl)amino group, a (2-methoxyphenyl)amino group, a (4-trifluoromethoxyphenyl)amino group, a (3-trifluoromethoxyphenyl)amino group, a (3,5-dimethoxyphenyl)amino group, a (2,5-dimethoxyphenyl)amino group, a (2,4,6-trimethoxyphenyl)amino group, an N-methyl-N-(4-trifluoromethylphenyl)amino group, an N-ethyl-N-(4-trifluoromethoxyphenyl)amino group, a 1-phenethylamino group, a 2-phenethylamino group, a 3-phenylpropylamino group, a 2-phenylpropylamino group, a 4-phenylbutylamino group, a 5-phenylpentylamino group, a 4-phenylpentylamino group, a 6-phenylhexylamino group, a 2-fluorobenzylamino group, a 3-fluorobenzylamino group, an N-phenyl-N-(4-fluorobenzyl)amino group, a 2-chlorobenzylamino group, a 3-chlorobenzylamino group, a 4-chlorobenzylamino group, a 2-bromobenzylamino group, an N-methyl-N-(3-bromobenzyl)amino group, a 4-bromobenzylamino group, a 2-iodobenzylamino group, a 3-iodobenzylamino group, a 4-iodobenzylamino group, a 2,3-difluorobenzylamino group, a 3,4-difluorobenzylamino group, a 3,5-difluorobenzylamino group, a 2,4-difluorobenzylamino group, a 2,6-difluorobenzylamino group, a 2,3-dichlorobenzylamino group, a 3,4-dichlorobenzylamino group, a 3,5-dichlorobenzylamino group, a 2,4-dichlorobenzylamino group, a 2,6-dichlorobenzylamino group, a 2-fluoro-4-bromobenzylamino group, a 4-chloro-3-fluorobenzylamino group, a 2,3,4-trichlorobenzylamino group, a 3,4,5-trifluorobenzylamino group, a 2,4,6-trichlorobenzylamino group, a 4-isopropylbenzylamino group, a 4-n-butylbenzylamino group, a 4-methylbenzylamino group, a 2-methylbenzylamino group, a 3-methylbenzylamino group, a 2,4-dimethylbenzylamino group, a 2,3-dimethylbenzylamino group, a 2,6-dimethylbenzylamino group, a 3,5-dimethylbenzylamino group, a 2,5-dimethylbenzylamino group, a 2,4,6-trimethylbenzylamino group, a 3,5-ditrifluoromethylbenzylamino group, a 2,3,4,5,6-pentafluorobenzylamino group, a 4-isopropoxybenzylamino group, a 4-n-butoxybenzylamino group, a 4-methoxybenzylamino group, a 2-methoxybenzylamino group, a 3-methoxybenzylamino group, a 2,4-dimethoxybenzylamino group, a 2,3-dimethoxybenzyl group, a 2,6-dimethoxybenzylamino group, a 3,5-dimethoxybenzylamino group, a 2,5-dimethoxybenzylamino group, a 2,4,6-trimethoxybenzylamino group, a 3,5-ditrifluoromethoxybenzylamino group, a 2-isopropoxybenzylamino group, a 3-chloro-4-methoxybenzylamino group, a 2-chloro-4-trifluoromethoxybenzylamino group, a 3-methyl-4-fluorobenzylamino group, a 4-bromo-3-trifluoromethylbenzylamino group, a 2-trifluoromethylbenzylamino group, a 3-trifluoromethylbenzylamino group, a 4-trifluoromethylbenzylamino group, a 2-pentafluoroethylbenzylamino group, a 3-pentafluoroethylbenzylamino group, a 4-pentafluoroethylbenzylamino group, a 2-trifluoromethoxybenzylamino group, a 3-trifluoromethoxybenzylamino group, a 4-trifluoromethoxybenzylamino group, a 2-pentafluoroethoxybenzylamino group, a 3-pentafluoroethoxybenzylamino group, a 4-pentafluoroethoxybenzylamino group, a 2-(2-trifluoromethylphenyl)ethylamino group, a 2-(3-trifluoromethylphenyl)ethylamino group, a 2-(4-trifluoromethylphenyl)ethylamino group, a 2-(2-trifluoromethoxyphenyl)ethylamino group, a 2-(3-trifluoromethoxyphenyl)ethylamino group, a 2-(4-trifluoromethoxyphenyl)ethylamino group, a 2-(2-pentafluoroethoxyphenyl)ethylamino group, a 2-(3-pentafluoroethoxyphenyl)ethylamino group, a 2-(4-pentafluoroethoxyphenyl)ethylamino group, a 3-(2-trifluoromethylphenyl) propylamino group, a 3-(3-trifluoromethylphenyl) propylamino group, a 3-(4-trifluoromethylphenyl) propylamino group, a 3-(2-trifluoromethoxyphenyl) propylamino group, a 3-(3-trifluoromethoxyphenyl) propylamino group, a 3-(4-trifluoromethoxyphenyl) propylamino group, a 3-(3-pentafluoroethoxyphenyl) propylamino group, a 3-(4-pentafluoroethoxyphenyl) propylamino group, a 4-(3-pentafluoroethoxyphenyl) butylamino group, a 5-(4-trifluoromethylphenyl) pentylamino group, a 4-(4-trifluoromethylphenyl) pentylamino group, a 4-(4-trifluoromethoxyphenyl) pentylamino group, a 6-(3-trifluoromethylphenyl) hexylamino group, a 6-(4-trifluoromethylphenyl)hexylamino group, a 6-(4-trifluoromethoxyphenyl)hexylamino group, an N-methyl-N-phenylamino group, an N-methyl-N-benzylamino group, and an N-phenyl-N-benzylamino group.

Examples of the carbamoyloxy group (wherein, on the amino group, at least one selected from the group consisting of a C1-C6 alkyl group and a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted] may be substituted) may include carbamoyloxy groups such as a carbamoyloxy group, a phenylcarbamoyloxy group, a 2-fluorophenylcarbamoyloxy group, a 3-fluorophenylcarbamoyloxy group, a 4-fluorophenylcarbamoyloxy group, a 2-chlorophenylcarbamoyloxy group, a 3-chlorophenylcarbamoyloxy group, a 4-chlorophenylcarbamoyloxy group, a 2-bromophenylcarbamoyloxy group, a 3-bromophenylcarbamoyloxy group, a 4-bromophenylcarbamoyloxy group, a 2-iodophenylcarbamoyloxy group, a 3-iodophenylcarbamoyloxy group, a 4-iodophenylcarbamoyloxy group, a 2,3-difluorophenylcarbamoyloxy group, a 3,4-difluorophenylcarbamoyloxy group, a 3,5-difluorophenylcarbamoyloxy group, a 2,4-difluorophenylcarbamoyloxy group, a 2,6-difluorophenylcarbamoyloxy group, a 2,3-dichlorophenylcarbamoyloxy group, a 3,4- dichlorophenylcarbamoyloxy group, a 3,5-dichlorophenylcarbamoyloxy group, a 2,4-dichlorophenylcarbamoyloxy group, a 2,6-dichlorophenylcarbamoyloxy group, a 3,4,5-trifluorophenylcarbamoyloxy group, a 2,3,4,5,6-pentafluorophenylcarbamoyloxy group, a 3,4,5-trichlorophenylcarbamoyloxy group, a 2,4,6-trifluorophenylcarbamoyloxy group, a 2,4,6-trichlorophenylcarbamoyloxy group, a 2-methylphenylcarbamoyloxy group, a 3-methylphenylcarbamoyloxy group, a 4-methylphenylcarbamoyloxy group, a 2-methyl-3-chlorophenylcarbamoyloxy group, a 3-methyl-4-chlorophenylcarbamoyloxy group, a 2-chloro-4-methylphenylcarbamoyloxy group, a 2-methyl-3-fluorophenylcarbamoyloxy group, a 2-trifluoromethylphenylcarbamoyloxy group, a 3-trifluoromethylphenylcarbamoyloxy group, a methylcarbamoyloxy group, an ethylcarbamoyloxy group, an n-propylcarbamoyloxy group, an n-butylcarbamoyloxy group, an n-hexylcarbamoyloxy group, an n-penylcarbamoyloxy group, an N-methyl-N-phenylcarbamoyloxy group, an N,N-dimethylcarbamoyloxy group, an N-methyl-N-ethylcarbamoyloxy group, an N-(2-fluorophenyl)-N-methylcarbamoyloxy group, an N-(3-fluorophenyl)-N-methylcarbamoyloxy group, an N-(4-fluorophenyl)-N-methylcarbamoyloxy group, an N-(2-chlorophenyl)-N-methylcarbamoyloxy group, an N-(3-chlorophenyl)-N-methylcarbamoyloxy group, an N-(4-chlorophenyl)-N-methylcarbamoyloxy group, an N-(4-bromophenyl)-N-methylcarbamoyloxy group, an N-(2-iodophenyl)-N-methylcarbamoyloxy group, an N-(3-iodophenyl)-N-methylcarbamoyloxy group, an N-(4-iodophenyl)-N-methylcarbamoyloxy group, an N-(2,3-difluorophenyl)-N-methylcarbamoyloxy group, an N-(3,4-difluorophenyl)-N-methylcarbamoyloxy group, an N-(3,5-difluorophenyl)-N-methylcarbamoyloxy group, an N-(2,4-difluorophenyl)-N-methylcarbamoyloxy group, an N-(2,6-difluorophenyl)-N-methylcarbamoyloxy group, an N-(2,3-dichlorophenyl)-N-methylcarbamoyloxy group, an N-(3,4-dichlorophenyl)-N-methylcarbamoyloxy group, an N-(3,5-dichlorophenyl)-N-methylcarbamoyloxy group, an N-(2,4-dichlorophenyl)-N-methylcarbamoyloxy group, an N-(2,6-dichlorophenyl)-N-methylcarbamoyloxy group, an N-(3,4,5-trifluorophenyl)-N-methylcarbamoyloxy group, an N-(3,4,5-trichlorophenyl)-N-methylcarbamoyloxy group, an N-(2,4,6-trifluorophenyl)-N-methylcarbamoyloxy group, an N-(2,4,6-trichlorophenyl)-N-methylcarbamoyloxy group, an N-(2-methylphenyl)-N-methylcarbamoyloxy group, an N-(3-methylphenyl)-N-methylcarbamoyloxy group, an N-(4-methylphenyl)-N-methylcarbamoyloxy group, an N-(2-methyl-3-chlorophenyl)-N-methylcarbamoyloxy group, an N-(3-methyl-4-chlorophenyl)-N-methylcarbamoyloxy group, an N-(2-chloro-4-methylphenyl)-N-methylcarbamoyloxy group, an N-(2-methyl-3-fluorophenyl)-N-methylcarbamoyloxy group, an N-(2-trifluoromethylphenyl)-N-methylcarbamoyloxy group, an N-(4-trifluoromethylphenyl)-N-methylcarbamoyloxy group, an N-phenyl-N-phenylcarbamoyloxy group, an N-phenyl-N-(2-fluorophenyl)carbamoyloxy group, an N-phenyl-N-(3-fluorophenyl)carbamoyloxy group, an N-phenyl-N-(4-fluorophenyl)carbamoyloxy group, an N-phenyl-N-(2-chlorophenyl)carbamoyloxy group, an N-phenyl-N-(3-chlorophenyl)carbamoyloxy group, an N-phenyl-N-(4-chlorophenyl)carbamoyloxy group, an N-phenyl-N-(2-bromophenyl)carbamoyloxy group, an N-phenyl-N-(3-bromophenyl)carbamoyloxy group, an N-phenyl-N-(4-bromophenyl)carbamoyloxy group, an N-phenyl-N-(2-iodophenyl)carbamoyloxy group, an N-phenyl-N-(3-iodophenyl)carbamoyloxy group, an N-phenyl-N-(4-iodophenyl)carbamoyloxy group, an N-phenyl-N-(2,3-difluorophenyl)carbamoyloxy group, an N-phenyl-N-(3,4-difluorophenyl)carbamoyloxy group, an N-phenyl-N-(3,5-difluorophenyl)carbamoyloxy group, an N-phenyl-N-(2,4-difluorophenyl)carbamoyloxy group, an N-phenyl-N-(2,6-difluorophenyl)carbamoyloxy group, an N-phenyl-N-(2,3-dichlorophenyl)carbamoyloxy group, an N-phenyl-N-(3,4-dichlorophenyl)carbamoyloxy group, an N-phenyl-N-(3,5-dichlorophenyl)carbamoyloxy group, an N-phenyl-N-(2,4-dichlorophenyl)carbamoyloxy group, an N-phenyl-N-(2,6-dichlorophenyl)carbamoyloxy group, an N-phenyl-N-(3,4,5-trifluorophenyl)carbamoyloxy group, an N-phenyl-N-(3,4,5-trichlorophenyl)carbamoyloxy group, an N-phenyl-N-(2,4,6-trifluorophenyl)carbamoyloxy group, an N-phenyl-N-(2,4,6-trichlorophenyl)carbamoyloxy group, an N-phenyl-N-(2-methylphenyl)carbamoyloxy group, an N-phenyl-N-(3-methylphenyl)carbamoyloxy group, an N-phenyl-N-(4-methylphenyl)carbamoyloxy group, an N-phenyl-N-(2-methyl-3-chlorophenyl)carbamoyloxy group, an N-phenyl-N-(3-methyl-4-chlorophenyl)carbamoyloxy group, an N-phenyl-N-(2-chloro-4-methylphenyl)-carbamoyloxy group, an N-phenyl-N-(2-methyl-3-fluorophenyl)carbamoyloxy group, an N-phenyl-N-(2-trifluoromethylphenyl)carbamoyloxy group, an N-phenyl-N-(3-trifluoromethylphenyl) carbamoyloxy group, an N-phenyl-N-(4-trifluoromethylphenyl)carbamoyloxy group, a 2-pentafluoroethylphenylcarbamoyloxy group, a 3-pentafluoroethylphenylcarbamoyloxy group, a 4-pentafluoroethylphenylcarbamoyloxy group, a 2-isopropylphenylcarbamoyloxy group, a 3-isopropylphenylcarbamoyloxy group, a 4-isopropylphenylcarbamoyloxy group, a 2-tert-butylphenylcarbamoyloxy group, a 3-tert-butylphenylcarbamoyloxy group, a 4-tert-butylphenylcarbamoyloxy group, a 2-sec-butylphenylcarbamoyloxy group, a 3-sec-butylphenylcarbamoyloxy group, a 4-sec-butylphenylcarbamoyloxy group, a 2-n-heptafluoropropylphenylcarbamoyloxy group, a 3-n-heptafluoropropylphenylcarbamoyloxy group, a 4-n-heptafluoropropylphenylcarbamoyloxy group, a 4-n-pentylphenylcarbamoyloxy group, a 4-n-hexylphenylcarbamoyloxy group, a 2,4-dimethylphenylcarbamoyloxy group, a 2,4,6-trimethylphenylcarbamoyloxy group, a 3,4-dimethoxyphenylcarbamoyloxy group, a 3,4,5-trimethoxyphenylcarbamoyloxy group, a 2-methoxyphenylcarbamoyloxy group, a 3-methoxyphenylcarbamoyloxy group, a 4-methoxyphenylcarbamoyloxy group, a 2-methoxy-3-chlorophenylcarbamoyloxy group, a 2-fluoro-3-methoxyphenylcarbamoyloxy group, a 2-fluoro-4-methoxyphenylcarbamoyloxy group, a 2,6-dimethoxyphenylcarbamoyloxy group, a 2,3,4-trifluorophenylcarbamoyloxy group, a 3,4,5-trifluorophenylcarbamoyloxy group, a 2-trifluoromethoxyphenylcarbamoyloxy group, a 3-trifluoromethoxyphenylcarbamoyloxy group, a 4-trifluoromethoxyphenylcarbamoyloxy group, a 2-pentafluoroethoxyphenylcarbamoyloxy group, a 3-pentafluoroethoxyphenylcarbamoyloxy group, a 4-pentafluoroethoxyphenylcarbamoyloxy group, a 2-isopropoxyphenylcarbamoyloxy group, a 3-isopropoxyphenylcarbamoyloxy group, a 4-isopropoxyphenylcarbamoyloxy group, a 2-tert-butoxyphenylcarbamoyloxy group, a 3-tert-butoxyphenylcarbamoyloxy group, a 4-tert-butoxyphenylcarbamoyloxy group, a 2-sec-butoxyphenylcarbamoyloxy group, a 3-sec-butoxyphenylcarbamoyloxy group, a 4-sec-butoxyphenylcarbamoyloxy group, a 2-n-heptafluoropropoxyphenylcarbamoyloxy group, a 3-n-heptafluoropropoxyphenylcarbamoyloxy group, a 4-n-heptafluoropropoxyphenylcarbamoyloxy group, a 4-n-pentyloxyphenylcarbamoyloxy group, and a 4-n-hexyloxyphenylcarbamoyloxy group (wherein, on the amino group, 1 or 2 groups selected from the group consisting of a C1-C6 alkyl group and a phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted] may be substituted).

Examples of the halogen substituted or unsubstituted C1-C10 alkyl group may include: the above described halogen substituted or unsubstituted C1-C6 alkyl group; C1-C10 alkyl groups such as a heptyl group, an octyl group, a nonyl group, a decyl group, a 7-fluoroheptyl group, a 7,7,6-trifluoroheptyl group, a 7,7,7,6,6,5,5-heptafluoroheptyl group, a 8-chlorooctyl group, a 8,8-dibromooctyl group, a 6,7,8-trifluorooctyl group, a 8,8,8,7,7,6,6-heptafluorooctyl group, a 8,8,8,7,7-pentachlorooctyl group, a 9-iodononyl group, a 9,9-dibromononyl group, a 9,9,9,8,8-pentachlorononyl group, a 9,9,9,8,8,7,7-heptafluorononyl group, a 10-chlorodecyl group, a 10,10-dibromodecyl group, a 10,10,10,9-tetrachlorodecyl group, and a 10,10,10,9,9,9,8,8-heptafluorodecyl group; and C1-C10 alkyl groups wherein 1 to 7 halogen atoms are substituted.

In addition to the above described phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted), examples of the phenyl group [wherein, on the phenyl ring, at least one selected from the group consisting of a C1-C4 alkylenedioxy group, a cyano group, a phenoxy group, a C1-C6 alkylthio group, a C1-C6 alkanoyl group, a phenyl group, a phenyl C1-C6 alkyl group, a halogen atom, a halogen substituted or unsubstituted C1-C10 alkyl group, and a halogen substituted or unsubstituted C1-C10 alkoxy group may be substituted] may further include phenyl groups such as a 4-cyanophenyl group, a 3-cyanophenyl group, a 2-cyanophenyl group, a 3,4-dicyanophenyl group, a 3,4,5-tricyanophenyl group, a 4-phenoxyphenyl group, a 3-phenoxyphenyl group, a 2-phenoxyphenyl group, a 3,4-diphenoxyphenyl group, a 2,4,6-triphonoxyphenyl group, a 4-methylthiophenyl group, a 3-methylthiophenyl group, a 2-methylthiophenyl group, a 3,4-dimethylthiophenyl group, a 2,4,6-trimethylthiophenyl group, a 4-acetylphenyl group, a 3-acetylphenyl group, a 2-acetylphenyl group, a 3,4-diacetylphenyl group, a 2,4,6-triacetylphenyl group, a 4-biphenyl group, a 3-biphenyl group, a 2-biphenyl group, a 3,4-diphenylphenyl group, a 2,4,6-triphenylphenyl group, a 4-heptyloxyphenyl group, a 3-octyloxyphenyl group, a 2-nonyloxyphenyl group, a 4-decyloxyphenyl group, a 2,4-diheptyloxyphenyl group, a 2,4,6-triheptyloxyphenyl group, a 4-(7,7-dichloroheptyloxy)phenyl group, a 4-benzylphenyl group, a 3-benzylphenyl group, a 2-benzylphenyl group, a 2,4-dibenzylphenyl group, a 2,4,6-tribenzylphenyl group, a 4-octylphenyl group, a 4-heptylphenyl group, a 3-octylphenyl group, a 3-(8,8,8-trifluorooctyl)phenyl group, a 2-nonylphenyl group, a 4-decylphenyl group, a 2,4-dioctylphenyl group, a 2,4,6-trioctyldiphenyl group, a 4-phenyl-3-chlorophenyl group, a 4-phenoxy-3-methylthiophenyl group, a 4-heptyloxy-3-trifluoromethoxyphenyl group, a 4-octyl-2-trifluoromethylphenyl group, a 4-benzyl-2-methylphenyl group, a 3,4-ethylenedioxyphenyl group, and a 3,4-methylenedioxyphenyl group [wherein, on the phenyl ring, 1 to 5 groups, and preferably 1 to 3 groups selected from the group consisting of the above described C1-C4 alkylenedioxy group, cyano group, phenoxy group, the above described C1-C6 alkylthio group, the above described C1-C6 alkanoyl group, phenyl group, the above described phenyl C1-C6 alkyl group, the above described halogen atom, the above described halogen substituted or unsubstituted C1-C6 alkyl group, and the above described halogen substituted or unsubstituted C1-C6 alkoxy group may be substituted (in a case where the substituent is a C1-C4 alkylenedioxy group, 1 or 2 groups are preferably substituted)).

Examples of the carbamoyloxy substituted C1-C6 alkyl group (wherein, on the amino group, at least one selected from the group consisting of a C1-C6 alkyl group, a phenyl C1-C6 alkyl group, a C3-C8 cycloalkyl group, a naphthyl group, a 2,3-dihydro-1H-indenyl group, a 2,3-dihydrobenzofuryl group, and a phenyl group [wherein, on the phenyl ring, at least one selected from the group consisting of a C1-C4 alkylenedioxy group, a cyano group, a phenoxy group, a C1-C6 alkylthio group, a C1-C6 alkanoyl group, a phenyl group, a phenyl C1-C6 alkyl group, a halogen atom, a halogen substituted or unsubstituted C1-C10 alkyl group, and a halogen substituted or unsubstituted C1-C10 alkoxy group may be substituted], may be substituted), may include carbamoyloxy substituted C1-C6 alkyl groups such as a carbamoyloxymethyl group, a 2-carbamoyloxyethyl group, a 1-carbamoyloxyethyl group, a 3-carbamoyloxypropyl group, a 4-carbamoyloxybutyl group, a 5-carbamoyloxypentyl group, a 6-carbamoyloxyhexyl group, a phenylcarbamoyloxymethyl group, a 2-methylphenylcarbamoyloxymethyl group, a 3-methylphenylcarbamoyloxymethyl group, a 4-methylphenylcarbamoyloxymethyl group, a 2,3-dimethylphenylcarbamoyloxymethyl group, a 2,4-dimethylphenylcarbamoyloxymethyl group, a 2,6-dimethylphenylcarbamoyloxymethyl group, a 2,4,6-trimethylphenylcarbamoyloxymethyl group, a 2-trifluoromethylphenylcarbamoyloxymethyl group, a 3-trifluoromethylphenylcarbamoyloxymethyl group, a 4-trifluoromethylphenylcarbamoyloxymethyl group, a 2,3-ditrifluoromethylphenylcarbamoyloxymethyl group, a 2,4-ditrifluoromethylphenylcarbamoyloxymethyl group, a 2,6-ditrifluoromethylphenylcarbamoyloxymethyl group, a 2-pentafluoroethylphenylcarbamoyloxymethyl group, a 3-pentafluoroethylphenylcarbamoyloxymethyl group, a 4-pentafluoroethylphenylcarbamoyloxymethyl group, a 2-(n-propylphenyl)carbamoyloxymethyl group, a 3-(n-propylphenyl)carbamoyloxymethyl group, a 4-(n-propylphenyl)carbamoyloxymethyl group, a 2-(phenylcarbamoyloxy)ethyl group, a 2-(3-trifluoromethylphenylcarbamoyloxy)ethyl group, a 2-(4-trifluoromethylphenylcarbamoyloxy)ethyl group, a 2-(2,3-ditrifluoromethylphenylcarbamoyloxy)ethyl group, a 2-(2,4-ditrifluoromethylphenylcarbamoyloxy)ethyl group, a 2-(2,6-ditrifluoromethylphenylcarbamoyloxy)ethyl group, a 2-(2-pentafluoroethylphenylcarbamoyloxy)ethyl group, a 2-(3-pentafluoroethylphenylcarbamoyloxy)ethyl group, a 2-(4-pentafluoroethylphenylcarbamoyloxy)ethyl group, a 3-(phenylcarbamoyloxy)propyl group, a 3-(3-trifluoromethylphenylcarbamoyloxy)propyl group, a 3-(4-trifluoromethylphenylcarbamoyloxy)propyl group, a 3-(2,3-ditrifluoromethylphenylcarbamoyloxy)propyl group, a 3-(2,4-ditrifluoromethylphenylcarbamoyloxy)propyl group, a 3-(2,6-ditrifluoromethylphenylcarbamoyloxy)-propyl group, a 3-(2-pentafluoroethylphenyl-carbamoyloxy)propyl group, a 3-(3-pentafluoroethylphenylcarbamoyloxy)propyl group, a 3-(4-pentafluoroethylphenylcarbamoyloxy)propyl group, a 4-(4-trifluoromethylphenylcarbamoyloxy)butyl group, a 5-(4-trifluoromethylphenylcarbamoyloxy)pentyl group, a 6-(4-trifluoromethylphenylcarbamoyloxy)hexyl group, a (2-fluorophenylcarbamoyloxy)methyl group, a 2-(3-fluorophenylcarbamoyloxy)ethyl group, a 1-(4-fluorophenylcarbamoyloxy)ethyl group, a 3-(2-chlorophenylcarbamoyloxy)propyl group, a 4-(3-chlorophenylcarbamoyloxy)butyl group, a 5-(4-chlorophenylcarbamoyloxy)pentyl group, a 6-(2-bromophenylcarbamoyloxy)hexyl group, a (3-bromophenylcarbamoyloxy)methyl group, a 2-(4-bromophenylcarbamoyloxy)ethyl group, a 1-(2-iodophenylcarbamoyloxy)ethyl group, a 3-(3-iodophenylcarbamoyloxy)propyl group, a 4-(4-iodophenylcarbamoyloxy)butyl group, a 5-(2,3-difluorophenylcarbamoyloxy)pentyl group, a 6-(3,4-difluorophenylcarbamoyloxy)hexyl group, a (3,5-difluorophenylcarbamoyloxy)methyl group, a 2-(2,4-difluorophenylcarbamoyloxy)ethyl group, a 1-(2,6-difluorophenylcarbamoyloxy)ethyl group, a 3-(2,3-dichlorophenylcarbamoyloxy)propyl group, a 4-(3,4-dichlorophenylcarbamoyloxy)butyl group, a 5-(3,5-dichlorophenylcarbamoyloxy)pentyl group, a 6-(2,4-dichlorophenylcarbamoyloxy)hexyl group, a (2,6-dichlorophenylcarbamoyloxy)methyl group, a 2-(3,4,5-trifluorophenylcarbamoyloxy)ethyl group, a 1-(2,3,4,5,6-pentafluorophenylcarbamoyloxy)ethyl group, a 3-(3,4,5-trichlorophenylcarbamoyloxy)propyl group, a 4-(2,4,6-trifluorophenylcarbamoyloxy)butyl group, a 5-(2,4,6-trichlorophenylcarbamoyloxy)pentyl group, a (2-methyl-3-chlorophenylcarbamoyloxy)methyl group, a (3-methyl-4-chlorophenylcarbamoyloxy)methyl group, a (2-chloro-4-methylphenylcarbamoyloxy)methyl group, a (2-methyl-3-fluorophenylcarbamoyloxy)methyl group, an ethylcarbamoyloxymethyl group, an n-butylcarbamoyloxymethyl group, an n-hexylcarbamoyloxymethyl group, an n-pentylcarbamoyloxymethyl group, an N-methyl-N-phenylcarbamoyloxymethyl group, an N,N-dimethylcarbamoyloxymethyl group, an N-methyl-N-ethylcarbamoyloxymethyl group, a 2-(N-(2-fluorophenyl)-N-methylcarbamoyloxy)ethyl group, a 1-(N-(3-fluorophenyl)-N-methylcarbamoyloxy)ethyl group, a 3-(N-(4-fluorophenyl)-N-methylcarbamoyloxy)propyl group, a 4-(N-(2-chlorophenyl)-N-methylcarbamoyloxy)butyl group, a 5-(N-(3-chlorophenyl)-N-methylcarbamoyloxy)pentyl group, a 6-(N-(4-chlorophenyl)-N-methylcarbamoyloxy)hexyl group, an (N-(4-bromophenyl)-N-methylcarbamoyloxy)methyl group, a 2-(N-(2-iodophenyl)-N-methylcarbamoyloxy)ethyl group, a 1-(N-(3-iodophenyl)-N-methylcarbamoyloxy)ethyl group, a 3-(N-(4-iodophenyl)-N-methylcarbamoyloxy)propyl group, a 4-(N-(2,3-difluorophenyl)-N-methylcarbamoyloxy)butyl group, a 5-(N-(3,4-difluorophenyl)-N-methylcarbamoyloxy)pentyl group, a 6-(N-(3,5-difluorophenyl)-N-methylcarbamoyloxy)hexyl group, an (N-(2,4-difluorophenyl)-N-methylcarbamoyloxy)methyl group, a 2-(N-(2,6-difluorophenyl)-N-methylcarbamoyloxy)ethyl group, a 1-(N-(2,3-dichlorophenyl)-N-methylcarbamoyloxy)ethyl group, a 3-(N-(3,4-dichlorophenyl)-N-methylcarbamoyloxy)propyl group, an (N-(3,5-dichlorophenyl)-N-methylcarbamoyloxy)methyl group, a 4-(N-(2,4-dichlorophenyl)-N-methylcarbamoyloxy)butyl group, a 5-(N-(2,6-dichlorophenyl)-N-methylcarbamoyloxy)pentyl group, a 6-(N-(3,4,5-trifluorophenyl)-N-methylcarbamoyloxy)hexyl group, an (N-(3,4,5-trichlorophenyl)-N-methylcarbamoyloxy)methyl group, a 2-(N-(2,4,6-trifluorophenyl)-N-methylcarbamoyloxy)ethyl group, a 1-(N-(2,4,6-trichlorophenyl)-N-methylcarbamoyloxy)ethyl group, a 3-(N-(2-methylphenyl)-N-methylcarbamoyloxy)propyl group, a 4-(N-(3-methylphenyl)-N-methylcarbamoyloxy)butyl group, a 5-(N-(4-methylphenyl)-N-methylcarbamoyloxy)hexyl group, a 6-(N-(2-methyl-3-chlorophenyl)-N-methylcarbamoyloxy)hexyl group, an (N-(3-methyl-4-chlorophenyl)-N-methylcarbamoyloxy)methyl group, a 2-(N-(2-chloro-4-methylphenyl)-N-methylcarbamoyloxy)ethyl group, a 1-(N-(2-methyl-3-fluorophenyl)-N-methylcarbamoyloxy)ethyl group, a 3-(N-(2-trifluoromethylphenyl)-N-methylcarbamoyloxy)propyl group, a 4-(N-(4-trifluoromethylphenyl)-N-methylcarbamoyloxy)butyl group, a 2-(N-(4-trifluoromethylphenyl)-N-methylcarbamoyloxy)ethyl group, a 5-(N-phenyl-N-phenylcarbamoyloxy)pentyl group, a 6-(N-phenyl-N-(2-fluorophenyl)carbamoyloxy)hexyl group, an (N-phenyl-N-(3-fluorophenyl)carbamoyloxy)methyl group, a 2-(N-phenyl-N-(4-fluorophenyl)-carbamoyloxy)ethyl group, a 1-(N-phenyl-N-(2-chlorophenyl)carbamoyloxy)ethyl group, a 1-(N-phenyl-N-(3-chlorophenyl)carbamoyloxy)ethyl group, a 3-(N-phenyl-N-(4-chlorophenyl)carbamoyloxy)propyl group, a 4-(N-phenyl-N-(2-bromophenyl)carbamoyloxy)butyl group, a 5-(N-phenyl-N-(3-bromophenyl)carbamoyloxy)pentyl group, a 6-(N-phenyl-N-(4-bromophenyl)-carbamoyloxy)hexyl group, an (N-phenyl-N-(2-iodophenyl)carbamoyloxy)methyl group, a 1-(N-phenyl-N-(3-iodophenyl)carbamoyloxy)ethyl group, a 2-(N-phenyl-N-(4-iodophenyl)carbamoyloxy)ethyl group, a 1-(N-phenyl-N-(2,3-difluorophenyl)carbamoyloxy)ethyl group, a 3-(N-phenyl-N-(3,4-difluorophenyl)carbamoyloxy)propyl group, a 4-(N-phenyl-N-(3,5-difluorophenyl)-carbamoyloxy)butyl group, a 5-(N-phenyl-N-(2,4-difluorophenyl)carbamoyloxy)pentyl group, a 6-(N-phenyl-N-(2,6-difluorophenyl)carbamoyloxy)hexyl group, an (N-phenyl-N-(2,3-dichlorophenyl)carbamoyloxy)methyl group, a 2-(N-phenyl-N-(3,4-dichlorophenyl)-carbamoyloxy)ethyl group, a 1-(N-phenyl-N-(3,5-dichlorophenyl)carbamoyloxy)ethyl group, a 3-(N-phenyl-N-(2,4-dichlorophenyl)carbamoyloxy)propyl group, a 4-(N-phenyl-N-(2,6-dichlorophenyl)carbamoyloxy)butyl group, a 5-(N-phenyl-N-(3,4,5-trifluorophenyl)-carbamoyloxy)pentyl group, a 6-(N-phenyl-N-(3,4,5-trichlorophenyl)carbamoyloxy)hexyl group, an (N-phenyl-N-(2,4,6-trifluorophenyl)carbamoyloxy)methyl group, a 2-(N-phenyl-N-(2,4,6-trichlorophenyl)carbamoyloxy)ethyl group, a 1-(N-phenyl-N-(2-methylphenyl)-carbamoyloxy)ethyl group, a 3-(N-phenyl-N-(3-methylphenyl)carbamoyloxy)propyl group, a 4-(N-phenyl-N-(4-methylphenyl)carbamoyloxy)butyl group, a 5-(N-phenyl-N-(2-methyl-3-chlorophenyl)carbamoyloxy)pentyl group, a 6-(N-phenyl-N-(3-methyl-4-chlorophenyl)-carbamoyloxy)hexyl group, an (N-phenyl-N-(2-chloro-4-methylphenyl)carbamoyloxy)methyl group, an (N-phenyl-N-(2-methyl-3-fluorophenyl)carbamoyloxy)methyl group, a 2-(N-phenyl-N-(2-trifluoromethylphenyl)-carbamoyloxy)ethyl group, a 1-(N-phenyl-N-(3-trifluoromethylphenyl)carbamoyloxy)ethyl group, a 3-(N-phenyl-N-(4-trifluoromethylphenyl)carbamoyloxy)propyl group, a 2-isopropylphenylcarbamoyloxymethyl group, a 3-isopropylphenylcarbamoyloxymethyl group, a 4-isopropylphenylcarbamoyloxymethyl group, a 2-tert-butylphenylcarbamoyloxymethyl group, a 4-n-butylphenylcarbamoyloxymethyl group, a 2-methyl-4-chlorophenylcarbamoyloxymethyl group, a 3-tert-butylphenylcarbamoyloxymethyl group, a 4-tert-butylphenylcarbamoyloxymethyl group, a 2-sec-butylphenylcarbamoyloxymethyl group, a 3-sec-butylphenylcarbamoyloxymethyl group, a 4-sec-butylphenylcarbamoyloxymethyl group, a 4-pentylphenylcarbamoyloxymethyl group, a 4-hexylphenylcarbamoyloxymethyl group, a 3,4-dimethoxyphenylcarbamoyloxymethyl group, a 3,4,5-trimethoxyphenylcarbamoyloxymethyl group, a 2-methoxyphenylcarbamoyloxymethyl group, a 3-methoxyphenylcarbamoyloxymethyl group, a 4-methoxyphenylcarbamoyloxymethyl group, a 2-methoxy-3-chlorophenylcarbamoyloxymethyl group, a 2-(2-fluoro-3-methoxyphenylcarbamoyloxy)ethyl group, a 1-(2-fluoro-4-methoxyphenylcarbamoyloxy)ethyl group, a 3-[(2,6-dimethoxyphenylcarbamoyloxy)propyl group, a 4-(2,3,4-trifluorophenylcarbamoyloxy)butyl group, a 5-(3,4,5-trifluorophenylcarbamoyloxy)pentyl group, a 6-(2- trifluoromethoxyphenylcarbamoyloxy)hexyl group, a 3-trifluoromethoxyphenylcarbamoyloxymethyl group, a 4-trifluoromethoxyphenylcarbamoyloxymethyl group, a 2-(4-trifluoromethoxyphenylcarbamoyloxy)ethyl group, a 2-(N-methyl-N-(4-trifluoromethoxyphenyl)carbamoyloxy)ethyl group, a 3-trifluoromethylphenylcarbamoyloxymethyl group, a 4-trifluoromethylphenylcarbamoyloxymethyl group, a 3-trifluoromethyl-4-chlorophenylcarbamoyloxymethyl group, a 3,5-ditrifluoromethoxyphenylcarbamoyloxymethyl group, a 2,4-dichlorophenylcarbamoyloxymethyl group, a 2-chlorophenylcarbamoyloxymethyl group, a 3-chlorophenylcarbamoyloxymethyl group, a 4-chlorophenylcarbamoyloxymethyl group, a 3,5-dichlorophenylcarbamoyloxymethyl group, a 3,4-dichlorophenylcarbamoyloxymethyl group, a 2-fluorophenylcarbamoyloxymethyl group, a 3-fluorophenylcarbamoyloxymethyl group, a 4-fluorophenylcarbamoyloxymethyl group, a 2-pentafluoroethoxyphenylcarbamoyloxymethyl group, a 3-pentafluoroethoxyphenylcarbamoyloxymethyl group, an 4-pentafluoroethoxyphenylcarbamoyloxymethyl group, a 2-isopropoxyphenylcarbamoyloxymethyl group, a 3-isopropoxyphenylcarbamoyloxymethyl group, a 4-isopropoxyphenylcarbamoyloxymethyl group, a 2-tert-butoxyphenylcarbamoyloxymethyl group, a 4-n-butoxyphenylcarbamoyloxymethyl group, a 3-methoxyphenylcarbamoyloxymethyl group, a 4-methoxyphenylcarbamoyloxymethyl group, a 4-ethoxyphenylcarbamoyloxymethyl group, a 3-tert-butoxyphenylcarbamoyloxymethyl group, a 4-tert-butoxyphenylcarbamoyloxymethyl group, a 2-sec-butoxyphenylcarbamoyloxymethyl group, a 3-sec-butoxyphenylcarbamoyloxymethyl group, a 4-sec-butoxyphenylcarbamoyloxymethyl group, a 2-n-heptafluoropropoxyphenylcarbamoyloxymethyl group, a 3-n-heptafluoropropoxyphenylcarbamoyloxymethyl group, a 4-n-heptafluoropropoxyphenylcarbamoyloxymethyl group, a 4-n-pentyloxyphenylcarbamoyloxymethyl group, a 4-n-hexyloxyphenylcarbamoyloxymethyl group, a 4-cyanophenylcarbamoyloxymethyl group, an (N-methyl-N-(3-cyanophenyl)carbamoyloxy)methyl group, a 2-cyanophenylcarbamoyloxymethyl group, a 3,4-dicyanophenylcarbamoyloxymethyl group, a 3,4,5-tricyanophenylcarbamoyloxymethyl group, a 4-phenoxyphenylcarbamoyloxymethyl group, an (N-methyl-N-(3-phenoxyphenyl)carbamoyloxy)methyl group, a 2-phenoxyphenylcarbamoyloxymethyl group, a 3,4-diphenoxyphenylcarbamoyloxymethyl group, a 2,4,6-triphenoxyphenylcarbamoyloxymethyl group, a 4-methylthiophenylcarbamoyloxymethyl group, an (N-methyl-N-(4-methylthiophenyl)carbamoyloxy)methyl group, a 3-methylthiophenylcarbamoyloxymethyl group, a 2-methylthiophenylcarbamoyloxymethyl group, a 3,4-dimethylthiophenylcarbamoyloxymethyl group, a 2,4,6-trimethylthiophenylcarbamoyloxymethyl group, a 4-acetylphenylcarbamoyloxymethyl group, a 3-acetylphenylcarbamoyloxymethyl group, a 2-acetylphenylcarbamoyloxymethyl group, a 3,4-diacetylphenylcarbamoyloxymethyl group, an (N-methyl-N-(3,4-diacetylphenyl)carbamoyloxy) methyl group, a 2,4,6-triacetylphenylcarbamoyloxymethyl group, a 4-biphenylcarbamoyloxymethyl group, a 3-biphenylcarbamoyloxymethyl group, a 2-biphenylcarbamoyloxymethyl group, an (N-methyl-N-(2-biphenyl)carbamoyloxy)methyl group, a 3,4-diphenylcarbamoyloxymethyl group, a 2,4,6-triphenylphenylcarbamoyloxymethyl group, a 4-n-heptyloxyphenylcarbamoyloxymethyl group, an (N-methyl-N-4-(n-heptyloxyphenyl)carbamoyloxy)methyl group, a 3-n-octyloxyphenylcarbamoyloxymethyl group, a 2-n-nonyloxyphenylcarbamoyloxymethyl group, a 4-n-decyloxyphenylcarbamoyloxymethyl group, a 2,4-di-n-heptyloxyphenylcarbamoyloxymethyl group, a 2,4,6-tri-n-heptyloxyphenylcarbamoyloxymethyl group, a 4-(7,7-dichloroheptyloxy)phenylcarbamoyloxymethyl group, a 4-benzylphenylcarbamoyloxymethyl group, an (N-methyl-N-(4-benzylphenyl)carbamoyloxy)methyl group, a 3-benzylphenylcarbamoyloxymethyl group, a 2-benzylphenylcarbamoyloxymethyl group, a 2,4-dibenzylphenylcarbamoyloxymethyl group, a 2,4,6-tribenzylphenylcarbamoyloxymethyl group, a 4-n-octylphenylcarbamoyloxymethyl group, an (N-methyl-N-(4-n-octylphenyl)carbamoyloxy)methyl group, a 3-n-heptylphenylcarbamoyloxymethyl group, a 2-n-octylphenylcarbamoyloxymethyl group, a 3-(8,8,8-trifluorooctyl)phenylcarbamoyloxymethyl group, a 4-n-nonylphenylcarbamoyloxymethyl group, a 3-n-decylphenylcarbamoyloxymethyl group, a 2,4-di-n-octylphenylcarbamoyloxymethyl group, a 2,4,6-tri-n-octyldiphenylcarbamoyloxymethyl group, a 4-phenyl-3-chlorophenylcarbamoyloxymethyl group, a 4-phenoxy-3-methylthiophenylcarbamoyloxymethyl group, a 4-n-heptyloxy-3-trifluoromethoxyphenylcarbamoyloxymethyl group, a 4-n-octyl-2-trifluoromethylphenyl-carbamoyloxymethyl group, a 4-benzyl-2-methylphenylcarbamoyloxymethyl group, a 3,4-ethylenedioxyphenylcarbamoyloxymethyl group, a 3,4-methylenedioxyphenylcarbamoyloxymethyl group, a benzylcarbamoyloxymethyl group, a 2-phenylethylcarbamoyloxymethyl group, a cyclohexylcarbamoyloxymethyl group, a 1-naphthylcarbamoyloxymethyl group, a 2-naphthylcarbamoyloxymethyl group, a 5-(2,3-dihydro-1H-indenyl) carbamoyloxymethyl group, a 5-(2,3-dihydrobenzofuryl) carbamoyloxymethyl group, an (N-methyl-N-(3,4-methylenedioxyphenyl)carbamoyloxy)methyl group, an (N-methyl-N-benzylcarbamoyloxy)methyl group, an (N-methyl-N-(2-phenylethyl)carbamoyloxy)methyl group, an (N-methyl-N-cyclohexylcarbamoyloxy)methyl group, an (N-methyl-N-(1-naphthyl)carbamoyloxy)methyl group, an (N-methyl-N-(2-naphthyl)carbamoyloxy)methyl group, an (N-methyl-N-(5-(2,3-dihydro-1H-indenyl))-carbamoyloxy) methyl group, and an (N-methyl-N-(2,3-dihydro-5-benzofuryl)carbamoyloxy)methyl group (wherein, on the amino group, 1 or 2 groups selected from the following groups may be substituted: a C1-C6 alkyl group, the above described phenyl C1-C6 alkyl group, the above described C3-C8 cycloalkyl group, naphthyl group, 2,3-dihydro-1H-indenyl group, 2,3-dihydrobenzofuryl group, and the above described phenyl group [wherein, on the phenyl ring, 1 to 5 groups, and preferably 1 to 3 groups selected from the group consisting of a C1-C4 alkylenedioxy group, a cyano group, a phenoxy group, a C1-C6 alkylthio group, a C1-C6 alkanoyl group, a phenyl group, a phenyl C1-C6 alkyl group, a halogen atom, a halogen substituted or unsubstituted C1-C10 alkyl group, and a halogen substituted or unsubstituted C1-C10 alkoxy group may be substituted (in a case where the substituent is a C1-C4 alkylenedioxy group, 1 or 2 groups are preferably substituted))).

Examples of the C1-C6 alkanoyl substituted C1-C6 alkyl group may include an acetylmethyl group, a 2-propionylethyl group, a 1-buthyrylethyl group, a 2-acetylethyl group, a 3-acetylpropyl group, a 4-acetylbutyl group, a 4-isobuthyrylbutyl group, a 5-pentanoylpentyl group, a 6-acetylhexyl group, a 6-tert-butylcarbonylhexyl group, a 1,1-dimethyl-2-hexanoylethyl group, and a 2-methyl-3-acetylpropyl group.

In addition to the above described phenoxy C1-C6 alkyl group (wherein, on the phenyl ring at least one selected from the group consisting of a halogen atom, a halogen substituted or unsubstituted C1-C6 alkyl group, and a halogen substituted or unsubstituted C1-C6 alkoxy group may be substituted), examples of the phenoxy C1-C6 alkyl group (wherein, on the phenyl ring, at least one selected from the following groups may be substituted: a halogen atom; a C1-C4 alkylenedioxy group; a C1-C6 alkoxycarbonyl group; a phenyl group; a phenoxy group; a pyrrolyl group; a benzothiozolyl group; a 1,2,4-triazolyl group; an imidazolyl group; an isoxazolyl group; a benzoxazolyl group; a benzotriazolyl group; a cyano group; a nitro group; a C2-C6 alkenyl group; a C1-C6 alkanoyl group; a C1-C6 alkoxycarbonyl substituted C1-C6 alkyl group; a C1-C6 alkanoyl substituted C1-C6 alkyl group; a group —N($R^{11B}$)$R^{12B}$ (wherein $R^{11B}$ and $R^{12B}$, which may be identical or different, each represent a hydrogen atom, a C1-C6 alkyl group, a C1-C6 alkanoyl group, or a phenyl group, and $R^{11B}$ and $R^{12B}$ may bind to each other adjacent thereto directly or through a nitrogen, oxygen or sulfur atom, so as to form a 5-7 membered saturated heterocyclic ring together with the nitrogen atom, wherein, on the heterocyclic ring, at least one selected from the group consisting of a C1-C6 alkoxycarbonyl group and an amino group [wherein, on the amino group, at least one selected from a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) and a C1-C6 alkyl group may be substituted] may be substituted); a phenyl C1-C6 alkoxy group; a phenyl C1-C6 alkyl group; a C1-C6 alkylthio group; a C3-C8 cycloalkyl group; a halogen substituted or unsubstituted C1-C6 alkyl group; and a halogen substituted or unsubstituted C1-C6 alkoxy group), may further include phenoxy C1-C6 alkyl groups such as a 3,4-methylenedioxyphenoxymethyl group, a 3,4-ethylenedioxyphenoxymethyl group, a 4-ethoxycarbonylphenoxymethyl group, a 3-methoxycarbonylphenoxymethyl group, a 2-ethoxycarbonylphenoxymethyl group, a 2,4-diethoxycarbonylphenoxymethyl group, a 2,4,6-triethoxycarbonylphenoxymethyl group, a 2-ethoxycarbonyl-4-methylphenoxymethyl group, a 2-methoxycarbonyl-4-methoxyphenoxymethyl group, a 2-methoxycarbonyl-3-methoxyphenoxymethyl group, a 2-(4-ethoxycarbonylphenoxy)ethyl group, a 4-cyanophenoxymethyl group, a 3-cyanophenoxymethyl group, a 2-cyanophenoxymethyl group, a 2,4-dicyanophenoxymethyl group, a 2,4,6-tricyanophenoxymethyl group, a 2-(4-cyanophenoxy)ethyl group, a 4-nitrophenoxymethyl group, a 3-nitrophenoxymethyl group, a 2-nitrophenoxymethyl group, a 2,4-dinitrophenoxymethyl group, a 2,4,6-trinitrophenoxymethyl group, a 2-(4-nitrophenoxy)ethyl group, a 4-allylphenoxymethyl group, a 3-allylphenoxymethyl group, a 2-allylphenoxymethyl group, a 3,4-diallylphenoxymethyl group, a 3,4,5-triallylphenoxymethyl group, a 2-(4-allylphenoxy)ethyl group, a 2-(3-allylphenoxy)ethyl group, a 3-diethylaminophenoxymethyl group, a 3-anilinophenoxymethyl group, a 4-acetylaminophenoxymethyl group, a 2,4,6-tri(diethylamino)phenoxymethyl group, a 2-anilinophenoxymethyl group, a 2,4-diacetylaminophenoxymethyl group, a 2-(3-diethylaminophenoxy)ethyl group, a 2-(3-anilinophenoxy)ethyl group, a 2-(4-(2-acetylethyl)phenoxy)ethyl group, a 4-(2-acetylethyl)phenoxymethyl group, a 3-acetylmethylphenoxymethyl group, 2-(3-acetylpropyl)phenoxymethyl group, a 2,4-di(2-acetylethyl)phenoxymethyl group, a 2,4,6-tri(2-acetylethyl)phenoxymethyl group, a 4-methoxycarbonylmethylphenoxymethyl group, a 3-ethoxycarbonylmethylphenoxymethyl group, a 2-methoxycarbonylmethylphenoxymethyl group, a 2,4-dimethoxycarbonylmethylphenoxymethyl group, a 2,4,6-trimethoxycarbonylmethylphenoxymethyl group, a 2-(4-methoxycarbonylmethylphenoxy)ethyl group, a 4-propionylphenoxymethyl group, a 4-acetylphenoxymethyl group, a 3-propionylphenoxymethyl group, a 2-acetylphenoxymethyl group, a 2,4-dipropionylphenoxymethyl group, a 2,4,6-triacetylphenoxymethyl group, a 2-(4-propionylphenoxy)ethyl group, a 2-benzylphenoxymethyl group, a 3-benzylphenoxymethyl group, a 4-benzylphenoxymethyl group, a 2,3-dibenzylphenoxymethyl group, a 3,4,5-tribenzylphenoxymethyl group, a 4-methylthiophenoxymethyl group, a 3-methylthiophenoxymethyl group, a 2-methylthiophenoxymethyl group, a 2,4-dimethylthiophenoxymethyl group, a 2,4,6-trimethylthiophenoxymethyl group, a 2-(4-methylthiophenoxy)ethyl group, a 4-cyclopentylphenoxymethyl group, a 3-cyclohexylphenoxymethyl group, a 4-cyclohexylphenoxymethyl group, a 2-cycloheptylphenoxymethyl group, a 2,4-dicyclopentylphenoxymethyl group, a 2,4-cyclopentyl-6-cyclooctylphenoxymethyl group, a 2-(4-cyclohexylphenoxy)ethyl group, a 2-(4-cyclopentylphenoxy)ethyl group, a 4-n-octyloxyphenoxymethyl group, a 2-(4-n-octyloxyphenoxy)ethyl group, a 4-phenylphenoxymethyl group, a 3-phenylphenoxymethyl group, a 2-phenylphenoxymethyl group, a 2,4-diphenylphenoxymethyl group, a 2,4,6-triphenylphenoxymethyl group, a 2-(4-phenylphenoxy)ethyl group, a 4-phenoxyphenoxymethyl group, a 3-phenoxyphenoxymethyl group, a 2-phenoxyphenoxymethyl group, a 2,4-diphenoxyphenoxymethyl group, a 2,4,6-triphenoxyphenoxymethyl group, a 2-(3-phenoxyphenoxy)ethyl group, a 4-benzyloxyphenoxymethyl group, a 3-benzyloxyphenoxymethyl group, a 2-benzyloxyphenoxymethyl group, a 2,4-dibenzyloxyphenoxymethyl group, a 2,4,6-tribenzyloxyphenoxymethyl group, a 2-(4-benzyloxyphenoxy)ethyl group, a 2,4-dibenzylphenoxymethyl group, a 2,4,6-tribenzylphenoxymethyl group, a 2-(4-benzylphenoxy)ethyl group, a 4-(1-pyrrolyl)phenoxymethyl group, a 3-(1-pyrrolyl)phenoxymethyl group, a 2-(1-pyrrolyl)phenoxymethyl group, a 2,4-di(1-pyrrolyl)phenoxymethyl group, a 2,4,6-tri (1-pyrrolyl)phenoxymethyl group, a 2-(2-benzothiazolyl) phenoxymethyl group, a 2-(2-benzothiazolyl)phenoxymethyl group, a 3-(2-benzothiazolyl)phenoxymethyl group, a 2,4,6-tri(5-benzothiazolyl)phenoxymethyl group, a 2,4-di(6-benzothiazolyl)phenoxymethyl group, a 4-(1-1,2,4-triazolyl) phenoxymethyl group, a 3-(1-1,2,4-triazolyl)phenoxymethyl group, a 2-(1-1,2,4-triazolyl)phenoxymethyl group, a 4-(3-1,2,4-triazolyl)phenoxymethyl group, a 2,4-di(5-1,2,4-triazolyl)phenoxymethyl group, a 2,4,6-tri(1-1,2,4-triazolyl)phenoxymethyl group, a 4-(5-isoxazolyl)phenoxymethyl group, a 3-(3-isoxazolyl)phenoxymethyl group, a 2-(4-isoxazolyl) phenoxymethyl group, a 2-(5-isoxazolyl)phenoxymethyl group, a 2,4-di(5-isoxazolyl)phenoxymethyl group, a 2,4,6-tri(5-isoxazolyl)phenoxymethyl group, a 4-(1-imidazolyl) phenoxymethyl group, a 3-(2-imidazolyl)phenoxymethyl group, a 2-(4-imidazolyl)phenoxymethyl group, a 2,4-di(1-imidazolyl)phenoxymethyl group, a 2,4,6-tri(1-imidazolyl) phenoxymethyl group, a 4-(1-benzotriazolyl)phenoxymethyl group, a 3-(1-benzotriazolyl)phenoxymethyl group, a 2-(1-benzotriazolyl)phenoxymethyl group, a 2-(1-benzotriazolyl) phenoxymethyl group, a 2,4-di(1-benzotriazolyl)phenoxymethyl group, a 2,4,6-tri(1-benzotriazolyl)phenoxymethyl group, a 4-(6-benzimidazolyl)phenoxymethyl group, a 3-(5-benzimidazolyl)phenoxymethyl group, a 2-(2-benzimidazolyl)phenoxymethyl group, a 2-(1-benzotriazolyl)phenoxymethyl group, a 2,4-di(2-benzimidazolyl) phenoxymethyl group, a 2,4,6-tri(2-benzimidazolyl) phenoxymethyl group, a 4-(4-tert-butoxycarbonyl-1- piperazinyl)phenoxymethyl group, a 2-(4-(4-(4-(N-(4-chlorophenyl)-N-methylamino))-1-piperidyl)phenoxy)ethyl group, a 2-(4-(1-1,2,4-triazolyl)phenoxy)ethyl group, a 2-(2-(5-isoxazolyl)phenoxy)ethyl group, a 2-(2-methoxy-4-allylphenoxy)ethyl group, a 2-(2-fluoro-4-nitrophenoxy)ethyl group, a 2-(2-ethoxy-5-allylphenoxy)ethyl group, a 2-fluoro-4-nitrophenoxymethyl group, a 2-methoxy-4-allylphenoxymethyl group, a 2-ethoxy-5-allylphenoxymethyl group, and a 2-methyl-4-acetylphenoxymethyl group (wherein, on the phenyl ring, 1 to 5 groups, and preferably 1 to 3 groups selected from the following groups may be substituted: a halogen atom; the above described C1-C4 alkylenedioxy group; the above described C1-C6 alkoxycarbonyl group; a phenyl group; a phenoxy group; a pyrrolyl group; a benzothiozolyl group; a 1,2,4-triazolyl group; an imidazolyl group; an isoxazolyl group; a benzoxazolyl group; a benzotriazolyl group; a cyano group; a nitro group; the above described C2-C6 alkenyl group; the above described C1-C6 alkanoyl group; the above described C1-C6 alkoxycarbonyl substituted C1-C6 alkyl group; the above described C1-C6 alkanoyl substituted C1-C6 alkyl group; a group —N($R^{11B}$)$R^{12B}$ (wherein $R^{11B}$ and $R^{12B}$, which may be identical or different, each represent a hydrogen atom, the above described C1-C6 alkyl group, the above described C1-C6 alkanoyl group, or a phenyl group, and the above described $R^{11B}$ and $R^{12B}$ may bind to each other adjacent thereto directly or through a nitrogen, oxygen or sulfur atom, so as to form a 5-7 membered saturated heterocyclic ring together with the nitrogen atom, wherein, on the heterocyclic ring, 1 to 3 groups selected from the group consisting of a C1-C6 alkoxycarbonyl group and an amino group [wherein, on the amino group, 1 or 2 groups selected from a phenyl group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted) and a C1-C6 alkyl group may be substituted] may be substituted); the above described phenyl C1-C6 alkoxy group; the above described phenyl C1-C6 alkyl group; the above described C1-C6 alkylthio group; the above described C3-C8 cycloalkyl group; the above described halogen substituted or unsubstituted C1-C6 alkyl group; and the above described halogen substituted or unsubstituted C1-C10 alkoxy group (in a case where the substituent is a C1-C4 alkylenedioxy group, 1 or 2 groups may be substituted)).

Examples of the tetrahydropyranyloxy C1-C6 alkyl group may include a (2-tetrahydropyranyloxy)methyl group, a 2-(3-tetrahydropyranyloxy)ethyl group, a 1-(4-tetrahydropyranyloxy)ethyl group, a 2-(2-tetrahydropyranyloxy)ethyl group, a 3-(2-tetrahydropyranyloxy)propyl group, a 4-(2-tetrahydropyranyloxy)butyl group, a 4-(3-tetrahydropyranyloxy)butyl group, a 5-(2-tetrahydropyranyloxy)pentyl group, a 6-(2-tetrahydropyranyloxy)hexyl group, a 6-(2-tetrahydropyranyloxy)hexyl group, a 1,1-dimethyl-2-(4-tetrahydropyranyloxy)ethyl group, and a 2-methyl-3-(3-tetrahydropyranyloxy)propyl group.

Examples of the furyl C1-C6 alkoxy substituted C1-C6 alkyl group (wherein, on the furan ring, at least one C1-C6 alkoxycarbonyl group may be substituted) may include furyl C1-C6 alkoxy substituted C1-C6 alkyl groups such as a ((2-furyl)methoxy)methyl group, a (2-(3-furyl)ethoxy)methyl group, a (3-(2-furyl)propoxy)methyl group, a (2-(3-furyl)propoxy)methyl group, a (4-(2-furyl)butoxy)methyl group, a (5-(3-furyl)pentoxy)methyl group, a (4-(2-furyl)pentoxy)methyl group, a (6-(3-furyl)hexyloxy)methyl group, a 2-((2-furyl)methoxy)ethyl group, a 1-(2-(3-furyl)ethoxy)ethyl group, a 3-(3-(2-furyl)propoxy)propyl group, a 4-(2-(3-furyl)propoxy)butyl group, a 5-(4-(2-furyl)butoxy)hexyl group, a 1,1-dimethyl-2-(5-(3-furyl)pentoxy)ethyl group, a 2-methyl-3-(4-(2-furyl)pentoxy)propyl group, a 2-(6-(3-furyl)hexyloxy)ethyl group, a ((5-ethoxycarbonyl-2-furyl)methoxy)methyl group, a ((4-methoxycarbonyl-2-furyl)methoxy)methyl group, a ((3-propoxycarbonyl-2-furyl)methoxy)methyl group, a ((5-butoxycarbonyl-2-furyl)methoxy)methyl group, a ((4-pentyloxycarbonyl-2-furyl)methoxy)methyl group, a ((3-hexyloxycarbonyl-2-furyl)methoxy)methyl group, a ((3,5-diethoxycarbonyl-2-furyl)methoxy)methyl group, and a ((3,4,5-triethoxycarbonyl-2-furyl)methoxy)methyl group (wherein, on the furan ring, 1 to 3 C1-C6 alkoxycarbonyl groups may be substituted).

Examples of the C3-C8 cycloalkyl C1-C6 alkyl group may include a cyclohexylmethyl group, a 2-cyclopropylethyl group, a 1-cyclopentylethyl group, a 3-cyclobutylpropyl group, a 4-cyclohexylbutyl group, a 5-cycloheptylpentyl group, a 6-cyclooctylhexyl group, a 1,1-dimethyl-2-cyclohexylethyl group, and a 2-methyl-3-cyclohexylpropyl group.

Examples of the tetrazolyl C1-C6 alkoxy substituted C1-C6 alkyl group (wherein, on the tetrazole ring, a group selected from the group consisting of the following groups may be substituted: a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted), a phenyl C1-C6 alkyl group, and a C3-C8 cycloalkyl C1-C6 alkyl group), may include tetrazolyl C1-C6 alkoxy substituted C1-C6 alkyl groups such as a ((5-tetrazolyl)methoxy)methyl group, a (2-(5-tetrazolyl)ethoxy)methyl group, a (3-(5-tetrazolyl)propoxy)methyl group, a (2-(5-tetrazolyl)propoxy)methyl group, a (4-(5-tetrazolyl)butoxy)methyl group, a (5-(5-tetrazolyl)pentoxy)methyl group, a (4-(1-tetrazolyl)pentoxy)methyl group, a (6-(5-tetrazolyl)hexyloxy)methyl group, a (2-(1-tetrazolyl)methoxy)ethyl group, a 1-(2-(5-tetrazolyl)ethoxy)ethyl group, a 3-(3-(1-tetrazolyl)propoxy)propyl group, a 4-(2-(5-tetrazolyl)propoxy)butyl group, a 5-(4-(1-tetrazolyl)butoxy)hexyl group, a 1,1-dimethyl-2-(5-(5-tetrazolyl)pentoxy)ethyl group, a 2-methyl-3-(4-(1-tetrazolyl)pentoxy)propyl group, a 2-(6-(5-tetrazolyl)hexyloxy)ethyl group, a ((1-(2-phenylethyl)-5-tetrazolyl)methoxy)methyl group, a ((1-cyclohexylmethyl-5-tetrazolyl)methoxy)methyl group, a ((5-benzyl-1-tetrazolyl)methoxy)methyl group, a ((1-cyclopentylmethyl-5-tetrazolyl)methoxy)methyl group, a ((5-(2-cyclohexylethyl)-1-tetrazolyl)methoxy)methyl group, a ((1-benzyl-5-tetrazolyl)methoxy)methyl group, a ((1-cycloheptylmethyl-5-tetrazolyl)methoxy)methyl group, a ((1-(3-phenylpropyl)-5-tetrazolyl)methoxy)methyl group, a (1-phenyl-5-tetrazolyl)methoxymethyl group, a ((1-(4-trifluoromethoxyphenyl)-5-tetrazolyl)methoxymethyl group, a ((1-(4-trifluoromethylphenyl)-5-tetrazolyl)methoxy)methyl group, a ((1-(4-chlorophenyl)-5-tetrazolyl)methoxy)methyl group (wherein, on the tetrazole ring, a group selected from the group consisting of the following groups may be substituted: a phenyl group (wherein, on the phenyl ring, 1 to 5 groups, and preferably 1 to 3 groups selected from the group consisting of a halogen atom, a halogen substituted or unsubstituted linear or branched alkyl group containing 1 to 6 carbon atoms, and a halogen substituted or unsubstituted linear or branched alkoxy group containing 1 to 6 carbon atoms, may be substituted), the above described phenyl C1-C6 alkyl group, and the above described C3-CB cycloalkyl C1-C6 alkyl group).

Examples of the isoxazolyl C1-C6 alkoxy substituted C1-C6 alkyl group (wherein, on the isoxazole ring, at least one C1-C6 alkyl group may be substituted) may include isoxazolyl C1-C6 alkoxy substituted C1-C6 alkyl groups such as a ((3-isoxazolyl)methoxy)methyl group, a (2-(4-isoxazolyl)ethoxy)methyl group, a (3-(5-isoxazolyl)propoxy) methyl group, a (2-(3-isoxazolyl)propoxy)methyl group, a (4-(4-isoxazolyl)butoxy)methyl group, a (5-(5-isoxazolyl) pentoxy)methyl group, a (4-(3-isoxazolyl)pentoxy)methyl group, a (6-(4-isoxazolyl)hexyloxy)methyl group, a (2-(5-isoxazolyl)methoxy)ethyl group, a 1-(2-(3-isoxazolyl) ethoxy)ethyl group, a 3-(3-(4-isoxazolyl)propoxy)propyl group, a 4-(2-(5-isoxazolyl)propoxy)butyl group, a 5-(4-(3-isoxazolyl)butoxy)hexyl group, a 1,1-dimethyl-2-(5-(4-isoxazolyl)pentoxy)ethyl group, a 2-methyl-3-(4-(5-isoxazolyl) pentoxy)propyl group, a 2-(6-(3-isoxazolyl)hexyloxy)ethyl group, a ((5-methyl-3-isoxazolyl)methoxy)methyl group, a ((4-ethyl-3-isoxazolyl)methoxy)methyl group, a ((3-n-propyl-4-isoxazolyl)methoxy)methyl group, a ((5-n-butyl-3-isoxazolyl)methoxy)methyl group, a ((4-n-pentyl-3-isoxazolyl)methoxy)methyl group, a ((3-n-hexyl-5-isoxazolyl) methoxy)methyl group, and a ((4,5-dimethyl-3-isoxazolyl) methoxy)methyl group (wherein, on the isoxazole ring, the above described 1 to 2 C1-C6 alkyl groups may be substituted).

Examples of the benzothienyl C1-C6 alkoxy substituted C1-C6 alkyl group (wherein, on the benzothiophene ring, at least one selected from the group consisting of a halogen atom, a halogen substituted or unsubstituted C1-C6 alkyl group, and a halogen substituted or unsubstituted C1-C6 alkoxy group may be substituted) may include benzothienyl C1-C6 alkoxy substituted C1-C6 alkyl groups such as a ((3-benzothienyl)methoxy)methyl group, a ((2-benzothienyl) ethoxy)methyl group, a (3-(4-benzothienyl)propoxy)methyl group, a (2-(5-benzothienyl)propoxy)methyl group, a (4-(6-benzothienyl)butoxy)methyl group, a (5-(7-benzothienyl) pentoxy)methyl group, a (4-(3-benzothienyl)pentoxy)methyl group, a (6-(2-benzothienyl)hexyloxy)methyl group, a 2-((4-benzothienyl)methoxy)ethyl group, a 1-(2-(5-benzothienyl) ethoxy)ethyl group, a 3-(3-(6-benzothienyl)propoxy)propyl group, a 4-(2-(7-benzothienyl)propoxy)butyl group, a 5-(4-(3-benzothienyl)butoxy)hexyl group, a 1,1-dimethyl-2-(5-(3-benzothienyl)pentoxy)ethyl group, a 2-methyl-3-(4-(5-benzothienyl)pentoxy)propyl group, a 2-(6-(3-benzothienyl) hexyloxy)ethyl group, a ((5-methyl-3-benzothienyl) methoxy)methyl group, a ((4-ethyl-3-benzothienyl) methoxy)methyl group, a ((5-chloro-3-benzothienyl) methoxy)methyl group, a ((6-methyl-3-benzothienyl) methoxy)methyl group, a ((4-trifluoromethyl-3-benzothienyl)methoxy)methyl group, a ((3-methoxy-5-benzothienyl)methoxy)methyl group, a ((5-trifluoromethoxy-3-benzothienyl)methoxy)methyl group, a ((4,5-dichloro-3-benzothienyl)methoxy)methyl group, a ((2,4,5-trifluoro-3-benzothienyl)methoxy)methyl group, a ((4,5-dichloro-2-methyl-3-benzothienyl)methoxy)methyl group, and a ((4,5-dichloro-2-methoxy-3-benzothienyl)methoxy) methyl group (wherein, on the benzothiophene ring, 1 to 3 groups selected from the group consisting of the above described halogen atom, the above described halogen substituted or unsubstituted C1-C6 alkyl group, and the above described halogen substituted or unsubstituted C1-C6 alkoxy group may be substituted).

Examples of the 1,3,4-oxadiazolyl C1-C6 alkoxy substituted C1-C6 alkyl group (wherein, on the 1,3,4-oxadiazole ring, a phenyl group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted]) may include 1,3,4-oxadiazolyl C1-C6 alkoxy substituted C1-C6 alkyl groups such as a ((2-1,3,4-oxadiazolyl)methoxy)methyl group, a (2-(2-1,3,4-oxadiazolyl)ethoxy)methyl group, a (3-(2-1,3,4-oxadiazolyl) propoxy)methyl group, a (2-(2-1,3,4-oxadiazolyl)propoxy) methyl group, a (4-(2-1,3,4-oxadiazolyl)butoxy)methyl group, a (5-(2-1,3,4-oxadiazolyl)pentoxy)methyl group, a (4-(2-1,3,4-oxadiazolyl)pentoxy)methyl group, a (6-(2-1,3,4-oxadiazolyl)hexyloxy)methyl group, a 2-((2-1,3,4-oxadiazolyl)methoxy)ethyl group, a 1-(2-(2-1,3,4-oxadiazolyl) ethoxy)ethyl group, a 3-(3-(2-1,3,4-oxadiazolyl)propoxy) propyl group, a 4-(2-(2-1,3,4-oxadiazolyl)propoxy)butyl group, a 5-((2-1,3,4-oxadiazolyl)methoxy)pentyl group, a 6-(4-(2-1,3,4-oxadiazolyl)butoxy)hexyl group, a 1,1-dimethyl-2-(5-(2-1,3,4-oxadiazolyl)pentoxy)ethyl group, a 2-methyl-3-(4-(2-1,3,4-oxadiazolyl)pentoxy)propyl group, a 2-(6-(2-1,3,4-oxadiazolyl)hexyloxy)ethyl group, a (5-(4-methylphenyl)-2-1,3,4-oxadiazolyl)methoxymethyl group, a (5-(4-chlorophenyl)-2-1,3,4-oxadiazolyl)methoxymethyl group, a (5-(4-trifluoromethylphenyl)-2-1,3,4-oxadiazolyl) methoxymethyl group, a (5-(4-methoxyphenyl)-2-1,3,4-oxadiazolyl)methoxymethyl group, a (5-(4-trifluoromethoxyphenyl)-2-1,3,4-oxadiazolyl)methoxymethyl group, a (5-(2,4-dichlorophenyl)-2-1,3,4-oxadiazolyl)methoxymethyl group, a (5-(2,4,6-trimethylphenyl)-2-1,3,4-oxadiazolyl) methoxymethyl group, and a (5-(2,4-dimethoxyphenyl)-2-1,3,4-oxadiazolyl)methoxymethyl group (wherein, on the 1,3,4-oxadiazole ring, the above described phenyl group may be substituted [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted]).

Examples of the C2-C6 alkynyloxy substituted C1-C6 alkyl group may include an ethynyloxymethyl group, a 2-ethynyloxymethyl group, a 2-(2-ethynyloxy)ethyl group, a 1-(2-butynyloxy)ethyl group, a 2-(3-butynyloxy)ethyl group, a 3-(1-methyl-2-propynyloxy)propyl group, a 4-(2-pentynyloxy)butyl group, a 4-(2-hexynyloxy)butyl group, a 5-(2-propynyloxy)pentyl group, a 6-(2-propynyloxy)hexyl group, a 6-(2-butynyloxy)hexyl group, a 1,1-dimethyl-2-(2-propynyloxy)ethyl group, and a 2-methyl-3-(2-propynyloxy)propyl group.

Examples of the naphthyl C1-C6 alkoxy substituted C1-C6 alkyl group may include a (1-naphthyl)methoxymethyl group, a (2-(2-naphthyl)ethoxy)methyl group, a (3-(1-naphthyl)propoxy)methyl group, a (2-(2-naphthyl)propoxy)methyl group, a (4-(2-naphthyl)butoxy)methyl group, a (5-(2-naphthyl)pentoxy)methyl group, a (4-(1-naphthyl)pentoxy) methyl group, a (6-(1-naphthyl)hexyloxy)methyl group, a 2-(1-naphthyl)methoxy)ethyl group, a 1-(2-(2-naphthyl) ethoxy)ethyl group, a 3-(3-(2-naphthyl)propoxy)propyl group, a 4-(2-(2-naphthyl)propoxy)butyl group, a 5-(4-(1-naphthyl)butoxy)pentyl group, a 6-(5-(2-naphthyl)pentoxy) hexyl group, a 1,1-dimethyl-2-(4-(1-naphthyl)pentoxy)ethyl group, and a 2-methyl-3-(6-(1-naphthyl)hexyloxy)propyl group.

Examples of the 1,2,4-oxadiazolyl C1-C6 alkoxy substituted C1-C6 alkyl group [wherein, on the 1,2,4-oxadiazole ring, a phenyl group may be substituted] may include 1,2,4-oxadiazolyl C1-C6 alkoxy substituted C1-C6 alkyl groups such as a ((3-1,2,4-oxadiazolyl)methoxy)methyl group, a (2-(5-1,2,4-oxadiazolyl)ethoxy)methyl group, a (3-(3-1,2,4-oxadiazolyl)propoxy)methyl group, a (2-(5-1,2,4-oxadiazolyl)propoxy)methyl group, a (4-(3-1,2,4-oxadiazolyl) butoxy)methyl group, a (5-(5-1,2,4-oxadiazolyl)pentoxy) methyl group, a (4-(3-1,2,4-oxadiazolyl)pentoxy)methyl group, a (6-(3-1,2,4-oxadiazolyl)hexyloxy)methyl group, a 2-((5-1,2,4-oxadiazolyl)methoxy)ethyl group, a 1-(2-(3-1,2,4-oxadiazolyl)ethoxy)ethyl group, a 3-(3-(5-1,2,4-oxadiazolyl)propoxy)propyl group, a 4-(2-(3-1,2,4-oxadiazolyl)propoxy)butyl group, a 5-((3-1,2,4-oxadiazolyl)methoxy)pentyl group, a 6-(4-(5-1,2,4-oxadiazolyl)butoxy)hexyl group, a 1,1-dimethyl-2-(5-(3-1,2,4-oxadiazolyl)pentoxy)ethyl group, a 2-methyl-3-(4-(5-1,2,4-oxadiazolyl)pentoxy)propyl group, a 2-(6-(3-1,2,4-oxadiazolyl)hexyloxy)ethyl group, a (5-phenyl-3-1,2,4-oxadiazolyl)methoxymethyl group, and a (3-phenyl-5-1,2,4-oxadiazolyl)methoxymethyl group [wherein, on the 1,2,4-oxadiazole ring, a phenyl group may be substituted].

Examples of the pyridyl C1-C6 alkoxy substituted C1-C6 alkyl group [wherein, on the pyridine ring, at least one selected from the group consisting of a halogen atom, a halogen substituted or unsubstituted C1-C6 alkyl group, and a halogen substituted or unsubstituted C1-C6 alkoxy group may be substituted] may include pyridyl C1-C6 alkoxy substituted C1-C6 alkyl groups such as a (2-pyridyl)methoxymethyl group, a (2-(3-pyridyl)ethoxy)methyl group, a (3-(4-pyridyl)propoxy)methyl group, a (2-(2-pyridyl)propoxy) methyl group, a (4-(3-pyridyl)butoxy)methyl group, a (5-(4-pyridyl)pentoxy)methyl group, a (4-(2-pyridyl)pentoxy) methyl group, a (6-(3-pyridyl)hexyloxy)methyl group, a (2-(4-pyridyl)methoxy)ethyl group, a 1-(2-(2-pyridyl)ethoxy) ethyl group, a 3-(3-(3-pyridyl)propoxy)propyl group, a 4-(2-(4-pyridyl)propoxy)butyl group, a 5-((2-pyridyl)methoxy) pentyl group, a 6-(4-(2-pyridyl)butoxy)hexyl group, a 1,1-dimethyl-2-(5-(3-pyridyl)pentoxy)ethyl group, a 2-methyl-3-(4-(4-pyridyl)pentoxy)propyl group, a 2-(6-(2-pyridyl) hexyloxy)ethyl group, a (2-trifluoromethyl-5-pyridyl) methoxymethyl group, a (4-chloro-2-pyridyl) methoxymethyl group, a (3-trifluoromethyl-2-pyridyl) methoxymethyl group, a (2-methoxy-4-pyridyl) methoxymethyl group, a (2-trifluoromethoxy-5-pyridyl) methoxymethyl group, a (2,4-dibromo-3-pyridyl) methoxymethyl group, a (2,4,6-trimethyl-5-pyridyl) methoxymethyl group, a (2,4-dimethoxy-5-pyridyl) methoxymethyl group, and a (2,4,6-trifluoro-3-pyridyl) methoxymethyl group [wherein, on the pyridine ring, 1 to 3 groups selected from the group consisting of the above described halogen atom, the above described halogen substituted or unsubstituted C1-C6 alkyl group, and the above described halogen substituted or unsubstituted C1-C6 alkoxy group may be substituted].

Examples of the thiazolyl C1-C6 alkoxy substituted C1-C6 alkyl group [wherein, on the thiazole ring, at least one selected from the group consisting of a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) and a lower alkyl group may be substituted], may include thiazolyl C1-C6 alkoxy substituted C1-C6 alkyl groups such as a (4-thiazolyl)methoxymethyl group, a (2-(2-thiazolyl)ethoxy) methyl group, a (3-(5-thiazolyl)propoxy)methyl group, a (2-(4-thiazolyl)propoxy)methyl group, a (4-(2-thiazolyl)butoxy)methyl group, a (5-(4-thiazolyl)pentoxy)methyl group, a (4-(5-thiazolyl)pentoxy)methyl group, a (6-(4-thiazolyl) hexyloxy)methyl group, a (2-(2-thiazolyl)methoxy)ethyl group, a 1-(2-(5-thiazolyl)ethoxy)ethyl group, a 3-(3-(4-thiazolyl)propoxy)propyl group, a 4-(2-(2-thiazolyl)propoxy) butyl group, a 5-((4-thiazolyl)methoxy)pentyl group, a 6-(4-(5-thiazolyl)butoxy)hexyl group, a 1,1-dimethyl-2-(5-(4-thiazolyl)pentoxy)ethyl group, a 2-methyl-3-(4-(2-thiazolyl) pentoxy)propyl group, a 2-(6-(5-thiazolyl)hexyloxy)ethyl group, a (2-(4-methylphenyl)-4-thiazolyl)methoxymethyl group, a (2-(4-chlorophenyl)-4-thiazolyl)methoxymethyl group, a (2-(4-trifluoromethylphenyl)-4-thiazolyl)methoxymethyl group, a (5-(4-methoxyphenyl)-4-thiazolyl)methoxymethyl group, a (2-(4-trifluoromethoxyphenyl)-4-thiazolyl)methoxymethyl group, a (5-(2,4-dichlorophenyl)-2-thiazolyl)methoxymethyl group, a (4-(2,4,6-trimethylphenyl)-2-thiazolyl)methoxymethyl group, a (4-(2,4-dimethoxyphenyl)-2-thiazolyl)methoxymethyl group, a (2-methyl-4-thiazolyl)methoxymethyl group, a (2,5-dimethyl-5-thiazolyl)methoxymethyl group, and a (2-phenyl-4-methyl-5-thiazolyl)methoxymethyl group [wherein, on the thiazole ring, 1 or 2 groups selected from the group consisting of the above described phenyl group (wherein, on the phenyl ring, 1 to 5 groups, and preferably 1 to 3 groups selected from the group consisting of a halogen atom, a halogen substituted or unsubstituted linear or branched C1-C6 alkyl group containing 1 to 6 carbon atoms, and a halogen substituted or unsubstituted linear or branched C1-C6 alkoxy group containing 1 to 6 carbon atoms, may be substituted) and a linear or branched alkyl group containing 1 to 6 carbon atoms, may be substituted].

Examples of the 1,2,3,4-tetrahydronaphthyl C1-C6 alkoxy substituted C1-C6 alkyl group [wherein, on the 1,2,3,4-tetrahydronaphthalene ring, at least one C1-C6 alkyl group may be substituted] may include 1,2,3,4-tetrahydronaphthyl C1-C6 alkoxy substituted C1-C6 alkyl groups such as a (6-1,2,3,4-tetrahydronaphthyl)methoxymethyl group, a (2-(2-1,2,3,4-tetrahydronaphthyl)ethoxy)methyl group, a (3-(3-1,2,3,4-tetrahydronaphthyl)propoxy)methyl group, a (2-(4-1,2,3,4-tetrahydronaphthyl)propoxy)methyl group, a (4-(5-1,2,3,4-tetrahydronaphthyl)butoxy)methyl group, a (5-(6-1,2,3,4-tetrahydronaphthyl)pentoxy)methyl group, a (4-(6-1,2,3,4-tetrahydronaphthyl)pentoxy)methyl group, a (6-(5-1,2,3,4-tetrahydronaphthyl)hexyloxy)methyl group, a 2-((6-1,2,3,4-tetrahydronaphthyl)methoxy)ethyl group, a 1-(2-(6-1,2,3,4-tetrahydronaphthyl)ethoxy)ethyl group, a 3-(3-(5-1,2,3,4-tetrahydronaphthyl)propoxy)propyl group, a 4-(2-(5-1,2,3,4-tetrahydronaphthyl)propoxy)butyl group, a 5-(4-(6-1,2,3,4-tetrahydronaphthyl)butoxy)pentyl group, a 6-(5-(5-1,2,3,4-tetrahydronaphthyl)pentoxy)hexyl group, a 1,1-dimethyl-2-(4-(6-1,2,3,4-tetrahydronaphthyl)pentoxy)ethyl group, a 2-methyl-3-(6-(6-1,2,3,4-tetrahydronaphthyl)hexyloxy)propyl group, a (1,1,4,4-tetramethyl-6-1,2,3,4-tetrahydronaphthyl)methoxymethyl group, a (1,1,4-trimethyl-6-1,2,3,4-tetrahydronaphthyl)methoxymethyl group, a (1,1-dimethyl-6-1,2,3,4-tetrahydronaphthyl)methoxymethyl group, a (1,1-dimethyl-7-1,2,3,4-tetrahydronaphthyl)methoxymethyl group, a (1-methyl-6-1,2,3,4-tetrahydronaphthyl)methoxymethyl group, a (1,4-dimethyl-6-1,2,3,4-tetrahydronaphthyl)methoxymethyl group, a (1,1,4,4-tetraethyl-6-1,2,3,4-tetrahydronaphthyl)methoxymethyl group, a (1,1-dimethyl-4-ethyl-6-1,2,3,4-tetrahydronaphthyl)methoxymethyl group, a (1,1-di-n-propyl-6-1,2,3,4-tetrahydronaphthyl) methoxymethyl group, a (4,4-di-n-butyl-6-1,2,3,4-tetrahydronaphthyl)methoxymethyl group, a (1-n-pentyl-6-1,2,3,4-tetrahydronaphthyl)methoxymethyl group, a (1,4-di-n-hexyl-6-1,2,3,4-tetrahydronaphthyl)methoxymethyl group, and a (1-methyl-5-n-propyl-4-ethyl-6-1,2,3,4-tetrahydronaphthyl)methoxymethyl group [wherein, on the 1,2,3,4-tetrahydronaphthalene ring, the above described 1 to 4 C1-C6 alkyl groups may be substituted].

Examples of the carbamoyl C1-C6 alkoxy substituted C1-C6 alkyl group [wherein, on the amino group, at least one selected from the group consisting of a C3-C8 cycloalkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) may be substituted] may include carbamoyl C1-C6 alkoxy substituted C1-C6 alkyl groups such as a carbamoylmethoxymethyl group, a 2-(carbamoylethoxy)methyl group, a (3-carbamoylpropoxy)methyl group, a (2-carbamoylpropoxy)methyl group, a (4-carbamoylbutoxy)methyl group, a (5-carbamoylpentoxy) methyl group, a (4-carbamoylpentoxy)methyl group, a (6-carbamoylhexyloxy)methyl group, a (2-carbamoylmethoxy)ethyl group, a 1-(2-carbamoylethoxy)ethyl group, a 3-(3-carbamoylpropoxy)propyl group, a 4-(2-carbamoylpropoxy)butyl group, a 5-(carbamoylmethoxy)pentyl group, a 4-(2-carbamoylpropoxy)butyl group, a 6-(4-carbamoylbutoxy)hexyl group, a 1,1-dimethyl-2-(5-carbamoylpentoxy) ethyl group, a 2-methyl-3-(4-carbamoylpentoxy)propyl group, a 2-(6-carbamoylhexyloxy)ethyl group, an (N-(4-methylphenyl)carbamoyl)methoxymethyl group, an (N-(4-chlorophenyl)carbamoyl)methoxymethyl group, an (N-(4-trifluoromethylphenyl)carbamoyl)methoxymethyl group, an (N-(4-methoxyphenyl)carbamoyl)methoxymethyl group, an (N-(4-trifluoromethoxyphenyl)carbamoyl)methoxymethyl group, an (N-(2,4-dichlorophenyl)-carbamoyl)methoxymethyl group, an (N-(2,4,6-trimethylphenyl)carbamoyl)methoxymethyl group, an (N-(2,4-dimethoxyphenyl)carbamoyl) methoxymethyl group, an (N-cyclohexylcarbamoyl) methoxymethyl group, an (N-cyclopentylcarbamoyl) methoxymethyl group, an (N-cycloheptylcarbamoyl) methoxymethyl group, an (N-cyclooctylcarbamoyl) methoxymethyl group, an (N-cyclobutylcarbamoyl) methoxymethyl group, an (N-cyclopropylcarbamoyl) methoxymethyl group, an (N-cyclopropyl-N-cyclohexylcarbamoyl)methoxymethyl group, an (N,N-dicyclohexylcarbamoyl)methoxymethyl group, an (N-cyclopropyl-N-(4-fluoromethylphenyl)carbamoyl)-methoxymethyl group, and an (N-cyclohexyl-N-(4-fluoromethylphenyl)carbamoyl)methoxymethyl group (wherein, on the amino group, 1 or 2 groups selected from the group consisting of the above described C3-C8 cycloalkyl group and the above described phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted] may be substituted).

Examples of the benzofuryl C1-C6 alkoxy substituted C1-C6 alkyl group [wherein, on the benzofuran ring, at least one cyano group may be substituted] may include benzofuryl C1-C6 alkoxy substituted C1-C6 alkyl groups such as a (2-benzofuryl)methoxymethyl group, a (2-(3-benzofuryl) ethoxy)methyl group, a (3-(4-benzofuryl)propoxy)methyl group, a (2-(5-benzofuryl)propoxy)methyl group, a (4-(6-benzofuryl)butoxy)methyl group, a (5-(7-benzofuryl)pentoxy)methyl group, a (4-(2-benzofuryl)pentoxy)methyl group, a (6-(3-benzofuryl)hexyloxy)methyl group, a (2-(2-benzofuryl)methoxy)ethyl group, a 1-(2-(3-benzofuryl) ethoxy)ethyl group, a 3-(3-(4-benzofuryl)propoxy)propyl group, a 4-(2-(5-benzofuryl)propoxy)butyl group, a 5-(4-(6-benzofuryl)butoxy)pentyl group, a 6-(5-(7-benzofuryl)pentoxy)hexyl group, a 1,1-dimethyl-2-(4-(2-benzofuryl)pentoxy)ethyl group, a 2-methyl-3-(6-(3-benzofuryl)hexyloxy) propyl group, a (7-cyano-2-benzofuryl)methoxymethyl group, a (6-cyano-2-benzofuryl)methoxymethyl group, a (5-cyano-2-benzofuryl)methoxymethyl group, a (4-cyano-2-benzofuryl)methoxymethyl group, a (3-cyano-2-benzofuryl) methoxymethyl group, a (2-cyano-5-benzofuryl)methoxymethyl group, a (6,7-dicyano-2-benzofuryl)methoxymethyl group, and a (3,4,5-tricyano-2-benzofuryl)methoxymethyl group [wherein, on the benzofuran ring, 1 to 3 cyano groups may be substituted].

Examples of the C7-C10 alkoxy group may include an n-heptyloxy group, an n-octyloxy group, an n-nonyloxy group, an n-decyloxy group, a 5-methylhexyloxy group, a 4,4-dimethylpentyloxy group, a 6-methylheptyloxy group, and a 5,5,5-trimethylpentyloxy group.

Examples of the phenoxy group [wherein, on the phenyl ring, at least one selected from the group consisting of a phenyl C1-C6 alkoxy group, a C3-C8 cycloalkyl group, a C7-C10 alkoxy group, and a phenoxy group is substituted] may include phenoxy groups such as a 4-benzyloxyphenoxy group, a 4-cyclohexylphenoxy group, a 4-n-octyloxyphenoxy group, a 4-cyclopentylphenoxy group, a 3-phenoxyphenoxy group, a 3-benzyloxyphenoxy group, a 3-cyclohexylphenoxy group, a 3-n-octyloxyphenoxy group, a 3-cyclopentylphenoxy group, a 4-phenoxyphenoxy group, a 2-benzyloxyphenoxy group, a 2-cyclohexylphenoxy group, a 2-n-heptyloxyphenoxy group, a 2-cyclopentylphenoxy group, a 2-phenoxyphenoxy group, a 4-(2-phenylethoxy) phenoxy group, a 4-cyclooctylphenoxy group, a 4-n-nonyloxyphenoxy group, a 4-cyclopropylphenoxy group, a 2,3-diphenoxyphenoxy group, a 4-(3-phenylpropoxy)phenoxy group, a 4-cycloheptylphenoxy group, a 4-n-decyloxyphenoxy group, a 4-cyclobutylphenoxy group, a 2,4,6-triphenoxyphenoxy group, a 4-(4-phenylbutoxy)phenoxy group, a 2,4-dicyclohexylphenoxy group, a 2,4-di-n-octyloxyphenoxy group, a 2,4,6-tricyclopentylphenoxy group, a 3-phenoxy-4-benzyloxyphenoxy group, a 4-(5-phenylpentyloxy)phenoxy group, a 4-cyclohexyl-3-phenoxyphenoxy group, a 2,4,6-tri-n-octyloxyphenoxy group, a 4-cyclopentyl-2-benzyloxyphenoxy group, a 3-phenoxy-2-cyclohexylphenoxy group, a 4-(6-phenylhexyloxy)phenoxy group, a 3,4,5-tribenzyloxyphenoxy group, and a 2,4-dibenzyloxyphenoxy group, provided that, on the phenyl ring, 1 to 3 groups selected from the group consisting of the above described phenyl C1-C6 alkoxy group, the above described C3-C8 cycloalkyl group, the above described C7-C10 alkoxy group, and the above described phenoxy group, are substituted.

Examples of the 2,3-dihydrobenzofuryloxy group [wherein, on the 2,3-dihydrobenzofuran ring, at least one oxo group may be substituted] may include 2,3-dihydrobenzofuryloxy groups such as a (2-, 3-, 4-, 5-, 6- or 7-)2,3-dihydrobenzofuryloxy group, a 3-oxo-6-2,3-dihydrobenzofuryloxy group, and a 2-oxo-5-2,3-dihydrobenzofuryloxy group, provided that, on the 2,3-dihydrobenzofuran ring, 1 or 2 oxo groups may be substituted.

Examples of the benzothiazolyloxy group [wherein, on the benzothiazole ring, at least one C1-C6 alkyl group may be substituted] may include benzothiazolyloxy groups such as a (2-, 4-, 5-, 6- or 7-)benzothiazolyloxy group, a 2-methyl-5-benzothiazolyloxy group, a 2-ethyl-5-benzothiazolyloxy group, a 2-n-propyl-5-benzothiazolyloxy group, a 2-tert-butyl-5-benzothiazolyloxy group, a 2-n-pentyl-5-benzothiazolyloxy group, a 2-n-hexyl-5-benzothiazolyloxy group, a 2,5-dimethyl-6-benzothiazolyloxy group, and a 4,5,6-trimethyl-2-benzothiazolyloxy group, provided that, on the benzothiazole ring, the above described 1 to 3 C1-C6 alkyl groups may be substituted.

Examples of the furyl C1-C6 alkoxy group [wherein, on the furan ring, at least one C1-C6 alkoxycarbonyl group may be substituted] may include furyl C1-C6 alkoxy groups such as a (2- or 3-)furylmethoxy group, a 2-((2- or 3-)furyl)ethoxy group, a 1-((2- or 3-)furyl)ethoxy group, a 3-((2- or 3-)furyl) propoxy group, a 2-((2- or 3-)furyl)propoxy group, a 4-((2- or 3-)furyl)butoxy group, a 5-((2- or 3-)furyl)pentoxy group, a 4-((2- or 3-)furyl)pentoxy group, a 6-((2- or 3-)furyl)hexyloxy group, a 2-methyl-3-((2- or 3-)furyl)propoxy group, a 1,1-dimethyl-2-((2- or 3-)furyl)ethoxy group, a 2-ethoxycarbonyl-5-furylmethoxy group, a 2-ethoxycarbonyl-5-furylmethoxy group, a 2-methoxycarbonyl-4-furylmethoxy group, a 2-propoxycarbonyl-3-furylmethoxy group, a 2-butoxycarbonyl-5-furylmethoxy group, a 2-pentyloxycarbonyl-5-furylmethoxy group, a 2-hexyloxycarbonyl-5-furylmethoxy group, a 2,3-diethoxycarbonyl-5-furylmethoxy group, and a 2,3,4-trimethoxycarbonyl-5-furylmethoxy group, provided that, on the furan ring, the above described 1 to 3 C1-C6 alkoxycarbonyl groups may be substituted.

Examples of the tetrazolyl C1-C6 alkoxy group [wherein, on the tetrazole ring, at least one selected from the group consisting of a phenyl C1-C6 alkyl group and a C3-C8 cycloalkyl C1-C6 alkyl group may be substituted] may include tetrazolyl C1-C6 alkoxy groups such as a (1-, 2- or 5-)tetrazolylmethoxy group, a 2-((1-, 2- or 5-)tetrazolyl) ethoxy group, a 1-((1-, 2- or 5-)tetrazolyl)ethoxy group, a 3-((1-, 2- or 5-)tetrazolyl)propoxy group, a 2-((1-, 2- or 5-)tetrazolyl)propoxy group, a 4-((1-, 2- or 5-)tetrazolyl)butoxy group, a 5-((1-, 2- or 5-)tetrazolyl)pentoxy group, a 4-((1-, 2- or 5-)tetrazolyl)pentoxy group, a 6-((1-, 2- or 5-)tetrazolyl) hexyloxy group, a 2-methyl-3-((1-, 2- or 5-)tetrazolyl)propoxy group, a 1,1-dimethyl-2-((1-, 2- or 5-)tetrazolyl)ethoxy group, a 1-(2-phenylethyl)-5-tetrazolylmethoxy group, a 1-cyclohexylmethyl-5-tetrazolylmethoxy group, a 5-benzyl-1-tetrazolylmethoxy group, a 5-(2-cyclopentylethyl)-1-tetrazolylmethoxy group, a 1-benzyl-5-tetrazolylmethoxy group, a 1-(3-phenylpropyl)-5-tetrazolylmethoxy group, a 1-(4-phenylbutyl)-5-tetrazolylmethoxy group, a 1-(5-phenylpentyl)-5-tetrazolylmethoxy group, a 1-(6-phenylhexyl)-5-tetrazolylmethoxy group, a 1-cyclobutylmethyl-5-tetrazolylmethoxy group, a 1-(3-cyclopropylpropyl)-5-tetrazolylmethoxy group, a 1-(4-cycloheptylbutyl)-5-tetrazolylmethoxy group, a 1-(5-cyclooctylpentyl)-5-tetrazolylmethoxy group, and a 1-(6-cyclohexylhexyl)-5-tetrazolylmethoxy group, provided that, on the tetrazole ring, one group selected from the group consisting of the above described phenyl C1-C6 alkyl group and the above described C3-C8 cycloalkyl C1-C6 alkyl group may be substituted.

Examples of the 1,2,4-oxadiazolyl C1-C6 alkoxy group [wherein, on the 1,2,4-oxadizole ring, a phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted)) may include 1,2,4-oxadiazolyl C1-C6 alkoxy groups such as a (3- or 5-)1,2,4-oxadiazolylmethoxy group, a 2-((3- or 5-)1,2,4-oxadiazolyl)ethoxy group, a 1-((3- or 5-)1,2,4-oxadiazolyl)ethoxy group, a 3-((3- or 5-)1,2,4-oxadiazolyl)propoxy group, a 2-((3- or 5-)1,2,4-oxadiazolyl)propoxy group, a 4-((3- or 5-)1,2,4-oxadiazolyl)butoxy group, a 5-((3- or 5-)1,2,4-oxadiazolyl)pentoxy group, a 4-((3- or 5-)1,2,4-oxadiazolyl)pentoxy group, a 6-((3- or 5-)1,2,4-oxadiazolyl) hexyloxy group, a 2-methyl-3-((3- or 5-)1,2,4-oxadiazolyl) propoxy group, a 1,1-dimethyl-2-((3- or 5-)1,2,4-oxadiazolyl)ethoxy group, a 3-(4-tert-butylphenyl)-5-1,2,4-oxadiazolylmethoxy group, a 3-phenyl-5-1,2,4-oxadiazolylmethoxy group, a 3-(4-chlorophenyl)-5-1,2,4-oxadiazolylmethoxy group, a 3-(4-trifluoromethylphenyl)-5-1,2,4-oxadiazolylmethoxy group, a 5-(4-trifluoromethoxyphenyl)-3-1,2,4-oxadiazolylmethoxy group, a 5-(4-methoxyphenyl)-3-1,2,4-oxadiazolylmethoxy group, a 5-(2,4-dimethylphenyl)-3-1,2,4-oxadiazolylmethoxy group, a 3-(2,4,6-trimethylphenyl)-5-1,2,4-oxadiazolylmethoxy group, a 3-(2,4-dimethylphenyl)-5-1,2,4-oxadiazolylmethoxy group, a 5-(2,4,6-trimethoxyphenyl)-3-1,2,4-oxadiazolylmethoxy group, a 3-(2,4-dibromophenyl)-5-1,2,4-oxadiazolylmethoxy group, a 3-(2,4,6-trifluorophenyl)-5-1,2,4-oxadiazolylmethoxy group, a 3-(3,5-dichlorophenyl)-5-1,2,4-oxadiazolylmethoxy group, a 3-(2-methyl-5-chlorophenyl)-5-1,2,4-oxadiazolylmethoxy group, a 3-(3-methoxy-5-chlorophenyl)-5-1,2,4-oxadiazolylmethoxy group, and a 3-(2,3,4,5,6-pentafluorophenyl)-5-1,2,4-oxadiazolylmethoxy group, provided that, on the 1,2,4-oxadiazole ring, the above described phenyl group may be substituted (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted).

Examples of the benzothienyl C1-C6 alkoxy group [wherein, on the benzothiophene ring, at least one halogen atom may be substituted] may include benzothienyl C1-C6 alkoxy groups such as a (2-, 3-, 4-, 5-, 6- or 7-)benzothienylmethoxy group, a 2-((2-, 3-, 4-, 5-, 6- or 7-)benzothienyl) ethoxy group, a 1-((2-, 3-, 4-, 5-, 6- or 7-)benzothienyl)ethoxy group, a 3-((2-, 3-, 4-, 5-, 6- or 7-)benzothienyl)propoxy group, a 2-((2-, 3-, 4-, 5-, 6- or 7-)benzothienyl)propoxy group, a 4-((2-, 3-, 4-, 5-, 6- or 7-)benzothienyl)-butoxy group, a 5-((2-, 3-, 4-, 5-, 6- or 7-)benzothienyl)pentoxy group, a 4-((2-, 3-, 4-, 5-, 6- or 7-)benzothienyl)pentoxy group, a 6-((2-, 3-, 4-, 5-, 6- or 7-)benzothienyl)hexyloxy group, a 2-methyl-3-((2-, 3-, 4-, 5-, 6- or 7-)benzothienyl) propoxy group, a 1,1-dimethyl-2-((2-, 3-, 4-, 5-, 6- or 7-)benzothienyl)ethoxy group, a 5-chloro-3-benzothienylmethoxy group, a 4-bromo-2-benzothienylmethoxy group, a 6-fluoro-5-benzothienylmethoxy group, a 7-iodo-4-1,2,4-oxadiazolylmethoxy group, a 4,5-dichloro-3-benzothienylmethoxy group, and a 3,4,5-trifluoro-2-benzothienylmethoxy group, provided that, on the benzothiophene ring, 1 to 3 halogen atoms may be substituted.

Examples of the isoxazolyl C1-C6 alkoxy group [wherein, on the isoxazole ring, at least one C1-C6 alkyl group may be substituted] may include isoxazolyl C1-C6 alkoxy groups such as a (3-, 4- or 5-)isoxazolylmethoxy group, a 2-((3-, 4- or 5-)isoxazolyl)ethoxy group, a 1-((3-, 4- or 5-)isoxazolyl) ethoxy group, a 3-((3-, 4- or 5-)isoxazolyl)propoxy group, a 2-((3-, 4- or 5-)isoxazolyl)propoxy group, a 4-((3-, 4- or 5-)isoxazolyl)butoxy group, a 5-((3-, 4- or 5-)isoxazolyl)pentoxy group, a 4-((3-, 4- or 5-)isoxazolyl)pentoxy group, a 6-((3-, 4- or 5-)isoxazolyl)hexyloxy group, a 2-methyl-3-((3-, 4- or 5-)isoxazolyl)propoxy group, a 1,1-dimethyl-2-((3-, 4- or 5-)isoxazolyl)ethoxy group, a (3,5-dimethyl-4-isoxazolyl)methoxy group, a (3-methyl-5-isoxazolyl) methoxy group, a (4-ethyl-5-isoxazolyl)methoxy group, a (5-n-propyl-4-isoxazolyl)methoxy group, a (3-tert-butyl-4-isoxazolyl)methoxy group, a (4-n-pentyl-5-isoxazolyl)methoxy group, and a (5-n-hexyl-5-isoxazolyl)methoxy group, provided that, on the isoxazole ring, the above described 1 or 2 C1-C6 alkyl groups may be substituted.

Examples of the 1,3,4-oxadiazolyl C1-C6 alkoxy group [wherein, on the 1,3,4-oxadiazole ring, at least one phenyl group may be substituted (wherein, on the phenyl ring, at least one C1-C6 alkyl group may be substituted)) may include 1,3,4-oxadiazolyl C1-C6 alkoxy groups such as a 2-1,3,4-oxadiazolylmethoxy group, a 2-(2-1,3,4-oxadiazolyl)ethoxy group, a 1-(2-1,3,4-oxadiazolyl)ethoxy group, a 3-(2-1,3,4-oxadiazolyl)propoxy group, a 2-(2-1,3,4-oxadiazolyl)propoxy group, a 4-(2-1,3,4-oxadiazolyl)butoxy group, a 5-(2-1,3,4-oxadiazolyl)pentoxy group, a 4-(2-1,3,4-oxadiazolyl) pentoxy group, a 6-(2-1,3,4-oxadiazolyl)hexyloxy group, a 2-methyl-3-(2-1,3,4-isoxazolyl)propoxy group, a 1,1-dimethyl-2-(2-1,3,4-oxadiazolyl)ethoxy group, a 2-(4-methylphenyl)-5-1,3,4-oxadiazolylmethoxy group, a 3-phenyl-5-1,3,4-oxadiazolylmethoxy group, a 2-(4-ethylphenyl)-5-1,3,4-oxadiazolylmethoxy group, a 3-(4-n-propylphenyl)-5-1,3,4-oxadiazolylmethoxy group, a 3-(4-sec-butylphenyl)-5-1,3,4-oxadiazolylmethoxy group, a 3-(4-n-pentylphenyl)-5-1,3,4-oxadiazolylmethoxy group, a 3-(2,4-dimethylphenyl)-5-1,3,4-oxadiazolylmethoxy group, a 3-(2,4,6-trimethylphenyl)-5-1,3,4-oxadiazolylmethoxy group, a 3-(3-n-hexylphenyl)-5-1,3,4-oxadiazolylmethoxy group, a 3-(2-methylphenyl)-5-1,3,4-oxadiazolylmethoxy group, and a 3-(3-methylphenyl)-5-1,3,4-oxadiazolylmethoxy group, provided that, on the 1,3,4-oxadiazole ring, one phenyl group may be substituted (wherein, on the phenyl ring, the above described 1 to 3 C1-C6 alkyl groups may be substituted).

Examples of the naphthyl C1-C6 alkoxy groups may include a (2- or 3-)naphthylmethoxy group, a 2-((2- or 3-)naphthyl)ethoxy group, a 1-((2- or 3-)naphthyl)ethoxy group, a 3-((2- or 3-)naphthyl)-propoxy group, a 2-((2- or 3-)naphthyl)propoxy group, a 4-((2- or 3-)naphthyl)butoxy group, a 5-((2- or 3-)naphthyl)pentoxy group, a 4-((1- or 2-)naphthyl)pentoxy group, a 6-((2- or 3-)naphthyl)hexyloxy group, a 2-methyl-3-((2- or 3-)naphthyl)propoxy group, and a 1,1-dimethyl-2-((2- or 3-)naphthyl)ethoxy group.

Examples of the pyridyl C1-C6 alkoxy group (wherein, on the pyridine ring, at least one halogen substituted or unsubstituted C1-C6 alkyl group may be substituted) may include pyridyl C1-C6 alkoxy groups such as a (1-, 2-, 3- or 4-)pyridylmethoxy group, a 2-((1-, 2-, 3- or 4-)pyridyl)ethoxy group, a 1-((1-, 2-, 3- or 4-)pyridyl)ethoxy group, a 3-((1-, 2-, 3- or 4-)pyridyl)propoxy group, a 2-((1-, 2-, 3- or 4-)pyridyl)propoxy group, a 4-((1-, 2-, 3- or 4-)pyridyl)butoxy group, a 5-((1-, 2-, 3- or 4-)pyridyl)pentoxy group, a 4-((1-, 2-, 3- or 4-)pyridyl)pentoxy group, a 6-((1-, 2-, 3- or 4-)pyridyl)hexyloxy group, a 2-methyl-3-((1-, 2-, 3- or 4-)pyridyl)propoxy group, a 1,1-dimethyl-2-((1-, 2-, 3- or 4-)pyridyl)ethoxy group, a 2-trifluoromethyl-5-pyridylmethoxy group, a 2-methyl-5-pyridylmethoxy group, a 2-ethyl-6-pyridylmethoxy group, a 3-n-propyl-2-pyridylmethoxy group, a 4-n-butyl-5-pyridylmethoxy group, a 3-n-pentyl-4-pyridylmethoxy group, a 2-n-hexyl-6-pyridylmethoxy group, a 2,3-ditrifluoromethyl-5-pyridylmethoxy group, a 3,4,5-tritrifluoromethyl-2-pyridylmethoxy group, a 2,4-dimethyl-5-pyridylmethoxy group, and a 3,4,5-trimethyl-2-pyridylmethoxy group, provided that, on the pyridine ring, 1 to 3 halogen substituted or unsubstituted C1-C6 alkyl groups may be substituted.

Examples of the thiazolyl C1-C6 alkoxy group [wherein, on the thiazole ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted)) may include thiazolyl C1-C6 alkoxy groups such as a (2-, 4- or 5-)thiazolylmethoxy group, a 2-((2-, 4- or 5-)thiazolyl) ethoxy group, a 1-((2-, 4- or 5-)thiazolyl)ethoxy group, a 3-((2-, 4- or 5-)thiazolyl)propoxy group, a 2-((2-, 4- or 5-)thiazolyl)propoxy group, a 4-((2-, 4- or 5-)thiazolyl)butoxy group, a 5-((2-, 4- or 5-)thiazolyl)pentoxy group, a 4-((2-, 4- or 5-)thiazolyl)pentoxy group, a 6-((2-, 4- or 5-)thiazolyl)hexyloxy group, a 2-methyl-3-((2-, 4- or 5-)thiazolyl)propoxy group, a 1,1-dimethyl-2-((2-, 4- or 5-)thiazolyl)ethoxy group, a 2-(4-trifluoromethylphenyl)-4-thiazolylmethoxy group, a 2-phenyl-4-thiazolylmethoxy group, a 2-(4-chlorophenyl)-4-thiazolylmethoxy group, a 2-(4-trifluoromethylphenyl)-5-thiazolylmethoxy group, a 2-(4-trifluoromethoxyphenyl)-4-thiazolylmethoxy group, a 5-(4-methoxyphenyl)-3-thiazolylmethoxy group, a 5-(2,4-dimethylphenyl)-2-thiazolylmethoxy group, a 4-(2,4,6-trimethylphenyl)-2-thiazolylmethoxy group, a 2-(2,4-dimethylphenyl)-5-thiazolylmethoxy group, a 2-(2,4,6-trimethoxyphenyl)-4-thiazolylmethoxy group, a 2-(2,4-dibromophenyl)-4-thiazolylmethoxy group, a 2-(2,4,6-trifluorophenyl)-5-thiazolylmethoxy group, a 2-(3,5-dichlorophenyl)-4-thiazolylmethoxy group, a 2-(2-methyl-5-chlorophenyl)-4-thiazolylmethoxy group, a 2-(3-methoxy-5-chlorophenyl)-4-thiazolylmethoxy group, a 2-(2,3,4,5,6-pentafluorophenyl)-4-thiazolylmethoxy group, and a 2,5-diphenyl-4-thiazolylmethoxy group, provided that, on the thiazole ring, the above described 1 or 2 phenyl groups may be substituted (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted).

Examples of the 1,2,3,4-tetrahydronaphthyl C1-C6 alkoxy group (wherein, on the 1,2,3,4-tetrahydronaphthalene ring, at least one C1-C6 alkyl group may be substituted) may include 1,2,3,4-tetrahydronaphthyl C1-C6 alkoxy groups such as a (1-, 2-, 5- or 6-)1,2,3,4-tetrahydronaphthylmethoxy group, a 2-((1-, 2-, 5- or 6-)1,2,3,4-tetrahydronaphthyl)ethoxy group, a 1-((1-, 2-, 5- or 6-)1,2,3,4-tetrahydronaphthyl)ethoxy group, a 3-((1-, 2-, 5- or 6-)1,2,3,4-tetrahydronaphthyl)propoxy group, a 2-((1-, 2-, 5- or 6-)1,2,3,4-tetrahydronaphthyl) propoxy group, a 4-((1- or 2-)1,2,3,4-tetrahydronaphthyl)butoxy group, a 5-((1- or 2-)1,2,3,4-tetrahydronaphthyl) pentoxy group, a 4-((1-, 2-, 5- or 6-)1,2,3,4-tetrahydronaphthyl)pentoxy group, a 6-((1-, 2-, 5- or 6-)1,2,3,4-tetrahydronaphthyl)hexyloxy group, a 2-methyl-3-((1-, 2-, 5- or 6-)1,2,3,4-tetrahydronaphthyl)propoxy group, a 1,1-dimethyl-2-((1-, 2-, 5- or 6-)1,2,3,4-tetrahydronaphthyl) ethoxy group, a (1,1,4,4-tetramethyl-6-1,2,3,4-tetrahydronaphthyl)methoxy group, a (1,1,4-trimethyl-6-1,2,3,4-tetrahydronaphthyl)methoxy group, a (1,1-dimethyl-6-1,2,3,4-tetrahydronaphthyl)methoxy group, a (4,4-dimethyl-6-1,2,3,4-tetrahydronaphthyl)methoxy group, a (1-methyl-6-1,2,3,4-tetrahydronaphthyl)methoxy group, a (1,4-dimethyl-6-1,2,3,4-tetrahydronaphthyl)methoxy group, a (1,1,4,4-tetraethyl-6-1,2,3,4-tetrahydronaphthyl)methoxy group, a (1,1-dimethyl-4-ethyl-6-1,2,3,4-tetrahydronaphthyl)methoxy group, a (1,1-di-n-propyl-6-1,2,3,4-tetrahydronaphthyl) methoxy group, a (4,4-di-n-butyl-6-1,2,3,4-tetrahydronaphthyl)methoxy group, a (1-n-pentyl-6-1,2,3,4-tetrahydronaphthyl)methoxy group, a (1,4-di-n-hexyl-6-1,2,3,4-tetrahydronaphthyl)methoxy group, and a (1-methyl-5-n-propyl-4-ethyl-6-1,2,3,4-tetrahydronaphthyl)methoxy group, provided that, on the 1,2,3,4-tetrahydronaphthalene ring, the above described 1 to 4 C1-C6 alkyl groups may be substituted.

Examples of the phenoxy C1-C6 alkoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) may include phenoxy C1-C6 alkoxy groups such as a phenoxymethoxy group, a 2-phenoxyethoxy group, a 1-phenoxyethoxy group, a 3-phenoxypropoxy group, a 2-phenoxypropoxy group, a 4-phenoxybutoxy group, a 5-phenoxypentoxy group, a 4-phenoxypentoxy group, a 6-phenoxyhexyloxy group, a 2-methyl-3-phenoxypropoxy group, a 1,1-dimethyl-2-phenoxyethoxy group, a 2-fluorophenoxymethoxy group, a 3-fluorophenoxymethoxy group, a 4-fluorophenoxymethoxy group, a 2-(2-fluorophenoxy)ethoxy group, a 2-(3-fluorophenoxy)ethoxy group, a 2-(4-fluorophenoxy)ethoxy group, a 2-chlorophenoxymethoxy group, a 3-chlorophenoxymethoxy group, a 4-chlorophenoxymethoxy group, a 2-fluoro-4-bromophenoxymethoxy group, a 4-chloro-3-fluorophenoxymethoxy group, a 2-chloro-4-fluorophenoxymethoxy group, a 3,4-dichlorophenoxymethoxy group, a 3,5-dichlorophenoxymethoxy group, a 2,3-dichlorophenoxymethoxy group, a 2,5-dichlorophenoxymethoxy group, a 2,3,4-trichlorophenoxymethoxy group, a 3,4,5-trifluorophenoxymethoxy group, a 2,3,4,5,6-pentafluorophenoxymethoxy group, a 2,4,6-trichlorophenoxymethoxy group, a 4-isopropylphenoxymethoxy group, a 4-n-butylphenoxymethoxy group, a 4-methylphenoxymethoxy group, a 2-methylphenoxymethoxy group, a 3-methylphenoxymethoxy group, a 2,4-dimethylphenoxymethoxy group, a 2,3-dimethylphenoxymethoxy group, a 2,6-dimethylphenoxymethoxy group, a 3,5-dimethylphenoxymethoxy group, a 2,5-dimethylphenoxymethoxy group, a 2,4,6-trimethylphenoxymethoxy group, a 4-ethylphenoxymethoxy group, a 4-isopropylphenoxymethoxy group, a 3,5-ditrifluoromethylphenoxymethoxy group, a 4-isopropoxyphenoxymethoxy group, a 4-n-butoxyphenoxymethoxy group, a 4-methoxyphenoxymethoxy group, a 2-methoxyphenoxymethoxy group, a 3-methoxyphenoxymethoxy group, a 2,4-dimethoxyphenoxymethoxy group, a 2,3-dimethoxyphenoxymethoxy group, a 2,6-dimethoxyphenoxymethoxy group, a 3,5-dimethoxyphenoxymethoxy group, a 2,5-dimethoxyphenoxymethoxy group, a 2,4,6-trimethoxyphenoxymethoxy group, a 3,5-ditrifluoromethoxyphenoxymethoxy group, a 2-isopropoxyphenoxymethoxy group, a 3-chloro-4-methoxyphenoxymethoxy group, a 2-chloro-4-trifluoromethoxyphenoxymethoxy group, a 3-methyl-4-fluorophenoxymethoxy group, a 4-bromo-3-trifluoromethylphenoxymethoxy group, a 2-(2-chlorophenoxy)ethoxy group, a 2-(3-chlorophenoxy)ethoxy group, a 2-(4-chlorophenoxy)ethoxy group, a 2-trifluoromethylphenoxymethoxy group, a 3-trifluoromethylphenoxymethoxy group, a 4-trifluoromethylphenoxymethoxy group, a 2-trifluoromethoxyphenoxymethoxy group, a 3-trifluoromethoxyphenoxymethoxy group, a 4-trifluoromethoxyphenoxymethoxy group, a 2-(2-trifluoromethylphenoxy)ethoxy group, a 2-(3-trifluoromethylphenoxy)ethoxy group, a 2-(4-trifluoromethylphenoxy)ethoxy group, a 2-(2-trifluoromethoxyphenoxy)ethoxy group, a 2-(3-trifluoromethoxyphenoxy)ethoxy group, a 2-(4-trifluoromethoxyphenoxy)ethoxy group, a 3-(2-trifluoromethylphenoxy)propoxy group, a 3-(3-trifluoromethylphenoxy)propoxy group, a 3-(4-trifluoromethylphenoxy)propoxy group, a 3-(2-trifluoromethylphenoxy)propoxy group, a 3-(3-trifluoromethoxyphenoxy)propoxy group, a 3-(4-trifluoromethoxyphenoxy)propoxy group, a 4-(3-trifluoromethylphenoxy)butoxy group, a 5-(4-trifluoromethylphenoxy)pentoxy group, a 4-(4-trifluoromethylphenoxy)pentoxy group, a 4-(4-trifluoromethoxyphenoxy)pentoxy group, a 6-(3-trifluoromethylphenoxy)hexyloxy group, a 6-(4-trifluoromethylphenoxy)hexyloxy group, and a 6-(4-trifluoromethoxyphenoxy)hexyloxy group, provided that, on the phenyl ring, 1 to 5 groups, and preferably 1 to 3 groups selected from the group consisting of the above described halogen atom, the above described halogen substituted or unsubstituted C1-C6 alkyl group, and the above described halogen substituted or unsubstituted C1-C6 alkoxy group may be substituted.

Examples of the carbamoyl C1-C6 alkoxy group [wherein, on the amino group, at least one selected from the group consisting of a C3-C8 cycloalkyl group and a phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) may be substituted] may include carbamoyl C1-C6 alkoxy groups such as a carbamoylmethoxy group, a 2-carbamoylethoxy group, a 3-carbamoylpropoxy group, a 2-carbamoylpropoxy group, a 4-carbamoylbutoxy group, a 5-carbamoylpentoxy group, a 4-carbamoylpentoxy group, a 6-carbamoylhexyloxy group, a 2-methyl-3-carbamoylpropoxy group, a 1,1-dimethyl-2-carbamoylethoxy group, an (N-(4-methylphenyl)carbamoyl)methoxy group, an (N-(4-chlorophenyl)carbamoyl)methoxy group, an (N-(4-trifluoromethylphenyl)carbamoyl)methoxy group, an (N-(4-methoxyphenyl)carbamoyl)methoxy group, an (N-(4-trifluoromethoxyphenyl)carbamoyl)methoxy group, an (N-(2,4-dichlorophenyl)carbamoyl)methoxy group, an (N-(2,4,6-trimethylphenyl)carbamoyl)methoxy group, an (N-(2,4-dimethoxyphenyl)carbamoyl)methoxy group, an (N-cyclohexylcarbamoyl)methoxy group, an (N-cyclopentylcarbamoyl)methoxy group, an (N-cycloheptylcarbamoyl)methoxy group, an (N-cyclooctylcarbamoyl)methoxy group, an (N-cyclobutylcarbamoyl)methoxy group, an (N-cyclopropylcarbamoyl)methoxy group, an (N-cyclopropyl-N-cyclohexylcarbamoyl)methoxy group, an (N,N-dicyclohexylcarbamoyl)methoxy group, an (N-cyclopropyl-N-(4-fluoromethylphenyl)carbamoyl)methoxy group, and an (N-cyclohexyl-N-(4-fluoromethylphenyl)carbamoyl)methoxy group, provided that, on the amino group, 1 or 2 groups selected from the group consisting of the above described C3-C8 cycloalkyl group and the above described phenyl group (wherein, on the phenyl-ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted) may be substituted.

Examples of the benzofuryl C1-C6 alkoxy group (wherein, on the benzofuran ring, at least one cyano group may be substituted) may include benzofuryl C1-C6 alkyl group such as a (2-benzofuryl)methoxy group, a 2-(3-benzofuryl)ethoxy group, a 3-(4-benzofuryl)propoxy group, a 2-(5-benzofuryl)propoxy group, a 4-(6-benzofuryl)butoxy group, a 5-(7-benzofuryl)pentoxy group, a 4-(2-benzofuryl)pentoxy group, a 6-(3-benzofuryl)hexyloxy group, a 2-(2-benzofuryl)methoxy group, a 1,1-dimethyl-2-(2-benzofuryl)ethoxy group, a 2-methyl-3-(3-benzofuryl)propoxy group, a (7-cyano-2-benzofuryl)methoxy group, a (6-cyano-2-benzofuryl)methoxy group, a (5-cyano-2-benzofuryl)methoxy group, a (4-cyano-2-benzofuryl)methoxy group, a (3-cyano-2-benzofuryl)methoxy group, a (2-cyano-5-benzofuryl)methoxy group, and a (6,7-dicyano-2-benzofuryl)methoxy group, a (3,4,5-tricyano-2-benzofuryl)methoxy group, provided that, on the benzofuran ring, 1 to 3 cyano groups may be substituted.

Examples of the naphthyloxy C1-C6 alkyl group (wherein, on the naphthalene ring, at least one C1-C6 alkoxy group may be substituted) may include naphthyloxy C1-C6 alkyl groups such as a (1- or 2-) naphthyloxymethyl group, a 2-((1- or 2-)naphthyloxy)ethyl group, a 1-((1- or 2-)naphthyloxy)ethyl group, a 3-((1- or 2-)naphthyloxy)propyl group, a 2-((1- or 2-)naphthyloxy)butyl group, a 5-((1- or 2-)naphthyloxy)pentyl group, a 4-((1- or 2-)naphthyloxy)pentyl group, a 6-((1- or 2-)naphthyloxy)hexyl group, a 2-methyl-3-((1- or 2-)naphthyloxy)propyl group, a 1,1-dimethyl-2-((1- or 2-)naphthyloxy)ethyl group, a 2-(4-methoxy-1-naphthyloxy)ethyl group, a (4-methoxy-1-naphthyloxy)methyl group, a 2-(3-ethoxy-1-naphthyloxy)ethyl group, a 2-n-propoxy-1-naphthyloxymethyl group, a 5-tert-butoxy-2-naphthyloxymethyl group, a 6-n-pentyloxy-3-naphthyloxymethyl group, a 7-n-hexyloxy-4-naphthyloxymethyl group, a 2-(2,4-dimethoxy- 1-naphthyloxy)ethyl group, and a 2-(1,2,3,4-tetramethoxy-5-naphthyloxy)ethyl group, provided that, on the naphthalene ring, the above described 1 to 4 C1-C6 alkoxy groups may be substituted.

Examples of the benzothiazolyloxy C1-C6 alkyl group (wherein, on the benzothiazole ring, at least one C1-C6 alkyl group may be substituted) may include benzothiazolyloxy C1-C6 alkyl groups such as a (2-, 4-, 5-, 6- or 7-)benzothiazolyloxymethyl group, a 2-((2-, 4-, 5-, 6- or 7-)benzothiazolyloxy)ethyl group, a 1-((2-, 4-, 5-, 6- or 7-)benzothiazolyloxy)ethyl group, a 3-((2-, 4-, 5-, 6- or 7-)benzothiazolyloxy) propyl group, a 2-((2-, 4-, 5-, 6- or 7-)benzothiazolyloxy) propyl group, a 4-((2-, 4-, 5-, 6- or 7-)benzothiazolyloxy)-butyl group, a 5-((2-, 4-, 5-, 6- or 7-)benzothiazolyloxy) pentyl group, a 4-((2-, 4-, 5-, 6- or 7-)benzothiazolyloxy) pentyl group, a 6-((2-, 4-, 5-, 6- or 7-)benzothiazolyloxy) hexyl group, a 2-methyl-3-((2-, 4-, 5-, 6- or 7-)benzothiazolyloxy)propyl group, a 1,1-dimethyl-2-((2-, 4-, 5-, 6- or 7-)benzothiazolyloxy)ethyl group, a 2-(2-methyl-5-benzothiazolyloxy)ethyl group, a (2-methyl-5-benzothiazolyloxy)methyl group, a 2-(4-ethyl-6-benzothiazolyloxy) ethyl group, a (2-n-propyl-4-benzothiazolyloxy)methyl group, a (5-tert-butyl-6-benzothiazolyloxy)methyl group, a (6-n-pentyl-7-benzothiazolyloxy)methyl group, a (7-n-hexyl-5-benzothiazolyloxy)methyl group, a 2-(2,4-dimethyl-5-benzothiazolyloxy)ethyl group, and a 2-(2,4,5-trimethyl-7-benzothiazolyloxy)ethyl group, provided that, on the benzothiazole ring, the above described 1 to 3 C1-C6 alkyl groups may be substituted.

Examples of the quinolyloxy C1-C6 alkyl group (wherein, on the quinoline ring, at least one C1-C6 alkyl group may be substituted) may include quinolyloxy C1-C6 alkyl groups such as a (2-, 3-, 4-, 5-, 6-, 7- or 8-)quinolyloxymethyl group, a 2-((2-, 3-, 4-, 5-, 6-, 7- or 8-)quinolyloxy)ethyl group, a 1-((2-, 3-, 4-, 5-, 6-, 7- or 8-)quinolyloxy)ethyl group, a 3-((2-, 3-, 4-, 5-, 6-, 7- or 8-)quinolyloxy)propyl group, a 2-((2-, 3-, 4-, 5-, 6-, 7- or 8-)quinolyloxy)propyl group, a 4-((2-, 3-, 4-, 5-, 6-, 7- or 8-)quinolyloxy)butyl group, a 5-((2-, 3-, 4-, 5-, 6-, 7- or 8-)quinolyloxy)pentyl group, a 4-((2-, 3-, 4-, 5-, 6-, 7- or 8-)quinolyloxy)pentyl group, a 6-((2-, 3-, 4-, 5-, 6-, 7- or 8-)quinolyloxy)hexyl group, a 2-methyl-3-((2-, 3-, 4-, 5-, 6-, 7- or 8-)quinolyloxy)propyl group, a 1,1-dimethyl-2-((2-, 3-, 4-, 5-, 6-, 7- or 8-)quinolyloxy)ethyl group, a 2-methyl-8-quinolyloxymethyl group, a (3-ethyl-7-quinolyloxy)methyl group, a (4-n-propyl-6-quinolyloxy)methyl group, a (5-n-butyl-4-quinolyloxy)methyl group, a (6-n-hexyl-5-quinolyloxy)methyl group, a (2-methyl-7-quinolyloxy)methyl group, a (7-n-pentyl-6-quinolyloxy)methyl group, a (8-methyl-2-quinolyloxymethyl) group, a (2,4-dimethyl-8-quinolyloxy)methyl group, and a (5,6,7-trimethyl-2-quinolyloxy)methyl group, provided that, on the quinoline ring, the above described 1 to 3 C1-C6 alkyl groups may be substituted.

Examples of the 2,3-dihydrobenzofuryloxy C1-C6 alkyl group (wherein, on the 2,3-dihydrobenzofuran ring, at least one selected from the group consisting of a C1-C6 alkyl group and an oxo group may be substituted) may include 2,3-dihydrobenzofuryloxy C1-C6 alkyl groups such as a (2-, 3-, 4-, 5-, 6- or 7-)2,3-dihydrobenzofuryloxymethyl group, a 2-((2-, 3-, 4-, 5-, 6- or 7-)2,3-dihydrobenzofuryloxy)ethyl group, a 1-((2-, 3-, 4-, 5-, 6- or 7-)2,3-dihydrobenzofuryloxy)ethyl group, a 3-((2-, 3-, 4-, 5-, 6- or 7-)2,3-dihydrobenzofuryloxy) propyl group, a 2-((2-, 3-, 4-, 5-, 6- or 7-)2,3-dihydrobenzofuryloxy)propyl group, a 4-((2-, 3-, 4-, 5-, 6- or 7-)2,3-dihydrobenzofuryloxy)butyl group, a 5-((2-, 3-, 4-, 5-, 6- or 7-)2,3-dihydrobenzofuryloxy)pentyl group, a 4-((2-, 3-, 4-, 5-, 6- or 7-)$_2$, 3-dihydrobenzofuryloxy)pentyl group, a 6-((2-, 3-, 4-, 5-, 6- or 7-)2,3-dihydrobenzofuryloxy)hexyl group, a 2-methyl-3-((2-, 3-, 4-, 5-, 6- or 7-)2,3-dihydrobenzofuryloxy)propyl group, a 1,1-dimethyl-2-((2-, 3-, 4-, 5-, 6- or 7-)2,3-dihydrobenzofuryloxy)ethyl group, a 2-(2,2-dimethyl-7-2,3-dihydrobenzofuryloxy)ethyl group, a (2,2-dimethyl-7-2,3-dihydrobenzofuryloxy)methyl group, a 2-(3-ethyl-6-2,3-dihydrobenzofuryloxy)ethyl group, a (4-n-propyl-5-2,3-dihydrobenzofuryloxy)methyl group, a (5-tert-butyl-6-2,3-dihydrobenzofuryloxy)methyl group, a (6-n-pentyl-7-2,3-dihydrobenzofuryloxy)methyl group, a (7-n-hexyl-5-2,3-dihydrobenzofuryloxy)methyl group, a 2-(2,4-dimethyl-5-2,3-dihydrobenzofuryloxy)ethyl group, a 2-(2,2,3-trimethyl-7-2,3-dihydrobenzofuryloxy)ethyl group, a (2-oxo-5-2,3-dihydrobenzofuryloxy)methyl group, a (3-oxo-6-2,3-dihydrobenzofuryloxy)methyl group, and a (2-oxo-3-methyl-5-2,3-dihydrobenzofuryloxy)methyl group, provided that, on the 2,3-dihydrobenzofuran ring, 1 to 3 groups selected from the group consisting of the above described C1-C6 alkyl group and oxo group may be substituted.

Examples of the 1,2,3,4-tetrahydronaphthyloxy C1-C6 alkyl group (wherein, on the 1,2,3,4-tetrahydronaphthalene ring, at least one oxo group may be substituted) may include 1,2,3,4-tetrahydronaphthyloxy C1-C6 alkyl groups such as a (1-, 2-, 5- or 6-)1,2,3,4-tetrahydronaphthyloxymethyl group, a 2-((1-, 2-, 5- or 6-)1,2,3,4-tetrahydronaphthyloxy)ethyl group, a 1-((1-, 2-, 5- or 6-)1,2,3,4-tetrahydronaphthyloxy) ethyl group, a 3-((1-, 2-, 5- or 6-)1,2,3,4-tetrahydronaphthyloxy)propyl group, a 2-((1-, 2-, 5- or 6-)1,2,3,4-tetrahydronaphthyloxy)propyl group, a 4-((1-, 2-, 5- or 6-)1,2,3,4-tetrahydronaphthyloxy)butyl group, a 5-((1-, 2-, 5- or 6-)1,2,3,4-tetrahydronaphthyloxy)pentyl group, a 4-((1- or 2-)1,2,3,4-tetrahydronaphthyloxy)pentyl group, a 6-((1- or 2-)1,2,3,4-tetrahydronaphthyloxy)hexyl group, a 2-methyl-3-((1-, 2-, 5- or 6-)1,2,3,4-tetrahydronaphthyloxy)propyl group, a 1,1-dimethyl-2-((1-, 2-, 5- or 6-)1,2,3,4-tetrahydronaphthyloxy)ethyl group, a (1-oxo-(2-, 5- or 6-)1,2,3,4-tetrahydronaphthyloxy)methyl group, a (1,4-dioxo-(2-, 5- or 6-)1,2,3,4-tetrahydronaphthyloxy)methyl group, and a 1,2,4-trioxo-(3-, 5-, 6-, 7- or 8-)1,2,3,4-tetrahydronaphthyloxy)methyl group, provided that, on the 1,2,3,4-tetrahydronaphthalene ring, 1 to 3 oxo groups may be substituted.

Examples of the 2,3-dihydro-1H-indenyloxy C1-C6 alkyl group (wherein, on the 2,3-dihydro-1H-indene ring, at least one oxo group may be substituted) may include 2,3-dihydro-1H-indenyloxy C1-C6 alkyl groups such as a (1-, 2-, 4- or 5-)2,3-dihydro-1H-indenyloxymethyl group, a 2-((1-, 2-, 4- or 5-)2,3-dihydro-1H-indenyloxy)ethyl group, a 1-((1-, 2-, 4- or 5-)2,3-dihydro-1H-indenyloxy)ethyl group, a 3-((1-, 2-, 4- or 5-)2,3-dihydro-1H-indenyloxy)propyl group, a 2-((1-, 2-, 4- or 5-)2,3-dihydro-1H-indenyloxy)propyl group, a 4-((1-, 2-, 4- or 5-)2,3-dihydro-1H-indenyloxy)butyl group, a 5-((1-, 2-, 4- or 5-)2,3-dihydro-1H-indenyloxy)pentyl group, a 4-((1-, 2-, 4- or 5-)2,3-dihydro-1H-indenyloxy)pentyl group, a 6-((1-, 2-, 4- or 5-)2,3-dihydro-1H-indenyloxy)hexyl group, a 2-methyl-3-((1-, 2-, 4- or 5-)2,3-dihydro-1H-indenyloxy)propyl group, a 1,1-dimethyl-2-((1-, 2-, 4- or 5-)2,3-dihydro-1H-indenyloxy)ethyl group, a (1-oxo-(2-, 3-, 4-, 5-, 6- or 7-)2,3-dihydro-1H-indenyloxy)methyl group, and a (1,3-dioxo-(2-, 4- or 5-)2,3-dihydro-1H-indenyloxy)methyl group, provided that, on the 2,3-dihydro-1H-indene ring, 1 or 2 oxo groups may be substituted.

Examples of the benzoxathiolanyloxy C1-C6 alkyl group (wherein, on the benzoxathiolane ring, at least one oxo group may be substituted) may include benzoxathiolanyloxy C1-C6 alkyl groups such as a (2-, 4-, 5-, 6- or 7-)benzoxathiolanyloxymethyl group, a 2-((2-, 4-, 5-, 6- or 7-)benzoxathiolanyloxy)ethyl group, a 1-((2-, 4-, 5-, 6- or 7-)benzoxathiolanyloxy)ethyl group, a 3-((2-, 4-, 5-, 6- or 7-)benzoxathiolanyloxy)-propyl group, a 2-((2-, 4-, 5-, 6- or 7-)benzoxathiolanyloxy)propyl group, a 4-((2-, 4-, 5-, 6- or 7-)benzoxathiolanyloxy)butyl group, a 5-((2-, 4-, 5-, 6- or 7-)benzoxathiolanyloxy)pentyl group, a 4-((2-, 4-, 5-, 6- or 7-)benzoxathiolanyloxy)pentyl group, a 6-((2-, 4-, 5-, 6- or 7-)benzoxathiolanyloxy)hexyl group, a 2-methyl-3-((2-, 4-, 5-, 6- or 7-)benzoxathiolanyloxy)-propyl group, a 1,1-dimethyl-2-((2-, 4-, 5-, 6- or 7-)benzoxathiolanyloxy)ethyl group, and a (2-oxo-(4-, 5-, 6- or 7-)benzoxathiolarnyloxy)-methyl group, provided that, on the benzoxathiolane ring, one oxo group may be substituted.

Examples of the isoquinolyloxy C1-C6 alkyl group may include a (1-, 3-, 4-, 5-, 6-, 7- or 8-)isoquinolyloxymethyl group, a 2-((1-, 3-, 4-, 5-, 6-, 7- or 8-)isoquinolyloxy)ethyl group, a 1-((1-, 3-, 4-, 5-, 6-, 7- or 8-)isoquinolyloxy)ethyl group, a 3-((1-, 3-, 4-, 5-, 6-, 7- or 8-)isoquinolyloxy)propyl group, a 2-((1-, 3-, 4-, 5-, 6-, 7- or 8-)isoquinolyloxy)propyl group, a 4-((1-, 3-, 4-, 5-, 6-, 7- or 8-)isoquinolyloxy)butyl group, a 5-((1-, 3-, 4-, 5-, 6-, 7- or 8-)isoquinolyloxy)pentyl group, a 4-((1-, 3-, 4-, 5-, 6-, 7- or 8-)isoquinolyloxy)pentyl group, a 6-((1-, 3-, 4-, 5-, 6-, 7- or 8-)isoquinolyloxy)hexyl group, a 2-methyl-3-((1-, 3-, 4-, 5-, 6-, 7- or 8-)isoquinolyloxy)propyl group, and a 1,1-dimethyl-2-((1-, 3-, 4-, 5-, 6-, 7- or 8-)isoquinolyloxy)ethyl group.

Examples of the pyridyloxy C1-C6 alkyl group may include a (2-, 3- or 4-)pyridyloxymethyl group, a 2-((2-, 3- or 4-)pyridyloxy)ethyl group, a 1-((2-, 3- or 4-)pyridyloxy)ethyl group, a 3-((2-, 3- or 4-)pyridyloxy)propyl group, a 2-((2-, 3- or 4-)pyridyloxy)propyl group, a 4-((2-, 3- or 4-)pyridyloxy) butyl group, a 5-((2-, 3- or 4-)pyridyloxy)pentyl group, a 4-((2-, 3- or 4-)pyridyloxy)pentyl group, a 6-((2-, 3- or 4-)pyridyloxy)hexyl group, a 2-methyl-3-((2-, 3- or 4-)pyridyloxy) propyl group, and a 1,1-dimethyl-2-((2-, 3- or 4-)pyridyloxy) ethyl group.

Examples of the dibenzofuryloxy C1-C6 alkyl group may include a (1-, 2-, 3- or 4-)dibenzofuryloxy-methyl group, a 2-((1-, 2-, 3-, 4-, 5-, 6-, 7- or 8-)dibenzofuryloxy)ethyl group, a 1-((1-, 2-, 3- or 4-)dibenzofuryloxy)ethyl group, a 3-((1-, 2-, 3- or 4-)dibenzofuryloxy)propyl group, a 2-((1-, 2-, 3- or 4-)dibenzofuryloxy)propyl group, a 4-((1-, 2-, 3- or 4-)dibenzofuryloxy)butyl group, a 5-((1-, 2-, 3- or 4-)dibenzofuryloxy)pentyl group, a 4-((1-, 2-, 3- or 4-)dibenzofuryloxy) pentyl group, a 6-((1-, 2-, 3- or 4-)dibenzofuryloxy)hexyl group, a 2-methyl-3-((1-, 2-, 3- or 4-)dibenzofuryloxy)propyl group, and a 1,1-dimethyl-2-((1-, 2-, 3- or 4-)dibenzofuryloxy)ethyl group.

Examples of the 2H-1-benzopyranyloxy C1-C6 alkyl group (wherein, on the 2H-1-benzopyran ring, at least one oxo group may be substituted) may include 2H-1-benzopyranyloxy C1-C6 alkyl groups such as a (2-, 3-, 4-, 5-, 6-, 7- or 8-)2H-1-benzopyranyloxymethyl group, a 2-((2-, 3-, 4-, 5-, 6-, 7- or 8-)2H-1-benzopyranyloxy)ethyl group, a 1-((2-, 3-, 4-, 5-, 6-, 7- or 8-)2H-1-benzopyranyloxy)ethyl group, a 3-((2-, 3-, 4-, 5-, 6-, 7- or 8-)2H-1-benzopyranyloxy)propyl group, a 2-((2-, 3-, 4-, 5-, 6-, 7- or 8-)2H-1-benzopyranyloxy) propyl group, a 4-((2-, 3-, 4-, 5-, 6-, 7- or 8-)2H-1-benzopyranyloxy)butyl group, a 5-((2-, 3-, 4-, 5-, 6-, 7- or 8-)2H-1-benzopyranyloxy)pentyl group, a 4-((2-, 3-, 4-, 5-, 6-, 7- or 8-)2H-1-benzopyranyloxy)pentyl group, a 6-((2-, 3-, 4-, 5-, 6-, 7- or 8-)2H-1-benzopyranyloxy)hexyl group, a 2-methyl-3-((2-, 3-, 4-, 5-, 6-, 7- or 8-)2H-1-benzopyranyloxy)propyl group, a 1,1-dimethyl-2-((2-, 3-, 4-, 5-, 6-, 7- or 8-)2H-1-benzopyranyloxy)ethyl group, and a (2-oxo-(3-, 4-, 5-, 6-, 7- or 8-)2H-1-benzopyranyloxy)methyl group, provided that, on the 2H-1-benzopyran ring, one oxo group may be substituted.

Examples of the benzoisoxazolyloxy C1-C6 alkyl group may include a (3-, 4-, 5-, 6- or 7-)benzoisoxazolyloxymethyl group, a 2-((3-, 4-, 5-, 6- or 7-)benzoisoxazolyloxy)ethyl group, a 1-((3-, 4-, 5-, 6- or 7-)benzoisoxazolyloxy)ethyl group, a 3-((3-, 4-, 5-, 6- or 7-)benzoisoxazolyloxy)propyl group, a 2-((3-, 4-, 5-, 6- or 7-)benzoisoxazolyloxy)propyl group, a 4-((3-, 4-, 5-, 6- or 7-)benzoisoxazolyloxy)butyl group, a 5-((3-, 4-, 5-, 6- or 7-)benzoisoxazolyloxy)pentyl group, a 4-((3-, 4-, 5-, 6- or 7-)benzoisoxazolyloxy)-pentyl group, a 6-((3-, 4-, 5-, 6- or 7-)benzoisoxazolyloxy)hexyl group, a 2-methyl-3-((3-, 4-, 5-, 6- or 7-)benzoisoxazolyloxy) propyl group, and a 1,1-dimethyl-2-((3-, 4-, 5-, 6- or 7-)benzoisoxazolyloxy)ethyl group.

Examples of the benzofurazanyloxy C1-C6 alkyl group may include a (4- or 5-)benzofurazanyloxymethyl group, a 2-((4- or 5-)benzofurazanyloxy)ethyl group, a 1-((4- or 5-)benzofurazanyloxy)ethyl group, a 3-((4- or 5-)benzofurazanyloxy)propyl group, a 2-((4- or 5-)benzofurazanyloxy) propyl group, a 4-((4- or 5-)benzofurazanyloxy)butyl group, a 5-((4- or 5-)benzofurazanyloxy)pentyl group, a 4-((4- or 5-)benzofurazanyloxy)pentyl group, a 6-((4- or 5-)benzofurazanyloxy)hexyl group, a 2-methyl-3-((4- or 5-)benzofurazanyloxy)propyl group, and a 1,1-dimethyl-2-((4- or 5-)benzofurazanyloxy)ethyl group.

Examples of the quinoxalyloxy C1-C6 alkyl group may include a (2-, 5- or 6-)quinoxalyloxymethyl group, a 2-((2-, 5- or 6-)quinoxalyloxy)ethyl group, a 1-((2-, 5- or 6-)quinoxalyloxy)ethyl group, a 3-((2-, 5- or 6-)quinoxalyloxy)propyl group, a 2-((2-, 5- or 6-)quinoxalyloxy)propyl group, a 4-((2-, 5- or 6-)quinoxalyloxy)butyl group, a 5-((2-, 5- or 6-)quinoxalyloxy)pentyl group, a 4-((2-, 5- or 6-)quinoxalyloxy)pentyl group, a 6-((2-, 5- or 6-)quinoxalyloxy)hexyl group, a 2-methyl-3-((2-, 5- or 6-)quinoxalyloxy)propyl group, and a 1,1-dimethyl-2-((2-, 5- or 6-)quinoxalyloxy)ethyl group.

Examples of the phenyl C2-C10 alkenyl group [wherein, on the phenyl ring, at least one selected from the following groups may be substituted: a halogen atom, a C1-C4 alkylenedioxy group, a C1-C6 alkylthio group, a benzoyl group, a cyano group, a nitro group, a C2-C6 alkanoyloxy group, an amino group which may have C1-C6 alkyl group(s) as substituent, a hydroxyl group, a phenyl C1-C6 alkoxy group, a phenoxy group, a halogen substituted or unsubstituted C1-C6 alkyl group, and a halogen substituted or unsubstituted C1-C6 alkoxy group), may include the above described phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted), as well as alkenyl groups containing 2 to 10 carbon atoms and having 1 to 3 double bonds, wherein, on the C2-C10 alkenyl group, 1 or 2 phenyl groups may be substituted, such as a 2-n-pentyl-3-phenyl-2-propenyl group, a 9-phenyl-2-nonenyl group, a 10-phenyl-2-decenyl group, a 8-phenyl-1,3-octadienyl group, a 9-phenyl-1,3,5-nonatrienyl group, a 10-2,4,6-decatrienyl group, a 3-(4-methylthiophenyl)-2-propenyl group, a 3-(3-methylthiophenyl)-2-propenyl group, a 3-(2-methylthiophenyl)-2-propenyl group, a 3-(3,4-dimethylthiophenyl)-2-propenyl group, a 3-(3,4,5-trimethylthiophenyl)-2-propenyl group, a 3-(4-benzoyl)-2-propenyl group, a 3-(3-benzoyl)-2-propenyl group, a 3-(2-benzoyl)-2-propenyl group, a 3-(3,4-dibenzoyl)-2-propenyl group, a 3-(2,4,6-tribenzoyl)-2-propenyl group, a 3-(4-cyanophenyl)-2-propenyl group, a 3-(3-cyanophenyl)-2-propenyl group, a 3-(2-cyanophenyl)-2-propenyl group, a 3-(3,4-dicyanophenyl)-2-propenyl group, a 3-(2,4,6-tricyanophenyl)-2-propenyl group, a 3-(4-acetyloxyphenyl)-2-propenyl group, a 3-(4-acetyloxy-3-methoxyphenyl)-2-propenyl group, a 3-(3- acetyloxyphenyl)-2-propenyl group, a 3-(2-acetyloxyphenyl)-2-propenyl group, a 3-(3,4-diacetyloxyphenyl)-2-propenyl group, a 3-(2,4,6-triacetyloxyphenyl)-2-propenyl group, a 3-(4-dimethylaminophenyl)-2-propenyl group, a 3-(4-dimethylaminophenyl)-2-propenyl group, a 3-(3-methylaminophenyl)-2-propenyl group, a 3-(2-(N-methyl-N-ethylamino)phenyl)-2-propenyl group, a 3-(2,4-dimethylaminophenyl)-2-propenyl group, a 3-(2,4,6-tri (dimethylamino)phenyl)-2-propenyl group, a 3-(2-hydroxyphenyl)-2-propenyl group, a 3-(3-hydroxyphenyl)-2-propenyl group, a 3-(4-hydroxyphenyl)-2-propenyl group, a 3-(3,5-dimethyl-4-hydroxyphenyl)-2-propenyl group, a 3-(3-methoxy-4-hydroxyphenyl)-2-propenyl group, a 3-(2-hydroxyphenyl)-2-propenyl group, a 3-(4-benzyloxyphenyl)-2-propenyl group, a 3-(4-benzyloxyphenyl)-2-propenyl group, a 3-(2-benzyloxyphenyl)-2-propenyl group, a 3-(2,4,6-tribenzyloxyphenyl)-2-propenyl group, a 3-(3,4-dibenzyloxyphenyl)-2-propenyl group, a 3-(4-phenoxyphenyl)-2-propenyl group, a 3-(3-phenoxyphenyl)-2-propenyl group, a 3-(2-phenoxyphenyl)-2-propenyl group, a 3-(2,4-diphenoxyphenyl)-2-propenyl group, a 3-(2,4,6-triphenoxyphenyl)-2-propenyl group, a 3-(3,4-methylenedioxyphenyl)-2-propenyl group, a 3-(2,3-ethylenedioxyphenyl)-2-propenyl group, and a 3-(3,4-ethylenedioxyphenyl)-2-propenyl group. The above phenyl C2-C10 alkenyl group includes both a trans form and a cis form. On the phenyl ring, 1 to 5 groups, and preferably 1 to 3 groups selected from the following groups may be substituted: a halogen atom, the above described C1-C4 alkylenedioxy group, the above described C1-C6 alkylthio group, benzoyl group, cyano group, nitro group, the above described C2-C6 alkanoyloxy group, the above described amino group which may have a C1-C6 alkyl group as a substituent, hydroxyl group, the above described phenyl C1-C6 alkoxy group, phenoxy group, the above described halogen substituted or unsubstituted C1-C6 alkyl group, and the above described halogen substituted or unsubstituted C1-C6 alkoxy group. In a case where the substituent is a C1-C4 alkylenedioxy group, 1 or 2 groups are preferably substituted on the phenyl ring.

Examples of the naphthyl C2-C6 alkenyl group may include alkenyl groups containing 2 to 6 carbon atoms and having 1 to 3 double bonds, wherein a naphthyl group is substituted, such as a 2-(1- or 2-)naphthylvinyl group, a 3-(1- or 2-)naphthyl-2-propenyl group, a 3-(1- or 2-)naphthyl-2-methyl-2-propenyl group, a 4-(1- or 2-)naphthyl-2-butenyl group, a 4-(1- or 2-)naphthyl-3-butenyl group, a 4-(1- or 2-)naphthyl-1,3-butadienyl group, a 5-(1- or 2-)naphthyl-1,3-pentadienyl group, a 6-(1- or 2-)naphthyl-3-hexadienyl group, a 6-(1- or 2-)naphthyl-2-hexenyl group, a 5-(1- or 2-)naphthyl-2-pentenyl group, and a 6-(1- or 2-)naphthyl-1,3,5-hexadienyl group. The above naphthyl C2-C6 alkenyl group includes both a trans form and a cis form.

Examples of the benzothienyl C2-C6 alkenyl group may include alkenyl groups containing 2 to 6 carbon atoms and having 1 to 3 double bonds, wherein a benzothienyl group is substituted, such as a 2-(2-, 3-, 4-, 5-, 6- or 7-)benzothienylvinyl group, a 3-(2-, 3-, 4-, 5-, 6- or 7-)benzothienyl-2-propenyl group, a 3-(2-, 3-, 4-, 5-, 6- or 7-)benzothienyl-2-methyl-2-propenyl group, a 4-(2-, 3-, 4-, 5-, 6- or 7-)benzothienyl-2-butenyl group, a 4-(2-, 3-, 4-, 5-, 6- or 7-)benzothienyl-3-butenyl group, a 4-(2-, 3-, 4-, 5-, 6- or 7-)benzothienyl-1,3-butadienyl group, a 5-(2-, 3-, 4-, 5-, 6- or 7-)benzothienyl-1,3-pentadienyl group, a 6-(2-, 3-, 4-, 5-, 6- or 7-)benzothienyl-1,3-hexadienyl group, a 6-(2-, 3-, 4-, 5-, 6- or 7-)benzothienyl-2-hexenyl group, a 5-(2-, 3-, 4-, 5-, 6- or 7-)benzothienyl-2-pentenyl group, and a 6-(2-, 3-, 4-, 5-, 6- or 7-)benzothienyl-1,3,5-hexatrienyl group. The above benzothienyl C2-C6 alkenyl group includes both a trans form and a cis form.

Examples of the benzothiazolyl C2-C6 alkenyl group [wherein, on the benzothiazole ring, at least one C1-C6 alkyl group may be substituted] may include alkenyl groups containing 2 to 6 carbon atoms and having 1 to 3 double bonds, wherein a benzothiazolyl group is substituted, such as a 2-(2-, 4-, 5-, 6- or 7-)benzothiazolylvinyl group, a 3-(2-, 4-, 5-, 6- or 7-)benzothiazolyl-2-propenyl group, a 3-(2-, 4-, 5-, 6- or 7-)benzothiazolyl-2-methyl-2-propenyl group, a 4-(2-, 4-, 5-, 6- or 7-)benzothiazolyl-2-butenyl group, a 4-(2-, 4-, 5-, 6- or 7-)benzothiazolyl-3-butenyl group, a 4-(2-, 4-, 5-, 6- or 7-)benzothiazolyl-1,3-butadienyl group, a 5-(2-, 4-, 5-, 6- or 7-)benzothiazolyl-1,3-pentadienyl group, a 6-(2-, 4-, 5-, 6- or 7-)benzothiazolyl-1,3-hexadienyl group, a 6-(2-, 4-, 5-, 6- or 7-)benzothiazolyl-2-hexenyl group, a 5-(2-, 4-, 5-, 6- or 7-)benzothiazolyl-2-pentenyl group, a 6-(2-, 4-, 5-, 6- or 7-)benzothiazolyl-1,3,5-hexadienyl group, a 3-(2-methyl-5-benzothiazolyl)-2-propenyl group, a 3-(2-ethyl-4-benzothiazolyl)-2-propenyl group, a 3-(2-n-propyl-6-benzothiazolyl)-2-propenyl group, a 3-(2-n-butyl-7-benzothiazolyl)-2-propenyl group, a 3-(4-n-pentyl-5-benzothiazolyl)-2-propenyl group, a 3-(5-n-hexyl-2-benzothiazolyl)-2-propenyl group, a 3-(2,4-dimethyl-5-benzothiazolyl)-2-propenyl group, and a 3-(2,4,5-trimethyl-7-benzothiazolyl)-2-propenyl group. The above benzothiazolyl C2-C6 alkenyl group includes both a trans form and a cis form.

Examples of the phenyl C1-C6 alkyl group [wherein, on the phenyl ring, at least one selected from the group consisting of a piperidinyl group (wherein, on the piperidine ring, at least one phenoxy group may be substituted [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted]) and a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) is substituted], may include phenyl C1-C6 alkyl groups such as a 4-(1-piperidyl)benzyl group, a 2,4-di(4-piperidyl)benzyl group, a 2,4,6-tri(2-piperidyl)benzyl group, a 4-(4-(4-trifluoromethoxyphenoxy)-1-piperidyl)benzyl group, a 4-(4-(4-trifluoromethylphenoxy)-1-piperidyl)benzyl group, a 4-(4-(4-chlorophenoxy)-1-piperidyl)benzyl group, a 4-(4-(3,4-di (trifluoromethoxy)phenoxy)-1-piperidyl)benzyl group, a 4-(4-(2,4,6-tri(trifluoromethyl)phenoxy)-1-piperidyl)benzyl group, a 4-(4-(2,4-dichlorophenoxy)-1-piperidyl)benzyl group, a 4-(4-(2,4,6-trifluorophenoxy)-1-piperidyl)benzyl group, a 3-(2,4-diphenoxy-3-piperidyl)benzyl group, a 2-(1,2,3-triphenoxy-4-piperidyl)benzyl group, a 4-(4-trifluoromethoxyphenoxy)benzyl group, a 4-(4-trifluoromethylphenoxy)benzyl group, a 4-(4-chlorophenoxy)benzyl group, a 4-(2,4-dichlorophenoxy)benzyl group, a 4-(3,4,5-trifluorophenoxy)benzyl group, a 4-(3-methylphenoxy)benzyl group, a 4-(2-methoxyphenoxy)benzyl group, a 4-(2,4-dimethylphenoxy)benzyl group, a 4-(3,4-dimethoxyphenoxy)benzyl group, a 4-(2,4,6-trimethylphenoxy)benzyl group, a 4-(3,4,5-trimethoxyphenoxy)benzyl group, a 2,4-diphenoxybenzyl group, a 2,4,6-triphenoxybenzyl group, and a 2-phenoxy-4-(1-piperidyl)benzyl group [wherein, on the phenyl ring, 1 to 3 groups selected from the group consisting of the above described piperidinyl group (wherein, on the piperidine ring, 1 to 3 phenoxy groups may be substituted [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted]) and the above described phenoxy group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted) is substituted].

Examples of the diphenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) may include C1-C6 alkyl groups wherein 2 phenyl groups is substituted [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted), such as a diphenylmethyl group, a 2,2-diphenylethyl group, a 1,1-diphenylethyl group, a 3,3-diphenylpropyl group, a 2,3-diphenylpropyl group, a 4,4-diphenylbutyl group, a 5,5-diphenylpentyl group, a 4,5-diphenylpentyl group, a 6,6-diphenylhexyl group, a 2-methyl-3,3-diphenylpropyl group, a 1,1-dimethyl-2,2-diphenylethyl group, a di(4-chlorophenyl)methyl group, a di(4-trifluoromethoxyphenyl)methyl group, a di(4-trifluoromethylphenyl)methyl group, a di(3-methoxyphenyl)methyl group, a di(2,4-dichlorophenyl)methyl group, a di(2-methylphenyl)methyl group, a di(2,4,6-trifluorophenyl) methyl group, a di(3,4-dimethoxyphenyl)methyl group, a di(2,4,6-trimethoxyphenyl)methyl group, a di(3,4-dimethylphenyl)methyl group, a di(2,4,6-trimethylphenyl)methyl group, and a 1-(4-trifluoromethoxyphenyl)-1-(4-chlorophenyl)methyl group.

Examples of the phenyl group [wherein, on the phenyl ring, at least one selected from the group consisting of a C1-C4 alkylenedioxy group, a phenyl group, a C1-C6 alkoxycarbonyl group, a hydroxyl group, and a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted), is substituted] may include phenyl groups such as a 4-biphenyl group, a 4-tert-butoxycarbonylphenyl group, a 4-ethoxycarbonylphenyl group, a 2-biphenyl group, a 4-hydroxyphenyl group, a 4-(4-chlorophenoxy)phenyl group, a 2,3-ethylenedioxyphenyl group, a 3-biphenyl group, a 3-tert-butoxycarbonylphenyl group, a 3-methoxycarbonylphenyl group, a 2,4-diphenylphenyl group, a 3-hydroxyphenyl group, a 4-(4-trifluoromethoxyphenoxy)phenyl group, a 2,3-methylenedioxyphenyl group, a 2,4,6-triphenyl group, a 2-tert-butoxycarbonylphenyl group, a 2-propoxycarbonylphenyl group, a 2-n-pentyloxyphenyl group, a 2-hydroxyphenyl group, a 4-(4-trifluoromethylphenoxy)phenyl group, a 3,4-ethylenedioxyphenyl group, a 2,4,6-trihydroxyphenyl group, a 4-n-hexyloxycarbonylphenyl group, a 2,4-diethoxycarbonylphenyl group, a 2-biphenyl group, a 3,4-dihydroxyphenyl group, a 4-(2,4-dichlorophenoxy)phenyl group, a 3-(2,4,6-trifluorophenoxy)phenyl group, a 2,4,6-triethoxycarbonylphenyl group, a 3-(2-methylphenoxy)phenyl group, a 4-(3-methylphenoxy)phenyl group, a 2-(4-methylphenoxy)phenyl group, a 3-(2,3-dimethylphenoxy)phenyl group, a 4-(2,4,5-trimethylphenoxy)phenyl group, a 3-(2-methoxyphenoxy) phenyl group, a 4-(3-methoxyphenoxy)phenyl group, a 2-(4-methoxyphenoxy)phenyl group, a 3-(3,4-dimethoxyphenoxy)phenyl group, a 4-(2,4,6-trimethoxyphenoxy)phenyl group, a 2-phenoxy-4-ethoxycarbonylphenyl group, and a 2-phenyl-3-phenoxyphenyl group [wherein, on the phenyl ring, 1 to 3 groups selected from the group consisting of the above described C1-C4 alkylenedioxy group, the above described phenyl group, the above described C1-C6 alkoxycarbonyl group, hydroxyl group, and the above described phenoxy group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted), is substituted].

Examples of the benzofuryl group [wherein, on the benzofuran ring, at least one selected from the group consisting of a halogen atom and a C1-C6 alkyl group may be substituted] may include benzofuryl groups such as a (2-, 3-, 4-, 5-, 6- or 7-)benzofuryl group, a 5-chloro-7-benzofuryl group, a 5-methyl-7-benzofuryl group, a 4-iodo-6-benzofuryl group, a 6-ethyl-7-benzofuryl group, a 6-bromo-5-benzofuryl group, a 7-n-propyl-4-benzofuryl group, a 7-fluoro-2-benzofuryl group, a 4-n-butyl-2-benzofuryl group, a 2,5-dichloro-7-benzofuryl group, a 5,6-dimethyl-7-benzofuryl group, a 3,5,6-trifluoro-2-benzofuryl group, a 3,4,5-trimethyl-3-benzofuryl group, a 5-chloro-4-methyl-7-benzofuryl group, and a 5-methyl-3-fluoro-8-benzofuryl group, provided that, on the benzofuran ring, 1 to 3 groups selected from the group consisting of the above described halogen atom and the above described C1-C6 alkyl group may be substituted.

Examples of the benzothiazolinyl group [wherein, on the benzothiazoline ring, at least one oxo group may be substituted] may include benzothiazolinyl groups such as a (2-, 4-, 5-, 6- or 7-)benzothiazolyl group and a 2-oxo-6-benzothiazolyl group, provided that, on the benzothiazoline ring, one oxo group may be substituted.

Examples of the benzothienyl group [wherein, on the benzothiophene ring, at least one halogen atom may be substituted] may include benzothienyl groups such as a (2-, 3-, 4-, 5-, 6- or 7-)benzothienyl group, a 5-fluoro-4-benzothienyl group, a 6-fluoro-2-benzothienyl group, a 2-chloro-3-benzothienyl group, a 3-bromo-6-benzothienyl group, a 4-iodo-5-benzothienyl group, a 2,4,6-trichloro-7-benzothienyl group, and a 4,5-difluoro-2-benzothienyl group, provided that, on the benzothiophene ring, 1 to 3 halogen atoms may be substituted.

Examples of the 1,2,3,4-tetrahydroquinolyl group (wherein, on the 1,2,3,4-tetrahydroquinoline ring, at least one selected from the group consisting of an oxo group and a C1-C6 alkyl group may be substituted) may include 1,2,3,4-tetrahydroquinolyl groups such as a (1-, 2-, 3-, 4-, 5-, 6-, 7- or 8-)1,2,3,4-tetrahydroquinolyl group, a 2-oxo-(1-, 3-, 4-, 5-, 6-, 7- or 8-)1,2,3,4-tetrahydroquinolyl group, a 2,4-dioxo-(1-, 3-, 5-, 6-, 7- or 8-)1,2,3,4-tetrahydroquinolyl group, a 3-oxo-(1-, 2-, 4-, 5-, 6-, 7- or 8-)1,2,3,4-tetrahydroquinolyl group, a 1-methyl-2-oxo-5-1,2,3,4-tetrahydroquinolyl group, a 2-methyl-1-1,2,3,4-tetrahydroquinolyl group, a 3-ethyl-2-1,2,3,4-tetrahydroquinolyl group, a 4-n-propyl-3-1,2,3,4-tetrahydroquinolyl group, a 5-n-butyl-4-1,2,3,4-tetrahydroquinolyl group, a 6-n-pentyl-5-1,2,3,4-tetrahydroquinolyl group, a 7-n-hexyl-6-1,2,3,4-tetrahydroquinolyl group, a 8-methyl-7-1,2,3,4-tetrahydroquinolyl group, a 4,6-dimethyl-5-1,2,3,4-tetrahydroquinolyl group, and a 5,6,7-trimethyl-4-1,2,3,4-tetrahydroquinolyl group, provided that, on the 1,2,3,4-tetrahydroquinoline ring, 1 to 3 groups selected from the group consisting of an oxo group and the above described C1-C6 alkyl group may be substituted.

Examples of the 1,2-dihydrohydroquinolyl group (wherein, on the 1,2-dihydrohydroquinoline ring, at least one oxo group may be substituted) may include 1,2-dihydrohydroquinolyl groups such as a (1-, 2-, 3-, 4-, 5-, 6-, 7- or 8-)1,2-dihydrohydroquinolyl group and a 2-oxo-(1-, 3-, 4-, 5-, 6-, 7- or 8-)1,2-dihydrohydroquinolyl group, provided that, on the 1,2-dihydrohydroquinoline ring, one oxo group may be substituted.

Examples of the 1,2,3,4-tetrahydro-quinazolinyl group [wherein, on the 1,2,3,4-tetrahydroquinazoline ring, at least one selected from the group consisting of an oxo group and a C1-C6 alkyl group may be substituted] may include 1,2,3,4-tetrahydroquinazolinyl groups such as a (1-, 2-, 3-, 4-, 5-, 6-, 7- or 8-)1,2,3,4-tetrahydroquinazolinyl group, a 2-oxo-(1-, 3-, 4-, 5-, 6-, 7- or 8-)1,2,3,4-tetrahydroquinazolinyl group, a 4-oxo-(1-, 2-, 3-, 5-, 6-, 7- or 8-)1,2,3,4-tetrahydroquinazolinyl group, a 2,4-dioxo-(1-, 3-, 5-, 6-, 7- or 8-)1,2,3,4-tetrahydroquinazolinyl group, a 1-methyl-2,4-dioxo-(3-, 5-, 6-, 7- or 8-)1,2,3,4-tetrahydroquinazolinyl group, a 3-ethyl-2,4-dioxo-(1-, 5-, 6-, 7- or 8-)1,2,3,4-tetrahydroquinazolinyl group, a 1,3-dimethyl-2,4-dioxo-(5-, 6-, 7- or 8-)1,2,3,4-tetrahydroquinazolinyl group, a 1-n-propyl-5-methyl-2-oxo-(3-, 4-, 6-, 7- or 8-)1,2,3,4-tetrahydroquinazolinyl group, a 1-n-butyl-6-methyl-4-oxo-(2-, 3-, 5-, 7- or 8-)1,2,3,4-tetrahydroquinazolinyl group, a 1-n-pentyl-7-methyl-2-oxo-(3-, 4-, 5-, 6- or 8-)1,2,3,4-tetrahydroquinazolinyl group, and a 1-n-hexyl-8-methyl-2,4-dioxo-(3-, 5-, 6- or 7-)1,2,3,4-tetrahydroquinazolinyl group, provided that, on the 1,2,3,4-tetrahydroquinazoline ring, 1 to 4 groups selected from the group consisting of an oxo group and the above described C1-C6 alkyl group may be substituted.

Examples of the benzothienyl substituted C1-C6 alkyl group [wherein, on the benzothiophene ring, at least one halogen atom may be substituted] may include benzothienyl substituted C1-C6 alkyl groups such as a 2-benzothienylmethyl group, a 3-benzothienylmethyl group, a 4-benzothienylmethyl group, a 5-benzothienylmethyl group, a 6-benzothienylmethyl group, a 7-benzothienylmethyl group, a 2-(2-benzothienyl)ethyl group, a 3-(2-benzothienyl)propyl group, a 4-(2-benzothienyl)butyl group, a 5-(2-benzothienyl)pentyl group, a 6-(2-benzothienyl)hexyl group, a 5-chloro-3-benzothienylmethyl group, a 3,4-dibromo-2-benzothienylmethyl group, and a 4,5,6-trichloro-2-benzothienylmethyl group, provided that, on the benzothiophene ring, 1 to 3 halogen atoms may be substituted].

Examples of the naphthyl substituted C1-C6 alkyl group may include a 1-naphthylmethyl group, a 2-naphthylmethyl group, a 2-(1-naphthyl)ethyl group, a 1-(2-naphthyl)ethyl group, a 3-(1-naphthyl)propyl group, a 3-(2-naphthyl)propyl group, a 4-(1-naphthyl)butyl group, a 4-(2-naphthyl)butyl group, a 5-(1-naphthyl)pentyl group, a 5-(2-naphthyl)pentyl group, a 6-(1-naphthyl)hexyl group, and a 6-(2-naphthyl)hexyl group.

Examples of the pyridyl substituted C1-C6 alkyl group [wherein, on the pyridine ring, at least one halogen atom may be substituted] may include pyridyl substituted C1-C6 alkyl groups such as a 2-pyridylmethyl group, a 3-pyridylmethyl group, a 4-pyridylmethyl group, a 2-(2-pyridyl)ethyl group, a 2-(3-pyridyl)ethyl group, a 2-(4-pyridyl)ethyl group, a 3-(2-pyridyl)propyl group, a 3-(3-pyridyl)propyl group, a 3-(4-pyridyl)propyl group, a 4-(2-pyridyl)butyl group, a 4-(3-pyridyl)butyl group, a 4-(4-pyridyl)butyl group, a 5-(2-pyridyl)pentyl group, a 5-(3-pyridyl)pentyl group, a 5-(4-pyridyl)pentyl group, a 6-(2-pyridyl)hexyl group, a 6-(3-pyridyl)hexyl group, a 6-(4-pyridyl)hexyl group, a 2-chloro-3-pyridylmethyl group, a 3-bromo-2-pyridylmethyl group, a 4-fluoro-2-pyridylmethyl group, a 2-(2-chloro-4-pyridyl)ethyl group, a 2-(3-chloro-5-pyridyl)ethyl group, a 2-(4-iodo-3-pyridyl)ethyl group, a 3-(2-bromo-5-pyridyl)propyl group, a 3-(3-fluoro-4-pyridyl)propyl group, a 3-(4-chloro-2-pyridyl)propyl group, a 4-(2-iodo-5-pyridyl)butyl group, a 4-(3-bromo-5-pyridyl)butyl group, a 4-(4-chloro-3-pyridyl)butyl group, a 5-(2-chloro-5-pyridyl)pentyl group, a 5-(3-fluoro-2-pyridyl)pentyl group, a 5-(4-bromo-2-pyridyl)pentyl group, a 6-(2-chloro-5-pyridyl)hexyl group, a 6-(3-fluoro-4-pyridyl)hexyl group, a 6-(4-bromo-2-pyridyl)hexyl group, a (2,6-dichloro-4-pyridyl)methyl group, and a (2,3,4-trichloro-6-pyridyl)methyl group, provided that, on the pyridine ring, 1 to 3 halogen atoms may be substituted as substituents.

Examples of the furyl substituted C1-C6 alkyl group [wherein, on the furan ring, at least one nitro group may be substituted] may include furyl substituted C1-C6 alkyl groups such as a 2-furylmethyl group, a 3-furylmethyl group, a 2-(2-furyl)ethyl group, a 3-(2-furyl)propyl group, a 3-(3-furyl)propyl group, a 4-(2-furyl)butyl group, a 4-(3-furyl)butyl group, a 5-(2-furyl)pentyl group, a 5-(3-furyl)pentyl group, a 6-(2-furyl)hexyl group, a 6-(3-furyl)hexyl group, a 5-nitro-2-furylmethyl group, a 5-nitro-3-furylmethyl group, a 2-(5-nitro-2-furyl)ethyl group, a 3-(5-nitro-2-furyl)propyl group, a 4-(5-nitro-2-furyl)butyl group, a 4-(5-nitro-3-furyl)butyl group, a 5-(5-nitro-2-furyl)pentyl group, a 5-(5-nitro-3-furyl)pentyl group, a 6-(5-nitro-2-furyl)hexyl group, a 6-(5-nitro-3-furyl)hexyl group, a (4,5-dinitro-2-furyl)methyl group, and a (2,4,5-trinitro-3-furyl)methyl group, provided that, on the furan ring, 1 to 3 nitro groups may be substituted as substituents.

Examples of the thienyl substituted C1-C6 alkyl group [wherein, on the thiophene ring, at least one halogen atom may be substituted) may include thienyl substituted C1-C6 alkyl groups such as a 2-thienylmethyl group, a 3-thienylmethyl group, a 2-(2-thienyl)ethyl group, a 3-(2-thienyl)propyl group; a 3-(3-thienyl)propyl group, a 4-(2-thienyl)butyl group, a 4-(3-thienyl)butyl group, a 5-(2-thienyl)pentyl group, a 5-(3-thienyl)pentyl group, a 6-(2-thienyl)hexyl group, a 6-(3-thienyl)hexyl group, a 5-chloro-2-thienylmethyl group, a 5-chloro-3-thienylmethyl group, a 2-(4-bromo-2-thienyl)ethyl group, a 3-(3-fluoro-2-thienyl)propyl group, a 4-(5-iodo-2-thienyl)butyl group, a 4-(4-chloro-3-thienyl)butyl group, a 5-(3-chloro-2-thienyl)pentyl group, a 5-(2-chloro-3-thienyl)pentyl group, a 6-(3-chloro-2-thienyl)hexyl group, a 6-(5-chloro-3-thienyl)hexyl group, a (4,5-dichloro-2-thienyl)methyl group, and a (2,4,5-trichloro-3-thienyl)methyl group, provided that, on the thiophene ring, 1 to 3 halogen atoms may be substituted as substituents.

Examples of the phenyl group (wherein, on the phenyl ring, at least one selected from the group consisting of a halogen atom and a halogen substituted or unsubstituted C1-C6 alkyl group may be substituted) may include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,3-difluorophenyl group, a 3,4-difluorophenyl group, a 3,5-difluorophenyl group, a 2,4-difluorophenyl group, a 2,6-difluorophenyl group, a 2,3-dichlorophenyl group, a 3,4-dichlorophenyl group, a 3,5-dichlorophenyl group, a 2,4-dichlorophenyl group, a 2,6-dichlorophenyl group, a 3,4,5-trifluorophenyl group, a 3,4,5-trichlorophenyl group, a 2,4,6-trifluorophenyl group, a 2,4,6-trichlorophenyl group, a 2-fluoro-4-bromophenyl group, a 4-chloro-3-fluorophenyl group, a 2,3,4-trichlorophenyl group, a 3,4,5-trifluorophenyl group, a 2,3,4,5,6-pentafluorophenyl group, a 2,4,6-trimethylphenyl group, a 4-n-butylphenyl group, a 2,4-dimethylphenyl group, a 2,3-dimethylphenyl group, a 2,6-dimethylphenyl group, a 3,5-dimethylphenyl group, a 2,5-dimethylphenyl group, a 3,5-ditrifluoromethylphenyl group, a 3-methyl-4-fluorophenyl group, a 4-bromo-3-trifluoromethylphenyl group, a 2-methylphenyl group, a 3-methylphenyl group, a 4-methylphenyl group, a 2-methyl-3-chlorophenyl group, a 3-methyl-4-chlorophenyl group, a 2-chloro-4-methylphenyl group, a 2-methyl-3-fluorophenyl group, a 2-trifluoromethylphenyl group, a 3-trifluoromethylphenyl group, a 4-trifluoromethylphenyl group, a 2-pentafluoroethylphenyl group, a 3-pentafluoroethylphenyl group, a 4-pentafluoroethylphenyl group, a 2-isopropylphenyl group, a 3-isopropylphenyl group, a 4-isopropylphenyl group, a 2-tert-butylphenyl group, a 3-tert-butylphenyl group, a 4-tert-butylphenyl group, a 2-sec-butylphenyl group, a 3-sec-butylphenyl group, a 4-sec-butylphenyl group, a 2-n-heptafluoropropylphenyl group, a 3-n-heptafluoropropylphenyl group, a 4-n-heptafluoropropylphenyl group, a 4-n-pentylphenyl group, a 4-n-hexylphenyl group, a 2,3,4-trifluorophenyl group, and a 2,4,6-trifluorophenyl group.

Examples of the thiazolyl substituted C1-C6 alkyl group (wherein, on the thiazole ring, at least one selected from the group consisting of a C1-C6 alkyl group and a phenyl group (wherein, on the phenyl ring, at least one selected from the group consisting of a halogen atom and a halogen substituted or unsubstituted C1-C6 alkyl group may be substituted) may be substituted] may include thiazolyl substituted C1-C6 alkyl groups such as a 4-thiazolylmethyl group, a 5-thiazolylmethyl group, a 2-methyl-4-thiazolylmethyl group, a 2-methyl-5-thiazolylmethyl group, a 2,5-dimethyl-4-thiazolylmethyl group, a 2,4-dimethyl-5-thiazolylmethyl group, a 2-methyl-5-phenyl-4-thiazolylmethyl group, a 2-methyl-4-phenyl-5-thiazolylmethyl group, a 2-phenyl-4-thiazolylmethyl group, a 2-phenyl-5-thiazolylmethyl group, a 2-phenyl-5-methyl-4-thiazolylmethyl group, a 2-phenyl-4-methyl-5-thiazolylmethyl group, a 2-methyl-5-(2-fluorophenyl)-4-thiazolylmethyl group, a 2-methyl-4-(2-fluorophenyl)-5-thiazolylmethyl group, a 2-(2-chlorophenyl)-4-thiazolylmethyl group, a 2-(2-bromophenyl)-5-thiazolylmethyl group, a 2-(2-fluorophenyl)-5-methyl-4-thiazolylmethyl group, a 2-(2-fluorophenyl)-4-methyl-5-thiazolylmethyl group, a 2-methyl-5-(3-iodophenyl)-4-thiazolylmethyl group, a 2-methyl-4-(3-fluorophenyl)-5-thiazolylmethyl group, a 2-(2,3-difluorophenyl)-4-thiazolylmethyl group, a 2-(3-fluorophenyl)-5-thiazolylmethyl group, a 2-(3-fluorophenyl)-5-methyl-4-thiazolylmethyl group, a 2-(3-fluorophenyl)-4-methyl-5-thiazolylmethyl group, a 2-methyl-5-(2,4,6-trichlorophenyl)-4-thiazolylmethyl group, a 2-methyl-4-(2,3,4,5,6-pentafluorophenyl)-5-thiazolylmethyl group, a 2-(4-fluorophenyl)-4-thiazolylmethyl group, a 4-(2-fluorophenyl)-5-thiazolylmethyl group, a 2-(4-fluorophenyl)-5-methyl-4-thiazolylmethyl group, a 2-(4-fluorophenyl)-4-methyl-5-thiazolylmethyl group, a 2-methyl-5-(2-chlorophenyl)-4-thiazolylmethyl group, a 2-methyl-4-(2-chlorophenyl)-5-thiazolylmethyl group, a 2-(2-chlorophenyl)-4-thiazolylmethyl group, a 2-(2-chlorophenyl)-5-thiazolylmethyl group, a 2-(2-chlorophenyl)-5-methyl-4-thiazolylmethyl group, a 2-(2-chlorophenyl)-4-methyl-5-thiazolylmethyl group, a 2-methyl-5-(3-chlorophenyl)-4-thiazolylmethyl group, a 2-methyl-4-(3-chlorophenyl)-5-thiazolylmethyl group, a 2-(3-chlorophenyl)-4-thiazolylmethyl group, a 2-(2-fluorophenyl)-5-thiazolylmethyl group, a 2-(3-chlorophenyl)-5-methyl-4-thiazolylmethyl group, a 2-(3-chlorophenyl)-4-methyl-5-thiazolylmethyl group, a 2-methyl-5-(4-chlorophenyl)-4-thiazolylmethyl group, a 2-methyl-4-(4-chlorophenyl)-5-thiazolylmethyl group, a 2-(4-chlorophenyl)-4-thiazolylmethyl group, a 2-(4-chlorophenyl)-5-thiazolylmethyl group, a 2-(4-chlorophenyl)-5-methyl-4-thiazolylmethyl group, a 2-(4-chlorophenyl)-4-methyl-5-thiazolylmethyl group, a 2-(2-thiazolyl)ethyl group, a 2-(4-thiazolyl)ethyl group, a 2-(5-thiazolyl)ethyl group, a 2-(2-methyl-4-thiazolyl)ethyl group, a 2-(2-methyl-5-thiazolyl)ethyl group, a 2-(2,5-dimethyl-4-thiazolyl)ethyl group, a 2-(2,4-dimethyl-5-thiazolyl)ethyl group, a 2-(2-methyl-5-phenyl-4-thiazolyl)ethyl group, a 2-(2-methyl-4-phenyl-5-thiazolyl)ethyl group, a 2-(2-phenyl-4-thiazolyl)ethyl group, a 2-(2-phenyl-5-thiazolyl)ethyl group, a 2-(2-phenyl-5-methyl-4-thiazolyl)ethyl group, a 3-(2-thiazolyl)propyl group, a 2-(4-thiazolyl)propyl group, a 3-(5-thiazolyl)propyl group, a 3-(2-methyl-4-thiazolyl)propyl group, a 2-(2-methyl-5-thiazolyl)propyl group, a 3-(2,5-dimethyl-4-thiazolyl)propyl group, a 3-(2,4-dimethyl-5-thiazolyl)propyl group, a 3-(2-methyl-5-phenyl-4-thiazolyl)propyl group, a 3-(2-methyl-4-phenyl-5-thiazolyl)propyl group, a 2-(2-phenyl-4-thiazolyl)propyl group, a 3-(3-phenyl-5-thiazolyl)propyl group, a 3-(2-phenyl-5-methyl-4-thiazolyl)propyl group, a 4-(2-thiazolyl)butyl group, a 4-(4-thiazolyl)butyl group, a 3-(5-thiazolyl)butyl group, a 4-(2-methyl-4-thiazolyl)butyl group, a 4-(2-methyl-5-thiazolyl)butyl group, a 4-(2,5-dimethyl-4-thiazolyl)butyl group, a 4-(2,4-dimethyl-5-thiazolyl)butyl group, a 4-(2-methyl-5-phenyl-4-thiazolyl)butyl group, a 4-(2-methyl-4-phenyl-5-thiazolyl)butyl group, a 4-(2-phenyl-4-thiazolyl)butyl group, a 4-(4-phenyl-5-thiazolyl)butyl group, a 4-(2-phenyl-5-methyl-4-thiazolyl)butyl group, a 5-(2-thiazolyl)pentyl group, a 5-(4-thiazolyl)pentyl group, a 5-(5-thiazolyl)pentyl group, a 5-(2-methyl-4-thiazolyl)pentyl group, a 5-(2-methyl-5-thiazolyl)pentyl group, a 5-(2,5-dimethyl-4-thiazolyl)pentyl group, a 5-(2,4-dimethyl-5-thiazolyl)pentyl group, a 5-(2-methyl-5-phenyl-4-thiazolyl)pentyl group, a 5-(2-methyl-4-phenyl-5-thiazolyl)pentyl group, a 5-(2-phenyl-4-thiazolyl)pentyl group, a 5-(4-phenyl-5-thiazolyl)pentyl group, a 5-(2-phenyl-5-methyl-4-thiazolyl)pentyl group, a 6-(2-thiazolyl)hexyl group, a 6-(4-thiazolyl)hexyl group, a 6-(5-thiazolyl)hexyl group, a 6-(2-methyl-4-thiazolyl)hexyl group, a 6-(2-methyl-5-thiazolyl)hexyl group, a 6-(2,5-dimethyl-4-thiazolyl)hexyl group, a 6-(2,4-dimethyl-5-thiazolyl)hexyl group, a 6-(2-methyl-5-phenyl-4-thiazolyl)hexyl group, a 6-(2-methyl-4-phenyl-5-thiazolyl)hexyl group, a 6-(2-phenyl-4-thiazolyl)hexyl group, a 6-(4-phenyl-5-thiazolyl)hexyl group, a 6-(2-phenyl-5-methyl-4-thiazolyl)hexyl group, a 2-(2,3-dimethylphenyl)-4-thiazolylmethyl group, a 2-(3-methylphenyl)-5-thiazolylmethyl group, a 2-(3-trifluoromethylphenyl)-5-methyl-4-thiazolylmethyl group, a 2-(3-ethylphenyl)-4-methyl-5-thiazolylmethyl group, a 2-(2-trifluoroethylphenyl)-4-methyl-5-thiazolylmethyl group, and a 2-methyl-5-(2,4,6-trimethylphenyl)-4-thiazolylmethyl group, provided that, on the thiazole ring, 1 or 2 groups selected from the group consisting of a C1-C6 alkyl group and a phenyl group (wherein, on the phenyl ring, 1 to 5 groups, and preferably 1 to 3 groups selected from the group consisting of a halogen atom and a halogen substituted or unsubstituted C1-C6 alkyl group may be substituted) may be substituted;

Examples of the tetrazolyl substituted C1-C6 alkyl group [wherein, on the tetrazole ring, at least one C1-C6 alkyl group may be substituted] may include tetrazolyl substituted C1-C6 alkyl groups such as a 5-(1H)-tetrazolylmethyl group, a 2-(5-(1H)-tetrazolyl)ethyl group, a 1-(5-(1H)-tetrazolyl)ethyl group, a 3-(5-(1H)-tetrazolyl)propyl group, a 4-(5-(1H)-tetrazolyl)butyl group, a 5-(5-(1H)-tetrazolyl)pentyl group, a 6-(5-(1H)-tetrazolyl)hexyl group, a 2-methyl-3-(5-(1H)-tetrazolyl)propyl group, a 1,1-dimethyl-2-(5-(1H)-tetrazolyl)ethyl group, a 1-methyl-5-(1H)-tetrazolylmethyl group, a 1-ethyl-5-(1H)-tetrazolylmethyl group, a 1-n-propyl-5-(1H)- tetrazolylmethyl group, a 1-n-butyl-5-(1H)-tetrazolylmethyl group, a 1-n-pentyl-5-(1H)-tetrazolylmethyl group, a 1-n-hexyl-5-(1H)-tetrazolylmethyl group, a 2-(1-methyl-5-(1H)-tetrazolyl)ethyl group, a 2-(1-ethyl-5-(1H)-tetrazolyl)ethyl group, a 2-(1-n-propyl-5-(1H)-tetrazolyl)ethyl group, a 2-(1-n-butyl-5-(1H)-tetrazolyl)ethyl group, a 2-(1-n-pentyl-5-(1H)-tetrazolyl)ethyl group, and a 2-(1-n-hexyl-5-(1H)-tetrazolyl)ethyl group; provided that, on the tetrazole ring, one C1-C6 alkyl group may be substituted.

Examples of the isoxazolyl substituted C1-C6 alkyl group [wherein, on the isoxazole ring, at least one C1-C6 alkyl group may be substituted] may include isoxazolyl substituted C1-C6 alkyl groups such as a (3-, 4- or 5-isoxazolyl)methyl group, a 2-(3-, 4- or 5-isoxazolyl)ethyl group, a 1-(3-, 4- or 5-isoxazolyl)ethyl group, a 3-(3-, 4- or 5-isoxazolyl)propyl group, a 4-(3-, 4- or 5-isoxazolyl)butyl group, a 5-(3-, 4- or 5-isoxazolyl)pentyl group, a 6-(3-, 4- or 5-isoxazolyl)hexyl group, a 3-methyl-2-(3-, 4- or 5-isoxazolyl)propyl group, a 1,1-dimethyl-2-(3-, 4- or 5-isoxazolyl)ethyl group, a (3-methyl-4-isoxazolyl)methyl group, a (4-ethyl-3-isoxazolyl)methyl group, a (5-n-propyl-3-isoxazolyl)methyl group, a (4-n-butyl-5-isoxazolyl)methyl group, a (5-n-pentyl-3-isoxazolyl) methyl group, a (3-n-hexyl-4-isoxazolyl)methyl group, a (3,4-dimethyl-5-isoxazolyl)methyl group, a 2-(3-methyl-4-isoxazolyl)ethyl group, a 1-(4-ethyl-3-isoxazolyl)ethyl group, a 3-(5-n-propyl-3-isoxazolyl)propyl group, a 4-(4-n-butyl-5-isoxazolyl)butyl group, a 5-(5-n-pentyl-3-isoxazolyl)pentyl group, a 6-(3-n-hexyl-4-isoxazolyl)hexyl group, and a 2-(3,4-dimethyl-5-isoxazolyl)ethyl group, provided that, on the isoxazole ring, 1 or 2 C1-C6 alkyl groups may be substituted.

Examples of the 1,2,4-oxadiazolyl substituted C1-C6 alkyl group [wherein, on the 1,2,4-oxadiazole ring, at least one phenyl group may be substituted (wherein, on the phenyl ring, a C1-C6 alkyl group may be substituted)) may include 1,2,4-oxadiazolyl substituted C1-C6 alkyl groups such as a (3- or 5-)1,2,4-oxadiazolylmethyl group, a 2-((3- or 5-)1,2,4-oxadiazolyl)ethyl group, a 1-((3- or 5-)1,2,4-oxadiazolyl)ethyl group, a 3-((3- or 5-)1,2,4-oxadiazolyl)propyl group, a 4-((3- or 5-)1,2,4-oxadiazolyl)butyl group, a 5-((3- or 5-)1,2,4-oxadiazolyl)pentyl group, a 6-((3- or 5-)1,2,4-oxadiazolyl)hexyl group, a 3-methyl-2-((3- or 5-)1,2,4-oxadiazolyl)propyl group, a 1,1-dimethyl-2-((3- or 5-)1,2,4-oxadiazolyl)ethyl group, a (3-phenyl-5-1,2,4-oxadiazolyl)methyl group, a (5-phenyl-3-1,2,4-oxadiazolyl)methyl group, a (3-(3-methylphenyl)-5-1,2,4-oxadiazolyl)methyl group, a (5-(3,4-dimethylphenyl)-3-1,2,4-oxadiazolyl)methyl group, a (3-(2,4,6-trimethylphenyl)-5-1,2,4-oxadiazolyl)methyl group, a (5-(2-ethylphenyl)-3-1,2,4-oxadiazolyl)methyl group, a 2-((3-n-propylphenyl)-5-1,2,4-oxadiazolyl)ethyl group, a 1-(5-(4-n-butylphenyl)-3-1,2,4-oxadiazolyl)ethyl group, a 3-(3-(3-n-pentylphenyl)-5-1,2,4-oxadiazolyl)propyl group, a 4-(5-(5-n-hexylphenyl)-3-1,2,4-oxadiazolyl)butyl group, a 5-(3-(3-ethyl-4-methylphenyl)-5-1,2,4-oxadiazolyl)pentyl group, and a 6-(5-(2-methylphenyl)-3-1,2,4-oxadiazolyl)hexyl group, provided that, on the 1,2,4-oxadiazole ring, one phenyl group may be substituted, provided that (wherein, on the phenyl ring, 1 to 3 C1-C6 alkyl groups may be substituted).

Examples of the benzofurazanyl substituted C1-C6 alkyl group may include 4-benzofurazanylmethyl, 5-benzofurazanylmethyl, 6-benzofurazanylmethyl, 7-benzofurazanylmethyl, 1-(4-benzofurazanyl)ethyl, 2-(5-benzofurazanyl)ethyl, 3-(6-benzofurazanyl)propyl, 4-(7-benzofurazanyl)butyl, 5-(4-benzofurazanyl)pentyl, 6-(5-benzofurazanyl)hexyl, 2-methyl-3-(6-benzofurazanyl)propyl, and 1,1-dimethyl-2-(7-benzofurazanyl)ethyl.

The phenylamino group [wherein a C1-C6 alkyl group may be substituted on position N of the phenylamino group, and wherein, on the phenyl ring of the phenylamino group, at least one halogen substituted or unsubstituted C1-C6 alkoxy group may be substituted] may be an unsubstituted phenylamino group (alias: anilino group), or a phenylamino group wherein the above defined 1 to 3 halogen substituted or unsubstituted C1-C6 alkoxy groups are substituted. Examples of the phenylamino group may include a phenylamino group, a 2-methoxyphenylamino group, a 3-methoxyphenylamino group, a 4-methoxyphenylamino group, a 2-ethoxyphenylamino group, a 3-ethoxyphenylamino group, a 4-ethoxyphenylamino group, a 4-n-propoxyphenylamino group, a 4-tert-butoxyphenylamino group, a 4-n-butoxyphenylamino group, a 2-trifluoromethoxyphenylamino group, a 3-trifluoromethoxyphenylamino group, a 4-trifluoromethoxyphenylamino group, a 2-pentafluoroethoxyphenylamino group, a 3-pentafluoroethoxyphenylamino group, a 2,3-dimethoxyphenylamino group, a 3,4,5-trimethoxyphenylamino group, a 4-n-pentyloxyphenylamino group, a 4-n-hexyloxyphenylamino group, a 3,5-ditrifluoromethoxyphenylamino group, an N-phenyl-N-methylamino group, an N-(2-methoxyphenyl)-N-ethylamino group, an N-(3-methoxyphenyl)-N-n-propylamino group, an N-(4-methoxyphenyl)-N-n-butylamino group, an N-(2-ethoxyphenyl)-N-n-pentylamino group, an N-(3-ethoxyphenyl)-N-n-hexylamino group, an N-(4-ethoxyphenyl)-N-methylamino group, an N-(4-n-propoxyphenyl)-N-ethylamino group, an N-(4-tert-butoxyphenyl)-N-n-propylamino group, an N-(4-n-butoxyphenyl)-N-n-butylamino group, an N-(2-trifluoromethoxyphenyl)-N-n-pentylamino group, an N-(3-trifluoromethoxyphenyl)-N-n-hexylamino group, an N-(4-trifluoromethoxyphenyl)-N-methylamino group, an N-(2-pentafluoroethoxyphenyl)-N-ethylamino group, an N-(3-pentafluoroethoxyphenyl)-N-n-propylamino group, an N-(2,3-dimethoxyphenyl)-N-methylamino group, an N-(3,4,5-trimethoxyphenyl)-N-methylamino group, an N-(4-n-pentyloxyphenyl)-N-methylamino group, an N-(4-n-hexyloxyphenyl)-N-methylamino group, and an N-(3,5-ditrifluoromethoxyphenyl)-N-methylamino group.

Examples of the phenoxy group (wherein, on the phenyl ring, a halogen substituted or unsubstituted C1-C6 alkoxy group may be substituted) may include phenoxy groups such as a phenoxy group, a 2-methoxyphenoxy group, a 3-methoxyphenoxy group, a 4-methoxyphenoxy group, a 4-isopropoxyphenoxy group, a 4-n-butoxyphenoxy group, a 2,4-dimethoxyphenoxy group, a 2,3-dimethoxyphenoxy group, a 2,3,4,5,6-pentamethoxyphenoxy group, a 3,5-dimethoxyphenoxy group, a 2,5-dimethoxyphenoxy group, a 2,4,6-trimethoxyphenoxy group, a 3,5-di(trifluoromethoxy)phenoxy group, a 4-methoxy-3-trifluoromethoxyphenoxy group, a 2,6-dimethoxyphenoxy group, a 2-trifluoromethoxyphenoxy group, a 3-trifluoromethoxyphenoxy group, a 4-trifluoromethoxyphenoxy group, a 2,3-di(trifluoromethoxy)phenoxy group, a 2,4-di(trifluoromethoxy)phenoxy group, a 2-pentafluoroethoxyphenoxy group, a 3-pentafluoroethoxyphenoxy group, a 4-pentafluoroethoxyphenoxy group, a 2-isopropoxyphenoxy group, a 3-isopropoxyphenoxy group, a 4-isopropoxyphenoxy group, a 2-tert-butoxyphenoxy group, a 3-tert-butoxyphenoxy group, a 4-tert-butoxyphenoxy group, a 2-sec-butoxyphenoxy group, a 3-sec-butoxyphenoxy group, a 4-sec-butoxyphenoxy group, a 4-n-hexyloxyphenoxy group, a 2-n-heptafluoropropoxyphenoxy group, a 3-n-heptafluoropropoxyphenoxy group, and a 4-n-heptafluoropropoxyphenoxy group, provided that, on the phenyl ring, 1 to 5 groups, and preferably 1 to 3 groups selected from the group consisting of halogen substituted or unsubstituted C1-C6 alkoxy groups may be substituted.

Examples of the amino group (wherein, on the amino group, at least one selected from the group consisting of a C1-C6 alkyl group and a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) may be substituted as a substituent) may include amino groups such as an amino group, a methylamino group, a dimethylamino group, an ethylamino group, a diethylamino group, an n-propylamino group, an n-butylamino group, an n-pentylamino group, a 3-n-hexylamino group, a phenylamino group, a (4-chlorophenyl)amino group, a (4-bromophenyl)amino group, a (2,4-dichlorophenyl)amino group, a (2,4,6-trichlorophenyl) amino group, a (2,3,4,5,6-pentafluorophenyl)amino group, a (4-fluorophenyl)amino group, a (4-iodophenyl)amino group, a (4-chlorophenyl)amino group, a (3-methylphenyl)amino group, a (4-trifluoromethylphenyl)amino group, a (4-trifluoromethylphenyl)amino group, a 3-(4-trifluoromethylphenyl) amino group, a (3,4-dimethylphenyl)amino group, a (3,4,5-trimethylphenyl)amino group, a (2-methoxyphenyl)amino group, a (4-trifluoromethoxyphenyl)amino group, a 3-(4-trifluoromethoxyphenyl)amino group, a (3,5-dimethoxyphenyl)amino group, a (2,5-dimethoxyphenyl)amino group, a (2,4,6-trimethoxyphenyl)amino group, an N-methyl-N-(4-trifluoromethylphenyl)amino group, and an N-ethyl-N-(4-trifluoromethoxyphenyl)amino group, provided that, on the amino group, 1 or 2 groups selected from the group consisting of a C1-C6 alkyl group and a phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted] may be substituted as substituents.

Examples of the piperidyl group [wherein, on the piperidine ring, at least one selected from the group consisting of a phenoxy group (wherein, on the phenyl ring, a halogen substituted or unsubstituted C1-C6 alkoxy group may be substituted as a substituent) and an amino group (wherein, on the amino group, at least one selected from the group consisting of a C1-C6 alkyl group and a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted] may be substituted as a substituent) may be substituted], may include piperidyl groups such as a 2-piperidyl group, a 3-piperidyl group, a 4-piperidyl group, a 2,4-diamino-1-piperidyl group, a 2,4,6-triamino-1-piperidyl group, a 4-amino-3-phenoxy-1-piperidyl group, a 4-phenoxy-2-amino-1-piperidyl group, a 2-amino-1-piperidyl group, a 3-amino-1-piperidyl group, a 4-amino-1-piperidyl group, a 4-methylamino-1-piperidyl group, a 4-ethylamino-1-piperidyl group, a 4-n-propylamino-1-piperidyl group, a 4-dimethylamino-1-piperidyl group, a 4-diethylamino-1-piperidyl group, a 4-di-n-propylamino-1-piperidyl group, a 4-phenylamino-1-piperidyl group, a 4-(N-phenyl-N-methylamino)-1-piperidyl group, a 4-(2-fluorophenylamino)-1-piperidyl group, a 4-(3-fluorophenylamino)-1-piperidyl group, a 4-(4-fluorophenylamino)-1-piperidyl group, a 4-(2-chlorophenylamino)-1-piperidyl group, a 4-(2,3-chlorophenylamino)-1-piperidyl group, a 4-(4-chlorophenylamino)-1-piperidyl group, a 4-(2,3-dichlorophenylamino)-1-piperidyl group, a 4-(2,4,6-trifluorophenylamino)-1-piperidyl group, a 4-(2,4-dichlorophenylamino)-1-piperidyl group, a 4-(3,4-dichlorophenylamino)-1-piperidyl group, a 4-(3,5-dichlorophenylamino)-1-piperidyl group, a 4-(2,3,4,5,6-pentafluorophenylamino)-1-piperidyl group, a 4-(2-trifluoromethylphenylamino)-1-piperidyl group, a 4-(2-methylphenylamino)-1-piperidyl group, a 4-(2,3-dimethylphenylamino)-1-piperidyl group, a 4-(2-trifluoromethylphenylamino)-1-piperidyl group, a 4-(2,4,6-trimethylphenylamino)-1-piperidyl group, a 4-(4-trifluoromethylphenylamino)-1-piperidyl group, a 4-(2-pentafluoroethylphenylamino)-1-piperidyl group, a 4-(3-pentafluoroethylphenylamino)-1-piperidyl group, a 4-(4-pentafluoroethylphenylamino)-1-piperidyl group, a 4-(2-trifluoromethoxyphenylamino)-1-piperidyl group, a 4-(2-methoxyphenylamino)-1-piperidyl group, a 4-(2,3-dimethoxyphenylamino)-1-piperidyl group, a 4-(2,4,6-trimethoxyphenylamino)-1-piperidyl group, a 4-(N-methyl-N-(2,4,6-trimethoxyphenylamino))-1-piperidyl group, a 4-(N-methyl-N-(3,4-dimethylphenylamino))-1-piperidyl group, a 4-(3-trifluoromethoxyphenylamino)-1-piperidyl group, a 4-(4-trifluoromethoxyphenylamino)-1-piperidyl group, a 4-(2-pentafluoroethoxyphenylamino)-1-piperidyl group, a 4-(3-pentafluoroethoxyphenylamino)-1-piperidyl group, a 4-(4-pentafluoroethoxyphenylamino)-1-piperidyl group, a 4-(2-fluorophenylamino)-1-piperidyl group, a 4-(3-fluorophenylamino)-1-piperidyl group, a 4-(4-fluorophenylamino)-1-piperidyl group, a 4-phenoxy-1-piperidyl group, a 2,4-diphenoxy-1-piperidyl group, a 2,4,6-triphenoxy-1-piperidyl group, a 4-(2-methoxyphenoxy)-1-piperidyl group, a 1-(3-methoxyphenoxy)-4-piperidyl group, a 1-(4-methoxyphenoxy)-4-piperidyl group, a 2-(2-ethoxyphenoxy)-3-piperidyl group, a 3-(3-ethoxyphenoxy)-4-piperidyl group, a 4-(4-ethoxyphenoxy)-5-piperidyl group, a 3-(4-n-propoxyphenoxy)-2-piperidyl group, a 2-(4-tert-butoxyphenoxy)-1-piperidyl group, a 1-(4-n-butoxyphenoxy)-2-piperidyl group, a 2-(2-trifluoromethoxyphenoxy)-3-piperidyl group, a 3-(3-trifluoromethoxyphenoxy)-4-piperidyl group, a 4-(4-trifluoromethoxyphenoxy)-3-piperidyl group, a 3-(2-pentafluoroethoxyphenoxy)-2-piperidyl group, a 6-(3-pentafluoroethoxyphenoxy)-1-piperidyl group, a 1-(2,3-dimethoxyphenoxy)-4-piperidyl group, a 4-(3,4,5-trimethoxyphenoxy)-1-piperidyl group, a 4-(4-n-pentyloxyphenoxy) group, and a 4-(4-n-hexyloxyphenoxy)-1-piperidyl group, provided that, on the piperidine ring, 1 to 3 groups selected from the group consisting of a phenoxy group (wherein, on the phenyl ring, 1 to 5, and preferably 1 to 3 halogen substituted or unsubstituted C1-C6 alkoxy groups may be substituted as substituents) and an amino group (wherein, on the amino group, 1 or 2 groups selected from the group consisting of a C1-C6 alkyl group and a phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted] may be substituted as substituents) may be substituted.

Examples of the piperazinyl group [wherein, on the piperazine ring, at least one selected from the following groups may be substituted: a C1-C6 alkoxycarbonyl group, a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted), a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted), and a benzoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted)), may include piperazinyl groups such as a (1-, 2- or 3-)piperazinyl group, a 4-tert-butoxycarbonyl-1-piperazinyl group, a 4-ethoxycarbonyl-1-piperazinyl group, a 4-methoxycarbonyl-1-piperazinyl group, a 2,4-dimethoxycarbonyl-1-piperazinyl group, a 2,4,6-triethoxycarbonyl-1-piperazinyl group, a 4-(4-trifluoromethoxybenzyl)-1-piperazinyl group, a 4-(4-chlorobenzyl)-1-piperazinyl group, a 4-(4-methoxybenzyl)-1-piperazinyl group, a 4-(4-bromobenzyl)-1-piperazinyl group, a 4-(4-methylbenzyl)-1-piperazinyl group, a 4-(2,4-dichlorobenzyl)-1-piperazinyl group, a 4-(3',4-dimethoxybenzyl)-1-piperazinyl group, a 4-(2,4,6-trifluorobenzyl)-1-piperazinyl group, a 4-(3,4-dimethylbenzyl)-1-piperazinyl group, a 4-(2,4,6-trimethoxybenzyl)-1'-piperazinyl group, a 4-(2,4,6-trimethylbenzyl)-1-piperazinyl group, a 4-(4-iodobenzyl)-1-piperazinyl group, a 4-(4-trifluoromethylbenzyl)-1-piperazinyl group, a 4-(3,4-dichlorobenzyl)-1-piperazinyl group, a 4-(3-(4-trifluoromethylphenyl)-2-propenyl)-1-piperazinyl group, a 4-(3-(4-trifluoromethylphenyl)-2-propenyl)-1-piperazinyl group, a 4-(4-trifluoromethylbenzoyl)-1-piperazinyl group, a 4-(3-(4-chlorophenyl)-2-propenyl)-1-piperazinyl group, a 4-(3-(4-methylphenyl)-2-propenyl)-1-piperazinyl group, a 4-(3-(4-methoxyphenyl)-2-propenyl)-1-piperazinyl group, a 4-(3-(3,4-dimethylphenyl)-2-propenyl)-1-piperazinyl group, a 4-(3-(3,4-dimethoxyphenyl)-2-propenyl)-1-piperazinyl group, a 4-(3-(3,4,5-trimethylphenyl)-2-propenyl)-1-piperazinyl group, a 4-(3-(3,4,5-trimethoxyphenyl)-2-propenyl)-1-piperazinyl group, a 4-(3-(3,4-dichlorophenyl)-2-propenyl)-1-piperazinyl group, a 4-(3-(2,4,6-trifluorophenyl)-2-propenyl)-1-piperazinyl group, a 4-(3-(4-iodophenyl)-2-propenyl)-1-piperazinyl group, a 4-(3-(3-bromophenyl)-2-propenyl)-1-piperazinyl group, a 4-(4-fluorobenzyl)-1-piperazinyl group, a 4-(4-methylbenzoyl)-1-piperazinyl group, a 4-(4-methoxybenzoyl)-1-piperazinyl group, a 4-(3,4-dimethylbenzoyl-1-piperazinyl group, a 4-(2,4-dimethylbenzoyl-1-piperazinyl group, a 4-(3,4,5-trimethylbenzoyl-1-piperazinyl group, a 4-(2,4,6-trimethoxybenzoyl-1-piperazinyl group, a 4-(4-chlorobenzoyl)-1-piperazinyl group, a 4-(2,4,6-trifluorobenzoyl)-1-piperazinyl group, a 4-(4-bromobenzoyl)-1-piperazinyl group, a 4-(4-iodobenzoyl)1-piperazinyl group, a 4-(3,4-dichlorobenzoyl)-1-piperazinyl group, a 4-(4-fluorobenzoyl)-1-piperazinyl group, a 4-benzyl-3-(3-phenyl-2-propenyl)-1-piperazinyl group, and a 4-benzoyl-3,5-dibenzyl-1-piperazinyl group, provided that, on the piperazine ring, 1 to 3 groups selected from the following groups may be substituted: the above described C1-C6 alkoxycarbonyl group, the above described phenyl C1-C6 alkyl group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted), the above described phenyl C2-C6 alkenyl group (which is unsubstituted, or which is composed of 1 or 2 phenyl groups, wherein 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted, and alkenyl groups containing 2 to 6 carbon atoms and having 1 to 3 double bonds), and the above described benzoyl group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted).

Examples of the homopiperazinyl group [wherein, on the homopiperazine ring, at least one selected from the group consisting of a C1-C6 alkoxycarbonyl group and a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) may be substituted] may include homopiperazinyl groups such as a (1-, 2-, 3-, 4-, 5-, 6- or 7-)homopiperazinyl group, a 3,4-dibenzyl-1-homopiperazinyl group, a 2,7-dibenzyl-1-homopiperazinyl group, a 2,3,4-tribenzyl-1-homopiperazinyl group, a 2,4,6-tribenzyl-1-homopiperazinyl group, a 4-benzyl-1-homopiperazinyl group, a 4-(2-phenethyl)-1-homopiperazinyl group, a 4-(3-phenylpropyl)-1-homopiperazinyl group, a 4-(4-phenylbutyl)-1-homopiperazinyl group, a 4-(5-phenylpentyl)-1-homopiperazinyl group, a 4-(6-phenylhexyl)-1-homopiperazinyl group, a 4-(2-fluorobenzyl)-1-homopiperazinyl group, a 4-(3-fluorobenzyl)-1-homopiperazinyl group, a 4-(4-fluorobenzyl)-1-homopiperazinyl group, a 4-(2-chlorobenzyl)-1-homopiperazinyl group, a 4-(3-chlorobenzyl)-1-homopiperazinyl group, a 4-(4-chlorobenzyl)-1-homopiperazinyl group, a 4-(2,3-dichlorobenzyl)-1-homopiperazinyl group, a 4-(2,4-dichlorobenzyl)-1-homopiperazinyl group, a 4-(3,4-dichlorobenzyl)-1-homopiperazinyl group, a 4-(3,5-dichlorobenzyl)-1-homopiperazinyl group, a 4-(3,4,5-trichlorobenzyl)-1-homopiperazinyl group, a 4-(2,3,4,5,6-pentafluorobenzyl)-1-homopiperazinyl group, a 4-(2-trifluoromethylbenzyl)-1-homopiperazinyl group, a 4-(3-trifluoromethylbenzyl)-1-homopiperazinyl group, a 4-(4-trifluoromethylbenzyl)-1-homopiperazinyl group, a 4-(4-methylbenzyl)-1-homopiperazinyl group, a 4-(3,4-dimethylbenzyl)-1-homopiperazinyl group, a 4-(2,4,6-trimethylbenzyl)-1-homopiperazinyl group, a 4-(2-pentafluoroethylbenzyl)-1-homopiperazinyl group, a 4-(3-pentafluoroethylbenzyl)-1-homopiperazinyl group, a 4-(4-pentafluoroethylbenzyl)-1-homopiperazinyl group, a 4-(2-trifluoromethoxybenzyl)-1-homopiperazinyl group, a 4-(3-trifluoromethoxybenzyl)-1-homopiperazinyl group, a 4-(4-trifluoromethoxybenzyl)-1-homopiperazinyl group, a 4-(4-methoxybenzyl)-1-homopiperazinyl group, a 4-(3,4-dimethoxybenzyl)-1-homopiperazinyl group, a 4-(2,4,6-trimethoxybenzyl)-1-homopiperazinyl group, a 4-(2-pentafluoroethoxybenzyl)-1-homopiperazinyl group, a 4-(3-pentafluoroethoxybenzyl)-1-homopiperazinyl group, a 4-(4-pentafluoroethoxybenzyl)-1-homopiperazinyl group, a 4-(2-(4-trifluoromethoxyphenyl)ethyl)-1-homopiperazinyl group, a 4-(3-(4-trifluoromethoxyphenyl)propyl)-1-homopiperazinyl group, a 4-(4-(4-trifluoromethoxyphenyl)butyl)-1-homopiperazinyl group, a 4-(5-(4-trifluoromethoxyphenyl)pentyl)-1-homopiperazinyl group, a 4-(6-(4-trifluoromethoxyphenyl)hexyl)-1-homopiperazinyl group, a 4-(2-(4-trifluoromethylphenyl)ethyl)-1-homopiperazinyl group, a 4-(3-(4-trifluoromethylphenyl)propyl)-1-homopiperazinyl group, a 4-(4-(4-trifluoromethylphenyl)butyl)-1-homopiperazinyl group, a 4-(5-(4-trifluoromethylphenyl)pentyl)-1-homopiperazinyl group, a 4-(6-(4-trifluoromethylphenyl)hexyl)-1-homopiperazinyl group, a 4-tert-butoxycarbonyl-(1-, 2-, 3-, 5-, 6- or 7-)homopiperazinyl group, a 4-methoxycarbonyl(1-, 2-, 3-, 5-, 6- or 7-)homopiperazinyl, group, and a 4-ethoxycarbonylcarbonyl(1-, 2-, 3-, 5-, 6- or 7-)homopiperazinyl group, provided that, on the homopiperazine ring, 1 to 3 groups selected from the group consisting of the above described C1-C6 alkoxycarbonyl group and a phenyl C1-C6 alkyl group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted) may be substituted.

Examples of the phenoxy substituted phenyl group (wherein, on the phenyl ring, at least one halogen substituted or unsubstituted C1-C6 alkoxy group may be substituted) may include phenoxy substituted phenyl groups such as a 2-phenoxyphenyl group, a 2,3-diphenoxyphenyl group, a 2,4,6-triphenoxyphenyl group, a 3-(2-methoxyphenoxy)phenyl group, a 4-(3-methoxyphenoxy)phenyl group, a 2-(4-methoxyphenoxy)phenyl group, a 3-(4-isopropoxyphenoxy)phenyl group, a 4-(4-n-butoxyphenoxy)phenyl group, a 2-(2,4-dimethoxyphenoxy)phenyl group, a 3-(2,3-dimethoxyphenoxy)phenyl group, a 4-(2,3,4,5,6-pentamethoxyphenoxy)phenyl group, a 2-(3,5-dimethoxyphenoxy)phenyl group, a 3-(2,5-dimethoxyphenoxy)phenyl group, a 4-(2,4,6-trimethoxyphenoxy)phenyl group, a 2-(3,5-di(trifluoromethoxy)phenoxy)phenyl group, a 3-(4-methoxy-3-trifluoromethoxyphenoxy)phenyl group, a 4-(2,6-dimethoxyphenoxy)phenyl group, a 2-(2-trifluoromethoxyphenoxy)phenyl group, a 3-(3-trifluoromethoxyphenoxy)phenyl group, a 4-(4-trifluoromethoxyphenoxy)phenyl group, a 2-(2,3-di(trifluoromethoxy)phenoxy)phenyl group, a 3-(2,4-di(trifluoromethoxy)phenoxy)phenyl group, a 4-(2-pentafluoroethoxyphenoxy)phenyl group, a 2-(3-pentafluoroethoxyphenoxy)phenyl group, a 3-(4-pentafluoroethoxyphenoxy)phenyl group, a 4-(2-isopropoxyphenoxy)phenyl group, a 2-(3-isopropoxyphenoxy)phenyl group, a 3-(4-isopropoxyphenoxy)phenyl group, a 4-(2-tert-butoxyphenoxy)phenyl group, a 2-(3-tert-butoxyphenoxy)phenyl group, a 3-(4-tert-butoxyphenoxy)phenyl group, a 4-(2-sec-butoxyphenoxy)phenyl group, a 3-(3-sec-butoxyphenoxy)phenyl group, a 4-(4-sec-butoxyphenoxy)phenyl group, a 2-(4-n-hexyloxyphenoxy)phenyl group, a 3-(2-n-heptafluoropropoxyphenoxy)phenyl group, a 4-(3-n-heptafluoropropoxyphenoxy)phenyl group, and a 2-(4-n-heptafluoropropoxyphenoxy)phenyl group, provided that, on the phenyl ring, 1 to 5, and preferably 1 to 3 halogen substituted or unsubstituted C1-C6 alkoxy groups may be substituted Examples of the phenoxy group [wherein, on the phenyl ring, at least one selected from the group consisting of a halogen substituted or unsubstituted C1-C6 alkoxy group and a phenoxy substituted phenyl group (wherein, on the phenyl ring, at least one halogen substituted or unsubstituted C1-C6 alkoxy group may be substituted) may be substituted] may include phenoxy groups such as a phenoxy group, a 2-methoxyphenoxy group, a 3-methoxyphenoxy group, a 4-methoxyphenoxy group, a 4-isopropoxyphenoxy group, a 4-n-butoxyphenoxy group, a 2,4-dimethoxyphenoxy group, a 2,3-dimethoxyphenoxy group, a 2,3,4,5,6-pentamethoxyphenoxy group, a 3,5-dimethoxyphenoxy group, a 2,5-dimethoxyphenoxy group, a ~2,4,6-trimethoxyphenoxy group, a 3,5-di(trifluoromethoxy)phenoxy group, a 4-methoxy-3-trifluoromethoxyphenoxy group, a 2,6-dimethoxyphenoxy group, a 2-trifluoromethoxyphenoxy group, a 3-trifluoromethoxyphenoxy group, a 4-trifluoromethoxyphenoxy group, a 2,3-di(trifluoromethoxy)phenoxy group, a 2,4-di(trifluoromethoxy)phenoxy group, a 2-pentafluoroethoxyphenoxy group, a 3-pentafluoroethoxyphenoxy group, a 4-pentafluoroethoxyphenoxy group, a 2-isopropoxyphenoxy group, a 3-isopropoxyphenoxy group, a 4-isopropoxyphenoxy group, a 2-tert-butoxyphenoxy group, a 3-tert-butoxyphenoxy group, a 4-tert-butoxyphenoxy group, a 2-sec-butoxyphenoxy group, a 3-sec-butoxyphenoxy group, a 4-sec-butoxyphenoxy group, a 4-n-hexyloxyphenoxy group, a 2-n-heptafluoropropoxyphenoxy group, a 3-n-heptafluoropropoxyphenoxy group, a 4-n-heptafluoropropoxyphenoxy group, a 2-(2-phenoxyphenyl)phenoxy group, a 2,3-di(2-phenoxyphenyl)phenoxy group, a 2,3-di(2-phenoxyphenyl)-4-methoxyphenoxy group, a 2,4-dimethoxy-3-(3-phenoxyphenyl)phenoxy group, a 3-(2,3-diphenoxyphenyl)phenoxy group, a 4-(2,4,6-triphenoxyphenyl)phenoxy group, a 2-(3-(2-methoxyphenoxy)phenyl)phenoxy group, a 3-(4-(3-methoxyphenoxy)phenyl)phenoxy group, a 4-(2-(4-methoxyphenoxy)phenyl)phenoxy, group, a 2-(3-(4-isopropoxyphenoxy)phenyl)phenoxy group, a 3-(4-(4-n-butoxyphenoxy)phenyl)phenoxy group, a 4-(2'-(2,4-dimethoxyphenoxy)phenyl)phenoxy group, a 2-(3-(2,3-dimethoxyphenoxy)phenyl)phenoxy group, a 3-(4-(2,3,4,5,6-pentamethoxyphenoxy)phenyl)phenoxy group, a 4-(2-(3,5-dimethoxyphenoxy)phenyl)phenoxy group, a 2-(3-(2,5-dimethoxyphenoxy)phenyl)phenoxy group, a 3-(4-(2,4,6-trimethoxyphenoxy)phenyl)phenoxy group, a 4-(2-(3,5-di(trifluoromethoxy)phenoxy)phenyl)phenoxy group, a 2-(3-(4-methoxy-3-trifluoromethoxyphenoxy)phenyl)phenoxy group, a 3-(4-(2,6-dimethoxyphenoxy)phenyl)phenoxy group, a 4-(2-(2-trifluoromethoxyphenoxy)phenyl)phenoxy group, a 2-(3-(3-trifluoromethoxyphenoxy)phenyl)phenoxy group, a 3-(4-(4-trifluoromethoxyphenoxy)phenyl)phenoxy group, a 4-(2-(2,3-di(trifluoromethoxy)phenoxy)phenyl)phenoxy group, a 2-(3-(2,4-di(trifluoromethoxy)phenoxy)phenyl)phenoxy group, a 3-(4-(2-pentafluoroethoxyphenoxy)phenyl)phenoxy group, a 4-(2-(3-pentafluoroethoxyphenoxy)phenyl)phenoxy group, a 2-(3-(4-pentafluoroethoxyphenoxy)phenyl)phenoxy group, a 3-(4-(2-isopropoxyphenoxy)phenyl)phenoxy group, a 4-(2-(3-isopropoxyphenoxy)phenyl)phenoxy group, a 2-(3-[(4-isopropoxyphenoxy)phenyl)phenoxy group, a 3-(2-(2-tert-butoxyphenoxy)phenyl)phenoxy group, a 4-(2-(3-tert-butoxyphenoxy)phenyl)phenoxy group, a 2-(3-(4-tert-butoxyphenoxy)phenyl)phenoxy group, a 3-(4-(2-sec-butoxyphenoxy)phenyl)phenoxy group, a 2-(2-(3-sec-butoxyphenoxy)phenyl)phenoxy group, a 2-(3-(4-sec-butoxyphenoxy)phenyl)phenoxy group, a 4-(2-(4-n-hexyloxyphenoxy)phenyl)phenoxy group, a 2-(3-(2-n-heptafluoropropoxyphenoxy)phenyl)phenoxy group, a 3-(4-(3-n-heptafluoropropoxyphenoxy)phenyl)phenoxy group, and a 4-(2-(4-n-heptafluoropropoxyphenoxy)phenyl)phenoxy group, provided that, on the phenyl ring, 1 to 5 groups, and preferably 1 to 3 groups selected from the group consisting of a halogen substituted or unsubstituted C1-C6 alkoxy group and a phenoxy substituted phenyl group (wherein, on the phenyl ring, 1 to 5, and preferably. 1 to 3 halogen substituted or unsubstituted C1-C6 alkoxy groups may be substituted) may be substituted.

Examples of the homopiperazinyl group (wherein, on the homopiperazine ring, at least one selected from the following groups may be substituted: a C1-C6 alkoxycarbonyl group, a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a phenyl C1-C6 alkoxycarbonyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a phenylcarbamoyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a phenyl C2-C6 alkenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], and a benzoyl group [wherein, on the phenyl ring, at least one selected from the group consisting of a halogen atom, a halogen substituted or unsubstituted C1-C6 alkyl group, and a halogen substituted, or unsubstituted C1-C6 alkoxy group may be substituted]), may include homopiperazinyl groups such as a (1-, 2-, 3-, 4-, 5-, 6- or 7-)homopiperazinyl group, a 4-tert-butoxycarbonyl-1-homopiperazinyl group, a 4-ethoxycarbonyl-1-homopiperazinyl group, a 4-methoxycarbonyl-1-homopiperazinyl group, a 2,4-dimethoxycarbonyl-1-homopiperazinyl group, a 2,4,6-triethoxycarbonyl-1-homopiperazinyl group, a 4-(4-trifluoromethoxybenzyl)-1-homopiperazinyl group, a 4-(4-chlorobenzyl)-1-homopiperazinyl group, a 4-(4-methoxybenzyl)-1-homopiperazinyl group, a 4-(4-bromobenzyl)-1-homopiperazinyl group, a 4-(4-methylbenzyl)-1-homopiperazinyl group, a 4-(2,4-dichlorobenzyl)-1-homopiperazinyl group, a 4-(3,4-dimethoxybenzyl)-1-homopiperazinyl group, a 4-(2,4,6-trifluorobenzyl)-1-homopiperazinyl group, a 4-(3,4-dimethylbenzyl)-1-homopiperazinyl group, a 4-(2,4,6-trimethoxybenzyl)-1-homopiperazinyl group, a 4-(2,4,6-trimethylbenzyl)-1-homopiperazinyl group, a 4-(4-iodobenzyl)-1-homopiperazinyl group, a 4-(4-trifluoromethylbenzyl)-1-homopiperazinyl group, a 4-(3,4-dichlorobenzyl)-1-homopiperazinyl group, a 4-(3-(4-trifluoromethylphenyl)-2-propenyl)-1-homopiperazinyl group, a 4-(3-(4-trifluoromethylphenyl)-2-propenyl)-1-homopiperazinyl group, a 4-(4-trifluoromethylbenzoyl)-1-homopiperazinyl group, a 4-(3-(4-chlorophenyl)-2-propenyl)-1-homopiperazinyl group, a 4-(3-(4-methylphenyl)-2-propenyl)-1-homopiperazinyl group, a 4-(3-(4-methoxyphenyl)-2-propenyl)-1-homopiperazinyl group, a 4-(3-(3,4-dimethylphenyl)-2-propenyl)-1-homopiperazinyl group, a 4-(3-(3',4-dimethxoyphenyl)-2-propenyl)-1-homopiperazinyl group, a 4-(3-(3,4,5-trimethylphenyl)-2-propenyl)-1-homopiperazinyl group, a 4-(3-(3,4,5-trimethoxyphenyl)-2-propenyl)-1-homopiperazinyl group, a 4-(3-(3,4-dichlorophenyl)-2-propenyl)-1-homopiperazinyl group, a 4-(3-(2,4,6-,trifluorophenyl)-2-propenyl)-1-homopiperazinyl group, a 4-(3-(4-iodophenyl)-2-propenyl)-1-homopiperazinyl group, a 4-(3-(3-bromophenyl)-2-propenyl)-1-homopiperazinyl group, a 4-(4-fluorobenzyl)-1-homopiperazinyl group, a 4-(4-methylbenzoyl)-1-homopiperazinyl group, a 4-(4-methoxybenzoyl)-1-homopiperazinyl group, a 4-(3,4-dimethylbenzoyl)-1-homopiperazinyl group, a 4-(2,4-dimethoxybenzoyl)-1-homopiperazinyl group, a 4-(3,4,5-trimethylbenzoyl)-1-homopiperazinyl group, a 4-(2,4,6-trimethoxybenzoyl)-1-homopiperazinyl group, a 4-(4-chlorobenzoyl)-1-homopiperazinyl group, a 4-(2,4,6-trifluorobenzoyl)-1-homopiperazinyl group, a 4-(4-bromobenzoyl)-1-homopiperazinyl group, a 4-(4-iodobenzoyl)-1-homopiperazinyl group, a 4-(3,4-dichlorobenzoyl)-1-homopiperazinyl group, a 4-(4-fluorobenzoyl)-1-homopiperazinyl group, a 4-benzyl-3-(3-phenyl-2-propenyl)-1-homopiperazinyl group, a 4-benzoyl-3,5-dibenzyl-1-homopiperazinyl group, a 2,7-dibenzyl-4-phenyl-homopiperazinyl group, a 4-(4-trifluoromethylphenyl)-1-homopiperazinyl group, a 4-(4-trifluoromethoxyphenyl)-1-homopiperazinyl group, a 4-(4-chlorophenyl)-1-homopiperazinyl group, a 4-(4 methoxyphenyl)-1-homopiperazinyl group, a 4-(4-methylphenyl)-1-homopiperazinyl group, a 4-(2,4-dimethoxyphenyl)-1-homopiperazinyl group, a 4-(2,4-dimethylphenyl)-1-homopiperazinyl group, a 4-(2,4,6-trimethoxyphenyl)-1-homopiperazinyl group, a 4-(2,4,6-trimethylphenyl)-1-homopiperazinyl group, a 4-(3,4-dichlorophenyl)-1-homopiperazinyl group, a 4-(2,4,6-trifluorophenyl)-1-homopiperazinyl group, a 4-(4-bromophenyl)-1-homopiperazinyl group, a 4-(4-iodophenyl)-1-homopiperazinyl group, a 4-(4-fluorophenyl)-1-homopiperazinyl group, a 4-(4-trifluoromethoxybenzyloxycarbonyl)-1-homopiperazinyl group, a 4-(4-chlorobenzyloxycarbonyl)-1-homopiperazinyl group; a 4-(4-methoxybenzyloxycarbonyl)-1-homopiperazinyl group, a 4-(4-bromobenzyloxycarbonyl)-1-homopiperazinyl group, a 4-(4-methylbenzyloxycarbonyl)-1-homopiperazinyl group, a 4-(2,4-dichlorobenzyloxycarbonyl)-1-homopiperazinyl group, a 4-(3,4-dimethoxybenzyloxycarbonyl)-1-homopiperazinyl group, a 4-(2,4,6-trifluorobenzyloxycarbonyl)-1-homopiperazinyl group, a 4-(3,4-dimethylbenzyloxycarbonyl)-1-homopiperazinyl group, a 4-(2,4,6-trimethoxybenzyloxycarbonyl)-1-homopiperazinyl group, a 4-(2,4,6-trimethylbenzyloxycarbonyl)-1-homopiperazinyl group, a 4-(4-iodobenzyloxycarbonyl)-1-homopiperazinyl group, a 4-(4-trifluoromethylbenzyloxycarbonyl)-1-homopiperazinyl group, a 4-(3,4-dichlorobenzyloxycarbonyl)-1-homopiperazinyl group, a 4-(4-trifluoromethoxyphenylcarbamoyl)-1-homopiperazinyl group, a 4-(4-chlorophenylcarbamoyl)-1-homopiperazinyl group, a 4-(4-methoxyphenylcarbamoyl)-1-homopiperazinyl group, a 4-(4-bromophenylcarbamoyl)-1-homopiperazinyl group, a 4-(4-methylphenylcarbamoyl)-1-homopiperazinyl group, a 4-(2,4-dichlorophenylcarbamoyl)-1-homopiperazinyl group, a 4-(3,4-dimethoxyphenylcarbamoyl)-1-homopiperazinyl group, a 4-(2,4,6-trifluorophenylcarbamoyl)-1-homopiperazinyl group, a 4-(3,4-dimethylphenylcarbamoyl)-1-homopiperazinyl group, a 4-(2,4,6-trimethoxyphenylcarbamoyl)-1-homopiperazinyl group, a 4-(2,4,6-trimethylphenylcarbamoyl)-1-homopiperazinyl group, a 4-(4-iodophenylcarbamoyl)-1-homopiperazinyl group, a 4-(4-trifluoromethylphenylcarbamoyl)-1-homopiperazinyl group, a 3,4-di(phenylcarbamoyl)-1-homopiperazinyl group, a 4-(2-(4-trifluoromethylphenyl)ethyl)-1-homopiperazinyl group, and a 4-(3-(4-trifluoromethylphenyl)propyl)-1-homopiperazinyl group, provided that, on the homopiperazine ring, 1 to 3 groups selected from the following groups may be substituted: the above described C1-C6 alkoxycarbonyl group, the above described phenyl C1-C6 alkyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], the above described phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], the above described phenyl C1-C6 alkoxycarbonyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], the above described phenylcarbamoyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted cl-C6 alkoxy group may be substituted], the above described phenyl C2-C6 alkenyl group [which is unsubstituted, or which is composed of 1 or 2 phenyl groups, wherein 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted, and alkenyl groups containing 2 to 6 carbon atoms and having 1 to 3 double bonds), and the above described benzoyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted-C1-C6 alkoxy group may be substituted].

Examples of the 1,2,3,4-tetrahydroisoquinolyl group (wherein, on the 1,2,3,4-tetrahydroisoquinoline ring, at least one amino group may be substituted [wherein, on the amino group, at least one selected from the group consisting of a phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) and a C1-C6 alkyl group may be substituted]), may include 1,2,3,4-tetrahydroisoquinolyl groups such as a 1,2,3,4-tetrahydro(1-, 2-, 3-, 4-, 5-, 6-, 7- or 8-)isoquinolyl group, a 4,6-diamino-1,2,3,4-tetrahydro-2-isoquinolyl group, a 4,6,7-triamino-1,2,3,4-tetrahydro-2-isoquinolyl group, a 7-(N-methyl-N-(4-trifluoromethoxybenzyl)amino)-1,2,3,4-tetrahydro-2-isoquinolyl group, a 6-(4-trifluoromethoxyphenoxy)-1,2,3,4-tetrahydro-2-isoquinolyl group, a 7-(N-methyl-N-(4-trifluoromethylbenzyl)amino)-1,2,3,4-tetrahydro-2-isoquinolyl group, a 7-(N-methyl-N-(4-chlorobenzyl)amino)-1,2,3,4-tetrahydro-2-isoquinolyl group, a 7-(N-(4-chlorobenzyl)amino)-1,2,3,4-tetrahydro-2-isoquinolyl group, a 7-(N-methyl-N-(2,4,6-tri (trifluoromethoxy)benzyl)amino)-1,2,3,4-tetrahydro-2-isoquinolyl group, a 7-(N-methyl-N-(2,4-di(trifluoromethyl) benzyl)amino)-1,2,3,4-tetrahydro-2-isoquinolyl group, and a 7-(N-methyl-N-(2,3-diiodobenzyl)amino)-1,2,3,4-tetrahydro-2-isoquinolyl group, provided that, on the 1,2,3,4-tetrahydroisoquinoline ring, 1 to 3 amino groups may be substituted [wherein, on the amino group, 1 or 2 groups selected from the group consisting of the above described phenyl C1-C6 alkyl group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted) and the above described C1-C6 alkyl group may be substituted].

Examples of the oxazolyl group (wherein, on the oxazole ring, at least one selected from the following groups may be substituted: a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted], a C1-C6 alkyl group, and a piperidyl group [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted))), may include oxazolyl groups such as a (2-, 4- or 5-)oxazolyl group, a 4-(4-chlorophenyl)-2-oxazolyl group, a 4-(4-trifluoromethoxyphenyl)-2-oxazolyl group, a 2-(4-trifluoromethylphenyl)-4-oxazolyl group, a 4-(4-trifluoromethylphenyl)-2-oxazolyl group, a 2-(4-trifluoromethoxyphenyl)-4-oxazolyl group, a 4-(3,4-dichlorophenyl)-2-oxazolyl group, a 5-(4-bromophenyl)-2-oxazolyl group, a 4-(4-fluorophenyl)-2-oxazolyl group, a 5-(4-Iodophenyl)-2-oxazolyl group, a 2-(2,4,6-trifluorophenyl)-4-oxazolyl group, a 4-(4-methylphenyl)-2-oxazolyl group, a 4-(3-methoxyphenyl)-2-oxazolyl group, a 2-(3,4-dimethylphenyl)-5-oxazolyl group, a 4-(2,4-dimethoxyphenyl)-2-oxazolyl group, a 4-(2,4,6-trimethylphenyl)-2-oxazolyl group, a 4-(3,4,5-trimethoxyphenyl)-2-oxazolyl group, a 4,5-diphenyl-2-oxazolyl group, a 2,4-diphenyl-5-oxazolyl group, and a 4-methyl-5-(4-(4-trifluoromethoxyphenoxy)-(1-, 2- or 3-)piperidyl)-2-oxazolyl group, provided that, on the oxazole ring, 1 or 2 groups selected from the following groups may be substituted: a phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted], the above described C1-C6 alkyl group, and the below described piperidyl group [wherein, on the piperidine ring, 1 to 3 phenoxy groups may be substituted (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted)).

Examples of the isoindolinyl group (wherein, on the isoindoline ring, at least one selected from the group consisting of a halogen atom, a halogen substituted or unsubstituted C1-C6 alkyl group, and a halogen substituted or unsubstituted C1-C6 alkoxy group may be substituted) may include isoindolinyl groups such as a (1-, 2-, 4- or 5-)isoindolinyl group, a 4-chloro-(1-, 2-, 3-, 5-, 6- or 7-)-isoindolinyl group, a 4-trifluoromethyl-(1-, 2-, 3-, 5-, 6- or 7-)-isoindolinyl group, a 4-trifluoromethoxy-(1-, 2-, 3-, 5-, 6- or 7-)-isoindolinyl group, a 5-methyl-(1-, 2-, 3-, 4-, 6- or 7-)-isoindolinyl group, a 4-methoxy-(1-, 2-, 3-, 5-, 6- or 7-)isoindolinyl group, a 3,4-difluoro-(1-, 2-, 5-, 6- or 7-)isoindolinyl group, a 4,5,6-trichloro(1-, 2-, 3- or 7-)isoindolinyl group, a 4,5-dimethyl (1-, 2-, 3-, 6- or 7-)isoindolinyl group, a 4,5,6-trimethyl(1-, 2-, 3- or 7-)isoindolinyl group, a 4,5-dimethoxy(1-, 2-, 3-, 6- or 7-)isoindolinyl group, a 4,5,6-trimethoxy(1-, 2-, 3- or 7-)isoindolinyl group, and a 1,1-dimethyl-5-bromo-(2-, 3-, 4-, 6- or 7-)isoindolinyl group, provided that, on the isoindoline ring, 1 to 3 groups selected from the group consisting of the above described halogen atom, the above described halogen substituted or unsubstituted C1-C6 alkyl group, and the above described halogen substituted or unsubstituted C1-C6 alkoxy group may be substituted.

Examples of the piperazinyl group [wherein, on the piperazine ring, at least one phenyl group may be substituted (wherein, on the phenyl ring, at least one selected from the group consisting of a halogen atom, a halogen substituted or unsubstituted-C1-C6 alkyl group, and a halogen substituted or unsubstituted C1-C6 alkoxy group may be substituted)) may include piperazinyl groups such as a (1-, 2- or 3-)piperazinyl group, a 4-phenyl-1-piperazinyl group, a 2,4-diphenyl-1-piperazinyl group, a 2,4,5-triphenyl-1-piperazinyl group, a 4-(4-trifluoromethoxyphenyl)-1-piperazinyl group, a 4-(4-trifluoromethylphenyl)-1-piperazinyl group, a (4-chlorophenyl-1-piperazinyl)methyl group, a 4-(2,4-dichlorophenyl)-1-piperazinyl group, a 4-(2,4,6-trifluorophenyl)-1-piperazinyl group, a 2,4-di(trifluoromethyl)phenyl-1-piperazinyl group, and a 2,4,6-tri(trifluoromethoxy)phenyl-1-piperazinyl group, provided that, on the piperazine ring, the above described 1 to 3 phenyl groups may be substituted (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted).

Examples of the thiazolyl group (wherein, on the thiazole ring, at least one selected from the following groups may be substituted: a phenoxy C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted]; a phenyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted]; a phenyl C1-C6 alkyl group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted]; a group —$(W_1)oNR^{31}R^{32}$ [wherein $W_1$ and o are the same as described above, and $R^{31}$ and $R^{32}$, which may be identical or different, each represent a hydrogen atom, C1-C6 alkyl group, phenyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted), or phenyl C1-C6 alkyl group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted)); a piperazinyl group [wherein, on the piperazine ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted)); a piperidyl group [wherein, on the piperidine ring, at least one selected from the group consisting of a phenoxy group (wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted) and a phenyl C1-C6 alkyl group may be substituted]; and a phenoxy group [wherein, on the phenyl ring, at least one selected from the group consisting of a halogen atom, a halogen substituted or unsubstituted C1-C6 alkyl group, and a halogen substituted or unsubstituted C1-C6 alkoxy group may be substituted]), may include thiazolyl groups such as a (2-, 4- or 5-)thiazolyl group, a 2-((4-fluoromethoxyphenoxy)methyl)-4-thiazolyl group, a 4-((4-fluoromethoxyphenoxy)methyl)-2-thiazolyl group, a 2-((4-fluoromethylphenoxy)methyl)-4-thiazolyl group, a 2-((4-chlorophenoxy)methyl)-4-thiazolyl group, a 2-((3-methoxyphenoxy)methyl)-4-thiazolyl group, a 2-((2-methylphenoxy)methyl)-5-thiazolyl group, a 2-((2,4-dimethoxyphenoxy)methyl)-5-thiazolyl group, a dimethylphenoxy)methyl)-4-thiazolyl group, a 5-((2,4,6-trimethoxyphenoxy)methyl)-2-thiazolyl group, a 2-((3,4,5-trimethylphenoxy)methyl)-4-thiazolyl group, a 2-((2,4,6-trifluorophenoxy)methyl)-4-thiazolyl group, a 4-((3,4-dichlorophenoxy)methyl)-2-thiazolyl group, a 2-((4-bromophenoxy)methyl)-4-thiazolyl group, a 2-((4-iodophenoxy)methyl)-4-thiazolyl group, a 4-((4-fluorophenoxy)methyl)-2-thiazolyl group, a 2,5-diphenoxymethyl-4-thiazolyl group, a 4,5-diphenoxymethyl-2-thiazolyl group, a 2-(4-fluorophenyl)-4-thiazolyl group, a 4-(4-fluorophenyl)-2-thiazolyl group, a 2-(4-chlorophenyl)-4-thiazolyl group, a 4-(4-chlorophenyl)-2-thiazolyl group, a 2-(4-trifluoromethylphenyl)-4-thiazolyl group, a 2-(4-trifluoromethoxyphenyl)-4-thiazolyl group, a 4-(4-trifluoromethylphenyl)-2-thiazolyl group, a 4-(4-trifluoromethoxyphenyl)-2-thiazolyl group, a 2-(3,4-dichlorophenyl)-4-thiazolyl group, a 4-(3,4-dichlorophenyl)-2-thiazolyl group, a 4-(2,4,6-trifluorophenyl)-2-thiazolyl group, a 5-(4-bromophenyl)-2-thiazolyl group, a 5-(4-fluorophenyl)-4-thiazolyl group, a 2-(4-iodophenyl)-5-thiazolyl group, a 2-(4-methylphenyl)-4-thiazolyl group, a 2-(4-methoxyphenyl)-4-thiazolyl group, a 2-(2,4-dimethylphenyl)-5-thiazolyl group, a 4-(3,4-dimethoxyphenyl)-2-thiazolyl group, a 4-(2,4,6-trimethylphenyl)-5-thiazolyl group, a 5-(3,4,5-trimethoxyphenyl)-4-thiazolyl group, a 2,4-diphenyl-5-thiazolyl group, a 4,5-diphenyl-2-thiazolyl group, a 2-phenyl-5-phenoxymethyl-4-thiazolyl group, a 2-(4-fluorobenzyl)-4-thiazolyl group, a 2-(4-chlorobenzyl)-4 thiazolyl group, a 2-(4-trifluoromethylbenzyl)-4-thiazolyl group, a 2-(4-trifluoromethoxybenzyl)-4-thiazolyl group, a 2-(3,4-dichlorobenzyl)-4-thiazolyl group, a 4-(2,4,6-trifluorobenzyl)-2-thiazolyl group, a 5-(4-bromobenzyl)-2-thiazolyl group, a 5-(4-fluorobenzyl)-4-thiazolyl group, a 2-(4-iodobenzyl)-5-thiazolyl group, a 2-(4-methylbenzyl)-4-thiazolyl group, a 2-(4-methoxybenzyl)-4-thiazolyl group, a 2-(2,4-dimethylbenzyl)-5-thiazolyl group, a 4-(3,4-dimethoxybenzyl)-2-thiazolyl group, a 4-(2,4,6-trimethylbenzyl)-5-thiazolyl group, a 5-(3,4,5-trimethoxybenzyl)-4-thiazolyl group, a 2,4-dibenzyl-5-thiazolyl group, a 4,5-dibenzyl-2-thiazolyl group, a 2-benzyl-5-phenoxymethyl-4-thiazolyl group, a 4-(4-chlorobenzyl)amino-2-thiazolyl group, a 4-(4-trifluoromethoxybenzyl)amino-2-thiazolyl group, a 4-(4-trifluoromethylbenzyl)amino-2-thiazolyl group, a 4-(N-methyl-N-(4-chlorobenzyl)amino)-2-thiazolyl group, a 4-(N-methyl-N-(4-trifluoromethoxybenzyl)amino)-2-thiazolyl group, a 4-(N-methyl-N-(4-trifluoromethylbenzyl)amino)-2-thiazolyl group, a 4-(4-chlorophenyl)amino-2-thiazolyl group, a 4-(4-trifluoromethoxyphenyl)amino-2-thiazolyl group, a 4-(4-trifluoromethylphenyl)amino-2-thiazolyl group, a 4-(N-methyl-N-(4-chlorophenyl)amino)-2-thiazolyl group, a 4-(N-methyl-N-(4-trifluoromethoxyphenyl)amino)-2-thiazolyl group, a 4-(N-methyl-N-(4-trifluoromethylphenyl)amino)-2-thiazolyl group, a 4-(4-chlorobenzyl)aminomethyl-2-thiazolyl group, a 4-(4-trifluoromethoxybenzyl)aminomethyl-2-thiazolyl group, a 4-(4-trifluoromethylbenzyl)aminomethyl-2-thiazolyl group, a 4-(N-methyl-N-(4-chlorobenzyl)aminomethyl)-2-thiazolyl group, a 4-(N-methyl-N-(4-trifluoromethoxybenzyl)aminomethyl)-2-thiazolyl group, a 4-(N-methyl-N-(4-trifluoromethylbenzyl)aminomethyl)-2-thiazolyl group, a 4-(4-chlorophenyl)aminomethyl-2-thiazolyl group, a 4-(4-trifluoromethoxyphenyl) aminomethyl-2-thiazolyl group, a 4-(4-trifluoromethylphenyl)aminomethyl-2-thiazolyl group, a 4-(N-methyl-N-(4-chlorophenyl)aminomethyl)-2-thiazolyl group, a 4-(N-methyl-N-(4-trifluoromethoxyphenyl)aminomethyl)-2-thiazolyl group, a 4-(N-methyl-N-(4-trifluoromethylphenyl)aminomethyl)-2-thiazolyl group, a 4-(4-bromobenzyl)amino-2-thiazolyl group, a 4-(4-methoxybenzyl)amino-2-thiazolyl group, a 4-(4-methylbenzyl)amino-2-thiazolyl group, a 4-(N-methyl-N-(3,4-dichlorobenzyl)amino)-2-thiazolyl group, a 4-(N-methyl-N-(2,4-dimethoxybenzyl)amino)-2-thiazolyl group, a 4-(N- methyl-N-(3,4-dimethylbenzyl)amino)-2-thiazolyl group, a 4-(4-bromophenyl)amino-2-thiazolyl group, a 4-(4-methoxyphenyl)amino-2-thiazolyl group, a 4-(4-methylphenyl)amino-2-thiazolyl group, a 4-(N-methyl-N-(3,4-dichlorophenyl)amino)-2-thiazolyl group, a 4-(N-methyl-N-(3,4-dimethoxyphenyl)amino)-2-thiazolyl group, a 4-(N-methyl-N-(2,4-dimethylphenyl)amino)-2-thiazolyl group, a 4-(4-bromobenzyl)aminomethyl-2-thiazolyl group, a 4-(4-methoxybenzyl)aminomethyl-2-thiazolyl group, a 4-(4-methylbenzyl)aminomethyl-2-thiazolyl group, a 4-(N-methyl-N-(3,4-dichlorobenzyl)aminomethyl)-2-thiazolyl group, a 4-(N-methyl-N-(4-methoxybenzyl)aminomethyl)-2-thiazolyl group, a 4-(N-methyl-N-(3,4-dimethylbenzyl)aminomethyl)-2-thiazolyl group, a 4-(4-bromophenyl)aminomethyl-2-thiazolyl group, a 4-(4-methoxyphenyl)aminomethyl-2-thiazolyl group, a 4-(4-methylphenyl)aminomethyl-2-thiazolyl group, a 4-(N-methyl-N-(3,4-dichlorophenyl)aminomethyl)-2-thiazolyl group, a 4-(N-methyl-N-(2,4-dimethoxyphenyl)aminomethyl)-2-thiazolyl group, a 4-(N-methyl-N-(3,4-dimethylphenyl)aminomethyl)-2-thiazolyl group, a 4-(4-fluorobenzyl)amino-2-thiazolyl group, a 4-(2,4,6-trimethoxybenzyl)amino-2-thiazolyl group, a 4-(3,4,5-trimethylbenzyl)amino-2-thiazolyl group, a 4-(N-methyl-N-(4-iodobenzyl)amino)-2-thiazolyl group, a 4-(N-methyl-N-(2,4,6-trifluorobenzyl)amino)-2-thiazolyl group, a 4-(N-methyl-N-(4-iodobenzyl)amino)-2-thiazolyl group, a 4-(4-fluorophenyl)amino-2-thiazolyl group, a 4-(2,4,6-trimethoxyphenyl)amino-2-thiazolyl group, a 4-(3,4,5-trimethylphenyl)amino-2-thiazolyl group, a 4-(N-methyl-N-(4-iodophenyl)amino)-2-thiazolyl group, a 4-(N-methyl-N-(2,4,6-trifluorophenyl)amino)-2-thiazolyl group, a 4-(4-fluorobenzyl)aminomethyl-2-thiazolyl group, a 4-(3,4,6-trimethoxybenzyl)aminomethyl-2-thiazolyl group, a 4-(2,4,6-trimethylbenzyl)aminomethyl-2-thiazolyl group, a 4-(N-methyl-N-(4-iodobenzyl)aminomethyl)-2-thiazolyl group, a 4-(N-methyl-N-(2,46-trifluorobenzyl)aminomethyl)-2-thiazolyl group, a 4-(4-fluorophenyl)aminomethyl-2-thiazolyl group, a 4-(2,4,6-trimethoxyphenyl)aminomethyl-2-thiazolyl group, a 4-(3,4,5-trimethylphenyl)aminomethyl-2-thiazolyl group, a 4-(N-methyl-N-(4-iodophenyl)aminomethyl)-2-thiazolyl group, a 4-(N-methyl-N-(2,4,6-trifluorophenyl)aminomethyl)-2-thiazolyl group, a 4-(N-methyl-N-(4-trifluoromethylphenyl)aminomethyl)-2-thiazolyl group, a 4-(4-trifluoromethoxyphenoxy)-2-thiazolyl group, a 4-(4-trifluoromethylphenoxy)-2-thiazolyl group, a 4-(4-chlorophenoxy)-2-thiazolyl group, a 4-(3,4-dichlorophenoxy)-2-thiazolyl group, a 4-(4-methoxyphenoxy)-2-thiazolyl group, a 4-(4-methylphenoxy)-2-thiazolyl group, a 4-(3,4-dimethoxyphenoxy)-2-thiazolyl group, a 5-(2,4-dimethylphenoxy)-4-thiazolyl group, a 4-(2,4,6-trimethoxyphenoxy)-5-thiazolyl group, a 4-(3,4,5-trimethylphenoxy)-2-thiazolyl group, a 4-(4-fluorophenoxy)-2-thiazolyl group, a 2-(4-bromophenoxy)-5-thiazolyl group, a 2-(4-iodophenoxy)-4-thiazolyl group, a 5-(2,4,6-trifluorophenoxy)-2-thiazolyl group, a 4-(4-(4-trifluoromethylphenyl)-1-piperazinyl)-2-thiazolyl group, a 4-(4-(4-trifluoromethoxyphenyl)-1-piperazinyl)-2-thiazolyl group, a 4-(4-(4-chlorophenyl)-1-piperazinyl)-2-thiazolyl group, a 4-(4-(4-trifluoromethylphenoxy)-1-piperazinyl)-2-thiazolyl group, a 4-(4-(4-trifluoromethoxyphenoxy)-1-piperazinyl)-2-thiazolyl group, a 4-(4-(4-chlorophenoxy)-1-piperazinyl)-2-thiazolyl group, a 5-(3,4-diphenyl-1-piperazinyl)-2-thiazolyl group, a 2-(3,4,5-triphenyl-1-piperazinyl)-4-thiazolyl group, a 5-(3,4,5-triphenoxy-1-piperazinyl)-4-thiazolyl group, a 4-(3,4-diphenoxy-1-piperazinyl)-5-thiazolyl group, a 4-(4-(4-trifluoromethoxyphenyl)-1-piperazinyl)-5-phenoxy-2-thiazolyl group, a 4-(4-(4-trifluoromethoxyphenoxy)-1-piperazinyl)-5-phenoxy-2-thiazolyl group, a 4-phenyl-2-thiazolyl group, a 2-phenyl-4-thiazolyl group, and a 2-(4-benzyl-(1-, 2- or 3-)piperidyl)-(4- or 5-)thiazolyl group, provided that, on the thiazole ring, 1 or 2 groups selected from the following groups may be substituted: the above described phenoxy C1-C6 alkyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted]; the above described phenyl group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted]; the above described phenyl C1-C6 alkyl group [Wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted]; a group —$(W_1)oNR^{31}R^{32}$ (wherein $W_1$ and o are the same as described above, and $R^{31}$ and $R^{32}$, which may be identical or different, each represent a hydrogen atom, the above described C1-C6 alkyl group, the above described phenyl group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted), or the above described phenyl C1-C6 alkyl group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted)); the above described piperazinyl group [wherein, on the piperazine ring, at least 1 to 3 phenyl groups may be substituted (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted)); the above described piperidyl group [wherein, on the piperidine ring, 1 to 3 groups selected from the group consisting of a phenoxy group (wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted) and the above described phenyl C1-C6 alkyl group may be substituted]; and a phenoxy group [wherein, on the phenyl ring, 1 to 5 groups, and preferably 1 to 3 groups selected from the group consisting of a halogen atom, a halogen substituted or unsubstituted C1-C6 alkyl group, and a halogen substituted or unsubstituted C1-C6 alkoxy group may be substituted].

A naphthyl substituted C1-C6 alkyl group (wherein, on the naphthalene ring, at least one C1-C6 alkoxy group may be substituted) includes, in addition to naphthyl substituted C1-C6 alkyl group as described above, a naphthyl C1-C6 alkyl group (wherein, on the naphthalene ring, 1 to 4 C1-C6 alkoxy groups may be substituted), for example, a 2-(6-methoxy-2-naphthyl)methyl group, (4-methoxy-1-naphthyl)methyl group, 2-(4-methoxy-1-naphthyl)ethyl group, (4-methoxy-1-naphthyl)methyl group, 2-(3-ethoxy-1-naphthyl)ethyl group, 2-n-propoxy-1-naphthylmethyl group, 5-tert-butoxy-2-naphthyl methyl group, 6-n-pentyloxy-3-naphthylmethyl group, 7-n-hexyloxy-4-naphthylmethyl group, 2-(2,4- dimethoxy-1-naphthyloxy)ethyl group, 2-(1,1,4,4-tetramethoxy-5-naphthioloxy)ethyl group or the like.

An imidazolyl group (wherein, on the imidazole ring, at least one selected from the group consisting of a halogen atom and a nitro group may be substituted) includes an imidazolyl group (wherein, on the imidazole ring, 1 to 3 substituents selected from the group consisting of a halogen atom and a nitro group may be substituted), for example, a (1-, 2-, 4- or 5-)imidazolyl group, 2-chloro-4-nitro-(1- or 5-) imidazolyl group, 2-bromo-(1-, 4- or 5-)imidazolyl group, 4-fluoro-(1-, 2- or 5-)imidazolyl group, 2,5-dichloro(1- or 4-)imidazolyl group, 2,4,5-trichloro-1-imidazolyl group, 2-nitro-(1-, 4- or 5-)imidazolyl group, 4-nitro-(1-, 2- or 5-)imidazolyl group, 2,5-dinitro-(1- or 4-)imidazolyl group, 2,4,5-trinitro-1-imidazolyl group or the like.

A phenyl C1-C6 alkyl group (wherein, on the phenyl ring, at least one selected from the group consisting of a benzofuryl group, a halogen atom, a halogen substituted or unsubstituted C1-C6 alkyl group and a halogen substituted or unsubstituted C1-C6 alkoxy group may be substituted) includes, in addition to a phenyl C1-C6 alkyl group as described above (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl C1-C6 alkyl group having a linear or branched alkyl group containing 1 to 6 carbon atoms on the alkyl moiety (wherein on the phenyl ring, 1 to 5 preferably 1 to 3 substituents selected from the group consisting of a benzofuryl group, a halogen atom, a halogen substituted or unsubstituted C1-C6 alkyl group and a halogen substituted or unsubstituted C1-C6 alkoxy group may be substituted), for example, a 4-((2-, 3-, 4-, 5-, 6- or 7-)benzofuryl)benzyl group, 2-((2-, 3-, 4-, 5-, 6- or 7-)benzofuryl)benzyl group, 3-((2-, 3-, 4-, 5-, 6- or 7-)benzofuryl)benzyl group, 2,4-di((2-, 3-, 4-, 5-, 6- or 7-)benzofuryl)benzyl group, 2,4,6-tri((2-, 3-, 4-, 5-, 6- or 7-)benzofuryl) benzyl group, 2-trifluoromethyl-4-(2-, 3-, 4-, 5-, 6- or 7-)benzofuryl)benzyl group, 3-trifluoromethoxy-4-(2-, 3-, 4-, 5-, 6- or 7-)benzofuryl)benzyl group, 4-chloro-3-(2-, 3-, 4-, 5-, 6- or 7-)benzofuryl)benzyl group or the like.

A furyl C1-C6 alkyl group [wherein, on the furan ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a furyl C1-C6 alkyl group having a linear or branched alkyl group containing 1 to 6 carbon atoms on the alkyl moiety [wherein, on the furan ring, 1 to 3 phenyl groups as described above (wherein, on the phenyl ring, 1 to 5, preferably 1 to 3 substituents selected from the group consisting of a halogen atoms a halogen substituted or unsubstituted C1-C6 alkyl group and a halogen substituted or unsubstituted C1-C6 alkoxy group may be substituted) may be substituted], for example, a (2- or 3-)furylmethyl group, 1-((2- or 3-)furyl) ethyl group, 2-((2- or 3-)furyl)ethyl group, 3-((2- or 3-)furyl) propyl group, 2-((2- or 3-)furyl)propyl group, 4-((2- or 3-)furyl)butyl group, 5-((2- or 3-)furyl)pentyl group, 4-((2- or 3-)furyl)pentyl group, 6-((2- or 3-)furyl)hexyl group, 1,1-dimethyl-2-((2- or 3-)furyl)ethyl group, 2-methyl-3-((2- or 3-)furyl)propyl group, 2-(4-chlorophenyl)-(3-, 4- or 5-)furylmethyl group, 2-(2-chloro-5-trifluoromethylphenyl)-(3-, 4- or 5-)furylmethyl group, 2-(4-trifluoromethoxyphenyl)-(3-, 4- or 5-)furylmethyl group, 2-(2,4-dichlorophenyl)-(3-, 4- or 5-)furylmethyl group, 2-(2,4,6-trifluorophenyl)-(3-, 4- or 5-)furylmethyl group, 2-(4-methylphenyl)-(3-, 4- or 5-)furylmethyl group, 2-(4-methoxyphenyl)-(3-, 4- or 5'-)furylmethyl group, 2-(2,4-dimethylphenyl)-(3-, 4- or 5-)furylmethyl group, 2-(3,4-dimethoxyphenyl)-(3-, 4- or 5-)furylmethyl group, 2-(2,4,6-trimethylphenyl)-(3-, 4- or 5-)furylmethyl group, 2-(3,4,5-trimethoxyphenyl)-(3-, 4- or 5-)furylmethyl group, 2,4-diphenyl(3- or 5-)furylmethyl group, 2,4,5-triphenyl-3-furylmethyl group or the like.

A pyridyl C1-C6 alkyl group [wherein, on the pyridine ring, at least one selected from the group consisting of a furyl group and a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes, in addition to a pyridyl C1-C6 alkyl group as described above, a pyridyl C1-C6 alkyl group having a linear or branched alkyl group containing 1 to 6 carbon atoms on the alkyl moiety [wherein, on the pyridine ring, 1 to 3 substituents selected from the group consisting of a furyl group and a phenyl group as described above (wherein, on the phenyl ring, 1 to 5, preferably 1 to 3 substituents selected from the group consisting of a benzofuryl group, a halogen atom, a halogen substituted or unsubstituted C1-C6 alkyl group and a halogen substituted or unsubstituted C1-C6 alkoxy group may be substituted) may be substituted], for example, a 3-(2- or 3-)furyl-(2-, 4-, 5- or 6-)pyridylmethyl group, 2-(4-trifluoromethoxyphenyl)-(3-, 4-, 5- or 6-)pyridylmethyl group, 2-(4-trifluoromethylphenyl)-(3-, 4-, 5- or 6-)pyridylmethyl group, 2-(4-methoxyphenyl)-(3-, 4-, 5- or 6-)pyridylmethyl group, 2-(4-methylphenyl)-(3-, 4-, 5- or 6-)pyridylmethyl group, 2-(3-chloro-4-fluorophenyl)-(3-, 4-, 5- or 6-)pyridylmethyl group, 2-(2,4-dimethoxyphenyl)-(3-, 4-, 5- or 6-)pyridylmethyl group, 2-(3,4,5-trimethoxyphenyl)-(3-, 4-, 5- or 6-)pyridylmethyl group, 2-(2,4-dimethylphenyl)-(3-, 4-, 5- or 6-)pyridyl methyl group, 2-(2,4,6-trimethylphenyl)-(3-, 4-, 5- or 6-)pyridylmethyl group, 2-(2,4,6-trichlorophenyl)-(3-, 4-, 5- or 6-)pyridylmethyl group, 2-(3-chloro-4-trifluoromethoxyphenyl)-(3-, 4-, 5- or 6-)pyridylmethyl group, 2,4-di(2- or 3-)furyl(5- or 6-)pyridylmethyl group, 2,4,6-triphenyl(3- or 5-)pyridylmethyl group, 2-furyl-5-phenyl(3-, 4- or 6-)pyridylmethyl group or the like.

A benzothienyl C1-C6 alkyl group (wherein, on the benzothiophene ring, at least one halogen atom may be substituted) includes a benzothienyl substituted C1-C6 alkyl group which may be substituted by 1 to 3' halogen atoms on the benzofuran ring, for example, a 2-benzothienylmethyl group, 1-(2-benzothienyl)ethyl group, 2-(4-benzothienyl)ethyl group, 3-(5-benzothienyl)propyl group, 4-(6-benzothienyl) butyl group, 5-(7-benzothienyl)pentyl group, 6-(2-benzothienyl) hexyl group, 4-fluoro-2-benzothienylmethyl group, 5-fluoro-2-benzothienylmethyl group, 6-fluoro-2-benzothienylmethyl group, 7-fluoro-2-benzothienylmethyl group, 4-chloro-2-benzothienylmethyl group, 5-chloro-2-benzothienylmethyl group, 6-chloro-2-benzothienylmethyl group, 7-chloro-2-benzothienylmethyl group, 4-bromo-2-benzothienylmethyl group, 5-bromo-2-benzothienylmethyl group, 6-bromo-2-benzothienylmethyl group, 7-bromo-2-benzothienylmethyl group, 4-iodo-2-benzothienylmethyl group, 5-iodo-2-benzothienylmethyl group, 6-iodo-2-benzothienylmethyl group, 7-iodo-2-benzothienylmethyl group, 4-fluoro-3-benzothienylmethyl group, 5-fluoro-3-benzothienylmethyl group, 6-fluoro-3-benzothienylmethyl group, 7-fluoro-3-benzothienylmethyl group, 4-chloro-3-benzothienylmethyl group, 5-chloro-3-benzothienylmethyl group, 6-chloro-3-benzothienylmethyl group, 7-chloro-3-benzothienylmethyl group, 4-bromo-3-benzothienylmethyl group, 5-bromo-3-benzothienylmethyl group, 6-bromo-3-benzothienylmethyl group, 7-bromo-3-benzothienylmethyl group, 4-iodo-3-benzothienylmethyl group, 5-iodo-3-benzothienylmethyl group, 6-iodo-3-benzothienylmethyl group, 7-iodo-3-benzothienylmethyl group, 2-(4-fluoro-2-benzothienyl)ethyl group, 2-(5-fluoro-2-benzothienyl)ethyl group, 2-(6-fluoro-2-benzothienyl)ethyl group, 2-(7-fluoro-2-benzothienyl)ethyl group, 2-(4-chloro-2-benzothienyl) ethyl group, 2-(5-chloro-2-benzothienyl)ethyl group, 2-(6-chloro-2-benzothienyl)ethyl group, 2-(7-chloro-2-benzothienyl)ethyl group, 2-(4-fluoro-3-benzothienyl) methyl group, 2-(5-fluoro-3-benzothienyl)methyl group, 2-(6-fluoro-3-benzothienyl)ethyl group, 2-(7-fluoro-3-benzothienyl)ethyl group, 2-(4-chloro-3-benzothienyl)ethyl group, 2-(5-chloro-3-benzothienyl)ethyl group, 2-(6-chloro-3-benzothienyl)ethyl group, 2-(7-chloro-3-benzothienyl) ethyl group, 2-(4-fluoro-2-benzothienyl)ethyl group, 6-(5-fluoro-2-benzothienyl)hexyl group, 6-(6-fluoro-2-benzothienyl)hexyl group, 6-(7-fluoro-2-benzothienyl)hexyl group, 6-(4-chloro-2-benzothienyl)hexyl group, 6-(5-chloro-2-benzothienyl)hexyl group, 6-(6-chloro-2-benzothienyl) hexyl group, 6-(7-chloro-2-benzothienyl)hexyl group, 6-(4-fluoro-3-benzothienyl)methyl group, 6-(5-fluoro-3-benzothienyl)hexyl group, 6-(6-fluoro-3-benzothienyl)hexyl group, 6-(7-fluoro-3-benzothienyl)hexyl group, 6-(4-chloro-3-benzothienyl)hexyl group, 6-(5-chloro-3-benzothienyl) hexyl group, 6-(6-chloro-3-benzothienyl)hexyl group, 6-(7-chloro-3-benzothienyl)hexyl group, (2,4-dibromo-3-benzothienyl)methyl group, (4,5,6-trichloro-3-benzothienyl) methyl group or the like.

A benzofuryl C2-C6 alkenyl group (wherein, on the benzofuran ring, at least one selected from the group consisting of a halogen atom, a halogen substituted or unsubstituted C1-C6 alkyl group and a halogen substituted or unsubstituted C1-C6 alkoxy group may be substituted) includes a benzofuryl group, which is a group consisting of a benzofuryl group unsubstituted or substituted by 1 to 3 substituents selected from the group consisting of a halogen atom, a halogen substituted or unsubstituted C1-C6 alkyl group and a halogen substituted or unsubstituted C1-C6 alkoxy group, and a linear or branched alkenyl group containing 2 to 6 carbon atoms and having 1 to 3 double bonds. The benzofuryl C2-C6 alkenyl group includes both trans and cis forms. The benzofuryl C2-C6 alkenyl group includes 2-((2-, 3-, 4-, 5-, 6- or 7-)benzofuryl)vinyl group, 3-((2-, 3-, 4-, 5-, 6- or 7-)benzofuryl)-2-propenyl group, 3-((2-, 3-4-, 5-, 6- or 7-)benzofuryl)-2-methyl-2-propenyl group, 4-((2-, 3-, 4-, 5-, 6- or 7-)benzofuryl)-2-butenyl group, 4-((2-, 3-, 4-, 5-, 6- or 7-)benzofuryl)-3-butenyl group, 4-((2-, 3-, 4-, 5-, 6- or 7-)benzofuryl)-1,3-butadienyl group, 5-((2-, 3-, 4-, 5-, 6- or 7-)benzofuryl)-1,3,5-hexatrienyl group, 6-((2-, 3-, 4-, 5-, 6- or 7-)benzofuryl)-1,3-hexadienyl group, 3-(6-trifluoromethyl(2-(2-, 3-, 4-, 5- or 7-)benzofuryl)-2-propenyl group, 3-(5-trifluoromethoxy(2-, 3-, 4-, 5- or 7-)benzofuryl)-2-propenyl group, 3-(7-chloro-(2-, 3-, 4-, 5- or 7-)benzofuryl)-2-propenyl group, 3-(2,6-dimethyl-(3-, 4-, 5- or 7-)benzofuryl)-2-propenyl group, 3-(3,6-dimethoxy(2-, 3-, 4-, 5- or 7-)benzofuryl)-2-propenyl group, 3-(4,5,6-trimethyl(2-, 3- or 7-)benzofuryl)-2-propenyl group, 3-(3,5,6-trimethoxy(2-, 4- or 7-)benzofuryl)-2-propenyl group, 3-(3-chloro-6-trifluoromethyl(2-, 3-, 4-, 5- or 7-)benzofuryl)-2-propenyl group or the like.

A thiazolyl group [wherein, on the thiazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a thiazolyl group [wherein, on the thiazole ring, 1 to 2 phenyl groups as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a (2-, 4- or 5-)thiazolyl group, 4-phenyl-(2- or 5-) thiazolyl group, 2-phenyl-(4- or 5-)thiazolyl group, 5-phenyl-(2- or 4-)thiazolyl group, 2,5-diphenyl-4-thiazolyl group, 2,4-diphenyl-5-thiazolyl group, 2-(4-trifluoromethylphenyl)-(4- or 5-)thiazolyl group, 2-(4-trifluoromethoxyphenyl)-(4- or 5-)thiazolyl group, 2-(4-chlorophenyl)-(4- or 5-)thiazolyl group, 2-(3-chloro-4-trifluoromethylphenyl)-(4- or 5-)thiazolyl group, 2-(4-methylphenyl)-(4- or 5-)thiazolyl group, 2-(2,4-dimethylphenyl)-(4- or 5-)thiazolyl group, 2-(3,4,6-trimethylphenyl)-(4- or 5-)thiazolyl group, 2-(4-methoxyphenyl)-(4- or 5-)thiazolyl group, 2-(2,4-dimethoxyphenyl)-(4- or 5-)thiazolyl group, 2-(3,4,6-trimethoxyphenyl)-(4- or 5-)thiazolyl group, 2-(2,4-dichlorophenyl)-(4- or 5-)thiazolyl group, 2-(3,4,6-trifluorophenyl)-(4- or 5-)thiazolyl group or the like.

An isoindolinyloxy group [wherein, on the isoindoline ring, at least one selected from the group consisting of a C1-C6 alkoxycarbonyl group, phenyl C1-C6 alkyl group (wherein, on the phenyl ring, at least one selected from the group consisting of a benzofuryl group, a halogen atom, a halogen substituted or unsubstituted C1-C6 alkyl group and a halogen substituted or unsubstituted C1-C6 alkoxy group may be substituted), a phenyl C2-C6 alkenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a furyl C1-C6 alkyl group [wherein, on the furan ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted), a pyridyl C1-C6 alkyl group [wherein, on the pyridine ring, at least one selected from the group consisting of a furyl group and a phenyl group (wherein, on the phenyl ring, at least one selected from the group consisting of a benzofuryl group, a halogen atom, a halogen substituted or unsubstituted C1-C6 alkyl group and a halogen substituted or unsubstituted C1-C6 alkoxy group may be substituted) may be substituted), a benzofuryl C1-C6 alkyl group (wherein, on the benzofuran ring, at least one selected from the group consisting of a halogen atom, a halogen substituted or unsubstituted C1-C6 alkyl group and a halogen substituted or unsubstituted C1-C6 alkoxy group may be substituted), a benzothienyl C1-C6 alkyl group (wherein, on the benzothiophene ring, at least one halogen atom may be substituted), a benzofuryl C2-C6 alkenyl group (wherein, on the benzofuryl ring, at least one selected from the group consisting of a halogen atom, a halogen substituted or unsubstituted C1-C6 alkyl group and a halogen substituted or unsubstituted C1-C6 alkoxy group may be substituted), a thiazolyl group [wherein, on the thiazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted) and a phenoxy C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes an isoindolinyloxy group [wherein, on the isoindoline ring, 1 to 3 substituents selected from the group consisting of a linear or branched C1-C6 alkoxycarbonyl group containing 1 to 6 carbon atoms as described above, a phenyl C1-C6 alkyl group having a linear or branched alkyl group on the alkyl moiety as described above (wherein, on the phenyl ring, 1 to 5, preferably 1 to 3 substituents selected from the group consisting of a benzofuryl group, a halogen atom, a halogen substituted or unsubstituted C1-C6 alkyl group and a halogen substituted or unsubstituted C1-C6 alkoxy group may be substituted), a phenyl C2-C6 alkenyl group having a linear or branched alkenyl group containing 2 to 6 carbon atoms on the alkenyl moiety and having 1 to 3 double bonds as described above, and including both trans and cis forms (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a furyl C1-C6 alkyl group having a linear or branched alkyl group containing 1 to 6 carbon atoms on the alkyl moiety as described above [wherein, on the furan ring, 1 to 3 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a pyridyl C1-C6 alkyl group having a linear or branched alkyl group containing 1 to 6 carbon atoms on the alkyl moiety as described above [wherein, on the pyridine ring, 1 to 3 substituents selected from the group consisting of a furyl group and a phenyl group (wherein, on the phenyl ring, 1 to 5, preferably 1 to 3 substituents selected from the group consisting of a benzofuryl group, a halogen atom, a halogen substituted or unsubstituted C1-C6 alkyl group and a halogen substituted or unsubstituted C1-C6 alkoxy group may be substituted) may be substituted], a benzofuryl C1-C6 alkyl group having a linear or branched alkyl group containing 1 to 6 carbon atoms on the alkyl moiety as described above (wherein, on the benzofuran ring, 1 to 3 substituents selected from the group consisting of a halogen atom, a halogen substituted or unsubstituted C1-C6 alkyl group and a halogen substituted or unsubstituted C1-C6 alkoxy group may be substituted), a benzothienyl C1-C6 alkyl group having a linear or branched alkyl group containing 1 to 6 carbon atoms on the alkyl moiety as described above (wherein, on the benzothiophene ring, 1 to 3 halogen atoms may be substituted), a benzofuryl C2-C6 alkenyl group having a linear or branched alkenyl group containing 2 to 6 carbon atoms on the alkenyl moiety and having 1 to 3 double bonds as described above, and including both trans and cis forms (wherein, on the benzofuran ring, 1 to 3 substituents selected from the group consisting a halogen atom, a halogen substituted or unsubstituted C1-C6 alkyl group and a halogen substituted or unsubstituted C1 to C6 alkoxy group may be substituted), a thiazolyl group as described above [wherein, on the thiazole ring, 1 to 2 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted] and a phenoxy C1-C6 alkyl group having a linear or branched alkyl group containing 1 to 6 carbon atoms on the alkyl moiety as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a (1-, 2-, 3- or 4-)isoindolinyloxy group, 1-tert-butoxycarbonyl-(2-, 3- or 4-)isoindolinyloxygroup, 1-(2-(4-chlorophenyl)-(3-, 4- or 5-)furylmethyl)-(2-, 3- or 4-)isoindolinyloxy group, 1-(2-(2-chloro-5-trifluoromethylphenyl)-(3-, 4- or 5-)furylmethyl)-(2-, 3- or 4-)isoindolinyloxy group, 1-(3-trifluoromethyl-4-chlorobenzyl)-(2-, 3- or 4-)isoindolinyloxy group, 1-(4-((2-, 3-, 4-, 5-, 6- or 7-)benzofuryl)benzyl)-(2-, 3- or 4-)isoindolinyloxy group, 1-(3-((2- or 3-)furyl)-(2-, 4-, 5- or 6-)pyridylmethyl)-(2-, 3- or 4-)isoindolinyloxy group, 1-(2-(4-trifluoromethoxyphenyl)-(3-, 4-, 5- or 6-)pyridylmethyl)-(2-, 3- or 4-)isoindolinyloxy group, 1-(2-(3-chloro-4-fluorophenyl)-(3-, 4-, 5- or 6-)pyridylmethyl)-(2-, 3- or 4-)isoindolinyloxy group, 1-(6-trifluoromethyl (2-, 3-, 4-, 5- or 7-)benzofurylmethyl)-(2-, 3- or 4-)isoindolinyloxy group, 1-(5-chloro-(2-, 3-, 4-, 6- or 7-)benzothienylmethyl)-(2-, 3- or 4-)isoindolinyloxy group, 1-(6-chloro(2-, 3-, 4-, 5-, or 7-)benzofurylmethyl)-(2-, 3- or 4-)isoindolinyloxy group, 1-(5-trifluoromethoxy(2-, 3-, 4-, 6- or 7-)benzofurylmethyl)-(2-, 3- or 4-)isoindolinyloxy group, 1-(3-(6-trifluoromethyl(2-, 3-, 4-, 5- or 7-)benzofuryl)-2-propenyl)-(2-, 3- or 4-)isoindolinyloxy group, 1-(5-chloro-(2-, 3-, 4-, 6- or 7-)benzofurylmethyl)-(2-, 3- or 4-)isoindolinyloxy group, 1-(2-(4-trifluoromethylphenyl)-(4- or 5-)thiazolylmethyl)-(2-, 3- or 4-)isoindolinyloxy group, 1-(2-(4-trifluoromethoxyphenoxy)ethyl)-(2-, 3- or 4-)isoindolinyloxy group, 1,3-diethoxycarbonyl-(2- or 4-)isoindolinyloxy group, 2-phenoxymethyl-4-((2-, 3-, 4-, 5-, 6- or 7-)benzofurylmethyl)-(1-, 3-, 5-, 6- or 7-)isoindolinyloxy group, 2-((2- or 3-)furylmethyl)-4,5-dimethoxycarbonyl-(1-, 3-, 6- or 7-)isoindolinyloxy group or the like.

A benzothiazolydinyloxy group [wherein, on the benzothiazolydine ring, at least one selected from the group consisting of an oxo group and a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a benzothiazolidinyloxy group [wherein, on the benzothiazolidine ring, 1 to 3 substituents selected from the group consisting of an oxo group and a phenyl C1-C6 alkyl group having a linear or branched alkyl group containing 1 to 6 carbon atoms on the alkyl moiety as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a (2-, 3-, 4-, 5-, 6- or 7-)benzothiazolydinyloxy group, 3(4-trifluoromethoxybenzyl)-2-oxo-(4-, 5-, 6- or 7-)benzothiazolydinyloxy group, 3-(4-trifluoromethylbenzyl)-(2-, 4-, 5-, 6- or 7-)benzothiazolydinyloxy group, 3-(4-chlorobenzyl)-(2-, 4-, 5-, 6- or 7-)benzothiazolydinyloxy group, 3-(4-methylbenzyl)-(2-, 4-, 5-, 6- or 7-)benzothiazolydinyloxy group, 3-(3,4-dimethylbenzyl)-(2-, 4-, 5-, 6- or 7-)benzothiazolydinyloxy group, 3-(2,4,6-trimethylbenzyl)-(2-, 4-, 5-, 6- or 7-)benzothiazolydinyloxy group, 3-(4-methoxybenzyl)-(2-, 4-, 5-, 6- or 7-)benzothiazolydinyloxy group, 3-(3,4-dimethoxybenzyl)-(2-, 4-, 5-, 6- or 7-)benzothiazolydinyloxy group, 3-(3,4,5-trimethoxybenzyl)-(2-, 4-, 5-, 6- or 7-)benzothiazolydinyloxy group, 3-(4-fluorobenzyl)-(2-, 4-, 5-6- or 7-)benzothiazolydinyloxy group, 3-(3,4-dichlorobenzyl)-(2-, 4-, 5-, 6- or 7-)benzothiazolydinyloxy group, 3-(2,4,6-trifluorobenzyl)-(2-, 4-, 5-, 6- or 7-)benzothiazolydinyloxy group, 2-oxo-(2-, 4-, 5-, 6- or 7-)benzothiazolydinyloxy group, 2,3-dibenzyl(4-, 5-, 6- or 7-)benzothiazolydinyloxy group, 2,3,5-tribenzyl(4-, 5-, 6- or 7-)benzothiazolydinyloxy group or the like.

An indolyloxy group [wherein, on the indole ring, at least one phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes an indolyloxy group. [wherein, on the indole ring, 1 to 3 phenyl C1-C6 alkyl groups having a linear or branched alkyl group containing 1 to 6 carbon atoms on the alkyl moiety as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a (1-, 2-, 3-, 4-, 5-, 6- or 7-)indolyloxy group, 1-(4-trifluoromethoxybenzyl)-(2-, 3-, 4-, 5-, 6- or 7-)indolyloxy group, 1-(4-trifluoromethylbenzyl)-(2-, 3-, 4-, 5-, 6- or 7-)indolyloxy group, 1-(4-chlorobenzyl)-(2-, 3-, 4-, 5-, 6- or 7-)indolyloxy group, 2-(4-methylbenzyl)-(1-, 3-, 4-, 5-, 6- or 7-)indolyloxy group, 3-(3,4-dimethylbenzyl)-(1-, 2-, 4-, 5-, 6- or 7-)indlyloxy group, 4-(2,4,6-trimethylbenzyl)-(1-, 2-, 3-, 5-, 6- or 7-)indolyloxy group, 5-(4-methoxybenzyl)-(1-, 2-, 3-, 4-, 6- or 7-)indolyloxy group, 6-(3,4-dimethoxybenzyl)-(1-, 2-, 3-, 4-, 5- or 7-)indolyloxy group, 7-(3,4,5-trimethoxybenzyl)-(1-, 2-, 3-, 4-, 5- or 6-)indolyloxy group, 1-(4-fluorobenzyl)-(2-, 3-, 4-, 5-, 6- or 7-)indolyloxy group, 1-(3,4-dichlorobenzyl)-(2-, 3-, 4-, 5-, 6- or 7-)indolyloxy group, 1-(2,4,6 trifluorobenzyl)-(2-, 3-, 4-, 5-, 6- or 7-)indolyloxy group, 1,3-dibenzyl(2-, 4-, 5-, 6- or 7-)indolyloxy group, 1,3,5-tribenzyl(2-, 4-, 6- or 7-)indolyloxy group or the like.

A pyrrolidinyl group [wherein, on the pyrrolidine ring, at least one amino group (wherein, on the amino group, at least one selected from the group consisting of a C1-C6 alkyl group and a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted) is substituted] includes a pyrrolidinyl group [wherein, on the pyrrolidine ring, 1 to 3 amino groups (wherein, on the amino group, 1 to 5, preferably 1 to 3 substituents selected from the group consisting of a C1-C6 alkyl group as described above and a phenyl group as described above (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted) are substituted], for example, a 3-(N-methyl-N-(3,4-dichlorophenyl)amino)-(1-, 2-, 4- or 5-)pyrrolidinyl group, 3-amino-(1-, 2-, 4- or 5-)pyrrolidinyl group, 2,3-diamino-(1-, 4- or 5-)pyrrolidinyl group, 2,3,5-triamino-(1- or 4-)pyrrolidinyl, 3-(N-methyl-N-(4-methylphenyl)amino)-(1-, 2-, 4- or 5-)pyrrolidinyl group, 3-(N-ethyl-N-(3-methoxyphenyl)amino)-(1-, 2-, 4- or 5-)pyrrolidinyl group, 3-(N-(4-trifluoromethylphenyl)amino)-(1-, 2-, 4- or 5-)pyrrolidinyl group, 3-(N-(4-trifluoromethoxyphenyl)amino)-(1-, 2-, 4- or 5-)pyrrolidinyl group, 3-(N-methyl-N-(3,4,5-trifluorophenyl)amino)-(1-, 2-, 4- or 5-)pyrrolidinyl group, 3-(N-methyl-N-(3-chloro-4-trifluoromethylphenyl)amino)-(1-, 2-, 4- or 5-)pyrrolidinyl group, 3-(N-phenylamino)-(1-, 2-, 4- or 5-)pyrrolidinyl group, 3-methylamino-(1-, 2-, 4- or 5-)pyrrolidinyl group, 3-methylamino(1-, 2-, 4- or 5-)pyrrolidinyl group or the like.

An indolinyl group (wherein, on the indoline ring, at least one halogen atom may be substituted) includes an indolinyl group (wherein, on the indoline ring, 1 to 3 halogen atoms may be substituted), for example, a (1-, 2-, 3-, 4-, 5-, 6- or 7-)indolinyl group, 5-bromo-(1-, 2-, 3-, 4-, 6- or 7-)indolinyl group, 4-chloro-(1-, 2-, 3-, 5-, 6- or 7-)indolinyl group, 6-fluoro-(1-, 2-, 3-, 4-, 5- or 7-)indolinyl group, 5,7-dichloro-(1-, 2-, 3-, 4- or 6-)indolinyl group, 3,5,6-trifluoro-(1-, 2-, 4- or 7-)indolinyl group or the like.

An indolinyloxy group [wherein, on the indoline ring, at least one selected from the group consisting of a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) and an oxo group may be substituted] includes an indolinyloxy group [wherein, on the indoline ring, 1 to 3 substituents selected from the group consisting of a phenyl C1-C6 alkyl group having a linear or branched alkyl group containing 1 to 6 carbon atoms on the alkyl moiety as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and an oxo group may be substituted], for example, a (1-, 2-, 3-, 4-, 5-, 6- or 7-)indolinyloxy group, 1-(4-trifluoromethoxybenzyl)-2,3-dioxo(1-, 2-, 3-, 4-, 5-, 6- or 7-)indolinyloxy group, 1-(4-trifluoromethoxybenzyl)-2-oxo(3-, 4-, 5-, 6- or 7-)indolinyloxy group, 1-(4-trifluoromethylbenzyl)-(2-, 3-, 4-, 5-, 6- or 7-)indolinyloxy group, 1-(4-chlorobenzyl)-(2-, 3-, 4-, 5-, 6- or 7-)indolinyloxy group, 3-(4-methylbenzyl)-(1-, 2-, 4-, 5-, 6- or 7-)indolinyloxy group, 4-(3,4-dimethylbenzyl)-(1-, 2-, 3-, 5-, 6- or 7-)indolinyloxy group, 2-(2,4,6-trimethylbenzyl)-(1-, 3-, 4-, 5-, 6- or 7-)indolinyloxy group, 5-(4-methoxybenzyl)-(1-, 2-, 3-, 4-, 6- or 7-)indolinyloxy group, 6-(3,4-dimethoxybenzyl)-(1-, 2-, 3-, 4-, 5- or 7-)indolinyloxy group, 7-(3,4,5-trimethoxybenzyl)-(1-, 2-, 3-, 4,5- or 6-)indolinyloxy group, 1-(4-fluorobenzyl)-(2-, 3-, 4-, 5-, 6- or 7-)indolinyloxy group, 1-(3,4-dichlorobenzyl)-(2-, 3-, 4-, 5-, 6- or 7-)indolinyloxy group, 1-(2,4,6-trifluorobenzyl)-(2-, 3-, 4-, 5-, 6- or 7-)indolinyloxy, 2-oxo-(1-, 3-, 4-, 5-, 6-, or 7-)indolinyloxy group, 1,3-dibenzyl(2-, 4-, 5-, 6- or 7-)indolinyloxy group, 1,5,6-tribenzyl(1-, 2-, 3-, 4- or 7-)indolinyloxy group, 2,3-dioxo(1-, 4-, 5-, 6- or 7-)indolinyloxy group or the like.

A pyrrolyl group [wherein, on the pyrrole ring, at least one selected from the group consisting of a C1-C6 alkyl group and a phenyl C1-C6 alkyl group (wherein, on the phenyl ring, at least one selected from the group consisting of a halogen atom, a halogen substituted or unsubstituted C1-C6 alkyl group and halogen substituted or unsubstituted C1-C6 alkoxy group may be substituted) may be substituted] includes a pyrrolyl group [wherein, on the pyrrole ring, 1 to 3 substituents selected from the group consisting of a C1-C6 alkyl group as described above and a phenyl C1-C6 alkyl group having a linear or branched alkyl group containing 1 to 6 carbon atoms on the alkyl moiety as described above (wherein, on the phenyl ring; 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted may be substituted), for example, a (1-, 2- or 3-)pyrrolyl group, 1-(4-trifluoromethoxybenzyl)-(2- or, 3-)pyrrolyl group, 1-(4-trifluoromethylbenzyl)-(2- or 3-)pyrrolyl group, 1-(4-chlorobenzyl)-(2- or 3-)pyrrolyl group, 1-(4-methoxybenzyl)-(2- or 3-)pyrrolyl group, 1-(4-methylbenzyl)-(2- or 3-)pyrrolyl group, 1-(3,4-dimethoxybenzyl)-(2- or 3-)pyrrolyl group, 1-(2,4,6-trimethoxybenzyl)-(2- or 3-)pyrrolyl group, 1-(3,4-dimethylbenzyl)-(2- or 3-)pyrrolyl group, 1-(2,4,6-trimethylbenzyl)-(2- or 3-)pyrrolyl group, 1-(2,4,6-trifluorobenzyl)-(2- or 3-)pyrrolyl group, 1-(2,6-dichlorobenzyl)-(2- or 3-)pyrrolyl group, 1-benzyl-(2- or 3-)pyrrolyl group, 1,2-dibenzyl-(3-, 4- or 5-)pyrrolyl group, 1,2,4-tribenzyl-(3- or 5-)pyrrolyl group, 2-(3-chloro-4-trifluoromethoxybenzyl)-(1-, 3-, 4- or 5-)pyrrolyl group, 1-methyl-(2- or 3-)pyrrolyl group, 1-ethyl-(2- or 3-)pyrrolyl group, 1-n-propyl-(2- or 3-)pyrrolyl group, 1-n-butyl-(2- or 3-)pyrrolyl group, 1-n-pentyl-(2- or 3-)pyrrolyl group, 1-hexyl-(2- or 3-)pyrrolyl group, 1,3-dimethyl-(2-, 4- or -5)pyrrolyl group, 1,3,4-trimethyl-(2- or 5-)pyrrolyl group, 1-benzyl-3-methyl-(2-, 4- or 5-)pyrrolyl group or the like.

A phenylthio group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) includes a phenylthio group unsubstituted or having 1 to 5, preferably 1 to 3 substituents selected from the group consisting of a halogen atom, a halogen substituted or unsubstituted C1-C6 alkyl group and a halogen substituted or unsubstituted C1-C6 alkoxy group as defined above, examples of which include a phenylthio group, 2-fluorophenylthio group, 3-fluorophenylthio group, 4-fluorophenylthio group, 2-chlorophenylthio group, 3-chlorophenylthio group, 4-chlorophenylthio group, 2-bromophenylthio group, 3-bromophenylthio group, 4-bromophenyl group, 2-iodophenylthio group, 3-iodophenylthio group, 4-iodophenylthio group, 2,3-difluorophenylthio group, 3,4-difluorophenyl group, 3,5-difluorophenylthio group, 2,4-difluorophenylthio group, 2,6-difluorophenylthio group, 2,3-dichlorophenylthio group, 3,4-dichlorophenylthio group, 3,5-dichlorophenylthio group, 2,4-dichlorophenylthio group, 2,6-dichlorophenylthio group, 3,4,5-trifluorophenylthio group, 3,4,5-trichlorophenylthio group, 2,4,6-trifluorophenylthio group, 2,4,6-trichlorophenylthio group, 2-fluoro-4-bromophenylthio group, 4-chloro-3-fluorophenylthio group, 2,3,4-trichlorophenylthio group, 2,3,4,5,6-pentafluorophenylthio group, 2,4,6-trimethylphenylthio group, 4-n-butylphenylthio group, 2,4-dimethylphenylthio group, 2,3-dimethylphenylthio group, 2,6-dimethylphenylthio group, 3,5-dimethylphenylthio group, 2,5-dimethylphenylthio group, 3,5-ditrifluoromethylphenylthio group, 4-n-butoxyphenylthio group, 2,4-dimethoxyphenylthio group, 2,3-dimethoxyphenylthio group, 2,6-dimethoxyphenylthio group, 3,5-dimethoxyphenylthio group, 2,5-dimethoxyphenylthio group, 2,4,6-trimethoxyphenylthio group, 3,5-ditrifluoromethoxyphenylthio group, 3-chloro-4-methoxyphenylthio group, 2-chloro-4-trifluoromethoxyphenylthio group, 3-methyl-4-fluorophenylthio group, 4-bromo-3-trifluoromethylphenylthio group, 2-methylphenylthio group, 3-methylphenylthio group, 4-methylphenylthio group, 2-methyl-3-chlorophenylthio group, 3-methyl-4-chlorophenylthio group, 2-chloro-4-methylphenylthio group, 2-methyl-3-fluorophenylthio group, 2-trifluoromethylphenylthio group, 3-trifluoromethylphenylthio group, 4-trifluoromethylphenylthio group, 2-pentafluoroethylphenylthio group, 3-pentafluoroethylphenylthio group, 4-pentafluoroethylphenylthio group, 2-isopropylphenylthio group, 3-isopropylphenylthio group, 4-isopropylphenylthio group, 2-tert-butylphenylthio group, 3-tert-butylphenylthio group, 4-tert-butylphenylthio group, 2-sec-butylphenylthio group, 3-sec-butylphenylthio group, 4-sec-butylphenylthio group, 2-n-hepafluoropropylphenylthio group, 3-n-heptafluoropropylphenylthio group, 4-n-heptafluoropropylphenylthio group, 4-pentylphenylthio group, 4-hexylphenylthio group, 2-methoxyphenylthio group, 3-methoxyphenylthio group, 4-methoxyphenylthio group, 3-chloro-2-methoxyphenylthio group, 2-fluoro-3-methoxyphenylthio group, 2-fluoro-4-methoxyphenylthio group, 2,3,4-trifluorophenylthio group, 2-trifluoromethoxyphenylthio group, 3-trifluoromethoxyphenylthio group, 4-trifluoromethoxyphenylthio group, 3-fluoro-2-trifluoromethoxyphenylthio group, 2-fluoro-3-trifluoromethoxyphenylthio group, 3-fluoro-4-trifluoromethoxyphenylthio group, 3-chloro-2-trifluoromethoxyphenylthio group, 2-chloro-3-trifluoromethoxyphenylthio group, 3-chloro-4-trifluoromethoxyphenylthio group, 2-pentafluoroethoxyphenylthio group, 3-pentafluoroethoxyphenylthio group, 4-pentafluoroethoxyphenylthio group, 3-chloro-2-pentafluoroethoxyphenylthio group, 2-chloro-3-pentafluoroethoxyphenylthio group, 3-chloro-4-pentafluoroethoxyphenylthio group, 2-isopropoxyphenylthio group, 3-isopropoxyphenylthio group, 4-isopropoxyphenylthio group, 2-tert-butoxyphenylthio group, 3-tert-butoxyphenylthio group, 4-tert-butoxyphenylthio group, 2-sec-butoxyphenylthio group, 3-sec-butoxyphenylthio group, 4-sec-butoxyphenylthio group, 2-n-heptafluoropropoxyphenylthio group, 3-n-heptafluoropropoxyphenylthio group, 4-n-heptafluoropropoxyphenylthio group, 4-n-pentoxyphenylthio group, 4-n-hexyloxyphenylthio group or the like.

A piperazinyl group (wherein, on the piperazine ring, at least one selected from the group consisting of a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl group [wherein, on the phenyl ring, at least one selected from the group consisting of a phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a halogen atom, a halogen substituted or unsubstituted C1-C6 alkyl group and a halogen substituted or unsubstituted C1-C6 alkoxy group may be substituted] and a phenyl C2-C6 alkenyl group [wherein, on the phenyl ring, at least one selected from the group consisting of a halogen atom, a halogen substituted or unsubstituted C1-C6 alkyl group and a halogen substituted or unsubstituted C1-C6 alkoxy group may be substituted] may be substituted] includes, in addition to a piperazinyl group as described above. [wherein, on the piperazinyl ring, at least one phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a piperazinyl group [wherein, on the piperazine ring, 1 to 3 substituents selected from the group consisting of a phenyl C1-C6 alkyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a phenyl group [wherein, on the phenyl ring, 1 to 5, preferably 1 to 3 substituents selected from the group consisting of a phenoxy group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a halogen atom, a halogen substituted or unsubstituted C1-C6 alkyl group and a halogen substituted or unsubstituted C1-C6 alkoxy group may be substituted] and a phenyl C2-C6 alkenyl group having a linear or branched alkenyl group containing 2 to 6 carbon atoms on the alkenyl moiety as and having 1 to 3 double bonds as described later, and including both trans and cis forms [wherein, on the phenyl ring, 1 to 5, preferably. 1 to 3 substituents selected from the group consisting of a halogen atom, a halogen substituted or unsubstituted C1-C6 alkyl group and a halogen substituted or unsubstituted C1-C6 alkoxy group may be substituted] may be substituted], for example, 4-(3-(4-trifluoromethylphenyl)-2-propenyl)-(1-, 2- or 3-)piperazinyl group, 4-(4-methoxyphenyl)-(1-, 2- or 3-)piperazinyl group, 4-(3,4-dimethylphenyl)-(1-, 2- or 3-)piperazinyl group, 4-(4-fluorophenyl)-(1-, 2- or 3-)piperazinyl group, 4-(4-trifluoromethylphenyl)-(1-, 2- or 3-)piperazinyl group, 4-(4-methylphenyl)-(1-, 2- or 3-)piperazinyl group, 4-(3,4-dichlorophenyl)-(1-, 2- or 3-)piperazinyl group, 4-(4-trifluoromethoxyphenyl)-(1-, 2- or 3-)piperazinyl group, 4-(4-(4-chlorophenoxy)phenyl)-(1-, 2- or 3-)piperazinyl group or the like.

A naphthyl C1-C6 alkyl group includes a naphthylalkyl group having a linear or branched alkyl group containing 1 to 6 carbon atoms on the alkyl moiety, for example, a ((1- or 2-)naphthyl)methyl group, 1-((1- or 2-)naphthyl)ethyl group, 2-((1- or 2-)naphthyl)ethyl group, 3-((1- or 2-)naphthyl)propyl group, 2-((1- or 2-)naphthyl)propyl group, 4-((1- or 2-)naphthyl)butyl group, 5-((1- or 2-)naphthyl)pentyl group, 4-((1- or 2-)naphthyl)pentyl group, 6-((1- or 2-)naphthyl) hexyl group, 2-methyl-3-((1- or 2-)naphthyl)propyl group, 1,1-dimethyl-2-((1- or 2-)naphthyl)ethyl group or the like.

A piperazinyl group [wherein, on the piperazine ring, at least one selected from the group consisting of a C1-C6 alkoxycarbonyl group, a furyl C1-C6 alkyl group [wherein, on the furan ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a pyridyl C1-C6 alkyl group [wherein, on the pyridine ring, at least one selected from the group consisting of a furyl group and a phenyl group (wherein, on the phenyl ring, at least one selected from the group consisting of a halogen atom, a halogen substituted or unsubstituted C1-C6 alkyl group and a halogen substituted or unsubstituted, C1-C6 alkoxy group may be substituted) may be substituted], a benzothienyl C1-C6 alkyl group (wherein, on the benzothiophene ring, at least one selected from the group consisting of a halogen atom, a halogen substituted or unsubstituted C1-C6 alkyl group and a halogen substituted or unsubstituted C1-C6 alkoxy group may be substituted), a phenyl C2-C6 alkenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a benzofuryl C1-C6 alkyl group [wherein, on the benzofuran ring, at least one selected from the group consisting of a halogen atom, a halogen substituted or unsubstituted C1-C6 alkyl group and a halogen substituted or unsubstituted C1-C6 alkoxy group may be substituted], a benzofuryl C2-C6 alkenyl group [wherein, on the benzofuran ring, at least one selected from the group consisting of a halogen atom, a halogen substituted or unsubstituted C1-C6 alkyl group and a halogen substituted or unsubstituted C1-C6 alkoxy group may be substituted], a thiazolyl C1-C6 alkyl group [wherein, on the thiazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a phenoxy C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), an indolyl C1-C6 alkyl group (wherein, on the indole ring, at least one selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group (wherein, on the phenyl ring, at least one selected from the group consisting of benzofuryl group, a halogen atom, a halogen substituted or unsubstituted C1-C6 alkyl group and a halogen substituted or unsubstituted C1-C6 alkoxy group may be substituted) may be substituted] includes, in addition to a piperazinyl group as described above [wherein, on the piperazine ring, at least one phenyl C1-C6 alkyl group (wherein, on the phenyl ring, at least one selected from the group consisting of benzofuryl group, a halogen atom, a halogen substituted or unsubstituted C1-C6 alkyl group and a halogen substituted or unsubstituted C1-C6 alkoxy group may be substituted) may be substituted], a piperazinyl group which may be substituted on the piperazine ring by 1 to 3 substituents selected from the group consisting of a C1-C6 alkoxycarbonyl group as described later, a furyl C1-C6 alkyl group having a linear or branched alkyl group containing 1 to 6 carbon atoms on the alkyl moiety as described later [wherein, on the furan ring, 1 to 3 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkyl group may be substituted) may be substituted], a pyridyl C1-C6 alkyl group having a linear or branched alkyl group containing 1 to 6 carbon atoms on the alkyl moiety as described later [wherein, on the pyridine ring, 1 to 3 substituents selected from the group consisting of a furyl group and a phenyl group (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a benzothienyl C1-C6 alkyl group having a linear or branched alkyl group containing 1 to 6 carbon atoms on the alkyl moiety as described later (wherein, on the benzothiophene ring, 1 to 3 substituents selected from the group consisting of a halogen atom, a halogen substituted or unsubstituted C1-C6 alkyl group and a halogen substituted or unsubstituted C1-C6 alkoxy group may be substituted), a phenyl C2-C6 alkenyl group having a linear or branched alkenyl group containing 2 to 6 carbon atoms on the alkenyl moiety and having 1 to 3 double bonds as described later, and including both trans and cis forms (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a benzofuryl C1-C6 alkyl group having a linear or branched alkyl group containing 1 to 6 carbon atoms on the alkyl moiety as described later [wherein, on the benzofuran ring, 1 to 3 substituents selected from the group consisting of a halogen atom, a halogen substituted or unsubstituted C1-C6 alkyl group and a halogen substituted or unsubstituted C1-C6 alkoxy group may be substituted], a benzofuryl C2-C6 alkenyl group having a linear or branched alkenyl group having a linear or branched alkenyl group containing 2 to 6 carbon atoms and having 1 to 3 double bonds on the alkenyl moiety as described later, and including both trans and cis forms [wherein, on the benzofuran ring, 1 to 3 substituents selected from the group consisting of a halogen atom, a halogen substituted or unsubstituted C1-C6 alkyl group and a halogen substituted or unsubstituted C1-C6 alkoxy group may be substituted], a thiazolyl C1-C6 alkyl group having a linear or branched alkyl group containing 1 to 6 carbon atoms on the alkyl moiety as described later [wherein, on the thiazole ring, 1 or 2 phenyl groups (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], a phenoxy C1-C6 alkyl group having a linear or branched alkyl group containing 1 to 6 carbon atoms on the alkyl moiety as described later (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), an indolyl C1-C6 alkyl group having a linear or branched alkyl group containing 1 to 6 carbon atoms on the alkyl moiety as described later (wherein, on the indole ring, 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group as described later (wherein, on the phenyl ring, 1 to 5, preferably 1 to 3 substituents selected from the group consisting of a benzofuryl ring, a halogen atom, a halogen substituted or unsubstituted C1-C6 alkyl group and a halogen substituted or unsubstituted C1-C6 alkoxy group may be substituted), for example, a 4-tert-butoxycarbonyl-(1-, 2- or 3-)piperazinyl group, 4-(4-((2-, 3-, 4-, 5-, 6- or 7-)benzofuryl)benzyl)-(1-, 2- or 3-)piperazinyl group, 4-(3-((2- or 3-)furyl)pyridyl)methyl)-(1-, 2- or 3-)piperazinyl group, 4-(2-(4-trifluoromethoxyphenyl)pyridylmethyl)-(1-, 2- or 3-)piperazinyl group, 4-(2-(3-chloro-4-fluorophenyl)pyridylmethyl)-(1-, 2- or 3-)piperazinyl group, 4-(5-trifluoromethyl(2-, 3-, 4-, 6- or 7-)benzofurylmethyl)-(1-, 2- or 3-)piperazinyl group, 4-(6-trifluoromethyl-(2-, 3-, 4-, 5- or 7-)benzofurylmethyl)-(1-, 2- or 3-)piperazinyl group, 4-(5-chloro(2-, 3-, 4-, 6- or 7-)benzothienylmethyl)-(1-, 2-, or 3-)piperazinyl group, 4-(6-chloro(2-, 3-, 4-, 5- or 7-)benzofurylmethyl)-(1-, 2- or 3-)piperazinyl group, 4-(5-trifluoromethoxy(2-, 3-, 4-, 6- or 7-)benzofurylmethyl)-(1-, 2- or 3-)piperazinyl group, 4-(3-(4-trifluoromethylphenyl)-2-propenyl)-(1-, 2- or 3-)piperazinyl group, 4-(3-(3,4-dichlorophenyl)-2-propenyl)-(1-, 2- or 3-)piperazinyl group, 4-(3-(4-chlorophenyl)-2-propenyl)-(1-, 2- or 3-)piperazinyl group, 4-(3-(6-trifluoromethyl(2-, 3-, 4-, 5- or 7-)benzofuryl)-2-propenyl)-(1-, 2- or 3-)piperazinyl group, 4-(3-(5-chloro(2-, 3-, 4-, 5- or 7-)benzofuryl))-2-propenyl)-(1-, 2- or 3-)piperazinyl group, 4-(5-chloro(2-, 3-, 4-, 6- or 7-)benzofurylmethyl)-(1-, 2- or 3-)piperazinyl group, 4-(2-(4-trifluoromethylphenyl)-(4- or 5-)thiazolylmethyl)-(1-, 2- or 3-)piperazinyl group, 4-(2-(4-trifluoromethoxyphenoxy)ethyl)-(1-, 2- or 3-)piperazinyl group, 4-(3-(4-trifluoromethoxyphenyl)-2-propenyl)-(1-, 2- or 3-)piperazinyl group, 4-(5-trifluoromethoxy(1-, 2-, 3-, 4-, 6- or 7-)indolylmethyl)-(1-, 2- or 3-)piperazinyl group, 4-(2-(4-chlorophenyl)-(3-, 4- or 5-)furylmethyl)-(1-, 2- or 3-)piperazinyl group, 4-(2-(2-chloro-5-trifluoromethylphenyl)-(3-, 4- or 5-)furylmethyl)-(1-, 2- or 3-)piperazinyl group or the like.

A benzothienyl C1-C6 alkyl group (wherein, on the benzothiophene ring, at least one selected from the group consisting of a halogen atom, a halogen substituted or unsubstituted C1-C6 alkoxy group and a halogen substituted or unsubstituted C1-C6 alkyl group may be substituted) includes a benzothienyl C1-C6 alkyl group having a linear or branched alkyl group containing 1 to 6 carbon atoms on the alkyl moiety (wherein, on the benzothiophene ring, 1 to 3 substituents selected from the group consisting of a halogen substituted or unsubstituted C1-C6 alkoxy group and a halogen substituted or unsubstituted C1-C6 alkyl group may be substituted), for example, ((2-, 3-, 4-, 5-, 6- or 7-)benzothienyl)methyl group, 1-((2-, 3-, 4-, 5-, 6- or 7-)benzothienyl) ethyl group, 2-((2-, 3-, 4-, 5-, 6- or 7-)benzothienyl)ethyl group, 3-((2-, 3-, 4-, 5-, 6- or 7-)benzothienyl)propyl group, 2-((2-, 3-, 4-, 5-, 6- or 7-)benzothienyl)propyl group, 4-((2-, 3-, 4-, 5-, 6- or 7-)benzothienyl)butyl group, 5-((2-, 3-, 4-, 5-, 6- or 7-)benzothienyl)pentyl group, 4-((2-, 3-, 4-, 5-, 6- or 7-)benzothienyl)pentyl group, 6-((2-, 3-, 4-, 5-, 6- or 7-)benzothienyl)hexyl group, 2-methyl-3-((2-, 3-, 4-, 5-6- or 7-)benzothienyl)propyl group, 1,1-dimethyl-2-((2-, 3-, 4-, 5-, 6- or 7-)benzothienyl)ethyl group, 5-chloro-(2-, 3-, 4-, 6- or 7-)benzothienylmethyl group, 5-methyl-(2-, 3-, 4-, 6- or 7-)benzothienylmethyl group, 5-methoxy-(2-, 3-, 4-, 6- or 7-)benzothienylmethyl group, 5-trifluoromethyl-(2-, 3-, 4-, 6- or 7-)-benzothienylmethyl group, 5-trifluoromethoxy-(2-, 3-, 4-, 6- or 7-)benzothienylmethyl group, 5,6-dichloro-(2-, 3-, 4- or 7-)benzothienylmethyl group, 4,5,6-trifluoro-(2-, 3- or 7-)benzothienylmethyl group, 5-chloro-6-trifluoromethoxy-(2-, 3-, 4- or 7-)-benzothienylmethyl group, 2,5-dimethyl-(3-, 4-, 6- or 7-)benzothienylmethyl group, 2,5,6-trimethyl-(3-, 4-, 6- or 7-)benzothienylmethyl group or the like.

A thiazolyl C1-C6 alkyl group [wherein, on the thiazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a thiazolyl C1-C6 alkyl group a linear or branched alkyl group containing 1 to 6 carbon atoms on the alkyl moiety [wherein, on the thiazole ring, 1 to 2 phenyl groups as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a ((2-, 4- or 5-)thiazolyl)methyl group, 1-((2-, 4- or 5-)thiazolyl)ethyl group, 2-((2-, 4- or 5-)thiazolyl)ethyl group, 3-((2-, 4- or 5-)thiazolyl)propyl group, 2-((2-, 4- or 5-)thiazolyl)propyl group, 4-((2-, 4- or 5-)thiazolyl)butyl group, 5-((2-, 4- or 5-)thiazolyl)pentyl group, 4-((2-, 4- or 5-)thiazolyl)pentyl group, 6-((2-, 4- or 5-)thiazolyl)hexyl group, 2-methyl-3-((2-, 4- or 5-)thiazolyl)propyl group, 1,1-dimethyl-2-((2-, 4- or 5-)thiazolyl)ethyl group, 2-(4-trifluoromethylphenyl)-(4- or 5-)thiazolylmethyl group, 2-(4-trifluoromethylphenyl)-(4- or 5-)thiazolylmethyl group, 2-(4-trifluoromethoxyphenyl)-(4- or 5-)thiazolylmethyl group, 4-(3-methylphenyl)-(2- or 5-)thiazolylmethyl group, 5-(2-methoxyphenyl)-(2- or 5-)thiazolylmethyl group, 4-(4-chlorophenyl)-(2- or 5-)thiazolylmethyl group, 2-(2-, 4-dimethylphenyl)-(4- or 5-)thiazolylmethyl group, 2-(2,4,6-trimethylphenyl)-(4- or 5-)thiazolylmethyl group, 2-(3,4-dimethoxyphenyl)-(4- or 5-)thiazolylmethyl group, 2-(3,4,5-trimethoxyphenyl)-(4- or 5-)thiazolylmethyl group, 2-(3-chloro-4-trifluoromethylphenyl)-(4- or 5-)thiazolylmethyl group, 4-(3,4-dichlorophenyl)-(2- or 5-)thiazolylmethyl group, 2-(3,4,6-trifluorophenyl)-(4- or 5-)thiazolylmethyl group, 2,4-diphenyl(4- or 5-)thiazolylmethyl group or the like.

An indolyl C1-C6 alkyl group (wherein, on the indole ring, at least one selected from the group consisting of a halogen atom, a halogen substituted or unsubstituted C1-C6 alkyl group and a halogen substituted or unsubstituted C1-C6 alkoxy group may be substituted) includes an indolyl C1-C6 alkyl group having a linear or branched alkyl group containing 1 to 6 carbon atoms on the alkyl moiety (wherein, on the indole ring, 1 to 3 substituents selected from the group consisting of a halogen atom, a halogen substituted or unsubstituted C1-C6 alkyl group and a halogen substituted or unsubstituted C1-C6 alkoxy group may be substituted), for example, a ((1-, 2-, 3-, 4-, 5-, 6- or 7-)indolyl)methyl group, 1-((1-, 2-, 3-, 4-, 5-, 6- or 7-)indolyl)ethyl group, 2-((1-, 2-, 3-, 4-, 5-, 6- or 7-)indolyl)ethyl group, 3-((1-, 2-, 3-, 4-, 5-, 6- or 7-)indolyl)propyl group, 2-((1-, 2-, 3-, 4-, 5-, 6- or 7-)indolyl) propyl group, 4-((1-, 2-, 3-, 4-, 5-, 6- or 7-)indolyl)butyl group, 5-((1-, 2-, 3-, 4-, 5-, 6- or 7-)indolyl)pentyl group, 4-(1-, 2-, 3-, 4-, 5-, 6- or 7-)indolyl)pentyl group, 6-((1-, 2-, 3-, 4-, 5-, 6- or 7-)indolyl)hexyl group, 2-methyl-3-((1-, 2-, 3-, 4-, 5-, 6- or 7-)indolyl)propyl group, 1,1-dimethyl-2-((1-, 2-, 3-, 4-, 5-, 6- or 7-)indolyl)ethyl group, 2-trifluoromethyl-(1-, 3-, 4-, 5-, 6- or 7-) indolylmethyl group, 5-trifluoromethyl-(1-, 2-, 3-, 4-, 6- or 7-)indolylmethyl group, 2-trifluoromethoxy-(1-, 3-, 4-, 5-, 6- or 7-)indolylmethyl group, 4-methyl-(1-, 2-, 3-, 5-, 6- or 7-)indolylmethyl group, 5-methoxy-(1-, 2-, 3-, 4-, 6- or 7-)indolylmethyl group, 4-chloro-(1-, 2-, 3-, 5-, 6- or 7-)indolylmethyl group, 2,4-dimethyl-(1-, 3-, 5-, 6- or 7-)indolylmethyl group, 2,4,6-trimethyl-(1-, 3-, 5- or 7-)indolylmethyl group, 3,4-dimethoxy-(1-, 2-, 5-, 6- or 7-)indolylmethyl group, 3,4,5-trimethoxy-(1-, 2-, 6- or 7-)indolylmethyl group, 3-chloro-4-trifluoromethyl-(1-, 2-, 5-, 6- or 7-)indolylmethyl group, 3,4-dichloro-(1-, 2-, 5-, 6- or 7-)indolylmethyl group, 3,4,6-trifluoro-(1-, 2-, 5- or 7-)indolylmethyl group, 5-trifluoromethoxy-(1-, 2-, 3-, 4-, 6- or 7-)indolylmethyl group, 5-trifluoromethoxy-6-chloro-(1-, 2-, 3-, 4- or 7-)indolylmethyl group, 1,3-dimethyl-5-fluoro-(2-, 4-, 6- or 7-)indolylmethyl group or the like.

A phenyl C1-C6 alkyl group (wherein, on the phenyl ring, at least one selected from the group consisting of a benzofuryl group, a halogen atom, a halogen substituted or unsubstituted C1-C6 alkyl group and a halogen substituted or unsubstituted C1-C6 alkoxy group may be substituted) includes, in addition to a phenyl C1-C6 alkyl group as described above (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a phenyl C1-C6 alkyl group having a linear or branched alkyl group containing 1 to 6 carbon atoms on the alkyl moiety (wherein, on the phenyl ring, 1 to 5, preferably 1 to 3 substituents selected from the group consisting of a benzofuryl group, a halogen atom, a halogen substituted or unsubstituted C1-C6 alkyl group and a halogen substituted or unsubstituted C1-C6 alkoxy group may be substituted), for example, 4-((2-, 3-, 4-, 5-, 6- or 7-)benzofuryl)benzyl group, 2-((2-, 3-, 4-, 5-, 6- or 7-)benzofuryl)benzyl group, 3-((2-, 3-, 4-, 5-, 6- or 7-)benzofuryl)benzyl group, 3,4-di((2-, 3-, 4-, 5-, 6- or 7-)benzofuryl)benzyl group, 2,4,6-tri((2-, 3-, 4-, 5-, 6- or 7-)benzofuryl)benzyl group, 3-chloro-4-((2-, 3-, 4-, 5-, 6- or 7-)benzofuryl)benzyl group or the like.

A phenyl C1-C6 alkyl group [wherein, on the phenyl group, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a phenyl C1-C6 alkyl group having a linear or branched alkyl group containing 1 to 6 carbon atoms on the alkyl moiety [wherein, on the phenyl ring, 1 to 3 phenyl groups as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a 4-phenylbenzyl group, 3-phenylbenzyl group, 2-phenylbenzyl group, 2,4-diphenylbenzyl group, 2,4,6-triphenylbenzyl group, 4-(4-trifluoromethoxyphenyl)benzyl group, 2-(3-trifluoromethylphenyl)benzyl group, 4-(2-fluorophenyl)benzyl group, 3-(4-chlorophenyl) benzyl group, 4-(4-methoxyphenyl)benzyl group, 3-(4-methylphenyl)benzyl group, 2-(3,4-dimethoxyphenyl)benzyl group, 4-(3,4-dimethylphenyl)benzyl group, 3-(3,4,6-trimethoxyphenyl)benzyl group, 2-(2,4,5-trimethylphenyl) benzyl group, 4-(3,4-dichlorophenyl)benzyl group, 2-(2,4,6-trifluorophenyl)benzyl group, 4-(3-chloro-4-trifluoromethoxyphenyl)benzyl group, 2-(4-(2-fluorophenyl)phenyl)ethyl group, 3-(2-(3,4-dimethoxyphenyl)phenyl)propyl group, 4-(2-(2,4,5-trimethylphenyl)phenyl)butyl group, 5-(4-(3-chloro-4-trifluoromethoxyphenyl)phenyl)pentyl group, 6-(2-(3-trifluoromethylphenyl)phenyl)hexyl group, 1-(4-(4-trifluoromethoxyphenyl)phenyl)ethyl group or the like.

A phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group is substituted) includes is a phenoxy group having 1 to 5, preferably 1 to 3 substituents selected from the group consisting of a halogen atom, a halogen substituted or unsubstituted C1-C6 alkyl group and a halogen substituted or unsubstituted C1-C6 alkoxy group as defined above, examples of which include a 2-fluorophenoxy group, 3-fluorophenoxy group, 4-fluorophenoxy group, 2-chlorophenoxy group, 3-chlorophenoxy group, 4-chlorophenoxy group, 2-bromophenoxy group, 3-bromophenoxy group, 4-bromophenoxy group, 2-iodophenoxy group, 3-iodophenoxy group, 4-iodophenoxy group, 2,3-difluorophenoxy group, 3,4-difluorophenoxy group, 3,5-difluorophenoxy group, 2,4-difluorophenoxy group, 2,6-difluorophenoxy group, 2,3-dichlorophenoxy group, 3,4-dichlorophenoxy group, 3,5-dichlorophenoxy group, 2,4-dichlorophenoxy group, 2,6-dichlorophenoxy group, 3,4,5-trifluorophenoxy group, 3,4,5-trichlorophenoxy group, 2,4,6-trifluorophenoxy group, 2,4,6-trichlorophenoxy group, 2-fluoro-4-bromophenoxy group, 4-chloro-3-fluorophenoxy group, 2,3,4-trichlorophenoxy group, 3,4,5-trifluorophenoxy group, 2,3,4,5,6-pentafluorophenoxy group, 2,4,6-trimethylphenoxy group, 4-n-butylphenoxy group, 2,4-dimethylphenoxy group, 2,3-dimethylphenoxy group, 2,6-dimethylphenoxy group, 3,5-dimethylphenoxy group, 2,5-dimethyl phenoxy group, 3,5-ditrifluoromethylphenoxy group, 4-n-butoxyphenoxy group, 2,4-dimethoxyphenoxy group, 2,3-dimethoxyphenoxy group, 2,6-dimethoxyphenoxy group, 3,5-dimethoxyphenoxy group, 2,5-dimethoxyphenoxy group, 2,4,6-trimethoxyphenoxy group, 3,5-ditrifluoromethoxyphenoxy group, 3-chloro-4-methoxyphenoxy group, 2-chloro-4-trifluoromethoxyphenoxy group, 3-methyl-4-fluorophenoxy group, 4-bromo-3-trifluoromethylphenoxy group, 2-methylphenoxy group, 3-methylphenoxy group, 4-15' methylphenoxy group, 2-methyl-3-chlorophenoxy group, 3-methyl-4-chlorophenoxy group, 2-chloro-4-methylphenoxy group, 2-methyl-3-fluorophenoxy group, 2-trifluoromethylphenoxy group, 3-trifluoromethylphenoxy group, 4-trifluoromethylphenoxy group, 2-pentafluoroethylphenoxy group, 3-pentafluoroethylphenoxy group, 4-pentafluoroethylphenoxy group, 2-isopropylphenoxy group, 3-isopropylphenoxy group, 4-isopropylphenoxy group, 2-tert-butylphenoxy group, 3-tert-butylphenoxy group, 4-tert-butylphenoxy group, 2-sec-butylphenoxy group, 3-sec-butylphenoxy group, 4-sec-butylphenoxy group, 2-n-heptafluoropropylphenoxy group, 3-n-heptafluoropropylphenoxy group, 4-n-heptafluoropropylphenoxy group, 4-n-pentylphenoxy group, 4-n-hexylphenoxy group, 2-methoxyphenoxy group, 3-methoxyphenoxy group, 4-methoxyphenoxy group, 3-chloro-2-methoxyphenoxy group, 2-fluoro-3-methoxyphenoxy group, 2-fluoro-4-methoxyphenoxy group, 2,6-dimethoxyphenoxy group, 2,3,4-trifluorophenoxy group, 2,4,6-trifluorophenoxy group, 2-trifluoromethoxyphenoxy group, 3-trifluoromethoxyphenoxy group, 4-trifluoromethoxyphenoxy group, 3-fluoro-2-trifluoromethoxyphenoxy group, 2-fluoro-3-trifluoromethoxyphenoxy group, 3-fluoro-4-trifluoromethoxyphenoxy group, 3-chloro-2-trifluoromethoxyphenoxy group, 2-chloro-3-trifluoromethoxyphenoxy group, 3-chloro-4-trifluoromethoxyphenoxy group, 2-pentafluoroethoxyphenoxy group, 3-pentafluoroethoxyphenoxy group, 4-pentafluoroethoxyphenoxy group, 3-chloro-2-pentafluoroethoxyphenoxy group, 2-chloro-3-pentafluoroethoxyphenoxy group, 3-chloro-4-pentafluoroethoxyphenoxy group, 2-isopropoxyphenoxy group, 3-isopropoxyphenoxy group, 4-isopropoxyphenoxy group, 2-tert-butoxyphenoxy group, 3-tert-butoxyphenoxy group, 4-tert-butoxyphenoxy group, 2-sec-butoxyphenoxy group, 3-sec-butoxyphenoxy group, 4-sec-butoxyphenoxy group, 2-n-heptafluoropropoxyphenoxy group, 3-n-heptafluoropropoxyphenoxy group, 4-n-heptafluoropropoxyphenoxy group, 4-n-pentoxyphenoxy group, 4-n-hexyloxyphenoxy group or the like.

A phenyl C1-C6 alkyl group [wherein, on the phenyl ring, at least one phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group is substituted) is substituted] includes a phenyl C1-C6 alkyl group having a linear or branched alkyl group containing 1 to 6 carbon atoms on the alkyl moiety [wherein, on the phenyl ring, 1 to 3 phenoxy groups as described above (wherein, on the phenyl ring, 1 to 3 substituents selected from the group consisting of a halogen atom, a halogen substituted or unsubstituted C1-C6 alkyl group and a halogen substituted or unsubstituted C1-C6 alkoxy group are substituted) are substituted], for example, a 4-(4-trifluoromethoxyphenyl) benzyl group, 2,4-di(4-trifluoromethoxyphenyl)benzyl group, 2-(3-trifluoromethylphenoxy)benzyl group, 4-(2-fluorophenoxy)benzyl group, 2,4,6-tri(2-fluorophenoxy) benzyl group, 3-(4-chlorophenoxy)benzyl group, 4-(4-methoxyphenoxy)benzyl group, 3-(4-methylphenoxy)benzyl group, 2-(3,4-dimethoxyphenoxy)benzyl group, 4-(3,4-dimethylphenoxy)benzyl group, 3-(3,4,6-trimethoxyphenoxy) benzyl group, 2-(2,4,5-trimethylphenoxy)benzyl group, 4-(3,4-dichlorophenoxy)benzyl group, 2-(2,4,6-trifluorophenoxy)benzyl group, 4-(3-chloro-4-trifluoromethoxyphenoxy)benzyl group, 2-(4-(2-fluorophenoxy)phenyl)ethyl group, 3-(2-(3,4-dimethoxyphenoxy)phenyl)propyl group, 4-(2-(2,4,5-trimethylphenoxy)phenyl)butyl group, 5-(4-(3-chloro-4-trifluoromethoxyphenoxy)phenyl)pentyl group, 6-(2-(3-trifluoromethylphenoxy)phenyl)hexyl group, 1-(4-(4-trifluoromethoxyphenoxy)phenyl)ethyl group or the like.

A thiazolyl group (wherein, on the thiazole ring, at least one phenyl group may be substituted) includes a thiazolyl group (wherein, on the thiazole ring, 1 or 2 phenyl groups may be substituted), for example, (2-, 4- or 5-)thiazolyl group, 2-phenyl-(4- or 5-)thiazolyl group, 4-phenyl-(2- or 5-)thiazolyl group, 5-phenyl-(2- or 4-)thiazolyl group, 2,5-diphenyl-4-thiazolyl group, 2,4-diphenyl-5-thiazolyl group, 4,5-diphenyl-2-thiazolyl group.

A phenoxy C1-C6 alkyl group (wherein, on the phenyl ring, at least one selected from the group consisting of a phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted), a halogen atom, a halogen substituted or unsubstituted C1-C6 alkyl group and a halogen substituted or unsubstituted C1-C6 alkoxy group may be substituted) includes, in addition to a phenoxy C1-C6 alkyl group as described above (which may be substituted by at least one selected from the group consisting of a halogen atom, a halogen substituted or unsubstituted C1-C6 alkyl group and a halogen substituted or unsubstituted C1-C6 alkoxy group), a phenoxy C1-C6 alkyl group having a linear or branched alkyl group containing 1 to 6 carbon atoms on the alkyl moiety (wherein, on the phenyl ring, 1 to 3 substituents selected from the group consisting of a phenyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted), a halogen atom, a halogen substituted or unsubstituted C1-C6 alkyl group and a halogen substituted or unsubstituted C1-C6 alkoxy group may be substituted), for example, a 4-phenylphenoxymethyl group, 3-phenylphenoxymethyl group, 2-phenylphenoxymethyl group, 2,4-diphenylphenoxymethyl group, 2,4,6-triphenylphenoxymethyl group, 4-(4-trifluoromethoxyphenyl) phenoxymethyl group, 2-(3-trifluoromethylphenyl)phenoxymethyl group, 4-(2-fluorophenyl)phenoxymethyl group, 3-(4-chlorophenyl)phenoxymethyl group, 4-(4-methoxyphenyl)phenoxymethyl group, 3-(4-methylphenyl)phenoxymethyl group, 2-(3,4-methoxyphenyl)phenoxymethyl group, 4-(3,4-dimethylphenyl)phenoxymethyl group, 3-(3,4,6-trimethoxyphenyl)phenoxymethyl group, 2-(2,4,5-trimethylphenyl)phenoxymethyl group, 4-(3,4-dichlorophenyl) phenoxymethyl group, 2-(2,4,6-trifluorophenyl) phenoxymethyl group, 4-(3-chloro-4-trifluoromethoxyphenyl)phenoxymethyl group, 2-(4-phenylphenoxy)ethyl group, 2-(4-(2-fluorophenyl)phenoxy) ethyl group, 3-(2-(3,4-dimethoxyphenyl)phenoxy)propyl group, 4-(2-(2,4,5-trimethylphenyl)phenoxy)butyl group, 5-(4-(3-chloro-4-trifluoromethoxyphenyl)phenoxy)pentyl group, 6-(2-(3-trifluoromethylphenyl)phenoxy)hexyl group, 2-(4-(4-trifluoromethylphenyl)phenoxy)ethyl group, 2-(4-(4-trifluoromethoxyphenyl)phenoxy)ethyl group or the like.

A piperidyl group [wherein, on the piperidine ring, at least one selected from the group consisting of a phenoxy group (on the phenyl ring, at least one selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group may be substituted] includes, in addition the above-described pieridyl group, a piperidyl group [wherein, on the piperidine ring, at least one phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted], a piperidyl group [wherein, on the piperidine ring, 1 to 3 substituents selected from the group consisting of a phenoxy group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) and a phenyl C1-C6 alkyl group may be substituted), for example, a 4-benzyl-(1-, 2- or 3-)piperidyl group, 3-benzyl-(1-, 2-, 4-, 5- or 6-)piperidyl group, 2-benzyl-(1-, 3-, 4-, 5- or 6-)piperidyl group, 2,4-dibenzyl-(1-, 3-, 5- or 6-)piperidyl group, 2,3,4-tribenzyl-(1-, 5- or 6-)piperidyl group, 4-phenoxy-3-benzyl-(1-, 2-, 5- or 6-)piperidyl group or the like.

A benzofuryl C1-C6 alkyl group (wherein, on the benzofuran ring, at least one halogen substituted or unsubstituted C1-C6 alkyl group may be substituted) includes a benzofuryl C1-C6 alkyl group having a linear or branched alkyl group containing 1 to 6 carbon atoms on the alkyl moiety (wherein, on the benzofuran ring, 1 to 3 halogen substituted or unsubstituted C1-C6 alkyl groups may be substituted), for example, a ((2-, 3-, 4-, 5-, 6- or 7-)benzofuryl)methyl group, 1-((2-, 3-, 4-, 5-, 6- or 7-)benzofuryl)ethyl group, 2-((2-, 3-, 4-, 5-, 6- or 7-)benzofuryl)ethyl group, 3-((2-, 3-, 4-, 5-, 6- or 7-)benzofuryl)propyl group, 2-((2-, 3-, 4-, 5-, 6- or 7-)benzofuryl) propyl group, 4-((2-, 3-, 4-, 5-, 6- or 7-)benzofuryl)butyl group, 5-((2-, 3-, 4-, 5-, 6- or 7-)benzofuryl)pentyl group, 4-((2-, 3-, 4-, 5-, 6- or 7-)benzofuryl)pentyl group, 6-((2-, 3-, 4-, 5-, 6- or 7-)benzofuryl)hexyl group, 2-methyl-3-((2-, 3-, 4-, 5-, 6- or 7-)benzofuryl)propyl group, 1,1-dimethyl-2-((2-, 3-, 4-, 5-, 6- or 7-)benzofuryl)ethyl group, 2-trifluoromethyl-(3-, 4-, 5-, 6- or 7-)benzofurylmethyl group, 5-trifluoromethyl-(2-, 3-, 4-, 6- or 7-)benzofurylmethyl group, 4-methyl-(2-, 3-, 5-, 6- or 7-)benzofurylmethyl group, 2,4-dimethyl-(3-, 5-, 6- or 7-)benzofurylmethyl group, 2,4,6-trimethyl-(3-, 5- or 7-)benzofurylmethyl group, 4-trifluoromethyl-(2-, 3-, 5-, 6- or 7-)benzofurylmethyl group, 6-trifluoromethyl-(2-, 3-, 4-, 5- or 7-)benzofurylmethyl group or the like.

A piperidylcarbonyl C1-C6 alkyl group [wherein, on the piperidine ring, at least one phenoxy group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes a piperidylcarbonyl C1-C6 alkyl group having a linear or branched alkyl group containing 1 to 6 carbon atoms on the alkyl moiety (wherein, on the piperidine ring 1 to 3 phenoxy groups as described above) (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) is substituted, for example, (4-phenoxy-1-piperidylcarbonyl) methyl group, 2-(3-phenoxy-2-piperidylcarbonyl)ethyl group, 3-(2-phenoxy-3-piperidylcarbonyl)propyl group, 4-(1-phenoxy-4-piperidylcarbonyl)butyl group, 5-(4-phenoxy-1-piperidylcarbonyl)pentyl group, 6-(1-phenoxy-2-piperidylcarbonyl) hexyl group, 1-(4-trifluoromethoxyphenoxy)-4-piperidylcarbonylmethyl group, 4-(4-trifluoromethoxyphenoxy)-1-piperidylcarbonylmethyl group, 4-(4-trifluoromethylphenoxy)-1-piperidylcarbonylmethyl group, 4-(3-methoxyphenoxy)-1-piperidylcarbonylmethyl group, 1-(2-methylphenoxy)-4-piperidylcarbonylmethyl group, 4-(4-chlorophenoxy)-1-piperidylcarbonylmethyl group, 4-(3,4-di(trifluoromethoxy) phenoxy)-1-piperidylcarbonylmethyl group, 4-(2,4,6-tri (trifluoromethyl)phenoxy)-1-piperidylcarbonylmethyl group, 4-(3,4-dimethylphenoxy)-1-piperidylcarbonylmethyl group, 4-(2,4,6-trimethoxyphenoxy)-4-piperidylcarbonylmethyl group, 2-(3,4-dichlorophenoxy)-1-piperidylcarbonylmethyl group, 3-(2,4,6-tribromophenoxy)-1-piperidylcarbonylmethyl group, (1,2,6-triphenoxy-4-piperidylcarbonyl) methyl group, (2,4-diphenoxy-1-piperidylcarbonyl)methyl group or the like.

An oxazolyl C1-C6 alkyl group [wherein, on the oxazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes an oxazolyl C1-C6 alkyl group having a linear or branched alkyl group containing 1 to 6 carbon atoms on the alkyl moiety [wherein, on the oxazole ring, 1 or 2 phenyl groups as described above (wherein, on the phenyl ring, 1 to 5, preferably 1 to 3 substituents selected from the group consisting of a, halogen atom, a halogen substituted or unsubstituted C1-C6 alkyl group and a halogen substituted or unsubstituted C1-C6 alkoxy group may be substituted) may be substituted), for example, ((2-, 4-, or 5-)oxazolyl)methyl group, 1-((2-, 4- or 5-)oxazolyl)ethyl group, 2-((2-, 4- or 5-)oxazolyl)ethyl group, 3-((2-, 4- or 5-)oxazolyl) propyl group, 2-((2-, 4- or 5-)oxazolyl)propyl group, 4-((2-, 4- or 5-)oxazolyl)butyl group, 5-((2-, 4- or 5-)oxazolyl)pentyl group, 4-((2-, 4- or 5-)oxazolyl)pentyl group, 6-((2-, 4- or 5-)oxazolyl)hexyl group, 2-methyl-3-((2-, 4- or 5-)oxazolyl) propyl group, 1,1-dimethyl-2-((2-, 4- or 5-)oxazolyl)ethyl group, 4-(4-trifluoromethoxyphenyl)-(2- or 5-)oxazolylmethyl group, 4-(4-chlorophenyl)-(2- or 5-)oxazolylmethyl group, 4-(4-trifluoromethylphenyl)-(2- or 5-)oxazolylmethyl group, 4-(4-methylphenyl)-(2- or 5-)oxazolylmethyl group, 4-(4-methoxyphenyl)-(2- or 5-)oxazolylmethyl group, 4-(2,4-dichlorophenyl)-(2- or 5-)oxazolylmethyl group, 4-(2,4,6-trifluorophenyl)-(2- or 5-)oxazolylmethyl group, 2-(3,4-dimethylphenyl)-(4- or 5-)oxazolylmethyl group, 5-(3,4,6-trimethylphenyl)-(2- or 4-)oxazolylmethyl group, 2-(3,4-dimethoxyphenyl)-(4- or 5-)oxazolylmethyl group, 4-(2,4,6-trimethoxyphenyl)-(2- or 5-)oxazolylmethyl group, 4-(3-chloro-4-trifluoromethoxyphenyl)-(2- or 5-)oxazolylmethyl group, 2,4-diphenyl-5-oxazolylmethyl group, 4,5-diphenyl-2-oxazolylmethyl group, 2,5-diphenyl-5-oxazolylmethyl group or the like.

An isooxazolyl group [wherein, on the isooxazoline ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes an isooxazolyl group [wherein, on the isooxazoline ring, 1 or 2 phenyl groups as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, (3-, 4- or 5-)isooxazolyl group, 3-phenyl-(4- or 5-)isooxazolyl group, 4-phenyl-(3- or 5-)isooxazolyl group, 5-phenyl-(3- or 4-)isooxazolyl group, 3,4-diphenyl-5-isooxazolyl group, 3,5-diphenyl-4-isooxazolyl group, 4,5-diphenyl-3-isooxazolyl group, 3-(4-trifluorophenyl)-(4- or 5-)isooxazolyl group, 4-(4-chlorophenyl)-(3- or 5-)isooxazolyl group, 3-(4-trifluoromethylphenyl)-(4- or 5-)isooxazolyl group, 4-(4-methylphenyl)-(3- or 5-)isooxazolyl group, 3-(4-methoxyphenyl)-(4- or 5-)isooxazolyl group, 4-(2,4-dichlorophenyl)-(3- or 5-)isooxazolyl group, 3-(2,4,6-trifluorophenyl)-(4- or 5-)isooxazolyl group, 3-(3,4-diphenylmethyl)-(4- or 5-)isooxazolyl group, 5-(3,4,6-trimethylphenyl)-(3- or 4-)isooxazolyl group, 3-(3,4-dimethoxyphenyl)-(4- or 5-)isooxazolyl group, 4-(2,4,6- trimethoxyphenyl)-(3- or 5-)isooxazolyl group, 3-(3-chloro-4-trifluoromethoxyphenyl)-(4- or 5-)isooxazolyl group or the like.

A benzooxazolyl group (wherein, on the benzooxazole ring, at least one halogen atom may be substituted) includes a benzooxazolyl group (wherein, on the benzooxazole ring, 1 to 3 halogen atoms may be substituted), for example, a (2-, 4-, 5-, 6- or 7-)benzooxazolyl group, 5-chloro-(2-, 4-, 6- or 7-) benzooxazolyl group, 6-chloro-(2-, 4-, 5- or 7-)benzooxazolyl group, 5-fluoro(2-, 4-, 6- or 7-)benzooxazolyl group, 6-bromo-(2-, 4-, 5- or 7-)benzooxazolyl group, 5-iodo-(2-, 4-, 6- or 7-)benzooxazolyl group, 5,6-dichloro-(2-, 4- or 7-)benzooxazolyl group, 4,5,6-trifluoro-(2- or 7-)benzooxazolyl group, 5-fluoro-6-chloro-(2-, 4- or 7-)benzooxazolyl group or the like.

A benzoimidazolyl group [wherein, on the benzoimidazole ring, at least one selected from the group consisting of a halogen atom and a phenyl C1-C6 alkyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted) includes a benzoimidazolyl group [wherein, on the benzoimidazole ring, 1 to 3 substituents selected from the group consisting of a halogen atom and a phenyl C1-C6 alkyl group as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a (2-, 4-, 5-, 6- or 7-)benzoimidazolyl group, 1-(4-trifluoromethoxybenzyl)-5,6-dichloro-(2-, 4- or 7-)benzoimidazolyl group, 5-chloro-(1-, 2-, 4-, 6- or 7-)benzoimidazolyl group, 6-chloro-(1-, 2-, 4-, 5- or 7-)benzoimidazolyl group, 5-fluoro-(1-, 2-, 4-, 6- or 7-)benzoimidazolyl group, 6-bromo-(1-, 2-, 4-, 5- or 7-)benzoimidazolyl group, 5-iodo-(1-, 2-, 4-, 6- or 7-)benzoimidazolyl group, 5,6-dichloro-(1-, 2-, 4- or 7-)benzoimidazolyl group, 4,5,6-trifluoro-(1-, 2- or 7-)benzoimidazolyl group, 5-fluoro-6-chloro-(1-, 2-, 4- or 7-)benzoimidazolyl group, 1-benzyl-(2-, 4-, 5-, 6- or 7-)benzoimidazolyl group, 1-(4-trifluoromethylbenzyl)-(2-, 4-, 5-, 6- or 7-)benzoimidazolyl group, 1-(4-chlorobenzyl)-(2-, 4-, 5-, 6- or 7-)benzoimidazolyl group, 1-(3-methylbenzyl)-(2-, 4-, 5-, 6- or 7-)benzoimidazolyl group, 1-(2-methoxybenzyl)-(2-, 4-, 5-, 6- or 7-)benzoimidazolyl group, 1-(3,4-dimethylbenzyl)-(2-, 4-, 5-, 6- or 7-)benzoimidazolyl group, 1-(2,4,6-trimethylbenzyl)-(2-, 4-, 5-, 6- or 7-)benzoimidazolyl group, 1-(3,4-dimethoxybenzyl)-(2-, 4-, 5-, 6- or 7-)benzoimidazolyl group, 1-(2,4,5-trimethoxybenzyl)-(2-, 4-, 5-, 6- or 7-)benzoimidazolyl group, 1-(3,4-dichlorobenzyl)-(2-, 4-, 5-, 6- or 7-)benzoimidazolyl group, 1-(2,4,6-trifluorobenzyl)-(2-, 4-, 5-, 6- or 7-)benzoimidazolyl group, 1-(3-chloro-4-trifluoromethylbenzyl)-(2-, 4-, 5-, 6- or 7-)benzoimidazolyl group, (1,5-benzyl-(2-, 4-, 6- or 7-)benzoimidazolyl group, 1,5,6-tribenzyl-(2-, 4- or 7-)benzoimidazolyl group, or the like.

An imidazolyl group [wherein, on the imidazole ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is substituted] includes an imidazolyl group [wherein, on the imidazole ring, 1 or 2 phenyl groups as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) are substituted], for example, a 2-phenyl-(4- or 5-)imidazolyl group, 4-phenyl-(2- or 5-)imidazolyl group, 2,4-diphenyl-5-imidazolyl group, 2,4-diphenyl-5-imidazolyl group, 4,5-diphenyl-2-imidazolyl group, 2-(4-trifluoromethoxyphenyl)-(4- or 5-)imidazolyl group, 2-(4-trifluorophenyl)-(4- or 5-)imidazolyl group, 4-(4-chlorophenyl)-(2- or 5-)imidazolyl group, 4-(4-trifluoromethylphenyl)-(2- or 5-)imidazolyl group, 4-(4-methylphenyl)-2-imidazolyl group, 2-(4-methoxyphenyl)-(4- or 5-)imidazolyl group, 4-(2,4-dichlorophenyl)-(2- or 5-)imidazolyl group, 2-(2,4,6-trifluorophenyl)-(4- or 5-)imidazolyl group, 2-(3,4-diphenylmethyl)-(4- or 5-)imidazolyl group, 5-(3,4,6-trimethylphenyl)-(2- or 4-)imidazolyl group, 2-(3,4-dimethoxyphenyl)-(4- or 5-)imidazolyl group, 4-(2,4,6-trimethoxyphenyl)-(2- or 5-)imidazolyl group, 5-(3-chloro-4-trifluoromethoxyphenyl)-(2- or 4-)imidazolyl group or the like.

A phenylsulfinyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) is a phenylsulfinyl group unsubstituted or having 1 to 5, preferably 1 to 3 substituents selected from the group consisting of a halogen atom, a halogen substituted or unsubstituted C1-C6 alkyl group and a halogen substituted or unsubstituted C1-C6 alkoxy group as defined above, examples of which include a phenylsulfinyl group, 2-fluorophenylsulfinyl group, 3-fluorophenylsulfinyl group, 4-fluorophenylsulfinyl group, 2-chlorophenylsulfinyl group, 3-chlorophenylsulfinyl group, 4-chlorophenylsulfinyl group, 2-bromophenylsulfinyl group, 3-bromophenylsulfinyl group, 4-bromophenylsulfinyl group, 2-iodophenylsulfinyl group, 3-iodophenylsulfinyl group, 4-iodophenylsulfinyl group, 2,3-difluorophenylsulfinyl group, 3,4-difluorophenylsulfinyl group, 3,5-difluorophenylsulfinyl group, 2,4-difluorophenylsulfinyl group, 2,6-difluorophenylsulfinyl group, 2,3-dichlorophenylsulfinyl group, 3,4-dichlorophenylsulfinyl group, 3,5-dichlorophenylsulfinyl group, 2,4-dichlorophenylsulfinyl group, 2,6-dichlorophenylsulfinyl group, 3,4,5-trifluorophenylsulfinyl group, 3,4,5-trichlorophenylsulfinyl group, 2,4,6-trifluorophenylsulfinyl group, 2,4,6-trichlorophenylsulfinyl group, 2-fluoro-4-bromophenylsulfinyl group, 4-chloro-3-fluorophenylsulfinyl group, 2,3,4-trichlorophenylsulfinyl group, 2,3,4,5,6-pentafluorophenylsulfinyl group, 2,4,6-trimethylphenylsulfinyl group, 4-n-butylphenylsulfinyl group, 2,4-dimethylphenylsulfinyl group, 2,3-dimethylphenylsulfinyl group, 2,6-dimethylphenylsulfinyl group, 3,5-dimethylphenylsulfinyl group, 2,5-dimethylphenylsulfinyl group, 3,5-ditrifluoromethylphenylsulfinyl group, 4-n-butoxyphenylsulfinyl group, 2,4-dimethoxyphenylsulfinyl group, 2,3-dimethoxyphenylsulfinyl group, 2,6-dimethoxyphenylsulfinyl group, 3,5-dimethoxyphenylsulfinyl group, 2,5-dimethoxyphenylsulfinyl group, 2,4,6-trimethoxyphenylsulfinyl group, 3,5-ditrifluoromethoxyphenylsulfinyl group, 3-chloro-4-methoxyphenylsulfinyl group, 2-chloro-4-trifluoromethoxyphenylsulfinyl group, 3-methyl-4-fluorophenylsulfinyl group, 4-bromo-3-trifluoromethylphenylsulfinyl group, 2-methylphenylsulfinyl group, 3-methylphenylsulfinyl group, 4-methylphenylsulfinyl group, 2-methyl-3-chlorophenylsulfinyl group, 3-methyl-4-chlorophenylsulfinyl group, 2-chloro-4-methylphenylsulfinyl group, 2-methyl-3-fluorophenylsulfinyl group, 2-trifluoromethylphenylsulfinyl group, 3-trifluoromethylphenylsulfinyl group, 4-trifluoromethylphenylsulfinyl group, 2-pentafluoroethylphenylsulfinyl group, 3-pentafluoroethylphenylsulfinyl group, 4-pentafluoroethylphenylsulfinyl group, 2-isopropylphenylsulfinyl group, 3-isopropylphenylsulfinyl group, 4-isopropylphenylsulfinyl group, 2-tert-butylphenylsulfinyl group, 3-tert-butylphenylsulfinyl group, 4-tert-butylphenylsulfinyl group, 2-sec-butylphenylsulfinyl group, 3-sec-butylphenylsulfinyl group, 4-sec-butylphenylsulfinyl group, 2-n-heptafluoropropylphenylsulfinyl group, 3-n-heptafluoropropylphenylsulfinyl group, 4-n-heptafluoropropylphenylsulfinyl group, 4-n-pentylphenylsulfinyl group, 4-n-hexylphenylsulfinyl group, 2-methoxyphenylsulfinyl group, 3-methoxyphenylsulfinyl group, 4-methoxyphenylsulfinyl group, 3-chloro-2-methoxyphenylsulfinyl group, 2-fluoro-3-methoxyphenylsulfinyl group, 2-fluoro-4-methoxyphenylsulfinyl group, 2,3,4-trifluorophenylsulfinyl group, 2-trifluoromethoxyphenylsulfinyl group, 3-trifluoromethoxyphenylsulfinyl group, 4-trifluoromethoxyphenylsulfinyl group, 3-fluoro-2-trifluoromethoxyphenylsulfinyl group, 2-fluoro-3-trifluoromethoxyphenylsulfinyl group, 3-fluoro-4-trifluoromethoxyphenylsulfinyl group, 3-chloro-2-trifluoromethoxyphenylsulfinyl group, 2-chloro-3-trifluoromethoxyphenylsulfinyl group, 3-chloro-4-trifluoromethoxyphenylsulfinyl group, 2-pentafluoroethoxyphenylsulfinyl group, 3-pentafluoroethoxyphenylsulfinyl group, 4-pentafluoroethoxyphenylsulfinyl group, 3-chloro-2-pentafluoroethoxyphenylsulfinyl group, 2-chloro-3-pentafluoroethoxyphenylsulfinyl group, 3-chloro-4-pentafluoroethoxyphenylsulfinyl group, 2-isopropoxyphenylsulfinyl group, 3-isopropoxyphenylsulfinyl group, 4-isopropoxyphenylsulfinyl group, 2-tert-butoxyphenylsulfinyl group, 3-tert-butoxyphenylsulfinyl group, 4-tert-butoxyphenylsulfinyl group, 2-sec-butoxyphenylsulfinyl group, 3-sec-butoxyphenylsulfinyl group, 4-sec-butoxyphenylsulfinyl group, 2-n-heptafluoropropoxyphenylsulfinyl group, 3-n-heptafluoropropoxyphenylsulfinyl group, 4-n-heptafluoropropoxyphenylsulfinyl group, 4-n-pentoxyphenylsulfinyl group, 4-n-hexyloxyphenylsulfinyl group or the like.

A pyridyl C1-C6 alkyl group [wherein, on the pyridyl ring, at least one phenyl group (wherein, on the phenyl ring, at least one selected from the group consisting of a halogen atom, a halogen substituted or unsubstituted C1-C6 alkyl group and a halogen substituted or unsubstituted C1-C6 alkoxy group may be substituted) may be substituted] includes, in addition to a pyridyl C1-C6 alkyl group as described above, a pyridyl C1-C6 alkyl group having a linear or branched alkyl group containing 1 to 6 carbon atoms on the alkyl moiety [wherein, on the pyridine ring, 1 to 3 phenyl groups as described above (wherein, on the phenyl ring, 1 to 5, preferably 1 to 3 substituents selected from the group consisting of a halogen atom, a halogen substituted or unsubstituted C1-C6 alkyl group and a halogen substituted or unsubstituted C1-C6 alkoxy group may be substituted) may be substituted], for example, a 2-(4-trifluoromethoxyphenyl)-(3-, 4-, 5- or 6-)pyridylmethyl group, 2-(4-trifluoromethylphenyl)-(3-, 4-, 5- or 6-)pyridylmethyl group, 2-(4-methoxyphenyl)-(3-, 4-, 5- or 6-)pyridylmethyl group, 2-(4-methylphenyl)-(3-, 4-, 5- or 6-)pyridylmethyl group, 2-(3-chloro-4-fluorophenyl)-(3-, 4-, 5- or 6-)pyridylmethyl group, 2-(2,4-dimethoxyphenyl)-(3-, 4-, 5 or 6-)pyridylmethyl group, 2-(3,4,5-trimethoxyphenyl)-(3-, 4-, 5 or 6-)pyridylmethyl group, 2-(2,4-dimethylphenyl)-(3-, 4-, 5- or 6-)pyridylmethyl group, 2-(2,4,6-trimethylphenyl)-(3-, 4-, 5- or 6-)pyridylmethyl group, 2-(2,4,6-trichlorophenyl)-(3-, 4-, 5- or 6-)pyridylmethyl group, 2-(3-chloro-4-trifluoromethoxyphenyl)-(3-, 4-, 5- or 6-)pyridylmethyl group, 2,4,6-triphenyl-(3- or 5-)pyridylmethyl group, 2,5-diphenyl-(3-, 4- or 6-)pyridylmethyl group or the like.

A 4H-1,3-benzodioxinyl group (wherein, on the 4H-1,3-benzodioxine ring, at least one halogen atom may be substituted) includes a 4H-1,3-benzodioxinyl group (wherein, on the 4H-1,3-benzodioxine ring, 1 to 4 halogen atoms may be substituted), for example, a (2-, 4-, 5-, 6-, 7- or 8-)4H-1,3-benzodioxinyl group, 2,2,4,4-tetrafluoro-(5-, 6-, 7- or 8-)4H-1,3-benzodioxinyl group, 2-chloro-(2-, 4-, 5-, 6-, 7- or 8-)4H-1,3-benzodioxinyl group, 4-bromo-(2-, 4-, 5-, 6-, 7- or 8-)4H-1,3-benzodioxinyl group, 2,4-dichloro-(2-, 4-, 5-, 6-, 7- or 8-)4H-1,3-benzodioxinyl group, 2,4,6-trifluoro-(2-, 4-, 5-, 7- or 8-)4H-1,3-benzodioxinyl group or the like.

The methods for preparing the compounds of the present invention are explained in detail below.

Reaction scheme 1

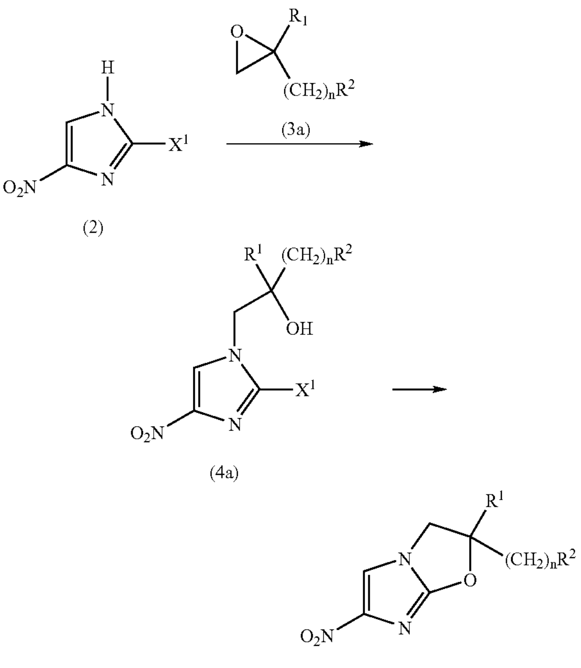

(2)
(3a)
(4a)
(1)

wherein $R^1$, $R^2$ and n are the same as above, and $X^1$ represents a halogen atom or nitro group.

According to reaction scheme 1, the compound of the present invention represented by general formula (1) is produced by reacting a 4-nitroimidazole compound represented by general formula (2) with an epoxy compound represented by general formula (3a) in the presence or absence of a basic compound to obtain a compound represented by general formula (4a), and then subjecting the obtained compound to a ring closure reaction.

The molar ratio of the compound of general formula (2) to the compound of general formula (3a) may be generally between 1:0.5 and 1:5, and preferably between 1:0.5 and 1:3.

Known compounds can be widely used as a basic compound herein. Examples of such a basic compound include inorganic basic compounds such as a metal hydride, metal alcoholate, hydroxide, carbonate or hydrogencarbonate, and organic basic compounds such as acetate.

Specific examples of a metal hydride include sodium hydride and potassium hydride. Specific examples of a metal alcoholate include sodium methoxide, sodium ethoxide and potassium tert-butoxide. Specific examples of a hydroxide include sodium hydroxide and potassium hydroxide. Specific examples of a carbonate include sodium carbonate and potassium carbonate. Specific examples of a hydrogencarbonate include sodium hydrogencarbonate and potassium hydrogencarbonate. In addition to the above compounds, sodium amide and the like may also be included in the inorganic basic compounds.

Specific examples of acetate include sodium acetate and potassium acetate. In addition to these compounds, specific examples of organic basic compounds include triethylamine, trimethylamine, diisopropyl-ethylamine, pyridine, dimethylaniline, 1-methyl-pyrrolidine, N-methylmorpholine, 1,5-diazabicyclo-[4.3.0]nonene-5(DBN), 1,8-diazabicyclo[5.4.0]undecene-7(DBU), and 1,4-diazabicyclo[2.2.2]octane (DABCO).

The molar ratio of the above basic compound to the compound of general formula (2) may be generally between 0.1:1 and 2:1, preferably between 0.1:1 and 1:1, and more preferably between 0.1:1 and 0.5:1.

The reaction of the compound of general formula (2) with the compound of general formula (3a) is generally carried out in an appropriate solvent.

Common solvents can be widely used as the above solvent, as long as it does not inhibit the reaction. Examples of such a solvent include aprotic polar solvents such as dimethylformamide (DMF), dimethylsulfoxide (DMSO) or acetonitrile, ketone solvents such as acetone or methylethylketone, hydrocarbon solvents such as benzene, toluene, xylene, tetralin or liquid paraffin, alcohol solvents such as methanol, ethanol, isopropanol, n-butanol or tert-butanol, ether solvents such as tetrahydrofuran (THF), dioxane, dipropyl ether, diethyl ether or diglyme, ester solvents such as ethyl acetate or methyl acetate, and mixed solvents thereof. Water may be contained in these solvents.

The reaction of the compound of general formula (2) with the compound of general formula (3a) is carried out, for example, as follows: The compound of general formula (2) is dissolved in a reaction solvent, and while stirring, a basic compound is added to the mixture cooled on ice or at up to room temperature (30° C.) Thereafter, the mixture is stirred at room temperature to 80° C. for 30 minutes to 1 hour, and the compound of general formula (3a) is then added thereto. Thereafter, the mixture is further stirred generally at room temperature to 100° C., and preferably 50° C. to 80° C., generally for 30 minutes to 60 hours, and preferably for 1 to 50 hours.

The compound (2) used as a starting material is known. The compound (3a) includes a novel compound, and a method for producing the compound will be explained later.

The compound of the present invention represented by general formula (1) is produced by subjecting the compound represented by general formula (4a) to a ring closure reaction. The ring closure reaction is carried out by dissolving the above obtained compound represented by general formula (4a) in a reaction solvent and then adding a basic compound thereto followed by stirring.

Herein, as a reaction solvent and a basic compound, there can be used the same reaction solvent and the same basic compound as used in the above reaction of the compound of general formula (2) with the compound of general formula (3a).

The molar ratio of the basic compound to the compound of general formula (4a) is generally equal to 1:1 or higher, preferably between 1:1 and 5:1, and more preferably between 1:1 and 2:1.

The reaction temperature for the ring closure reaction is generally 0° C. to 150° C., preferably room temperature to 120° C., and more preferably 50° C. to 100° C. The reaction time is generally 30 minutes to 48 hours, preferably 1 to 24 hours, and more preferably 1 to 12 hours.

In the present invention, the reaction mixture can be directly subjected to the following ring closure reaction without isolating the compound of general formula (4a) generated as a result of the reaction of the compound of general formula (2) with the compound of general formula (3a). For example, the compound of general formula (2) is reacted with the compound of general formula (3a) at room temperature to 80° C., and thereafter, a basic compound is added to the obtained reaction mixture followed by stirring at 50° C. to 100° C. Otherwise, after the compound of general formula (2) is reacted with the compound of general formula (3a) at room temperature to 80° C., the obtained reaction mixture is concentrated, and the residue is dissolved in a high boiling solvent. Thereafter, a basic compound is added to the obtained solution followed by stirring at 50° C. to 100° C., so as to produce a compound of interest represented by general formula (1).

Alternatively, in the reaction of the compound of general formula (2) with the compound of general formula (3a), a basic compound is used at a molar ratio of the basic compound to the compound (2) that is between 0.9:1 and 2:1. The stirring is carried out at 50° C. to 100° C., so that the reaction of the compound of general formula (2) with the compound of general formula (3a) is carried out in a single process to produce a compound of interest represented by general formula (1).

Reaction scheme 2

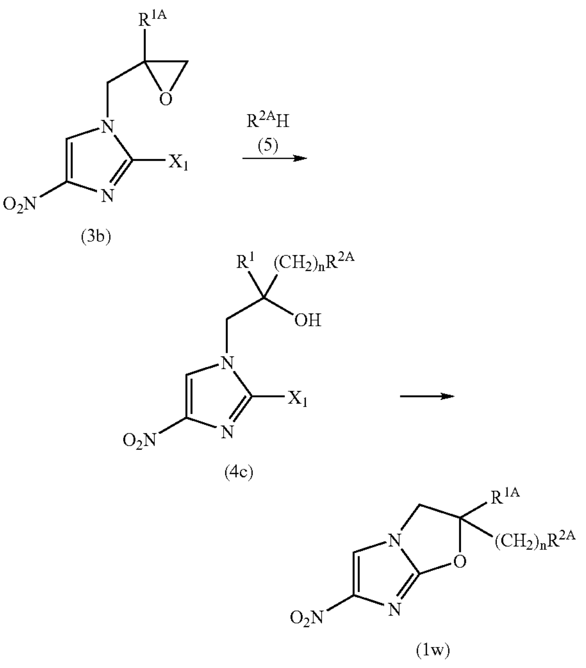

(3b)

(4c)

(1w)

wherein $X^1$ is the same as above, $R^{1A}$ represents a hydrogen atom or a C1-6 alkyl group and $R^{2A}$ represents a group of (a) to (y) as defined above.

According to reaction scheme 2, the compound of the present invention represented by general formula (1w) is produced by reacting a compound represented by general formula (3b) with a compound represented by general formula (5) or a salt thereof, so as to obtain a compound represented by general formula (4c), and then subjecting the obtained compound represented by general formula (4c) to a ring closure reaction, in the presence of a basic compound.

The compound (3b) is novel, and a method for producing the compound will be explained later (reaction scheme 6). Further, the compound (5) includes a novel compound. An example of methods for producing the above compound will be described later in Reference Example 2.

The molar ratio of the compound of general formula (3b) to the compound of general formula (5) may be generally between 1:0.5 and 1:5, and preferably between 1:0.5 and 1:2.

The reaction of the compound of general formula (3b) with the compound of general formula (5) is carried out in the presence of a basic compound in an appropriate solvent.

As a basic compound and a reaction solvent, there can be used the same basic compound and the same reaction solvent as used in the above reaction of the compound of general formula (2) with the compound of general formula (3a). The molar ratio of the basic compound to the compound of general formula (3b) is generally a catalytic amount, preferably between 0.1:1 and 3:1, and more preferably between 0.1:1 and 2:1.

The salt of the compound (5) can be used instead of using the compound (5) and a basic compound. Examples of such a salt include alkali metal salts such as a sodium salt or a potassium salt of the compound (5).

The reaction of the compound of general formula (3b) with the compound of general formula (5) is carried out, generally at room temperature to 150° C., preferably at room temperature to 120° C., and more preferably at room temperature to 80° C. The reaction time is generally 10 minutes to 48 hours, preferably 10 minutes to 24 hours, and more preferably 10 minutes to 2 hours.

The compound of the present invention represented by general formula (1w) is produced by subjecting the compound represented by general formula (4c) to a ring closure reaction. The ring closure reaction is carried out by dissolving the above obtained compound represented by general formula (4c) in a reaction solvent and then adding a basic compound thereto followed by stirring at a certain temperature.

Herein, as a reaction solvent and a basic compound, there can be used the same reaction solvent and the same basic compound as used in the above reaction of the compound of general formula (3b) with the compound of general formula (5).

The molar ratio of the basic compound to the compound of general formula (4c) is generally equal to 1:1 or higher, preferably between 1:1 and 5:1, and more preferably between 1:1 and 2:1.

The reaction temperature for the ring closure reaction is generally 0° C. to 150° C., preferably room temperature to 120° C., and more preferably 50° C. to 100° C. The reaction time is generally 10 minutes to 48 hours, preferably 10 minutes to 24 hours, and more preferably 20 minutes to 4 hours.

In the present invention, the reaction mixture can be directly subjected to the following ring closure reaction without isolating the compound of general formula (4c) generated as a result of the reaction of the compound of general formula (3b) with the compound of general formula (5), so as to produce a compound of interest that is the compound of the present invention represented by general formula (1w).

If a basic compound is used to the compound (5) at a molar ratio of equal to 1:1 or higher and the reaction is carried out at 50° C. to 100° C., the compound of the present invention represented by general formula (1w) can be produced in a single process without isolating an intermediate (4c). In the case of using the alkali metal salt (e.g., a sodium salt or a potassium salt) of the compound (5), the same thing can be said.

Reaction scheme 3

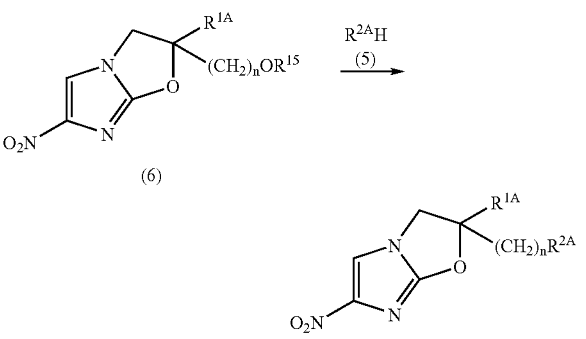

(6)

(1w)

wherein $R^{1A}$, $R^{2A}$ and n are the same as above, and $R^{15}$ represents a C1-6 alkylsulfonyl group, or a benzenesulfonyl group which may be substituted C1-6 alkyl group on the benzene ring.

Herein, a C1-6 alkylsulfonyl group is a group consisting of an alkyl group having 1 to 6 carbon atoms and a sulfonyl group, and example of a C1-6 alkylsulfonyl group includes a methanesulfonyl group, ethanesulfonyl group, propanesulfonyl group, butanesulfonyl group, pentanesulfonyl group, hexanesulfonyl group and the like.

Examples of a benzenesulfonyl group which may be substituted C1-6 alkyl group on the benzene ring includes a benzenesulfonyl group which may have 1 to 3 C1-6 alkyl groups on the benzene ring, such as a benzenesulfonyl group, o-toluenesulfonyl group, m-toluenesulfonyl group, p-toluenesulfonyl group, 2-ethylbenzenesulfonyl group, 3-ethylbenzenesulfonyl group, 4-ethylbenzenesulfonyl group, 2-propyl-benzenesulfonyl group, 3-propylbenzenesulfonyl group, 4-propylbenzenesulfonyl group, 2,3-dimethyl-benzenesulfonyl group, 2,4-dimethylbenzenesulfonyl group, 2,4,6-trimethylbenzenesulfonyl group and the like.

The reaction of the compound (6) with the compound represented by general formula (5) is carried out in an appropriate solvent in the presence of a basic compound.

Any known solvent can be used herein, as long as it does not inhibit the present reaction. Examples of such a solvent include water, aprotic polar solvents such as DMF, DMSO or acetonitrile, hydrocarbon solvents such as benzene, toluene, xylene, tetralin, liquid paraffin or cyclohexane, alcohol solvents such as ethanol, isopropanol, n-butanol or tert-butanol, ether solvents such as THF, dioxane, dipropyl ether, diethyl ether or diglyme, ethyl acetate, acetone, and mixed solvents thereof.

As a basic compound, there can be used the same basic compound as used in the above reaction of the compound of general formula (2) with the compound of general formula (3a).

The molar ratio of the basic compound to the compound (6) is generally equal to 1:1 or higher, preferably between 1:1 and 5:1, and more preferably between 1:1 and 2:1.

The molar ratio of the compound represented by general formula (5) to the compound (6) may be generally equal to 1:1 or higher, preferably between 0.9:1 and 2:1, and more preferably between 0.9:1 and 1.5:1.

The reaction temperature is generally room temperature to 150° C., preferably room temperature to 100° C., and more preferably 60° C. to 100° C. The reaction time is generally 10 minutes to 24 hours, preferably 10 minutes to 12 hours, and more preferably 20 minutes to 7 hours.

Next, the methods for preparing the starting materials and intermediates to obtain the compounds of the present invention are explained.

Reaction scheme 4

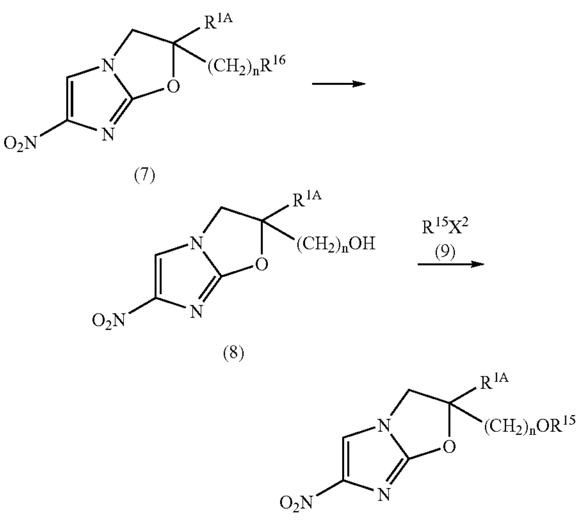

(7)

(8)

(6)

wherein $R^{1A}$, $R^{15}$ and n are the same as above, $R^{16}$ represents a C1-6 alkoxy-C1-6 alkoxyl group or a C1-6 alkanoyloxy group, and $X^2$ represents a halogen atom.

A compound of general formula (8) is produced by the hydrolysis of a compound of general formula (7).

Hydrolysis of the compound (7) is carried out under acidic conditions. The hydrolysis is carried out, for example, by suspending or dissolving the compound (7) in an appropriate solvent, and adding acid to the obtained solution followed by stirring at 0° C. to 120° C. Example of the used solvent may include water, alcohol solvents such as methanol, ethanol, isopropanol or ethylene glycol, acetonitrile, acetone, toluene, DMF, DMSO, acetic acid, trifluoroacetic acid, and mixed solvents thereof. Examples of the used acid may include organic acids such as trifluoroacetic acid or acetic acid, and inorganic acids such as hydrochloric acid, bromic acid, hydrobromic acid or sulfuric acid. Organic acids such as trifluoroacetic acid or acetic acid can also be used as reaction solvents. The reaction temperature is generally 0° C. to 120° C., preferably room temperature to 100° C., and more preferably room temperature to 80° C. The reaction time is generally 30 minutes to 24 hours, preferably 30 minutes to 12 hours, and more preferably 1 to 8 hours.

Hydrolysis of the compound (7) can be carried out under basic condition. The hydrolysis is carried out, for example, by suspending or dissolving the compound (7) in an appropriate solvent, and adding base to the obtained solution followed by stirring at 0° C. to 120° C. Example of the used solvent may include water, alcohol solvents such as methanol, ethanol, isopropanol or ethylene glycol, and mixed solvents thereof. Examples of the used base may include alkali metal hydroxides such as sodium hydroxide or potassium hydroxide, alkali metal carbonates such as sodium carbonate or potassium carbonate, and acetates such as sodium acetate. The reaction temperature is generally 0° C. to 120° C., preferably room temperature to 100° C., and more preferably room temperature to 80° C. The reaction time is generally 30 minutes to 24 hours, preferably 30 minutes to 12 hours, and more preferably 1 to 8 hours.

For the reaction of the compound (8) with the compound (9), the reaction conditions for the common sulfonylation reaction of alcohol can be widely applied. For example, the compound (8) is dissolved in an appropriate solvent, and the compound (9) is added to the obtained solution in the presence of a basic compound followed by stirring at 0° C. to 150° C., so that the compound (6) can be obtained.

Any known solvent can be used herein, as long as it does not inhibit the sulfonylation reaction. Examples of such a solvent include halogenated hydrocarbon solvents such as methylene chloride or chloroform, aprotic polar solvents such as DMF, DMSO or acetonitrile, aromatic hydrocarbon solvents such as benzene, toluene or xylene, hydrocarbon solvents such as tetralin, liquid paraffin or cyclohexane, ether solvents such as THF, dioxane, dipropyl ether, diethyl ether or diglyme, ethyl acetate, acetone, and mixed solvents thereof.

The compound (9) is used to the compound (8) at a molar ratio of generally equal to 1:1 or higher, preferably between 1:1 and 2:1, and more preferably between 1:1 and 1.1:1.

As a basic compound, there can be used the same basic compound as used in the above reaction of the compound of general formula (2) with the compound of general formula (3a).

The molar ratio of the basic compound to the compound (8) is generally equal to 1:1 or higher, preferably between 1:1 and 5:1, and more preferably between 1:1 and 2:1.

In the present sulfonylation reaction, 4-dimethylaminopyridine, 4-(1-pyrrolidinyl)pyridine or the like can be used as a catalyst.

The reaction temperature is generally 0° C. to 150° C., preferably 0° C. to 100° C., and more preferably 0° C. to 60° C. The reaction time is generally 30 minutes to 48 hours, preferably 1 to 24 hours, and more preferably 1 to 4 hours.

Reaction scheme 5

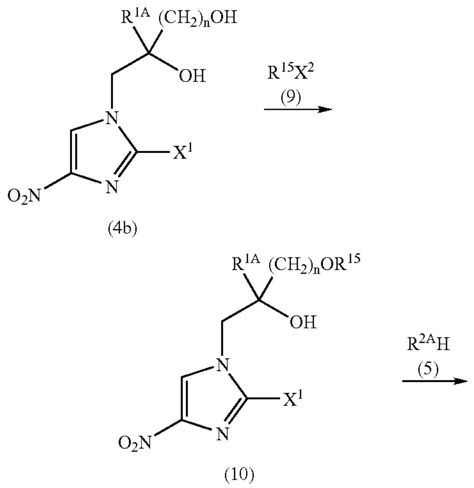

(4b)

(10)

-continued

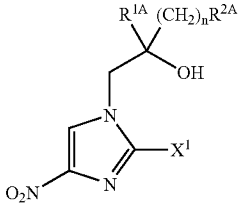

(4c)

wherein $R^{1A}$, $R^{2A}$, $R^{15}$, $X^1$ and n are the same as above.

A reaction to lead from the compound (4b) into a compound (10) is carried out, for example, under the same reaction conditions for the reaction to lead from the compound (8) into the compound (6) as shown in reaction scheme 4.

A reaction to lead from the compound (10) into a compound (4c) is carried out, for example, under the same reaction conditions for the reaction to lead from the compound (6) into the compound (1w) as shown in reaction scheme 3.

Reaction scheme 6

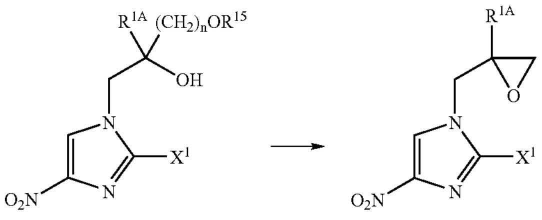

(10a) (3b)

wherein $R^{1A}$, $R^{15}$ and $X^1$ are the same as above.

A reaction to lead from a compound (10a) into a compound (3b) is carried out in an appropriate solvent in the presence of a basic compound.

Any solvent can be widely used herein, as long as it does not inhibit the reaction. Examples of such a solvent may include aprotic polar solvents such as DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

The same basic compound as used in the reaction of the compound represented by the above general formula (2) with the compound represented by the above general formula (3a) can be used herein.

The molar ratio of such a basic compound to the compound (10a) may be generally equal to 1:1 or higher, preferably between 1:1 and 5:1, and more preferably between 1:1 and 2:1.

The reaction temperature for this reaction is generally 0° C. to 150° C., preferably 0° C. to 100° C., and more preferably 0° C. to 60° C. The reaction time is generally 30 minutes to 48 hours, preferably 1 to 24 hours, and more preferably 1 to 4 hours.

Reaction scheme 7

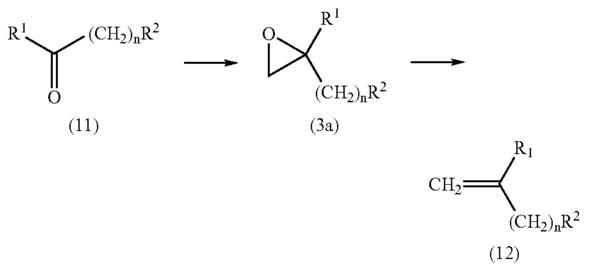

wherein $R^1$, $R^2$ and n are the same as above.

A reaction to lead from a compound (11) into a compound (3a) is carried out, for example, by treating the compound (11) with trimethylsulfoxonium iodide in an appropriate solvent in the presence of a basic compound.

Any solvent can be widely used herein, as long as it does not inhibit the reaction. Examples of such a solvent may include aprotic polar solvents such as DMSO or acetonitrile, hydrocarbon solvents such as benzene, toluene, xylene, tetralin or liquid paraffin, ether solvents such as THF, dioxane, dipropyl ether, diethyl ether or diglyme, and mixed solvents thereof.

Examples of a basic compound may include sodium hydride, sodium amide, metal alcoholates such as sodium methoxide, sodium ethoxide or potassium tert-butoxide.

The molar ratio of such a basic compound to the compound (11) may be generally equal to 1:1 or higher, preferably between 1:1 and 3:1, and more preferably between 1:1 and 1.5:1.

Moreover, the molar ratio of trimethyl-sulfoxonium iodide to the compound (11) may be generally equal to 1:1 or higher, preferably between 1:1 and 3:1, and more preferably between 1:1 and 1.5:1.

The reaction temperature for this reaction is generally 0° C. to 80° C., preferably 10° C. to 50° C., and more preferably 20° C. to 35° C. The reaction time is generally 1 to 24 hours, preferably 1 to 12 hours, and more preferably 1 to 4 hours.

A reaction to lead from a compound (12) into the compound (3a) is carried out, for example, by treating the compound (12) with peroxide in an appropriate solvent.

Any reaction solvent can be widely used herein, as long as it does not inhibit the reaction. Examples of such a solvent may include water, alcohol solvents such as methanol or ethanol, aprotic polar solvents such as DMF, DMSO or acetonitrile, hydrocarbon solvents such as benzene, toluene, xylene, tetralin, liquid paraffin or cyclohexane, halogenated hydrocarbon solvents such as methylene chloride, chloroform or dichloroethane, ether solvents such as THF, dioxane, dipropyl ether, diethyl ether or diglyme, and mixed solvents thereof.

Examples of peroxide include metachloro-perbenzoic acid (mCPBA), perbenzoic acid, peracetic acid and hydrogen peroxide.

The molar ratio of such peroxide to the compound (12) may be generally between 1:1 and 2:1, preferably between 1:1 and 1.5:1, and more prefer-ably between 1:1 and 1.3:1.

The reaction temperature for this reaction is generally 0° C. to 80° C., preferably 0° C. to 50° C., and more preferably 20° C. to 35° C. The reaction time is generally 10 minutes to 24 hours, preferably 1 to 12 hours, and more preferably 1 to 8 hours.

For example, one type of the compounds (3a) being optically active is produced from the compound (12) as follows.

Such an optically active compound (3a) can be produced by what is called Sharpless epoxidation. This is to say, the compound can be produced by epoxidation with cumene hydroperoxide or tert-butyl hydroperoxide, in the coexistence of Ti (O-iso-$C_3H_7$)$_4$ and optically active C1-C6 alkyl tartarate such as diethyl tartarate (D- or L-form) as catalysts, instead of using a peroxide in the above reaction to lead from the compound (12) into the compound (3a).

Any solvent can be widely used herein, as long as it does not inhibit the reaction. Examples of such a solvent may include aprotic polar solvents such as acetonitrile, hydrocarbon solvents such as benzene, toluene, xylene, tetralin, liquid paraffin or cyclohexane, halogenated hydrocarbon solvents such as methylene chloride, chloroform or dichloroethane, ether solvents such as THF, dioxane, dipropyl ether, diethyl ether or diglyme, and mixed solvents thereof.

The molar ratio of cumene hydroperoxide or tert-butyl hydroperoxide to the compound (6) may be generally between 0.1:1 and 2:1, preferably between 0.1:1 and 1.5:1, and more preferably between 0.1:1 and 1:1.

The molar ratio of Ti(O-iso-$C_3H_7$)$_4$ to the compound (12) may be generally between 0.1:1 and 2:1, preferably between 0.1:1 and 1.5:1, and more preferably between 0.1:1 and 1:1.

The molar ratio of optically active C1-C6 tartarates (D- or L-form) to the compound (12) may be generally between 1:1 and 2:1, preferably between 1:1 and 1.5:1, and more preferably between 1:1 and 1.3:1.

The reaction temperature for this reaction is generally −50° C. to 30° C., preferably −20° C. to 20° C., and more preferably −20° C. to 5° C. The reaction time is generally 1 to 48 hours, preferably 4 to 24 hours, and more preferably 4 to 12 hours.

Reaction scheme 8

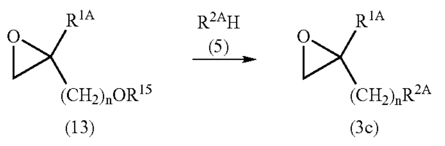

(13) (3c)

wherein $R^{1A}$, $R^{2A}$, $R^{15}$ and n are the same as above.

A reaction to lead from a compound (13) into a compound (3c) is carried out, for example, under the same reaction conditions for the reaction to lead from the compound (6) into the compound (1w) as shown in reaction scheme 3.

Reaction scheme 9

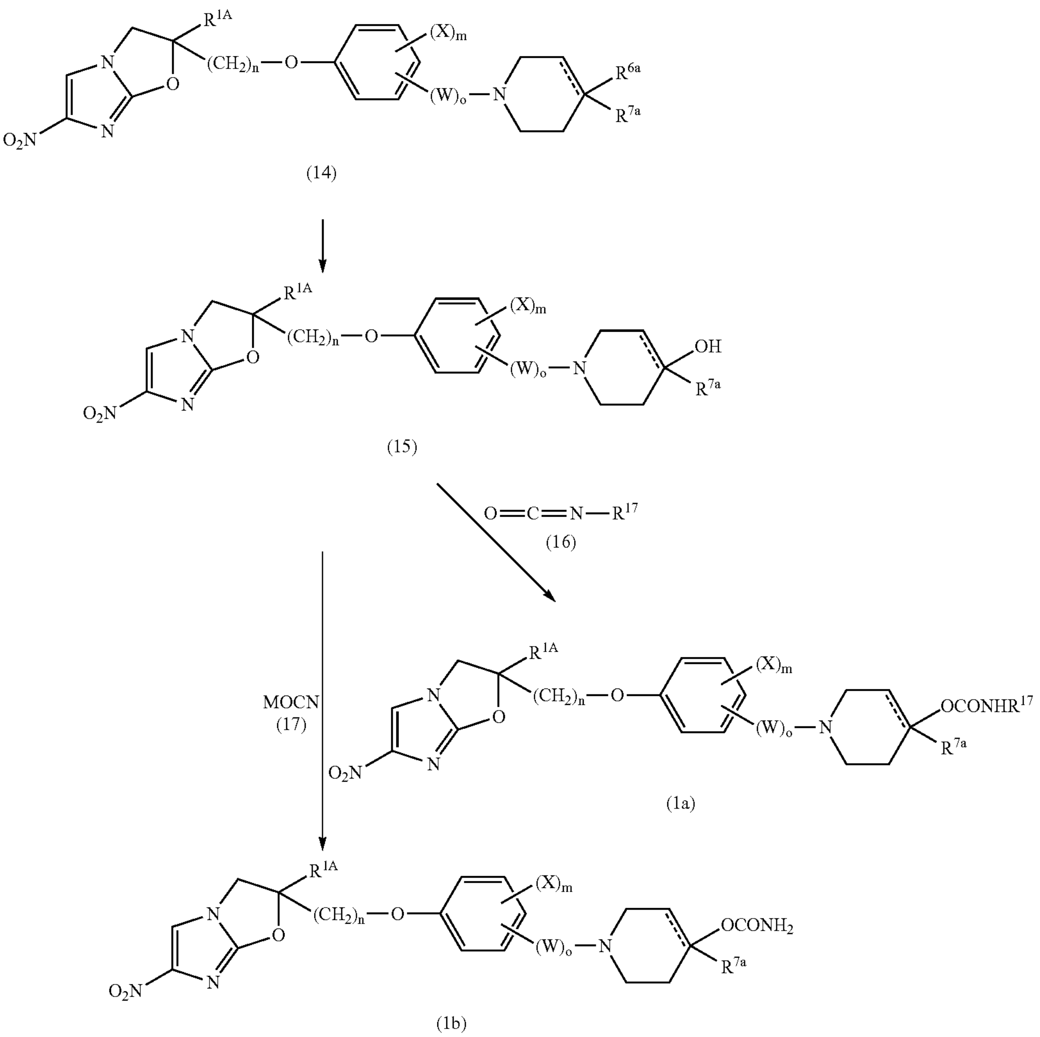

(14)

(15)

(1a)

(1b)

(wherein $R^{1A}$, X, n, m, W and o are the same as above. $R^{7a}$ represents a hydrogen atom, hydroxyl group, C1-6 alkoxy group or phenyl group (which may be substituted with a halogen atom(s) on the phenyl ring). The dotted line on the piperidine ring represents a bond which may be a double bond. When the dotted line is a double bond, a hydroxyl group should be substituted on the piperidine ring. $R^{6a}$ represents a tetrahydropyranyl group. $R^{17}$ represents a C1-6 alkyl group or phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring). M represents an alkali metal such as sodium, potassium, etc.).

A reaction to lead from a compound (14) into a compound (15) is carried out in the presence or absence of an appropriate solvent in the presence of an acid.

Any solvent can be widely used herein, as long as it does not affect the reaction. Examples of such a solvent may include water, halogenated hydrocarbons such as dichloromethane, chloroform or carbon tetrachloride, lower alcohols such as methanol, ethanol or isopropanol, ketones such as acetone or methyl ethyl ketone, ethers such as dioxane, tetrahydrofuran, ethylene glycol monomethyl ether or ethylene glycol dimethyl ether, aliphatic acids such as formic acid or acetic acid, an mixed solvents thereof.

Examples of such an acid may include, for example, mineral acids such as hydrochloric acid, sulfuric acid or hydrobromic acid, organic acids such as formic acid, trifluoroacetic acid or acetic acid, or aromatic sulfonic acids such as pyridinium p-toluenesulfonic acid, p-toluenesulfonic acid or the like. Although the amount of such an acid used may be suitably selected from a wide range without any particular limitation, it may be generally about 0.1-10 moles to 1 mole of the usual compound (14), preferably about 0.1-2 moles.

The reaction proceeds suitably at generally about 0-200° C., preferably room temperature to about 150° C., and is generally completed in about 0.5-50 hours.

The reaction of the compound (15) with compound (16) or (17) may be carried out in the presence or absence of a basic compound, preferably in its absence in an appropriate inert solvent or without any solvent.

Examples of a basic compound used herein include, for example, organic bases such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU) or 1,4-diazabicyclo[2.2.2]octane (DABCO), and inorganic bases including carbonates such as sodium carbonate, potassium carbonate, sodium hydrogencarbonate or potassium hydrogencarbonate, metal hydroxides such as sodium hydroxide, potassium hydroxide or calcium hydroxide, potassium hydride, sodium hydride, potassium, sodium, sodium amide, metallic alcoholates such as sodium methylate or sodium ethylate, or the like.

Examples of a solvent used include, for example, halogenated hydrocarbons such as chloroform, dichloromethane, dichloroethane or carbon tetrachloride, aromatic hydrocarbons such as benzene, toluene or xylene, ethers such as diethyl ether, diisopropyl ether, tetrahydrofuran or dimethoxyethane, esters such as methyl acetate, ethyl acetate or isopropyl acetate, alcohols such as methanol, ethanol, isopropanol, propanol, butanol, 3-methoxy-1-butanol, ethylcellosolve or methylcellosolve, and aprotic polar solvents such as acetonitrile, pyridine, acetone, water, N,N-dimethylacetamide, N,N-dimethylformamide, dimethylsulfoxide or hexamethylphosphoric triamide or mixed solvents thereof.

The molar ratio of the compound (16) or (17) to the compound (15) may be generally between about 1:1 and 5:1 each, preferably between about 1:1 and 3:1.

The reaction is performed generally at the temperature of about 0-200° C., preferably room temperature to around 150° C. generally for about 5 minutes to 30 hours required.

In the reaction system, boron compounds such as boron trifluoride etherate complex and halogenated copper compounds such as copper(I) chloride may be added.

In the reaction of the compound (15) with the compound (17), it proceeds advantageously when an organic acid such as trifluoroacetic acid is added in the reaction system.

Reaction scheme 10

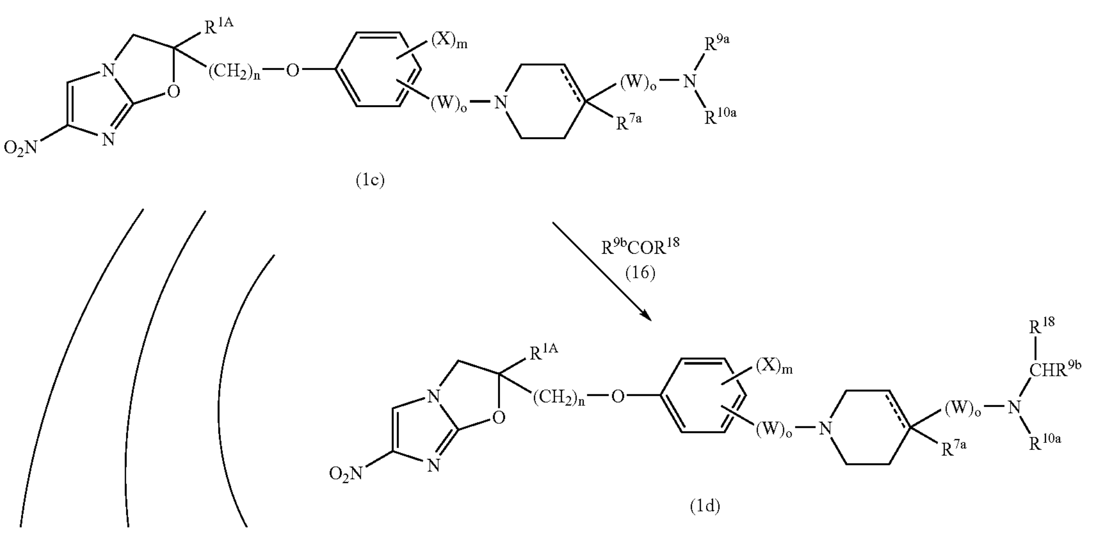

-continued

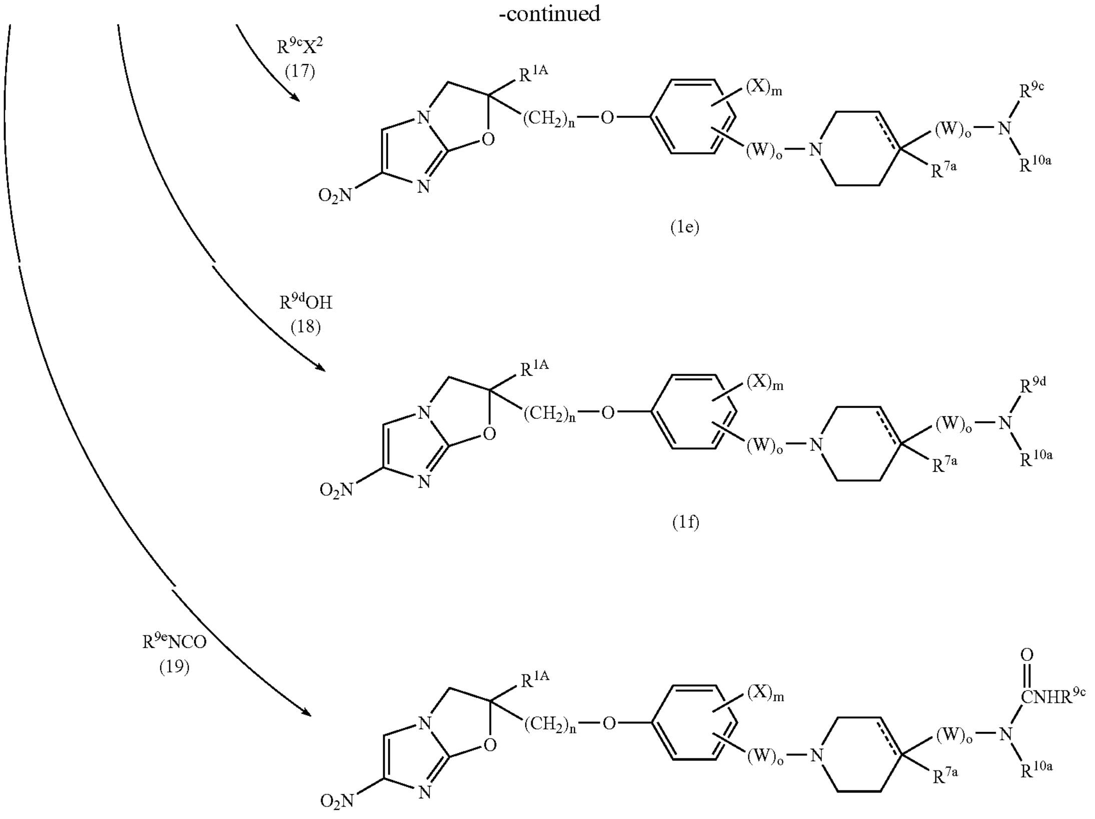

(1e)

(1f)

(1g)

(wherein $R^{1A}$, X, n, m, W, $R^{7a}$, $X^2$ and o are the same as above. Two Ws in general formulas (1c) to (1 g) may be same or different. $R^{9a}$ represents a hydrogen atom.)

$R^{10a}$ represents a hydrogen atom; C1-6 alkyl group which may have a hydroxyl group as a substituent; C1-6 alkanoyl group; C1-6 alkoxycarbonyl group; phenyl C1-6 alkoxycarbonyl group (which may be substituted with at least one of groups selected from the group consisting of a halogen atom, halogen-substituted or unsubstituted C1-6 alkyl group and halogen-substituted or unsubstituted C1-6 alkoxy group, as a substituent on the phenyl ring); phenyl group (wherein, on the phenyl ring, at least one selected from the group consisting of a halogen atom, halogen-substituted or unsubstituted C1-6 alkyl group, halogen-substituted or unsubstituted C1-6 alkoxy group, amino group which may have a group selected from the group consisting of a C1-6 alkanoyl group and C1-6 alkyl group as a substituent, C1-6 alkoxycarbonyl group, phenyl group, phenoxy group (wherein, on the phenyl ring, at least one selected from the group consisting of a halogen atom, halogen-substituted or unsubstituted C1-6 alkyl group and halogen-substituted or unsubstituted C1-6 alkoxy group, may be substituted), aminosulfonyl group, 1,2,3,4-tetrahydroquinolyl group (which may be substituted with at least one oxo group as substituent on the 1,2,3,4-tetrahydroquinoline ring), C1-6 alkylsulfonyl group, C3-8 cycloalkyl group, nitro group, cyano group, C1-6 alkylthio group, phenylsulfonyl group (which may be substituted with at least one selected from the group consisting of a halogen atom, halogen-substituted or unsubstituted C1-6 alkyl group and halogen-substituted or unsubstituted C1-6 alkoxy group, as a substituent on the phenyl ring), hydroxyl group-substituted C1-6 alkyl group and a group:

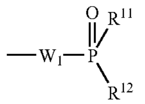

(wherein $W_1$ represents a C1-6 alkylene group. $R^{11}$ and $R^{12}$ represent a C1-6 alkoxy group which may be same or different) may be substituted); a phenyl C1-6 alkyl group (wherein, on the phenyl ring at least one selected from the group consisting of a C1-4 alkylene dioxy group, phenyl group (which may be substituted with at least one selected from the group consisting of a halogen atom, halogen-substituted or unsubstituted C1-6 alkyl group, halogen-substituted or unsubstituted C1-6 alkoxy group on the phenyl ring), group $—N(R^{11A})R^{12A}$($R^{11A}$ and $R^{12A}$ represent a hydrogen atom, C1-6 alkyl group or phenyl group which may be same or different, and $R^{11A}$ and $R^{12A}$ may be combined each other together with an adjacent nitrogen atom through a nitrogen atom, oxygen atom or sulfur atom or not through them to form a 5- to 7-membered saturated heterocycle), phenoxy group (which may be substituted with at least one selected from the group consisting of a halogen atom, halogen-substituted or unsubstituted C1-6 alkyl group, halogen-substituted or unsubstituted C1-6 alkoxy group on the phenyl ring), phenyl C1-6 alkoxy group, C1-6 alkoxy group substituted with an amino group which may have a C1-6 alkyl group as a substituent, halogen atom, halogen-substituted or unsubstituted C1-6 alkyl group, and halogen-substituted or unsubstituted $C_{1-10}$ alkoxy group, may be substituted as a substituent); benzofuryl C1-6 alkyl group (which may be substituted with at least one selected from the group consisting of a halogen atom, halogen-substituted or unsubstituted C1-6 alkyl group, halogen-substituted or unsubstituted C1-6 alkoxy group on the benzofuran ring); phenylsulfonyl group (which may be substituted with at least one selected from the group consisting of a halogen atom, halogen-substituted or unsubstituted C1-6 alkyl group, halogen-substituted or unsubstituted C1-6 alkoxy group and C1-4 alkylenedioxy group on the phenyl ring); phenoxydicarbonyl group (which may be substituted with at least one selected from the group consisting of a halogen atom, halogen-substituted or unsubstituted C1-6 alkyl group and halogen-substituted or unsubstituted C1-6 alkoxy group, as a substituent on the phenyl ring); phenyl $C_{2-6}$ alkenyl group (which may be substituted with at least one selected from the group consisting of a halogen atom, halogen-substituted or unsubstituted C1-6 alkyl group and halogen-substituted or unsubstituted C1-6 alkoxy group on the phenyl ring); C1-6 alkoxy-substituted C1-6 alkyl group; C2-6 alkenyl group; C1-6 alkoxy-substituted C2-6 alkanoyl group; C3-8 cycloalkyl-substituted C1-6 alkyl group; phenoxy C1-6 alkyl group (which may be substituted with at least one selected from the group consisting of a halogen atom, halogen-substituted or unsubstituted C1-6 alkyl group and halogen-substituted or unsubstituted C1-6 alkoxy group on the phenyl ring); benzoyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring); phenylcarbamoyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring); pyridyl group; pyridyl C1-6 alkyl group; imidazolyl C1-6 alkyl group; 1,2,3,4-tetrahydroquinolyl group (which may be substituted with at least one group selected from the group consisting of an oxo group and C1-6 alkyl group as substituent on the 1,2,3,4-tetrahydroquinoline ring); quinolyl group; indolyl group; amino group which may have a C1-6 alkyl group as a substituent; indazolyl group; naphthyl group; C3-8 cycloalkyl group; amino-substituted C1-6 alkyl group which may have a C1-6 alkyl group as a substituent; cyano group-substituted C1-6 alkyl group; furyl group C1-6 alkyl group; group:

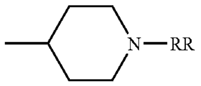

(wherein RR presents a phenyl group (which may be substituted with at least one of groups selected from the group consisting of a halogen atom, halogen-substituted or unsubstituted C1-6 alkyl group and halogen-substituted or unsubstituted C1-6 alkoxy group, as a substituent on the phenyl ring)); or piperazinyl-substituted C1-6 alkyl group (which may be substituted with at least one phenyl group (which may be substituted with at least one selected from the group consisting of a halogen atom, halogen-substituted or unsubstituted C1-6 alkyl group and halogen-substituted or unsubstituted C1-6 alkoxy group on the phenyl ring) as a substituent on the piperazine ring).

$R^{9b}$ represents a hydrogen atom; C1-6 alkyl group which may have a hydroxy group as a substituent; phenyl group (which may be substituted with at least one selected from the group consisting of a C1-4 alkylenedioxy group, phenyl group (which may be substituted with at least one selected from the group consisting of a halogen atom, halogen-substituted or unsubstituted C1-6 alkyl group and halogen-substituted or unsubstituted C1-6 alkoxy group on the phenyl group), group —$N(R^{11A})R^{12A}$($R^{11A}$ and $R^{12A}$ represent a hydrogen atom, C1-6 alkyl group or phenyl group which may be same or different, and $R^{11A}$ and $R^{12A}$ may be combined each other together with an adjacent nitrogen atom through a nitrogen atom, oxygen atom or sulfur atom or not through them to form a 5- to 7-membered saturated heterocycle), phenoxy group (which may be substituted with at least one selected from the group consisting of a halogen atom, halogen-substituted or unsubstituted C1-6 alkyl group and halogen-substituted or unsubstituted C1-6 alkoxy group on the phenyl ring), phenyl C1-6 alkoxy group, amino-substituted C1-6 alkoxy group which may have a C1-6 alkyl group as a substituent, a halogen atom, halogen-substituted or unsubstituted C1-6 alkyl group and halogen-substituted or unsubstituted C1-10 alkoxy group, as a substituent on the phenyl ring); phenyl C1-6 alkyl group (which may be substituted with at least one selected from the group consisting of a C1-4 alkylenedioxy group, phenyl group (which may be substituted with at least one selected from the group consisting of a halogen atom, halogen-substituted or unsubstituted C1-6 alkyl group and halogen-substituted or unsubstituted C1-6 alkoxy group on the phenyl ring), group —$N(R^{11A})R^{12A}$ ($R^{11A}$ and $R^{12A}$ represent a hydrogen atom, C1-6 alkyl group or phenyl group which may be same or different, and $R^{11A}$ and $R^{12A}$ may be combined each other together with an adjacent nitrogen atom through a nitrogen atom, oxygen atom or sulfur atom or not through them to form a 5- to 7-membered saturated heterocycle), phenoxy group (which may be substituted with at least one selected from the group consisting of a halogen atom, halogen-substituted or unsubstituted C1-6 alkyl group and halogen-substituted or unsubstituted C1-6 alkoxy group on the phenyl ring), phenyl C1-6 alkoxy group, amino-substituted C1-6 alkoxy group which may have a C1-6 alkyl group as a substituent, halogen atom, halogen-substituted or unsubstituted C1-6 alkyl group and halogen-substituted or unsubstituted C1-10 alkoxy group, as a substituent on the phenyl ring); benzofuryl (which may be substituted with at least one of groups selected from the group consisting of a halogen atom, halogen-substituted or unsubstituted C1-6 alkyl group, halogen-substituted or unsubstituted C1-6 alkoxy group-on the benzofuran ring); benzofuryl C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the benzofuran ring); C1-6 alkoxy-substituted C1-6 alkyl group; C3-8 cycloalkyl-substituted C1-6 alkyl group; C3-8 cycloalkyl group; phenoxy C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group, as a substituent on the phenyl ring); pyridyl group; pyridyl C1-6 alkyl group; imidazolyl group; imidazolyl C1-6 alkyl group; amino-substituted C1-6 alkyl group which may have a C1-6 alkyl group as a substituent; cyano-substituted C1-6 alkyl group; furyl-substituted C1-6 alkyl group; furyl group; piperazinyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring) as a substituent on the piperazine ring); or piperazinyl-substituted C1-6 alkyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring) as a substituent on the piperazine ring).

$R^{9c}$ represents a C1-6 alkyl group which may have a hydroxy group as a substituent; C1-6 alkoxycarbonyl group; phenyl C1-6 alkoxycarbonyl group (which may be substituted with at least one of groups selected from the group consisting of a halogen atom, halogen-substituted or unsubstituted C1-6 alkyl group and halogen-substituted or unsubstituted C1-6 alkoxy group, as a substituent on the phenyl group); phenyl group (which may be substituted with at least one of groups selected from the group consisting of a halogen atom, halogen-substituted or unsubstituted C1-6 alkyl group, halogen-substituted or unsubstituted C1-6 alkoxy group, amino group which may have a group from the group consisting of a C1-6 alkanoyl group and C1-6 alkyl group as a substituent, C1-6 alkoxycarbonyl group, phenyl group, phenoxy group (which may be substituted with at least one of groups selected from the group consisting of a halogen atom, halogen-substituted or unsubstituted C1-6 alkyl group and halogen-substituted or unsubstituted C1-6 alkoxy group, as a substituent on the phenyl ring), aminosulfonyl group, 1,2,3,4-tetrahydroquinolyl group (which may be substituted with at least one oxo group as substituent on the 1,2,3,4-tetrahydroquinoline ring), C1-6 alkylsulfonyl group, C3-8 cycloalkyl group, nitro group, cyano group, C1-6 alkylthio group, phenylsulfonyl group (which may be substituted with at least one of groups selected from the group consisting of a halogen atom, halogen-substituted or unsubstituted C1-6 alkyl group and halogen-substituted or unsubstituted C1-6 alkoxy group, as a substituent on the phenyl ring), a hydroxyl group-substituted C1-6 alkyl group and a group:

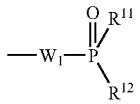

(wherein $W_1$ represents a C1-6 alkylene group, and $R^{11}$ and $R^{12}$ represent a C1-6 alkoxy group which may be same or different)); a phenyl C1-6 alkyl group (which may be substituted with at least one of groups selected from the group consisting of a C1-4 alkylene dioxy group, phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring), group —$N(R^{11A})R^{12A}$($R^{11A}$ and $R^{12A}$ represent a hydrogen atom, C1-6 alkyl group or phenyl group which may be same or different, and $R^{11A}$ and $R^{12A}$ may be combined each other together with an adjacent nitrogen atom through a nitrogen atom, oxygen atom or sulfur atom or not through them to form a 5- to 7-membered saturated heterocycle), phenoxy group (which may be substituted with at least one of groups selected from the group consisting of a halogen atom, halogen-substituted or unsubstituted C1-6 alkyl group and halogen-substituted or unsubstituted C1-6 alkoxy group on the phenyl ring), phenyl C1-6 alkoxy group, amino-substituted C1-6 alkoxy group which may have a C1-6 alkyl group as a substituent, halogen atom, halogen-substituted or unsubstituted C1-6 alkyl group and halogen-substituted or unsubstituted C1-10 alkoxy group, as a substituent on the phenyl ring); benzofuryl C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the benzofuran ring); phenylsulfonyl group (which may be substituted with at least one of groups selected from the group consisting of a halogen atom, halogen-substituted or unsubstituted C1-6 alkyl group, halogen-substituted or unsubstituted C1-6 alkoxy group and halogen-substituted or unsubstituted C1-4 alkylene dioxy group on the phenyl ring); phenyl C2-6 alkenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring); C1-6 alkoxy-substituted C1-6 alkyl group; C2-6 alkenyl group; C3-8 cycloalkyl group-substituted C1-6 alkyl group; phenoxy C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring); pyridyl group; pyridyl C1-6 alkyl group; imidazolyl C1-6 alkyl group; 1,2,3,4-tetrahydroquinolyl group (which may be substituted with at least one group selected from the group consisting of an oxo group and C1-6 alkyl group as substituent on the 1,2,3,4-tetrahydroquinoline ring); quinolyl group; indolyl group; indazolyl group; naphthyl group; C3-8 cycloalkyl group; amino-substituted C1-6 alkyl group which may have a C1-6 alkyl group as a substituent; cyano-substituted C1-6 alkyl group; furyl-substituted C1-6 alkyl group; group:

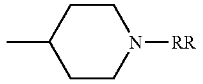

(wherein RR presents a phenyl group (which may be substituted with at least one of groups selected from the group consisting of a halogen atom, halogen-substituted or unsubstituted C1-6 alkyl group and halogen-substituted or unsubstituted C1-6 alkoxy group, as a substituent on the phenyl ring)); or piperazinyl-substituted C1-6 alkyl group (which may be substituted with at least one phenyl group (which may be substituted with at least one selected from the group consisting of a halogen atom, halogen-substituted or unsubstituted C1-6 alkyl group and halogen-substituted or unsubstituted C1-6 alkoxy group on the phenyl ring) as a substituent on the piperazine ring).

$R^{9d}$ represents a C1-6 alkanoyl group; phenoxydicarbonyl group (which may be substituted with at least one of groups selected from the group consisting of a halogen atom, halogen-substituted or unsubstituted C1-6 alkyl group and halogen-substituted or unsubstituted C1-6 alkoxy group on the phenyl group); C1-6 alkoxy-substituted C2-6 alkanoyl group or benzoyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring).

$R^{9e}$ represents a phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl group).

$R^{18}$ represents a hydrogen atom or C1-6 alkyl group.

The dotted line on the piperidine ring represents a bond which may be a double bond. When the dotted line is a double bond, a group-(W)oNR$^{9a}$R$^{10a}$, group-(W)oN(CHR$^{18}$R$^{9b}$) R$^{10a}$, group-(W)oNR$^{9c}$R$^{10a}$, group-(W)oNR$^{9d}$R$^{10a}$ or group-(W)oN(CONHR$^{9e}$) R$^{10a}$ should be substituted.

The total number of carbons of CHR$^{18}$R$^{9b}$ constituting the group-N(R$^{10a}$) CHR$^{18}$R$^{9b}$ in general formula (1d) should not exceed 6.

The reaction of the compound (1c) with the compound (16) is carried out in the presence of a reducing agent without a solvent or in an appropriate solvent.

The molar ratio of the compound (16) to the compound (1c) may be generally at least 1:1, preferably 1:1 to large excess.

Examples of the solvents used in the reaction may include, for example, water, lower alcohols such as methanol, ethanol, isopropanol, butanol, tert-butanol or ethylene glycol, acetonitrile, aliphatic acids such as formic acid, acetic acid or trifluoroacetic acid, ethers such as diethyl ether, tetrahydrofuran, dioxane, monoglyme or diglyme, aromatic hydrocarbons such as benzene, toluene or xylene, halogenated hydrocarbons such as dichloromethane, dichloroethane, chloroform, carbon tetrachloride or an mixed solvents thereof, or the like.

Examples of the reducing agents may include, for example, formic acid, alkali metal formates such as sodium formate, reducing agents such as sodium borohydride, sodium cyano borohydride, sodium triacetoxyborohydride, lithium aluminum hydride or mixed reducing agents thereof, catalytic hydrogen-reducing agents such as palladium-black, palladium-carbon, platinum oxide, platinum-black or Raney nickel, or the like.

When formic acid and the alkali metal formates are used as a reducing agent, the reaction temperature is appropriate generally at about room temperature to 200° C., preferably around about 50-150° C., and the reaction is completed in about 10 minutes to 10 hours. The molar ratio of formic acid to the compound (1c) may be large excess.

Also, when a reducing agent is used, the reaction temperature is appropriate generally at −80-100° C., preferably at −80-70° C., and the reaction is completed in about 30 minutes to 100 hours. The molar ratio of the reducing agent to the compound (1c) may be generally between about 1:1 and 20:1, preferably between about 1:1 and 6:1. Particularly, when lithium aluminum hydride is used as a reducing agent, preferred is use of ethers such as diethyl ether, tetrahydrofuran, dioxane, monoglyme or diglyme and aromatic hydrocarbons such as benzene, toluene or xylene. Amines such as trimethylamine, triethylamine or N-ethyldiisopropylamine and molecuar sieves such as molecular sieves 3A (MS-3A), molecular sieves 4A (MS-4A) or the like may be added in the reaction system.

Further, when the catalytic hydrogen-reducing agents are used, the reaction may be carried out generally in a hydrogen atmosphere of about ordinary pressure to 20 atm, preferably about ordinary pressure to 10 atm or in the presence of hydrogen-donating agents such as formic acid, ammonium formate, cyclohexene or hydrazine hydrate, generally at a temperature of about −30-100° C., preferably about 0-60° C., and the reaction is generally completed in about 1-12 hours. The catalytic hydrogen-reducing agents may be used generally in an amount of about 0.1-40 wt % based on the compound (1c), and preferably about 1-20 wt %.

The reaction of the compound (1c) with the compound (17) is conducted generally in an appropriate solvent in the presence or absence of a basic compound.

Examples of an inert solvent may include, for example, aromatic hydrocarbons such as benzene, toluene or xylene, ethers such as diethyl ether, tetrahydrofuran, dioxane, monoglyme or diglyme, halogenated hydrocarbons such as dichloromethane, dichloroethane, chloroform or carbon tetrachloride, lower alcohols such as methanol, ethanol, isopropanol, butanol, tert-butanol or ethylene glycol, aliphatic acids such as acetic acid, esters such as ethyl acetate or methyl acetate, ketones such as acetone or methylethyl ketone, acetonitrile, pyridine, dimethylsulfoxide, N,N-dimethylformamide, hexamethylphosphoric triamide or mixed solvents thereof.

The basic compounds may include, for example, carbonates such as sodium carbonate, potassium carbonate, sodium hydrogencarbonate, potassium hydrogencarbonate or cesium carbonate, metal hydroxides such as sodium hydroxide, potassium hydroxide or calcium hydroxide, sodium hydride, potassium hydride, potassium, sodium, sodium amide, metallic alcoholates such as sodium methylate, sodium ethylate or sodium n-butoxide, organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo [5.4.0]undecene-7 (DBU) or 1,4-diazabicyclo [2.2.2]octane (DABCO) or a mixture thereof.

The basic compounds may be used at the molar ratio to the compound (1c) of at least 1:1, preferably between 1:1 and 10:1.

The compound (17) be used at the molar ratio to the compound (1c) of at least 1:1, preferably between 1:1 and 10:1.

The reaction is carried out generally at 0-200° C., preferably at about 0-150° C., and is generally completed in about 5 minutes to 80 hours.

Alkali metal halides such as sodium iodide or potassium iodide may be added or phase-transfer catalysts may be added in the reaction system.

Examples of the phase-transfer catalysts herein may include, for example, catalysts such as tetrabutylammonium chloride, tetrabutylammonium bromide, tetrabutylammonium fluoride, tetrabutylammonium iodide, tetrabutylammonium hydroxide, tetrabutylammonium hydrogensulfite, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride or tetramethylammonium chloride, quaternary ammonium salts substituted with groups selected from the group consisting of C1-18 straight or branched chain alkyl groups, a phenyl C1-6 alkyl group and phenyl group, phosphonium salts substituted with C1-18 straight or branched chain alkyl groups such as tetrabutylphosphonium chloride or pyridinium salts substituted with C1-18 straight or branched chain alkyl groups such as 1-dodecanylpyridinium chloride.

The phase-transfer catalysts may be used generally at the molar ratio to the compound (1c) of between 0.1:1 and 1:1, preferably between 0.1:1 and 0.5:1.

The reaction of the compound (1c) with the compound (18) is by a method wherein the compound (1c) and carboxylic acid of the compound (18) are reacted with usual amide-coupling generation reactions.

Conditions for a known amide bond formation reaction can be widely applied herein. Examples of such an amide bond formation reaction include (a) mixed acid anhydride method, that is, a method of reacting carboxylic acid (18) with alkyl haloformate to obtain a mixed acid anhydride and reacting the mixed acid anhydride with amine (1c), (b) active ester method, that is, a method of converting carboxylic acid (18) into active ester such as p-nitrophenyl ester, N-hydroxy succinic acid imide ester or 1-hydroxybenzotriazole ester, or into active amide such as benzoxazoline-2-thione, and then reacting this with amine (1c), (c) carbodiimide method, that is, a method of carrying out the condensation reaction of carboxylic acid (18) with amine (1c) in the presence of an activator such as dicyclohexylcarbodiimide, 1-(3-dimethylaminopropyl)-3-ethylcarbodiimide (WSC) or carbonyldiimidazole, and (d) other methods including a method of converting carboxylic acid (18) into carboxylic anhydride by using a dehydrator such as acetic anhydride and reacting the carboxylic anhydride with amine (1c), a method of reacting ester of carboxylic acid (18) and lower alcohol with amine (1c) at high pressure and high temperature, and a method of reacting acid halide of carboxylic acid (18), i.e., carboxylic acid halide, with amine (1c).

The mixed acid anhydride used in (a) mixed acid anhydride method as described above is obtained by a common Schotten-Baumann reaction. The mixed acid anhydride is reacted with amine (1c) generally without subjecting to isolation, so as to produce the compound of the present invention represented by general formula (1f).

The above Schotten-Baumann reaction is carried out in the presence of a basic compound.

Compounds that are commonly used for the Schotten-Baumann reaction can be used herein as basic compounds. Examples of such a basic compound include: organic bases such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0)undecene-7 (DBU) or 1,4-diazabicyclo[2.2.2]octane (DABCO); inorganic bases including carbonates such as sodium carbonate, potassium carbonate, sodium hydrogencarbonate or potassium hydrogencarbonate, metal hydroxides such as sodium hydroxide, potassium hydroxide or calcium hydroxide, potassium hydride, sodium hydride, potassium, sodium, sodium amide, and metal alcoholates such as sodium methylate or sodium ethylate.

The reaction is carried out generally at −20° C. to 100° C., and preferably at 0° C. to 50° C. The reaction time is generally 5 minutes to 10 hours, and preferably 5 minutes to 2 hours.

The reaction of the obtained mixed acid anhydride with amine (1c) is carried out generally at −20° C. to 150° C., and preferably at 10° C. to 50° C. The reaction time is generally 5 minutes to 10 hours, and preferably 5 minutes to 5 hours. The mixed acid anhydride method is generally carried out in a solvent.

Any solvent that is commonly used for the mixed acid anhydride method can be used herein. Examples of such a solvent include halogenated hydrocarbons such as chloroform, dichloromethane, dichloroethane or carbon tetrachloride, aromatic hydrocarbons such as benzene, toluene or xylene, ethers such as diethyl ether, diisopropyl ether, tetrahydrofuran or dimethoxyethane, esters such as methyl acetate, ethyl acetate or isopropyl acetate, aprotic polar solvents such as N,N-dimethylacetamide, N,N-dimethylformamide, dimethylsulfoxide or hexamethylphosphoric acid triamide, and mixed solvents thereof.

Examples of alkyl haloformate used for the mixed acid anhydride method include methyl chloroformate, methyl bromoformate, ethyl chloroformate, ethyl bromoformate, and isobutyl chloroformate. The molar ratio among carboxylic acid (18), alkyl haloformate and amine (1c) may be generally equal to 1:1. Each of alkyl haloformate and carboxylic acid (18) can also be used to amine (1c) within the molar range between 1:1 and 1.5:1.

The above method (c) involving the condensation reaction in the presence of the above activator is carried out in an appropriate solvent in the presence or absence of a basic compound.

As a solvent and a basic compound used herein, any solvent used in the reaction of carboxylic acid halide with amine (1c) described as above in (d) other methods can be used.

The molar ratio of the activator to the compound (1c) may be at least equal to 1:1, and preferably between 1:1 and 5:1. When WSC is used as an activator, the reaction advantageously proceeds if 1-hydroxybenzotriazole is added into the reaction system.

The reaction is carried out generally at −20° C. to 180° C., and preferably at 0° C. to 150° C. The reaction time is generally 5 minutes to 90 hours.

When the method of reacting carboxylic acid halide with amine (1c) is adopted from (d) other methods described above, the reaction is carried out in the presence of a basic compound in an appropriate solvent.

Known basic compounds can be widely used herein. For example, any basic compound used in the above Schotten-Baumann reaction can be used.

Examples of the used solvent may include alcohols such as methanol, ethanol, isopropanol, propanol, butanol, 3-methoxy-1-butanol, ethyl cellosolve or methyl cellosolve, acetonitrile, pyridine, acetone, water, as well as solvents used for the above mixed acid anhydride method.

The molar ratio of amine (1c) to carboxylic acid halide is not particularly limited, but it may be appropriately selected from a wide range. The molar ratio of these compounds may be generally at least equal to 1:1, and preferably between 1:1 and 1:5.

The reaction is carried out generally at −20° C. to 180° C., and preferably at 0° C. to 150° C. The reaction time is generally 5 minutes to 50 hours.

The above amide bond formation reaction can also be carried out by reacting carboxylic acid (18) with amine (1c) in the presence of a phosphorus condensing agent such as diphenylphosphinic chloride, phenyl-N-phenyl phosphoramide chloridate, diethyl chlorophosphate, diethyl cyanophosphate, azide diphenyl phosphate, or bis(2-oxo-3-oxazolidinyl)phosphinic chloride.

This reaction is carried out in the presence of a solvent and a basic compound that are used for the above method of reacting carboxylic acid halide with amine (1c), generally at −20° C. to 150° C., and preferably at 0° C. to 100° C. The reaction time is generally 5 minutes to 30 hours. Each of the condensing agent and the carboxylic acid (18) is used to amine (1c) at a molar ratio of at least equal to 1:1, and preferably between 1:1 and 2:1.

The reaction of the compound (1c) with the compound (19) can be carried out under the same conditions for the reaction of the compound (15) with the compound (16) or (17) represented by the above reaction scheme 9.

Reaction Scheme 11

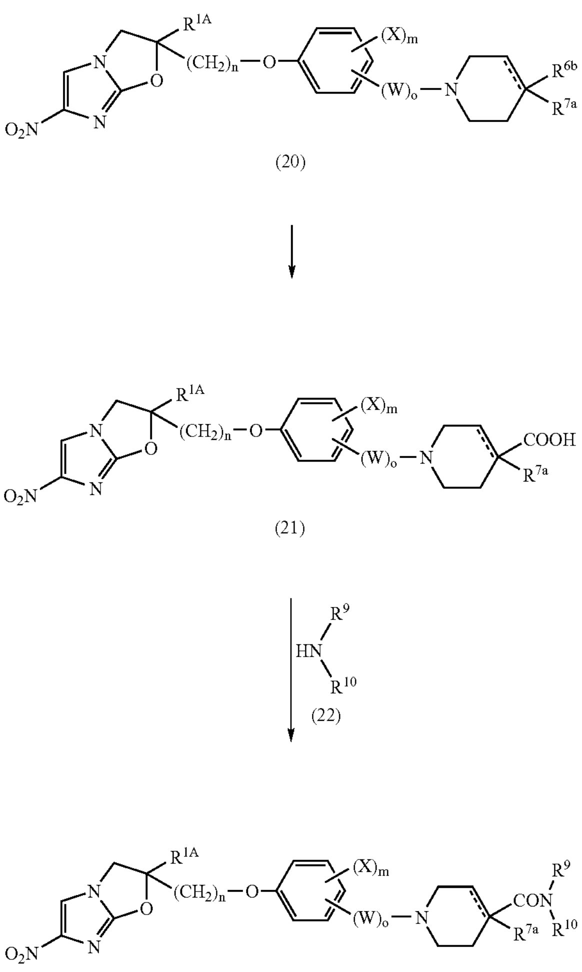

(20)

(21)

(22)

(1h)

(wherein $R^{1A}$, X, n, m, W, $R^{7a}$, $R^9$, $R^{10}$ and o are the same as above. $R^{6b}$ represents a C1-6 alkoxycarbonyl group. The dotted line on the piperidine ring represents a bond which may be a double bond. When the dotted line is a double bond, a group $R^{6b}$, COOH or —$CONR^9R^{10}$ should be substituted.).

A compound (21) is produced by hydrolyzing a compound (20).

The hydrolysis reaction is conducted in an appropriate solvent or without a solvent in the presence of an acid or basic compound.

The solvent used may include, for example, water, lower alcohols such as methanol, ethanol, isopropanol or tert-butanol, ketones such as acetone or methylethyl ketone, ethers such as diethyl ether, dioxane, tetrahydrofuran, monoglyme or diglyme, aliphatic acids such as acetic acid or formic acid, esters such as ethyl acetate or methyl acetate, halogenated hydrocarbons such as chloroform, dichloromethane, dichloroethane or carbon tetrachloride, dimethylsulfoxide, N,N-dimethylformamide, hexamethylphosphoric triamide or mixed solvents thereof.

The acid may include, for example, mineral acids such as hydrochloric acid, sulfuric acid or hydrobromic acid, organic acids such as formic acid, acetic acid, trifluoroacetic acid, or sulfonic acids such as p-toluenesulfonic acid.

The basic compound may include, for example, carbonates such as sodium carbonate, potassium carbonate, sodium hydrogencarbonate or potassium hydrogencarbonate, metal hydroxides such as sodium hydroxide, potassium hydroxide, calcium hydroxide or lithium hydroxide, or the like.

The acid or basic compound is used at its molar ratio to the compound (20) of at least 1:1, and preferably between 1:1 and 10:1, or may be used in large excess as a reaction solvent.

The reaction proceeds generally at about 0-200° C., preferably at about 0-150° C. and is generally completed in about 10 minutes to 30 hours.

After the above described hydrolysis treatment, a further treatment may be performed in about 1-30 minutes usually at 0-100° C., preferably at room temperature to around 70° C. in an appropriate solvent in the presence of a basic compound to complete the reaction. A solvent and basic compound used herein may use any solvent and basic compound which is used in the method wherein the carboxylic acid halide is reacted with the amine (1c) of the method (d) among reactions of the compound (1c) with the compound (18) in the above described Reaction Scheme 10.

The reaction of the compound (21) with the compound (22) is performed under the reaction conditions similar to those of the reaction of the compound (1c) with the compound (18) in the above described Reaction Scheme 10. The amount of the carboxylic acid (18) was based on the amine (1c) in the above described Reaction Scheme 10, while the amount of the amine (22) is based on the carboxylic acid (18) in the present reaction.

Reaction Scheme 12

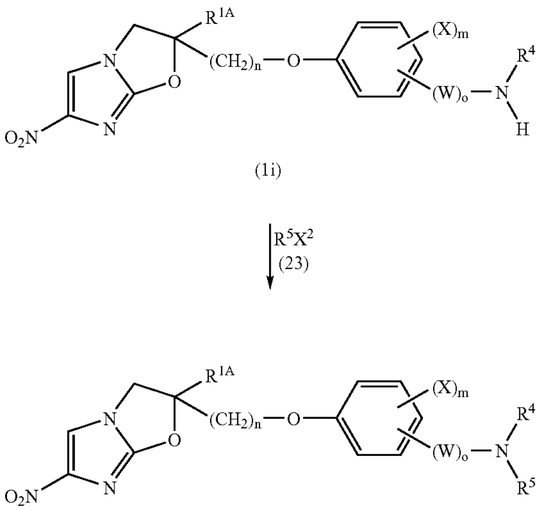

(1i)

(23)

(1j)

(wherein $R^{1A}$, n, X, m, W, o, $X^2$, $R^4$ and $R^5$ are the same as above.)

The reaction of a compound (1i) with a compound (23) is performed under the reaction conditions similar to those of the reaction of the compound (1c) with the compound (17) in the above described Reaction Scheme 10.

Reaction Scheme 13

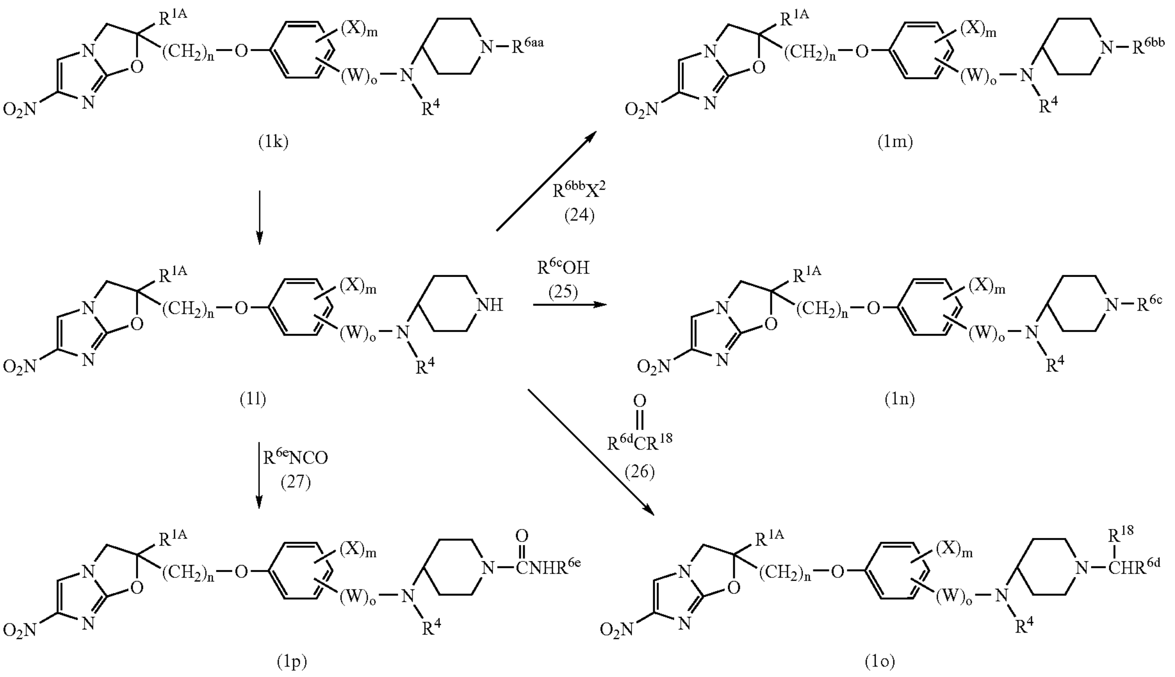

(wherein $R^{1A}$, n, $R^{18}$, X, m, W, o, $R^4$ and $X^2$ are the same as above.)

$R^{6aa}$ represents a C1-6 alkoxycarbonyl group.

$R^{6bb}$ represents: a C1-6 alkyl group; phenyl group (which may be substituted with at least one of groups selected from the group consisting of a C1-4 alkylenedioxy group, cyano group, nitro group, amino group which may have a C1-6 alkyl group as a substituent, amino-substituted sulfonyl group which may have a C1-6 alkyl group as a substituent, C1-6 alkoxycarbonyl group, C1-6 alkylthio group, phenoxy group, phenyl C1-6 alkoxy group, pyrrolidinyl group (which may be substituted with at least one oxo group on the pyrrolidine ring), imidazolyl group, isooxazolyl group, oxazolyl group, phenyl C1-6 alkyl group, phenyl group, amino C1-6 alkyl group which may a C1-6 alkyl group as a substituent, pyrrolidinyl C1-6 alkoxy group, halogen atom, halogen-substituted or unsubstituted C1-6 alkyl group and halogen-substituted or unsubstituted C1-6 alkoxy group on the phenyl ring); phenyl C1-6 alkoxycarbonyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring); benzofuryl C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the benzofuran ring); benzofuryl C2-6 alkenyl group (which may be substituted with at least one of groups selected from the group consisting of a halogen atom, halogen-substituted or unsubstituted C1-6 alkyl group and halogen-substituted or unsubstituted C1-6 alkoxy group on the benzofuran ring); phenoxy C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring); thiazolyl C1-6 alkyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring) on the thiazole ring); phenyl C1-6 alkyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring), halogen atom, halogen-substituted or unsubstituted C1-6 alkyl group and halogen-substituted or unsubstituted C1-6 alkoxy group on the phenyl ring); pyridyl C1-6 alkyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring) on the pyridine ring); C1-6 alkoxycarbonyl group; benzothienyl group; benzothienyl C1-6 alkyl group (which may be substituted with at least one halogen atom on the benzothiophene ring); indolyl C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the indole ring); 4H-1,3-benzodioxinyl group (wherein, on the 4H-1,3-benzodioxine ring, at least one halogen atom may be substituted); naphthyl group; quinolyl group; benzothiazolyl group (which may be substituted with at least one C1-6 alkyl group on the benzothiazole ring); 2,3-dihydro-1H-indenyl group (which may be substituted with at least one oxo group on the 2,3-dihydro-1H-indane ring); 9H-fluorenyl group or phenyl C2-6 alkenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring).

$R^{6c}$ represents a benzoyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring), halogen atom, halogen-substituted or unsubstituted C1-6 alkyl group and halogen-substituted or unsubstituted C1-6 alkoxy group on the phenyl ring).

$R^{6d}$ represents: a hydrogen atom; phenyl group (which may be substituted with at least one of groups selected from a phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring), a halogen atom, halogen-substituted or unsubstituted C1-6 alkyl group and halogen-substituted or unsubstituted C1-6 alkoxy group on the phenyl ring); benzofuryl C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the benzofuran ring); benzofuryl group (which may be substituted with at least one of groups selected from the group consisting of a halogen atom, halogen-substituted or unsubstituted C1-6 alkyl group and halogen-substituted or unsubstituted C1-6 alkoxy group on the benzofuran ring); phenoxy C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring); thiazolyl C1-6 alkyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring) on the thiazole ring); thiazolyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring) on the thiazole ring); phenyl C1-6 alkyl group (which may be substituted with at least one of groups selected from a phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring), halogen atom, halogen-substituted or unsubstituted C1-6 alkyl group and halogen-substituted or unsubstituted C1-6 alkoxy group on the phenyl ring); pyridyl C1-6 alkyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring) on the pyridine ring); benzothienyl C1-6 alkyl group (at least one halogen atom may be substituted on the benzothiophene ring); indolyl C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the indole ring); pyridyl group (which may be substituted with at least one phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring) on the pyridine ring); benzothienyl group (at least one halogen atom may be substituted on the benzothiophene ring); or indolyl group (which may be substituted with at least one of groups selected from the group consisting of a halogen atom, halogen-substituted or unsubstituted C1-6 alkyl group and halogen-substituted or unsubstituted C1-6 alkoxy group on the indole ring).

$R^{6e}$ represents a phenyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring).

The total number of carbons of the group-$CHR^{18}R^{6d}$ in general formula (1o) should not exceed 6. A reaction to lead from a compound (1k) into a compound (11) is performed under the reaction conditions similar to those of the reaction to lead from the compound (20) into the compound (21) in the above described Reaction Scheme 11.

A reaction of the compound (11) with a compound (24) is carried out under the reaction conditions similar to those of the reaction of the compound (1c) with the compound (17) in the above described Reaction Scheme 10.

A reaction of the compound (11) with a compound (25) is carried out under the reaction conditions similar to those of the reaction of the compound (1c) with the compound (18) in the above described Reaction Scheme 10.

A reaction of the compound (11) with a compound (26) is carried out under the reaction conditions similar to those of the reaction of the compound (1c) with the compound (16) in the above described Reaction Scheme 10.

A reaction of the compound (11) with a compound (27) is carried out under the reaction conditions similar to those of the reaction of the compound (1c) with the compound (19) in the above described Reaction Scheme 10.

Reaction Scheme 14

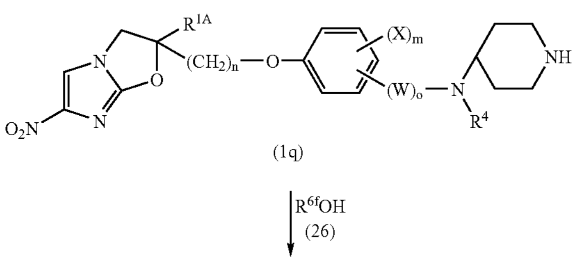

(1q)

-continued

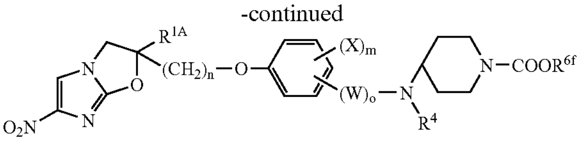

(1r)

(wherein $R^{1A}$, n, X, m, W, o and $R^4$ are the same as above. $R^{6f}$ represents a C1-6 alkyl group or phenyl C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring).)

The reaction of a compound (1q) with the compound (26) is conducted in appropriate solvent in the presence of a condensation agent.

Solvents used herein can use any solvent which is used in the method wherein the carboxylic acid halide is reacted with the amine (1c) of other methods (d) of reactions of the compound (1c) with the compound (18) in the above described Reaction Scheme 10.

A condensation agent may include, for example, N,N'-carbonyldiimidazole or the like. The molar ratio of the compound (26) and condensation agent used to the compound (1q) may be at least, preferably between about 1:1 and 2:1. The reaction is carried out generally at 0-150° C., preferably around 0-100° C. and completed in about 1-30 hours.

Reaction Scheme 15

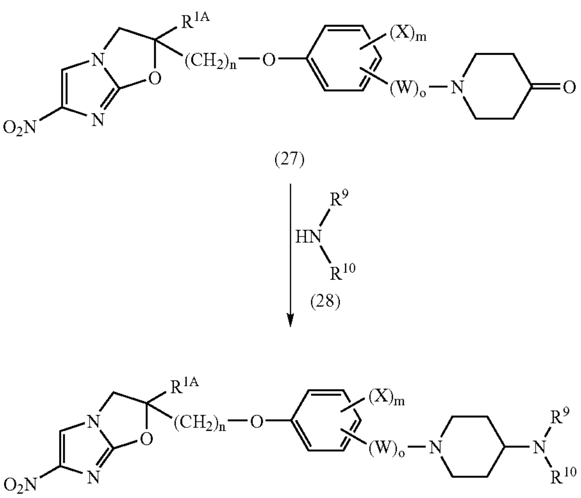

(27)

(28)

(1s)

(wherein $R^{1A}$, n, X, m, W, o, $R^9$ and $R^{10}$ are the same as above.)

A reaction of the compound (27) with a compound (28) is carried out under reaction conditions similar to those of the reaction of the compound (1c) with the compound (16) in the above described Reaction Scheme 10.

Reaction Scheme 16

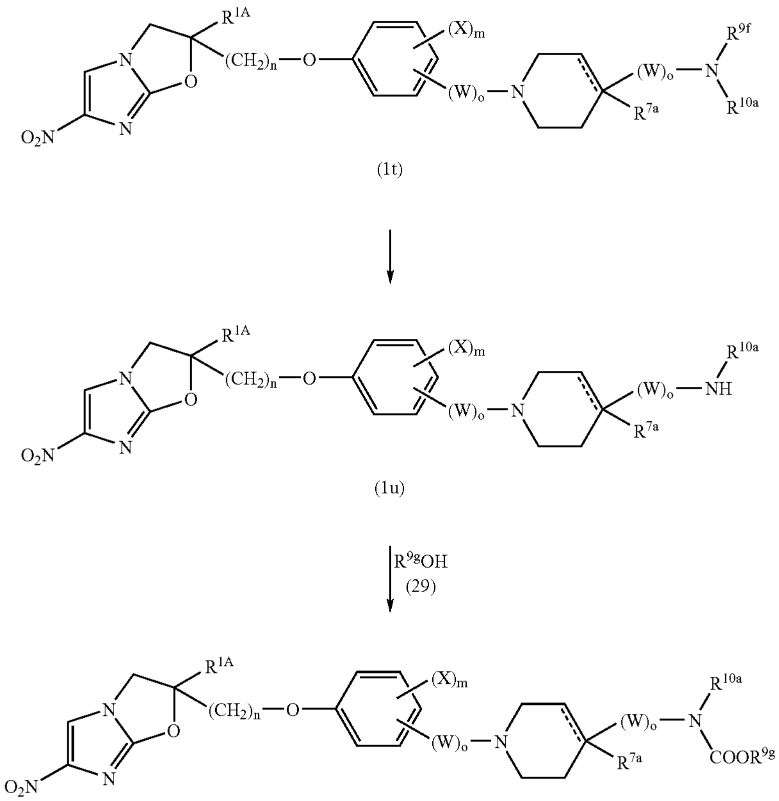

(1t)

(1u)

(29)

(1v)

(wherein $R^{1A}$, n, X, m, W, o, $R^{7a}$ and $R^{10a}$ are the same as above. Two Ws in general formulas (1t)-(1v) may be same or different. $R^{9f}$ represents a C1-6 alkoxycarbonyl group. The dotted line on the piperidine ring represents a bond which may be a double bond. When the dotted line is a double bond, a group —(W)oN$R^{9f}R^{10a}$, group —(W)oNH$R^{10a}$ or group —(W)oN$R^{10a}$(COO$R^{9g}$) should be substituted. $R^{9g}$ represents a C1-6 alkyl group or phenyl C1-6 alkyl group (which may be substituted with at least one of groups selected from the group consisting of a halogen atom, halogen-substituted or unsubstituted C1-6 alkyl group and halogen-substituted or unsubstituted C1-6 alkoxy group on the phenyl ring).)

A reaction to lead from the compound (1t) into the compound (1u) is carried out under reaction conditions similar to those of the reaction to lead from the compound (20) into the compound (21) in the above described Reaction Scheme 11.

A reaction of the compound (1u) with the compound (29) is carried out under reaction conditions similar to those of the reaction of the compound (1q) with the compound (26) in the above described Reaction Scheme 14.

The starting compound (14) in Reaction Scheme 9 and the starting compound (20) in Reaction Scheme 11 are new compounds. These compounds are readily manufactured, for example, according to the above Reaction Schemes 1 to 3 using the corresponding starting materials.

The compounds (final compounds) represented by general formula (1) of the present invention and intermediates obtained in the above described each Reaction Scheme embrace stereoisomers and optical isomers.

Each target compound obtained in the above described each Reaction Scheme can be isolated and purified from the reaction mixture, for example, by isolating crude reaction products by isolation operations such as filtration, concentration and extraction after cooling, followed by usual purification operations such as column chromatography and recrystallization.

The compound of the present invention includes a pharmaceutically acceptable salt of the compounds of the formula (1). Examples of such a salt include inorganic salts such as hydrochloride, hydrobromide, nitrate, sulfate or phosphate, and organic salts such as methanesulfonate, p-toluenesulfonate, acetate, citrate, tartrate, maleate, fumarate, malate or lactate.

Next, a medical preparation containing the compound of the present invention as an active ingredient will be explained.

The above medical preparation is obtained by preparing the compound of the present invention in the form of a common medical preparation. It is prepared using commonly used diluents or excipients such as a filler, expander, binder, wetting agent, disintegrator, surfactant or lubricant.

Such a medical preparation can be selected from among various forms, depending on therapeutic purposes. Typical examples of a preparation form include a tablet, pill, powder, liquid, suspension, emulsion, granule, capsule, suppository, and injection (liquid, suspension, etc.)

Known carriers can be widely used in making the medical preparation in a tablet form. Examples of such a carrier include excipients such as lactose, sucrose, sodium chloride, glucose, urea, starch, calcium carbonate, kaoline or crystalline cellulose; binders such as water, ethanol, propanol, simple syrup, glucose solution, starch solution, gelatin solution, carboxymethylcellulose, shellac, methylcellulose, potassium phosphate or polyvinylpyrrolidone; disintegrators such as dry starch, sodium alginate, agar powder, laminaran powder, sodium hydrogencarbonate, calcium carbonate, polyoxyethylene sorbitan fatty acid esters, sodium lauryl sulfate, monoglyceride stearate, starch or lactose; disintegration controllers such as sucrose, stearin, cacao butter or hydrogenated oil; absorption enhancers such as quaternary ammonium base or sodium lauryl sulfate, humectants such as glycerin or starch, adsorbents such as starch, lactose, kaoline, bentonite or colloidal silica, and lubricants such as purified talc, stearate, boric acid powder or polyethylene glycol.

Moreover, such tablets can be prepared as tablets with common tablet coating, such as a sugar coated tablet, gelatin coated tablet, enteric coated tablet, film coated tablet, double coated tablet, or multi-coated tablet.

Known carriers can be widely used in making the medical preparation in a pill form. Examples of such a carrier include excipients such as glucose, lactose, starch, cacao butter, hydrogenated vegetable oil, kaoline or talc, binders such as gum arabic powder, tragacanth powder, gelatin or ethanol, and disintegrators such as laminaran or agar.

Known carriers can be widely used in making the medical preparation in a suppository form. Examples of such a carrier include polyethylene glycol, cacao butter, higher alcohol, higher alcohol esters, gelatin, and semisynthetic glyceride.

In a case where the medical preparation is prepared as an injection such as a liquid, emulsion or suspension, these solutions are preferably sterilized and prepared to be isotonic to blood. Known diluents can be widely used in making the medical preparation in such a liquid, emulsion or suspension form. Examples of such a diluent include water, ethanol, propylene glycol, ethoxylated isostearyl alcohol, polyoxylated isostearyl alcohol, and polyoxyethylene sorbitan fatty acid esters. Moreover, in the case of using the medical preparation as an injection, a certain amount of common salts, glucose or glycerin that is sufficient to prepare an isotonic solution may be added to the medical preparation. Otherwise, a common solubilizing agent, buffer, soothing agent or the like may also be added to the medical preparation. Further, a coloring agent, preservative, perfume, flavor, sweetening agent or other pharmaceuticals may also be added thereto, if necessary.

The amount of the compound of the present invention contained in the medical preparation is not particularly limited, but it can be appropriately selected from a wide range. Generally, 1 to 70% by weight of the compound of the present invention is preferably contained in the medical preparation.

The method of administering the medical preparation of the present invention is not particularly limited. It is administered depending on various preparation forms, patients' age, sex, conditions of disease, or other conditions. For example, where the medical preparation adopts a tablet, pill, liquid, suspension, emulsion, granule or capsule form, it is administered orally. In the case of an injection, it can be administered intravenously, singly or in combination with a common auxiliary fluid such as glucose or amino acid. Moreover, if necessary, it can be singly administered intramuscularly, intradermally, subcutaneously or intraperitoneally. In the case of a suppository, it can be administered intrarectally.

The dose of the above medical preparation may be appropriately selected depending on usage, patients' age, sex, level of disease, or other conditions. Generally 0.01 to 100 mg, preferably 0.1 to 50 mg per kg of body weight of the medical preparation is administered once or divided into several times per day.

Since the above dose is altered depending on various conditions, the dose smaller than the above range may be sufficient in some cases, or the dose greater than the above range may be required in other cases.

The compound of the present invention has a specific effect against *Mycobacterium tuberculosis* such as acid-fast bacteria (Mycobacterium, atypical acid-fast bacteria). The compound of the present invention has an excellent effect against multi-drug-resistant *Mycobacterium tuberculosis*. The compound of the present invention has an antimicrobial action against anaerobic bacteria.

The compound of the present invention does not only show the above described activities in vitro, but it also expresses the above activities in oral administration.

The compound of the present invention does not induce diarrhea, which is induced by known antimicrobial agents having a wide spectrum for common bacteria such as Gram-positive bacteria or Gram-negative bacteria. In addition, it has lesser adverse reactions than existing agents. Accordingly, it can be a medical preparation, which can be administered for a long time.

The compound of the present invention can be distributed well in the tissues of the lung, the main organ that is infected by acid-fast bacteria, and it has properties such as sustained efficacy or excellent safety. Accordingly, a high therapeutic effect can be expected from the compound.

When compared with existing antitubercular agents, the compound of the present invention shows a strong bactericidal action even towards cytozoic bacteria such as *Mycobacterium tuberculosis* present in a human macrophage. Accordingly, it enables a reduction of reoccurrence rate of tuberculosis and the realization of a short-term chemotherapy. It is therefore expected that the compound of the present invention will also be used as a main preventive agent administered for a mixed infection by HIV and tuberculosis, which is considered to be a serious problem.

EXAMPLES

Formulation Example, Text Examples, Reference Examples and Examples will be described below.

Formulation Example 1

100 g of a compound of the invention, 40 g of Avicel (trade name, manufactured by Asahi Kasei Corporation), 30 g of corn starch and 2 g of magnesium stearate were mixed and ground, and then formed into tablets with a pestle of sugar-coat R10 mm.

A film coating agent containing 10 g of TC-5 (trade name, hydroxypropyl methylcellulose, manufactured by Shin-Etsu Chemical Co., Ltd.), 3 g of polyethylene glycol 6000, 40 g of castor oil and an appropriate amount of ethanol was used to coat the obtained tablets, producing a film-coated tablet having the composition described above.

Reference Example 1

Preparation of 1-(4-(tetrahydropyran-2-yloxy)phenyl)-4-(N-(4-chlorophenyl)-N-methylamino)piperidine 4-(N-(4-chlorophenyl)-N-methylamino)-piperidine (2.52 g, 11.22 mmol), 2-(4-bromophenoxy) tetrahydropyran (2.89 g, 11.22 mmol), palladium acetate (50 mg, 0.22 mmol), (S)-(−)-2,2-bis(diphenylphosphino)-1,1'-binaphthyl (BINAP) (212 mg, 0.34 mmol) and tert-butoxy sodium (1.51 g, 15.71 mmol) were refluxed with heating in toluene (30 ml) under nitrogen atmosphere for 3 hours. Ethyl acetate and water were added into the reaction solution and stirred, then the resulting precipitate was removed by filtration through Celite, thereafter the filtrate was extracted with ethyl acetate. The organic phase was washed with saturated brine, dried over magnesium sulfate, and then filtered. After the resulting filtrate was concentrated under reduced pressure, the residue was purified by silica gel column chromatography (n-hexane/ethyl acetate=20/1) to afford 1-(4-(tetrahydropyran-2-yloxy)phenyl)-4-(N-(4-chlorophenyl)-N-methylamino)piperidine (1.33 g, yield 30%) as a light yellow powder.

$^1$H-NMR ($CDCl_3$) δppm: 1.50-2.04 (10H, m), 2.68-2.80 (2H, m), 2.78 (3H, s), 3.50-3.70 (4H, m), 3.85-4.03 (1H, m), 5.31 (1H, t, J=5.7 Hz), 6.72 (2H, d, J=9.1 Hz), 6.90 (2H, d, J=9.2 Hz), 6.98 (2H, d, J=9.2 Hz), 7.17 (2H, d, J=9.1 Hz).

Reference Example 2

Preparation of 4-(4-(N-(4-chlorophenyl)-N-methylamino)piperidine-1-yl)phenol 1-(4-(Tetrahydropyran-2-yloxy)phenyl)-4-(N-(4-chlorophenyl)-N-methylamino)piperidine (1.33 g, 3.32 mmol) was suspended in ethanol (80 ml). To this mixture, pyridinium p-toluenesulfonate (0.25 g, 1 mmol) was added and then stirred at 70° C. for 8 hours. Ethanol was removed under reduced pressure, then to this residue, methylene chloride and a saturated aqueous sodium hydrogencarbonate solution were added and stirred. This was extracted with methylene chloride, dried over magnesium sulfate and then filtered. After the resulting filtrate was concentrated under reduced pressure, methylene chloride and n-hexane were added to the residue and the resulting precipitate was filtered to afford 4-(4-(N-(4-chlorophenyl)-N-methylamino)piperidine-1-yl)phenol (922.5 mg, yield 88%) as a light pink powder.

$^1$H-NMR ($CDCl_3$) δppm: 1.79-2.04 (4H, m), 2.67-2.79 (2H, m), 2.79 (3H, s), 3.56-3.68 (2H, m), 4.48 (1H, s), 6.69-6.80 (4H, m), 6.85-6.92 (2H, m), 7.14-7.21 (2H, m).

The following compounds were prepared similarly to Reference Examples 1 and 2. In the following table, Ph means a phenyl group or phenylene group.

Reference Example 3

(4-Chlorophenyl)-(4-hydroxyphenyl)methanone O-methyloxime

Ms: 261 ($M^+$).

Reference Example 4

(4-Hydroxyphenyl)-(4-trifluoromethylphenyl)methanone O-methyloxime

Ms: 295 ($M^+$).

TABLE 1

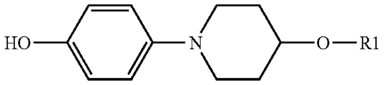

| Reference Example | R1 | $^1$HNMR or MS |
|---|---|---|
| 5 | —$CH_2C_6H_5$ | $^1$H NMR ($CDCl_3$) δ 1.79-1.89(2H, m), 2.01-2.08(2H, m), 2.77-2.87(2H, m), 3.33-3.41(2H, m), 3.53-3.56(2H, m), 4.59(2H, s), 4.63(1H, brs), 6.74(2H, d, J = 9.0 Hz), 6.87(2H, d, J = 9.0 Hz), 7.27-7.36(5H, m). |
| 6 | 4-$CF_3OPhCH_2$— | $^1$H NMR ($CDCl_3$) δ 1.76-1.90(2H, m), 2.00-2.10(2H, m), 2.84(2H, m). 3.33-3.42(2H, m), 3.51-3.60(1H, m), 4.53(1H, brs), 4.63(2H, s), 6.74(2H, d, J = 9.0 Hz), 6.87(2H, d, J = 9.0 Hz), 7.48(2H, d, J = 8.1 Hz), 7.60(2H, d, J = 8.2 Hz). |
| 7 | 4-$CF_3PhCH_2$— | $^1$H NMR ($CDCl_3$) δ 1.71-1.93(2H, m), 1.95-2.15(2H, m), 2.71-2.93(2H, m), 3.26-3.46(2H, m), 3.46-3.63(1H, m), 4.50(1H, s), 4.57(2H, s), 6.74(2H, d, J = 9.0 Hz), 6.87(2H, d, J = 8.9 Hz), 7.19(2H, d, J = 8.5 Hz), 7.39(2H, d, J = 8.4 Hz). |
| 8 | 4-$ClPhCH_2$— | $^1$H NMR ($CDCl_3$) δ 1.69-1.91(2H, m), 1.95-2.14(2H, m), 2.72-2.90(2H, m), 3.26-3.44(2H, m), 3.44-3.63(1H, m), 4.46(1H, broad s), 4.54(2H, s), 6.74(2H, d, J = 9.0 Hz), 6.87(2H, d, J = 9.0 Hz), 7.20-7.33(4H, m). |
| 9 | 3,4-$Cl_2PhCH_2$— | $^1$H NMR ($CDCl_3$) δ 1.71-1.93(2H, m), 1.93-2.18(2H, m), 2.70-2.93(2H, m), 3.22-3.45(2H, m), 3.45-3.65(1H, m), 4.52(2H, s), 4.85(1H, brs), 6.73(2H, d, J = 9.0 Hz), 6.82(2H, d, J = 9.0 Hz), 7.19(1H, dd, J = 8.2 Hz, 2.0 Hz), 7.41(1H, d, J= 8.2 Hz), 7.46(1H, d, J = 1.9 Hz). |
| 10 | 4-$CF_3OPh(CH_2)_2$— | Ms: 381(M+) |
| 11 | 4-$CF_3OPhCH$═$CHCH_2$— | Ms: 393(M+) |
| 12 | 4-$CF_3OPh(CH_2)_3$— | Ms: 395(M+) |

TABLE 2

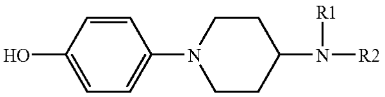

| Reference Example | R1 | R2 | NMR or MS |
|---|---|---|---|
| 13 | 4-ClPh— | —$CH_3$ | $^1$H NMR ($CDCl_3$) δ 1.79-2.04(4H, m), 2.67-2.79(2H. m), 2.79(3H, s), 3.56-3.68(2H, m), 4.48(1H, s), 6.69-6.80(4H, m), 6.85-6.92(2H, m), 7.14-7.21 (2H, m). |
| 14 | 4-$CF_3Ph$— | —H | $^1$H NMR ($CDCl_3$) δ 1.56-1.72(2H, m), 2.13-2.20(2H, m), 2.77-2.88(2H, m), 3.44-3.51(3H, m), 3.92(1H, d, J = 7.94 Hz), 4.86(1H, s), 6.59-6.63(2H, m), 6.72-6.79(2H, m), 6.85-6.92(2H, m), 7.38-7.42(2H, m). |
| 15 | —$CH_2C_6H_5$ | —H | $^1$H NMR ($CDCl_3$) δ 1.26-2.46(3H, m), 2.51-2.80(3H, m), 3.36-3.56(2H, m), 3.86(2H, s), 6.65-6.79(2H, m), 6.79-6.91(2H, m), 7.15-7.43(5H, m). |
| 16 | 4-$ClPhCH_2$— | —H | $^1$H NMR ($CDCl_3$) δ 1.34-1.87(2H, m), 1.88-2.11(2H, m), 2.51-2.74(3H, m), 3.26-3.57(m, 2H), 3.82(2H, s), 6.66-6.79(2H, m), 6.79-6.92(2H, m), 7.09-7.41(4H, m). |
| 17 | 3,4-$Cl_2PhCH_2$— | —H | $^1$H NMR ($CDCl_3$) δ 1.34-1.80(2H, m), 1.89-2.10(2H, m), 2.50-2.80(3H, m), 3.31-3.54(2H, m), 3.81(2H, s), 6.65-6.79(2H, m), 6.80-6.90(2H, m), 7.11-7.23(1H, d, J = 8.0 Hz), 7.33-7.42 (1H, d, J = 8.2 Hz), 7.43-7.50(1H, d, J = 2.0 Hz). |
| 18 | 4-$CF_3PhCH_2$— | —H | $^1$H NMR ($CDCl_3$) δ 1.40-1.86(2H, m), 1.87-2.12(2H, m), 2.50-2.80(3H, m), 3.38-3.56(2H, m), 3.92(2H, s), 6.66-6.80(2H, m), 6.80-6.93(2H, m), 7.47(2H, d, J = 8.2 Hz), 7.58(2H, d, J = 8.1 Hz). |
| 19 | 4-$CF_3OPhCH_2$— | —H | $^1$H NMR ($CDCl_3$) δ 1.45-1.70(2H, m), 1.88-2.16(2H, m), 2.48-2.83(3H, m), 3.33-3.57(2H, m), 3.85(2H, s), 6.62-6.78(2H, m), 6.80-6.93(2H, m), 7.17(2H, d, J = 8.4 Hz), 7.37(2H, d, J = 8.5 Hz). |
| 20 | | | $^1$H NMR ($CDCl_3$) δ 1.53-1.69(2H, m), 2.13-2.19(2H, m), 2.75-2.86(2H, m), 3.37-3.51 (3H, m), 3.63(1H, d, J = 7.86 Hz). 4.48(1H, s), 6.53-6.61 (2H, m), 6.72-6.80(2H, m). 6.85-6.92(2H, m), 7.01-7.05(2H, m). |
| 21 | 4-ClPh— | —H | $^1$H NMR ($CDCl_3$) δ 1.52-1.68(2H, m), 2.13-2.18(2H, m), 2.75-2.86(2H, m), 3.35-3.56(4H, m), 4.59(1H, brs), 6.51-6.58(2H, m), 6.70-6.79(2H, m), 6.85-6.93(2H, m), 7.10-7.15(2H, m). |
| 22 | —$CH_2C_6H_5$ | —$CH_3$ | Ms: 296(M+) |

TABLE 2-continued

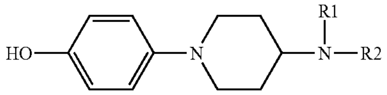

| Reference Example | R1 | R2 | NMR or MS |
|---|---|---|---|
| 23 | 4-$CH_3$OPh— | —$CH_3$ | MS: 366(M+) |
| 24 | 4-$CF_3$Ph— | —$CH_2CH_2OCH_3$ | Ms: 366(M+) |
| 25 | 4-$CF_3PhCH_2$— | —$C_6H_5$ | Ms: 426(M+) |
| 26 | $(CH_3)_3$COCO— | —H | Ms: 292(M+) |
| 27 | $(CH_3)_3$COCO— | —$C_2H_5$ | Ms: 320(M+) |

TABLE 3

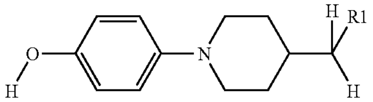

| Reference Example | R1 | NMR or MS |
|---|---|---|
| 28 | —$C_6H_5$ | Ms; 267(M+) |
| 29 | 4-$CF_3$OPhO— | $^1$H NMR($CDCl_3$) δ 1.48-1.63(2H, m), 1.87-1.98(3H, m), 2.62-2.72(2H, m), 3.51-3.57(2H, m), 3.83(2H, d, J = 5.88 Hz), 4.50(1H, brs), 6.73-6.78(2H, m), 6.84-6.91(4H, m), 7.12-7.16(2H, m). |
| 30 | 4-$CF_3OPhCH_2O$— | $^1$H NMR($CDCl_3$) δ 1.36-1.90(5H, m), 2.56-2.68(2H, m), 3.38(2H, d, J = 6.31 Hz), 3.44-3.53(2H, m), 4.51(2H, s), 4.66(1H, brs), 6.70-6.77(2H, m), 6.83-6.89(2H, m), 7.17-7.21(2H, m), 7.34-7.39(2H, m). |
| 31 | 4-$CF_3$OPh- | Ms; 351(M+) |
| 32 | 4-$CF_3$Ph- | $^1$H NMR($CDCl_3$) δ 1.31-1.86(5H, m), 2.43-2.77(4H, m), 3.34-3.58(2H, m), 4.57(1H, brs), 6.66-6.80(2H, m), 6.80-6.92(2H, m), 7.28(2H, d, J = 7.7 Hz), 7.55(2H, d, J = 8.1 Hz). |
| 33 | 4-ClPh- | Ms; 301(M+) |
| 34 | 3,4-$Cl_2$Ph- | Ms: 335(M+) |
| 35 | 4-$ClPhCH_2O$— | $^1$H NMR($CDCl_3$) δ 1.34-1.51(2H, m), 1.68-1.90(3H, m), 2.56-2.67(2H, m), 3.36(2H, d, J = 6.36 Hz), 3.46-3.52(2H, m), 4.43(1H, s), 4.48(2H, s), 6.71-6.78(2H, m), 6.83-6.89(2H, m), 7.27-7.34(4H, m). |
| 36 | 4-$CF_3PhCH_2O$— | $^1$H NMR($CDCl_3$) δ 1.37-1.54(2H, m), 1.68-1.90(3H, m), 2.57-2.68(2H, m), 3.39(2H, d, J = 6.29 Hz), 3.46-3.52(2H, m), 4.57(2H, s), 5.28(1H, s), 6.67-6.74(2H, m), 6.83-6.89(2H, m), 7.43-7.47(2H, m), 7.58-7.62(2H, m). |
| 37 | 4-ClPhO— | $^1$H NMR($CDCl_3$) δ 1.48-1.63(2H, m), 1.86-1.98(3H, m), 2.61-2.71(2H, m), 3.51-3.56(2H, m), 3.82(2H, d, J = 5.95 Hz), 4.49(1H, s), 6.73-6.91(6H, m), 7.19-7.25(2H, m). |
| 38 | 4-$CF_3$PhNH— | $^1$H NMR($CDCl_3$) δ 1.38-1.54(2H, m), 1.64-1.79(1H, m), 1.89(2H, d, J = 12.9 Hz), 2.62(2H, dt, J = 1.99, 11.98 Hz), 3.11(2H, t, J = 6.27 Hz), 3.52(2H, d, J = 11.98 Hz), 4.00-4.18(1H, brm), 4.46(1H, brs), 4.39-4.55(1H, brs), 6.60(2H, d, J = 8.56 Hz), 6.75(2H, d, J = 8.89 Hz), 6.87(2H, d, J = 8.89 Hz), 7.40(2H, d, J = 8.56 Hz) |
| 39 | 4-ClPhNH— | $^1$H NMR($CDCl_3$) δ 1.37-1.57(2H, m), 1.61-1.77(1H, m), 1.79-1.97(2H, m), 2.52-2.70(2H, m), 3.04(2H, d, J = 6.70 Hz), 3.51 (2H, d, J = 11.98 Hz), 3.76-4.76(2H, br), 6.48-6.58(2H, m), 6.71-6.81(2H, m), 6.83-6.92(2H, m), 7.08-7.17(2H, m) |
| 40 | 4-$CF_3$OPhNH— | $^1$H NMR ($CDCl_3$) δ 1.37-1.81(4H, m), 1.90(2H, d, J = 6.20 Hz), 2.63(2H, t, J = 11.68 Hz), 3.05(2H, d, J = 6.66 Hz), 3.52(2H, d, J = 11.99 Hz), 3.69-4.07(1H, br), 4.18-4.74(1H, br), 6.49-6.63(2H, m), 6.67-6.82(2H, m), 6.87(2H, d, J = 8.64 Hz), 7.03(2H, d, J = 8.64 Hz) |
| 41 | 4-$ClPhNHCO_2$— | $^1$H NMR (DMSO) δ 1.35-1.45(2H, m), 1.68-1.80(3H, m), 2.46-2.56(2H, m), 3.40-3.46(2H, m), 4.00(2H, d, J = 5.90 Hz), 6.61-6.65(2H, m), 6.67-6.81(2H, m), 7.31-7.35(2H, m), 7.45-7.51 (2H, m), 8.78(1H, s), 9.79(1H, s). |

TABLE 4

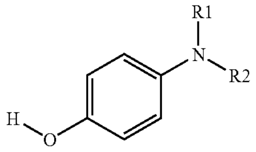

| Reference Example | R1 | R2 | NMR |
|---|---|---|---|
| 42 | —H | 4-$CF_3$OPhCH═CHCH$_2$— | $^1$H NMR ($CDCl_3$) δ 3.58(1H, brs), 3.89 (2H, d, J = 5.7 Hz), 4.24(1H, brs), 6.31 (1H, dt, J = 15.9, 5.7 |

TABLE 4-continued

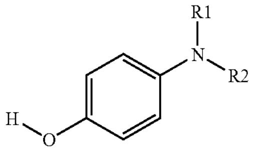

| Reference Example | R1 | R2 | NMR |
|---|---|---|---|
| | | | Hz), 6.57-6.62(3H, m), 6.69-6.73(2H, m), 7.13-7.16(2H, m), 7.36-7.38(2H, m). |

TABLE 5

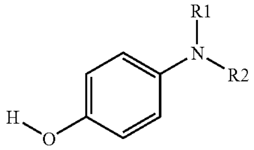

| Reference Example | R1 | R2 | NMR |
|---|---|---|---|
| 43 | —H | 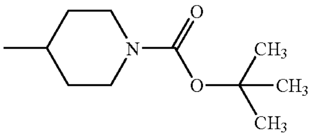 | $^1$H NMR ($CDCl_3$) δ 1.21-1.36(2H, m), 1.46(9H, s), 1.94-2.08(2H, m), 2.78-3.00(2H, brm), 3.08-3.26(1H, br), 3.27-3.38(1H, m), 3.87-4.22(2H, br). 4.29-4.58(1H, br), 6.50-6.58(2H, m), 6.66-6.75(2H, m) |
| 44 | —H | 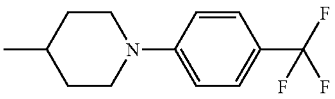 | $^1$H NMR ($CDCl_3$) δ 1.44-1.59(2H, m), 2.16(2H, d, J = 11.54 Hz), 2.92-3.03(2H, m), 3.14-3.32(1H, brs), 3.34-3.47(1H, m), 3.77(2H, d, J = 12.96 Hz), 4.15-4.33(1H, brs), 6.57(2H, d, J = 8.68 Hz), 6.72(2H, d, J = 8.68 Hz), 6.94(2H, d, J = 8.76 Hz), 7.47(2H, d, J = 8.76 Hz) |
| 45 | —H | 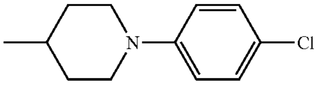 | $^1$H NMR ($CDCl_3$) δ 1.44-1.64(2H, m), 2.07-2.22(2H, m), 2.78-2.93(2H, m), 3.25-3.40(1H, m), 3.53-3.67(2H, m), 6.52-6.63(2H, m), 6.67-6.76(2H, m), 6.81-6.91(2H, m), 7.14-7.24(2H, m) |
| 46 | —H | 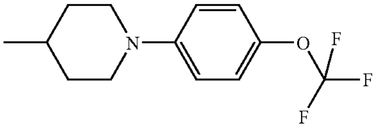 | $^1$H NMR ($CDCl_3$) δ 1.41-1.66(2H, m), 2.09-2.24(2H, m), 2.80-2.97(2H, m), 3.11-3.30(1H, brs), 3.30-3.42(1H, m), 3.53-3.70(2H, m), 4.16-4.34(1H, brs), 6.50-6.62(2H, m), 6.66-6.77(2H, m), 6.85-6.97(6H, m), 7.03-7.17 (2H, m) |
| 47 | —$CH_3$ | 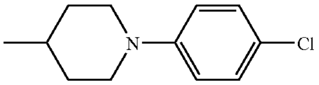 | $^1$H NMR ($CDCl_3$) δ 1.70-1.96(4H, brs), 2.59-2.86(5H, m), 3.37-3.58(1H, m), 3.60-3.82(2H, m), 4.36(1H, s), 6.63.-6.92(6H, m), 7.15-7.23(2H, m) |
| 48 | —$CH_3$ | 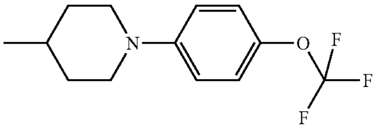 | $^1$H NMR ($CDCl_3$) δ 1.75-1.92(4H, brs), 2.64-2.84(5H, m), 3.37-3.52(1H, m), 3.63-3.79(2H, m), 4.39(1H, s), 6.67.-6.87(4H, m), 6.87-6.94(2H, m), 7.06-7.14(2H, m) |
| 49 | —$C_2H_5$ | 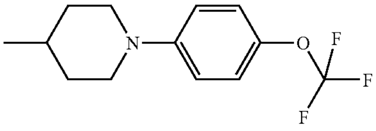 | $^1$H NMR ($CDCl_3$) δ 1.05(3H, t, J = 6.94 Hz), 1.65-1.82(2H, m), 1.82-1.99(2H, m), 2.65-2.83(2H, m), 3.04-3.27(2H, brs), 3.27-3.46(1H, brs), 3.56-3.80(2H, brm), 4.27-4.69(1H, brs), 6.63-6.94(6H, m), 7.03-7.14 (2H, m) |

TABLE 5-continued

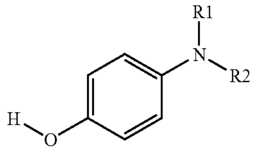

| Reference Example | R1 | R2 | NMR |
|---|---|---|---|
| 50 | —$CH_3$ | 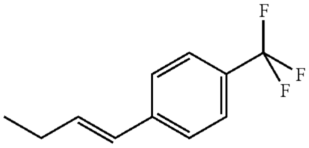 | $^1H$ NMR ($CDCl_3$) δ 2.90(3H, s), 4.00(2H, d, J = 5.4 Hz), 4.29(1H, brs), 6.34(1H, dt, J = 15.9, 5.4 Hz), 6.55(1H, d, J = 15.9 Hz), 6.71-6.79(4H, m), 7.42-7.44 (2H, m), 7.53-7.55(2H, m). |
| 51 | —$CH_3$ | 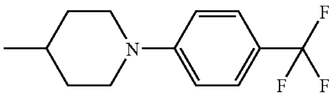 | $^1H$ NMR ($CDCl_3$) δ 1.72-1.91(4H, m), 2.72(3H, s), 2.79-2.93(2H, m), 3.45-3.56(1H, m), 3.87(2H, d, J = 12.74 Hz), 4.38(1H, s), 6.79(2H, d, J = 8.93 Hz), 6.82(2H, d, J = 8.93 Hz), 6.93(2H, d, J = 8.76 Hz), 7.47 (2H, d, J = 8.76 Hz) |

TABLE 6

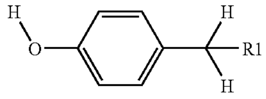

| Reference Example | R1 | NMR |
|---|---|---|
| 52 | 4-$CF_3$Ph- | $^1H$ NMR ($CDCl_3$) δ 3.96(2H, s), 4.66(1H, s), 6.75-6.79(2H, m), 7.01-7.06(2H, m), 7.26-7.29 (2H, m), 7.51-7.54(2H, m). |

TABLE 6-continued

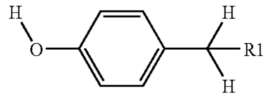

| Reference Example | R1 | NMR |
|---|---|---|
| 53 | 4-ClPh- | $^1H$ NMR ($CDCl_3$) δ 3.87(3H, brs), 6.74-6.78 (2H, m), 7.01-7.04(2H, m), 7.07-7.10(2H, m), 7.22-7.26(2H, m). |

TABLE 7

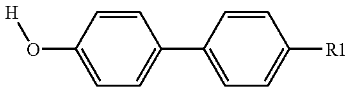

| Reference Example | R1 | NMR or MS |
|---|---|---|
| 54 | 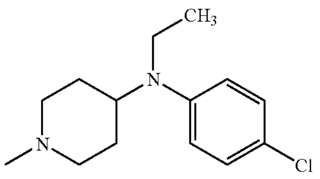 | Ms; 406(M+) |
| 55 | 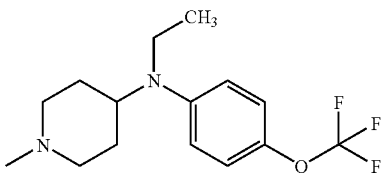 | $^1H$ NMR ($CDCl_3$) δ 1.17(3H, t, J = 7.01 Hz), 1.84-1.96 (4H, m), 2.79-2.91(2H, m), 3.31(3H, q, J = 7.01 Hz), 3.61-3.78(1H, m), 3.81-3.86(2H, m), 4.73(1H, s), 6.69-6.75(2H, m), 6.84-6.91(2H, m), 6.99-7.11(4H, m), 7.41-7.48(4H, m). |

TABLE 7-continued

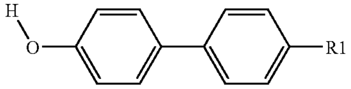

| Reference Example | R1 | NMR or MS |
|---|---|---|
| 56 | 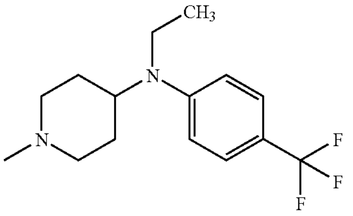 | $^1$H NMR ($CDCl_3$) δ 1.21(3H, t, J = 7.03 Hz), 1.90-1.98 (4H, m), 2.81-2.93(2H, m), 3.37(3H, q, J = 7.03 Hz), 3.74-3.88(3H, m), 4.75(1H, s), 6.73-6.79(2H, m), 6.84-6.91(2H, m), 6.98-7.04(2H, m), 7.42-7.49(6H, m). |
| 57 | 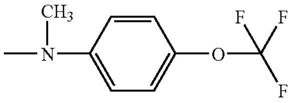 | $^1$H NMR ($CDCl_3$) δ 3.33(3H, s), 4.80(1H, brs), 6.87-6.91(2H, m), 6.96-7.02(2H, m), 7.07-7.14(4H, m), 7.42-7.51(4H, m). |
| 58 | 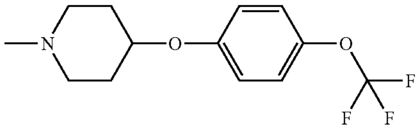 | $^1$H NMR ($CDCl_3$) δ 1.88-2.02(2H, m), 2.07-2.18(2H, m), 3.09-3.20(2H, m), 3.49-3.59(2H, m), 4.41-4.50(1H, m), 4.74(1H, s), 6.84-6.95(4H, m), 6.98-7.03(2H, m), 7.12-7.17(2H, m), 7.40-7.48(4H, m). |
| 59 | 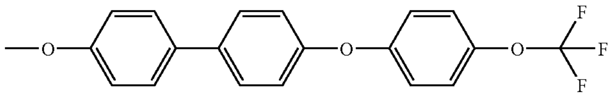 | $^1$H NMR (DMSO) δ 6.82-6.86(2H, m), 7.08-7.20(8H, m), 7.39-7.49(4H, m), 7.59-7.72(6H, m), 9.53(1H, s). |
| 60 | 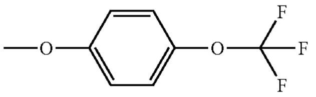 | $^1$H NMR ($CDCl_3$) δ 4.73(1H, s), 6.88-6.93(2H, m), 7.01-7.13(4H, m), 7.17-7.22(2H, m), 7.43-7.55(4H, m). |

TABLE 8

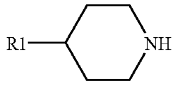

| Reference Example | R1 | MS |
|---|---|---|
| 61 | 4-$CF_3OPhCH_2$— | 260 $(M + 1)^+$ |
| 62 | 4-$CF_3OPhN(CH_3)$— | 224 $(M^+)$ |
| 63 | 4-$ClPhN(CH_3)$— | 224 $(M^+)$ |

TABLE 9

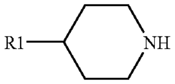

| Reference Example | R1 | NMR |
|---|---|---|
| 64 | 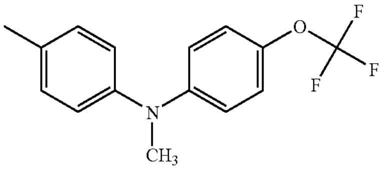 | CDCl3; 1.72-1.89(2H, m), 1.93-2.23(3H, m), 2.44-3.09(3H, m), 3.11-3.21 (1H, m), 3.28(3H, s), 3.42-3.56(1H, m), 6.82-6.91(2H, m), 6.94-7.10(4H, m), 7.13-7.24(2H, m). |

TABLE 10

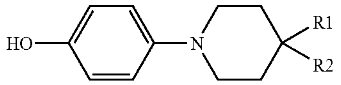

| Reference Example | R1 | R2 | NMR |
|---|---|---|---|
| 65 | —H | 4-$CF_3PhCH_2O(CH_2)_2$— | CDCl3; 1.35-1.67 (5H, m), 1.76-1.82 (2H, m), 2.55-2.66 (2H, m), 3.44-3.50 (2H, m), 3.57 (2H, t, J = 6.3 Hz), 4.38 (1H, s), 4.57 (2H, s), 6.72-6.78 (2H, m), 6.84-6.89 (2H, m), 7.43-7.48 (2H, m), 7.59-7.62 (2H, m) |
| 66 | —H | 4-$CF_3OPhCH_2OCH_2$— | CDCl3; 1.36-1.53 (2H, m), 1.65-1.82 (1H, m), 1.84-1.90 (2H, m), 2.56-2.67 (2H, m), 3.38 (2H, d, J = 6.3 Hz), 3.44-3.53 (2H, m), 4.51 (2H, s), 4.66 (1H, bs), 6.70-6.77 (2H, m), 6.83-6.89 (2H, m), 7.17-7.21 (2H, m), 7.34-7.39 (2H, m) |
| 67 | —H | 4-$CF_3OPhCH_2O(CH_2)_2$— | CDCl3; 1.37-1.66 (5H, m), 1.75-1.81 (2H, m), 2.55-2.65 (2H, m), 3.44-3.50 (2H, m), 3.55 (2H, t, J = 6.3 Hz), 4.44 (1H, s), 4.50 (2H, s), 6.72-6.78 (2H, m), 6.83-6.89 (2H, m), 7.18-7.22 (2H, m), 7.35-7.39 (2H, m) |
| 68 | —H | 4-FPhNH— | CDCl3; 1.51-1.66 (2H, m), 2.13-2.18 (2H, m), 2.74-2.85 (2H, m), 3.30-3.50 (4H, m), 4.50 (1H, s), 6.53-6.61 (2H, m), 6.73-6.78 (2H, m), 6.85-6.94 (4H, m) |
| 69 | —H | 4-$CF_3OPhNHCH_2$— | CDCl3; 7.03 (2H, d, J = 8.6 Hz), 6.87 (2H, d, J = 8.6 Hz), 6.82-6.67 (2H, m), 6.63-6.49(2H, m), 4.74-4.18(1H, br), 4.07-3.69 (1H, br), 3.53 (2H, d, J = 12.0 Hz), 3.05 (2H, d, J = 6.7 Hz), 2.63 (2H, t, J = 6.7 Hz), 1.90 (2H, d, J = 12.4 Hz), 1.81-1.37 (3H, m) |
| 70 | —H | 4-$ClPhNHCH_2$— | CDCl3; 7.17-7.08 (2H, m), 6.92-6.83 (2H, m), 6.81-6.71 (2H, m), 6.58-6.48(2H, m), 4.76-3.76(2H, br), 3.51 (2H, d, J = 12.0 Hz), 3.04 (2H, d, J = 6.7 Hz), 2.70-2.52 (2H, m), 1.88 (2H, d, J = 12.3 Hz), 1.77-1.61 (1H, m), 1.57-1.37 (2H, m) |
| 71 | —H | 3,5-$Cl_2PhNH$— | CDCl3; 1.48-1.64 (2H, m), 2.05-2.19 (2H, m), 2.71-2.88 (2H, m), 3.21-3.48 (3H, m), 3.75 (1H, d, J = 8.0 Hz), 4.71 (1H, bs), 6.46 (2H, d, J = 1.8 Hz) . . . |
| 72 | —H | 4-n-$C_3H_7$—PhNH— | CDCl3; 0.94 (3H, t, J = 7.3 Hz), 1.45-1.71 (4H, m), 2.05-2.21 (2H, m), 2.47 (2H, t, J = 7.3 Hz), 2.64-2.83 (2H, m), 3.29-3.52 (3H, m), 4.83 (1H, br), 6 . . . |

TABLE 11

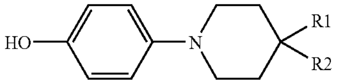

| Reference Example | R1 | R2 | NMR |
|---|---|---|---|
| 73 | —H | 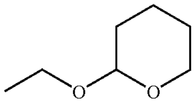 | CDCl3; 1.36-1.92 (10H, m), 2.56-2.68 (2H, m), 3.28 (1H, dd, J = 6.2 Hz, 9.5 Hz), 3.47-3.56 (3H, m), 3.65 (1H, dd, J = 6.6 Hz, 9.5 Hz), 3.82-3.92 (1H, m), 4.58-4.61 (1H, m), 4.76 (1H, bs), 6.70-6.78 (2H, m), 6.84-6.91 (2H, m) |
| 74 | —H | 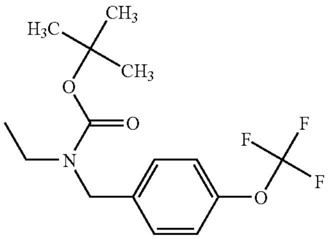 | CDCl3; 7.34-7.10 (4H, m), 6.85 (2H, d, J = 8.03 Hz), 6.75 (2H, d, J = 8.79 Hz), 4.60 (1H, s), 4.54-4.36 (2H, m), 3.55-3.40 (2H, m), 3.24-3.02 (2H, m), 2.66-2.44 (2H, m), 1.85-1.60 (3H, m), 1.56-1.31 (11H, m) |

TABLE 11-continued

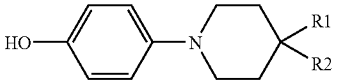

| Reference Example | R1 | R2 | NMR |
|---|---|---|---|
| 75 | —H | 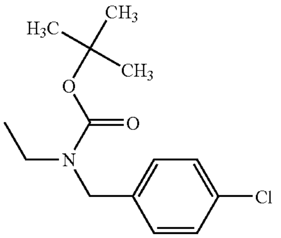 | CDCl3; 7.36-7.24 (2H, m), 7.23-7.07 (2H, m), 6.93-6.80 (2H, m), 6.80-6.72 (2H, m), 4.63 (1H, s), 4.51-4.34 (2H, m), 3.57-3.41 (2H, m), 3.26-2.99 (2H, m), 2.67-2.46 (2H, m), 1.85-1.61 (3H, m), 1.61-1.31 (11H, m) |
| 76 | —H | 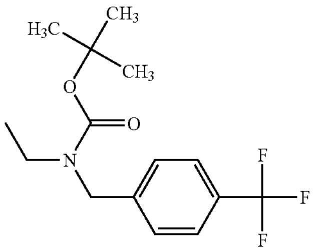 | CDCl3; 7.59(2H, d, J = 7.8 H), 7.42-7.28 (2H, m), 6.93-6.80 (2H, m), 6.75 (2H, d, J = 8.7 Hz), 4.69-4.41 (3H, m), 3.58-3.41 (2H, m), 3.26-3.02 (2H, m), 2.71-2.44 (2H, m), 1.91-1.62 (3H, m), 1.62-1.28 (11H, m) |

TABLE 12

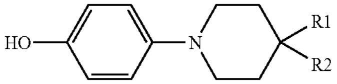

| Reference Example | R1 | R2 | MS |
|---|---|---|---|
| 77 | —H | 4-$CF_3OPhCH_2$— | 351 ($M^+$) |
| 78 | —H | 4-$CF_3OPh(CH_2)_3O$— | 395 ($M^+$) |
| 79 | —OH | 4-ClPH— | 303 ($M^+$) |
| 80 | —H | 4-$CF_3PhCH_2OCH_2$— | 364 $(M-1)^+$ |
| 81 | —H | 4-$ClPhCH_2O_2(CH_2)_2$— | 345 ($M^+$) |
| 82 | —H | 4-$ClPhNHCO(CH_2)_2$— | 374 ($M^+$) |
| 83 | —H | 4-$CF_3OPh(CH_2)_2$— | 365 ($M^+$) |
| 84 | —H | 3,4-$Cl_2PhNH$— | 336 $(M-1)^+$ |
| 85 | —H | 3-$CF_3OPhCH_2$— | 351 ($M^+$) |
| 86 | —H | 2-$CF_3OPhCH_2$— | 351 ($M^+$) |

TABLE 13

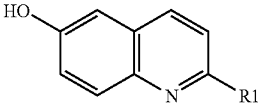

| Reference Example | R1 | MS |
|---|---|---|
| 87 | 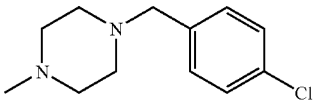 | 353 ($M^+$) |

TABLE 13-continued

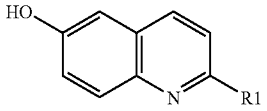

| Reference Example | R1 | MS |
|---|---|---|
| 88 | 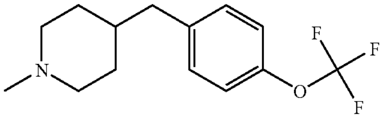 | 402 ($M^+$) |
| 89 | 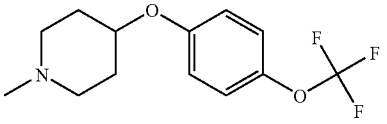 | 404 ($M^+$) |
| 90 | 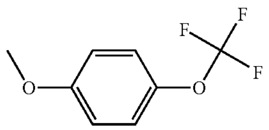 | 320 $(M-1)^+$ |
| 91 | 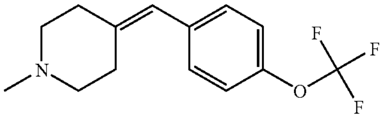 | 400 ($M^+$) |
| 92 | 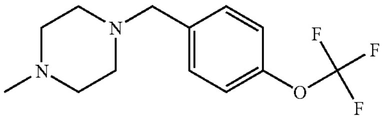 | 403 ($M^+$) |

TABLE 14
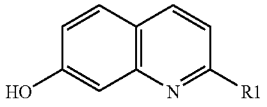
| Reference Example | R1 | MS |
|---|---|---|
| 93 | 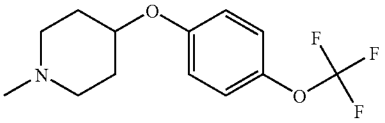 | 404 ($M^+$) |
| 94 | 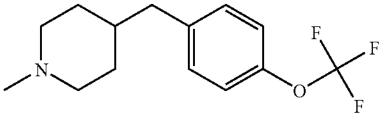 | 402 ($M^+$) |
TABLE 15
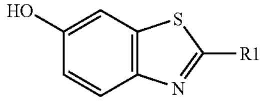
| Reference Example | R1 | MS |
|---|---|---|
| 95 | 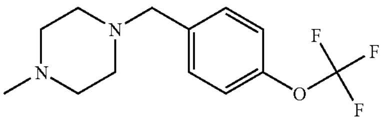 | 409 ($M^+$) |
| 96 | 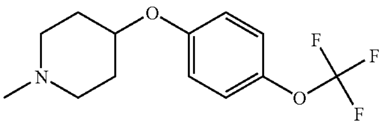 | 410 ($M^+$) |
| 97 | 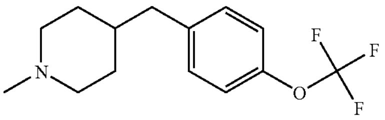 | 408 ($M^+$) |
| 98 | 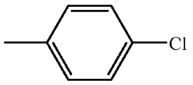 | 261 ($M^+$) |
TABLE 15-continued
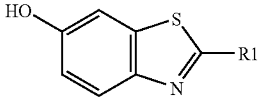
| Reference Example | R1 | MS |
|---|---|---|
| 99 | 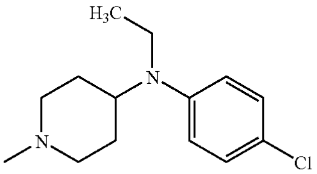 | 387 ($M^+$) |
TABLE 16
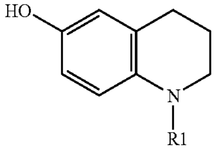
| Reference Example | R1 | MS |
|---|---|---|
| 100 | 4-$CF_3PhCH_2$— | 307 ($M^+$) |
| 101 | 4-$CF_3OPhCH_2$— | 323 ($M^+$) |
| 102 | 4-$ClPhCH_2$— | 273 ($M^+$) |
TABLE 17
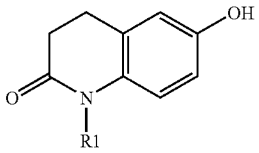
| Reference Example | R1 | MS |
|---|---|---|
| 103 | 4-$CF_3OPhCH_2$— | 337 ($M^+$) |
| 104 | 4-$ClPhCH_2$— | 287 ($M^+$) |
TABLE 18
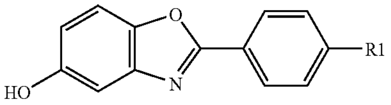
| Reference Example | R1 | MS |
|---|---|---|
| 105 | –Cl | 245 ($M^+$) |
| 106 | –H | 211 ($M^+$) |

TABLE 19

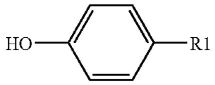

| Reference Example | R1 | NMR |
|---|---|---|
| 107 | 4-$CF_3$OPhCH═CHCH$_2$NH— | CDCl3; 3.52-3.75(1H, br), 3.89(2H, dd, J = 5.7, 1.4 Hz), 4.17-4.32(1H, br), 6.31(1H, td, J = 15.9, 5.7 Hz), 5.50-5.65(3H, m), 6.61(2H, d, J = 9.3 Hz), 7.15(2H, d, J = 8.4 Hz), 7.37(2H, d, J = 8.4 Hz). |
| 108 | 4-$CF_3$OPhCH═CHCONH— | (DMSO-D6); 6.72(2H, d, J = 8.7 Hz), 6.79(1H, d, J = 15.7 Hz), 7.41-7.49(4H, m), 7.55(1H, d, J = 15.7), 7.73(2H, d, J = 8.7 Hz), 9.10-9.34(1H, br), 9.90-10.02(1H, br). |
| 109 | 4-$CF_3$OPhCH═CHCON($CH_3$)— | (DMSO-D6); 3.38(3H, s), 6.11-6.16(1H, br), 6.35(1H, d, J = 15.5 Hz), 6.93(2H, d, J = 8.6 Hz), 7.07-7.15(4H, m), 7.33(1H, d, J = 8.6 Hz), 7.63(1H, d, J = 15.6 Hz). |
| 110 | 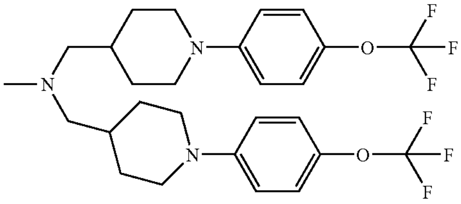 | CDCl3; 7.08(4H, d, J = 8.9 Hz), 6.87(4H, d, J = 8.9 Hz), 6.76(2H, d, J = 8.9 Hz), 6.65(2H, d, J = 8.9 Hz), 4.42-4.29(1H, br), 3.63(4H, d, J = 12.2 Hz), 3.14(4H, d, 6.5 Hz), 2.65(4H, t, J = 12.2 Hz), 1.81 (6H, d, J = 9.5 Hz), 1.44-1.27(4H, m) |
| 111 | 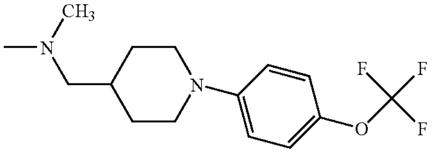 | CDCl3; 7.09(2H, d, J = 8.6 Hz), 6.94-6.84(2H, m), 6.81-6.73(2H, m), 6.63(2H, d, J = 8.9 Hz), 4.26(1H, s), 3.65(2H, d, J = 12.3 Hz), 3.12(2H, d, J = 6.8 Hz), 2.90(3H, s), 2.73-2.62(2H, m), 1.93-1.75(3H, m), 1.46-1.30(2H, m) |
| 112 | 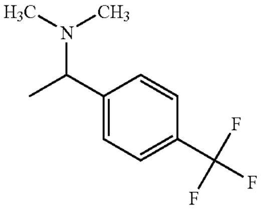 | CDCl3; 2.19(6H, s), 4.08(1H, s), 6.74(2H, d, J = 8.5 Hz), 7.24(2H, d, J = 8.5 Hz), 7.49-7.56(4H, m). |
| 113 | 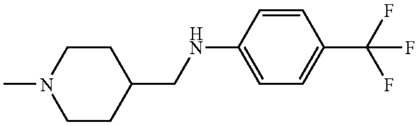 | CDCl3; 7.40(2H, d, J = 8.6 Hz), 6.87(2H, d, J = 8.9 Hz), 6.75(2H, d, J = 8.9 Hz), 6.60(2H, d, J = 8.6 Hz), 4.46(1H, s), 4.18-4.00(1H, br), 3.52(2H, d, J = 11.9 Hz), 3.11(2H, t, J = 6.3 Hz), 2.71-2.54(2H, m), 1.89(2H, d, J = 12.9 Hz), 1.79-1.64(1H, m), 1.53-1.38(2H, m) |

TABLE 20

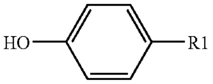

| Reference Example | R1 | MS |
|---|---|---|
| 114 | 4-$CF_3$PhCH═CHCH$_2$NH— | 293 ($M^+$) |
| 115 | 4-$CF_3$PhCH═CHCON($C_2H_5$)— | 321 ($M^+$) |
| 116 | 4-$CF_3$OPhCH$_2$OCONH— | 327 ($M^+$) |
| 117 | 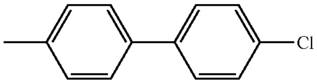 | 280 ($M^+$) |

TABLE 20-continued

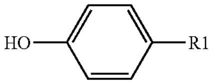

| Reference Example | R1 | MS |
|---|---|---|
| 118 | 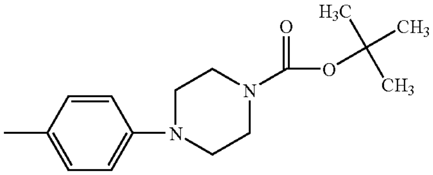 | 354 ($M^+$) |

TABLE 20-continued

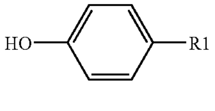

| Reference Example | R1 | MS |
|---|---|---|
| 119 | 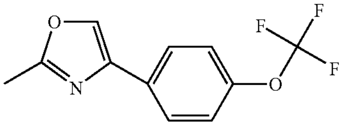 | 321 ($M^+$) |
| 120 | 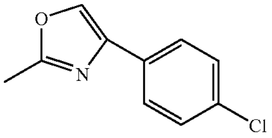 | 271 ($M^+$) |
| 121 | 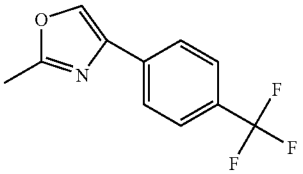 | 305 ($M^+$) |
| 122 | 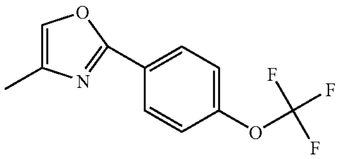 | 321 ($M^+$) |

TABLE 21

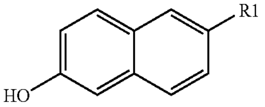

| Reference Example | R1 | MS |
|---|---|---|
| 123 | 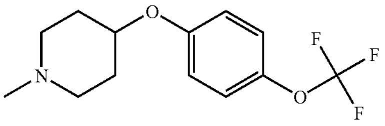 | 403 ($M^+$) |

Example 1

Preparation of (R)-2-methyl-6-nitro-2-(2-(4-(4-trifluoromethoxybenzyl)-piperazine-1-yl)benzothiazole-6-yloxymethyl)-2,3-dihydroimidazo[2,1-b]oxazole (R)-2-Chloro-1-(2-methyl-2-oxyranylmethyl)-4-nitro-1H-imidazole (51 mg, 0.23 mmol) and 6-hydroxy-2-(4-(4-trifluoromethoxybenzyl)-piperazine-1-yl)-benzothiazole (80 mg, 0.20 mmol) were dissolved in DMF (5 ml). To this mixture, sodium hydride (10 mg, 0.25 mmol) was added and stirred at 60° C. for 1.5 hours. After allowing to stand at room temperature, water was added to the reaction solution and extracted with ethyl acetate. The combined organic layer was washed with water and saturated brine, then dried over magnesium sulfate. This was filtered and then the filtrate was concentrated under reduced pressure. The residue was purified by silica gel column chromatography (n-hexane:ethyl acetate=1:3→ethyl acetate) and recrystallized from ethanol to afford (R)-2-methyl-6-nitro-2-(2-(4-(4-trifluoromethoxybenzyl)-piperazine-1-yl)benzothiazole-6-yloxymethyl)-2,3-dihydroimidazo[2,1-b]oxazole (40 mg, yield 33%) as colorless powdered crystals.

Melting point: 205.6-207.4° C.

Example 2

Preparation of (R)-2-methyl-6-nitro-2-(2-(4-(4-trifluoromethoxyphenoxy)piperidine-1-yl)pyridine-5-oxy)methyl-2,3-dihydro-imidazo[2,1-b]oxazole 5-hydroxy-2-(4-(4-trifluoromethoxy)-phenoxy)piperadine-1-yl)pyridine (0.67 g, 1.9 mmol) and (R)-2-chloro-1-(2-methyl-2-oxyranylmethyl)-4-nitro-1H-imidazole (0.51 g, 2.4 mmol) were dissolved in DMF (6.7 ml). To this mixture, sodium hydride (91 mg, 2.3 mmol) was added and stirred at 50-55° C. for 1 hour. Water was added to the reaction solution and extracted with methylene chloride. The organic layer was washed with saturated brine, dried over magnesium sulfate and then filtered under suction. The resulting filtrate was concentrated under reduced pressure. The residue was purified by silica gel column chromatography (methylene chloride/ethyl acetate=10/0, 9/1, 8/2), and further crystallized from methylene chloride/diisopropyl ether/ethyl acetate to afford (R)-2-methyl-6-nitro-2-(2-(4-(4-trifluoromethoxyphenoxy)piperidine-1-yl)pyridine-5-oxy)methyl-2,3-dihydro-imidazo[2,1-b]oxazole (0.30 g, yield 29%) as a light yellow powder.

$^1$H-NMR ($CDCl_3$) δppm: 1.77 (3H, s), 1.80-1.94 (2H, m), 1.94-2.17 (2H, m), 3.21-3.44 (2H, m), 3.67-3.89 (2H, m), 3.96-4.11 (2H, m), 4.19 (1H, d, J=10.4 Hz), 4.36-4.59 (2H, m), 6.65 (1H, d, J=9.2 Hz), 6.83-6.97 (2H, m), 7.02-7.20 (3H, m), 7.56 (1H, s), 7.87 (1H, d, J=3.0 Hz).

The following compounds were prepared similarly to the above described Example 2. In the following table, Ph means a phenyl group or phenylene group.

Example 3

(R)-2-(4-(4-(N-(4-chlorophenyl)-N-methylamino)piperidine-1-yl)phenoxymethyl)-2-methyl-6-nitro-2,3-dihydro-imidazo[2,1-b]oxazole Melting point: 173.7-175.1° C.

Example 4

(R)-2-methyl-6-nitro-2-(4-(4-(4-trifluoromethoxybenzyl)piperidine-1-yl)phenoxymethyl)-2,3-dihydroimidazo[2,1-b]oxazole $^1$H-NMR ($CDCl_3$) δppm: 1.23-1.52 (2H, m), 1.52-1.66 (3H, m), 1.66-1.89 (3H, m), 2.43-2.70 (4H, m), 3.50 (2H, d, J=12.1 Hz), 3.91-4.09 (2H, m), 4.16 (1H, d, J=10.1 Hz), 4.48 (1H, d, J=10.2 Hz), 6.66-6.81 (2H, m), 6.81-6.95 (2H, m), 7.05-7.23 (4H, m), 7.54 (1H, s).

Melting point: 210.9-212.4° C.

$[\alpha]_D$=−9.0° (concentration: 1.0, $CHCl_3$).

Example 5

(R)-2-(4-(4-(3,4-dichlorobenzyl)piperidine-1-yl)phenoxymethyl)-2-methyl-6-nitro-2,3-dihydroimidazo[2,1-b]oxazole $^1$H-NMR ($CDCl_3$) δppm: 1.24-1.52 (2H, m), 1.52-1.64 (4H, m), 1.64-1.73 (1H, m), 1.73-1.87 (4H, m), 2.38-2.68 (4H, m), 3.49 (2H, d, J=12.1 Hz), 3.91-4.09 (2H, m), 4.16 (1H, d, J=10.2 Hz), 4.49 (1H, d, J=10.2 Hz), 6.67-6.81 (2H, m), 6.81-6.92 (2H, m), 6.94-7.07 (1H, m), 7.25 (1H, s), 7.35 (1H, d, J=8.2 Hz), 7.55 (1H, s).

Melting point: 180.0-181.2° C.

$[\alpha]_D$=−8.5° (concentration: 1.0, $CHCl_3$).

Example 6

(R)-6-nitro-2-(4-(4-(4-trifluoromethoxybenzyloxymethyl)piperidine-1-yl)phenoxymethyl)-2,3-dihydroimidazo[2,1-b]oxazole Melting point: 140.4-141.7° C.

Example 7

(R)-2-methyl-6-nitro-2-(4-(4-(4-trifluoromethylbenzyloxymethyl)-piperidine-1-yl)phenoxymethyl)-2,3-dihydroimidazo[2,1-b]oxazole Melting point: 172.3-172.9° C.

Example 8

(R)-2-methyl-6-nitro-2-(4-(4-(3-(4-trifluoromethyphenyl)-2-propenyl)piperidine-1-yl)phenoxymethyl)-2,3-dihydroimidazo[2,1-b]oxazole Melting point: 199.7-202° C.

Example 9

(R)-2-methyl-6-nitro-2-(4-(4-(2-(4-trifluoromethoxyphenoxy)ethyl)piperazine-1-yl)phenoxymethyl)-2,3-dihydroimidazo[2,1-b]oxazole Melting point: 194.8-195.6° C.

Example 10

(R)-2-(4-(4-(N-(4-chlorophenyl)-N-ethylamino)piperidine-1-yl)phenoxymethyl)-2-methyl-6-nitro-2,3-dihydroimidazo[2,1-b]oxazole Melting point: 121.4-125° C.

Example 11

(R)-2-(4-(4-(N-ethyl-N-(4-trifluoromethoxyphenyl)amino)piperidine-1-yl)phenoxymethyl)-2-methyl-6-nitro-2,3-dihydroimidazo[2,1-b]oxazole Melting point: 122.5-122.8° C.

Example 12

(R)-2-(4-(4-(N-ethyl-N-(4-trifluoromethylphenyl)-amino)piperidine-1-yl)phenoxymethyl)-2-methyl-6-nitro-2,3-dihydroimidazo[2,1-b]oxazole Melting point: 105-108.5° C.

Example 13

(R)-2-(4-(4-(5-chlorobenzofuran-2-ylmethyl)piperadine-1-yl)phenoxymethyl)-2-methyl-6-nitro-2,3-dihydroimidazo[2,1-b]oxazole Melting point: 210.6-211.6° C.

Example 14

(R)-2-methyl-6-nitro-2-(2-(4-(4-trifluoromethoxybenzyl)piperadine-1-yl)benzothiazole-6-yloxymethyl)-2,3-dihydroimidazo[2,1-b]oxazole Melting point: 203.9-205.2° C.

Example 15

2-Methyl-6-nitro-2-(4-(4-(4-trifluoromethoxybenzyl)-piperidine-1-yl)phenoxymethyl)-2,3-dihydroimidazo[2,1-b]oxazole Melting point: 180.9-182.7° C.

Example 16

2-(4-(4-(3,4-Dichlorobenzyl)piperidine-1-yl)phenoxymethyl)-2-methyl-6-nitro-2,3-dihydroimidazo-[2,1-b]oxazole Melting point: 191.4-192.1° C.

Example 17

2-(4-(4-(N-(4-chlorophenyl)-N-methylamino)piperidine-1-yl)phenoxymethyl)-2-methyl-6-nitro-2,3-dihydroimidazo-[2,1-b]oxazole Melting point: 137.6-141.5° C.

Example 18

(R)-2-(4-(4-(N-(4-chlorophenyl)-N-methylamino)piperidine-1-yl)phenoxymethyl)-2-methyl-6-nitro-2,3-dihydroimidazo[2,1-b]oxazole, 4-toluenesulfonate.

Melting point: 212.6-214.1° C.

Example 19

(R)-2-(4-(4-(N-(4-chlorophenyl)-N-methylamino)-piperidine-1-yl)phenoxymethyl)-2-methyl-6-nitro-2,3-dihydroimidazo[2,1-b]oxazole, methanesulfonate Melting point: 171.2-172.8° C.

Example 20

(R)-2-(4-(4-(N-(4-chlorophenyl)-N-methylamino)-piperidine-1-yl)phenoxymethyl)-2-methyl-6-nitro-2,3-dihydroimidazo[2,1-b]oxazole, hydrochloride Melting point: 170.0-173.7° C.

Example 21

2-Methyl-6-nitro-2-(4-(4-(4-trifluoromethoxybenzyloxy-methyl)piperidine-1-yl)phenoxymethyl)-2,3-dihydroimidazo[2,1-b]oxazole Melting point: 153.1-153.7° C.

Example 22

(R)-(4-chlorophenyl)carbamic acid 1-(4-(2-methyl-6-nitro-2,3-dihydroimidazo[2,1-b]oxazole-2-yl-methoxy)phenyl)piperidine-4-ylmethyl ester Melting point: 211.6-212.3° C. (decomposed).

Example 23

2-Methyl-6-nitro-2-(4-(4-(4-trifluoromethylbenzyloxy-methyl)piperidine-1-yl)phenoxymethyl)-2,3-dihydroimidazo[2,1-b]oxazole Melting point: 138.7-139.5° C.

TABLE 22

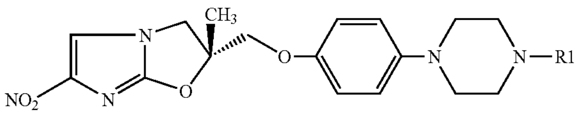

| Example | R1 | mp(° C.) |
|---|---|---|
| 24 | 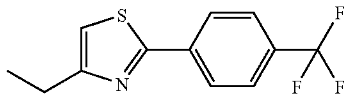 | 210.0-212.1 |
| 25 | 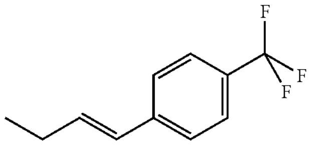 | 199.7-202.0 |
| 26 | 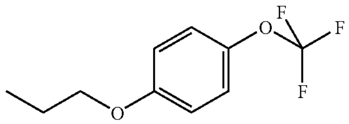 | 194.8-195.6 |
| 27 | 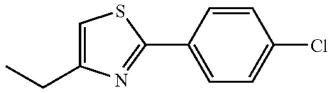 | 197.1-198.6 |
| 28 | 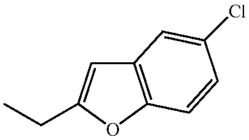 | 210.6-211.6 |

TABLE 23

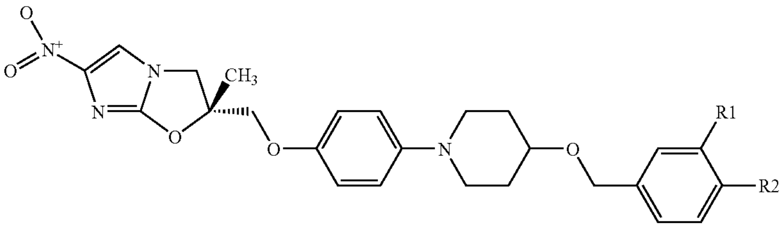

| Example | R1 | R2 | mp(° C.) |
|---|---|---|---|
| 29 | —H | —H | 210.9-213.8 |
| 30 | —H | —$OCF_3$ | 214.3-217.7 |
| 31 | —H | —$CF_3$ | 217.4-219.7 |
| 32 | —H | —Cl | 208.7-211.6 |
| 33 | —Cl | —Cl | 198.9-202.0 |

TABLE 24

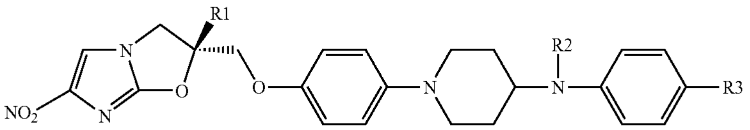

| Example | R1 | R2 | R3 | mp(° C.) |
|---|---|---|---|---|
| 34 | —$CH_3$ | —$CH_3$ | —Cl | 173.7-175.1 |
| 35 | —$CH_3$ | —H | —$CF_3$ | 178.4-181.1 dec |
| 36 | —$CH_3$ | —$CH_3$ | —$CF_3$ | 135.0-137.5 |
| 37 | —$CH_3$ | —H | —$OCF_3$ | 195.4-197.8 dec |
| 38 | —$CH_3$ | —$CH_3$ | —$OCF_3$ | 158.1-158.8 |
| 39 | —$CH_3$ | —H | —Cl | 187.0-189.5 |
| 40 | —$CH_3$ | —$CH_2CH_3$ | —Cl | 121.4-125.0 |
| 41 | —$CH_3$ | —$CH_2CH_3$ | —$CF_3$ | 105.0-108.5 |
| 42 | —$CH_3$ | 4-$CF_3PhCH_2$— | —H | 192.5-195.3 |
| 43 | —$CH_3$ | —$CH_2CH_2OH$ | —$CF_3$ | 147.3-148.6 |
| 44 | —$CH_3$ | —$CH_2CH_2OCH_3$ | —$CF_3$ | 89.5-93.4 |
| 45 | —$CH_3$ | —$C_3H_7$ | —$CF_3$ | 103.4-107.9 |
| 46 | —$CH_3$ | —$C_4H_9$ | —Cl | 122.1-124.0 |
| 47 | —$CH_3$ | $CH_3OCH_2CO$— | —$CF_3$ | 124.7-127.0 |
| 48 | —$CH_3$ | —$CH_2$-cyclo-$C_3H_5$ | —$CF_3$ | 157.6-160.4 |
| 49 | —$CH_3$ | —$C_4H_9$ | —$CF_3$ | 117.8-120.2 |
| 50 | —$CH_3$ | —$C_2H_5$ | —$OCF_3$ | 122.5-122.8 |
| 51 | —H | —$CH_3$ | —$OCF_3$ | 154.0-157.3 dec |
| 52 | —H | —$C_2H_5$ | —$CF_3$ | 172.0-174.2 |
| 53 | —H | —$CH_3$ | —$CF_3$ | 189.4-190.8 |
| 54 | —H | —H | —$CF_3$ | 179.2-180.7 |
| 55 | —H | —$CH_3$ | —Cl | 203.6-204.5 dec |

TABLE 25

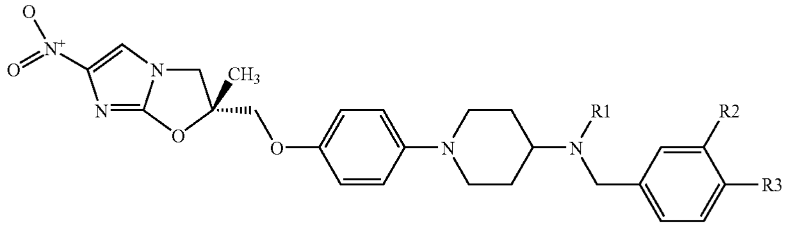

| Example | R1 | R2 | R3 | mp(° C.) or $^1$H NMR |
|---|---|---|---|---|
| 56 | —H | —H | —H | 215.9-217.2 |
| 57 | —H | —H | —Cl | 211.7-213.1 |
| 58 | —H | —Cl | —Cl | 199.5-204.0 |
| 59 | —H | —H | —$CF_3$ | 213.5-216.5 |
| 60 | —H | —H | —$OCF_3$ | 217.6-218.4 |
| 61 | —$CH_3$ | —H | —Cl | 195.4-199.1 |
| 62 | —$CH_3$ | —H | —$OCF_3$ | 204.8-207.0 |
| 63 | —$CH_3$ | —H | —H | 206.1-208.9 |
| 64 | —$CH_3$ | —Cl | —Cl | 182.1-185.7 |
| 65 | —$CH_3$ | —H | —$CF_3$ | 199.6-202.0 |
| 66 | —$COCH_3$ | —H | —Cl | 169.9-117.4 |
| 67 | 4-$CF_3OPhCH_2$— | —H | —$OCF_3$ | 115.4-117.4 |
| 68 | —$COCH_3$ | —Cl | —Cl | $^1$H NMR (DMSO) δ 1.42-1.87(8H, m), 2.11(3H, brs), 2.53-2.77(2H, m), 3.52(2H, d, J = 12.4 Hz), 4.15(1H, d, J = 11.9 Hz), 4.17(2H, s), 4.35(1H, d, J = 10.9 Hz), 4.51(2H, brs), 6.63-6.91(4H, m), 7.11-7.28(1H, m), 7.35-7.61(3H, m), 8.01(1H, s). |
| 69 | —$CO2C_6H_5$ | —H | —$CF_3$ | 137.0-140.0 |
| 70 | —$CO2C2H_5$ | —H | —$CF_3$ | 159.9-162.8 |
| 71 | —$C_2H_5$ | —H | —$CF_3$ | 132.5-136.7 |

TABLE 26

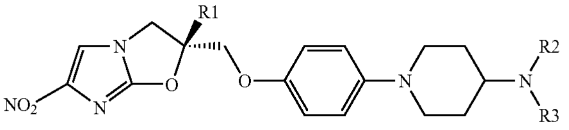

| Example | R1 | R2 | R3 | mp(° C.) |
|---|---|---|---|---|
| 72 | —$CH_3$ | —H | $(CH_3)_3COCO$— | 250.7-254.0 |
| 73 | —$CH_3$ | —H | 4-$ClPhCH_2OCO$— | 232.0-237.5 |
| 74 | —$CH_3$ | —$C_2H_5$ | $(CH_3)_3COCO$— | 165.0-167.2 |
| 75 | —$CH_3$ | —H | 4-$CF_3Ph(CH_2)_2$— | 161.2-163.5 |
| 76 | —$CH_3$ | —H | 4-$CF_3Ph(CH_2)_3$— | 194.9-196.7 |
| 77 | —$CH_3$ | —H | 4-$CF_3PhCH{=}CHCH_2$— | 212.3-214.7 dec |
| 78 | —$CH_3$ | —$CH_3$ | 4-$CF_3Ph(CH_2)_2$— | 144.0 |
| 79 | —$CH_3$ | —$CH_3$ | 4-$CF_3Ph(CH_2)_3$— | 172.2-173.0 |
| 80 | —$CH_3$ | —$CH_3$ | 4-$CF_3PhCH{=}CHCH_2$— | 212.4-214.5 dec |
| 81 | —$CH_3$ | —$CH_3$ | 4-$CF_3OPhCH_2CH_2OCO$— | 205.5-208.0 |
| 82 | —$CH_3$ | —H | 4-$ClPhCH_2OCO$— | 232.0-237.5 dec |
| 83 | —$CH_3$ | —$CH_3$ | 4-$ClPhCH_2OCO$— | 201.0-203.7 |
| 84 | —$CH_3$ | —$CH_3$ | 4-$CF_3PhCH_2OCO$— | 201.0-203.5 |

TABLE 27

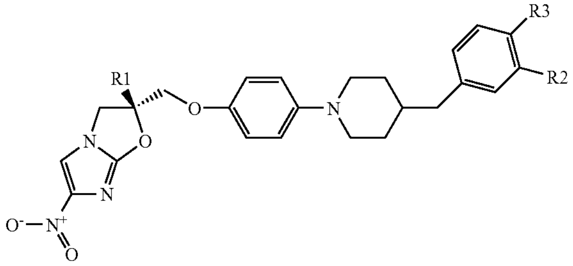

| Example | R1 | R2 | R3 | mp(° C.) |
|---|---|---|---|---|
| 85 | —$CH_3$ | —H | —H | 209.7-212.4 |
| 86 | —$CH_3$ | —H | —$OCF_3$ | 210.9-212.4 |
| 87 | —$CH_3$ | —H | —$OF_3$ | 199.5-203.1 |
| 88 | —$CH_3$ | —H | —Cl | 207.1-211.2 |
| 89 | —$CH_3$ | —Cl | —Cl | 180.0-181.2 |

TABLE 28

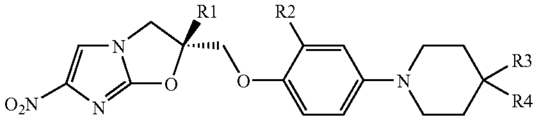

| Example | R1 | R2 | R3 | R4 | mp(° C.) or $^1$H NMR |
|---|---|---|---|---|---|
| 90 | —$CH_3$ | —H | —H | —OH | 228.0-229.5 dec |
| 91 | —$CH_3$ | —H | —H | $(CH_3)_3COCO$— | 218.5-219.0 dec |
| 92 | —$CH_3$ | —H | —H | —$CO_2H$ | $^1$H NMR (DMSO) δ 1.69(3H, s), 2.11(4H, brs), 2.64(1H, brs), 3.48(4H, brs), 4.20(1H, d, J = 11.0 Hz), 4.34(2H, s), 4.37(1H, d, J = 11.0 Hz), 7.03-7.08(2H, m), 7.69(2H, br), 8.16(1H, s), 12.44(1H, br). |
| 93 | —$CH_3$ | —H | —H | 4-$CF_3OPhNHCO$— | 251.0-254.7 dec |
| 94 | —$CH_3$ | —H | —OH | —$C_6H_5$ | 242.7-243.5 |
| 95 | —$CH_3$ | —H | —H | 4-$CF_3OPhCH_2OCH_2$— | 185.0-186.1 |
| 96 | —$CH_3$ | —H | —H | 4-$CF_3OPhOCH_2$— | 226.2-226.9 dec |
| 97 | —$CH_3$ | —H | —H | —$C_6H_5$ | 263.0-265.1 |
| 98 | —$CH_3$ | —H | —H | 4-$CF_3OPh(CH_2)_2O$— | 171.8-174.2 |
| 99 | —$CH_3$ | —H | —H | 4-$CF_3OPhCH{=}CHCH_2O$— | 213.7-217.4 |
| 100 | —$CH_3$ | —H | —$OC_2H_5$ | —$OC_2H_5$ | 153.0-156.8 |
| 101 | —$CH_3$ | —H | 4-ClPh- | —OH | 231.3-231.9 |
| 102 | —$CH_3$ | —H | —H | 4-$CF_3OPhOCH_2$— | 223.2-225.2 dec |
| 103 | —$CH_3$ | —H | —H | 4-$CF_3Ph(CH_2)_3O$— | 196.8-200.0 |
| 104 | —$CH_3$ | —$CH_2N(CH_3)_2$ | —H | 4-$CF_3OPhO$— | 186.6-190.5 |
| 105 | —$CH_3$ | —H | —H | cyclo-$C_6H_{11}CH_2O$— | 238.7-241.0 |
| 106 | —$CH_3$ | —H | —H | 4-$ClPhCH_2OCH_2$— | 175.3-175.5 |
| 107 | —$CH_3$ | —H | —H | 4-$CF_3PhCH_2OCH_2$— | 172.3-172.9 |
| 108 | —H | —H | —H | 4-$CF_3OPhCH_2OCH_2$— | 140.4-141.7 |
| 109 | —H | —H | —H | 4-$CF_3OPhCH_2O$— | 188.3-189.4 |
| 110 | —$CH_3$ | —H | —H | 4-$ClPhOCH_2$— | 220.2-223.1 |
| 111 | —H | —H | —H | 4-$CF_3PhOCH_2$— | 175.0-180 |
| 112 | —$CH_3$ | —H | —H | $NH_2COO$— | 208.7-209.9 dec |
| 113 | —$CH_3$ | —H | —H | 3,4-Cl2PhNHCOO— | 218.5-222.2 dec |
| 114 | —$CH_3$ | —H | —H | 4-$CF_3PhNHCOO$— | 224.0-226.6 dec |
| 115 | —$CH_3$ | —H | —H | 4-ClPhNHCOO— | 236.0-238.7 dec |
| 116 | —$CH_3$ | —H | —H | 4-$CF_3OPhNHCOO$— | 223.0-225.5 |
| 117 | —$CH_3$ | —H | —H | 4-$CF_3OPh(CH_2)_2$— | 239.4-241.3 |
| 118 | —$CH_3$ | —H | —H | 4-$CF_3OPh(CH_2)_3$— | 191.4-193.2 |
| 119 | —$CH_3$ | —H | —H | 4-$ClPhN(CH_3)COO$— | 224.6-224.9 |
| 120 | —$CH_3$ | —H | —H | 4-$ClPhN(C_2H_5)COO$— | 181.1-182.6 |

TABLE 29
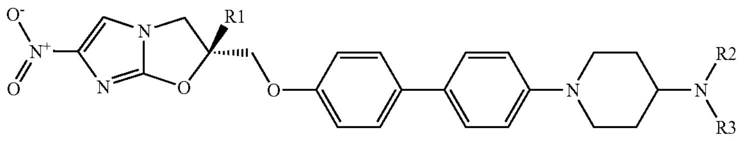
| Example | R1 | R2 | R3 | mp(° C.) or $^{1}$H NMR |
|---|---|---|---|---|
| 121 | —H | 4-ClPh- | —$C_2H_5$ | 217.6-219.4 dec |
| 122 | —$CH_3$ | 4-ClPh- | —$C_2H_5$ | 229.3-233.0 dec |
| 123 | —H | 4-$CF_3$OPh- | —$C_2H_5$ | 221.8-223.8 dec |
| 124 | —$CH_3$ | 4-$CF_3$OPh- | —$C_2H_5$ | 245.1-247.3 dec |
| 125 | —H | 4-$CF_3$Ph- | —$C_2H_5$ | $^{1}$H NMR ($CDCl_3$) δ 1.21(3H, t, J = 7.01 Hz), 191-1.98(4H, m), 2.82-2.94(2H, m), 3.37(2H, q, J = 7.01 Hz), 3.74-3.89(3H, m), 4.30-4.51(4H, m), 5.58-5.69(1H, m), 6.74-6.79(2H, m), 6.90-6.95(2H, m), 6.99-7.04(2H, m), 7.42-7.52(6H, m). |
| 126 | —$CH_3$ | 4-$CF_3$Ph- | —$C_2H_5$ | 251.8-253.5 dec |
TABLE 30
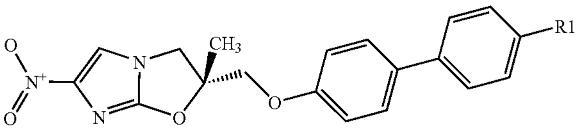
| Example | R1 | mp(° C.) or $^{1}$H NMR |
|---|---|---|
| 127 | —H | 237.7-239.6 |
| 128 | 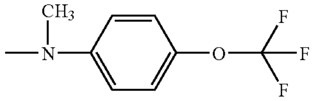 | 229.0-230.5 dec |
| 129 | 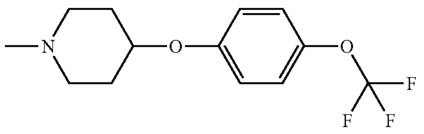 | 252.3-253.6 dec |
| 130 | 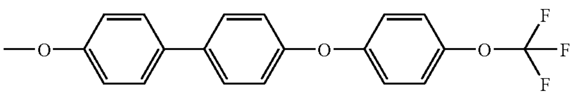 | $^{1}$H NMR (DMSO) δ 1.71(3H, s), 4.21(1H, d, J = 11.03 Hz), 4.34(2H, s), 4.40(1H, d, J = 11.03 Hz), 6.99(2H, d, J = 8.44 Hz), 7.10-7.20(8H, m), 7.42(2H, d, J = 8.44 Hz), 7.57-7.72(8H, m), 8.22(1H, s). |
| 131 | 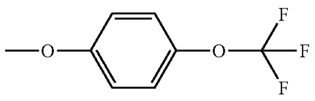 | 218.0-221.0 dec |
TABLE 31
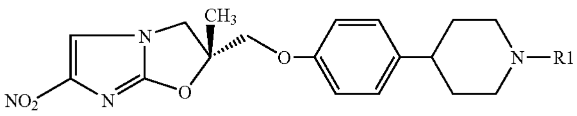
| Example | R1 | mp(° C.) |
|---|---|---|
| 132 | 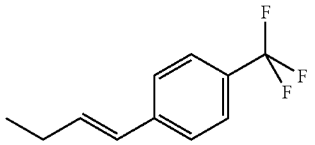 | 185.9-187.1 |
TABLE 31-continued
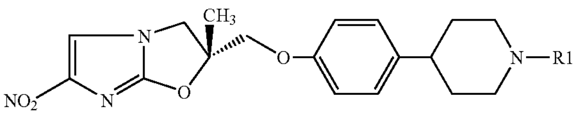
| Example | R1 | mp(° C.) |
|---|---|---|
| 133 | 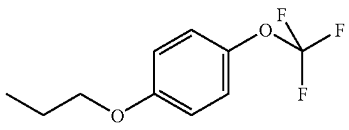 | 190.5-191.3 |

TABLE 31-continued

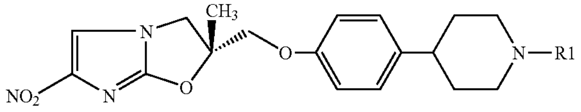

| Example | R1 | mp(° C.) |
|---|---|---|
| 134 | 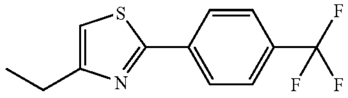 | 194.6-196.4 |

TABLE 31-continued

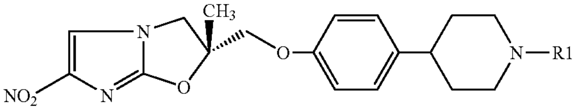

| Example | R1 | mp(° C.) |
|---|---|---|
| 135 | 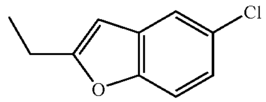 | 219.9-220.5 |

TABLE 32

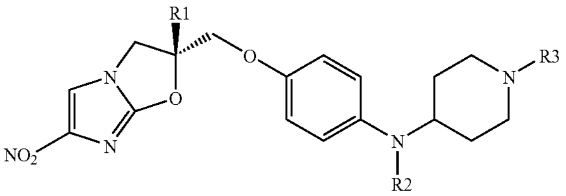

| Example | R1 | R2 | R3 | mp(° C.) or $^{1}$H NMR |
|---|---|---|---|---|
| 136 | —$CH_3$ | —$CH_3$ | 4-$CF_3$Ph- | 167.8-168.7 |
| 137 | —$CH_3$ | —$CH_3$ | 4-$CF_3$OPh$CH_2$— | 154.8-155.9 |
| 138 | —$CH_3$ | —$CH_3$ | 4-ClPh$CH_2$— | 149.6-153.4 |
| 139 | —$CH_3$ | —$CH_3$ | 4-$CF_3$Ph$CH_2$— | 145.0-146.9 |
| 140 | —$CH_3$ | —$CH_3$ | 4-$CF_3$OPh$CH_2$OCO— | 141.8-144.3 |
| 141 | —$CH_3$ | —$CH_3$ | 4-ClPh$CH_2$OCO— | 132.4-135.0 |
| 142 | —$CH_3$ | —$CH_3$ | 4-$CF_3$Ph$CH_2$OCO— | 152.2-155.6 |
| 143 | —$CH_3$ | —H | 4-$CF_3$PhCH═CH$CH_2$— | 160.5-163.7 |
| 144 | —$CH_3$ | —$C_2H_5$ | 4-$CF_3$OPh- | 125.2-128.1 |
| 145 | —$CH_3$ | —$CH_3$ | 4-$CF_3$OPh- | 137.9-139.2 |
| 146 | —$CH_3$ | —$CH_3$ | 4-ClPh- | 190.8-193.8 |
| 147 | —$CH_3$ | —H | 4-$CF_3$OPh | 145.6-149.3 |
| 148 | —$CH_3$ | —H | 4-ClPh- | 163.3-167.3 |
| 149 | —$CH_3$ | —H | 4-$CF_3$OPhO$(CH_2)_2$— | 140.9-143.1 |
| 150 | —$CH_3$ | —$CH_3$ | $(CH_3)_3$COCO— | 153.6-154.7 |
| 151 | —$CH_3$ | —H | 4-$CF_3$OPh$CH_2$— | 181.7-183.6 |
| 152 | —$CH_3$ | —H | 4-ClPh$CH_2$— | 183.7-186.6 |
| 153 | —$CH_3$ | —H | 4-$CF_3$Ph$CH_2$— | 173.0-176.3 |
| 154 | —$CH_3$ | —H | 4-ClPh$CH_2$OCO— | 125.2-127.6 |
| 155 | —$CH_3$ | —H | 4-$CF_3$OPh$CH_2$OCO— | 120.5-124.9 |
| 156 | —$CH_3$ | —H | 4-$CF_3$Ph$CH_2$OCO— | 103.5-107.3 |
| 157 | —$CH_3$ | —H | 4-$CF_3$Ph— | $^{1}$H NMR ($CDCl_3$) δ 1.46-1.62(2H, m), 1.76(3H, s), 2.08-2.21(2H, m), 2.90-3.05(2H, m), 3.35-3.47(1H, m), 3.70-3.83(2H, m), 3.98-4.06(2H, m), 4.16(1H, d, J = 10.20 Hz), 4.50(1H, d, J = 10.20 Hz), 6.53-6.65(2H, m), 6.69-6.77(2H, m), 6.89-6.98(2H, m), 7.43-7.51(2H, m), 7.55(1H, s) |
| 158 | —$CH_3$ | —H | $(CH_3)_3$COCO— | $^{1}$H NMR ($CDCl_3$) δ 1.20-1.37(2H, m), 1.46(9H, s), 1.76(3H, s), 1.94-2.07(2H, brm), 2.77-3.01(2H, brm), 3.23-3.41(2H, brm), 3.94-4.11(4H, m), 4.14(1H, d, J = 10.19 Hz), 4.49(1H, d, J = 10.15 Hz), 6.50-6.59(2H, m), 6.67-6.76(2H, m), 7.55(1H, s) |
| 159 | —$CH_3$ | —$CH_3$ | 4-$CF_3$OPhCO— | 129.2-132.0 |
| 160 | —$CH_3$ | —$CH_3$ | 4-$CF_3$OPhNHCO— | 179.0-182.5 |

TABLE 33
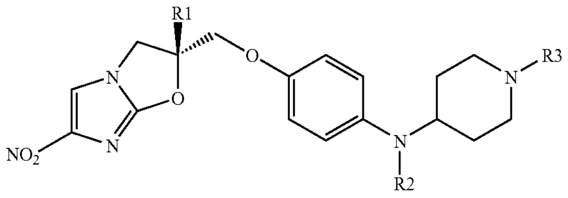
| Example | R1 | R2 | R3 | mp(° C.) |
|---|---|---|---|---|
| 161 | —$CH_3$ | —$CH_3$ | 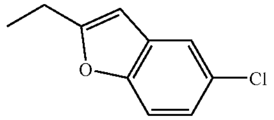 | 158.9-160.4 |
| 162 | —$CH_3$ | —$CH_3$ | 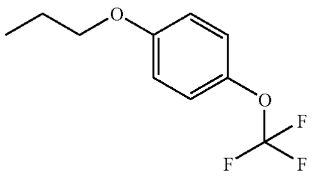 | 143.0-146.5 |
| 163 | —$CH_3$ | —$CH_3$ | 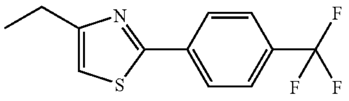 | 163.9-166.3 |
| 164 | —$CH_3$ | —H | 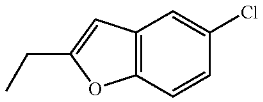 | 161.7-165.4 |
| 165 | —$CH_3$ | —H | 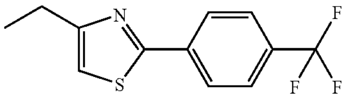 | 185.7-188.8 |
TABLE 34
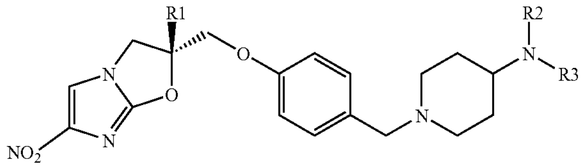
| Example | R1 | R2 | R3 | mp(° C.) or $^1H$ NMR |
|---|---|---|---|---|
| 166 | —$CH_3$ | 4-$CF_3$OPh— | —$CH_3$ | $^1H$ NMR ($CDCl_3$) δ 1.62-1.73(2H, m), 1.73-1.87(5H, m), 1.96-2.12(2H, m), 2.77(3H, s), 2.88-3.03(2H, m), 3.38-3.60(3H, m), 4.00-4.13(2H, m), 4.23(1H, d, J = 10.1 Hz), 4.50(1H, d, J = 10.2 Hz), 6.67-6.74(2H, m), 6.76-6.84(2H, m), 7.02-7.10(2H, m), 7.18-7.25(2H, m), 7.56(1H, s) |
| 167 | —$CH_3$ | 4-$CF_3$OPh$CH_2$OCO— | —$CH_3$ | 190.9-192.2 |
| 168 | —$CH_3$ | 4-$CF_3$OPh$CH_2$— | —$CH_3$ | 143.1-145.7 |
| 169 | —$CH_3$ | 4-$CF_3$OPhCO— | —$CH_3$ | 178.8-183.7 |
| 170 | —$CH_3$ | 4-$CF_3$OPhNHCO— | —$CH_3$ | $^1H$ NMR ($CDCl_3$) δ 1.74-1.87(5H, m), 2.50-2.68(2H, m), 2.68-2.83(2H, m), 2.97(3H, s), 3.42-3.56(2H, m), 3.97-4.17(4H, m), 4.29(1H, d, J = 10.3 Hz), 4.50(1H, d, J = 10.2 Hz), 4.55-4.66(1H, m), 6.46-6.55(1H, br), 6.84-6.93(2H, m), 7.10-7.18(2H, m), 7.37-7.44(2H, m), 7.49-7.57(2H, m), 7.58(1H, s) |

TABLE 35
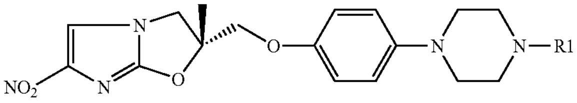
| Example | R1 | MS (M + 1) |
|---|---|---|
| 171 | 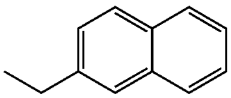 | 500 |
| 172 | 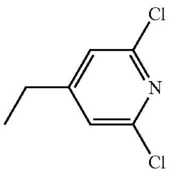 | 519 |
| 173 | 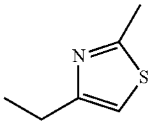 | 471 |
| 174 | 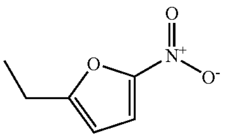 | 485 |
| 175 | 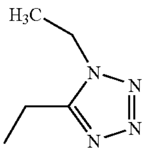 | 470 |
| 176 | 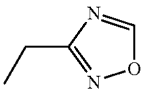 | 442 |
| 177 | 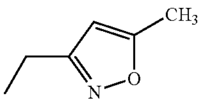 | 455 |
TABLE 35-continued
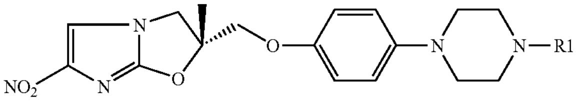
| Example | R1 | MS (M + 1) |
|---|---|---|
| 178 | 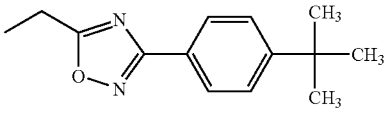 | 574 |
| 179 | 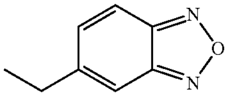 | 492 |
TABLE 36
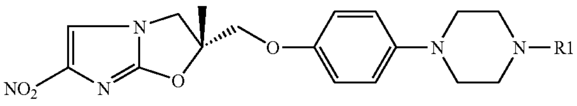
| Example | R1 | MS (M + 1) |
|---|---|---|
| 180 | 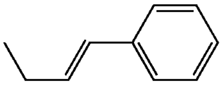 | 476 |
| 181 | 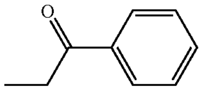 | 478 |
| 182 | 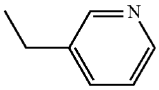 | 451 |
| 183 | 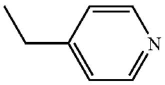 | 451 |
| 184 | 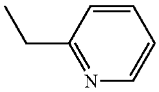 | 451 |
| 185 | 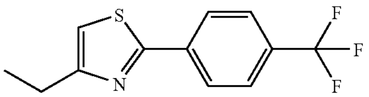 | 601 |
| 186 | 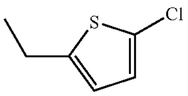 | 490 |
| 187 | 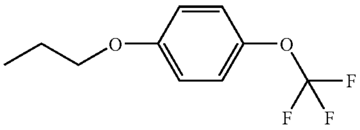 | 564 |

TABLE 37
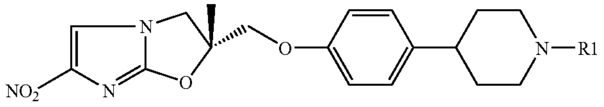
| Example | R1 | MS (M + 1) |
|---|---|---|
| 188 | 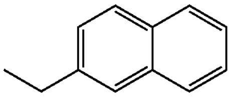 | 499 |
| 189 | 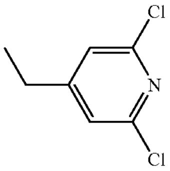 | 518 |
| 190 | 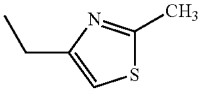 | 470 |
| 191 | 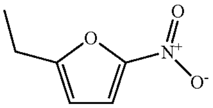 | 484 |
| 192 | 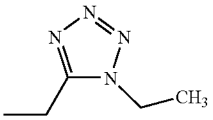 | 469 |
| 193 | 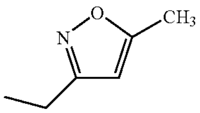 | 454 |
| 194 | 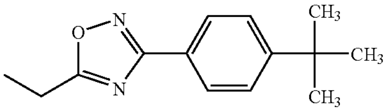 | 573 |
| 195 | 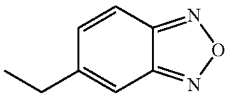 | 491 |
| 196 | 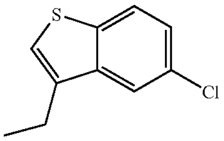 | 539 |
| 197 | 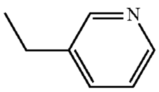 | 450 |
| 198 | 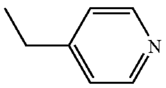 | 450 |

TABLE 38

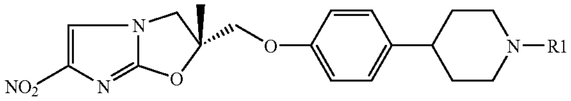

| Example | R1 | MS (M + 1) |
|---|---|---|
| 199 | 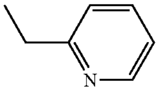 | 450 |
| 200 | 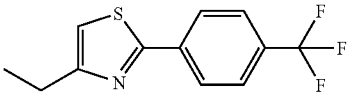 | 600 |

TABLE 38-continued

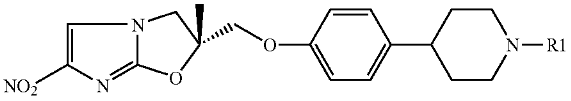

| Example | R1 | MS (M + 1) |
|---|---|---|
| 201 | 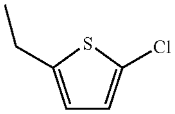 | 489 |

TABLE 39

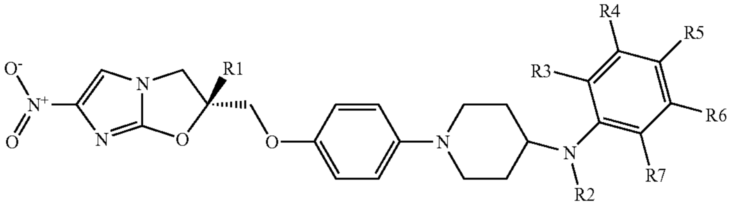

| Example | R1 | R2 | R3 | R4 | R5 | R6 | R7 | MS(M + 1) |
|---|---|---|---|---|---|---|---|---|
| 202 | $—CH_3$ | —H | —H | —H | —Cl | —H | —H | 484 |
| 203 | $—CH_3$ | $—CH_3$ | —H | —H | —Cl | —H | —H | 498 |
| 204 | $—CH_3$ | —H | —H | —H | —Cl | —Cl | —H | 518 |
| 205 | $—CH_3$ | —H | —H | —H | $—OCF_3$ | —H | —H | 534 |
| 206 | $—CH_3$ | —H | —H | $—CF_3$ | —H | $—CF_3$ | —H | 586 |
| 207 | $—CH_3$ | —H | —H | —H | $—C_4H_9$ | —H | —H | 506 |
| 208 | $—CH_3$ | —H | —H | —H | —H | —H | —H | 450 |
| 209 | $—CH_3$ | —H | —H | —H | $—OCH_3$ | —H | —H | 480 |
| 210 | $—CH_3$ | —H | —H | —H | —H | —H | —Cl | 484 |
| 211 | $—CH_3$ | —H | —H | —H | —H | —Cl | —H | 484 |
| 212 | $—CH_3$ | —H | —H | —H | $—CH_3$ | —H | —H | 464 |
| 213 | $—CH_3$ | —H | —H | $—OCH_3$ | $—OCH_3$ | $—OCH_3$ | —H | 540 |
| 214 | $—CH_3$ | —H | —H | —H | —H | $—OCF_3$ | —H | 534 |
| 215 | $—CH_3$ | —H | —H | —H | —F | —H | —H | 468 |
| 216 | $—CH_3$ | —H | —H | —H | $—N(CH_3)_2$ | —H | —H | 493 |
| 217 | $—CH_3$ | —H | —H | —H | $—OC_2H_5$ | —H | —H | 494 |
| 218 | $—CH_3$ | —H | —H | —H | $—C_2H_5$ | —H | —H | 478 |
| 219 | $—CH_3$ | —H | —H | —H | —H | $—CO_2C_2H_5$ | —H | 522 |
| 220 | $—CH_3$ | —H | —H | —H | —H | —H | $—OCF_3$ | 534 |
| 221 | $—CH_3$ | —H | —H | —H | —H | —H | $—OCHF_2$ | 516 |
| 222 | $—CH_3$ | —H | —H | —H | —Cl | —H | $—OCF_3$ | 568 |
| 223 | $—CH_3$ | —H | —H | —H | $—OC_6H_5$ | —H | —H | 542 |
| 224 | $—CH_3$ | —H | —H | —H | —H | —Cl | —Cl | 518 |
| 225 | $—CH_3$ | —H | —H | —H | —Cl | —H | —Cl | 518 |
| 226 | $—CH_3$ | —H | —H | —Cl | —H | —Cl | —H | 518 |
| 227 | $—CH_3$ | —H | —H | —H | —Cl | —Cl | —Cl | 552 |
| 228 | $—CH_3$ | —H | $—CH_3$ | —H | $—CH_3$ | —H | $—CH_3$ | 492 |
| 229 | $—CH_3$ | —H | —H | —H | $—OCH_3$ | —Cl | —H | 514 |
| 230 | $—CH_3$ | —H | —H | —H | $—CF_3$ | —H | —Cl | 552 |
| 231 | $—CH_3$ | —H | —F | —F | —F | —F | —F | 540 |
| 232 | $—CH_3$ | —H | —H | —H | $—NO_2$ | —H | —H | 495 |
| 233 | $—CH_3$ | —H | —H | —H | —CN | —H | —H | 475 |
| 234 | $—CH_3$ | —H | —H | —H | $—SCH_3$ | —H | —H | 496 |
| 235 | $—CH_3$ | $—CH_3$ | —H | —H | —Cl | —Cl | —H | 532 |
| 236 | $—CH_3$ | $—CH_3$ | —H | —H | $—OCF_3$ | —H | —H | 548 |
| 237 | $—CH_3$ | $—CH_3$ | —H | —H | $—C_4H_9$ | —H | —H | 520 |
| 238 | $—CH_3$ | $—CH_3$ | —H | —H | —H | —H | —H | 464 |

TABLE 40

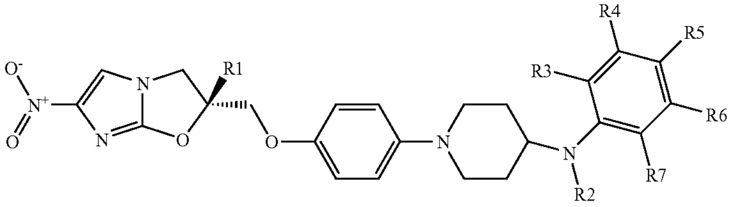

| Example | R1 | R2 | R3 | R4 | R5 | R6 | R7 | MS(M + 1) |
|---|---|---|---|---|---|---|---|---|
| 239 | —$CH_3$ | —$CH_3$ | —H | —H | —H | —H | —Cl | 498 |
| 240 | —$CH_3$ | —$CH_3$ | —H | —H | —H | —Cl | —H | 498 |
| 241 | —$CH_3$ | —$CH_3$ | —H | —H | —$CH_3$ | —H | —H | 478 |
| 242 | —$CH_3$ | —$CH_3$ | —H | —$OCH_3$ | —$OCH_3$ | —$OCH_3$ | —H | 554 |
| 243 | —$CH_3$ | —$CH_3$ | —H | —H | —H | —$OCF_3$ | —H | 548 |
| 244 | —$CH_3$ | —$CH_3$ | —H | —H | —F | —H | —H | 482 |
| 245 | —$CH_3$ | —$CH_3$ | —H | —H | —$N(CH_3)_2$ | —H | —H | 507 |
| 246 | —$CH_3$ | —$CH_3$ | —H | —H | —$OC_2H_5$ | —H | —H | 508 |
| 247 | —$CH_3$ | —$CH_3$ | —H | —H | —$C_2H_5$ | —H | —H | 492 |
| 248 | —$CH_3$ | —$CH_3$ | —H | —H | —$NHCOCH_3$ | —H | —H | 521 |
| 249 | —$CH_3$ | —$CH_3$ | —H | —H | —H | —$CO_2C_2H_5$ | —H | 536 |
| 250 | —$CH_3$ | —$CH_3$ | —H | —H | —H | —H | —$OCF_3$ | 548 |
| 251 | —$CH_3$ | —$CH_3$ | —H | —H | —H | —H | —$OCHF_2$ | 530 |
| 252 | —$CH_3$ | —$CH_3$ | —H | —H | —Cl | —H | —$OCF_3$ | 582 |
| 253 | —$CH_3$ | —$CH_3$ | —H | —H | —$OC_6H_5$ | —H | —H | 556 |
| 254 | —$CH_3$ | —$CH_3$ | —H | —H | —H | —Cl | —Cl | 532 |
| 255 | —$CH_3$ | —$CH_3$ | —H | —H | —Cl | —H | —Cl | 532 |
| 256 | —$CH_3$ | —$CH_3$ | —H | —Cl | —H | —Cl | —H | 532 |
| 257 | —$CH_3$ | —$CH_3$ | —H | —H | —Cl | —Cl | —Cl | 566 |
| 258 | —$CH_3$ | —$CH_3$ | —H | —H | —$OCH_3$ | —Cl | —H | 528 |
| 259 | —$CH_3$ | —$CH_3$ | —H | —H | —$SCH_3$ | —H | —H | 510 |

TABLE 41

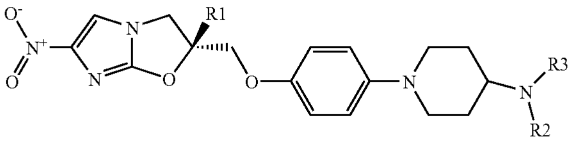

| Example | R1 | R2 | R3 | MS (M + 1) |
|---|---|---|---|---|
| 260 | —$CH_3$ | 4-$ClPhCH_2$— | —H | 498 |
| 261 | —$CH_3$ | —$CH_2C_6H_5$ | —H | 464 |
| 262 | —$CH_3$ | 2-$ClPhCH_2$— | —H | 498 |
| 263 | —$CH_3$ | 3-$ClPhCH_2$— | —H | 498 |
| 264 | —$CH_3$ | 4-$CH_3PhCH_2$— | —$CH_3$ | 492 |
| 265 | —$CH_3$ | 3,4,5-$(CH_3O)_3PhCH_2$— | —$CH_3$ | 568 |
| 266 | —$CH_3$ | —$CH_2C_6H_5$ | —$CH_2CH_2N(CH_3)_2$ | 535 |
| 267 | —$CH_3$ | 4-$CH_3OPhCH_2$— | —H | 494 |

TABLE 41-continued

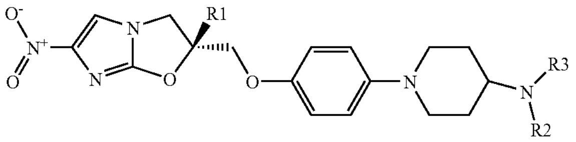

| Example | R1 | R2 | R3 | MS (M + 1) |
|---|---|---|---|---|
| 268 | —$CH_3$ | 4-$ClPhCH_2$— | —$CH_3$ | 512 |
| 269 | —$CH_3$ | 4-$FPhCH_2$— | —H | 482 |
| 270 | —$CH_3$ | 3,4-$(CH_3O)_2PhCH_2$— | —H | 524 |
| 271 | —$CH_3$ | —$CH_2CH_2OCH_3$ | —$CH_2CH_2OCH_3$ | 490 |
| 272 | —$CH_3$ | $(C_2H_5)_2N(CH_2)_2$— | —$C_2H_5$ | 501 |
| 273 | —$CH_3$ | -cyclo-$C_8H_{15}$ | —H | 484 |
| 274 | —$CH_3$ | 4-$ClPh(CH_2)_2$— | —H | 512 |
| 275 | —$CH_3$ | —$CH_2$-cyclo-$C_6H_{11}$ | —H | 470 |

TABLE 42

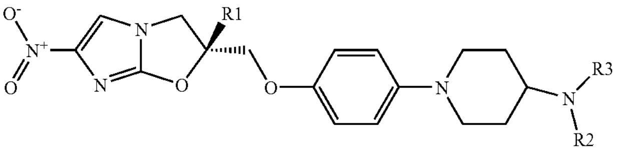

| Example | R1 | R2 | R3 | MS(M + 1) |
|---|---|---|---|---|
| 276 | —$CH_3$ | 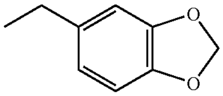 | —$CH_3$ | 522 |

TABLE 42-continued
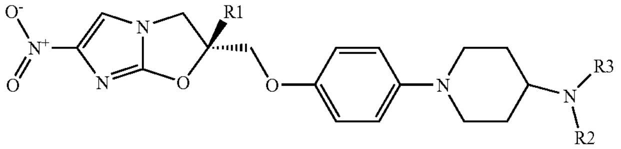
| Example | R1 | R2 | R3 | MS(M + 1) |
|---|---|---|---|---|
| 277 | —$CH_3$ | 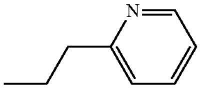 | —$CH_3$ | 493 |
| 278 | —$CH_3$ | 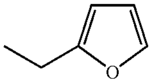 | —H | 454 |
| 279 | —$CH_3$ | 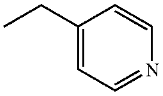 | —$C_2H_5$ | 493 |
| 280 | —$CH_3$ | 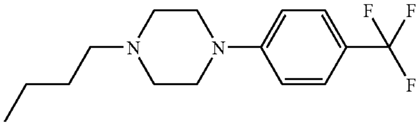 | —H | 644 |
TABLE 43
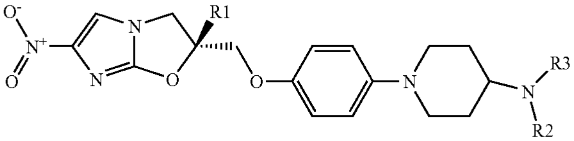
| Example | R1 | R2 | R3 | MS(M + 1) |
|---|---|---|---|---|
| 281 | —$CH_3$ | 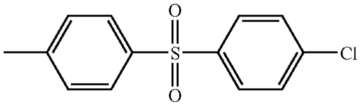 | —H | 624 |
| 282 | —$CH_3$ | 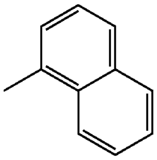 | —H | 500 |
| 283 | —$CH_3$ | 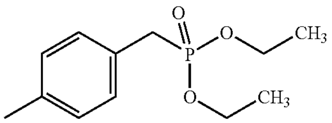 | —H | 600 |
| 284 | —$CH_3$ | 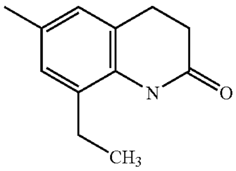 | —H | 547 |

TABLE 44
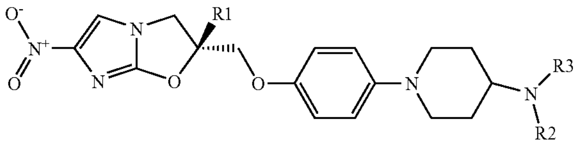
| Example | R1 | R2 | R3 | MS(M + 1) |
|---|---|---|---|---|
| 285 | —$CH_3$ | 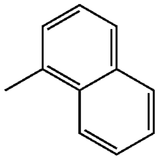 | —$CH_3$ | 514 |
| 286 | —$CH_3$ | 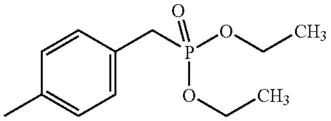 | —$CH_3$ | 614 |
| 287 | —$CH_3$ | 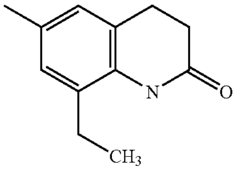 | —$CH_3$ | 561 |
TABLE 45
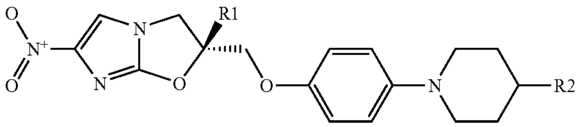
| Example | R1 | R2 | MS(M + 1) |
|---|---|---|---|
| 288 | —$CH_3$ | 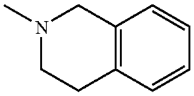 | 490 |
| 289 | —$CH_3$ | 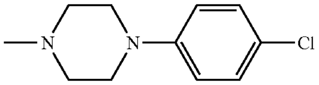 | 553 |
| 290 | —$CH_3$ | 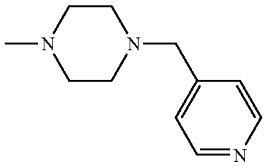 | 534 |
| 291 | —$CH_3$ | 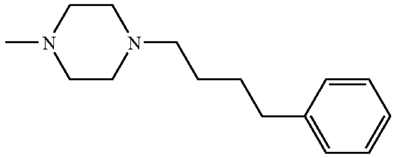 | 575 |

TABLE 45-continued
| 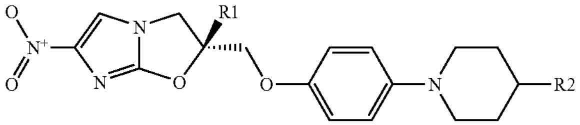 | | | |
|---|---|---|---|
| Example | R1 | R2 | MS(M + 1) |
| 292 | $—CH_3$ | 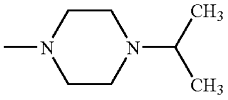 | 485 |
| 293 | $—CH_3$ | 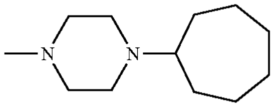 | 539 |
| 294 | $—CH_3$ | 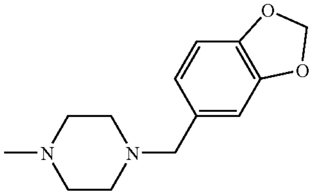 | 577 |
TABLE 46
| 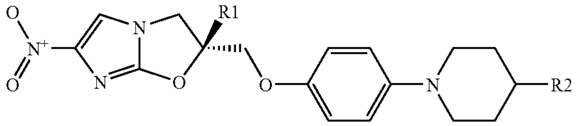 | | | |
|---|---|---|---|
| Example | R1 | R2 | MS(M + 1) |
| 295 | $—CH_3$ | 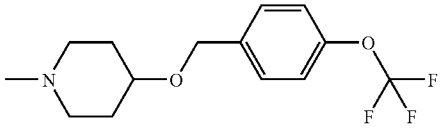 | 632 |
| 296 | $—CH_3$ | 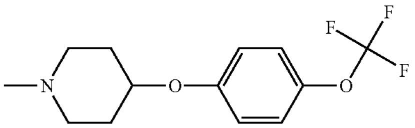 | 618 |
| 297 | $—CH_3$ | 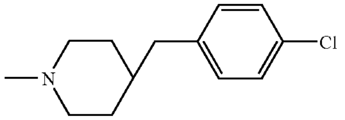 | 566 |
| 298 | $—CH_3$ | 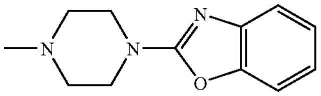 | 560 |
| 299 | $—CH_3$ | 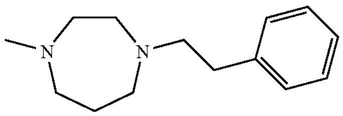 | 561 |

TABLE 46-continued

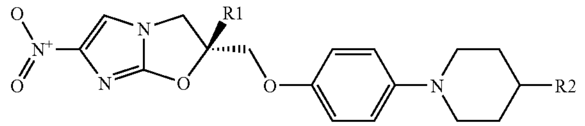

| Example | R1 | R2 | MS(M + 1) |
|---|---|---|---|
| 300 | —$CH_3$ | 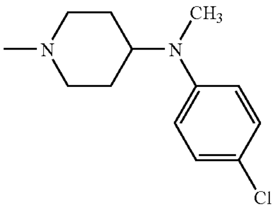 | 581 |

TABLE 47

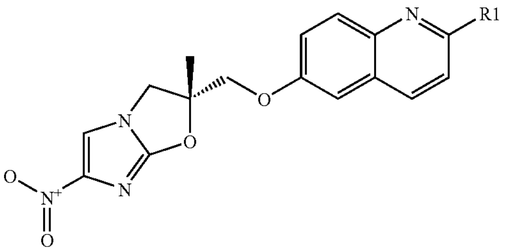

| Example | R1 | mp(° C.) |
|---|---|---|
| 301 | 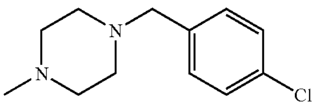 | 218.1-219.1 |

TABLE 47-continued

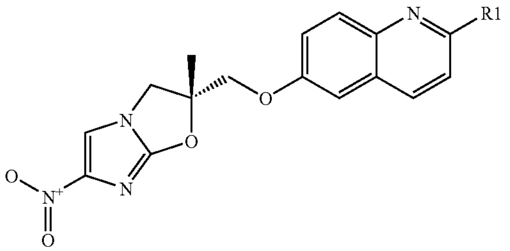

| Example | R1 | mp(° C.) |
|---|---|---|
| 302 | 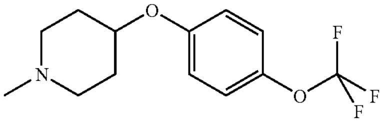 | 199.6-200.1 |

TABLE 48

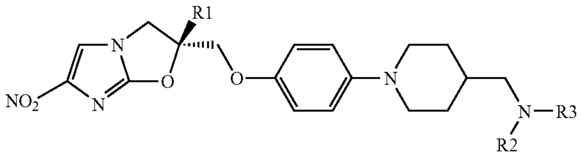

| Example | R1 | R2 | R3 | mp(° C.) or $^1$H NMR |
|---|---|---|---|---|
| 303 | —$CH_3$ | 4-$CF_3$OPh- | —$COCH_3$ | 148.6-149.1 |
| 304 | —$CH_3$ | 4-$CF_3$OPh- | —$C_2H_5$ | 116.8-119.2 |
| 305 | —$CH_3$ | 4-$CF_3$OPh- | —$CH_3$ | 135.6-140.9 |
| 306 | —$CH_3$ | 4-ClPh- | —$CH_3$ | 141.6-146.1 |
| 307 | —$CH_3$ | 4-$CF_3$Ph- | —$CH_3$ | 151.4-155.0 |
| 308 | —$CH_3$ | 4-$CF_3$OPh$CH_2$— | —$COCH_3$ | $^1$H NMR ($CDCl_3$) δ 1.29-1.51(2H, brm), 1.67-1.89(6H, brm), 2.13(1.5H, s), 2.20(1.5H, s), 2.46-2.72(2H, brm), 3.12-3.23(1H, brm), 3.27-3.36(1H, brm), 3.44-3.63(2H, brm), 3.96-4.10(2H, brm), 4.10-4.26(1H, brm), 4.49(1H, d, J = 10.15 Hz), 4.58(1H, s), 4.63(1H, s), 6.63-6.99(4H, brm), 7.12-7.30(4H, m), 7.56(1H, s) |
| 309 | —$CH_3$ | 4-$CF_3$OPh- | —H | 181.9-182.5 |
| 310 | —$CH_3$ | 4-ClPh- | —H | 177.6-179.1 |
| 311 | —$CH_3$ | 4-$CF_3$Ph- | —H | 164.7-165.8 |
| 312 | —$CH_3$ | 4-$CF_3$OPh$CH_2$— | —$C_2H_5$ | 163.9-165.2 |
| 313 | —$CH_3$ | 4-$CF_3$OPh$CH_2$— | —$CH_3$ | 180.5-180.8 |
| 314 | —$CH_3$ | 4-ClPh$CH_2$— | —$CH_3$ | 169.5-170.6 |
| 315 | —$CH_3$ | 4-$CF_3$Ph$CH_2$— | —$CH_3$ | 166.7-167.5 |

TABLE 48-continued

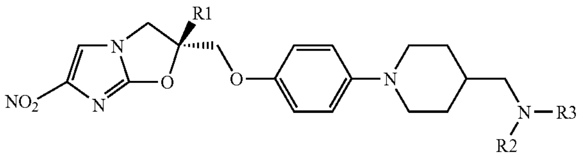

| Example | R1 | R2 | R3 | mp(° C.) or ¹H NMR |
|---|---|---|---|---|
| 316 | —$CH_3$ | 4-$CF_3OPhCH_2$— | —H | 163.9-167.6 |
| 317 | —$CH_3$ | 4-$ClPhCH_2$— | —H | 163.8-166.3 |
| 318 | —$CH_3$ | 4-$CF_3PhCH_2$— | —H | 157.0-160.8 |
| 319 | —$CH_3$ | 4-$CF_3OPhCH_2$— | $(CH_3)_3COCO$— | $^1$H NMR ($CDCl_3$) δ 1.29-1.56(11H, brm), 1.60-1.84(6H, m), 2.46-2.66(2H, brm), 3.00-3.24(2H, brm), 3.44-3.57(2H, brm), 3.97-4.08(2H, m), 4.17(1H, d,, J = 10.12 Hz), 4.35-4.55(3H, m), 6.70-6.80(2H, m), 6.81-6.95(2H, m), 7.12-7.20(2H, m), 7.20-7.32(2H, m), 7.50(1H, s) |
| 320 | —$CH_3$ | 4-$ClPhCH_2$— | $(CH_3)_3COCO$— | $^1$H NMR ($CDCl_3$) δ 1.29-1.54(11H, brm), 1.60-1.84(6H, m), 2.48-2.66(2H, brm), 3.00-3.22(2H, brm), 3.51(2H, d, J = 12.07 Hz). 3.96-4.08(2H, m)4.17(1H, d, J = 10.10 Hz), 4.34-4.46(2H, brm), 4.49(1H, d, J = 10.10 Hz), 6.76(2H, d, J = 8.97 Hz), 6.81-6.93(2H, brm), 7.07-7.21(2H, brm), 7.29(2H, d, J = 8.29 Hz), 7.55(1H, s) |
| 321 | —$CH_3$ | 4-$CF_3PhCH_2$— | $(CH_3)_3COCO$— | $^1$H NMR ($CDCl_3$) δ 1.31-1.57(11H, brm), 1.61-1.88(6H, m), 2.45-2.72(2H, brm), 3.03-3.28(2H, brm), 3.52(2H, d, J = 12.05 Hz), 3.96-4.08(2H, m), 4.17(1H, d, J = 10.15 Hz), 4.41-4.51(3H, m), 6.76(2H, d, J = 8.95 Hz), 6.83-6.96(2H, brm), 7.26-7.42(2H, brm), 7.55(1H, s), 7.59(2H, d, J = 7.95 Hz) |

TABLE 49

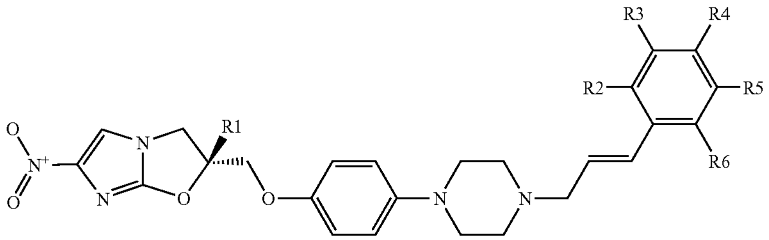

| Example | R1 | R2 | R3 | R4 | R5 | R6 | MS(M + 1) |
|---|---|---|---|---|---|---|---|
| 322 | —$CH_3$ | —H | —H | —H | —H | —$CH_3$ | 490 |
| 323 | —$CH_3$ | —H | —H | —H | —$CH_3$ | —H | 490 |
| 324 | —$CH_3$ | —H | —H | —H | —H | —$OCF_3$ | 560 |
| 325 | —$CH_3$ | —H | —H | —H | —$OCF_3$ | —H | 560 |
| 326 | —$CH_3$ | —H | —H | —F | —H | —$CH_3$ | 508 |
| 327 | —$CH_3$ | —H | —H | —Cl | —$CF_3$ | —H | 578 |
| 328 | —$CH_3$ | —H | —H | —$CH_3$ | —H | —H | 490 |
| 329 | —$CH_3$ | —H | —H | —$C(CH_3)_3$ | —H | —H | 532 |
| 330 | —$CH_3$ | —H | —H | —H | —H | —$CF_3$ | 544 |
| 331 | —$CH_3$ | —Cl | —H | —H | —H | —Cl | 544 |
| 332 | —$CH_3$ | —H | —Cl | —H | —Cl | —H | 544 |
| 333 | —$CH_3$ | —H | —H | —$SCH_3$ | —H | —H | 522 |
| 334 | —$CH_3$ | —H | —H | —$COC_6H_5$ | —H | —H | 580 |
| 335 | —$CH_3$ | —H | —H | —F | —$CF_3$ | —H | 562 |
| 336 | —$CH_3$ | —H | —H | —H | —$CF_3$ | —F | 562 |
| 337 | —$CH_3$ | —H | —H | —Cl | —H | —Cl | 544 |
| 338 | —$CH_3$ | —H | —Cl | —H | —H | —Cl | 544 |
| 339 | —$CH_3$ | —H | —Cl | —H | —Cl | —Cl | 578 |
| 340 | —$CH_3$ | —Cl | —H | —Cl | —Cl | —H | 578 |
| 341 | —$CH_3$ | —Cl | —H | —Cl | —H | —Cl | 578 |
| 342 | —$CH_3$ | —H | —H | —$OCH_3$ | —H | —H | 506 |
| 343 | —$CH_3$ | —H | —H | —H | —H | —$NO_2$ | 521 |
| 344 | —$CH_3$ | —H | —H | —Cl | —Cl | —H | 544 |
| 345 | —$CH_3$ | —H | —H | —Cl | —H | —H | 510 |
| 346 | —$CH_3$ | —H | —H | —H | —Cl | —H | 510 |
| 347 | —$CH_3$ | —H | —H | —CN | —H | —H | 501 |
| 348 | —$CH_3$ | —H | —H | —H | —CN | —H | 501 |
| 349 | —$CH_3$ | —H | —H | —H | —Cl | —Cl | 544 |

TABLE 49-continued
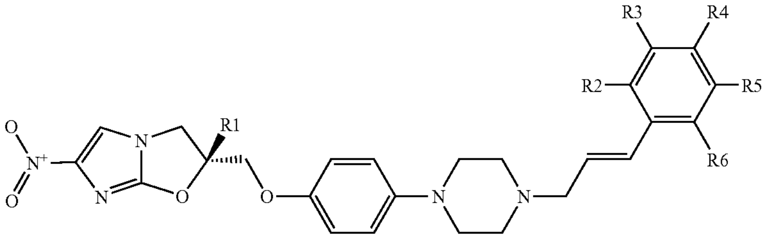
| Example | R1 | R2 | R3 | R4 | R5 | R6 | MS(M + 1) |
|---|---|---|---|---|---|---|---|
| 350 | $—CH_3$ | —H | —H | $—OCOCH_3$ | $—OCH_3$ | —H | 564 |
| 351 | $—CH_3$ | —H | —H | $—NO_2$ | —H | —H | 521 |
| 352 | $—CH_3$ | —H | —H | $—N(CH_3)_2$ | —H | —H | 519 |
| 353 | $—CH_3$ | —H | —H | —H | —H | —OH | 492 |
TABLE 50
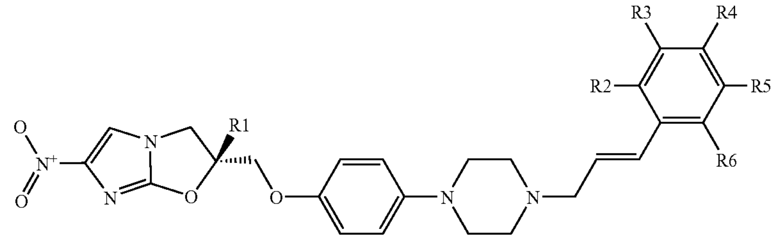
| Example | R1 | R2 | R3 | R4 | R5 | R6 | MS(M + 1) |
|---|---|---|---|---|---|---|---|
| 354 | $—CH_3$ | —H | $—OCH_3$ | —OH | $—OCH_3$ | —H | 552 |
| 355 | $—CH_3$ | —H | —H | —OH | $—OCH_3$ | —H | 522 |
| 356 | $—CH_3$ | —H | —H | $—C_2H_5$ | —H | —H | 504 |
| 357 | $—CH_3$ | —H | —H | $—C_6H_{13}$ | —H | —H | 560 |
| 358 | $—CH_3$ | —H | —H | $—OCH_2C_6H_5$ | —H | —H | 582 |
| 359 | $—CH_3$ | —H | —H | $—OC_6H_5$ | —H | —H | 568 |
| 360 | $—CH_3$ | —H | —H | $—CH(CH_3)_2$ | —H | —H | 518 |
| 361 | $—CH_3$ | —H | —H | $—OC_6H_{13}$ | —H | —H | 576 |
| 362 | $—CH_3$ | —H | —H | $—OCF_3$ | —H | —H | 560 |
TABLE 51
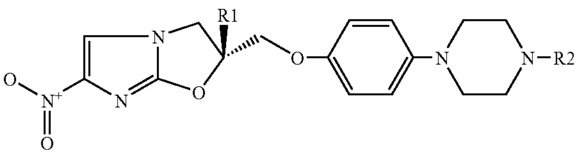
| Example | R1 | R2 | MS (M + 1) |
|---|---|---|---|
| 363 | $—CH_3$ | 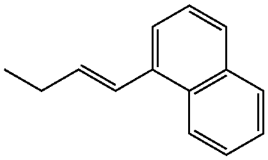 | 526 |
| 364 | $—CH_3$ | 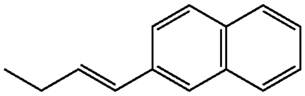 | 526 |
TABLE 51-continued
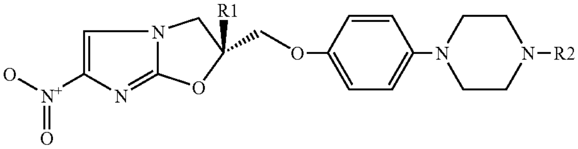
| Example | R1 | R2 | MS (M + 1) |
|---|---|---|---|
| 365 | $—CH_3$ | 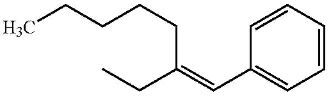 | 546 |
| 366 | $—CH_3$ | 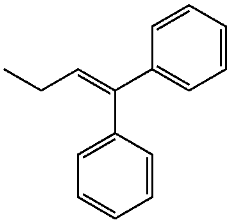 | 552 |

TABLE 51-continued
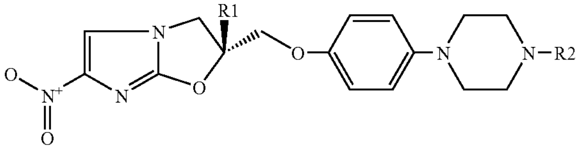
| Example | R1 | R2 | MS (M + 1) |
|---|---|---|---|
| 367 | —$CH_3$ | 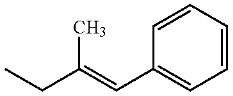 | 490 |
| 368 | —$CH_3$ | 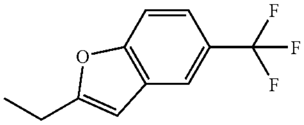 | 558 |
| 369 | —$CH_3$ | 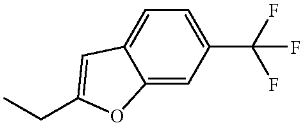 | 558 |
| 370 | —$CH_3$ | 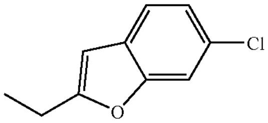 | 524 |
| 371 | —$CH_3$ | 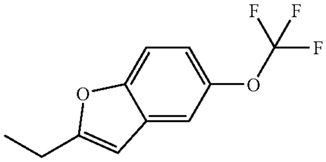 | 574 |
| 372 | —$CH_3$ | 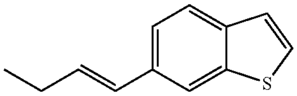 | 532 |
TABLE 52
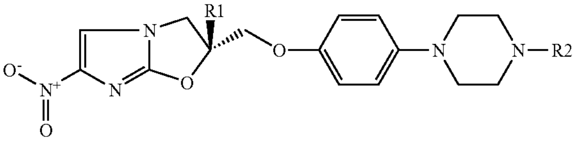
| Example | R1 | R2 | MS (M + 1) |
|---|---|---|---|
| 373 | —$CH_3$ | 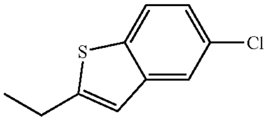 | 540 |
| 374 | —$CH_3$ | 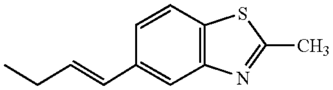 | 547 |
| 375 | —$CH_3$ | 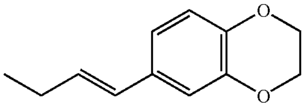 | 534 |
| 376 | —$CH_3$ | 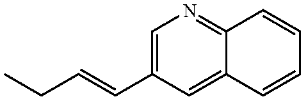 | 527 |
TABLE 53
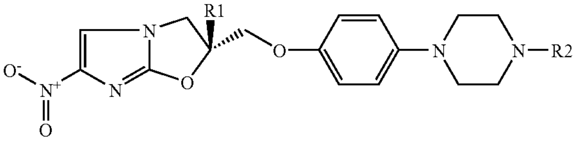
| Example | R1 | R2 | mp(° C.) |
|---|---|---|---|
| 377 | —$CH_3$ | 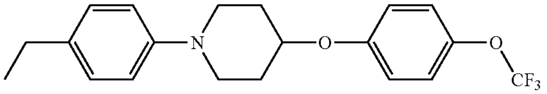 | 198.2-201.4 |
| 378 | —CH3 | 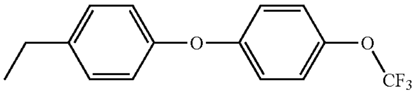 | 197.7-200.1 |
| 379 | —H | 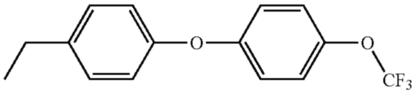 | 165.4-168.5 |

TABLE 53-continued
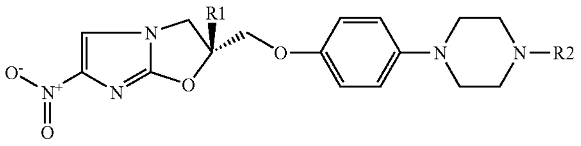
| Example | R1 | R2 | mp(° C.) |
|---|---|---|---|
| 380 | —CH3 | 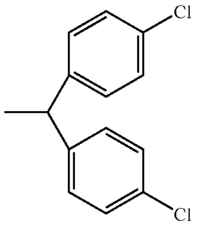 | |
| 381 | —CH3 | 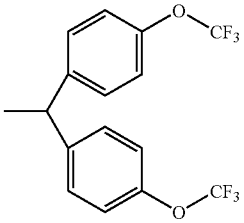 | |
TABLE 54
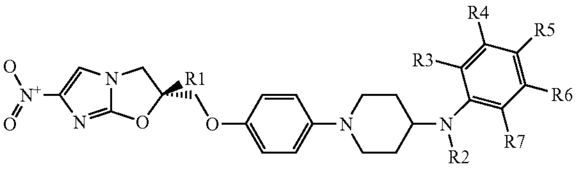
| Example | R1 | R2 | R3 | R4 | R5 | R6 | R7 | mp(° C.) |
|---|---|---|---|---|---|---|---|---|
| 382 | —$CH_3$ | —H | —H | —Cl | —H | —Cl | —H | 122-124 |
| 383 | —$CH_3$ | —$CH_3$ | —H | —Cl | —H | —Cl | —H | 166.5-167 |
| 384 | —$CH_3$ | —H | —H | —H | —$C_3H_7$ | —H | —H | 222-223 |
| 385 | —$CH_3$ | —$CH_3$ | —H | —H | —$C_3H_7$ | —H | —H | 198-199 |
| 386 | —$CH_3$ | —H | —H | —H | —F | —H | —H | 180.2-182.8 |
| 387 | —$CH_3$ | —$CH_3$ | —H | —H | —F | —H | —H | 175.7-177.4 |
| 388 | —$CH_3$ | —H | —H | —H | 4-$CF_3$OPhO— | —H | —H | 167.4-170.2 |
| 389 | —$CH_3$ | —$CH_3$ | —H | —H | 4-$CF_3$OPhO— | —H | —H | 167.4-170.2 |
| 390 | —$CH_3$ | —H | —H | —Cl | —Cl | —H | —H | |
TABLE 55
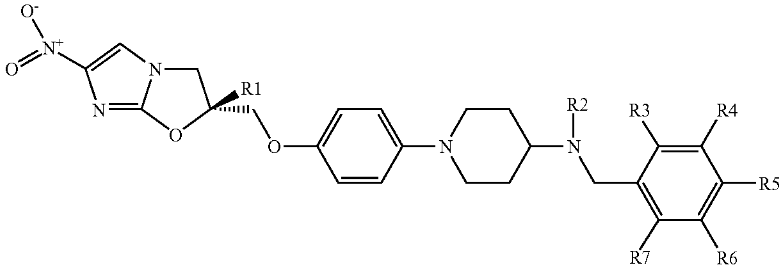
| Example | R1 | R2 | R3 | R4 | R5 | R6 | R7 | mp(° C.) |
|---|---|---|---|---|---|---|---|---|
| 391 | —$CH_3$ | —$CH_2CH_2OH$ | —H | —H | —$CF_3$ | —H | —H | 114.5-117.3 |
| 392 | —$CH_3$ | —$CH_3$ | —F | —H | —$CF_3$ | —H | —H | 197.5-199.2 |

TABLE 55-continued

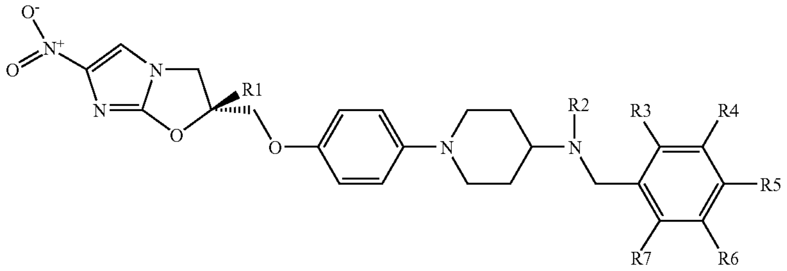

| Example | R1 | R2 | R3 | R4 | R5 | R6 | R7 | mp(° C.) |
|---|---|---|---|---|---|---|---|---|
| 393 | —$CH_3$ | —$CH_3$ | —$CF_3$ | —H | —H | —H | —H | 189.6-190.2 |
| 394 | —$CH_3$ | —$CH_3$ | —Cl | —Cl | —H | —H | —H | 176.9-178.2 |
| 395 | —$CH_3$ | —$CH_3$ | —Cl | —H | —Cl | —H | —H | 181.6-182.4 |
| 396 | —$CH_3$ | —$CH_3$ | —H | —$CF_3$ | —H | —$CF_3$ | —H | 193.8-195.3 |
| 397 | —H | —$CH_3$ | —H | —H | —$CF_3$ | —H | —H | 167.7-169.0 |

TABLE 56

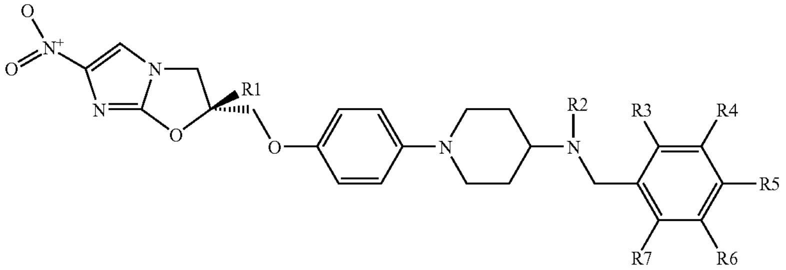

| Example | R1 | R2 | R3 | R4 | R5 | R6 | R7 | MS(M + 1) |
|---|---|---|---|---|---|---|---|---|
| 398 | —$CH_3$ | —$CH_2CH_2CN$ | —H | —H | —H | —H | —H | 517 |
| 399 | —$CH_3$ | —$C_2H_5$ | —Cl | —H | —H | —H | —Cl | 560 |
| 400 | —$CH_3$ | —$C_2H_5$ | —H | —H | —$CH(CH_3)_2$ | —H | —H | 534 |
| 401 | —$CH_3$ | —$C_2H_5$ | —H | —H | —$C_6H_5$ | —H | —H | 568 |
| 402 | —$CH_3$ | —$CH_3$ | —H | —H | —$C_2H_5$ | —H | —H | 506 |
| 403 | —$CH_3$ | —$CH_3$ | —H | —H | —$OC_6H_5$ | —H | —H | 570 |
| 404 | —$CH_3$ | —$CH_3$ | —H | —H | —$OCH_2C_6H_5$ | —H | —H | 584 |
| 405 | —$CH_3$ | —$CH_3$ | —H | —H | —$OC_8H_{17}$ | —H | —H | 606 |
| 406 | —$CH_3$ | —$CH_3$ | —H | —H | —$N(CH_3)_2$ | —H | —H | 521 |
| 407 | —$CH_3$ | —$CH_3$ | —H | —H | —$C_4H_9$ | —H | —H | 534 |
| 408 | —$CH_3$ | —$CH_3$ | —H | —H | —$CH_2CH(CH_3)_2$ | —H | —H | 534 |
| 409 | —$CH_3$ | —$CH_3$ | —H | —H | —$N(C_6H_5)_2$ | —H | —H | 645 |
| 410 | —$CH_3$ | —$CH_3$ | —H | —H | —$OCH(CH_3)_2$ | —H | —H | 536 |
| 411 | —$CH_3$ | —$CH_3$ | —H | —H | —$OC(CH_3)_3$ | —H | —H | 550 |
| 412 | —$CH_3$ | —$CH_3$ | —H | —H | —$O(CH_2)_3N(CH_3)_2$ | —H | —H | 579 |
| 413 | —$CH_3$ | —$CH_3$ | —H | —H | $N(C_4H_9)_2$ | —H | —H | 605 |

TABLE 57

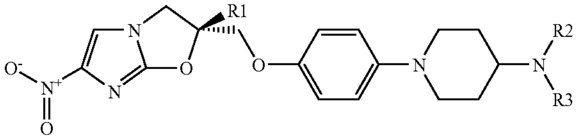

| Example | R1 | R2 | R3 | mp(° C.) |
|---|---|---|---|---|
| 414 | —$CH_3$ | $(CH_3)_3COCO$— | —$CH_3$ | |
| 415 | —H | $(CH_3)_3COCO$— | —$CH_3$ | |
| 416 | —$CH_3$ | 4-ClPh- | 4-ClPh- | 40.3-40.7 |
| 417 | —$CH_3$ | 4-$CF_3$Ph- | 4-$CF_3$Ph- | 104.0-108.0 |
| 418 | —$CH_3$ | 4-ClPh- | 4-$CF_3$Ph- | |
| 419 | —$CH_3$ | 4-$CF_3PhCH_2$— | —$CH_3$ | |
| 420 | —H | 4-$CF_3PhCH_2$— | —$CH_3$ | 167.7-169.0 |

TABLE 57-continued
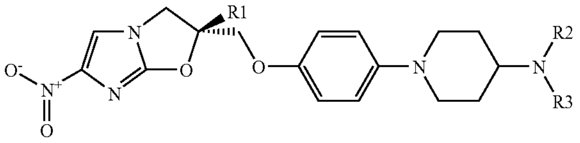
| Example | R1 | R2 | R3 | mp(° C.) |
|---|---|---|---|---|
| 421 | —$CH_3$ | -cyclo-$C_6H_{11}$ | —$CH_3$ | |
| 422 | —$CH_3$ | 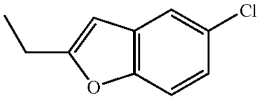 | —$CH_3$ | 207.4-210.0 |
| 423 | —$CH_3$ | 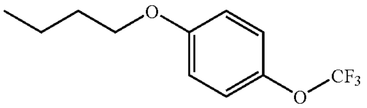 | —H | 165.2-168.9 |
| 424 | —$CH_3$ | 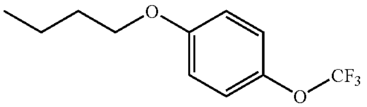 | —$CH_3$ | 163.0-163.9 |
| 425 | —$CH_3$ | 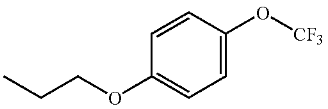 | —H | 198.3-199.0 |
| 426 | —$CH_3$ | 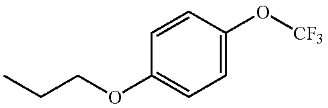 | —$CH_3$ | 185.7-187.7 |
| 427 | —H | 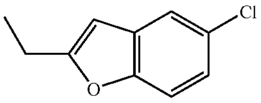 | —$CH_3$ | 219.6-221.1 |
TABLE 58
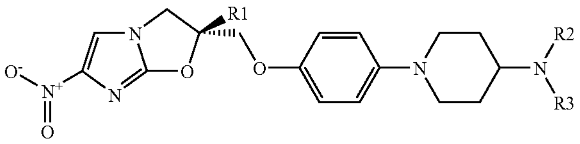
| Example | R1 | R2 | R3 | mp(° C.) |
|---|---|---|---|---|
| 428 | —$CH_3$ | 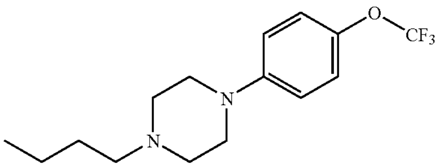 | —$CH_3$ | 190.8-194.2 |
| 429 | —$CH_3$ | 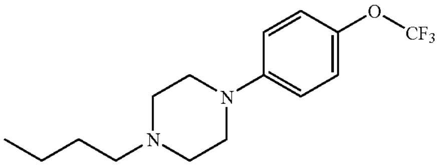 | —H | 203.0-207.6 dec |

TABLE 58-continued
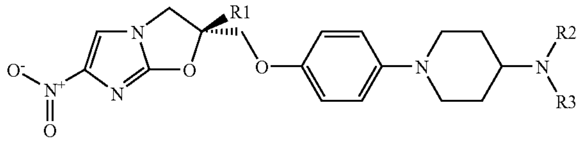
| Example | R1 | R2 | R3 | mp(° C.) |
|---|---|---|---|---|
| 430 | —$CH_3$ | 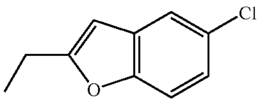 | —$CH_3$ | 207.4-210.0 |
| 431 | —H | 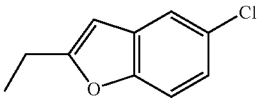 | —$CH_3$ | 219.6-221.1 |
| 432 | —$CH_3$ | 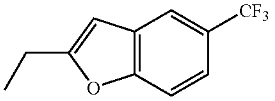 | —$CH_3$ | 194.2-196.0 |
| 433 | —H | 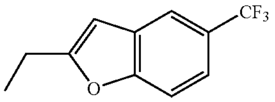 | —$CH_3$ | 174.0-175.3 |
TABLE 59
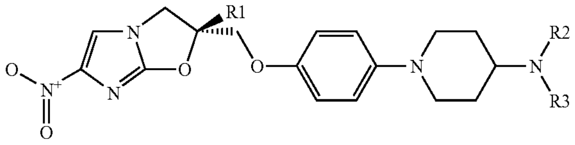
| Example | R1 | R2 | R3 | MS(M + 1) |
|---|---|---|---|---|
| 434 | —$CH_3$ | 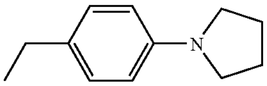 | —$CH_3$ | 547 |
| 435 | —$CH_3$ | 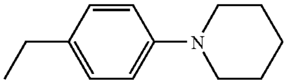 | —$CH_3$ | 561 |
| 436 | —$CH_3$ | 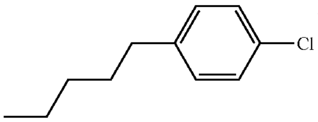 | —$C_2H_5$ | 568 |
| 437 | —$CH_3$ | 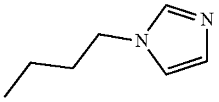 | —H | 482 |
| 438 | —$CH_3$ | 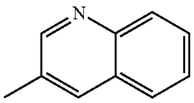 | —H | 501 |

TABLE 60

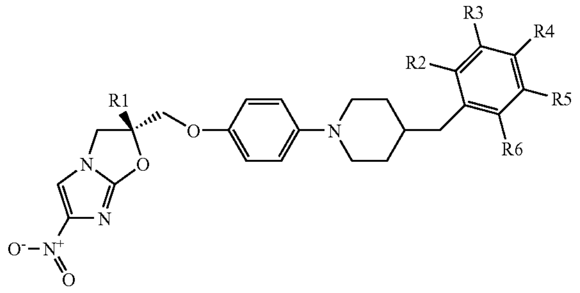

| Example | R1 | R2 | R3 | R4 | R5 | R6 | mp(° C.) |
|---|---|---|---|---|---|---|---|
| 439 | —H | —H | —H | —$OCF_3$ | —H | —H | 160.5-164.0 |
| 440 | —$CH_3$ | —H | —$OCF_3$ | —H | —H | —H | 187.4-189.8 |
| 441 | —H | —H | —$OCF_3$ | —H | —H | —H | 153.7-156.3 |
| 442 | —$CH_3$ | —$OCF_3$ | —H | —H | —H | —H | 205.8-208.5 |
| 443 | —H | —H | —H | —H | —H | —$OCF_3$ | 155.9-159.0 |

TABLE 61

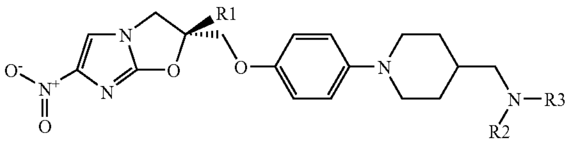

| Example | R1 | R2 | R3 | mp(° C.) |
|---|---|---|---|---|
| 444 | —$CH_3$ | 4-$CF_3$OPh- | —$COCH_3$ | 148.6-149.1 |
| 445 | —$CH_3$ | 4-$CF_3$OPh- | —$C_2H_5$ | 116.8-119.2 |
| 446 | —$CH_3$ | 4-$CF_3$OPh- | —$CH_3$ | 135.6-140.9 |
| 447 | —$CH_3$ | 4-ClPh- | —$CH_3$ | 141.6-146.1 |
| 448 | —$CH_3$ | 4-$CF_3$Ph- | —$CH_3$ | 151.4-155.0 |
| 449 | —$CH_3$ | 4-$CF_3$OPh$CH_2$— | —$COCH_3$ | |
| 450 | —$CH_3$ | 4-$CF_3$OPh- | —H | 181.9-182.5 |
| 451 | —$CH_3$ | 4-ClPh- | —H | 177.6-179.1 |
| 452 | —$CH_3$ | 4-$CF_3$Ph- | —H | 164.7-165.8 |
| 453 | —$CH_3$ | 4-$CF_3$OPh$CH_2$— | —$C_2H_5$ | 163.9-165.2 |
| 454 | —$CH_3$ | 4-$CF_3$OPh$CH_2$— | —$CH_3$ | 180.5-180.8 |
| 455 | —$CH_3$ | 4-ClPh$CH_2$— | —$CH_3$ | 169.5-170.6 |
| 456 | —$CH_3$ | 4-$CF_3$Ph$CH_2$— | —$CH_3$ | 166.7-167.5 |
| 457 | —$CH_3$ | 4-$CF_3$OPh$CH_2$— | —H | 163.9-167.6 |
| 458 | —$CH_3$ | 4-ClPh$CH_2$— | —H | 163.8-166.3 |
| 459 | —$CH_3$ | 4-$CF_3$Ph$CH_2$— | —H | 157.0-160.8 |
| 460 | —$CH_3$ | 4-$CF_3$OPh$CH_2$— | $(CH_3)_3$COCO— | |
| 461 | —$CH_3$ | 4-ClPh$CH_2$— | $(CH_3)_3$COCO— | |
| 462 | —$CH_3$ | 4-$CF_3$Ph$CH_2$— | $(CH_3)_3$COCO— | |
| 463 | —$CH_3$ | 4-$CF_3$OPh$CH_2$OCO— | —$CH_3$ | |
| 464 | —$CH_3$ | 4-$CF_3$OPhCO— | —$CH_3$ | |
| 465 | —$CH_3$ | 4-$CF_3$OPhNHCO— | —$CH_3$ | |

TABLE 62

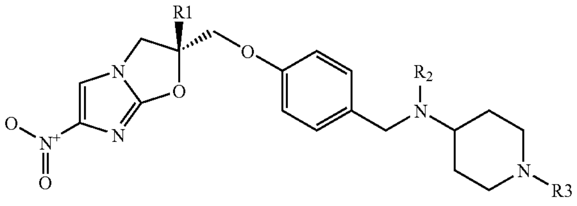

| Example | R1 | R2 | R3 | mp(° C.) |
|---|---|---|---|---|
| 466 | —$CH_3$ | —$CH_3$ | $(CH_3)_3$COCO— | 159.8-161.0 |
| 467 | —$CH_3$ | —$CH_3$ | 4-$CF_3$OPhCO— | 154.3-155.6 |
| 468 | —$CH_3$ | —$CH_3$ | 4-$CF_3$OPhNHCO— | 146.7-149.3 |

TABLE 62-continued

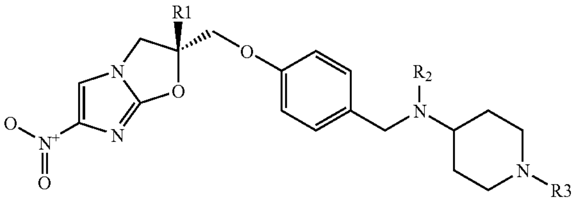

| Example | R1 | R2 | R3 | mp(° C.) |
|---|---|---|---|---|
| 469 | —$CH_3$ | —$CH_3$ | 4-$CF_3$OPh$CH_2$OCO— | 139.7-140.6 |
| 470 | —$CH_3$ | —$CH_3$ | 4-$CF_3$OPh$CH_2$— | 154.7-157.0 |

TABLE 63

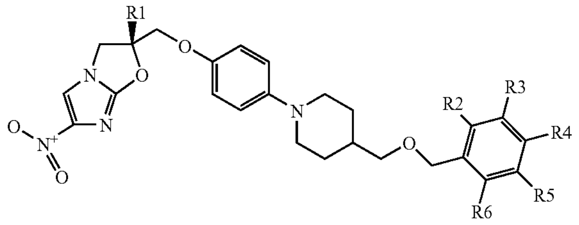

| Example | R1 | R2 | R3 | R4 | R5 | R6 | MS(M + 1) |
|---|---|---|---|---|---|---|---|
| 471 | —$CH_3$ | —Cl | —H | —H | —H | —H | 513 |
| 472 | —$CH_3$ | —H | —H | —$CH(CH_3)_2$ | —H | —H | 521 |
| 473 | —$CH_3$ | —H | —$CF_3$ | —H | —H | —H | 547 |
| 474 | —$CH_3$ | —H | —H | —$C(CH_3)_3$ | —H | —H | 535 |
| 475 | —$CH_3$ | —H | —H | —CN | —H | —H | 504 |
| 476 | —$CH_3$ | —H | —H | —$C_6H_5$ | —H | —H | 555 |
| 477 | —$CH_3$ | —$OCF_3$ | —H | —H | —H | —H | 563 |
| 478 | —$CH_3$ | —H | —$CH_3$ | —H | —H | —H | 493 |
| 479 | —$CH_3$ | —H | —H | —$OCF_3$ | —H | —H | 563 |
| 480 | —$CH_3$ | —H | —Cl | —H | —H | —H | 513 |
| 481 | —$CH_3$ | —H | —H | —F | —H | —H | 497 |
| 482 | —$CH_3$ | —H | —$OCH_3$ | —H | —H | —H | 509 |
| 483 | —$CH_3$ | —H | —Cl | —Cl | —H | —H | 547 |
| 484 | —$CH_3$ | —$CF_3$ | —H | —H | —H | —H | 547 |
| 485 | —$CH_3$ | —H | —$OC_6H_5$ | —H | —H | —H | 571 |
| 486 | —$CH_3$ | —H | —H | —$SCH_3$ | —H | —H | 525 |
| 487 | —$CH_3$ | —H | —$OCF_3$ | —H | —H | —H | 563 |
| 488 | —$CH_3$ | —Cl | —H | —F | —H | —H | 531 |
| 489 | —$CH_3$ | —H | —Cl | —H | —Cl | —H | 547 |
| 490 | —$CH_3$ | —Cl | —Cl | —H | —H | —H | 547 |
| 491 | —$CH_3$ | —H | —$CH_3$ | —H | —$CH_3$ | —H | 507 |
| 492 | —$CH_3$ | —Cl | —H | —H | —Cl | —H | 547 |
| 493 | —$CH_3$ | —H | —H | —$C_2H_5$ | —H | —H | 507 |
| 494 | —$CH_3$ | —H | —H | —Cl | —H | —H | 513 |
| 495 | —$CH_3$ | —H | —H | —$CF_3$ | —H | —H | 547 |
| 496 | —$CH_3$ | —H | —H | —$CH_3$ | —H | —H | 493 |
| 497 | —$CH_3$ | —H | —H | —H | —H | —H | 479 |

TABLE 64

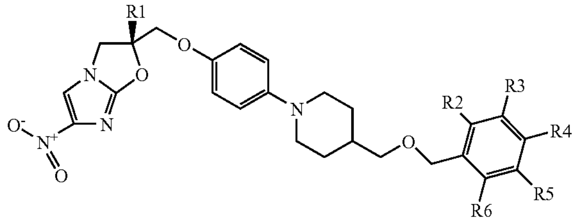

| Example | R1 | R2 | R3 | R4 | R5 | R6 | mp(° C.) |
|---|---|---|---|---|---|---|---|
| 498 | —H | —H | —H | —$CF_3$ | —H | —H | 126.8-129.0 |

TABLE 65

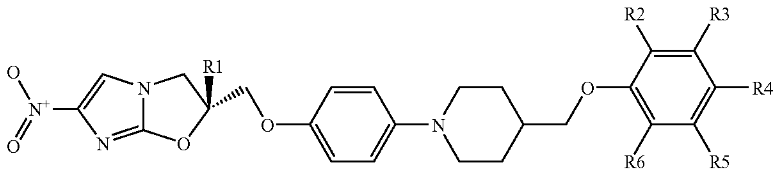

| Example | R1 | R2 | R3 | R4 | R5 | R6 | MS(M + 1) |
|---|---|---|---|---|---|---|---|
| 499 | —$CH_3$ | —H | —H | —$OCH_3$ | —H | —H | 495 |
| 500 | —$CH_3$ | —H | —H | —$OCH_3$ | —$OCH_3$ | —H | 525 |
| 501 | —$CH_3$ | —H | —H | —H | —H | —H | 465 |
| 502 | —$CH_3$ | —H | —H | —H | —H | —Cl | 499 |
| 503 | —$CH_3$ | —H | —H | —H | —Cl | —H | 499 |
| 504 | —$CH_3$ | —H | —H | —Cl | —H | —H | 499 |

TABLE 65-continued

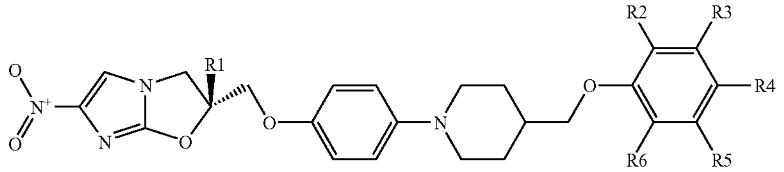

| Example | R1 | R2 | R3 | R4 | R5 | R6 | MS(M + 1) |
|---|---|---|---|---|---|---|---|
| 505 | $—CH_3$ | —H | —Cl | —Cl | —H | —H | 533 |
| 506 | $—CH_3$ | —H | —H | $—CH_3$ | —H | —H | 479 |
| 507 | $—CH_3$ | $—CH_3$ | —H | $—CH_3$ | —H | —H | 493 |
| 508 | $—CH_3$ | —H | —H | —F | —H | —H | 483 |
| 509 | $—CH_3$ | —H | —H | $—CO_2C_2H_5$ | —H | —H | 537 |
| 510 | $—CH_3$ | —H | —H | —CN | —H | —H | 490 |
| 511 | $—CH_3$ | —H | —H | —H | —H | $—CF_3$ | 533 |
| 512 | $—CH_3$ | —H | —H | —H | $—CF_3$ | —H | 533 |
| 513 | $—CH_3$ | —H | —H | $—CF_3$ | —H | —H | 533 |
| 514 | $—CH_3$ | —H | —H | $—OCF_3$ | —H | —H | 549 |
| 515 | $—CH_3$ | —H | —H | —H | —H | $—OCH(CH_3)_2$ | 523 |
| 516 | $—CH_3$ | —H | —H | $—CH_3$ | —H | $—CO_2C_2H_5$ | 551 |
| 517 | $—CH_3$ | —H | —H | $—OCH_3$ | —H | $—CO_2CH_3$ | 553 |
| 518 | $—CH_3$ | —H | —H | —Br | —H | —F | 561 |
| 519 | $—CH_3$ | —H | $—CH_3$ | —H | —H | —F | 497 |
| 520 | $—CH_3$ | —H | —H | $—C_3H_7$ | —H | —H | 507 |
| 521 | $—CH_3$ | —H | —H | —Cl | —F | —H | 517 |
| 522 | $—CH_3$ | —H | —H | $—NO_2$ | —H | —F | 528 |
| 523 | $—CH_3$ | —H | —H | $—CH_2CH{=}CH_2$ | —H | $—OCH_3$ | 535 |
| 524 | $—CH_3$ | —H | —H | —H | $—N(C_2H_5)_2$ | —H | 536 |
| 525 | $—CH_3$ | —H | $—CH{=}CHCH_3$(cis) | —H | —H | $—OC_2H_5$ | 549 |
| 526 | $—CH_3$ | —H | —H | $—CH(CH_3)_2$ | —H | —H | 507 |
| 527 | $—CH_3$ | —H | —H | $—CH_2CH_2COCH_3$ | —H | —H | 535 |
| 528 | $—CH_3$ | —H | —H | —H | $—NHC_6H_5$ | —H | 556 |
| 529 | $—CH_3$ | —H | —H | $—CH_2CO_2CH_3$ | —H | —H | 537 |
| 530 | $—CH_3$ | —H | —H | $—OCH_3$ | —H | —Cl | 529 |

TABLE 66

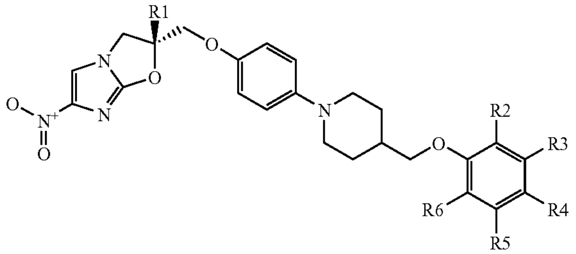

| Example | R1 | R2 | R3 | R4 | R5 | R6 | MS(M + 1) |
|---|---|---|---|---|---|---|---|
| 531 | $—CH_3$ | —H | —H | —H | $—CO_2CH_3$ | —H | 523 |
| 532 | $—CH_3$ | —H | —H | $—COC_2H_5$ | —H | —H | 521 |
| 533 | $—CH_3$ | —H | —H | $—COCH_3$ | —H | $—CH_3$ | 521 |
| 534 | $—CH_3$ | —H | —H | $—NHCOCH_3$ | —H | —H | 522 |
| 535 | $—CH_3$ | —H | $—CH_3$ | $—CH_3$ | $—CH_3$ | —H | 507 |
| 536 | $—CH_3$ | —H | —H | —H | —H | $—CH_2C_6H_5$ | 555 |
| 537 | $—CH_3$ | —H | $—OCH_3$ | —H | —H | $—CO_2CH_3$ | 553 |
| 538 | $—CH_3$ | —H | —H | $—SCH_3$ | —H | —H | 511 |
| 539 | $—CH_3$ | —H | —H | —H | —H | -2-BENZTHIAZOLYL | 598 |
| 540 | $—CH_3$ | —H | —H | -1-PYRRYL | —H | —H | 530 |
| 541 | $—CH_3$ | —H | —H | $—C_6H_5$ | —H | —H | 541 |
| 542 | $—CH_3$ | —H | —H | $—OCH_2C_6H_5$ | —H | —H | 571 |
| 543 | $—CH_3$ | —H | —H | $—CH_2C_6H_5$ | —H | —H | 555 |
| 544 | $—CH_3$ | —H | —H | -cyclo-$C_6H_{11}$ | —H | —H | 547 |
| 545 | $—CH_3$ | —H | —H | $—OC_8H_{17}$ | —H | —H | 593 |
| 546 | $—CH_3$ | —H | —H | -cyclo-$C_5H_9$ | —H | —H | 533 |
| 547 | $—CH_3$ | —H | —H | —H | $—OC_6H_5$ | —H | 557 |
| 548 | $—CH_3$ | —H | —H | $—C_6H_{13}$ | —H | —H | 549 |

TABLE 67
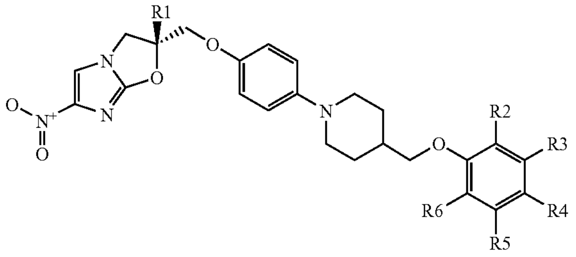
| Example | R1 | R2 | R3 | R4 | R5 | R6 | mp(° C.) |
|---|---|---|---|---|---|---|---|
| 549 | —H | —H | —H | —Cl | —H | —H | 198.6-202.5 |
| 550 | —H | —H | —H | —$CF_3$ | —H | —H | 197.0-200.9 |
TABLE 68
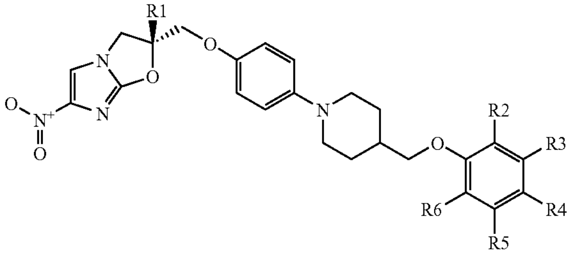
| Example | R1 | R2 | R3 | R4 | R5 | R6 | MS(M + 1) |
|---|---|---|---|---|---|---|---|
| 551 | —$CH_3$ | —H | —H | 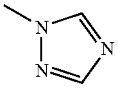 | —H | —H | 532 |
| 552 | —$CH_3$ | —H | —H | —H | —H | 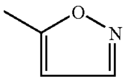 | 532 |
| 553 | —$CH_3$ | —H | —H | 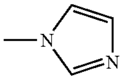 | —H | —H | 531 |
| 554 | —$CH_3$ | —H | —H | —$CH_3$ | —H | 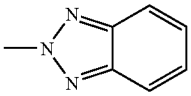 | 596 |
| 555 | —$CH_3$ | —H | —H | —H | —H | 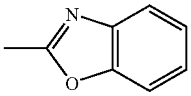 | 582 |
| 556 | —$CH_3$ | —H | —H | 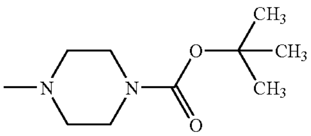 | —H | —H | 649 |

TABLE 69

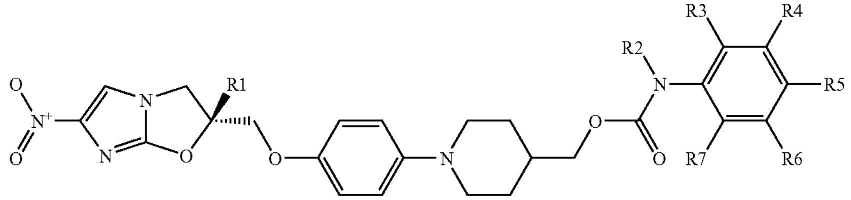

| Example | R1 | R2 | R3 | R4 | R5 | R6 | R7 | MS(M + 1) |
|---|---|---|---|---|---|---|---|---|
| 557 | —$CH_3$ | —H | —H | —H | —H | —H | —H | 508 |
| 558 | —$CH_3$ | —H | —Cl | —H | —H | —H | —H | 542 |
| 559 | —$CH_3$ | —H | —H | —H | —H | —Cl | —H | 542 |
| 560 | —$CH_3$ | —H | —H | —H | —Cl | —H | —H | 542 |
| 561 | —$CH_3$ | —H | —$OCH_3$ | —H | —H | —H | —H | 538 |
| 562 | —$CH_3$ | —H | —H | —H | —H | —$OCH_3$ | —H | 538 |
| 563 | —$CH_3$ | —H | —H | —H | —Cl | —Cl | —H | 576 |
| 564 | —$CH_3$ | —H | —H | —Cl | —H | —Cl | —H | 576 |
| 565 | —$CH_3$ | —H | —H | —$CF_3$ | —H | —H | —H | 576 |
| 566 | —$CH_3$ | —H | —H | —H | —$CF_3$ | —H | —H | 576 |
| 567 | —$CH_3$ | —H | —H | —H | —$OCF_3$ | —H | —H | 592 |
| 568 | —$CH_3$ | —H | —$CH_3$ | —H | —H | —H | —H | 522 |
| 569 | —$CH_3$ | —H | —H | —$CH_3$ | —H | —H | —H | 522 |
| 570 | —$CH_3$ | —H | —H | —H | —$CH_3$ | —H | —H | 522 |
| 571 | —$CH_3$ | —H | —F | —H | —H | —H | —H | 526 |
| 572 | —$CH_3$ | —H | —H | —F | —H | —H | —H | 526 |
| 573 | —$CH_3$ | —H | —H | —H | —F | —H | —H | 526 |
| 574 | —$CH_3$ | —H | —H | —H | —Cl | —H | —Cl | 576 |
| 575 | —$CH_3$ | —H | —H | —H | —CN | —H | —H | 533 |
| 576 | —$CH_3$ | —H | —H | —$CF_3$ | —H | —$CF_3$ | —H | 644 |
| 577 | —$CH_3$ | —H | —H | —H | —Cl | —$CF_3$ | —H | 610 |
| 578 | —$CH_3$ | —H | —H | —H | —$OC_6H_5$ | —H | —H | 600 |
| 579 | —$CH_3$ | —H | —H | —H | —$OC_2H_5$ | —H | —H | 552 |
| 580 | —$CH_3$ | —H | —H | —H | —$SCH_3$ | —H | —H | 554 |
| 581 | —$CH_3$ | —H | —H | —H | —$COCH_3$ | —H | —H | 550 |
| 582 | —$CH_3$ | —H | —H | —H | —$CH(CH_3)_2$ | —H | —H | 550 |
| 583 | —$CH_3$ | —H | —H | —H | —$C_4H_9$ | —H | —H | 564 |
| 584 | —$CH_3$ | —H | —H | —H | —Cl | —H | —$CH_3$ | 556 |
| 585 | —$CH_3$ | —H | —H | —H | —$OC_4H_9$ | —H | —H | 580 |
| 586 | —$CH_3$ | —H | —H | —H | —$C_6H_5$ | —H | —H | 584 |
| 587 | —$CH_3$ | —H | —H | —H | —$C(CH_3)_3$ | —H | —H | 564 |
| 588 | —$CH_3$ | —H | —H | —H | —$OC_7H_{15}$ | —H | —H | 622 |
| 589 | —$CH_3$ | —H | —H | —H | —$OCHF_2$ | —H | —H | 574 |
| 590 | —$CH_3$ | —H | —H | —H | —$CH_2C_6H_5$ | —H | —H | 598 |
| 591 | —$CH_3$ | —H | —H | —H | —$C_8H_{17}$ | —H | —H | 620 |

TABLE 70

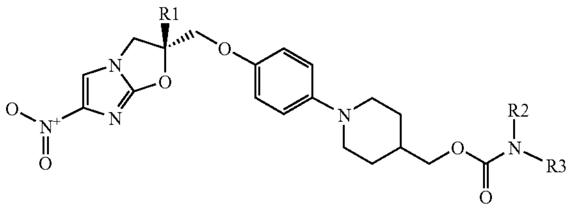

| Example | R1 | R2 | R3 | MS(M + 1) |
|---|---|---|---|---|
| 592 | —$CH_3$ | —$CH_2C_6H_5$ | —H | 522 |
| 593 | —$CH_3$ | —$(CH_2)_2C_6H_5$ | —H | 536 |
| 594 | —$CH_3$ | -cyclo-$C_6H_{11}$ | —H | 514 |
| 595 | —$CH_3$ | 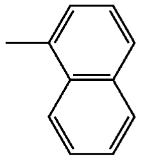 | —H | 558 |

TABLE 70-continued

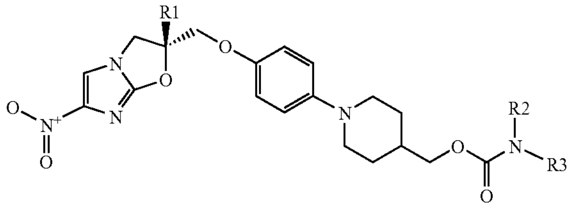

| Example | R1 | R2 | R3 | MS(M + 1) |
|---|---|---|---|---|
| 596 | —$CH_3$ | 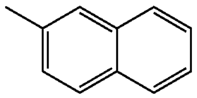 | —H | 558 |
| 597 | —$CH_3$ | 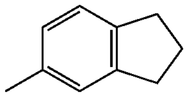 | —H | 548 |

TABLE 70-continued
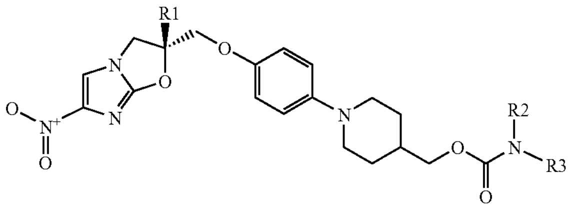
| Example | R1 | R2 | R3 | MS(M + 1) |
|---|---|---|---|---|
| 598 | —$CH_3$ | 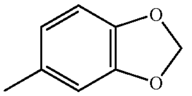 | —H | 552 |
| 599 | —$CH_3$ | 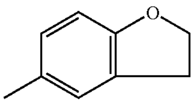 | —H | 550 |
TABLE 71
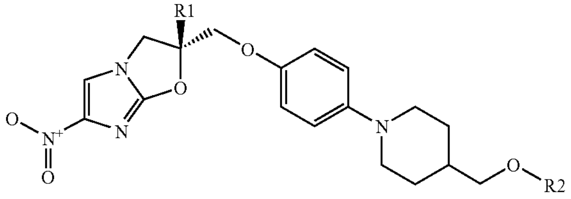
| Example | R1 | R2 | MS(M + 1) |
|---|---|---|---|
| 600 | —$CH_3$ | 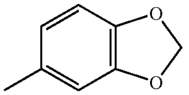 | 509 |
| 601 | —$CH_3$ | 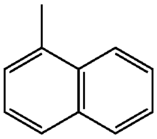 | 515 |
| 602 | —$CH_3$ | 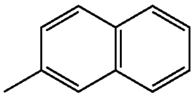 | 515 |
| 603 | —$CH_3$ | 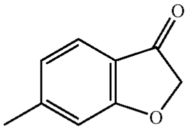 | 521 |
| 604 | —$CH_3$ | 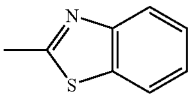 | 522 |
| 605 | —$CH_3$ | 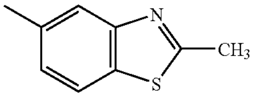 | 536 |
TABLE 71-continued
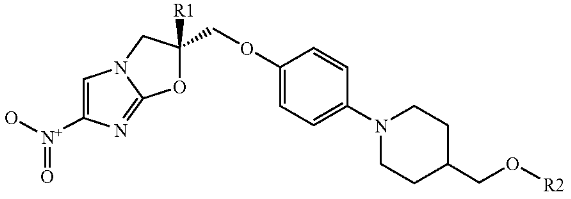
| Example | R1 | R2 | MS(M + 1) |
|---|---|---|---|
| 606 | —$CH_3$ | 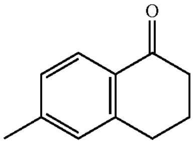 | 533 |
| 607 | —$CH_3$ | 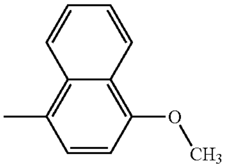 | 545 |
| 608 | —$CH_3$ | 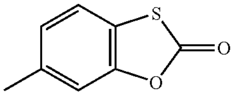 | 539 |
| 609 | —$CH_3$ | 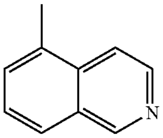 | 516 |
| 610 | —$CH_3$ | 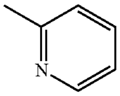 | 466 |
TABLE 72
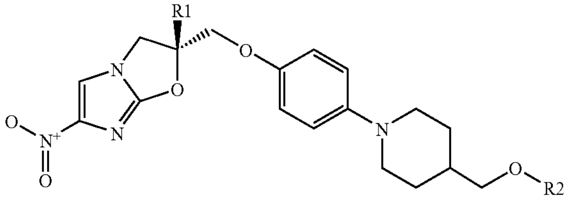
| Example | R1 | R2 | MS(M + 1) |
|---|---|---|---|
| 611 | —$CH_3$ | 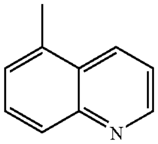 | 516 |
| 612 | —$CH_3$ | 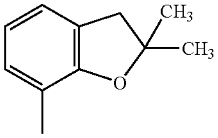 | 535 |

TABLE 72-continued
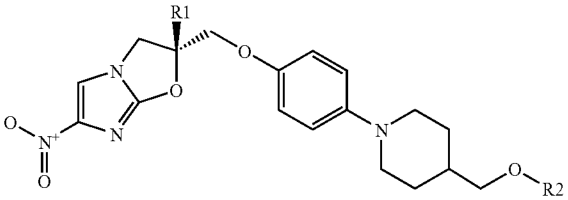
| Example | R1 | R2 | MS(M + 1) |
|---|---|---|---|
| 613 | —$CH_3$ | 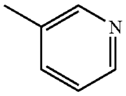 | 466 |
| 614 | —$CH_3$ | 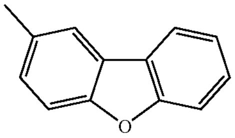 | 555 |
| 615 | —$CH_3$ | 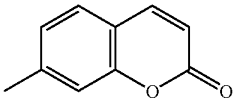 | 533 |
| 616 | —$CH_3$ | 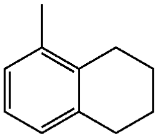 | 519 |
| 617 | —$CH_3$ | 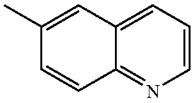 | 516 |
| 618 | —$CH_3$ | 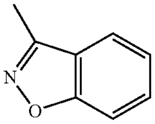 | 506 |
| 619 | —$CH_3$ | 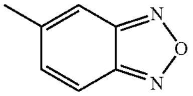 | 507 |
| 620 | —$CH_3$ | 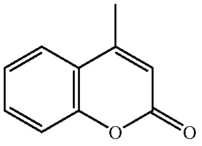 | |
| 621 | —$CH_3$ | 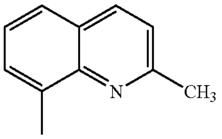 | 530 |
TABLE 73
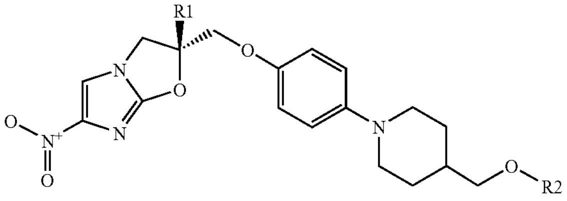
| Example | R1 | R2 | MS (M + 1) |
|---|---|---|---|
| 622 | —$CH_3$ | 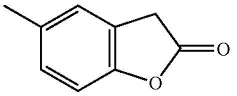 | |
| 623 | —$CH_3$ | 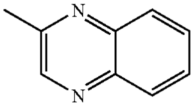 | 517 |
| 624 | —$CH_3$ | 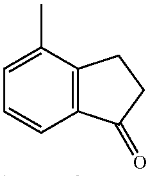 | 519 |
| 625 | —$CH_3$ | 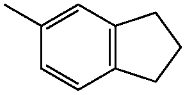 | 505 |
| 626 | —$CH_3$ | 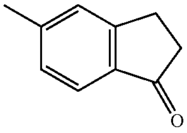 | 519 |
| 627 | —$CH_3$ | 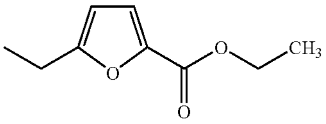 | 541 |
| 628 | —$CH_3$ | 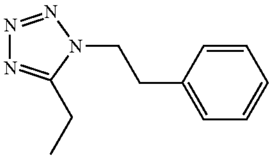 | 575 |
| 629 | —$CH_3$ | 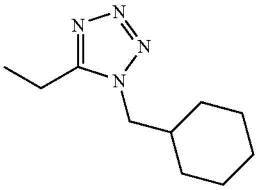 | 567 |
| 630 | —$CH_3$ | 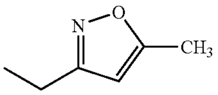 | 484 |
| 631 | —$CH_3$ | 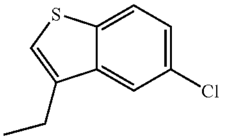 | 570 |

TABLE 74

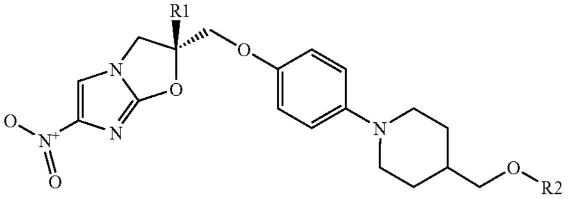

| Example | R1 | R2 | MS (M + 1) |
|---|---|---|---|
| 632 | $-CH_3$ | 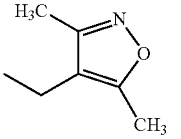 | 498 |
| 633 | $-CH_3$ | 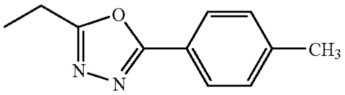 | 561 |
| 634 | $-CH_3$ | 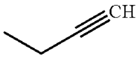 | 427 |
| 635 | $-CH_3$ | 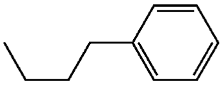 | 507 |
| 636 | $-CH_3$ | 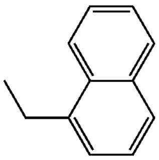 | 529 |
| 637 | $-CH_3$ | 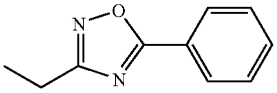 | 547 |
| 638 | $-CH_3$ | 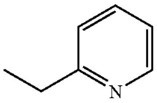 | 480 |
| 639 | $-CH_3$ | 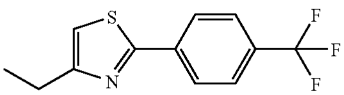 | 630 |
| 640 | $-CH_3$ | 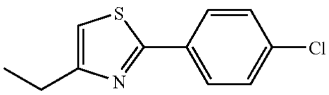 | 596 |
| 641 | $-CH_3$ | 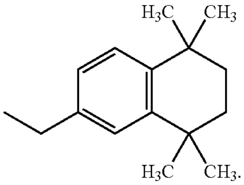 | 589 |

TABLE 75

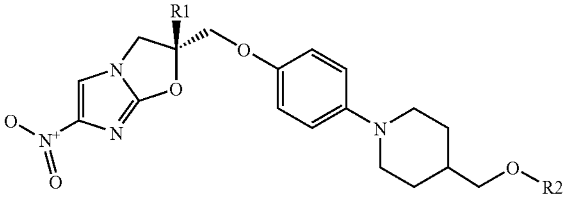

| Example | R1 | R2 | MS(M + 1) |
|---|---|---|---|
| 642 | $-CH_3$ | 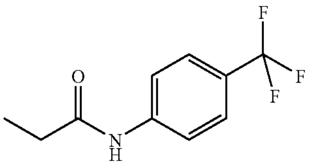 | 590 |
| 643 | $-CH_3$ | 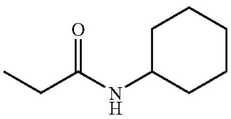 | 528 |
| 644 | $-CH_3$ | 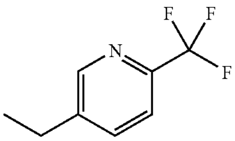 | 548 |
| 645 | $-CH_3$ | 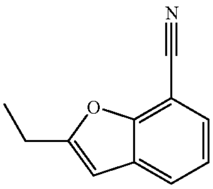 | 544 |

TABLE 76

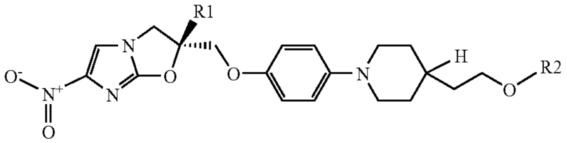

| Example | R1 | R2 | mp(° C.) |
|---|---|---|---|
| 646 | $-CH_3$ | $4-CF_3OPhCH_2-$ | 204.8-206.7 |
| 647 | $-CH_3$ | $4-CF_3PhCH_2-$ | 198.0-199.2 |
| 648 | $-CH_3$ | $4-ClPhCH_2-$ | 197.6-198.2 |
| 649 | $-CH_3$ | 4-ClPhNHCO— | 212.7-213.3 |
| 650 | $-CH_3$ | $4-ClPhN(CH_3)CO-$ | 189.4-191.6 |
| 651 | $-CH_3$ | $4-ClPhN(C_2H_5)CO-$ | 168.6-171.6 |
| 652 | $-CH_3$ | $4-CF_3PhNHCO-$ | 216.2-217.1 dec |
| 653 | $-CH_3$ | $4-CF_3OPhNHCO-$ | 218.3-218.5 dec |
| 654 | —H | $4-CF_3PhNHCO-$ | 179.9-180.7 |
| 655 | —H | $4-CF_3OPhNHCO-$ | 187.6-189.8 |
| 656 | $-CH_3$ | $4-CF_3PhN(CH_3)CO-$ | 195.8-199.1 |
| 657 | $-CH_3$ | $4-CF_3OPhN(CH_3)CO-$ | 181.0-184.2 |
| 658 | —H | $4-CF_3PhN(CH_3)CO-$ | 148.7-151.8 |
| 659 | —H | $4-CF_3OPhN(CH_3)CO-$ | 150.1-152.6 |

TABLE 77
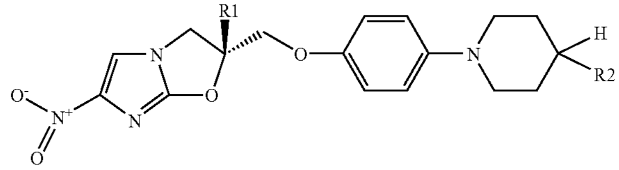
| Example | R1 | R2 | mp(° C.) |
|---|---|---|---|
| 660 | —$CH_3$ | 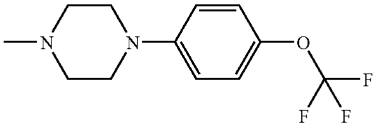 | 279-281 |
| 661 | —$CH_3$ | 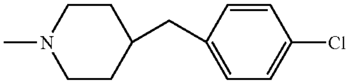 | 227-229 |
| 662 | —$CH_3$ | 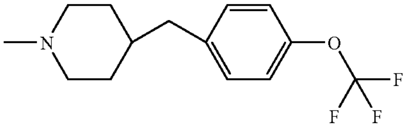 | 225-227 |
| 663 | —$CH_3$ | 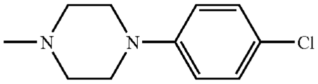 | 247-249 |
| 664 | —$CH_3$ | 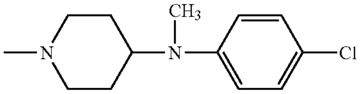 | 230.8-232 |
| 665 | —$CH_3$ | 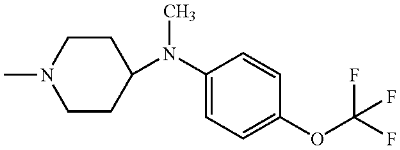 | 196-197 |
| 666 | —H | 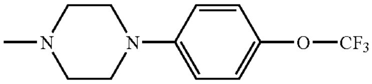 | 248-250 dec |
| 667 | —H | 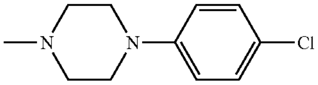 | 254-257 dec |
| 668 | —H | 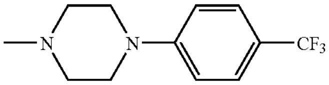 | 259-260.5 |
| 669 | —H | 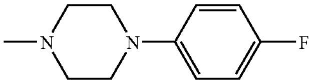 | 248.5-250 |
| 670 | —$CH_3$ | 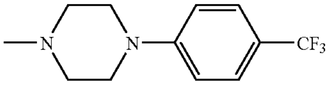 | 269-271 dec |
| 671 | —$CH_3$ | 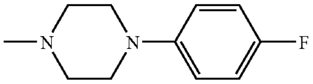 | 274-276 dec |

TABLE 78
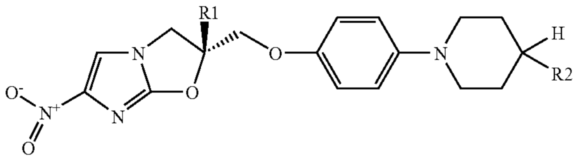
| Example | R1 | R2 | mp(° C.) |
|---|---|---|---|
| 672 | —H | 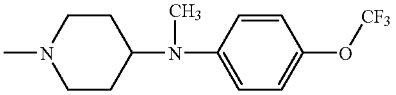 | 163-165 |
| 673 | —H | 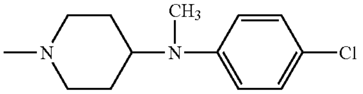 | 200-205 dec |
| 674 | —H | 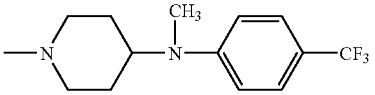 | 172-174 |
| 675 | —H | 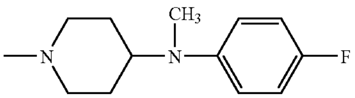 | 206.5-208 |
| 676 | $—CH_3$ | 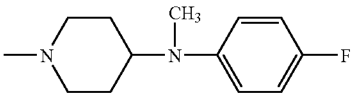 | 234-236 dec |
| 677 | $—CH_3$ | 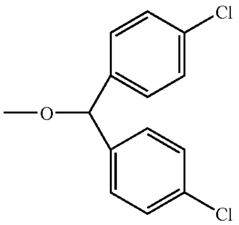 | |
| 678 | $—CH_3$ | 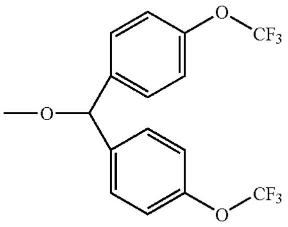 | |
| 679 | —H | $CF_3OPh(CH_2)_2—$ | |
| 680 | —H | $CF_3OPh(CH_2)_3—$ | |

TABLE 79
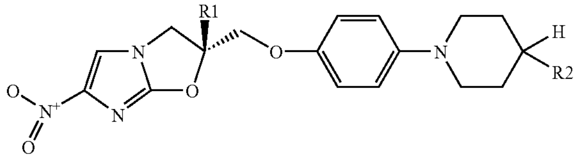
| Example | R1 | R2 | MS(M + 1) |
|---|---|---|---|
| 681 | —$CH_3$ | 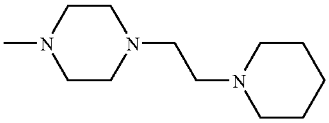 | 554 |
| 682 | —$CH_3$ | 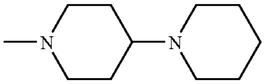 | 525 |
| 683 | —$CH_3$ | 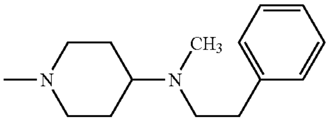 | 575 |
| 684 | —$CH_3$ | 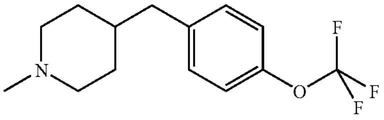 | 616 |
| 685 | —$CH_3$ | 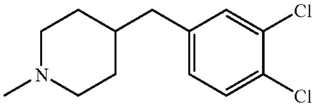 | 600 |
| 686 | —$CH_3$ | 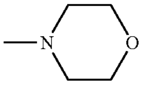 | 444 |
TABLE 80
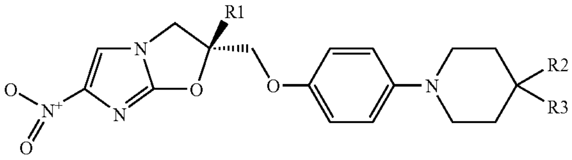
| Example | R1 | R2 | R3 | mp (° C.) |
|---|---|---|---|---|
| 687 | —$CH_3$ | —H | 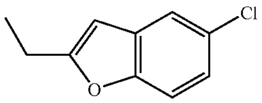 | 208.9-210.6 |
| 688 | —H | —H | 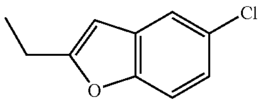 | 172.7-175.2 |
TABLE 80-continued
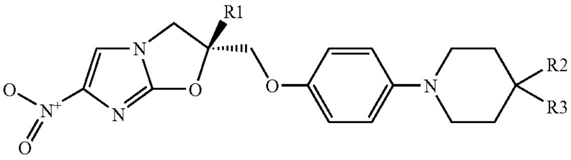
| Example | R1 | R2 | R3 | mp (° C.) |
|---|---|---|---|---|
| 689 | —$CH_3$ | —H | 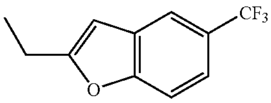 | 199.8-202.4 |
| 690 | —H | —H | 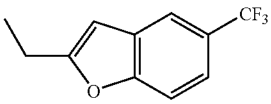 | 150.0-151.9 |

TABLE 81

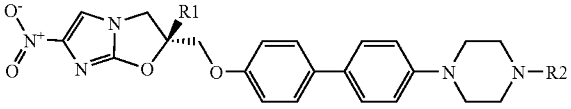

| Example | R1 | R2 | mp(° C.) |
|---|---|---|---|
| 691 | —$CH_3$ | $(CH_3)_3COCO$— | 261.0-266.3 dec |
| 692 | —$CH_3$ | —H | |
| 693 | —$CH_3$ | 4-$CF_3OPhCH_2$— | 238.2~240.3 dec. |
| 694 | —$CH_3$ | 4-$ClPhCH_2$— | 247.8~248.5 dec. |
| 695 | —$CH_3$ | 4-$CF_3PhCH_2$— | 247.7-248.4 dec |
| 696 | —$CH_3$ | 4-$CF_3PhCH{=}CHCH_2$— | 221.0-226.0 |
| 697 | —$CH_3$ | 4-$CF_3OPhCO$— | 248.0-252.0 |

TABLE 81-continued

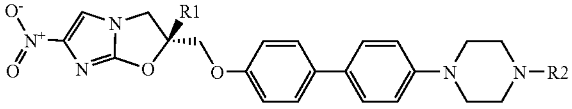

| Example | R1 | R2 | mp(° C.) |
|---|---|---|---|
| 698 | —$CH_3$ | 3,4-$Cl_2PhCH_2$— | 222.6-225.1 dec. |
| 699 | —$CH_3$ | 4-$FPhCH_2$— | 247.7-249.5 |
| 700 | —H | $(CH_3)_3COCO$— | 250 dec |
| 701 | —H | 4-$CF_3OPhCH_2$— | 200 dec |
| 702 | —H | 4-$CF_3PhCH_2$— | 200 dec |
| 703 | —H | 4-$ClPhCH_2$— | 200 dec |

TABLE 82

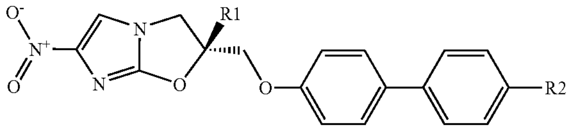

| Example | R1 | R2 | mp(° C.) |
|---|---|---|---|
| 704 | —$CH_3$ | 4-ClPh— | 250 dec. |
| 705 | —$CH_3$ | 4-$CF_3Ph$— | 266.2-271.2 dec |
| 706 | —$CH_3$ | 4-$CF_3OPh$— | 286.4-288.2 dec |
| 707 | —H | 4-ClPh— | |
| 708 | —H | 4-$CF_3Ph$— | 250 dec |
| 709 | —H | 4-$CF_3OPh$— | 270 dec |
| 710 | —$CH_3$ | 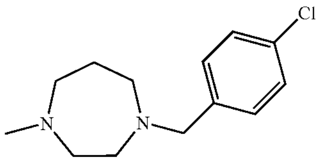 | 203.4-206.3 |
| 711 | —$CH_3$ | 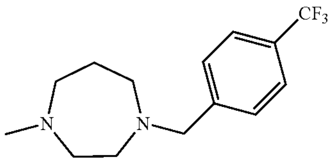 | 200.8-203.9 |
| 712 | —$CH_3$ | 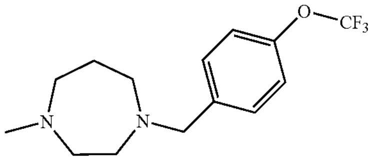 | 206.6-210.2 |
| 713 | —H | 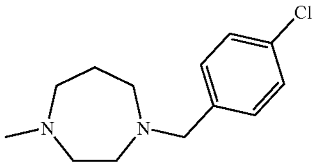 | 203.0-205.6 |
| 714 | —H | 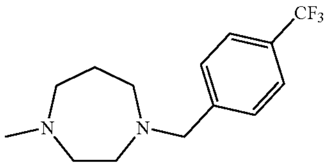 | 188.6-191.4 |

TABLE 82-continued

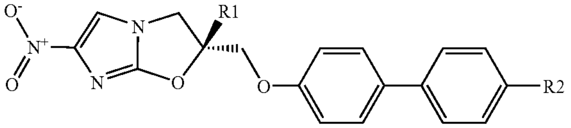

| Example | R1 | R2 | mp(° C.) |
|---|---|---|---|
| 715 | —H | 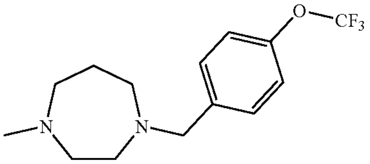 | 202.5-203.8 |

TABLE 83

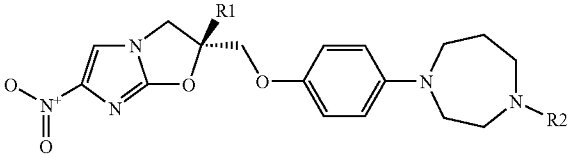

| Example | R1 | R2 | mp(° C.) |
|---|---|---|---|
| 716 | —$CH_3$ | $(CH_3)_3COCO$— | |
| 717 | —$CH_3$ | 4-$ClPhCH_2$— | 150.3-153.9 |
| 718 | —$CH_3$ | 4-$CF_3PhCH_2$— | 136.5-138.4 |
| 719 | —$CH_3$ | 4-$CF_3OPhCH_2$— | 150.6-153.5 |
| 720 | —$CH_3$ | 4-$CF_3Ph$— | 156.6-158.1 |
| 721 | —$CH_3$ | 4-$CF_3OPh$— | 134.0-137.9 |
| 722 | —$CH_3$ | 4-ClPh— | 149.7-151.2 |
| 723 | —$CH_3$ | 4-$CF_3OPhCH_2OCO$— | 90.2-93.0 |
| 724 | —$CH_3$ | 4-$Cl_3PhCH_2OCO$— | 86.7-89.0 |
| 725 | —$CH_3$ | 4-$ClPhCH_2OCO$— | 109.0-112.3 |
| 726 | —$CH_3$ | 4-ClPhNHCO— | |

TABLE 83-continued

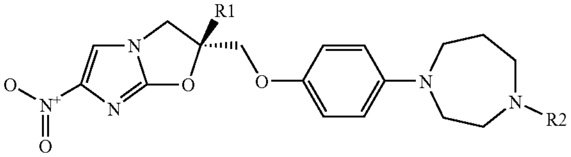

| Example | R1 | R2 | mp(° C.) |
|---|---|---|---|
| 727 | —$CH_3$ | 4-$CF_3$OPhNHCO— | 199.0-203.6 |
| 728 | —$CH_3$ | 4-$CF_3$PhNHCO— | 208.5-212.0 |
| 729 | —$CH_3$ | 4-$CF_3PhCH{=}CHCH_2$— | |
| 730 | —$CH_3$ | 4-$CF_3Ph(CH_2)_2$— | |
| 731 | —$CH_3$ | 4-$CF_3Ph(CH_2)_3$— | 149.5-154.0 (dihydrochloride) |
| 732 | —$CH_3$ | 4-ClPhCO— | |
| 733 | —$CH_3$ | 4-$CF_3$PhCO— | |
| 734 | —$CH_3$ | 4-$CF_3$OPhCO— | |

TABLE 84

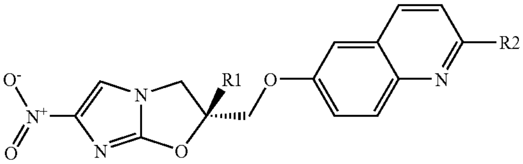

| Example | R1 | R2 | mp(° C.) |
|---|---|---|---|
| 735 | —$CH_3$ | 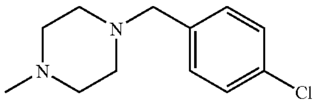 | 218.1-219.1 |
| 736 | —$CH_3$ | 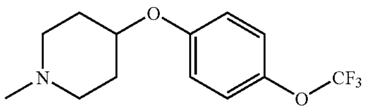 | 199.6-200.1 |
| 737 | —$CH_3$ | 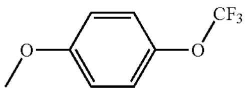 | 133.8-136.2 |

TABLE 84-continued
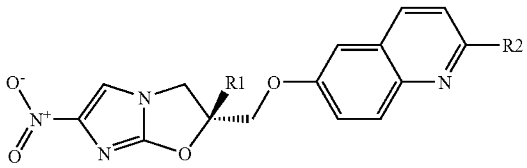
| Example | R1 | R2 | mp(° C.) |
|---|---|---|---|
| 738 | —$CH_3$ | 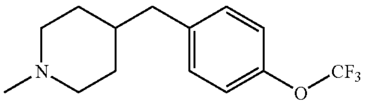 | 184.9-185.9 |
| 739 | —$CH_3$ | 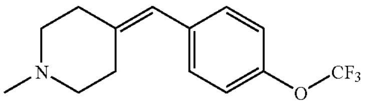 | 193.9-195.9 |
| 740 | —$CH_3$ | 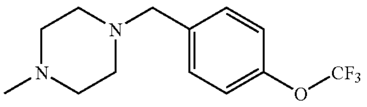 | 215.5-217.4 |
| 741 | —$CH_3$ | 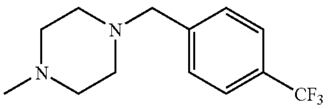 | 206.8-208.6 |
| 742 | —H | 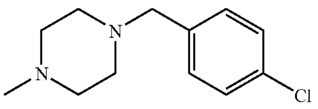 | 215.0-215.9 |
| 743 | —$CH_3$ | 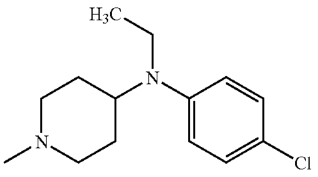 | 99.8-102.5 |
| 744 | —H | 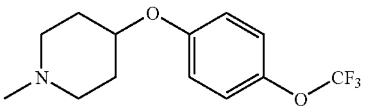 | 191.4-192.8 |
| 745 | —H | 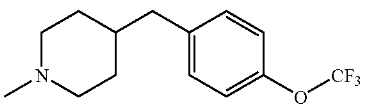 | 198.8-200.9 |

TABLE 85
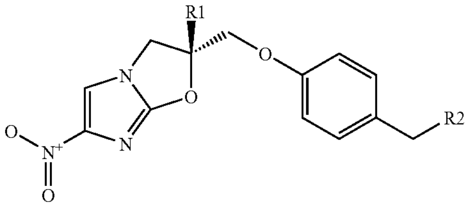
| Example | R1 | R2 | mp(° C.) |
|---|---|---|---|
| 746 | —$CH_3$ | 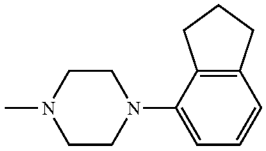 | 162.7-165.1 |
TABLE 85-continued
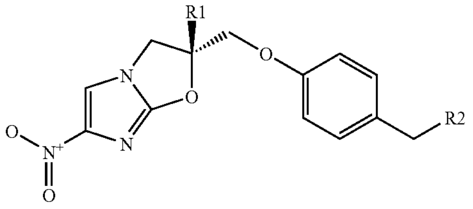
| Example | R1 | R2 | mp(° C.) |
|---|---|---|---|
| 747 | —$CH_3$ | 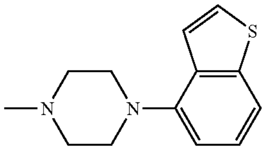 | 132.4-134.7 |
TABLE 86
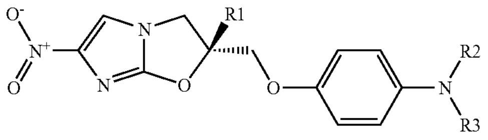
| Example | R1 | R2 | R3 | mp(° C.) |
|---|---|---|---|---|
| 748 | —$CH_3$ | —$CH_3$ | 4-$CF_3$PhCH═CHCH$_2$— | |
| 749 | —$CH_3$ | —$CH_3$ | 4-$CF_3$PhCH═CHCH$_2$— | 165.5-168.1 |
| 750 | —$CH_3$ | —H | 4-$CF_3$OPhCH═CHCH$_2$— | 193.3-195.3 |
| 751 | —$CH_3$ | —H | 4-$CF_3$OPhCH═CHCO— | 251.1-254.1 |
| 752 | —$CH_3$ | —$CH_3$ | 4-$CF_3$OPhCH═CHCO— | 161.7-163.4 |
| 753 | —$CH_3$ | —H | 4-$CF_3$PhCH═CHCH$_2$— | 193.4-196.2 |
| 754 | —$CH_3$ | —$C_2H_5$ | 4-$CF_3$PhCH═CHCH$_2$— | 143.8-145.1 |
| 755 | —$CH_3$ | —H | 4-$CF_3$OPhCH$_2$OCO— | 198.9-201.2 |
| 756 | —$CH_3$ | —$CH_3$ | 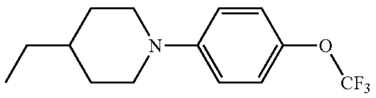 | 172.5-175.2 |
| 757 | —$CH_3$ | 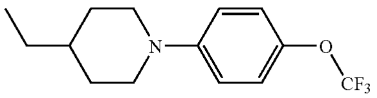 | 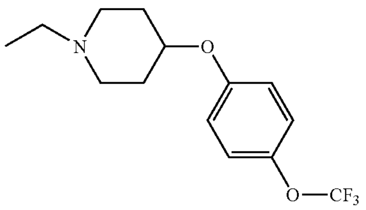 | 150.5-152.2 |

TABLE 87
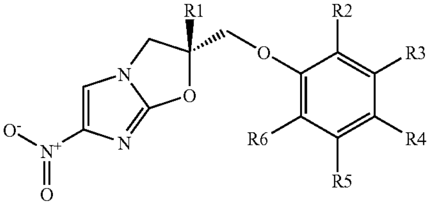
| Example | R1 | R2 | R3 | R4 | R5 | R6 | mp(° C.) |
|---|---|---|---|---|---|---|---|
| 758 | —$CH_3$ | —H | —H | 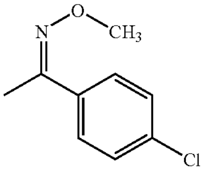 | —H | —H | |
| 759 | —$CH_3$ | —H | —H | 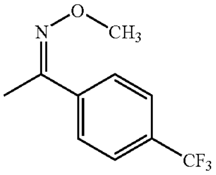 | —H | —H | 151.5-154.4 |
| 760 | —$CH_3$ | —H | —H | 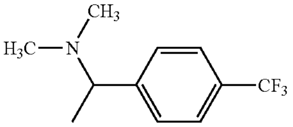 | —H | —H | 188.4-191.0 |
| 761 | —$CH_3$ | —H | —H | 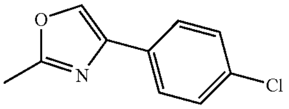 | —H | —H | 248.8-251.5 |
| 762 | —$CH_3$ | —H | —H | 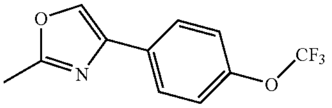 | —H | —H | 218.4-221.0 |
| 763 | —$CH_3$ | —H | —H | 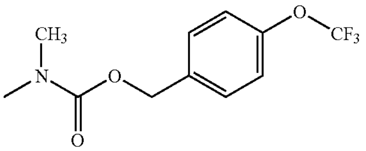 | —H | —H | 145.6-147.8 |
| 764 | —$CH_3$ | —H | —H | 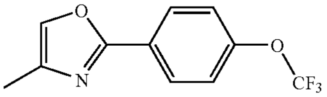 | —H | —H | 241.2-242.5 |
| 765 | —$CH_3$ | —H | —H | 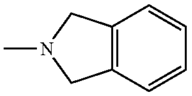 | —H | —H | |
| 766 | —$CH_3$ | —H | —H | 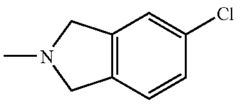 | —H | —H | |
| 767 | —$CH_3$ | —H | —H | 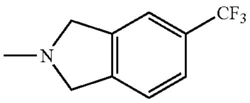 | —H | —H | |

TABLE 88
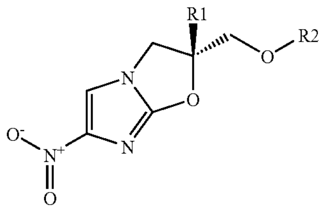
| Example | R1 | R2 | mp(° C.) |
|---|---|---|---|
| 768 | —$CH_3$ | 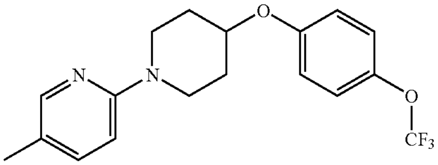 | 185.9-186.7 |
| 769 | —$CH_3$ | 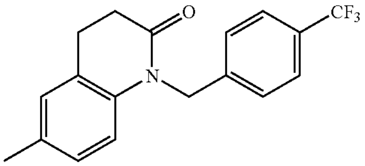 | 191.4-193.9 |
| 770 | —$CH_3$ | 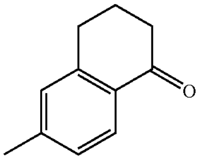 | 172.7-175.3 |
| 771 | —$CH_3$ | 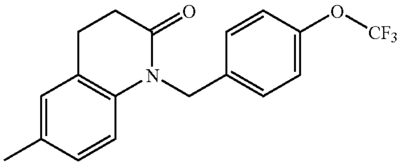 | 200.1-202.7 |
| 772 | —$CH_3$ | 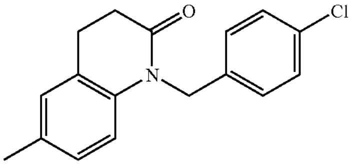 | 179.9-181.9 |
| 773 | —$CH_3$ | 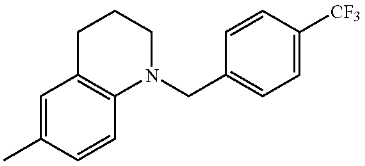 | 175.7-178.5 |
| 774 | —$CH_3$ | 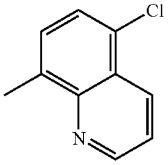 | 210 dec |

TABLE 88-continued
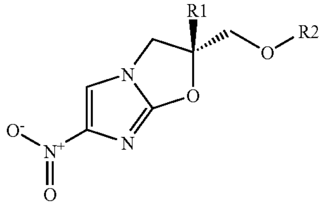
| Example | R1 | R2 | mp(° C.) |
|---|---|---|---|
| 775 | —$CH_3$ | 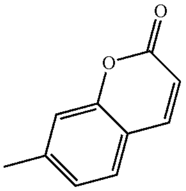 | 241.8-244.1 |
TABLE 89
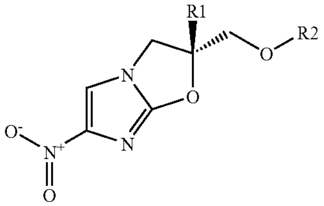
| Example | R1 | R2 | mp(° C.) |
|---|---|---|---|
| 776 | —$CH_3$ | 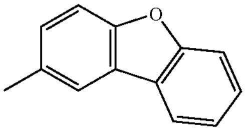 | 193.3-194.5 |
| 777 | —$CH_3$ | 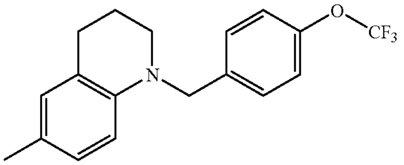 | 182.3-184.4 |
| 778 | —$CH_3$ | 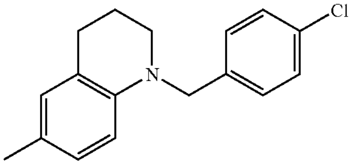 | 175.7-178.0 |
| 779 | —$CH_3$ | 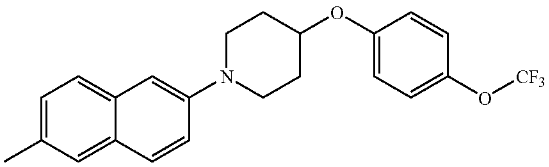 | |

TABLE 89-continued
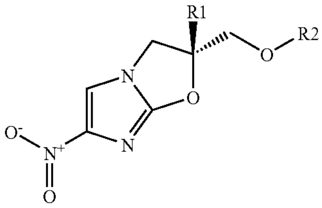
| Example | R1 | R2 | mp(° C.) |
|---|---|---|---|
| 780 | —$CH_3$ | 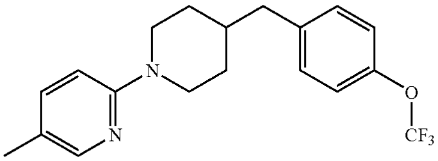 | |
| 781 | —H | 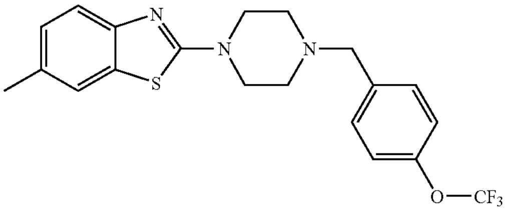 | 195.0-196.7 |
| 782 | —$CH_3$ | 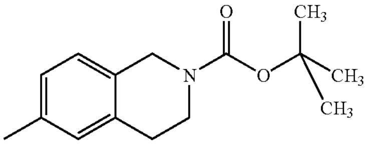 | 160.7-162.4 |
TABLE 90
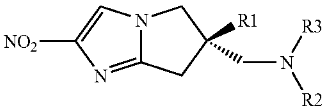
| Example | R1 | R2 | R3 | mp(° C.) |
|---|---|---|---|---|
| 783 | —$CH_3$ | —$CH_3$ | 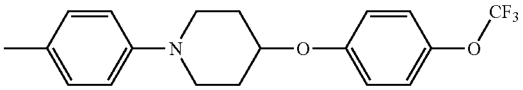 | 130.6-133.7 |
| 784 | —$CH_3$ | —$CH_3$ | 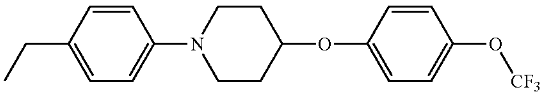 | 146.6-147.6 |
| 785 | —$CH_3$ | —$C_2H_5$ | 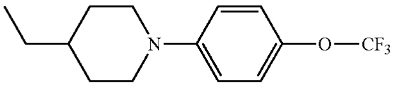 | 135-136 |
| 786 | —$CH_3$ | —$CH_3$ | 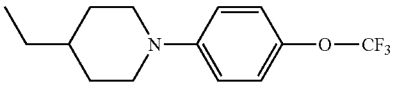 | 134-135.5 |

TABLE 90-continued
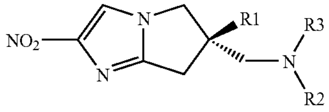
| Example | R1 | R2 | R3 | mp(° C.) |
|---|---|---|---|---|
| 787 | —$CH_3$ | —$CH_3$ | 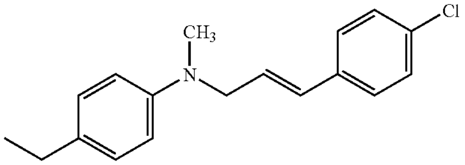 | 146-147 |
| 788 | —$CH_3$ | —$CH_3$ | 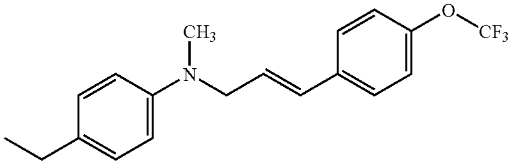 | 141-142 |
TABLE 91
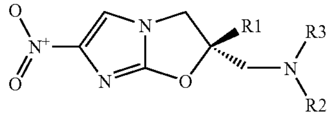
| Example | R1 | R2 | R3 |
|---|---|---|---|
| 789 | —$CH_3$ | —H | 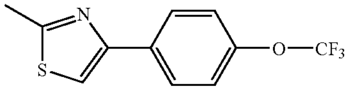 |
| 790 | —H | —H | 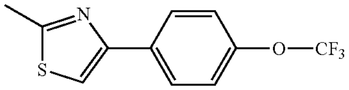 |
| 791 | —$CH_3$ | —H | 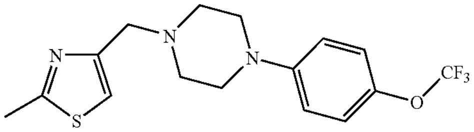 |
| 792 | —H | —H | 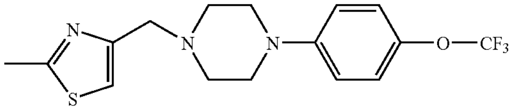 |
| 793 | —$CH_3$ | —H | 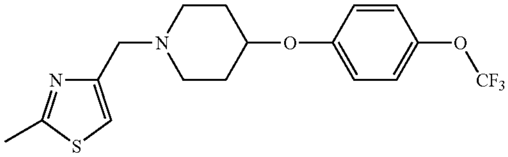 |
| 794 | —H | —H | 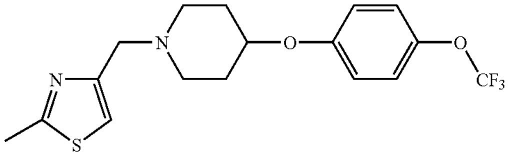 |

TABLE 92
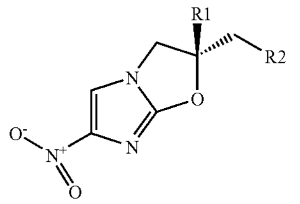
| Example | R1 | R2 | mp(° C.) |
|---|---|---|---|
| 795 | —$CH_3$ | 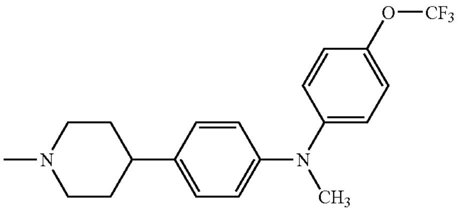 | |
| 796 | —$CH_3$ | 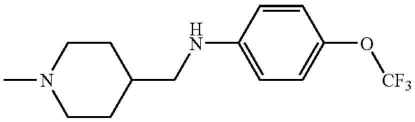 | 158-159 |
| 797 | —$CH_3$ | 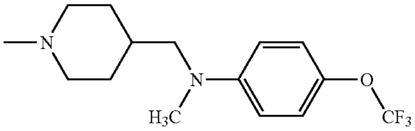 | 87-88 |
| 798 | —$CH_3$ | 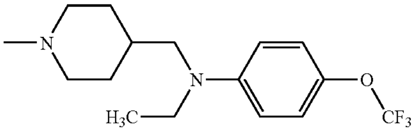 | 132-133 |
| 799 | —$CH_3$ | 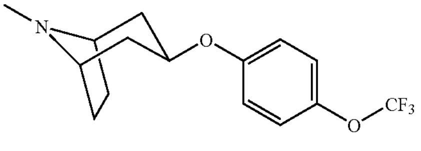 | |
| 800 | —$CH_3$ | 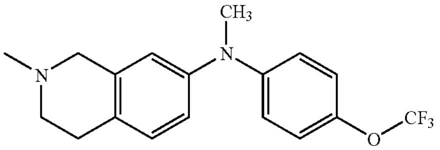 | 80.9-82.6 |
| 801 | —$CH_3$ | 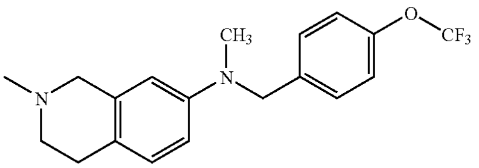 | 124.9-126.0 |
| 802 | —$CH_3$ | 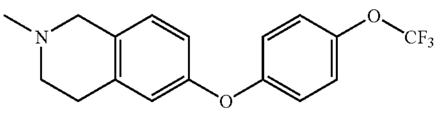 | 123.8-125.3 |

TABLE 92-continued
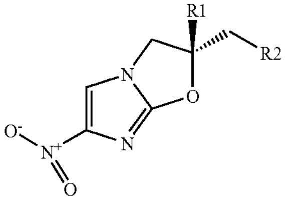
| Example | R1 | R2 | mp(° C.) |
|---|---|---|---|
| 803 | —$CH_3$ | 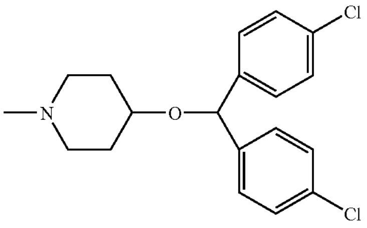 | 172-173.5 (maleate) |
TABLE 93
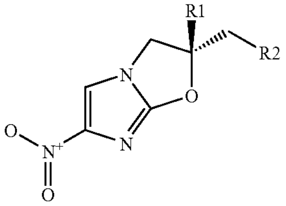
| Example | R1 | R2 | mp(° C.) |
|---|---|---|---|
| 804 | —$CH_3$ | 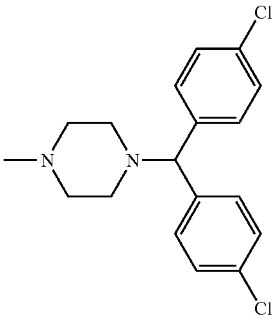 | |
| 805 | —$CH_3$ | 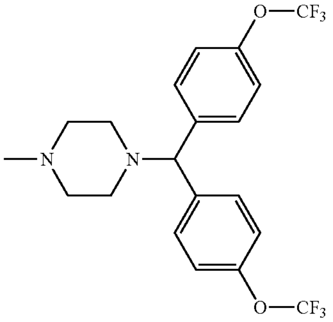 | |
| 806 | —$CH_3$ | 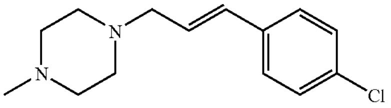 | 191.5-193 |

TABLE 93-continued
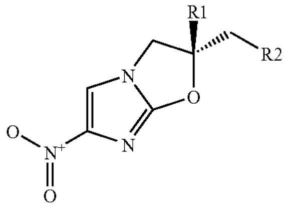
| Example | R1 | R2 | mp(° C.) |
|---|---|---|---|
| 807 | —$CH_3$ | 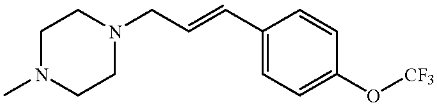 | 141.5-143 |
| 808 | —$CH_3$ | 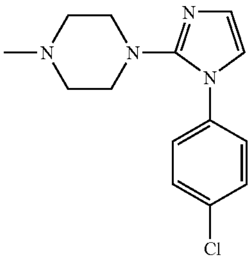 | 217-219 |
TABLE 94
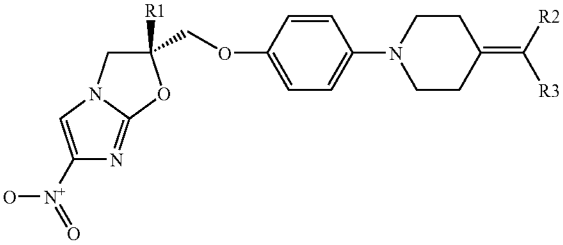
| Example | R1 | R2 | R3 | mp(° C.) |
|---|---|---|---|---|
| 809 | —$CH_3$ | —H | 4-$CF_3$OPh— | 182.0-184.2 |
| 810 | —H | —H | 4-$CF_3$OPh— | 143.9-146.7 |
TABLE 95
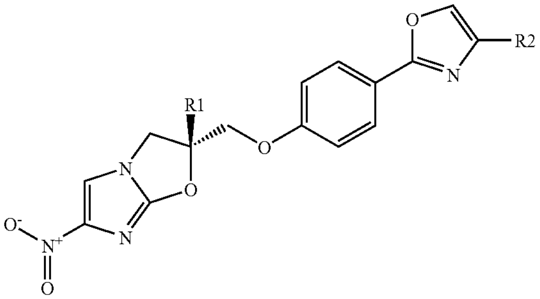
| Example | R1 | R2 | mp(° C.) |
|---|---|---|---|
| 811 | —$CH_3$ | 4-$CF_3$Ph— | 226.0-227.6 |
TABLE 96
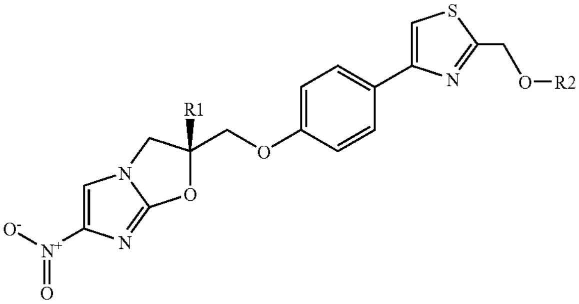
| Example | R1 | R2 | mp(° C.) |
|---|---|---|---|
| 812 | —$CH_3$ | 4-$CF_3$OPh— | 209.0-212.0 |
| 813 | —H | 4-$CF_3$OPh— | 208.0-210.9 |
TABLE 97
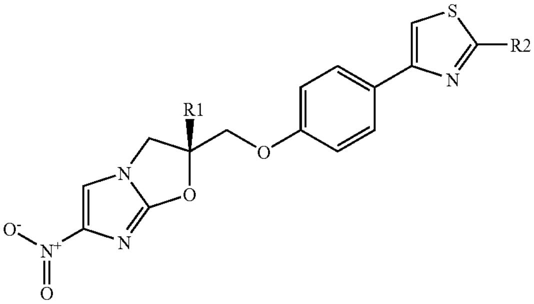
| Example | R1 | R2 | mp(° C.) | |
|---|---|---|---|---|
| 814 | —$CH_3$ | —$C_6H_5$ | 195.0-196.5 | |
| 815 | —H | —$C_6H_5$ | 232 | dec |

TABLE 97-continued
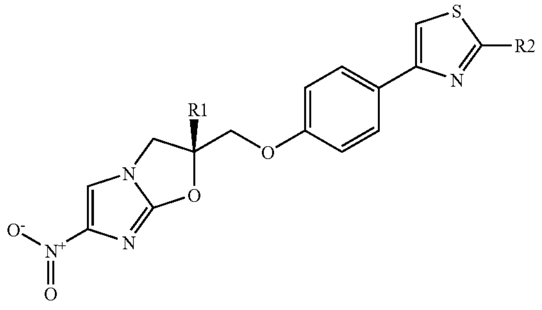
| Example | R1 | R2 | mp(° C.) |
|---|---|---|---|
| 816 | —$CH_3$ | 4-FPh— | 209.0-209.5 |
| 817 | —H | 4-FPh— | 228.0-231.0 |
| 818 | —$CH_3$ | 4-ClPh— | 213.0-216.0 |
| 819 | —H | 4-ClPh— | 243.0-246.0 dec |
| 820 | —$CH_3$ | 4-$CF_3$Ph— | 208.0-209.0 |
| 821 | —H | 4-$CF_3$Ph— | 208.0-211.0 |
| 822 | —$CH_3$ | 4-$CF_3$OPh— | 203.0-204.9 |
| 823 | —H | 4-$CF_3$OPh— | 218.0-219.4 |
| 824 | —$CH_3$ | 3,4-$Cl_2$Ph— | 220.0-221.0 |
TABLE 97-continued
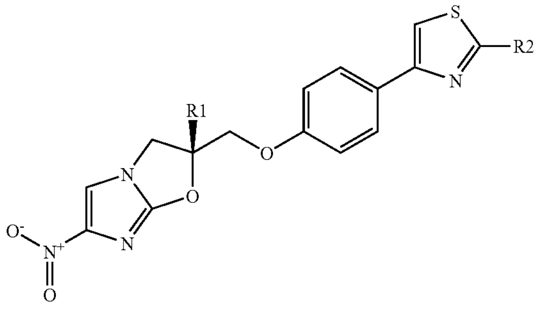
| Example | R1 | R2 | mp(° C.) |
|---|---|---|---|
| 825 | —H | 3,4-$Cl_2$Ph— | 210.5-212.0 |
| 826 | —$CH_3$ | —NHC6H5 | |
| 827 | —H | —NHC6H5 | |
| 828 | —$CH_3$ | 4-ClPh$CH_2$— | 196-197.5 |
| 829 | —H | 4-ClPh$CH_2$— | |
| 830 | —$CH_3$ | 4-$CF_3$OPh$CH_2$— | |
| 831 | —H | 4-$CF_3$OPh$CH_2$— | |
Table 98
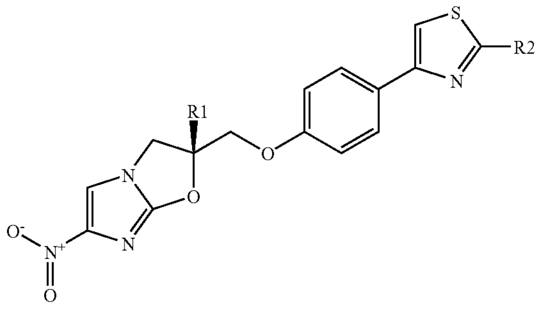
| Example | R1 | R2 | |
|---|---|---|---|
| 832 | —$CH_3$ | 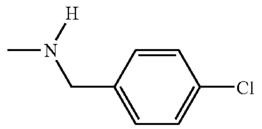 | 183.7-186.6 |
| 833 | —H | 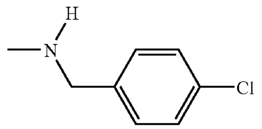 | 207.4-208.4 |
| 834 | —$CH_3$ | 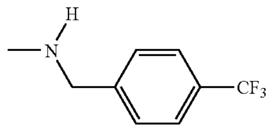 | 186.5-187.5 |
| 835 | —H | 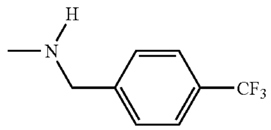 | 212.9-215.2 |

Table 98-continued
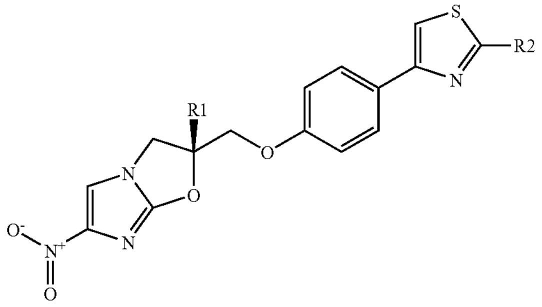
| Example | R1 | R2 | |
|---|---|---|---|
| 836 | —$CH_3$ | 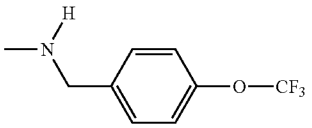 | 169-170 |
| 837 | —H | 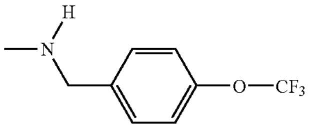 | 217-218.5 |
| 838 | —$CH_3$ | 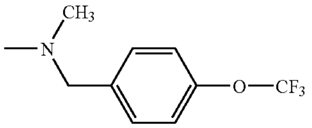 | |
| 839 | —$CH_3$ | 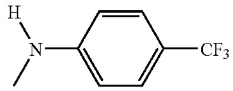 | |
| 840 | —H | 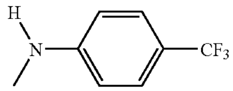 | |
| 841 | —$CH_3$ | 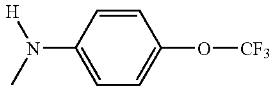 | |
TABLE 99
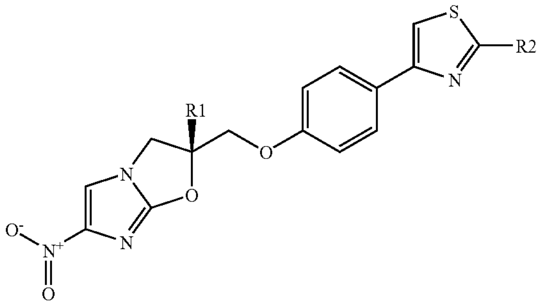
| Example | R1 | R2 |
|---|---|---|
| 842 | —H | 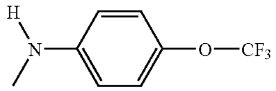 |

TABLE 99-continued
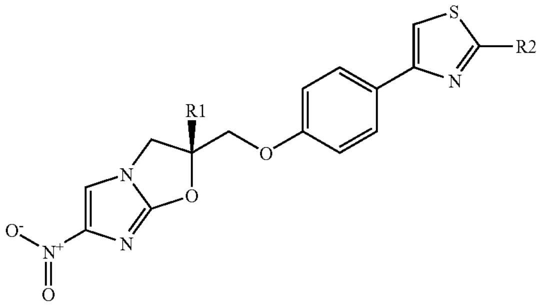
| Example | R1 | R2 | |
|---|---|---|---|
| 843 | —$CH_3$ | 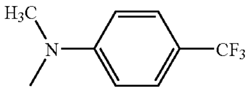 | |
| 844 | —$CH_3$ | 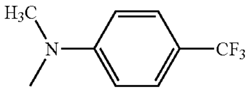 | |
| 845 | —H | 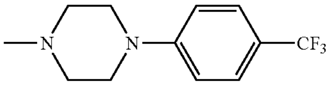 | |
| 846 | —$CH_3$ | 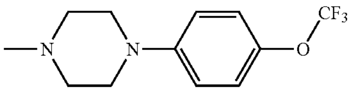 | 221.4-223.6 |
| 847 | —$CH_3$ | 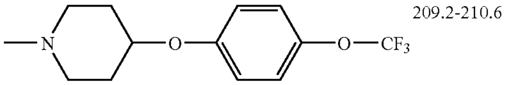 | 209.2-210.6 |
| 848 | —$CH_3$ | 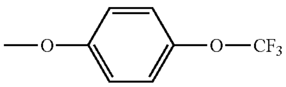 | |
| 849 | —$CH_3$ | 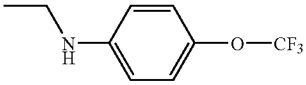 | |
| 850 | —H | 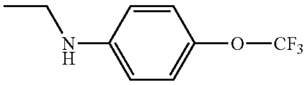 | |
| 851 | —H | 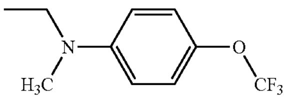 | |

TABLE 100
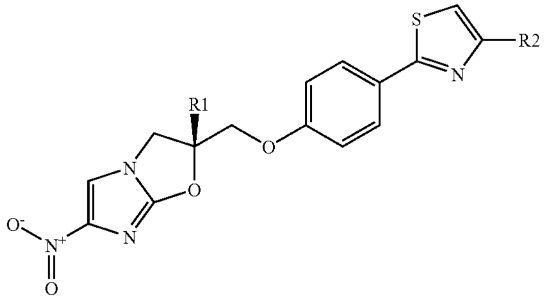
| Example | R1 | R2 | mp(° C.) | |
|---|---|---|---|---|
| 852 | —$CH_3$ | —$C_6H_5$ | 182.0-183.0 | |
| 853 | —H | —$C_6H_5$ | 257.0-259.0 | |
| 854 | —$CH_3$ | 4-ClPh— | 202.3-205.2 | |
| 855 | —H | 4-ClPh— | 231.0-233.5 | dec |
| 856 | —$CH_3$ | 4-FPh— | 230.5-233.0 | |
| 857 | —H | 4-FPh— | 215.0-217.5 | |
| 858 | —$CH_3$ | 4-$CF_3$Ph— | 229.0-232.0 | |
| 859 | —H | 4-$CF_3$Ph— | 179.0-182.0 | |
TABLE 100-continued
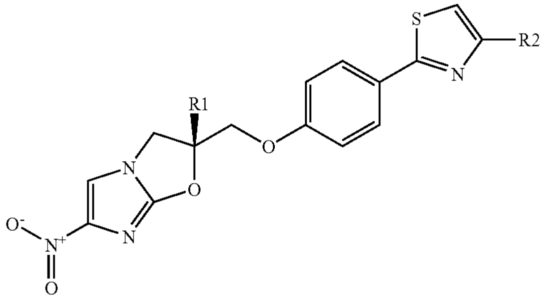
| Example | R1 | R2 | mp(° C.) |
|---|---|---|---|
| 860 | —$CH_3$ | 4-$CF_3$OPh— | 274.0-176.0 |
| 861 | —H | 4-$CF_3$OPh— | 185-188 |
| 862 | —$CH_3$ | 3,4-$Cl_2$Ph— | 206-208.5 |
| 863 | —H | 3,4-$Cl_2$Ph— | 190-193 |
| 864 | —$CH_3$ | 4-$CF_3$OPhO$CH_2$— | 201.3-202.2 |
| 865 | —H | 4-$CF_3$OPhO$CH_2$— | 191.5-194.5 |
TABLE 101
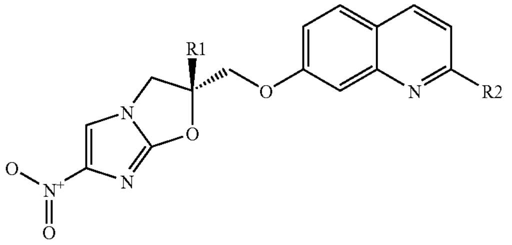
| Example | | R2 | mp(° C.) |
|---|---|---|---|
| 866 | —$CH_3$ | 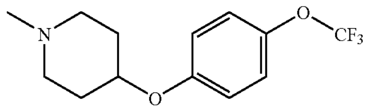 | 182.6-184.8 |
| 867 | —$CH_3$ | 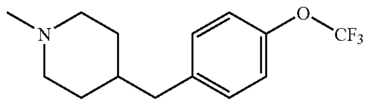 | 109.8-112.7 |
TABLE 102
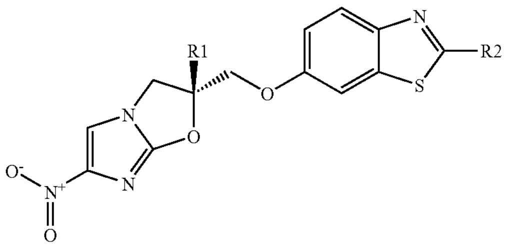
| Example | R1 | R2 | mp(° C.) |
|---|---|---|---|
| 868 | —$CH_3$ | 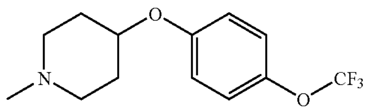 | 223.8-225.6 |

TABLE 102-continued
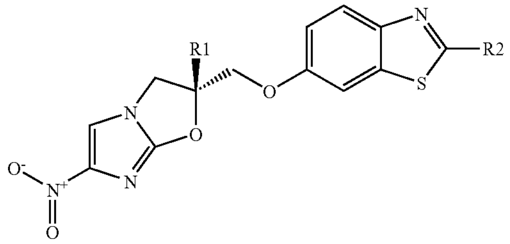
| Example | R1 | R2 | mp(° C.) |
|---|---|---|---|
| 869 | —$CH_3$ | 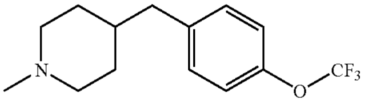 | 168.3-171.2 |
| 870 | —$CH_3$ | 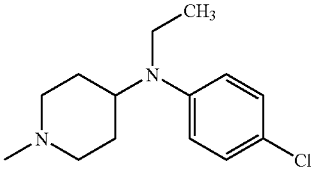 | 119.9-122.0 |
TABLE 103
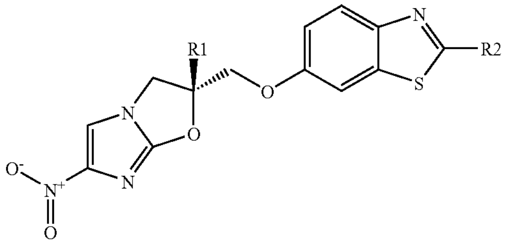
| Example | R1 | R2 | mp(° C.) |
|---|---|---|---|
| 871 | —$CH_3$ | —$C_6H_5$ | 249.3-250.0 |
| 872 | —$CH_3$ | 4-ClPh— | 257.8-258.2 |
| 873 | —H | —$C_6H_5$ | 249.2-252.1 dec |
| 874 | —H | 4-ClPh— | |
TABLE 104
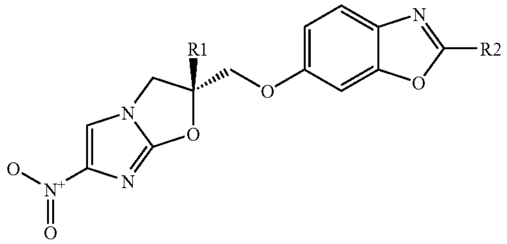
| Example | R1 | R2 |
|---|---|---|
| 875 | —$CH_3$ | 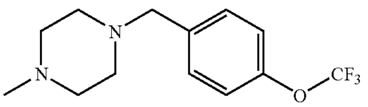 |
TABLE 105
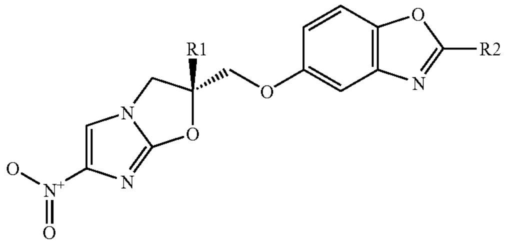
| Example | R1 | R2 | mp(° C.) |
|---|---|---|---|
| 876 | —$CH_3$ | —$C_6H_5$ | 221.2-222.1 |
| 877 | —$CH_3$ | 4-ClPh— | 229.8-232.1 |
| 878 | —H | —$C_6H_5$ | 246.2-247.0 |
| 879 | —H | 4-ClPh— | 260.4-260.9 |
TABLE 106
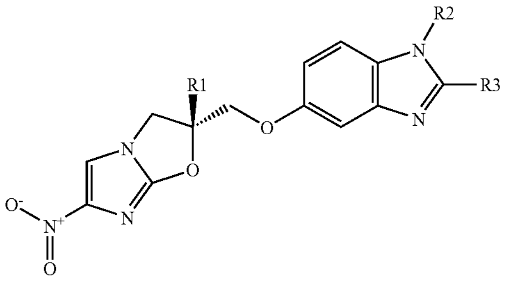
| Example | R1 | R2 | R3 | mp(° C.) |
|---|---|---|---|---|
| 880 | —$CH_3$ | —H | —$C_6H_5$ | 144.0-146.3 |
| 881 | —$CH_3$ | —H | 4-ClPh— | 191.0-193.9 dec |
| 882 | —H | —H | —$C_6H_5$ | |
| 883 | —H | —H | 4-ClPh— | 161.0-165.0 dec |
| 884 | —$CH_3$ | —$CH_3$ | —$C_6H_5$ | 121.0-126.1 dec |
| 885 | —$CH_3$ | —$CH_3$ | 4-ClPh— | 215.0-217.5 dec |

TABLE 106-continued
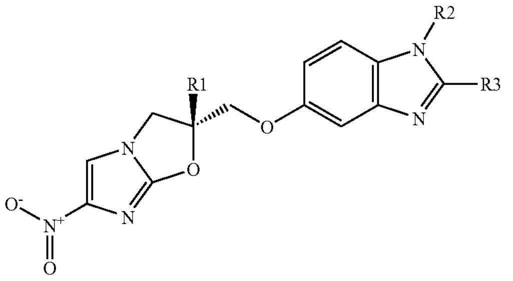
| Example | R1 | R2 | R3 | mp(° C.) |
|---|---|---|---|---|
| 886 | —H | —$CH_3$ | —$C_6H_5$ | 218.0-219.1 dec |
| 887 | —H | —$CH_3$ | 4-ClPh— | 183.0-186.6 dec |
Table 107
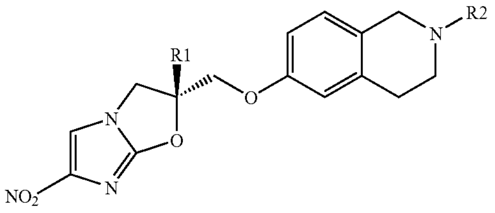
| Example | R1 | R2 | mp(° C.) |
|---|---|---|---|
| 888 | —$CH_3$ | 4-ClPh$CH_2$— | 180.9-183.1 |
| 889 | —$CH_3$ | 4-$CF_3$Oph$CH_2$— | 151.1-154.1 |
TABLE 108
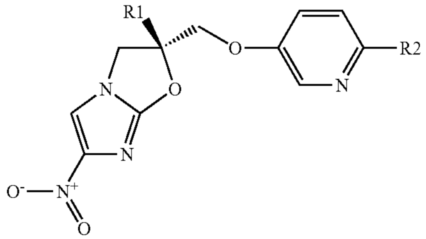
| Example | R1 | R2 | mp (° C.) |
|---|---|---|---|
| 890 | —$CH_3$ | 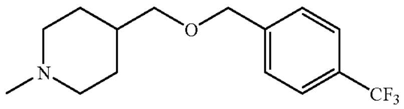 | 166.7-169.2 |
| 891 | —H | 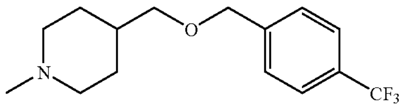 | 139.8-141.6 |
| 892 | —$CH_3$ | 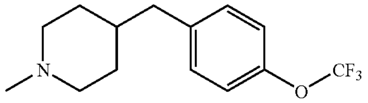 | |
| 893 | —H | 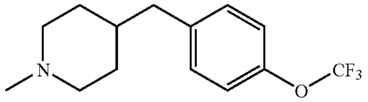 | 174.2-176.8 |
| 894 | —$CH_3$ | 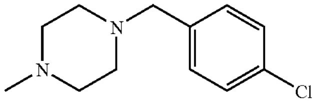 | 197.0-199.3 |
| 895 | —H | 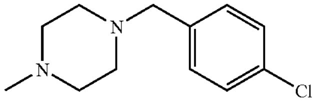 | 177.9-179.3 |
| 896 | —$CH_3$ | 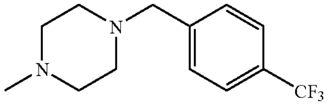 | 199.6-201.2 |

TABLE 108-continued
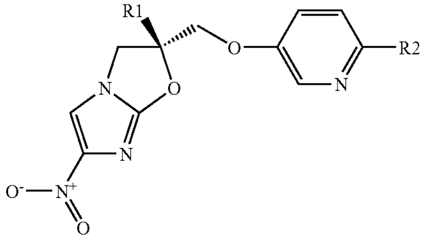
| Example | R1 | R2 | mp (° C.) |
|---|---|---|---|
| 897 | —H | 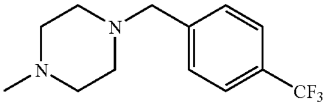 | 169.6-173.2 |
| 898 | —$CH_3$ | 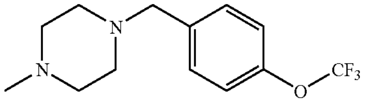 | 210.9-212.0 |
| 899 | —H | 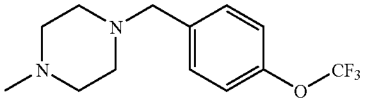 | 188.0-190.0 |
TABLE 109
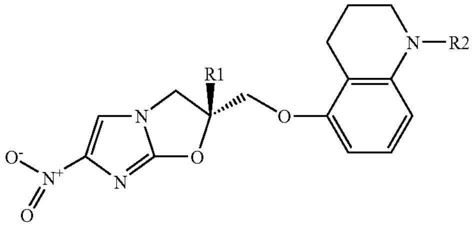
| Example | R1 | R2 | mp (° C.) |
|---|---|---|---|
| 900 | —$CH_3$ | 4-ClPh— | 238-239 |
| 901 | —$CH_3$ | 4-$CF_3$OPh— | 199-200 |
| 902 | —$CH_3$ | 4-ClPh$CH_2$— | 199-200 |
| 903 | —$CH_3$ | 4-$CF_3$OPh$CH_2$— | 172-173 |
TABLE 110
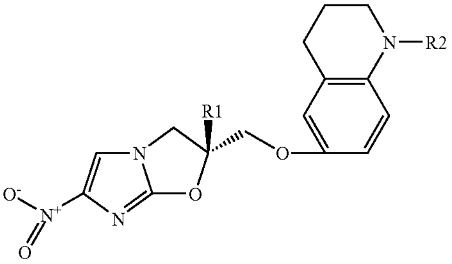
| Example | R1 | R2 | mp (° C.) | |
|---|---|---|---|---|
| 904 | —$CH_3$ | 4-ClPh— | 175.5-176.5 | |
| 905 | —$CH_3$ | 4-$CF_3$OPh— | 122.5-124 | dec |
TABLE 111
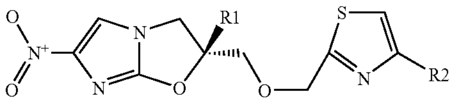
| Example | R1 | R2 |
|---|---|---|
| 906 | —$CH_3$ | 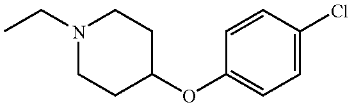 |
| 907 | —H | 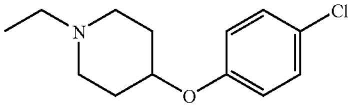 |
| 908 | —$CH_3$ | 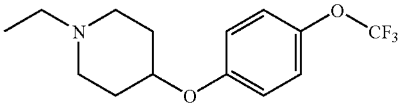 |
| 909 | —H | 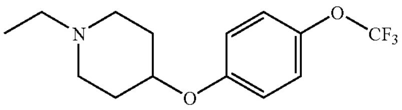 |

TABLE 111-continued
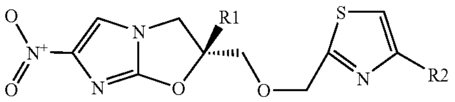
| Example | R1 | R2 |
|---|---|---|
| 910 | —$CH_3$ | 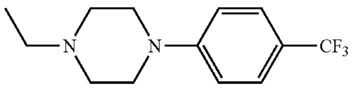 |
| 911 | —H | 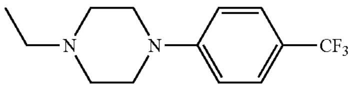 |
| 912 | —$CH_3$ | 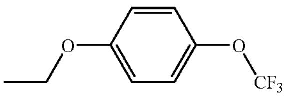 |
| 913 | —H | 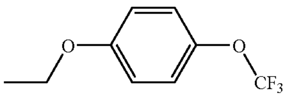 |
TABLE 111-continued
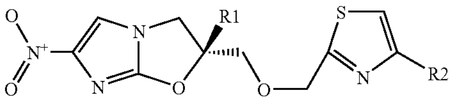
| Example | R1 | R2 |
|---|---|---|
| 914 | —$CH_3$ | 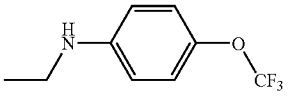 |
| 915 | —H | 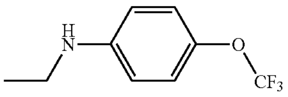 |
| 916 | —$CH_3$ | 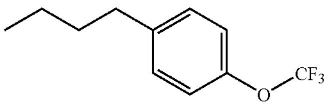 |
| 917 | —H | 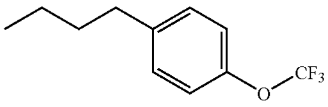 |
TABLE 112
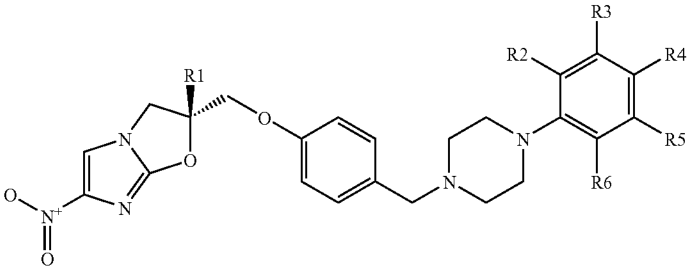
| Example | R1 | R2 | R3 | R4 | R5 | R6 | MS (M + 1) |
|---|---|---|---|---|---|---|---|
| 918 | —$CH_3$ | —H | —H | —$C_6H_5$ | —H | —H | 526 |
| 919 | —$CH_3$ | —H | —H | $(CH_3)_3COCO$— | | | |
| 920 | —$CH_3$ | —H | —H | —$CO_2C_2H_5$ | —H | —H | 522 |
| 921 | —$CH_3$ | —$C_6H_5$ | —H | —H | —H | —H | 526 |
| 922 | —$CH_3$ | —H | —H | —OH | —H | —H | |
| 923 | —$CH_3$ | —H | —H | 4-ClPhO— | | | 576 |

TABLE 113
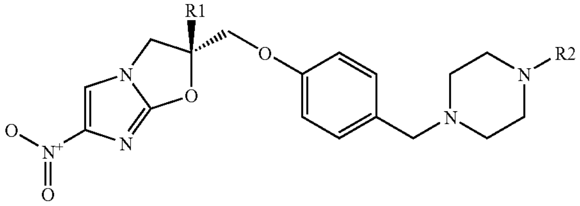
| Example | R1 | R2 | MS (M + 1) |
|---|---|---|---|
| 924 | —$CH_3$ | 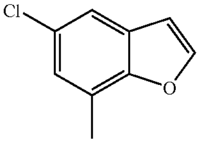 | 524 |
| 925 | —$CH_3$ | 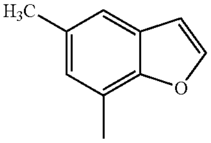 | 504 |
| 926 | —$CH_3$ | 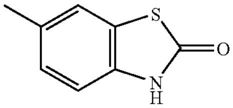 | 523 |
| 927 | —$CH_3$ | 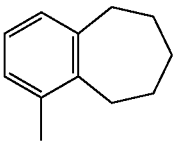 | |
| 928 | —$CH_3$ | 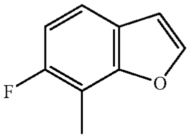 | 508 |
| 929 | —$CH_3$ | 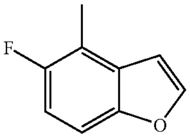 | |
| 930 | —$CH_3$ | 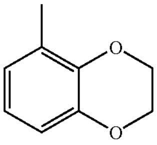 | |
| 931 | —$CH_3$ | 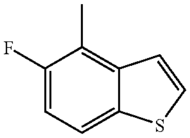 | |
| 932 | —$CH_3$ | 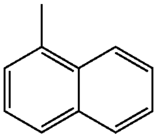 | 500 |
TABLE 114
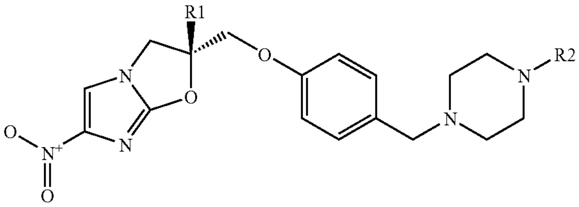
| Example | R1 | R2 | MS (M + 1) |
|---|---|---|---|
| 933 | —$CH_3$ | 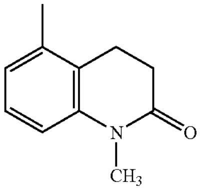 | 533 |
| 934 | —$CH_3$ | 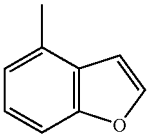 | 490 |
| 935 | —$CH_3$ | 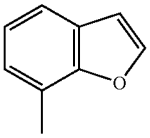 | 490 |
| 936 | —$CH_3$ | 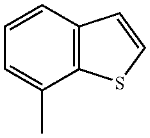 | 506 |
| 937 | —$CH_3$ | 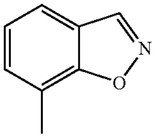 | 491 |
| 938 | —$CH_3$ | 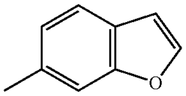 | 490 |
| 939 | —$CH_3$ | 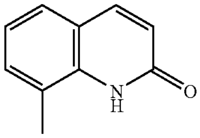 | 517 |
| 940 | —$CH_3$ | 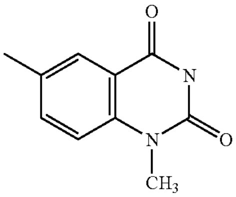 | 548 |
| 941 | —$CH_3$ | 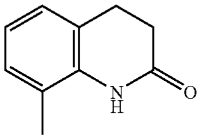 | 519 |

TABLE 115

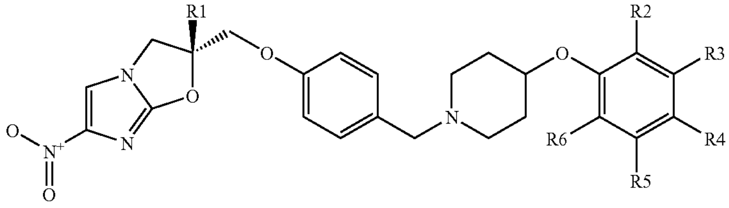

| Example | R1 | R2 | R3 | R4 | R5 | R6 | MS (M + 1) |
|---|---|---|---|---|---|---|---|
| 942 | —$CH_3$ | —H | —H | —$OCH_2C_6H_5$ | —H | —H | 571 |
| 943 | —$CH_3$ | —H | —H | —cyclo-$C_6H_{11}$ | —H | —H | 547 |
| 944 | —$CH_3$ | —H | —H | —$OC_8H_{17}$ | —H | —H | 593 |
| 945 | —$CH_3$ | —H | —H | —cyclo-$C_5H_9$ | —H | —H | 533 |
| 946 | —$CH_3$ | —H | —H | —H | —$OC_6H_5$ | —H | 557 |

TABLE 116

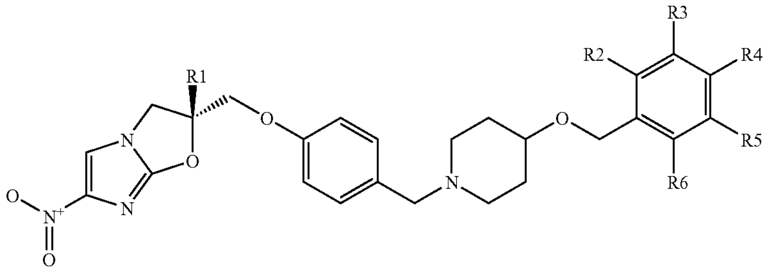

| Example | R1 | R2 | R3 | R4 | R5 | R6 | MS (M + 1) |
|---|---|---|---|---|---|---|---|
| 947 | —$CH_3$ | —H | —H | —Cl | —H | —H | 513 |
| 948 | —$CH_3$ | —Cl | —H | —H | —H | —H | 513 |
| 949 | —$CH_3$ | —H | —H | —$CH(CH_3)_2$ | —H | —H | 521 |
| 950 | —$CH_3$ | —H | —$CF_3$ | —H | —H | —H | 547 |
| 951 | —$CH_3$ | —H | —H | —$C(CH_3)_3$ | —H | —H | 535 |
| 952 | —$CH_3$ | —H | —H | —$CF_3$ | —H | —H | 547 |
| 953 | —$CH_3$ | —H | —H | —$CH_3$ | —H | —H | 493 |
| 954 | —$CH_3$ | —H | —H | —CN | —H | —H | 504 |
| 955 | —$CH_3$ | —H | —H | —$C_6H_5$ | —H | —H | 555 |
| 956 | —$CH_3$ | —$OCF_3$ | —H | —H | —H | —H | 563 |
| 957 | —$CH_3$ | —H | —$CH_3$ | —H | —H | —H | 493 |
| 958 | —$CH_3$ | —H | —H | —$OCF_3$ | —H | —H | 563 |
| 959 | —$CH_3$ | —H | —Cl | —H | —H | —H | 513 |
| 960 | —$CH_3$ | —H | —H | —F | —H | —H | 497 |
| 961 | —$CH_3$ | —H | —$OCH_3$ | —H | —H | —H | 509 |
| 962 | —$CH_3$ | —H | —Cl | —Cl | —H | —H | 547 |
| 963 | —$CH_3$ | —$CF_3$ | —H | —H | —H | —H | 547 |
| 964 | —$CH_3$ | —H | —H | —$CO_2CH_3$ | —H | —H | 537 |
| 965 | —$CH_3$ | —H | —$OC_6H_5$ | —H | —H | —H | 571 |
| 966 | —$CH_3$ | —H | —H | —$SCH_3$ | —H | —H | 525 |
| 967 | —$CH_3$ | —H | —H | —H | —H | —H | 479 |
| 968 | —$CH_3$ | —H | —$OCF_3$ | —H | —H | —H | 563 |
| 969 | —$CH_3$ | —Cl | —H | —F | —H | —H | 531 |
| 970 | —$CH_3$ | —H | —Cl | —H | —Cl | —H | 547 |
| 971 | —$CH_3$ | —Cl | —Cl | —H | —H | —H | 547 |
| 972 | —$CH_3$ | —H | —$CH_3$ | —H | —$CH_3$ | —H | 507 |
| 973 | —$CH_3$ | —Cl | —H | —H | —Cl | —H | 547 |
| 974 | —$CH_3$ | —H | —H | —$C_2H_5$ | —H | —H | 507 |

TABLE 117
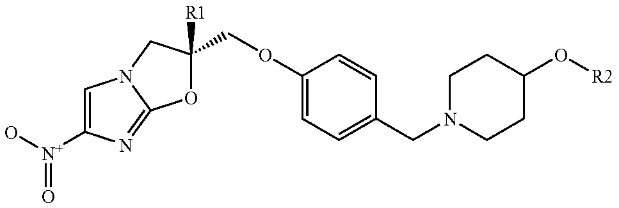
| Example | R1 | R2 | MS (M + 1) |
|---|---|---|---|
| 975 | —$CH_3$ | 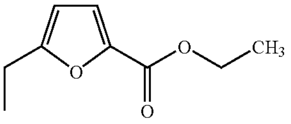 | 541 |
| 976 | —$CH_3$ | 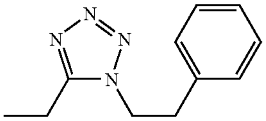 | 575 |
| 977 | —$CH_3$ | 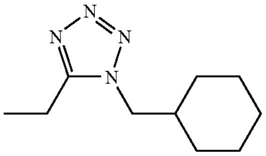 | 567 |
| 978 | —$CH_3$ | 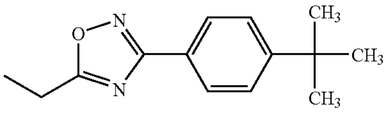 | 603 |
| 979 | —$CH_3$ | 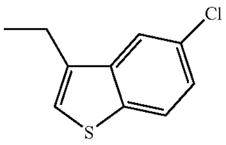 | 569 |
| 980 | —$CH_3$ | 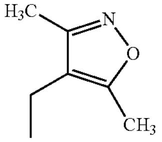 | |
| 981 | —$CH_3$ | 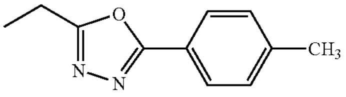 | 561 |
| 982 | —$CH_3$ | —$(CH_2)_3C_6H_5$ | 507 |
| 983 | —$CH_3$ | 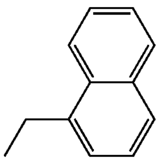 | 529 |
| 984 | —$CH_3$ | 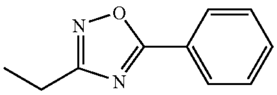 | 547 |

TABLE 117-continued
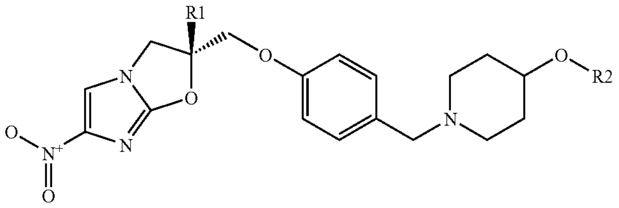
| Example | R1 | R2 | MS (M + 1) |
|---|---|---|---|
| 985 | —$CH_3$ | 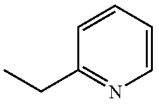 | |
TABLE 118
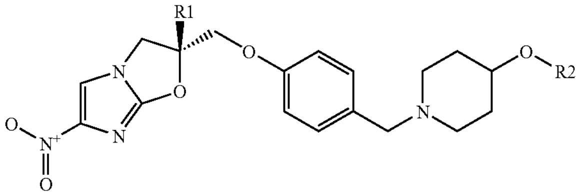
| Example | R1 | R2 | MS (M + 1) |
|---|---|---|---|
| 986 | —$CH_3$ | 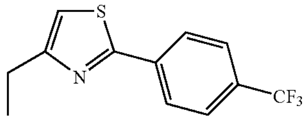 | 630 |
| 987 | —$CH_3$ | 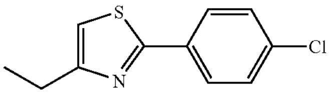 | 596 |
| 988 | —$CH_3$ | 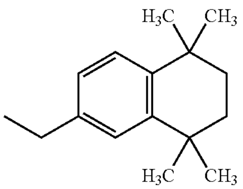 | 589 |
| 989 | —$CH_3$ | 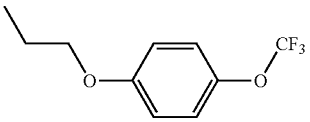 | 593 |
| 990 | —$CH_3$ | 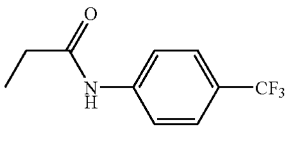 | 590 |
TABLE 118-continued
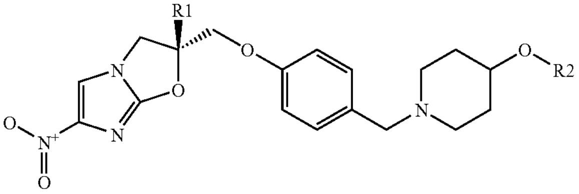
| Example | R1 | R2 | MS (M + 1) |
|---|---|---|---|
| 991 | —$CH_3$ | 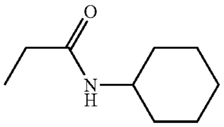 | |
| 992 | —$CH_3$ | 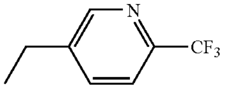 | 548 |
| 993 | —$CH_3$ | 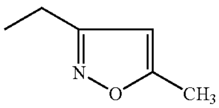 | |
| 994 | —$CH_3$ | 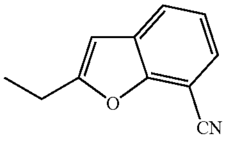 | 544 |

TABLE 119

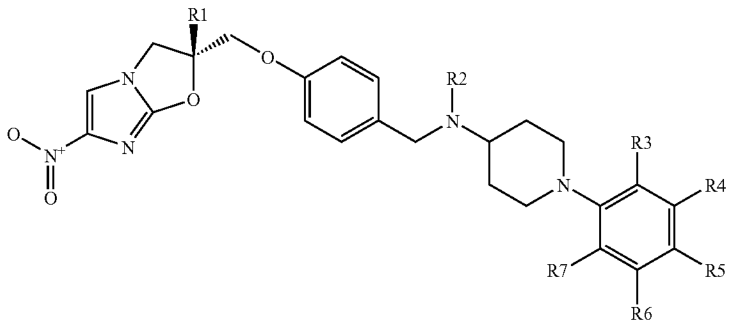

| Example | R1 | R2 | R3 | R4 | R5 | R6 | R7 | MS (M + 1) |
|---|---|---|---|---|---|---|---|---|
| 995 | —$CH_3$ | —$CH_3$ | —H | —H | —$OCF_3$ | —H | —H | 562 |
| 996 | —$CH_3$ | —$CH_3$ | —H | —H | —$CF_3$ | —H | —H | 546 |
| 997 | —$CH_3$ | —$CH_3$ | —H | —H | —CN | —H | —H | 503 |
| 998 | —$CH_3$ | —$CH_3$ | —H | —H | —$NO_2$ | —H | —H | 523 |
| 999 | —$CH_3$ | —$CH_3$ | —H | —H | —$N(CH_3)_2$ | —H | —H | 521 |
| 1000 | —$CH_3$ | —$CH_3$ | —$OCF_3$ | —H | —H | —H | —H | 562 |
| 1001 | —$CH_3$ | —$CH_3$ | —H | —$OCF_3$ | —H | —H | —H | 562 |
| 1002 | —$CH_3$ | —$CH_3$ | —H | —H | —$SO_2N(CH_3)_2$ | —H | —H | 585 |
| 1003 | —$CH_3$ | —$CH_3$ | —H | —H | —$CO_2C_2H_5$ | —H | —H | 550 |
| 1004 | —$CH_3$ | —$CH_3$ | —H | —$CF_3$ | —H | —H | —H | 546 |
| 1005 | —$CH_3$ | —$CH_3$ | —H | —$CF_3$ | —Cl | —H | —H | 580 |
| 1006 | —$CH_3$ | —$CH_3$ | —H | —H | —$CH_3$ | —H | —H | 492 |
| 1007 | —$CH_3$ | —$CH_3$ | —H | —H | —$C(CH_3)_3$ | —H | —H | 534 |
| 1008 | —$CH_3$ | —$CH_3$ | —$CF_3$ | —H | —H | —H | —H | 546 |
| 1009 | —$CH_3$ | —$CH_3$ | —Cl | —Cl | —H | —H | —H | 546 |
| 1010 | —$CH_3$ | —$CH_3$ | —H | —H | —$SCH_3$ | —H | —H | 524 |
| 1011 | —$CH_3$ | —$CH_3$ | —H | —H | —$CH(CH_3)_2$ | —H | —H | 520 |
| 1012 | —$CH_3$ | —$CH_3$ | —H | —H | —$OC_6H_5$ | —H | —H | 570 |
| 1013 | —$CH_3$ | —$CH_3$ | —H | —H | —$OC_6H_{13}$ | —H | —H | 578 |
| 1014 | —$CH_3$ | —$CH_3$ | —H | —H | —$C_6H_{13}$ | —H | —H | 562 |
| 1015 | —$CH_3$ | —$CH_3$ | —H | —H | —$OCH_2C_6H_5$ | —H | —H | 584 |
| 1016 | —$CH_3$ | —$CH_3$ | —Cl | —H | —Cl | —H | —H | 546 |
| 1017 | —$CH_3$ | —$CH_3$ | —H | —Cl | —Cl | —H | —Cl | 580 |
| 1018 | —$CH_3$ | —$CH_3$ | —Cl | —H | —H | —H | —H | 512 |
| 1019 | —$CH_3$ | —$CH_3$ | —H | —H | —$OCH_3$ | —H | —H | 508 |
| 1020 | —$CH_3$ | —$CH_3$ | —H | —Cl | —Cl | —H | —H | 546 |
| 1021 | —$CH_3$ | —$CH_3$ | —H | —H | —$OCHF_2$ | —H | —H | 544 |
| 1022 | —$CH_3$ | —$CH_3$ | —H | —F | —Cl | —H | —H | 530 |
| 1023 | —$CH_3$ | —$CH_3$ | —H | —H | 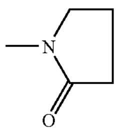 | —H | —H | 561 |
| 1024 | —$CH_3$ | —$CH_3$ | —H | —$CH_3$ | —Cl | —H | —H | 526 |
| 1025 | —$CH_3$ | —$CH_3$ | —H | —H | 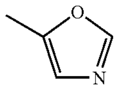 | —H | —H | 545 |

TABLE 120
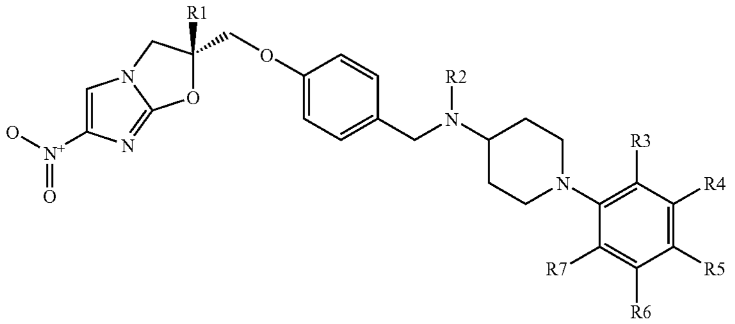
| Example | R1 | R2 | R3 | R4 | R5 | R6 | R7 | MS (M + 1) |
|---|---|---|---|---|---|---|---|---|
| 1026 | —$CH_3$ | —$CH_3$ | —H | —H | 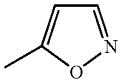 | —H | —H | |
| 1027 | —$CH_3$ | —$CH_3$ | —H | —H | 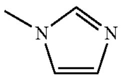 | —H | —H | |
| 1028 | —$CH_3$ | —$CH_3$ | —H | —H | —$CH_2C_6H_5$ | —H | —H | 568 |
| 1029 | —$CH_3$ | —$CH_3$ | —H | —H | 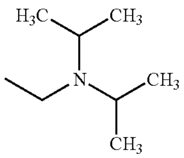 | —H | —H | 591 |
| 1030 | —$CH_3$ | —$CH_3$ | —H | —H | 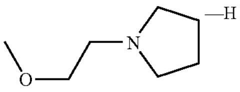 | —H | —H | |
| 1031 | —$CH_3$ | —$CH_3$ | —H | —Cl | —H | —H | —H | 512 |
| 1032 | —$CH_3$ | —$CH_3$ | —H | —H | —$C_6H_5$ | —H | —H | 554 |
TABLE 121
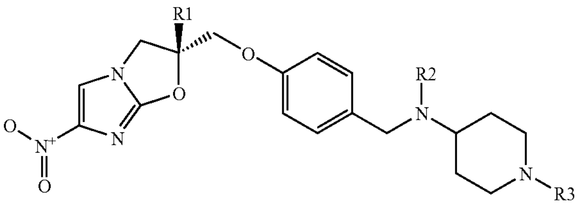
| Example | R1 | R2 | R3 | MS (M + 1) |
|---|---|---|---|---|
| 1033 | —$CH_3$ | —$CH_3$ | 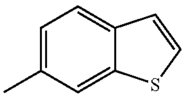 | 534 |
| 1034 | —$CH_3$ | —$CH_3$ | 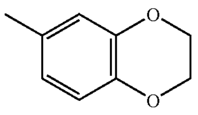 | 536 |
TABLE 121-continued
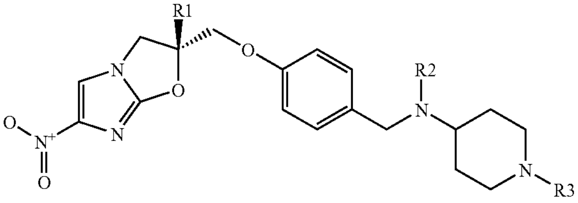
| Example | R1 | R2 | R3 | MS (M + 1) |
|---|---|---|---|---|
| 1035 | —$CH_3$ | —$CH_3$ | 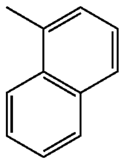 | 528 |
| 1036 | —$CH_3$ | —$CH_3$ | 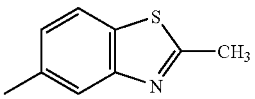 | 549 |

TABLE 121-continued

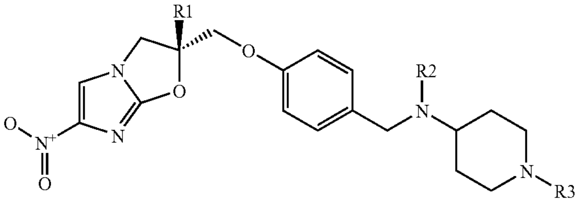

| Example | R1 | R2 | R3 | MS (M + 1) |
|---|---|---|---|---|
| 1037 | —$CH_3$ | —$CH_3$ | 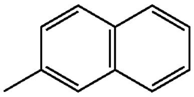 | 528 |
| 1038 | —$CH_3$ | —$CH_3$ | 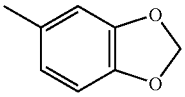 | 522 |
| 1039 | —$CH_3$ | —$CH_3$ | 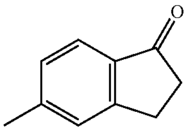 | 532 |

TABLE 121-continued

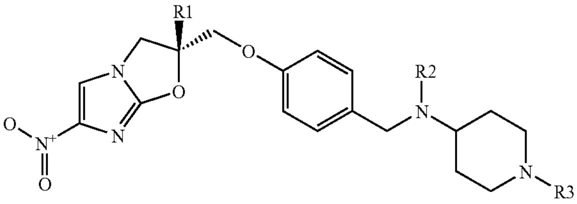

| Example | R1 | R2 | R3 | MS (M + 1) |
|---|---|---|---|---|
| 1040 | —$CH_3$ | —$CH_3$ | 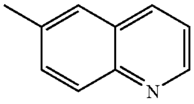 | 529 |
| 1041 | —$CH_3$ | —$CH_3$ | 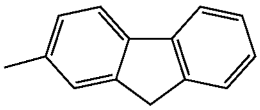 | 566 |

TABLE 122

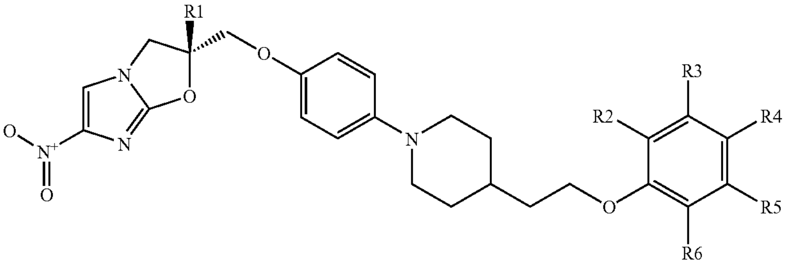

| Example | R1 | R2 | R3 | R4 | R5 | R6 | MS (M + 1) |
|---|---|---|---|---|---|---|---|
| 1042 | —$CH_3$ | —H | —H | —H | —$OCH_3$ | —H | 509 |
| 1043 | —$CH_3$ | —H | —H | —$OCH_3$ | —H | —H | 509 |
| 1044 | —$CH_3$ | —H | —$OCH_3$ | —$OCH_3$ | —H | —H | 539 |
| 1045 | —$CH_3$ | —H | —H | —H | —H | —H | 479 |
| 1046 | —$CH_3$ | —Cl | —H | —H | —H | —H | 513 |
| 1047 | —$CH_3$ | —H | —Cl | —H | —H | —H | 513 |
| 1048 | —$CH_3$ | —H | —H | —Cl | —H | —H | 513 |
| 1049 | —$CH_3$ | —H | —H | —Cl | —Cl | —H | 547 |
| 1050 | —$CH_3$ | —H | —H | —$CH_3$ | —H | —H | 493 |
| 1051 | —$CH_3$ | —H | —H | —$CH_3$ | —$CH_3$ | —H | 507 |
| 1052 | —$CH_3$ | —H | —H | —F | —H | —H | 497 |
| 1053 | —$CH_3$ | —H | —H | —$CO_2C_2H_5$ | —H | —H | 551 |
| 1054 | —$CH_3$ | —H | —H | —CN | —H | —H | 504 |
| 1055 | —$CH_3$ | —$CF_3$ | —H | —H | —H | —H | 547 |
| 1056 | —$CH_3$ | —H | —$CF_3$ | —H | —H | —H | 547 |
| 1057 | —$CH_3$ | —H | —H | —$CF_3$ | —H | —H | 547 |
| 1058 | —$CH_3$ | —$OCF_3$ | —H | —H | —H | —H | 563 |
| 1059 | —$CH_3$ | —H | —$OCF_3$ | —H | —H | —H | |
| 1060 | —$CH_3$ | —H | —H | —$OCF_3$ | —H | —H | |
| 1061 | —$CH_3$ | —H | —H | 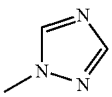 | —H | —H | 546 |
| 1062 | —$CH_3$ | 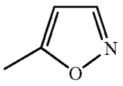 | —H | —H | —H | —H | 546 |

TABLE 122-continued

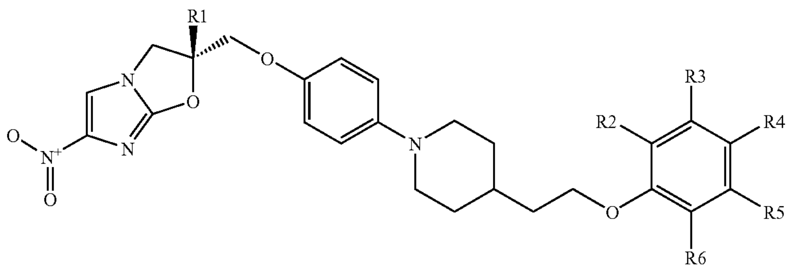

| Example | R1 | R2 | R3 | R4 | R5 | R6 | MS (M + 1) |
|---|---|---|---|---|---|---|---|
| 1063 | —$CH_3$ | —$OCH(CH_3)_2$ | —H | —H | —H | —H | 537 |
| 1064 | —$CH_3$ | —F | —H | —H | —$CH_3$ | —H | 511 |
| 1065 | —$CH_3$ | —H | —F | —Cl | —H | —H | |
| 1066 | —$CH_3$ | —F | —H | —$NO_2$ | —H | —H | 542 |
| 1067 | —$CH_3$ | —$OCH_3$ | —H | —$CH_2CH{=}CH_2$ | —H | —H | |
| 1068 | —$CH_3$ | —H | —$N(C_2H_5)_2$ | —H | —H | —H | |
| 1069 | —$CH_3$ | —$OC_2H_5$ | —H | —H | —$CH{=}CHCH_3$(cis) | —H | |

TABLE 123

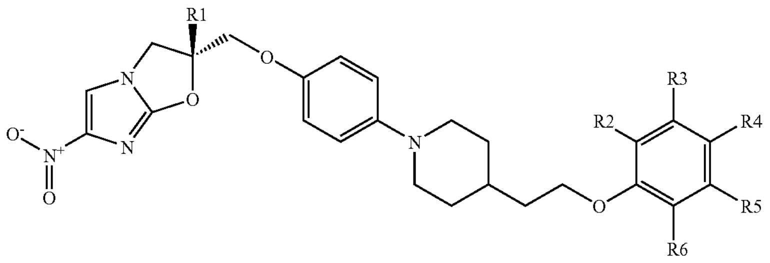

| Example | R1 | R2 | R3 | R4 | R5 | R6 | MS(M + 1) |
|---|---|---|---|---|---|---|---|
| 1070 | —$CH_3$ | —H | —H | —$CH(CH_3)_2$ | —H | —H | |
| 1071 | —$CH_3$ | —H | —H | —$CH_2CH_2COCH_3$ | —H | —H | |
| 1072 | —$CH_3$ | —H | —$NHC_6H_5$ | —H | —H | —H | |
| 1073 | —$CH_3$ | —H | —H | —$CH_2CO_2CH_3$ | —H | —H | |
| 1074 | —$CH_3$ | —Cl | —H | —$OCH_3$ | —H | —H | |
| 1075 | —$CH_3$ | —H | —H | —$COC_2H_5$ | —H | —H | |
| 1076 | —$CH_3$ | —H | —$CH_3$ | —$CH_3$ | —$CH_3$ | —H | |
| 1077 | —$CH_3$ | —H | —H | —$SCH_3$ | —H | —H | |
| 1078 | —$CH_3$ | —H | —H | 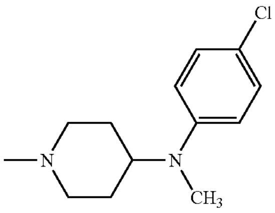 | —H | —H | |
| 1079 | —$CH_3$ | —H | —H | —$C_6H_5$ | —H | —H | |
| 1080 | —$CH_3$ | —H | —H | —$OCH_2C_6H_5$ | —H | —H | 585 |
| 1081 | —$CH_3$ | —H | —H | —$CH_2C_6H_5$ | —H | —H | 569 |
| 1082 | —$CH_3$ | —H | —H | —cyclo-$C_6H_{11}$ | —H | —H | 561 |
| 1083 | —$CH_3$ | —H | —H | —$OC_8H_{17}$ | —H | —H | 607 |
| 1084 | —$CH_3$ | —H | —H | —cyclo-$C_5H_9$ | —H | —H | 547 |
| 1085 | —$CH_3$ | —H | —$OC_6H_5$ | —H | —H | —H | 571 |
| 1086 | —$CH_3$ | —H | —H | —$C_6H_{13}$ | —H | —H | 563 |

TABLE 124
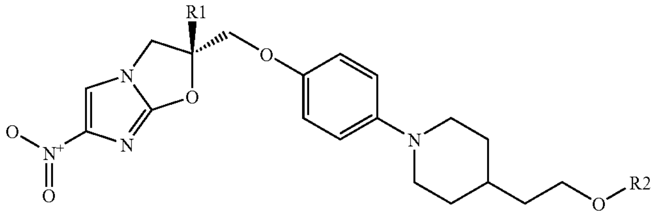
| Example | R1 | R2 | MS(M + 1) |
|---|---|---|---|
| 1087 | —$CH_3$ | 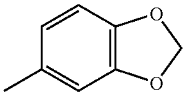 | 523 |
| 1088 | —$CH_3$ | 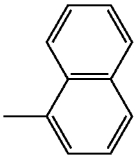 | 529 |
| 1089 | —$CH_3$ | 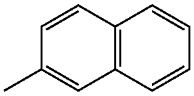 | 529 |
| 1090 | —$CH_3$ | 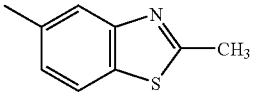 | 550 |
| 1091 | —$CH_3$ | 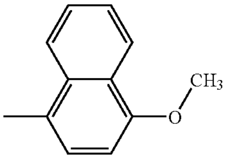 | |
| 1092 | —$CH_3$ | 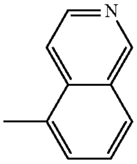 | 530 |
| 1093 | —$CH_3$ | 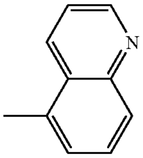 | |
| 1094 | —$CH_3$ | 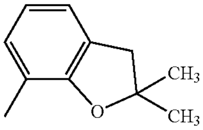 | |
| 1095 | —$CH_3$ | 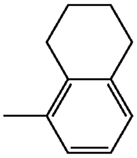 | |

TABLE 125

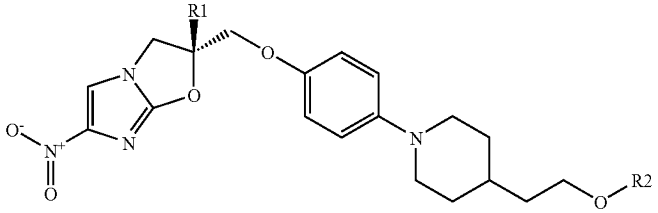

| Example | R1 | R2 |
|---|---|---|
| 1096 | —$CH_3$ | 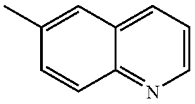 |
| 1097 | —$CH_3$ | 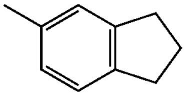 |

Example 1098

(R)-2-methyl-2-(4-(N-methyl-N-(1-methylpiperidine-4-yl)amino)phenoxymethyl)-6-nitro-2,3-dihydroimidazo[2,1-b]oxazole Example 1099

(R)-4-(1-(4-(2-methyl-6-nitro-2,3-dihydro-imidazo[2,1-b]oxazole-2-ylmethoxy)phenyl)-3-(4-trifluoromethoxyphenyl)ureido)-piperidine-1-carboxylic acid (4-trifluoromethoxyphenyl)amide Example 1100

6-Nitro-2-(4-(4-(4-trifluoromethylbenzyloxymethyl)piperidine-1-yl)phenoxymethyl)-2,3-dihydroimidazo[2,1-b]oxazole Melting point: 140.2-141.7° C.

Example 1101

(R)-2-methyl-6-nitro-2-(4-(4-(tetrahydropyran-2-yloxymethyl)piperidine-1-yl)phenoxymethyl)-2,3-dihydroimidazo[2,1-b]oxazole Melting point: 217.6-218.6° C.

Example 1102

(R)-2-methyl-6-nitro-2-(4-(4-(hydroxymethyl)piperidine-1-yl)phenoxymethyl)-2,3-dihydroimidazo[2,1-b]oxazole Example 1103

2-methyl-6-nitro-2-(4-(4-(4-trifluoromethoxyphenoxy)piperidine-1-yl)benzyl)-2,3-dihydroimidazo[2,1-b]oxazole Melting point: 184.9-186.8° C.

Example 1104

(R)-2-methyl-6-nitro-2-(4-(4-(4-trifluoromethoxyphenyl)carbamoyloxymethylpiperidin-1-yl)phenoxymethyl)-2,3-dihydroimidazo[2,1-b]oxazole Melting point: 211.6° C.-212.0° C. (decomposition)

Example 1105

(R)-2-(4-(4-(biphenyl-4-yloxymethyl)piperidin-1-yl)phenoxymethyl)-2-methyl-6-nitro-2,3-dihydroimidazo[2,1-b]oxazole Melting point: 245° C. (decomposition)

Example 1106

(R)-2-(1-benzyl-2-(4-(4-trifluoromethoxybenzyl)piperazin-1-yl)-1H-benzimidazol-5-yloxymethyl)-2-methyl-6-nitro-2,3-dihydroimidazo[2,1-b]oxazole Melting point: 101.3° C.-104.0° C.

Example 1107

(R)-2-methyl-6-nitro-2-(4-(4-(4-trifluoromethoxybenzyl)piperidin-1-ylmethyl)phenoxymethyl)-2,3-dihydroimidazo[2,1-b]oxazole Melting point: 172.5° C.-174.1° C.

Example 1108

2-(4-(4-(N-methyl-tert-butoxycarbonylamino)piperidin-1-ylmethyl)phenoxymethyl)-2-methyl-6-nitro-2,3-dihydroimidazo[2,1-b]oxazole Melting point: 138.5° C.-141.9° C.

Example 1109

(R)-2-(4'-(4-tert-butoxylcarbonyl-1,4-diazepan-1-yl)biphenyl-4-yloxymethyl)-2-methyl-6-nitro-2,3-dihydroimidazo[2,1-b]oxazole Melting point: 213.8° C.-215.7° C.

Example 1110

(R)-2-(4'-(4-tert-butoxycarbonyl-1,4-diazepan-1-yl)biphenyl-4-yloxymethyl)-6-nitro-2,3-dihydroimidazo[2,1-b]oxazole Melting point: 235.5° C.-237.5° C.

Example 1111

(S)-2-methyl-2-(N-methyl-N-(4-(N-methyl-N-(4-trifluoromethylcinnamyl)amino)benzyl)aminomethyl)-6-nitro-2,3-dihydroimidazo[2,1-b]oxazole Melting point: 153.5° C.-154.5° C.

Example 1112

(R)-2-methyl-6-nitro-2-(4-(2-oxo-2-(4-(4-trifluoromethoxyphenoxy)piperidin-1-yl)ethylaminocarbonyl)phenoxymethyl)-2,3-dihydroimidazo[2,1-b]oxazole Melting point: 186.9° C.-189.5° C.

Example 1113

2-methyl-6-nitro-2-(2-(4-(4-trifluoromethoxybenzyl)piperazin-1-yl)benzothiazol-6-yloxymethyl)-2,3-dihydroimidazo[2,1-b]oxazole Melting point: 172.6° C.-174.6° C.

Example 1114

2-(4-(4-(4-chlorophenoxymethyl)piperidin-1-yl)phenoxymethyl)-2-methyl-6-nitro-2,3-dihydroimidazo[2,1-b]oxazole Melting point: 190.0° C.-190.4° C.

Example 1115

2-(4-(4-(4-chlorophenoxymethyl)piperidin-1-yl)phenoxymethyl)-6-nitro-2,3-dihydroimidazo[2,1-b]oxazole Melting point: 191.2° C.-192.5° C.

Example 1116

6-nitro-2-(4-(4-(4-trifluoromethoxybenzyl)piperidin-1-yl)phenoxymethyl)-2,3-dihydroimidazo[2,1-b]oxazole Melting point: 132.7° C.-135.0° C.

Example 1117

2-methyl-6-nitro-2-(4-(4-(4-trifluoromethoxycinnamyl)piperazin-1-yl)phenoxymethyl)-2,3-dihydroimidazo[2,1-b]oxazole Melting point: 181.1° C.-182.2° C.

TABLE 126

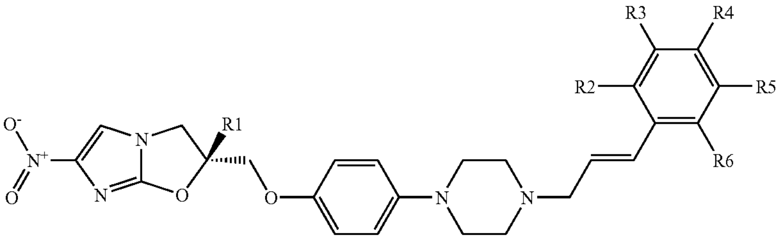

| Example | R1 | R2 | R3 | R4 | R5 | R6 | mp(° C.) |
|---|---|---|---|---|---|---|---|
| 1118 | —CH3 | —H | —H | —Br | —H | —H | 207.1-208.9 |
| 1119 | —CH3 | —H | —H | —Cl | —Cl | —H | 204.7-206.4 |
| 1120 | —CH3 | —H | —H | —CH3 | —H | —H | 210.4-211.9 |
| 1121 | —CH3 | —H | —H | —OCF3 | —H | —H | 213.0-214.9 |
| 1122 | —CH3 | —H | —H | —Cl | —H | —H | 198.6-201.2 |
| 1123 | —H | —H | —H | —CF3 | —H | —H | 172.1-174.7 |
| 1124 | —H | —H | —H | —Cl | —H | —H | 179.6-181.5 |
| 1125 | —H | —H | —Cl | —Cl | —H | —H | 189.1-190.7 |
| 1126 | —H | —H | —H | —Br | —H | —H | 202.6-204.4 |
| 1127 | —CH3 | —H | —H | —OCH3 | —H | —H | 218.5-220.6 |
| 1128 | —H | —H | —H | —OCF3 | —H | —H | 181.1-182.7 |
| 1129 | —CH3 | —H | —Cl | —H | —H | —H | 195 dec |
| 1130 | —CH3 | —H | —CF3 | —H | —CF3 | —H | 183 dec |
| 1131 | —CH3 | —H | —CF3 | —Cl | —H | —H | 196.1-197.4 |
| 1132 | —CH3 | —H | —CF3 | —F | —H | —H | 210.5 dec |
| 1133 | —CH3 | —Cl | —Cl | —H | —H | —H | 212 dec |

TABLE 127

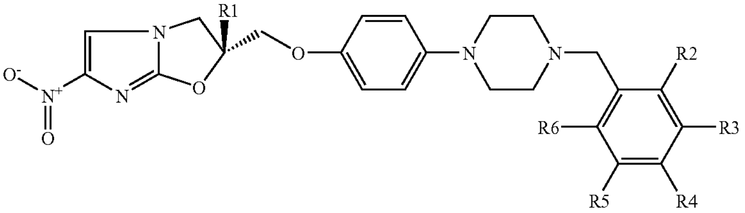

| Example | R1 | R2 | R3 | R4 | R5 | R6 | mp(° C.) |
|---|---|---|---|---|---|---|---|
| 1134 | —H | —H | —H | 4-ClPh— | —H | —H | 245-248 |
| 1135 | —$CH_3$ | —H | —H | 4-ClPh— | —H | —H | 241.7-243.5 |
| 1136 | —$CH_3$ | —H | —H | —$C_6H_5$ | —H | —H | 254.6-258.0 |
| 1137 | —H | —H | —H | 4-ClPhO— | —H | —H | 184.7-187.9 |
| 1138 | —$CH_3$ | —H | —H | 4-ClPhO— | —H | —H | 179.2-181.8 |
| 1139 | —H | —H | —H | —$C_6H_5$ | —H | —H | 256.0-258.2 |

TABLE 128

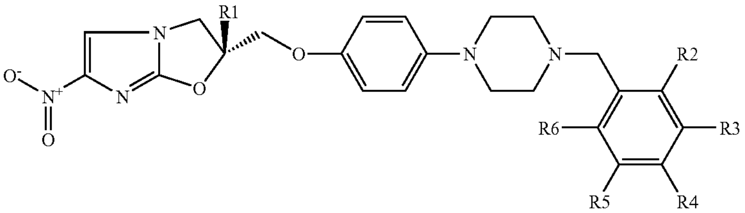

| Example | R1 | R2 | R3 | R4 | R5 | R6 | $^1H$ NMR |
|---|---|---|---|---|---|---|---|
| 1140 | —$CH_3$ | —H | —H | 4-$CF_3$Ph— | —H | —H | $^1H$ NMR($CDCl_3$) δ 1.75(3H, s), 2.52-2.74(4H, m), 2.99-3.22(4H, m), 3.62(2H, s), 3.92-4.09(2H, m), 4.17(1H, d, J = 10.2 Hz), 4.48(1H, d, J = 10.2 Hz), 6.66-6.82(2H, m), 6.82-6.94(2H, m), 7.43(2H, d, J = 8.2 Hz), 7.50-7.61 (3H, m), 7.69(4H, s). |
| 1141 | —$CH_3$ | —H | —H | 4-$CF_3$OPh— | —H | —H | $^1H$ NMR($CDCl_3$) δ 1.76(3H, s), 2.49-2.74(4H, m), 2.97-3.22(4H, m), 3.61(2H, s), 3.89-4.10(2H, m), 4.17(1H, d, J = 10.2 Hz), 4.49(1H, d, J = 10.2 Hz), 6.68-6.81(2H, m), 6.81-6.95(2H, m), 7.28(2H, d, J = 8.6 Hz), 7.43(2H, d, J = 8.2 Hz), 7.48-7.67(5H, m). |
| 1142 | —H | —H | —H | 4-$CF_3$Ph— | —H | —H | $^1H$ NMR($CDCl_3$) δ 2.51-2.76(4H, m), 3.00-3.24(4H, m), 3.62(2H, s), 4.14-4.53(4H, m), 5.47-5.68(1H, m), 6.68-6.97(4H, m), 7.44(2H, d, J = 8.2 Hz), 7.51-7.62(3H, m), 7.62-7.80(4H, m). |
| 1143 | —H | —H | —H | 4-$CF_3$OPh— | —H | —H | $^1H$ NMR($CDCl_3$) δ 2.53-2.73(4H, m), 3.02-3.21(4H, m), 3.57(2H, s), 4.15-4.50(4H, m), 5.49-5.66(1H, m), 6.72-6.95(4H, m), 7.28(2H, d, J = 20.1 Hz), 7.43(2H, d, J = 8.2 Hz), 7.52(2H, d, J = 8.3 Hz), 7.56-7.67(3H, m). |

TABLE 129

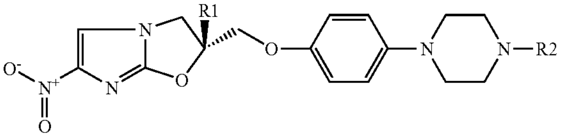

| Example | R1 | R2 | mp(° C.) |
|---|---|---|---|
| 1144 | —$CH_3$ | 4-ClPhCO$CH_2$— | 211-212 |
| 1145 | —$CH_3$ | 4-$CF_3$PhCO$CH_2$— | 197-198 |
| 1146 | —$CH_3$ | $(CH_3)_3$COCONH— | 254.1-255.9 |
| 1147 | —$CH_3$ | 4-$CF_3$OPhCO$CH_2$— | 200-202 |
| 1148 | —$CH_3$ | 4-$CF_3$Ph$CH_2$N($CH_3$)— | 201.1-203.7 |

TABLE 129-continued

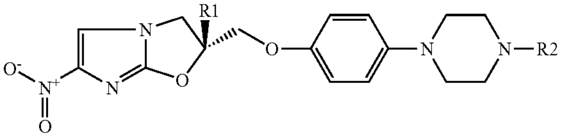

| Example | R1 | R2 | mp(° C.) |
|---|---|---|---|
| 1149 | —$CH_3$ | 4-$CF_3$OPh$CH_2$N($CH_3$)— | 208.9-210.3 |
| 1150 | —$CH_3$ | 4-ClPhNH$CH_2CH_2$— | 172-173 |
| 1151 | —$CH_3$ | 4-$CF_3$OPhNH$CH_2CH_2$— | 161-162 |
| 1152 | —$CH_3$ | 4-ClPhN($CH_3$)$CH_2CH_2$— | 179-180 |
| 1153 | —$CH_3$ | 4-ClPh$CH_2$N($CH_3$)— | 204.8-205.5 |

TABLE 129-continued
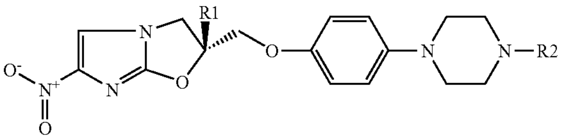
| Example | R1 | R2 | mp(° C.) |
|---|---|---|---|
| 1154 | —$CH_3$ | 4-$CF_3OPhN(CH_3)CH_2CH_2$— | 141-142.5 |
| 1155 | —$CH_3$ | 4-$CF_3PhNHCH_2CH_2$— | 159-160 |
TABLE 129-continued
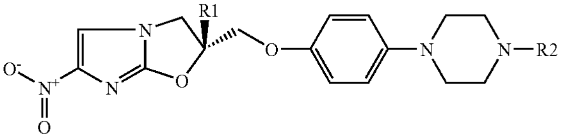
| Example | R1 | R2 | mp(° C.) |
|---|---|---|---|
| 1156 | —$CH_3$ | 4-$CF_3PhN(CH_3)CH_2CH_2$— | 177-178 |
| 1157 | —$CH_3$ | $PhC{\equiv}CCH_2$— | 186.0-189.0 |
TABLE 130
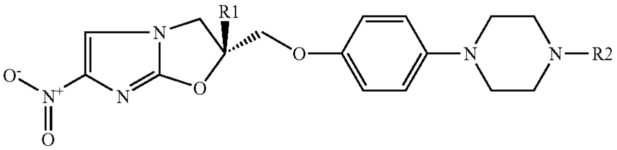
| Example | R1 | R2 | mp(° C.) |
|---|---|---|---|
| 1158 | —$CH_3$ | 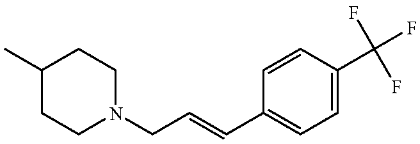 | 245-248 dec. |
| 1159 | —$CH_3$ | 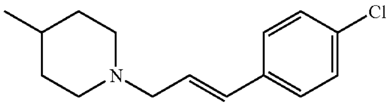 | 252-256 dec. |
| 1160 | —$CH_3$ | 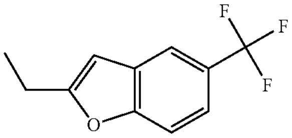 | 215.2-217.1 |
| 1161 | —$CH_3$ | 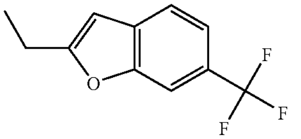 | 212.2-214.3 |
| 1162 | —H | 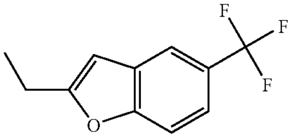 | 180.5-181.5 |
| 1163 | —$CH_3$ | 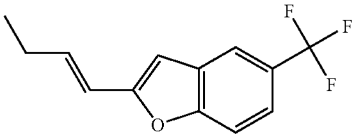 | 217.0-218.6 |
| 1164 | —$CH_3$ | 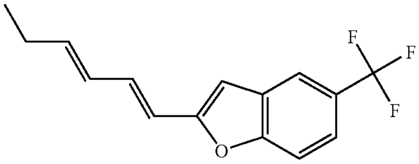 | 217.5-220.0 |

TABLE 130-continued
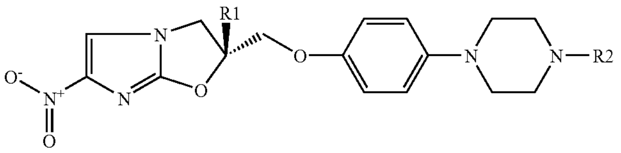
| Example | R1 | R2 | mp(° C.) |
|---|---|---|---|
| 1165 | —$CH_3$ | 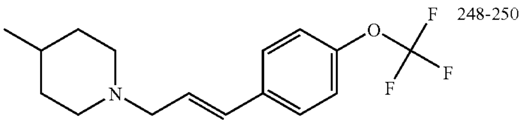 | 248-250 |
| 1166 | —H | 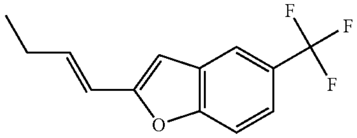 | 190.8-191.2 |
| 1167 | —H | 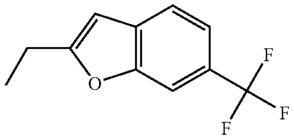 | 164.8-165.4 |
| 1168 | —$CH_3$ | 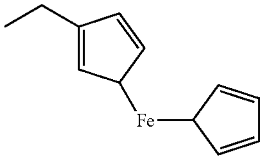 | 243.6-246.0 |
TABLE 131
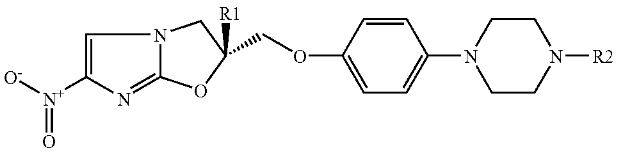
| Example | R1 | R2 | mp(° C.) |
|---|---|---|---|
| 1169 | —$CH_3$ | 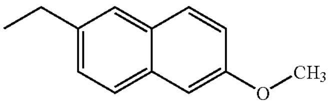 | 233.8-234.5 |
| 1170 | —$CH_3$ | 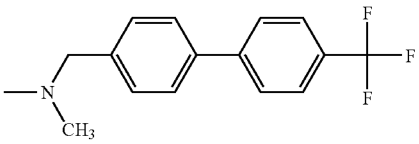 | 251.0-253.6 |
| 1171 | —$CH_3$ | 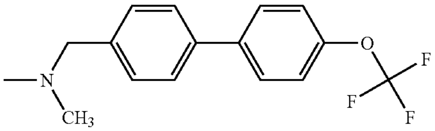 | 252.3-253.9 |

TABLE 131-continued
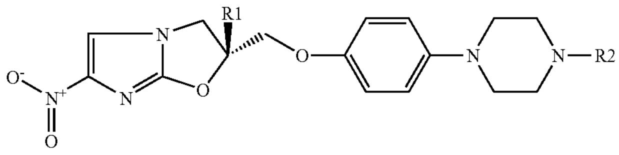
| Example | R1 | R2 | mp(° C.) |
|---|---|---|---|
| 1172 | —$CH_3$ | 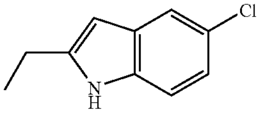 | 202-203 |
| 1173 | —$CH_3$ | 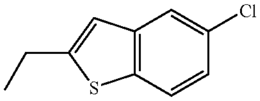 | 220-221.5 |
| 1174 | —$CH_3$ | 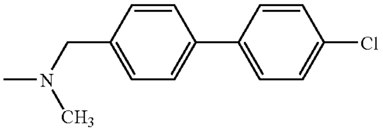 | 260.2-263.6 |
TABLE 132
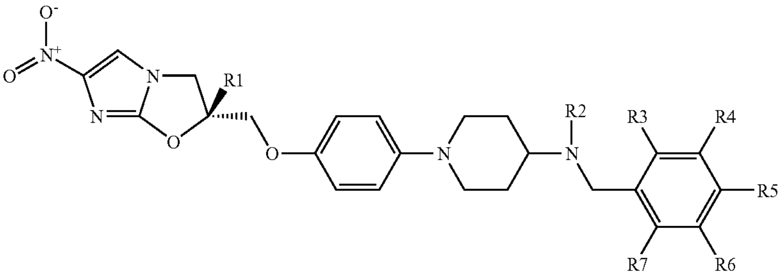
| Exaple | R1 | R2 | R3 | R4 | R5 | R6 | R7 | mp(° C.) |
|---|---|---|---|---|---|---|---|---|
| 1175 | —$CH_3$ | —$CH_3$ | —$CF_3$ | —H | —$CF_3$ | —H | —H | 176.7-178.3 |
| 1176 | —H | —$CH_3$ | —$CF_3$ | —H | —$CF_3$ | —H | —H | 135.7-137.6 |
| 1177 | —$CH_3$ | —$CH_3$ | —H | —H | 4-$CF_3$Ph— | —H | —H | 226.0-229.3 |
| 1178 | —$CH_3$ | —$CH_3$ | —H | —H | 4-ClPh— | —H | —H | 244.2-246.9 |
| 1179 | —$CH_3$ | —$CH_3$ | —H | —H | 4-ClPhO— | —H | —H | 189.5-194.1 |
| 1180 | —$CH_3$ | —$CH_3$ | —H | —H | 4-$CF_3$OPhO— | —H | —H | 200.0-203.5 |
| 1181 | —H | —$CH_3$ | —H | —H | 4-ClPh— | —H | —H | 237.4-239.0 |
| 1182 | —H | —$CH_3$ | —H | —H | 4-$CF_3$OPh— | —H | —H | 215.8-218.7 |
| 1183 | —H | —H | —H | —H | 4-$CF_3$OPh— | —H | —H | 233.7-235.8 |
| 1184 | —$CH_3$ | —H | —H | —H | —$C_6H_5$ | —H | —H | 241.2-243.7 |
| 1185 | —$CH_3$ | —$CH_3$ | —H | —H | —$C_6H_5$ | —H | —H | 227.2-229.5 |
| 1186 | —H | —$CH_3$ | —H | —H | —$C_6H_5$ | —H | —H | 229.8-231.7 |
| 1187 | —H | —H | —H | —H | —$C_6H_5$ | —H | —H | 248.4-253.6 |

TABLE 133
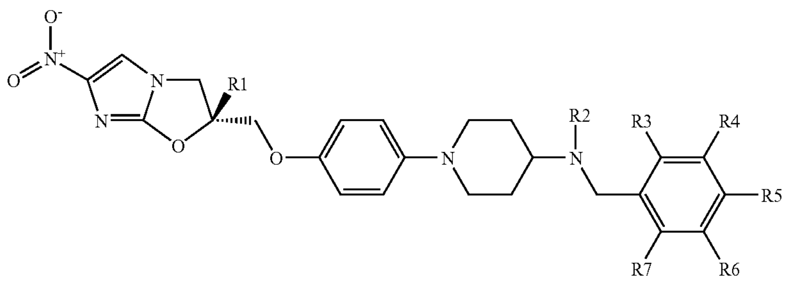
| Example | R1 | R2 | R3 | R4 | R5 | R6 | R7 | $^1$H NMR |
|---|---|---|---|---|---|---|---|---|
| 1188 | —$CH_3$ | —$CH_3$ | —H | —H | 4-$CF_3$OPh— | —H | —H | 1H NMR(CDCl3) δ 1.65-2.06 (7H, m), 2.26(3H, s), 2.47-2.77(3H, m), 3.51-3.72(4H, m), 3.92-4.09(2H, m), 4.17 (1H, d, J = 10.2 Hz), 4.49 (1H, d, J = 10.2Hz), 6.66-6.82(2H, m), 6.82-6.97(2H, m), 7.27(2H, d, J = 6.9 Hz), 7.40(2H, d, J = 8.2Hz), 7.46-7.66(5H, m). |
| 1189 | —H | —$CH_3$ | —H | —H | 4-$CF_3$Ph— | —H | —H | 1H NMR(CDCl3) δ 1.70-2.06 (4H, m), 2.30(3H, s), 2.44-2.78(3H, s), 3.48-3.75(4H, m), 4.17-4.53(4H, m), 5.48-5.70(1H, m), 6.71-6.85(2H, m), 6.85-6.98(2H, m), 7.42 (2H, d, J = 8.2 Hz), 7.51-7.61 (3H, m), 7.72(4H, s). |
TABLE 134
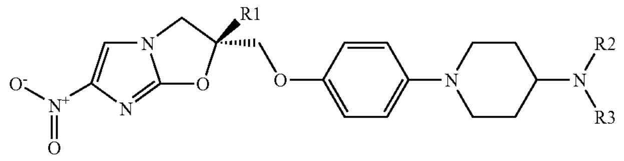
| Example | R1 | R2 | R3 | mp(° C.) |
|---|---|---|---|---|
| 1190 | —$CH_3$ | 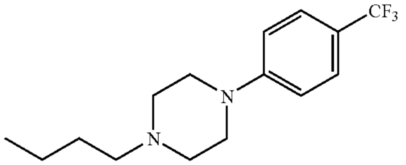 | —$CH_3$ | 181.4-183.3 |
| 1191 | —$CH_3$ | 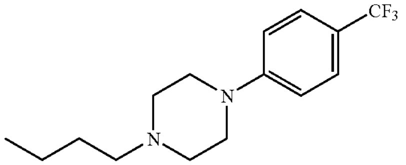 | —H | 185.0-188.8 |

TABLE 135
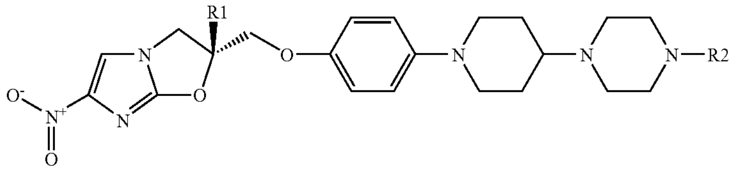
| Example | R1 | R2 | mp(° C.) |
|---|---|---|---|
| 1192 | —$CH_3$ | —$CH_3$ | 252-255 dec. |
| 1193 | —$CH_3$ | 4-$CF_3$PhCH═$CHCH_2$— | 232-234 |
| 1194 | —$CH_3$ | 4-ClPhCH═$CHCH_2$— | 231-232 |
| 1195 | —$CH_3$ | 4-$CF_3$OPhCH═$CHCH_2$— | 228-230 |
TABLE 136
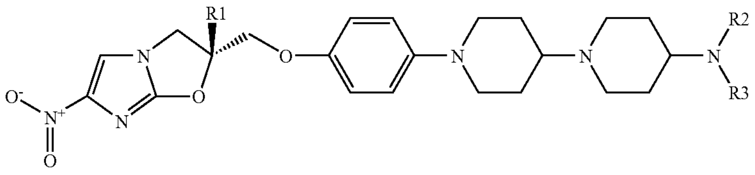
| Example | R1 | R2 | R3 | mp(° C.) |
|---|---|---|---|---|
| 1196 | —$CH_3$ | 4-$CF_3$Ph— | —$CH_3$ | 188-195 dec. |
| 1197 | —H | 4-$CF_3$Ph— | —$CH_3$ | 172-174 |
| 1198 | —$CH_3$ | 4-$CF_3$OPh— | —$C_2H_3$ | 196.5-198 |
| 1199 | —$CH_3$ | 4-ClPh— | —$C_2H_5$ | 184.5-186.5 |
| 1200 | —$CH_3$ | —$CH_3$ | —$CH_3$ | 250-252 |
TABLE 137
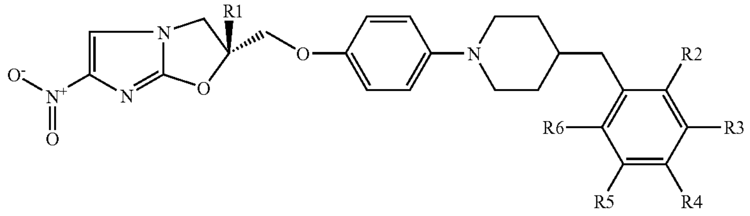
| Example | R1 | R2 | R3 | R4 | R5 | R6 | mp(° C.) |
|---|---|---|---|---|---|---|---|
| 1201 | —H | —H | —H | 4-$CF_3$Ph— | —H | —H | 196.0-198.2 |
| 1202 | —$CH_3$ | —H | —H | 4-$CF_3$OPh— | —H | —H | 229.4-230.1 |
| 1203 | —H | —H | —H | 4-$CF_3$OPh— | —H | —H | 185.7-187.2 |
| 1204 | —$CH_3$ | —H | —H | 4-ClPh— | —H | —H | 248.9-250.0 |
| 1205 | —H | —H | —H | 4-ClPh— | —H | —H | 236.2-238.8 |
| 1206 | —$CH_3$ | —H | —H | —$C_6H_5$ | —H | —H | 224.2-227.4 |
| 1207 | —H | —H | —H | —$C_6H_6$ | —H | —H | 235.8-237.4 |

TABLE 138
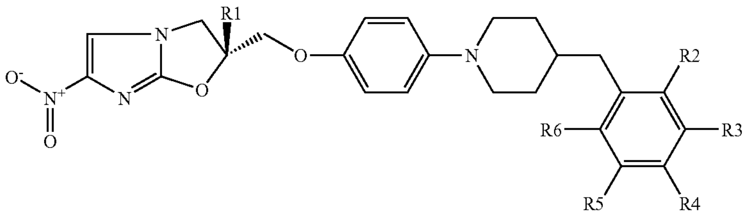
| Example | R1 | R2 | R3 | R4 | R5 | R6 | $^1$H NMR |
|---|---|---|---|---|---|---|---|
| 1208 | —$CH_3$ | —H | —H | 4-$CF_3$Ph— | —H | —H | 1H NMR(CDCl3) δ 1.30-1.54(2H, m), 1.58-1.98(6H, m), 2.44-2.72(4H, m), 3.36-3.62(2H, m), 3.91-4.08(2H, m), 4.16(1H, d, J = 10.2 Hz), 4.48(1H, d, J = 10.3 Hz), 6.66-6.81(2H, m), 6.81-6.94(2H, m), 7.18-7.32(2H, m), 7.44-7.59(3H, m), 7.61-7.75(4H, m). |
TABLE 139
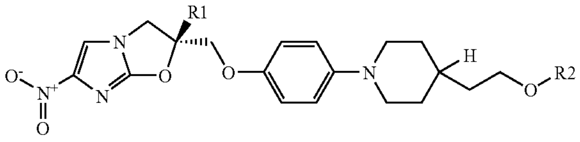
| Example | R1 | R2 | mp (° C.) | |
|---|---|---|---|---|
| 1209 | —$CH_3$ | —$CH_2OCH_3$ | 194.0-195.6 | |
| 1210 | —$CH_3$ | —H | 216.8-218.4 | dec. |
| 1211 | —H | —$CH_2OCH_3$ | 150.0-151.2 | |
TABLE 140
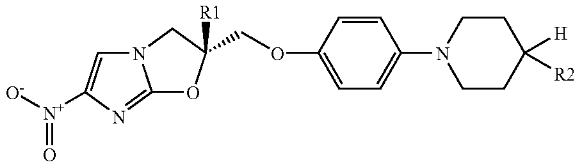
| Example | R1 | R2 | mp (° C.) |
|---|---|---|---|
| 1212 | —$CH_3$ | —$CH_2OCH_2OCH_3$ | 208.7-210.7 |
| 1213 | —$CH_3$ | —$CH_2OH$ | 171.0-173.8 |
TABLE 140-continued
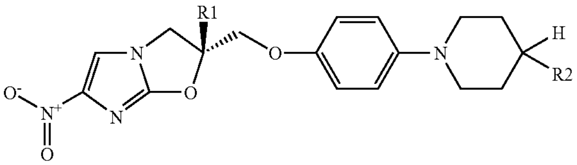
| Example | R1 | R2 | mp (° C.) |
|---|---|---|---|
| 1214 | —H | 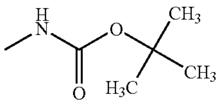 | 236.7-237.2 |
| 1215 | —$CH_3$ | 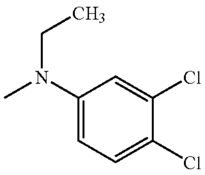 | 166.0-166.9 |
| 1216 | —$CH_3$ | 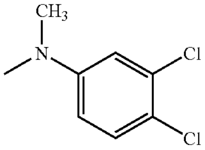 | 196.9-200.3 |
TABLE 141
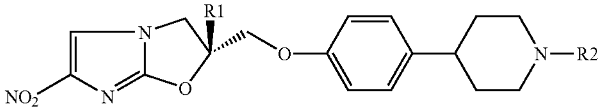
| Example | R1 | R2 | mp (° C.) |
|---|---|---|---|
| 1217 | —$CH_3$ | 3,4-$Cl_2$PhCH═CHCH$_2$— | 202.4-203.5 |
| 1218 | —$CH_3$ | 4-ClPhCH═CHCH$_2$— | 196.0-199.4 |

TABLE 141-continued
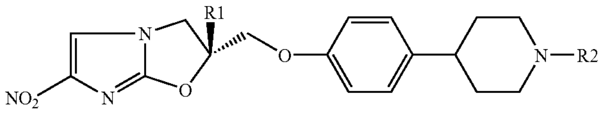
| Example | R1 | R2 | mp (° C.) |
|---|---|---|---|
| 1219 | —$CH_3$ | 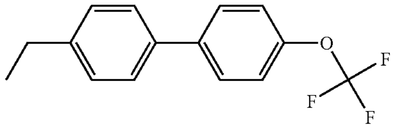 | 212.4-214.9 |
| 1220 | —$CH_3$ | 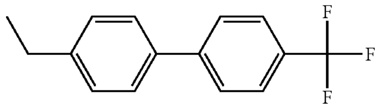 | 198.6-199.7 |
| 1221 | —$CH_3$ | 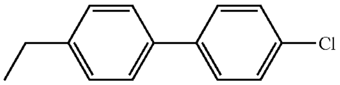 | 224.1-227.6 |
| 1222 | —$CH_3$ | 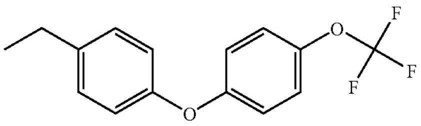 | 192.2-195.3 |
| 1223 | —$CH_3$ | 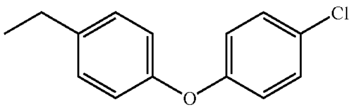 | 182.2-183.5 |
| 1224 | —$CH_3$ | 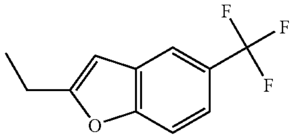 | 219.6-221.9 |
TABLE 142
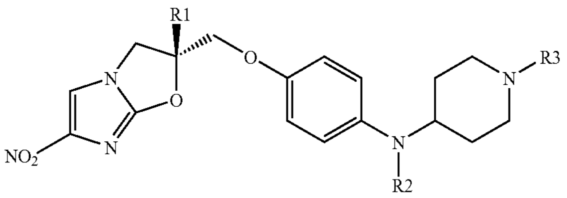
| Example | R1 | R2 | R3 | mp (° C.) |
|---|---|---|---|---|
| 1225 | —$CH_3$ | —$CH_3$ | 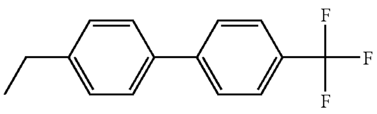 | 203.4-205.0 |
| 1226 | —$CH_3$ | —$CH_3$ | 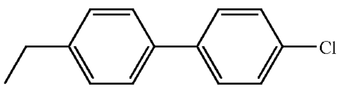 | 187.7-190.0 |

TABLE 142-continued
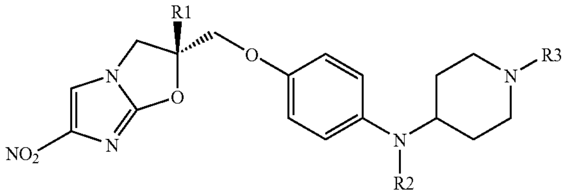
| Example | R1 | R2 | R3 | mp (° C.) |
|---|---|---|---|---|
| 1227 | —H | —$CH_3$ | 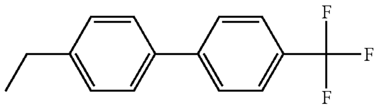 | 213.1-214.5 |
| 1228 | —H | —$CH_3$ | 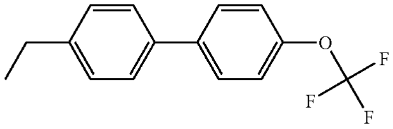 | 212.6-214.4 |
| 1229 | —H | —$CH_3$ | 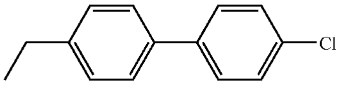 | 206.5-207.7 |
TABLE 143
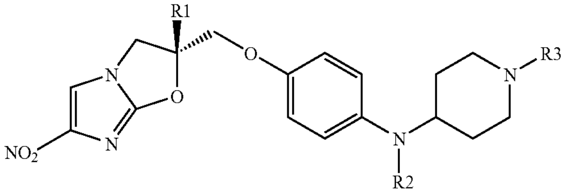
| Example | R1 | R2 | R3 | $^1$H NMR |
|---|---|---|---|---|
| 1230 | —H | —$CH_3$ | 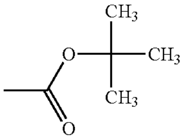 | 1H NMR (CDCl3) δ 1.46(9H, s), 1.54-1.84(4H, m), 2.57-2.85(6H, m), 3.39-3.65(1H, m), 4.04-4.52(7H, m), 5.49-5.67(1H, m), 6.69-6.86(4H, m), 7.58(1H, s). |
TABLE 144
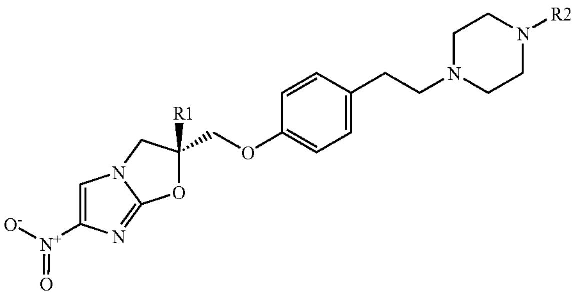
| Example | R1 | R2 | mp (° C.) |
|---|---|---|---|
| 1231 | —$CH_3$ | 4-$CF_3$OPh$CH_2$— | 164.6-167.5 |
| 1232 | —$CH_3$ | 4-$CF_3$OPhCH═CH$CH_2$— | 155.8-158.5 |
TABLE 145
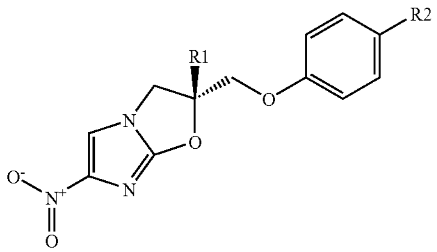
| Example | R1 | R2 | mp (° C.) |
|---|---|---|---|
| 1233 | —$CH_3$ | 4-ClPhS— | 182.8-184.6 |
| 1234 | —$CH_3$ | 4-$CF_3$OPhS— | 147.2-150.0 |
| 1235 | —$CH_3$ | 4-ClPh$SO_2$— | 223.5-224.9 |
| 1236 | —$CH_3$ | 4-$CF_3$OPhSO— | 128.0-130.7 |
| 1237 | —$CH_3$ | 4-$CF_3$OPh$SO_2$— | 171.2-174.1 |

TABLE 146
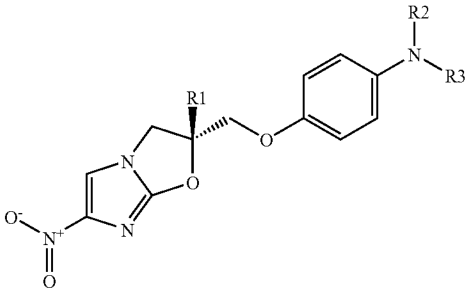
| Example | R1 | R2 | R3 | mp (° C.) |
| --- | --- | --- | --- | --- |
| 1238 | —$CH_3$ | —$CH_3$ | 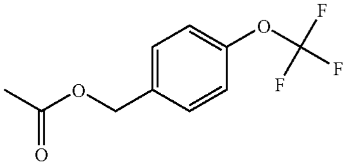 | 145.6-147.8 |
| 1239 | —$CH_3$ | —H | 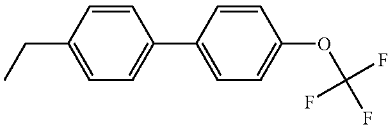 | 231.4-234.1 |
| 1240 | —$CH_3$ | —$CH_3$ | 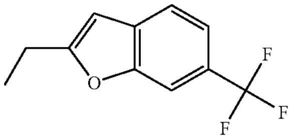 | 133.9-134.9 |
TABLE 147
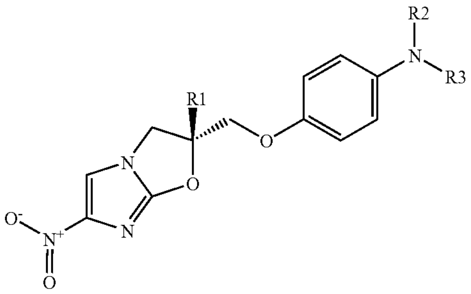
| Example | R1 | R2 | R3 | 1H NMR |
| --- | --- | --- | --- | --- |
| 1241 | —$CH_3$ | —$CH_3$ | 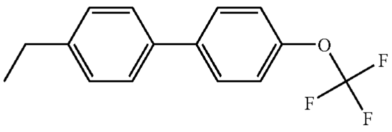 | 1H NMR(CDCl3) δ 1.75(3H, s), 2.98(3H, s), 4.00(1H, d, J = 10.1 Hz), 4.02(1H, d, J = 10.1 Hz), 4.16(1H, d, J = 10.1 Hz), 4.49(2H, s), 4.50(1H, d, J = 10.1 Hz), 6.70(2H, d, J = 9.2 Hz), 6.77(2H, d, J = 9.2 Hz), 7.28-7.31(4H, m), 7.50(2H, d, J = 8.2 Hz), 7.54(1H, s), 7.57(2H, d, J = 8.7 Hz). |

TABLE 148
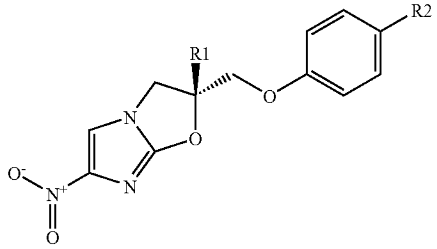
| Example | R1 | R2 | mp (° C.) |
|---|---|---|---|
| 1242 | —$CH_3$ | 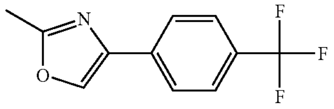 | 226.0-227.6 |
| 1243 | —$CH_3$ | 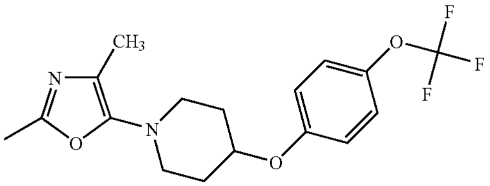 | 145.3-147.4 |
| 1244 | —$CH_3$ | 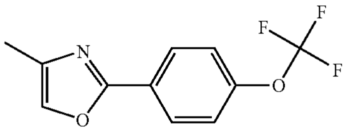 | 241.2-242.5 |
| 1245 | —$CH_3$ | 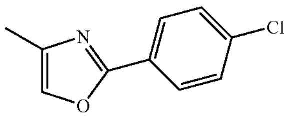 | 265.0-266.5 |
| 1246 | —$CH_3$ | 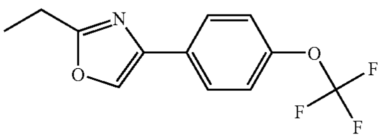 | 148.1-150.9 |
| 1247 | —$CH_3$ | 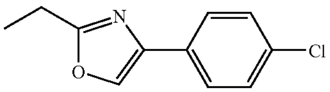 | 202.9-204.0 |
| 1248 | —$CH_3$ | 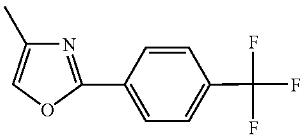 | 252.7-254.1 |
| 1249 | —$CH_3$ | 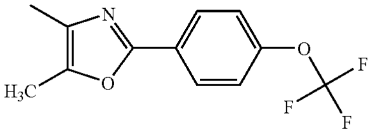 | 178.1-179.6 |
| 1250 | —$CH_3$ | 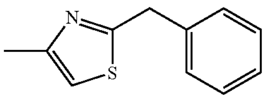 | 190.0-191.5 |

TABLE 148-continued
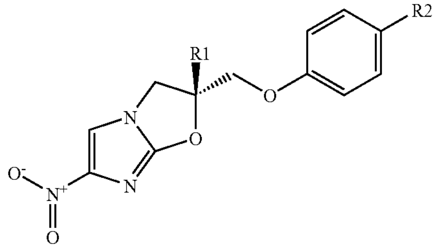
| Example | R1 | R2 | mp (° C.) |
|---|---|---|---|
| 1251 | —$CH_3$ | 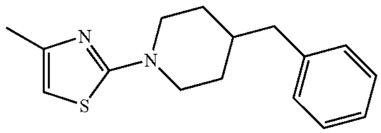 | 175 dec |
TABLE 149
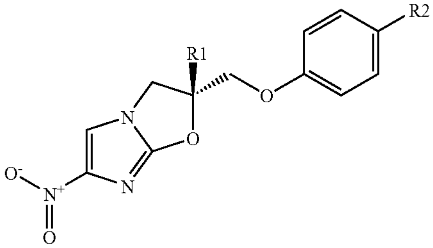
| Example | R1 | R2 | mp (° C.) |
|---|---|---|---|
| 1252 | —$CH_3$ | 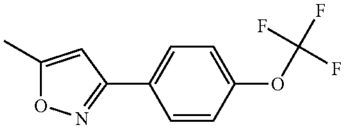 | 251.3-253.0 |
| 1253 | —$CH_3$ | 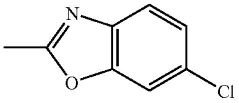 | 264.6-266.4 |
| 1254 | —$CH_3$ | 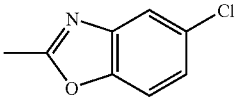 | 265.4-265.8 |
| 1255 | —$CH_3$ | 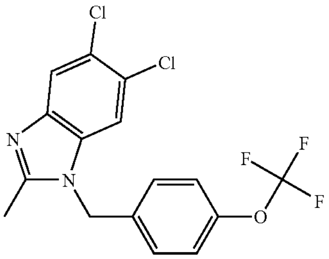 | 159.6-163.3 |
| 1256 | —$CH_3$ | 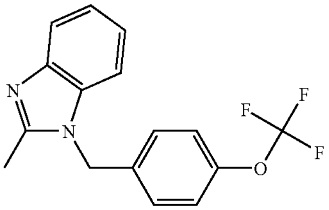 | 206.4-209.7 |

TABLE 150
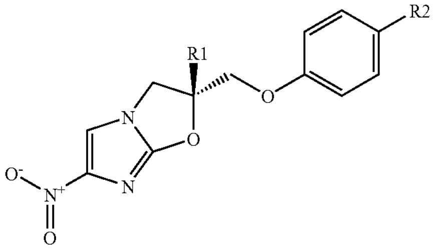
| Example | R1 | R2 | 1H NMR |
|---|---|---|---|
| 1257 | —$CH_3$ | 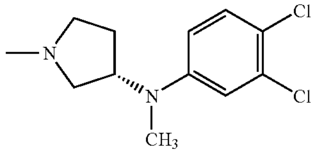 | 1H-NMR(CDCl3) δ ppm; 1.76(3H, s), 2.15-2.28(2H, m), 2.83(3H, s), 3.23-3.32(2H, m), 3.41-3.50(2H, m) 3.59-3.69(1H, m), 4.00(1H, d, J = 10.1 Hz), 4.02(1H, d, J = 10.2 Hz), 4.16(1H, d, J = 10.2 Hz), 4.50(2H, d, J = 10.1 Hz), 6.51(2H, d, J = 9.0 Hz), 6.66(1H, dd, J = 3.0 Hz, 9.0 Hz), 6.79(2H, d, J = 9.0 Hz), 6.86(1H, d, J = 3.0 Hz), 7.23(1H, d, J = 9.0 Hz), 7.55(1H, s) |
| 1258 | —$CH_3$ | 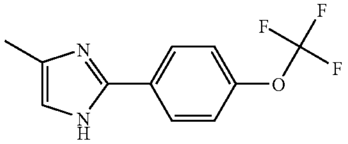 | 1H NMR(DMSO) δ ppm; 1.71(3H, s), 4.22(1H, d, J = 11.0 Hz), 4.37(2H, s), 4.41(1H, d, J = 11.0 Hz), 7.03(2H, d, J = 8.7 Hz), 7.62(2H, d, J = 8.5 Hz), 7.85(2H, d, J = 8.5 Hz), 7.98(1H, s), 8.19(1H, s), 8.22(2H, d, J = 8.7 Hz), 14.35(1H, brs). |
TABLE 151
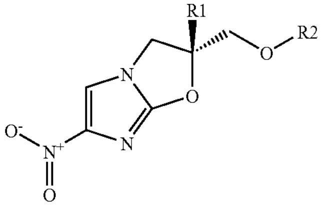
| Example | R1 | R2 | mp (° C.) |
|---|---|---|---|
| 1259 | —H | 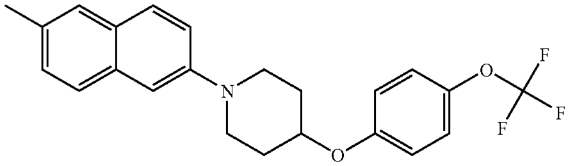 | 188.6-191.4 |
| 1260 | —$CH_3$ | 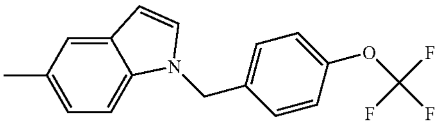 | 165.0-166.0 |
| 1261 | —$CH_3$ | 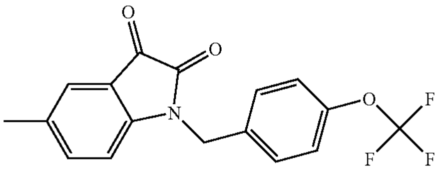 | 110-115 |
| 1262 | —$CH_3$ | 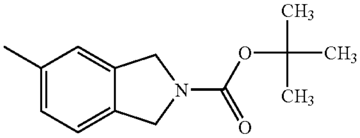 | 158.8-161.4 |

TABLE 151-continued
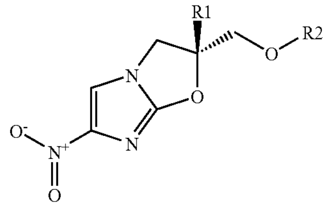
| Example | R1 | R2 | mp (° C.) |
|---|---|---|---|
| 1263 | —$CH_3$ | 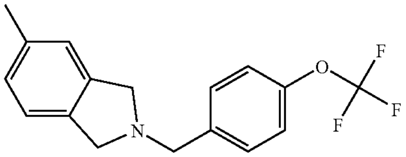 | 178.9-180.6 |
| 1264 | —$CH_3$ | 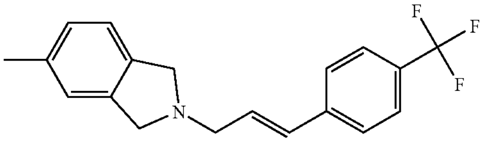 | 164.3-166.7 |
| 1265 | —$CH_3$ | 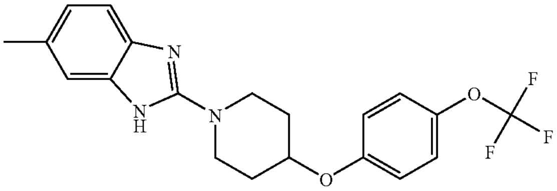 | 110.1-112.7 |
| 1266 | —$CH_3$ | 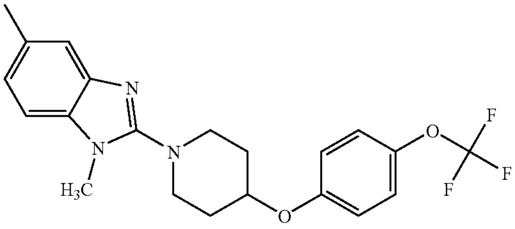 | 175.7-178.3 |
TABLE 152
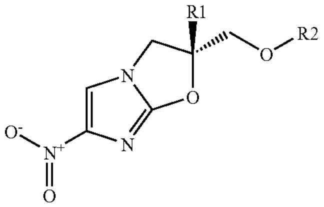
| Example | R1 | R2 | mp (° C.) |
|---|---|---|---|
| 1267 | —$CH_3$ | 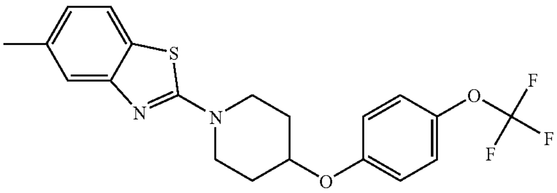 | 154.1-155.2 |

TABLE 152-continued
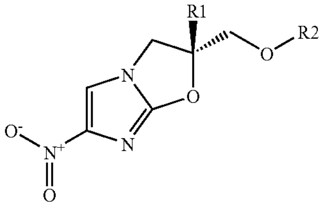
| Example | R1 | R2 | mp (° C.) |
|---|---|---|---|
| 1268 | —$CH_3$ | 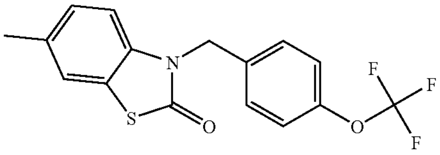 | 172.0-174.0 |
TABLE 153
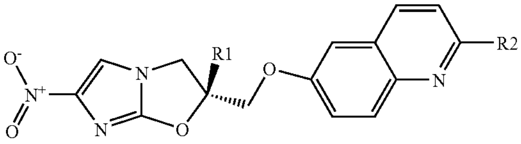
| Example | R1 | R2 | mp(° C.) |
|---|---|---|---|
| 1269 | —H | 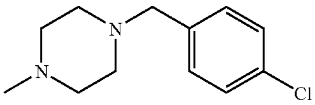 | 215.0-215.9 |
| 1270 | —H | 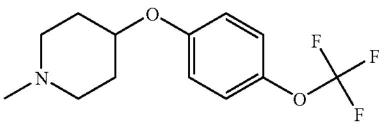 | 191.4-192.8 |
| 1271 | —H | 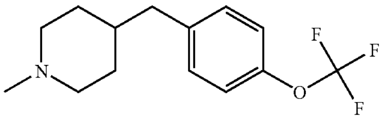 | 198.8-200.9 |
| 1272 | —H | 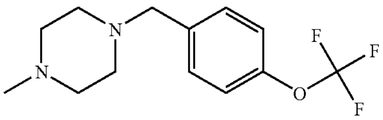 | 200 dec |
| 1273 | —$CH_3$ | —Cl | 182.2-184.7 |
| 1274 | —$CH_3$ | 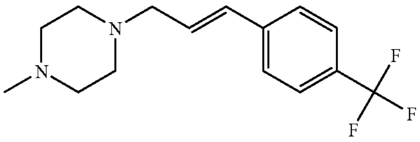 | 201.4-203.8 |
| 1275 | —H | 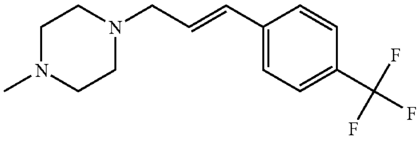 | 198.5-201.1 |

TABLE 153-continued
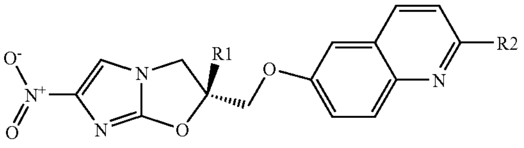
| Example | R1 | R2 | mp(° C.) |
|---|---|---|---|
| 1276 | —$CH_3$ | 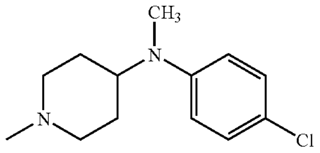 | 237.9-239.9 |
TABLE 154
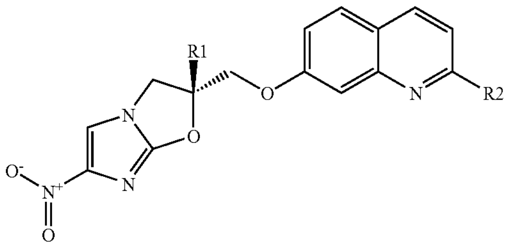
| Example | R1 | R2 | mp(° C.) |
|---|---|---|---|
| 1277 | —$CH_3$ | 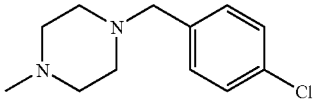 | 193.4-196.4 |
| 1278 | —$CH_3$ | 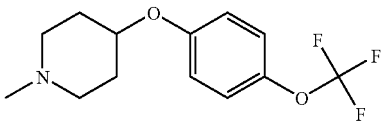 | 182.6-184.8 |
| 1279 | —$CH_3$ | 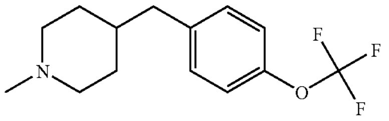 | 109.8-112.7 |
TABLE 155
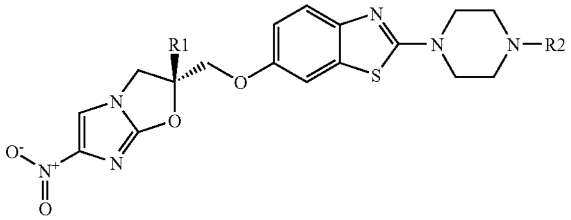
| Example | R1 | R2 | mp(° C.) |
|---|---|---|---|
| 1280 | —$CH_3$ | 4-$CF_3PhCH_2$— | 201.2-202.0 |
| 1281 | —$CH_3$ | 4-$ClPhCH_2$— | 194.4-195.7 |
| 1282 | —$CH_3$ | 4-$CF_3PhCH{=}CHCH_2$— | 184.2-186.7 |
| 1283 | —$CH_3$ | 4-$CF_3OPh$- | 256.1-258.7 |
| 1284 | —H | 4-$CF_3OPh$- | 254.6-255.6 |
TABLE 155-continued
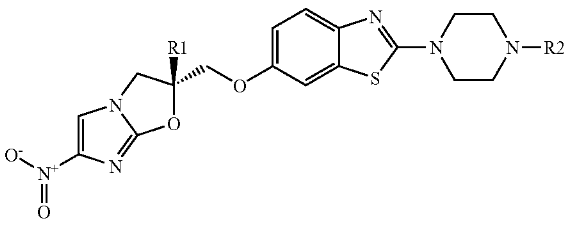
| Example | R1 | R2 | mp(° C.) |
|---|---|---|---|
| 1285 | —$CH_3$ | 4-$CF_3Ph$- | 270.6-271.6 |
| 1286 | —H | 4-$CF_3Ph$- | 256.8-259.5 |

TABLE 156
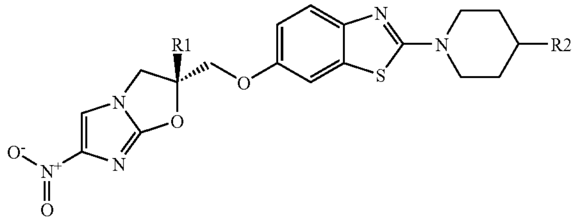
| Example | R1 | R2 | mp(° C.) |
|---|---|---|---|
| 1287 | —$CH_3$ | 4-$CF_3$OPhO— | 223.8-225.6 |
| 1288 | —$CH_3$ | 4-$CF_3$OPh$CH_2$— | 168.3-171.2 |
| 1289 | —$CH_3$ | 4-ClPhN($C_2H_5$)— | 119.9-122.0 |
| 1290 | —H | 4-$CF_3$PhO— | 199.7-202.0 |
| 1291 | —$CH_3$ | 4-ClPhN($CH_3$)— | 147.8-150.7 |
| 1292 | —H | 4-ClPhN($CH_3$)— | 128.4-130.9 |
TABLE 157
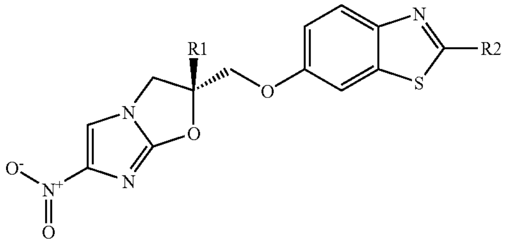
| Example | R1 | R2 | mp(° C.) |
|---|---|---|---|
| 1293 | —$CH_3$ | 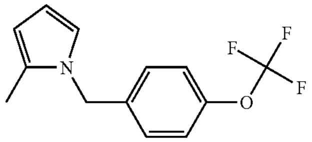 | 241.2-243.2 |
TABLE 157-continued
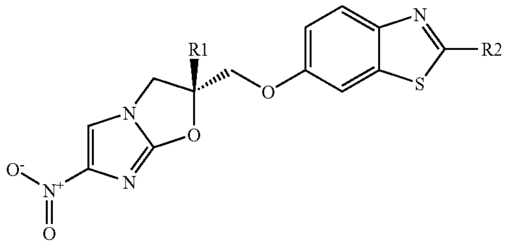
| Example | R1 | R2 | mp(° C.) |
|---|---|---|---|
| 1294 | —$CH_3$ | 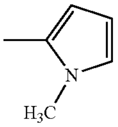 | 210.2-211.4 |
| 1295 | —$CH_3$ | 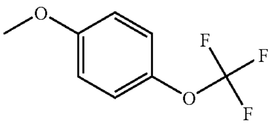 | 160.9-163.7 |
| 1296 | —$CH_3$ | 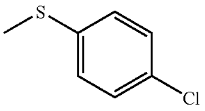 | 143.2-145.1 |
TABLE 158
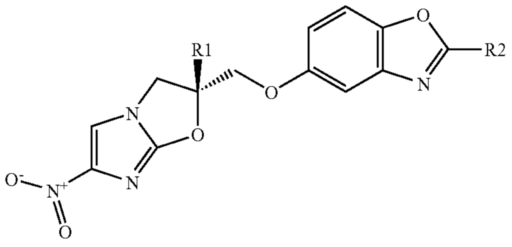
| Example | R1 | R2 | mp(° C.) |
|---|---|---|---|
| 1297 | —$CH_3$ | 4-$CF_3$Ph- | 252.5-255.6 |
| 1298 | —$CH_3$ | 4-$CF_3$OPh- | 242.7-243.1 |
| 1299 | —H | 4-$CF_3$OPh- | |
| 1300 | —$CH_3$ | 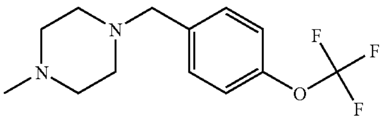 | 136.6-139.0 |

TABLE 158-continued
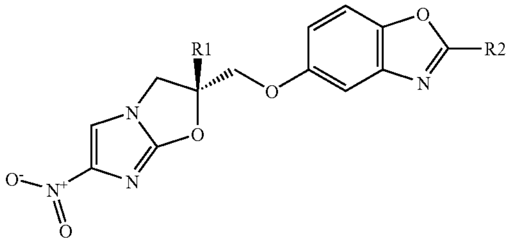
| Example | R1 | R2 | mp(° C.) |
|---|---|---|---|
| 1301 | —$CH_3$ | 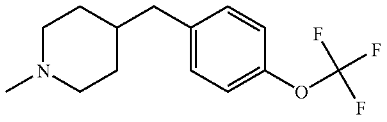 | 138.6-141.3 |
| 1302 | —H | 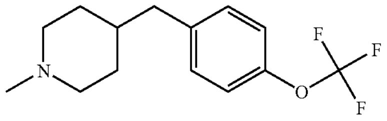 | 184.1-186.2 |
| 1303 | —$CH_3$ | 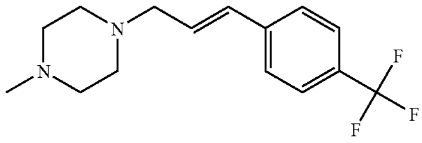 | 191.0-193.2 |
| 1304 | —$CH_3$ | 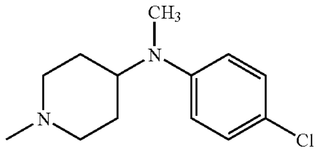 | 196.8-199.3 |
| 1305 | —H | 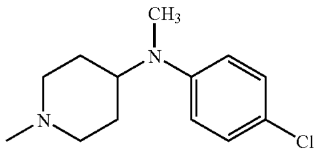 | 176.4-179.4 |
TABLE 159
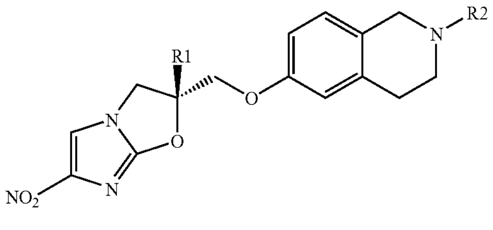
| Example | R1 | R2 | mp(° C.) |
|---|---|---|---|
| 1306 | —$CH_3$ | 4-$CF_3OPhCH_2$— | 151.1-154.1 |
| 1307 | —$CH_3$ | 4-$ClPhCH_2$— | 180.9-183.1 |
| 1308 | —$CH_3$ | 4-$CF_3OPh$- | 190.4-192.8 |

TABLE 160
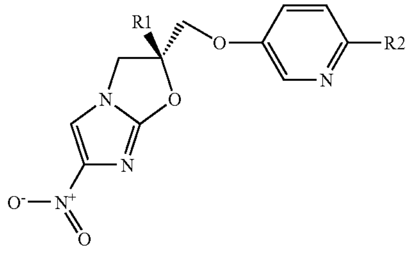
| Example | R1 | R2 | mp(° C.) |
|---|---|---|---|
| 1309 | —H | 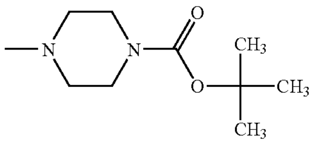 | 231.8-233.0 |
| 1310 | —$CH_3$ | 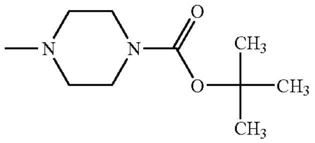 | 225.4-226.9 |
| 1311 | —H | 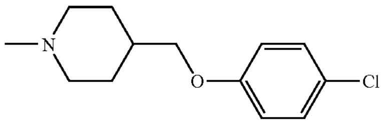 | 188.5-191.0 |
TABLE 161
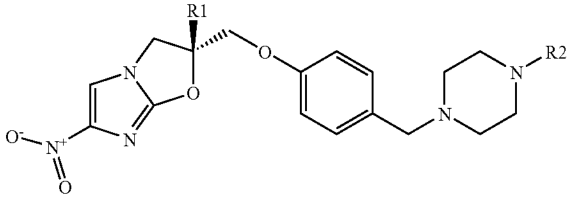
| Example | R1 | R2 | mp(° C.) |
|---|---|---|---|
| 1312 | —$CH_3$ | 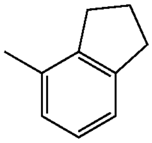 | 162.7-165.1 |
| 1313 | —$CH_3$ | 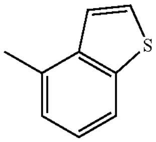 | 132.4-134.7 |

TABLE 162
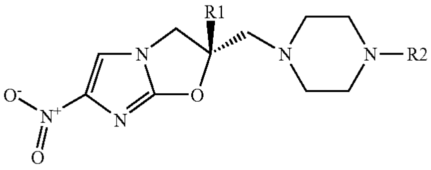
| Example | R1 | R2 | mp(° C.) |
|---|---|---|---|
| 1314 | $—CH_3$ | $4-CF_3PhCH{=}CHCH_2—$ | 152-153 |
| 1315 | $—CH_3$ | $4-(4-CF_3OPhO)PhCH_2—$ | 127.4-129.2 |
| 1316 | $—CH_3$ | $4-CF_3OPhO(CH_2)_2—$ | 121.6-122.2 |
| 1317 | $—CH_3$ | $4-ClPhO(CH_2)_2—$ | 121.8 dec |
| 1318 | $—CH_3$ | $3,4-Cl_2PhO(CH_2)_2—$ | 96.5-98.2 |
| 1319 | $—CH_3$ | 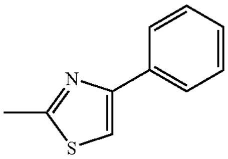 | 240-242 |
| 1320 | $—CH_3$ | 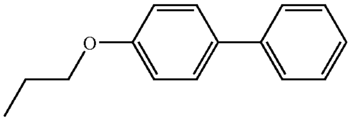 | 170.5 dec |
| 1321 | $—CH_3$ | 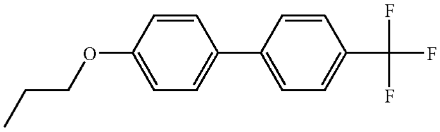 | 177.2 dec |
| 1322 | $—CH_3$ | 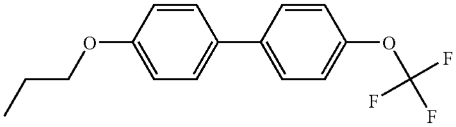 | 175.1-176.7 |
TABLE 163
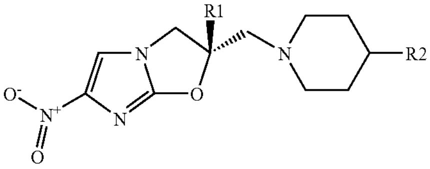
| Example | R1 | R2 | mp (° C.) |
|---|---|---|---|
| 1323 | $—CH_3$ | 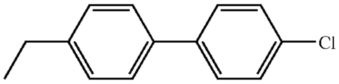 | 185.0-187.2 |
TABLE 163-continued
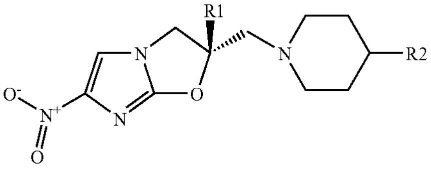
| Example | R1 | R2 | mp (° C.) |
|---|---|---|---|
| 1324 | $—CH_3$ | 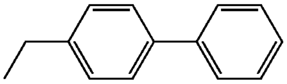 | 157.7-159.1 |

TABLE 164
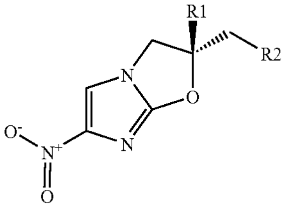
| Example | R1 | R2 | mp(° C.) |
|---|---|---|---|
| 1325 | —$CH_3$ | 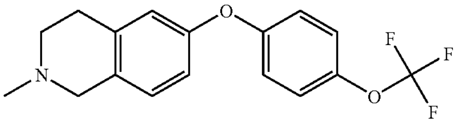 | 123.8-125.3 |
| 1326 | —$CH_3$ | 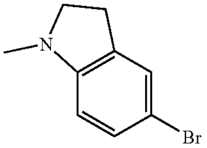 | 229.4-232.0 |
| 1327 | —$CH_3$ | 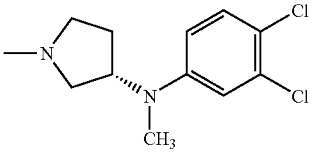 | 161.6-162.4 |
TABLE 165
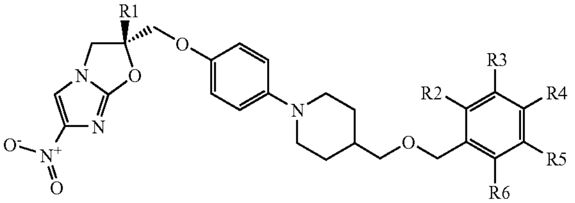
| Example | R1 | R2 | R3 | R4 | R5 | R6 | MS(M + 1) |
|---|---|---|---|---|---|---|---|
| 1328 | —$CH_3$ | —H | —H | —$OCH_3$ | —Cl | —H | 543 |
| 1329 | —$CH_3$ | —H | —H | —$CH_3$ | —$CH_3$ | —H | 507 |
| 1330 | —$CH_3$ | —H | —H | —$OCH_2C_6H_5$ | —H | —H | 585 |
| 1331 | —$CH_3$ | —$CH_3$ | —H | —$CH_3$ | —H | —$CH_3$ | 521 |
| 1332 | —$CH_3$ | —$CH_3$ | —H | —$CH_3$ | —$CH_3$ | —H | 521 |
| 1333 | —$CH_3$ | —H | —H | —CH═$CHC_6H_5$(trans) | —H | —H | 581 |
TABLE 166
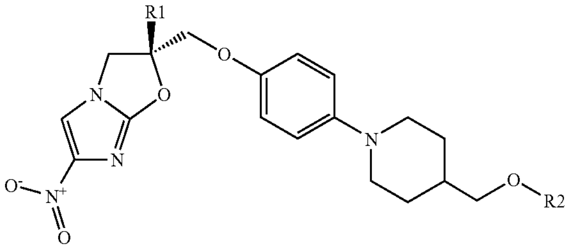
| Example | R1 | R2 | MS (M + 1) |
|---|---|---|---|
| 1334 | —$CH_3$ | 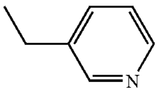 | 480 |
TABLE 166-continued
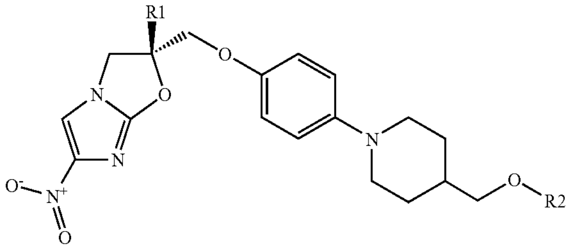
| Example | R1 | R2 | MS (M + 1) |
|---|---|---|---|
| 1335 | —$CH_3$ | 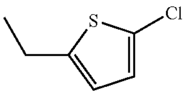 | 519 |

TABLE 166-continued

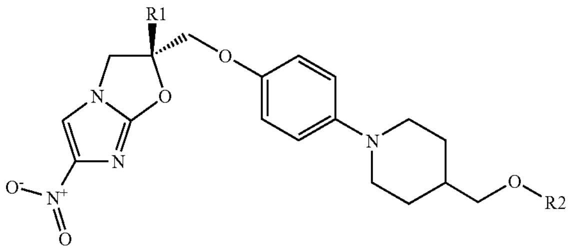

| Example | R1 | R2 | MS (M + 1) |
|---|---|---|---|
| 1336 | —$CH_3$ | 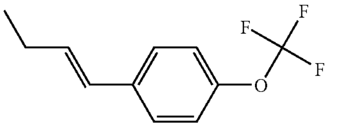 | 589 |
| 1337 | —$CH_3$ | 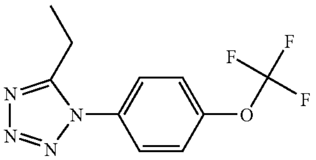 | 631 |
| 1338 | —$CH_3$ | 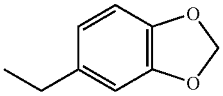 | 523 |
| 1339 | —$CH_3$ | 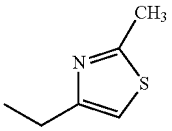 | 500 |
| 1340 | —$CH_3$ | 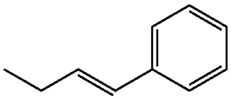 | 505 |
| 1341 | —$CH_3$ | 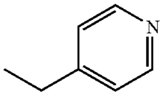 | 480 |

TABLE 167

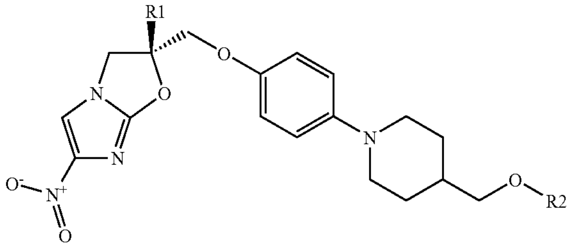

| Example | R1 | R2 | MS(M + 1) |
|---|---|---|---|
| 1342 | —$CH_3$ | 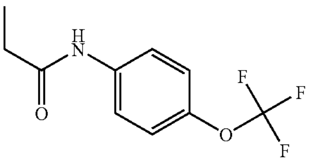 | 606 |

TABLE 167-continued

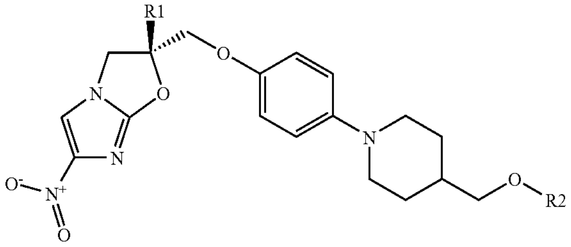

| Example | R1 | R2 | MS(M + 1) |
|---|---|---|---|
| 1343 | —$CH_3$ | 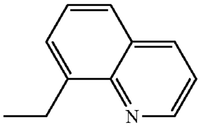 | 530 |
| 1344 | —$CH_3$ | 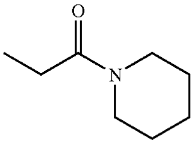 | 514 |

TABLE 168

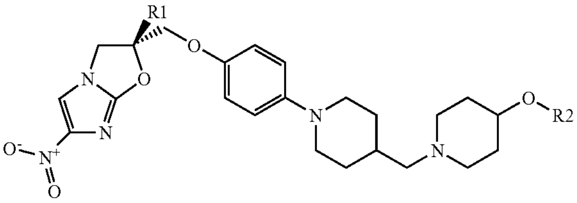

| Example | R1 | R2 | MS (M + 1) |
|---|---|---|---|
| 1345 | —$CH_3$ | 4-$CH_3$OPh— | 578 |
| 1346 | —$CH_3$ | 4-ClPh— | 582 |
| 1347 | —$CH_3$ | 3,4-$Cl_2$Ph— | 616 |
| 1348 | —$CH_3$ | 4-$CF_3$Ph— | 616 |
| 1349 | —$CH_3$ | 4-$CF_3$OPh— | 632 |
| 1350 | —$CH_3$ | 4-ClPh$CH_2$— | 596 |
| 1351 | —$CH_3$ | 4-$CF_3$Ph$CH_2$— | 630 |
| 1352 | —$CH_3$ | 4-$CH_3$Ph$CH_2$— | 576 |
| 1353 | —$CH_3$ | 4-$CF_3$OPh$CH_2$— | 646 |
| 1354 | —$CH_3$ | 3-$CH_3$OPh$CH_2$— | 592 |
| 1355 | —$CH_3$ | 3,4-$Cl_2$Ph$CH_2$— | 630 |

TABLE 169

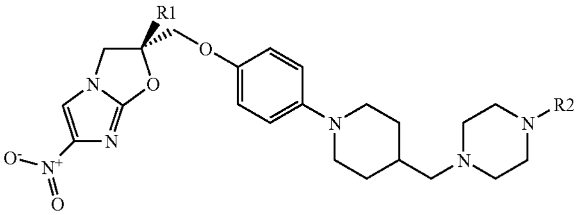

| Example | R1 | R2 | MS (M + 1) |
|---|---|---|---|
| 1356 | —$CH_3$ | 4-ClPh— | 567 |
| 1357 | —$CH_3$ | 4-$CH_3$OPh— | 563 |
| 1358 | —$CH_3$ | 4-$CF_3$Ph— | 601 |
| 1359 | —$CH_3$ | 4-$CH_3$Ph— | 547 |
| 1360 | —$CH_3$ | 3,4-$Cl_2$Ph— | 601 |
| 1361 | —$CH_3$ | 4-$CF_3$OPh— | 617 |

TABLE 170
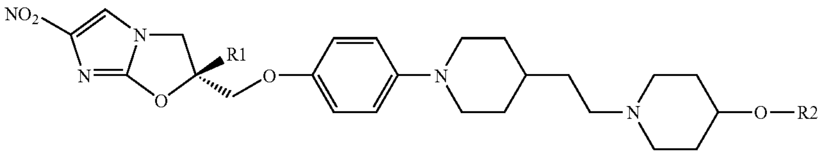
| Example | R1 | R2 | MS (M + 1) |
|---|---|---|---|
| 1362 | —$CH_3$ | 4-$CH_3$OPh— | 592 |
| 1363 | —$CH_3$ | 4-ClPh— | 596 |
| 1364 | —$CH_3$ | 3,4-$Cl_2$Ph— | 630 |
| 1365 | —$CH_3$ | 4-$CH_3$Ph— | 576 |
| 1366 | —$CH_3$ | 4-$CF_3$Ph— | 630 |
| 1367 | —$CH_3$ | 4-ClPh$CH_2$— | 610 |
| 1368 | —$CH_3$ | 4-$CF_3$Ph$CH_2$— | 644 |
| 1369 | —$CH_3$ | 4-$CF_3$OPh$CH_2$— | 660 |
| 1370 | —$CH_3$ | 3-$CH_3$OPh$CH_2$— | 606 |
| 1371 | —$CH_3$ | 3,4-$Cl_2$Ph$CH_2$— | 644 |
TABLE 171
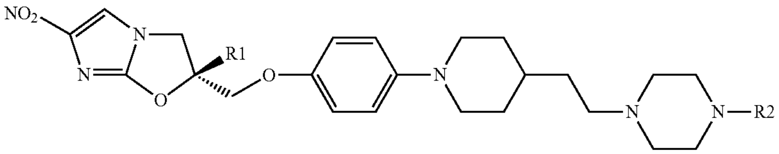
| Example | R1 | R2 | MS (M + 1) |
|---|---|---|---|
| 1372 | —$CH_3$ | 4-ClPh— | 581 |
| 1373 | —$CH_3$ | 4-$CF_3$Ph— | 615 |
| 1374 | —$CH_3$ | 4-$CH_3$Ph— | 561 |
| 1375 | —$CH_3$ | 3,4-$Cl_2$Ph— | 615 |
| 1376 | —$CH_3$ | 4-$CF_3$OPh— | 631 |
TABLE 172
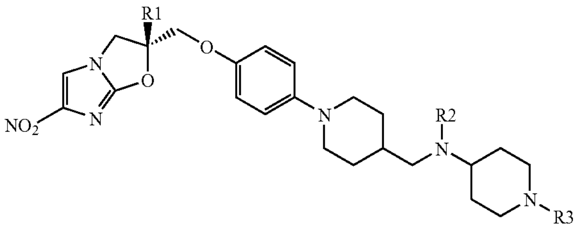
| Example | R1 | R2 | R3 | MS (M + 1) |
|---|---|---|---|---|
| 1377 | —$CH_3$ | —$CH_3$ | 4-$CF_3$OPh— | 645 |
| 1378 | —$CH_3$ | —$CH_3$ | 4-$CF_3$Ph— | 629 |
| 1379 | —$CH_3$ | —$CH_3$ | 4-$CH_3$Ph— | 575 |
| 1380 | —$CH_3$ | —$CH_3$ | 3,4-$Cl_2$Ph— | 629 |

TABLE 173
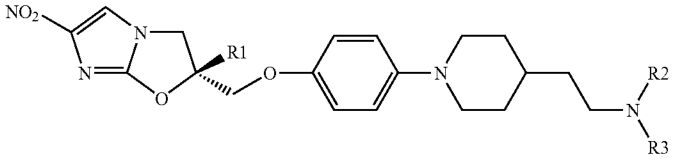
| Example | R1 | R2 | R3 | MS (M + 1) |
|---|---|---|---|---|
| 1381 | —$CH_3$ | —$CH_3$ | 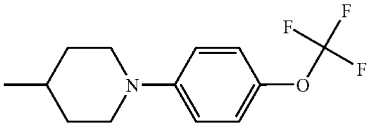 | 659 |
| 1382 | —$CH_3$ | —$CH_3$ | 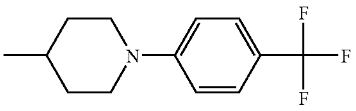 | 643 |
| 1383 | —$CH_3$ | —$CH_3$ | 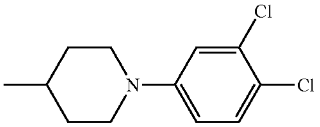 | 643 |
TABLE 174
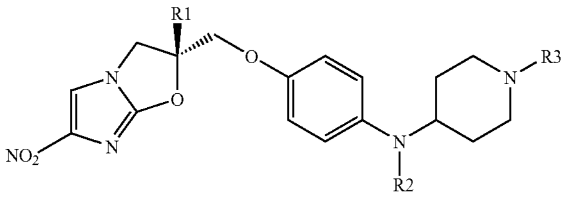
| Example | R1 | R2 | R3 | MS (M + 1) |
|---|---|---|---|---|
| 1384 | —$CH_3$ | —$CH_3$ | 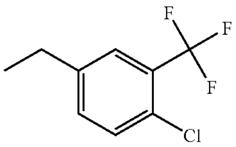 | 580 |
| 1385 | —$CH_3$ | —$CH_3$ | 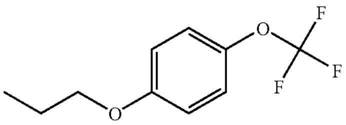 | 592 |
| 1386 | —$CH_3$ | —$CH_3$ | 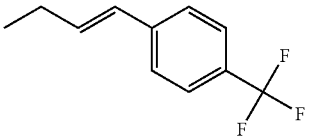 | 572 |
| 1387 | —$CH_3$ | —$CH_3$ | 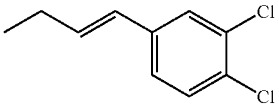 | 572 |

TABLE 174-continued
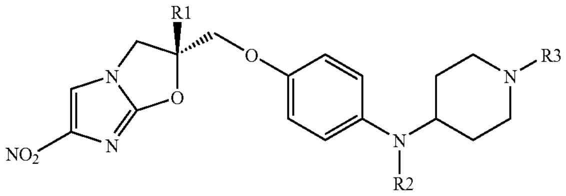
| Example | R1 | R2 | R3 | MS (M + 1) |
|---|---|---|---|---|
| 1388 | —$CH_3$ | —$CH_3$ | 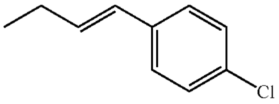 | 538 |
| 1389 | —$CH_3$ | —$CH_3$ | 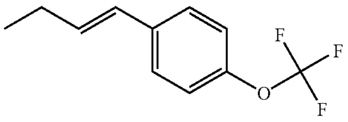 | 588 |
| 1390 | —$CH_3$ | —$CH_3$ | 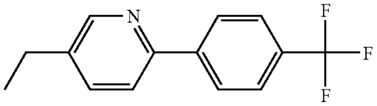 | 623 |
| 1391 | —$CH_3$ | —$CH_3$ | 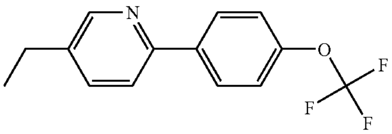 | 639 |
| 1392 | —$CH_3$ | —$CH_3$ | 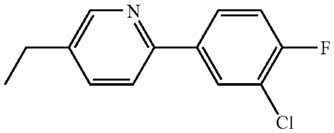 | 607 |
| 1393 | —$CH_3$ | —$CH_3$ | 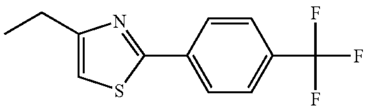 | 629 |
TABLE 175
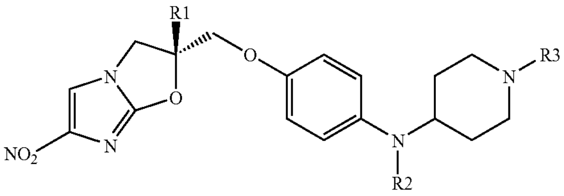
| Example | R1 | R2 | R3 | MS (M + 1) |
|---|---|---|---|---|
| 1394 | —$CH_3$ | —$CH_3$ | 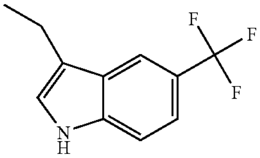 | 585 |

TABLE 175-continued
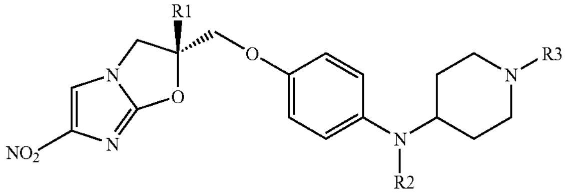
| Example | R1 | R2 | R3 | MS (M + 1) |
|---|---|---|---|---|
| 1395 | —$CH_3$ | —$CH_3$ | 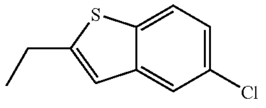 | 568 |
| 1396 | —$CH_3$ | —$CH_3$ | 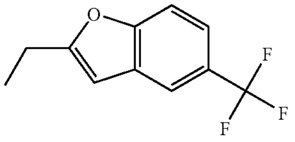 | 586 |
| 1397 | —$CH_3$ | —$CH_3$ | 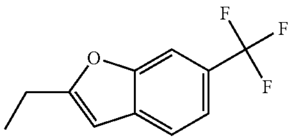 | 586 |
| 1398 | —$CH_3$ | —$CH_3$ | 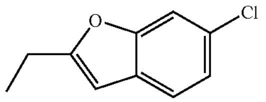 | 552 |
| 1399 | —$CH_3$ | —$CH_3$ | 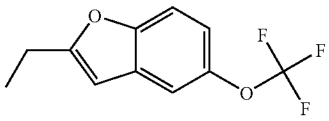 | 602 |
| 1400 | —$CH_3$ | —$CH_3$ | 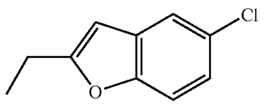 | 552 |
| 1401 | —$CH_3$ | —$CH_3$ | 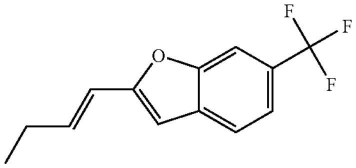 | 612 |
| 1402 | —$CH_3$ | —$CH_3$ | 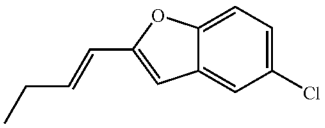 | 578 |

TABLE 176
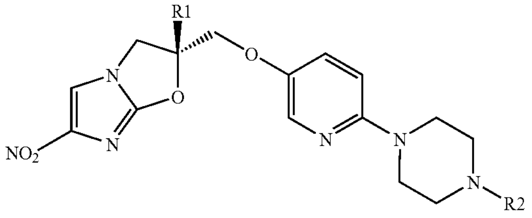
| Example | R1 | R2 | MS (M + 1) |
|---|---|---|---|
| 1403 | —$CH_3$ | 4-$CF_3$PhCH═CHCH$_2$— | 545 |
| 1404 | —$CH_3$ | 3,4-$Cl_2$PhCH═CHCH$_2$— | 545 |
| 1405 | —$CH_3$ | 4-ClPhCH═CHCH$_2$— | 511 |
| 1406 | —$CH_3$ | 4-$CF_3$OPhCH═CHCH$_2$— | 561 |
| 1407 | —$CH_3$ | 4-$CF_3$OPhO$(CH_2)_2$— | 565 |
| 1408 | —$CH_3$ | 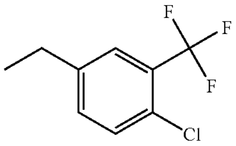 | 553 |
| 1409 | —$CH_3$ | 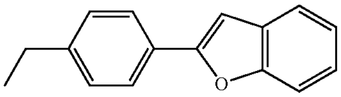 | 567 |
| 1410 | —$CH_3$ | 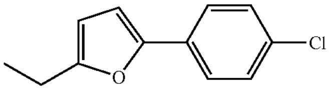 | 551 |
| 1411 | —$CH_3$ | 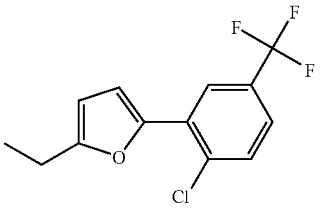 | 619 |
| 1412 | —$CH_3$ | 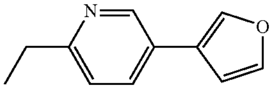 | 518 |
| 1413 | —$CH_3$ | 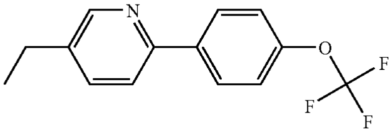 | 612 |
| 1414 | —$CH_3$ | 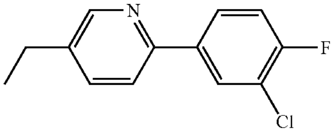 | 580 |
| 1415 | —$CH_3$ | 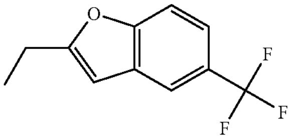 | 559 |

TABLE 177
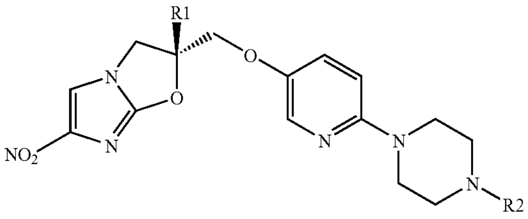
| Example | R1 | R2 | MS (M + 1) |
|---|---|---|---|
| 1416 | —$CH_3$ | 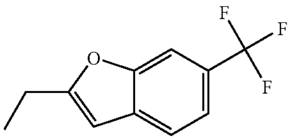 | 559 |
| 1417 | —$CH_3$ | 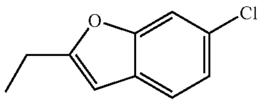 | 525 |
| 1418 | —$CH_3$ | 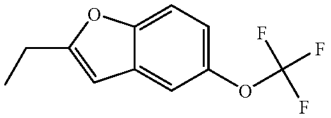 | 575 |
| 1419 | —$CH_3$ | 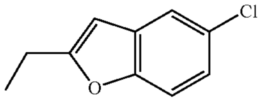 | 525 |
| 1420 | —$CH_3$ | 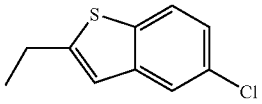 | 541 |
| 1421 | —$CH_3$ | 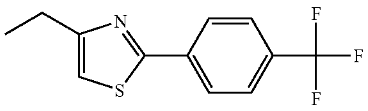 | 602 |
| 1422 | —$CH_3$ | 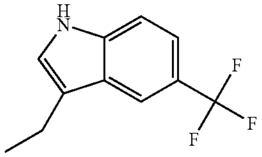 | 558 |
| 1423 | —$CH_3$ | 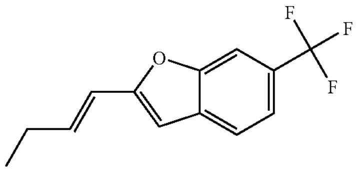 | 585 |
| 1424 | —$CH_3$ | 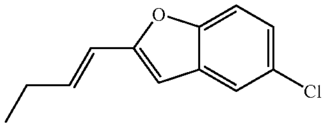 | 551 |

TABLE 178
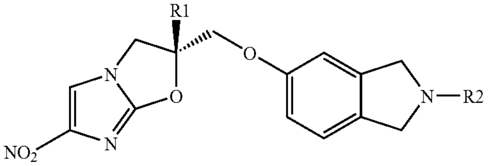
| Example | R1 | R2 | MS (M + 1) |
|---|---|---|---|
| 1425 | —$CH_3$ | 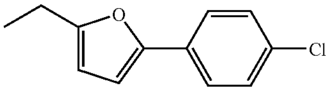 | 507 |
| 1426 | —$CH_3$ | 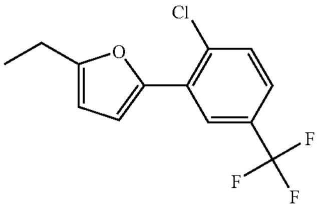 | 575 |
| 1427 | —$CH_3$ | 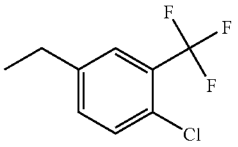 | 509 |
| 1428 | —$CH_3$ | 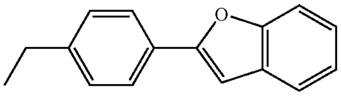 | 523 |
| 1429 | —$CH_3$ | 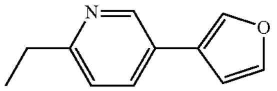 | 474 |
| 1430 | —$CH_3$ | 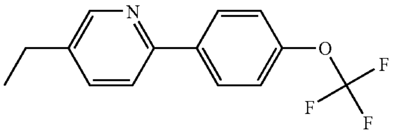 | 568 |
| 1431 | —$CH_3$ | 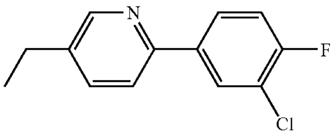 | 536 |
| 1432 | —$CH_3$ | 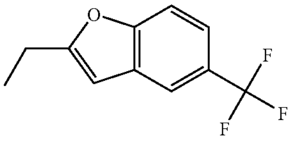 | 515 |
| 1433 | —$CH_3$ | 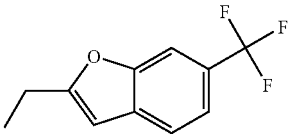 | 515 |
| 1434 | —$CH_3$ | 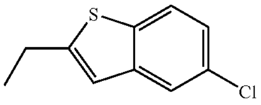 | 497 |

TABLE 179
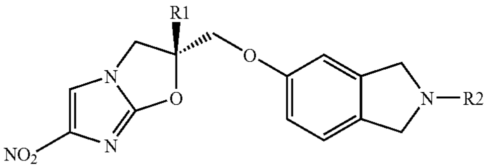
| Example | R1 | R2 | MS (M + 1) |
|---|---|---|---|
| 1435 | —$CH_3$ | 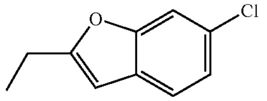 | 481 |
| 1436 | —$CH_3$ | 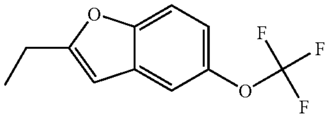 | 531 |
| 1437 | —$CH_3$ | 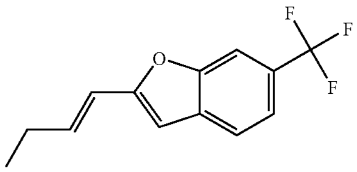 | 541 |
| 1438 | —$CH_3$ | 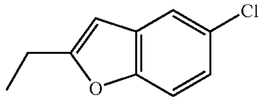 | 481 |
| 1439 | —$CH_3$ | 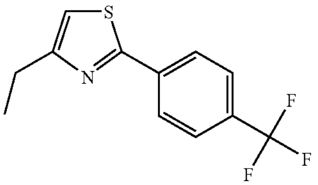 | 558 |
| 1440 | —$CH_3$ | 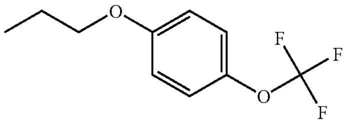 | 521 |
TABLE 180
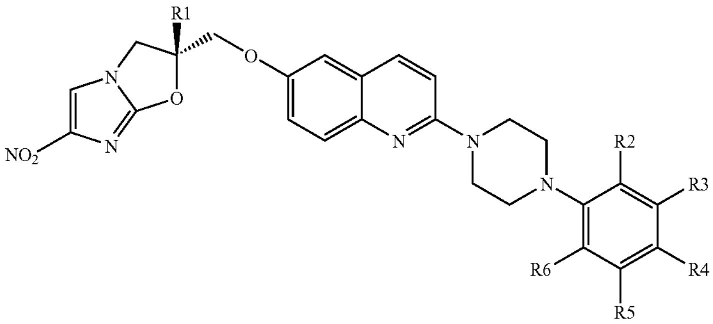
| Example | R1 | R2 | R3 | R4 | R5 | R6 | MS (M + 1) |
|---|---|---|---|---|---|---|---|
| 1441 | —$CH_3$ | —H | —H | —$OCH_3$ | —H | —H | 517 |
| 1442 | —$CH_3$ | —H | —H | —$CH_3$ | —$CH_3$ | —H | 515 |
| 1443 | —$CH_3$ | —H | —H | —F | —H | —H | 505 |

TABLE 180-continued
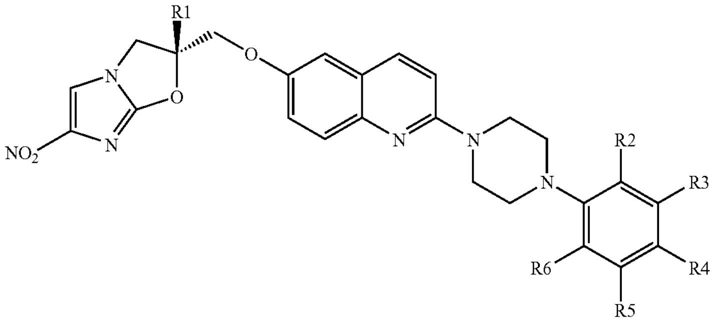
| Example | R1 | R2 | R3 | R4 | R5 | R6 | MS (M + 1) |
|---|---|---|---|---|---|---|---|
| 1444 | —$CH_3$ | —H | —H | —$CF_3$ | —H | —H | 555 |
| 1445 | —$CH_3$ | —H | —H | —$CH_3$ | —H | —H | 501 |
| 1446 | —$CH_3$ | —H | —H | —Cl | —Cl | —H | 555 |
| 1447 | —$CH_3$ | —H | —H | —$OCF_3$ | —H | —H | 571 |
| 1448 | —$CH_3$ | —H | —H | 4-ClPhO— | —H | —H | 613 |
TABLE 181
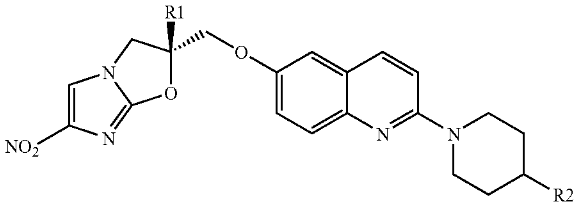
| Example | R1 | R2 | MS (M + 1) |
|---|---|---|---|
| 1449 | —$CH_3$ | 4-$CH_3$OPh— | 516 |
| 1450 | —$CH_3$ | 3,4-$Cl_2PhCH_2$— | 568 |
| 1451 | —$CH_3$ | 3,4-$Cl_2PhCH_2O$— | 584 |
| 1452 | —$CH_3$ | 4-$CH_3PhCH_2O$— | 530 |
| 1453 | —$CH_3$ | 4-$CF_3OPhCH_2O$— | 600 |
| 1454 | —$CH_3$ | 4-$ClPhCH_2O$— | 550 |
| 1455 | —$CH_3$ | 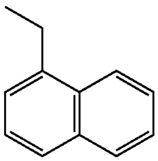 | 550 |
| 1456 | —$CH_3$ | 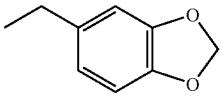 | 544 |
| 1457 | —$CH_3$ | 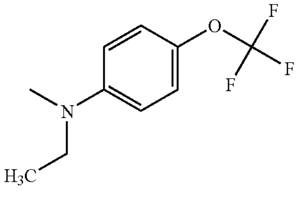 | 613 |
TABLE 181-continued
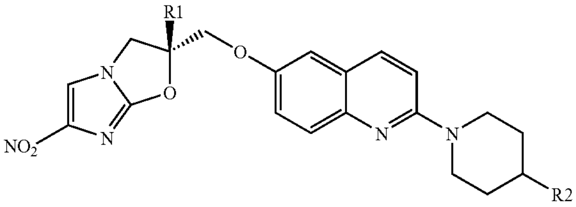
| Example | R1 | R2 | MS (M + 1) |
|---|---|---|---|
| 1458 | —$CH_3$ | 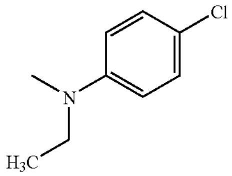 | 563 |
| 1459 | —$CH_3$ | 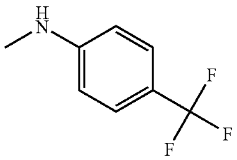 | 569 |
| 1460 | —$CH_3$ | 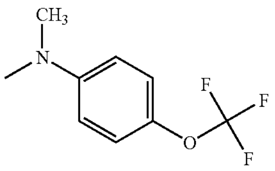 | 599 |

TABLE 182

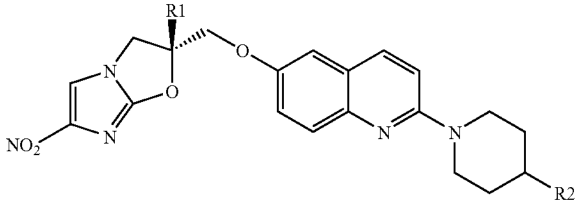

| Example | R1 | R2 | MS (M + 1) |
| --- | --- | --- | --- |
| 1461 | —$CH_3$ | 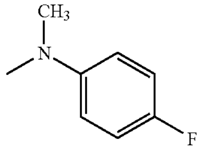 | 533 |
| 1462 | —$CH_3$ | 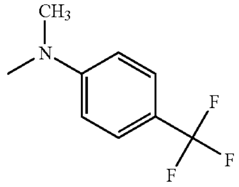 | 583 |

Example 1463

(R)-2-(4-(4-(4-chlorophenyl)oxazol-2-yl)phenoxymethyl)-2-methyl-6-nitro-2,3-dihydroimidazo[2,1-b]oxazole 1.73 g (7.9 mmol) of (R)-2-chloro-1-(2-methyl-2-oxyranylmethyl)-4-nitro-1H-imidazole, 1.80 g (6.6 mmol) of 4-(4-(4-chlorophenyl)oxazol-2-yl)phenol, and 0.42 g (2.0 mmol) of potassium phosphate were suspended in 15 ml of ethanol, and the mixture was heated under reflux with stirring for 3 hours in an argon atmosphere. The reaction solution was concentrated, and dichloromethane was then added to the residue to precipitate non-soluble product, which was then filtered off. The filtrate was concentrated, and the residue was dissolved in 20 ml of DMF to give a solution. 0.29 g (7.3 mmol) of 60% sodium hydride was added to the solution while cooled by ice, and the obtained mixture was stirred for 6 hours. Thereafter, the solvent was removed under a reduced pressure, and 100 ml of acetone and 10 ml of silica gel were added to the residue, followed by concentration. The residue was purified by silica gel column chromatography (dichloromethane:methanol=50:1 to 30:1), and the resultant product was crystallized from a mixed solvent consisting of dichloromethane and ethanol. The resultant product was then recrystallized from a mixed solvent consisting of acetone and water to obtain 1.15 g (yield: 38%) of light brown powders, (R)-2-(4-(4-(4-chlorophenyl)oxazol-2-yl)phenoxymethyl)-2-methyl-6-nitro-2,3-dihydroimidazo[2,1-b]oxazole.

Melting point: 248.8° C.-251.5° C.

Example 1464

6-((R)-2-methyl-6-nitro-2,3-dihydroimidazo[2,1-b]oxazol-2-ylmethoxy)-2-(4-(4-trifluoromethoxybenzyl)piperidin-1-yl)quinoline 0.65 g of (R)-2-chloro-1-(2-methyl-2-oxyranylmethyl)-4-nitro-1H-imidazole, 1.00 g of 6-hydroxy-2-(4-(4-trifluoromethoxybenzyl)piperidin-1-yl)quinoline, and 0.16 g of potassium phosphate were suspended in 10 ml of ethanol, and the mixture was heated under reflux with stirring for 4 hours in an argon atmosphere. The reaction solution was concentrated, and the residue was purified by silica gel column chromatography (from hexane:ethyl acetate=1:3 to ethyl acetate). The resultant product was concentrated, the residue was then dissolved in DMF (10 ml), and 99 mg of sodium hydride was then added thereto. The mixture was stirred at room temperature for 1 hour. Thereafter, water was added to the reaction solution, and repeated extraction was then carried out with ethyl acetate. The combined organic layer was washed with water and then with a saturated aqueous solution of sodium chloride, and then dried over sodium sulfate. The sodium sulfate was filtered off, and the filtrate was concentrated under a reduced pressure. The residue was purified by silica gel column chromatography (hexane:ethyl acetate from 1:1 to 1:3). The resultant product was recrystallized from ethanol to obtain 0.57 g (yield: 36%) of light yellow powdery crystals, 6-((R)-2-methyl-6-nitro-2,3-dihydroimidazo[2,1-b]oxazol-2-ylmethoxy)-2-(4-(4-trifluoromethoxybenzyl)piperidin-1-yl)quinoline.

Melting point: 184.9° C.-185.9° C.

Example 1465

6-((R)-2-methyl-6-nitro-2,3-dihydroimidazo[2,1-b]oxazol-2-ylmethoxy)-2-(4-(4-trifluoromethoxybenzyliden)piperidin-1-yl)quinoline 0.66 g of (R)-2-chloro-1-(2-methyl-2-oxyranylmethyl)-4-nitro-1H-imidazole, 0.94 g of 6-hydroxy-2-(4-(4-trifluoromethoxybenzyliden)-piperidin-1-yl)quinoline, and 0.15 g of potassium phosphate were suspended in 10 ml of ethanol, and the mixture was heated under reflux with stirring for 6 hours in an argon atmosphere. The reaction solution was concentrated, and the residue was purified by silica gel column chromatography (from hexane:ethyl acetate 1:3 to ethyl acetate). The resultant product was concentrated, the residue was then dissolved in DMF (10 ml), and 99 mg of sodium hydride was then added thereto. The mixture was stirred at room temperature for 3 hours. Thereafter, ethyl acetate was added to the reaction solution, and the mixture was then concentrated under a reduced pressure. The residue was purified by silica gel column chromatography (dichloromethane:methanol=50:1). The resultant product was recrystallized from ethanol to obtain 1.37 g (yield: 51%) of yellow powdery crystals, 6-((R)-2-methyl-6-nitro-2,3-dihydroimidazo[2,1-b]oxazol-2-ylmethoxy)-2-(4-(4-trifluoromethoxybenzyliden)piperidin-1-yl)quinoline.

Melting point: 193.9° C.-195.9° C.

Example 1466

(R)-2-methyl-6-nitro-2-(6-(4-(4-trifluoromethoxyphenoxy)piperidin-1-yl)naphthalene-2-yloxymethyl)-2,3-dihydroimidazo[2,1-b]oxazole 2.12 g of (R)-2-chloro-1-(2-methyl-2-oxyranylmethyl)-4-nitro-1H-imidazole, 3.02 g of 6-(4-(4-trifluoromethoxyphenoxy)piperidin-1-yl)naphthalene-2-ol, and 0.48 g of potassium phosphate were suspended in 30 ml of ethanol, and the mixture was heated under reflux with stirring for 6 hours in a nitrogen atmosphere. Thereafter, water was added to the reaction solution, and repeated extraction was carried out with dichloromethane. The combined organic layer was washed with a saturated aqueous solution of sodium chloride and then dried over anhydrous magnesium sulfate, followed by concentration. The residue was purified by silica gel column chromatography (from hexane:ethyl acetate=1:3 to ethyl acetate). The resultant product was concentrated to obtain 2.73 g of yellow powders. The obtained powders were dissolved in DMF (27 ml), and 0.21 g of sodium hydride was then added thereto, followed by stirring at room temperature for 2.5 hours. Thereafter, a saturated aqueous solution of sodium chloride was added to the reaction solution, and repeated extraction was then carried out with dichloromethane. The combined organic layer was washed with water and then with a saturated aqueous solution of sodium chloride, and then dried over anhydrous magnesium sulfate. The magnesium sulfate was filtered, and the filtrate was concentrated under a reduced pressure. The residue was purified by silica gel column chromatography (dichloromethane:ethyl acetate=4:1). The resultant product was recrystallized from a mixed solvent consisting of dichloromethane, ethyl acetate, and diisopropyl ether to obtain 1.05 g (yield: 24%) of light yellow powdery crystals, (R)-2-methyl-6-nitro-2-(6-(4-(4-trifluoromethoxyphenoxy)piperidin-1-yl)naphthalene-2-yloxymethyl)-2,3-dihydroimidazo[2,1-b]oxazole.

Melting point: 204.8° C.-207.9° C.

Example 1467

(R)-2-methyl-6-nitro-2-(4-(4-(4-trifluoromethoxybenzyloxy)piperidin-1-yl)phenoxymethyl)-2,3-dihydroimidazo[2,1-b]oxazole 0.305 g of 4-(4-(4-trifluoromethoxybenzyloxy)piperidin-1-yl)phenol was dissolved in DMF (5 ml), and 10 mg of sodium hydride was added thereto, followed by stirring at 70° C. to 80° C. for 20 minutes. Thereafter, 0.252 g of (R)-2-chloro-1-(2-methyl-2-oxyranylmethyl)-4-nitro-1H-imidazole was added to the reaction solution while cooled by ice, followed by stirring at 70° C. to 80° C. for 20 minutes. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over sodium sulfate. The sodium sulfate was filtered off, and the filtrate was concentrated under a reduced pressure. The residue was purified by silica gel column chromatography (from hexane:ethyl acetate=1:3 to ethyl acetate). The resultant product was recrystallized from a mixed solvent consisting of dichloromethane and ethyl acetate to obtain 88 mg (26.7%) of colorless powdery crystals, (R)-2-methyl-6-nitro-2-(4-(4-(4-trifluoromethoxybenzyloxy)piperidin-1-yl)phenoxymethyl)-2,3-dihydroimidazo[2,1-b]oxazole.

Melting point: 214.3° C.-217.7° C.

Example 1468

(R)-2-methyl-6-nitro-2-(4-(4-(4-trifluoromethylbenzyloxy)piperidin-1-yl)phenoxymethyl)-2,3-dihydroimidazo[2,1-b]oxazole 0.217 g of 4-(4-(4-trifluoromethylbenzyloxy)piperidin-1-yl)phenol was dissolved in DMF (5 ml), and 27 mg of sodium hydride was added thereto, followed by stirring at 70° C. to 80° C. for 20 minutes. Thereafter, 0.188 g of (R)-2-chloro-1-(2-methyl-2-oxyranylmethyl)-4-nitro-1H-imidazole was added to the reaction solution while cooled by ice, followed by stirring at 70° C. to 80° C. for 20 minutes. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over sodium sulfate. The sodium sulfate was filtered off, and the filtrate was concentrated under a reduced pressure. The residue was purified by silica gel column chromatography (from hexane: ethyl acetate=1:3 to ethyl acetate). The resultant product was recrystallized from a mixed solvent consisting of dichloromethane and ethyl acetate to obtain 88 mg (26.7%) of light yellow powders, (R)-2-methyl-6-nitro-2-(4-(4-(4-trifluoromethylbenzyloxy)piperidin-1-yl)phenoxymethyl)-2,3-dihydroimidazo[2,1-b]oxazole.

Melting point: 217.4° C.-219.7° C.

Example 1469

(R)-2-methyl-6-nitro-2-(4-(4-(4-trifluoromethoxybenzyl)piperidin-1-yl)phenoxymethyl)-2,3-dihydroimidazo[2,1-b]oxazole 8.41 g of 4-(4-(4-trifluoromethoxybenzyl)piperidin-1-yl)phenol was dissolved in DMF (84 ml), and 1.05 g of sodium hydride was added thereto, followed by stirring at 70° C. to 80° C. for 20 minutes. Thereafter, 7.29 g of (R)-2-chloro-1-(2-methyl-2-oxyranylmethyl)-4-nitro-1H-imidazole was added to the reaction solution while cooled by ice, followed by stirring at 70° C. to 80° C. for 20 minutes. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over sodium sulfate. The sodium sulfate was filtered off, and the filtrate was concentrated under a reduced pressure. The residue was purified by silica gel column chromatography (dichloromethane:ethyl acetate=9:1). The resultant product was recrystallized from a mixed solvent consisting of dichloromethane and ethyl acetate to obtain 4.65 g (36.5%) of light yellow powders, (R)-2-methyl-6-nitro-2-(4-(4-(4-trifluoromethoxybenzyl)piperidin-1-yl)phenoxymethyl)-2,3-dihydroimidazo[2,1-b]oxazole.

$^1$H-NMR ($CDCl_3$) δ ppm 1.23-1.52 (2H, m), 1.52-1.66 (3H, m), 1.66-1.89 (3H, m), 2.43-2.70 (4H, m), 3.50 (2H, d, J=12.1 Hz), 3.91-4.09 (2H, m), 4.16 (1H, d, J=10.1 Hz), 4.48 (1H, d, J=10.2 Hz), 6.66-6.81 (2H, m), 6.81-6.95 (2H, m), 7.05-7.23 (4H, m), 7.54 (1H, s)

Melting point: 210.9° C.-212.4° C.

$(\alpha)_D$=−9.0 deg. (c=1.0, $CHCl_3$)

Example 1470

(R)-2-(4-(4-(4-chlorobenzyl)piperidin-1-yl)phenoxymethyl)-2-methyl-6-nitro-2,3-dihydroimidazo[2,1-b]oxazole 1.036 g of 4-(4-(4-chlorobenzyl)piperidin-1-yl)phenol was dissolved in DMF (5 ml), and 151 mg of sodium hydride was added thereto, followed by stirring at 70° C. to 80° C. for 20 minutes. Thereafter, 1.04 g of (R)-2-chloro-1-(2-methyl-2-oxyranylmethyl)-4-nitro-1H-imidazole was added to the reaction solution while cooled by ice, followed by stirring at 70° C. to 80° C. for 20 minutes. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over sodium sulfate. The sodium sulfate was filtered off, and the filtrate was concentrated under a reduced pressure. The residue was purified by silica gel column chromatography (from hexane:ethyl acetate=1:3 to ethyl acetate). The resultant product was recrystallized from a mixed solvent consisting of dichloromethane and ethyl acetate to obtain 0.286 g (17.3%) of light yellow powdery crystals, (R)-2-(4-(4-(4-chlorobenzyl)piperidin-1-yl)phenoxymethyl)-2-methyl-6-nitro-2,3-dihydroimidazo[2,1-b]oxazole.

Melting point: 207.1° C.-211.2° C.

Example 1471

(R)-2-methyl-6-nitro-2-(4-(4-(4-trifluoromethoxycinnamyloxy)piperidin-1-yl)phenoxymethyl)-2,3-dihydroimidazo[2,1-b]oxazole 2.21 g of 4-(4-(4-trifluoromethoxycinnamyloxy)piperidin-1-yl)phenol was dissolved in DMF (22 ml), and 0.247 g of sodium hydride was added thereto, followed by stirring at 70° C. to 80° C. for 20 minutes. Thereafter, 1.71 g of (R)-2-chloro-1-(2-methyl-2-oxyranylmethyl)-4-nitro-1H-imidazole was added to the reaction solution while cooled by ice, followed by stirring at 70° C. to 80° C. for 20 minutes. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over anhydrous magnesium sulfate. The magnesium sulfate was filtered off, and the filtrate was concentrated under a reduced pressure. The residue was purified by silica gel column chromatography (dichloromethane:ethyl acetate=9:1). The resultant product was recrystallized from a mixed solvent consisting of dichloromethane and ethyl acetate to obtain 0.70 g (21.7%) of light yellow powdery crystals, (R)-2-methyl-6-nitro-2-(4-(4-(4-trifluoromethoxycinnamyloxy)piperidin-1-yl)phenoxymethyl)-2,3-dihydroimidazo[2,1-b]oxazole.

Melting point: 213.7° C.-217.4° C.

Example 1472

(R)-6-nitro-2-(4-(4-(4-trifluoromethoxybenzyloxy)piperidin-1-yl)phenoxymethyl)-2,3-dihydroimidazo[2,1-b]oxazole 4.60 g of 4-(4-(4-trifluoromethoxybenzyloxy)piperidin-1-yl)phenol was dissolved in DMF (46 ml), and 0.55 g of sodium hydride was added thereto, followed by stirring at 70° C. to 80° C. for 20 minutes. Thereafter, 3.57 g of (R)-2-chloro-1-oxyranylmethyl-4-nitro-1H-imidazole was added to the reaction solution while cooled by ice, followed by stirring at 70° C. to 80° C. for 20 minutes. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over sodium sulfate. The sodium sulfate was filtered off, and the filtrate was concentrated under a reduced pressure. The residue was purified by silica gel column chromatography (dichloromethane ethyl acetate from 9:1 to 6:4). The resultant product was recrystallized from a mixed solvent consisting of dichloromethane and ethyl acetate to obtain 0.99 g (14.8%) of light yellow powdery crystals, (R)-6-nitro-2-(4-(4-(4-trifluoromethoxybenzyloxy)piperidin-1-yl)phenoxymethyl)-2,3-dihydroimidazo[2,1-b]oxazole.

Melting point: 188.3° C.-189.4° C.

Example 1473

(R)-2-methyl-6-nitro-2-(4-(4-(2-(4-trifluoromethoxyphenyl)ethyl)piperidin-1-yl)phenoxymethyl)-2,3-dihydroimidazo[2,1-b]oxazole 1.01 g of (R)-2-chloro-1-(2-methyl-2-oxyranylmethyl)-4-nitro-1H-imidazole and 1.36 g of 4-(4-(2-(4-trifluoromethoxyphenyl)ethyl)piperidin-1-yl)phenol were dissolved in DMF (14 ml), and 0.18 g of sodium hydride was added thereto, followed by stirring at 50° C. for 1 hour. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over sodium sulfate. The sodium sulfate was filtered off, and the filtrate was concentrated under a reduced pressure. The residue was purified by silica gel column chromatography (dichloromethane:ethyl acetate from 9:1 to 8:2). The resultant product was recrystallized from a mixed solvent consisting of dichloromethane, ethyl acetate, and diisopropyl ether to obtain 0.70 g (34.4%) of light yellow powdery crystals, (R)-2-methyl-6-nitro-2-(4-(4-(2-(4-trifluoromethoxyphenyl)ethyl)piperidin-1-yl)phenoxymethyl)-2,3-dihydroimidazo[2,1-b]oxazole.

Melting point: 239.4° C.-241.3° C.

Example 1474

(R)-2-methyl-6-nitro-2-(6-(4-(4-trifluoromethoxyphenoxy)piperidin-1-yl)pyridin-3-yloxymethyl)-2,3-dihydroimidazo[2,1-b]oxazole 0.51 g of (R)-2-chloro-1-(2-methyl-2-oxyranylmethyl)-4-nitro-1H-imidazole and 0.67 g of 3-hydroxy-6-(4-(4-trifluoromethoxyphenoxy)piperidin-1-yl)pyridine were dissolved in DMF (6.7 ml), and 91 mg of sodium hydride was added thereto, followed by stirring at 50° C. for 1 hour. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over anhydrous magnesium sulfate. The magnesium sulfate was filtered, and the filtrate was concentrated under a reduced pressure. The residue was purified by silica gel column chromatography (dichloromethane ethyl acetate from 9:1 to 8:2). The resultant product was recrystallized from a mixed solvent consisting of dichloromethane, ethyl acetate, and diisopropyl ether to obtain 296 mg (29.1%) of light yellow powdery crystals, (R)-2-methyl-6-nitro-2-(6-(4-(4-trifluoromethoxyphenoxy)piperidin-1-yl)pyridin-3-yloxymethyl)-2,3-dihydroimidazo[2,1-b]oxazole.

Melting point: 185.9° C.-186.7° C.

Example 1475

(R)-6-nitro-2-(4-(4-(4-trifluoromethoxybenzyl)piperidin-1-yl)phenoxymethyl)-2,3-dihydroimidazo[2,1-b]oxazole 0.72 g of (R)-2-chloro-1-oxyranylmethyl-4-nitro-1H-imidazole and 1.00 g of 4-(4-(4-trifluoromethoxybenzyl)piperidin-1-yl)phenol were dissolved in DMF (10 ml), and 0.14 g of sodium hydride was added thereto, followed by stirring at 50° C. for 1 hour. Thereafter, the reaction solution was cooled to room temperature. Water was added to the reaction solution, and repeated extraction was carried out with ethyl acetate. The combined organic layer was washed with water and then with a saturated aqueous solution of sodium chloride, and then dried over anhydrous magnesium sulfate. The magnesium sulfate was filtered, and the filtrate was concentrated under a reduced pressure. The residue was purified by silica gel column chromatography (dichloromethane:ethyl acetate from 9:1 to 7:3). The resultant product was recrystallized from a mixed solvent consisting of dichloromethane, ethyl acetate, and diisopropyl ether to obtain 0.20 g (13.7%) of light yellow powdery crystals, (R)-6-nitro-2-(4-(4-(4-trifluoromethoxybenzyl)piperidin-1-yl)phenoxymethyl)-2,3-dihydroimidazo[2,1-b]oxazole.

Melting point: 160.5° C.-164.0° C.

Example 1476

(R)-2-methyl-6-nitro-2-(4-(4-(4-trifluoromethoxyphenyl)-1,4-diazepan-1-yl)phenoxymethyl)-2,3-dihydroimidazo[2,1-b]oxazole 2.21 g of (R)-2-chloro-1-(2-methyl-2-oxyranylmethyl)-4-nitro-1H-imidazole and 2.86 g of 4-(4-(4-trifluoromethoxyphenyl)-1,4-diazepan-1-yl)phenol were dissolved in DMF (29 ml), and 0.39 g of sodium hydride was added thereto, followed by stirring at 50° C. for 1 hour. Thereafter, the reaction solution was cooled to room temperature. Water was added to the reaction solution, and repeated extraction was carried out with dichloromethane. The combined organic layer was washed with water and then with a saturated aqueous solution of sodium chloride, and then concentrated. The residue was purified by silica gel column chromatography (from hexane:ethyl acetate=1:3 to ethyl acetate). The resultant product was then recrystallized from isopropyl alcohol to obtain 720 mg (16.6%) of red powders, (R)-2-methyl-6-nitro-2-(4-(4-(4-trifluoromethoxyphenyl)-1,4-diazepan-1-yl)phenoxymethyl)-2,3-dihydroimidazo[2,1-b]oxazole.

Melting point: 134.0° C.-137.9° C.

Example 1477

(R)-2-methyl-2-(4-(4-(N-methyl-N-(2-fluoro-4-trifluoromethylbenzyl)amino)piperidin-1-yl)phenoxymethyl)-6-nitro-2,3-dihydroimidazo[2,1-b]oxazole 0.80 g of (R)-2-methyl-2-(4-(4-(N-methyl-N-tert-butoxycarbonylamino)piperidin-1-yl)phenoxymethyl)-6-nitro-2,3-dihydroimidazo[2,1-b]oxazole was dissolved in 2 ml of trifluoroacetic acid and 2 ml of dichloromethane, followed by stirring at room temperature for 15 hours. Thereafter, the reaction solution was concentrated under a reduced pressure, and then, 2 ml of dichloromethane and 2 ml of triethylamine were added thereto. The mixture was stirred at room temperature for 5 minutes, and it was then concentrated under a reduced pressure. The residue was dissolved in 8 ml of dichloroethane, and then, 0.63 g of 2-fluoro-4-trifluoromethylbenzaldehyde and 0.70 g of triacetoxy sodium borohydride were added thereto while cooled by ice. The mixture was warmed to room temperature, and the mixture was then stirred for 24 hours. Thereafter, an aqueous solution of potassium carbonate and dichloromethane were added to the reaction solution. The mixture was stirred, and then extracted with dichloromethane. The organic layer was dried over magnesium sulfate, and then filtered. The obtained filtrate was concentrated under a reduced pressure. The residue was purified by silica gel column chromatography (dichloromethane:methanol=9:1). The resultant product was then crystallized from ethyl acetate to obtain 0.48 g (yield: 51.8%) of light yellow powders, (R)-2-methyl-2-(4-(4-(N-methyl-N-(2-fluoro-4-trifluoromethylbenzyl)amino)piperidin-1-yl)phenoxymethyl)-6-nitro-2,3-dihydroimidazo[2,1-b]oxazole.

Melting point: 197.5° C.-199.2° C.

Example 1478

(R)-2-methyl-2-(4-(4-(N-methyl-N-(2-trifluoromethylbenzyl)amino)piperidin-1-yl)phenoxymethyl)-6-nitro-2,3-dihydroimidazo[2,1-b]oxazole 0.80 g of (R)-2-methyl-2-(4-(4-(N-methyl-N-tert-butoxycarbonylamino)piperidin-1-yl)phenoxymethyl)-6-nitro-2,3-dihydroimidazo[2,1-b]oxazole was dissolved in 2 ml of trifluoroacetic acid and 2 ml of dichloromethane, followed by stirring at room temperature for 15 hours. Thereafter, the reaction solution was concentrated under a reduced pressure, and then, 2 ml of dichloromethane and 2 ml of triethylamine were added thereto. The mixture was stirred at room temperature for 5 minutes, and it was then concentrated under a reduced pressure. The residue was dissolved in 8 ml of dichloroethane, and then, 0.57 g of 2-trifluoromethylbenzaldehyde and 0.70 g of triacetoxy sodium borohydride were added thereto while cooled by ice. The mixture was warmed to room temperature, and the mixture was then stirred for 24 hours. Thereafter, an aqueous solution of potassium carbonate and dichloromethane were added to the reaction solution. The mixture was stirred, and then extracted with dichloromethane. The organic layer was dried over magnesium sulfate, and then filtered. The obtained filtrate was concentrated under a reduced pressure. The residue was purified by silica gel column chromatography (dichloromethane:methanol=9:1). The resultant product was then crystallized from ethyl acetate to obtain 0.47 g (yield: 52.4%) of light yellow powders, (R)-2-methyl-2-(4-(4-(N-methyl-N-(2-trifluoromethylbenzyl)amino)piperidin-1-yl)phenoxymethyl)-6-nitro-2,3-dihydroimidazo[2,1-b]oxazole.

Melting point: 189.6° C.-190.2° C.

Example 1479

(R)-2-methyl-2-(4-(4-(N-methyl-N-(3,5-bistrifluoromethylbenzyl)amino)piperidin-1-yl)phenoxymethyl)-6-nitro-2,3-dihydroimidazo[2,1-b]oxazole 0.80 g of (R)-2-methyl-2-(4-(4-(N-methyl-N-tert-butoxycarbonylamino)piperidin-1-yl)phenoxymethyl)-6-nitro-2,3-dihydroimidazo[2,1-b]oxazole was dissolved in 2 ml of trifluoroacetic acid and 2 ml of dichloromethane, followed by stirring at room temperature for 15 hours. Thereafter, the reaction solution was concentrated under a reduced pressure, and then, 2 ml of dichloromethane and 2 ml of triethylamine were added thereto. The mixture was stirred at room temperature for 5 minutes, and it was then concentrated under a reduced pressure. The residue was dissolved in 8 ml of dichloroethane, and then, 0.79 g of 3,5-bistrifluoromethylbenzaldehyde and 0.70 g of triacetoxy sodium borohydride were added thereto while cooled by ice. The mixture was warmed to room temperature, and the mixture was then stirred for 19 hours. Thereafter, an aqueous solution of potassium carbonate and dichloromethane were added to the reaction solution. The mixture was stirred, and then extracted with dichloromethane. The organic layer was dried over magnesium sulfate, and then filtered. The obtained filtrate was concentrated under a reduced pressure. The residue was purified by silica gel column chromatography (dichloromethane:methanol=9:1). The resultant product was then crystallized from ethyl acetate to obtain 0.55 g (yield: 54.9%) of light yellow powders, (R)-2-methyl-2-(4-(4-(N-methyl-N-(3,5-bistrifluoromethylbenzyl)amino)piperidin-1-yl)phenoxymethyl)-6-nitro-2,3-dihydroimidazo[2,1-b]oxazole.

Melting point: 193.8° C.-195.3° C.

Example 1480

(R)-2-methyl-6-nitro-2-(4-(4-(3-trifluoromethoxybenzyl)piperidin-1-yl)phenoxymethyl)-2,3-dihydroimidazo[2,1-b]oxazole 1.21 g of (R)-2-chloro-1-(2-methyl-2-oxyranylmethyl)-4-nitro-1H-imidazole and 1.56 g of 4-(4-(3-trifluoromethoxybenzyl)piperidin-1-yl)phenol were dissolved in DMF (16 ml), and 0.21 g of sodium hydride was then added thereto, followed by stirring at 50° C. for 1 hour. Thereafter, the reaction solution was cooled to room temperature. Water was added to the reaction solution, and the mixture was then extracted repeatedly with dichloromethane. The combined organic layer was washed with water and then with a saturated aqueous solution of sodium chloride, and then dried over anhydrous sodium sulfate. The sodium sulfate was filtered off, and the filtrate was concentrated under a reduced pressure. The residue was purified by silica gel column chromatography (dichloromethane:ethyl acetate from 9:1 to 8:2). The resultant product was recrystallized from a mixed solvent consisting of dichloromethane, ethyl acetate, and diisopropyl ether to obtain 0.80 g (33.8%) of light yellow powdery crystals, (R)-2-methyl-6-nitro-2-(4-(4-(3-trifluoromethoxybenzyl)piperidin-1-yl)phenoxymethyl)-2,3-dihydroimidazo[2,1-b]oxazole.

Melting point: 187.4° C.-189.8° C.

Example 1481

(R)-2-methyl-2-(4-(4-(N-methyl-N-(5-chlorobenzofuran-2-ylmethyl)amino)piperidin-1-yl)phenoxymethyl)-6-nitro-2,3-dihydroimidazo[2,1-b]oxazole 0.80 g of (R)-2-methyl-2-(4-(4-(N-methyl-N-tert-butoxycarbonylamino)piperidin-1-yl)phenoxymethyl)-6-nitro-2,3-dihydroimidazo[2,1-b]oxazole was dissolved in 2 ml of trifluoroacetic acid and 2 ml of dichloromethane, followed by stirring at room temperature for 15 hours. Thereafter, the reaction solution was concentrated under a reduced pressure, and then, 2 ml of dichloromethane and 2 ml of triethylamine were added thereto. The mixture was stirred at room temperature for 5 minutes, and it was then concentrated under a reduced pressure. The residue was dissolved in 8 ml of dichloroethane, and then, 0.59 g of 5-chlorobenzofuran-2-carbaldehyde and 0.70 g of triacetoxy sodium borohydride were added thereto while cooled by ice. The mixture was warmed to room temperature, and the mixture was then stirred for 22 hours. Thereafter, an aqueous solution of potassium carbonate and dichloromethane were added to the reaction solution. The mixture was stirred, and then extracted with dichloromethane. The organic layer was dried over magnesium sulfate, and then filtered. The obtained filtrate was concentrated under a reduced pressure. The residue was purified by silica gel column chromatography (dichloromethane:methanol=9:1). The resultant product was then crystallized from acetone to obtain 0.65 g (yield: 66.5%) of yellow powders, (R)-2-methyl-2-(4-(4-(N-methyl-N-(5-chlorobenzofuran-2-ylmethyl)amino)piperidin-1-yl)phenoxymethyl)-6-nitro-2,3-dihydroimidazo[2,1-b]oxazole.

Melting point: 207.4° C.-210.0° C.

Example 1482

(R)-2-methyl-6-nitro-2-(6-(4-(4-trifluoromethoxybenzyl)piperidin-1-yl)pyridin-3-yloxymethyl)-2,3-dihydroimidazo[2,1-b]oxazole 2.63 g of (R)-2-chloro-1-(2-methyl-2-oxyranylmethyl)-4-nitro-1H-imidazole and 3.41 g of 3-hydroxy-6-(4-(4-trifluoromethoxybenzyl)piperidin-1-yl)pyridine were dissolved in DMF (6.7 ml), and 0.46 g of sodium hydride was then added thereto, followed by stirring at 50° C. for 1.5 hours. Thereafter, the reaction solution was cooled to room temperature. Water was added to the reaction solution, and the mixture was then extracted repeatedly with dichloromethane. The combined organic layer was washed with water and then with a saturated aqueous solution of sodium chloride, and then dried over anhydrous magnesium sulfate. The magnesium sulfate was filtered, and the filtrate was concentrated under a reduced pressure. The residue was purified by silica gel column chromatography (dichloromethane:ethyl acetate from 9:1 to 6:4). The resultant product was recrystallized from a mixed solvent consisting of ethyl acetate and diisopropyl ether to obtain 1.46 g (28.3%) of light yellow powdery crystals, (R)-2-methyl-6-nitro-2-(6-(4-(4-trifluoromethoxybenzyl)piperidin-1-yl)pyridin-3-yloxymethyl)-2,3-dihydroimidazo 2,1-b]oxazole.

Melting point: 200.1° C.-202.9° C.

Example 1483

(R)-6-nitro-2-(4-(4-(2-(4-trifluoromethoxyphenyl)ethyl)piperidin-1-yl)phenoxymethyl)-2,3-dihydroimidazo[2,1-b]oxazole 0.75 g of (R)-2-chloro-1-oxyranylmethyl-4-nitro-1H-imidazole and 1.07 g of 4-(4-(2-(4-trifluoromethoxyphenyl)ethyl)piperidin-1-yl)phenol were dissolved in DMF (11 ml), and 0.14 g of sodium hydride was then added thereto, followed by stirring at 50° C. for 1 hour. Thereafter, the reaction solution was cooled to room temperature. Water was added to the reaction solution, and the mixture was then extracted repeatedly with dichloromethane. The combined organic layer was washed with water and then with a saturated aqueous solution of sodium chloride, and then dried over magnesium sulfate. The magnesium sulfate was filtered off, and the filtrate was concentrated under a reduced pressure. The residue was purified by silica gel column chromatography (dichloromethane:ethyl acetate from 9:1 to 6:4). The resultant product was recrystallized from a mixed solvent consisting of dichloromethane and diisopropyl ether to obtain 0.31 g (19.8%) of light yellow powdery crystals, (R)-6-nitro-2-(4-(4-(2-(4-trifluoromethoxyphenyl)ethyl)piperidin-1-yl)phenoxymethyl)-2,3-dihydroimidazo[2,1-b]oxazole.

Melting point: 208.9° C.-211.7° C.

Example 1484

(R)-2-methyl-2-(4-(4-(N-methyl-N-(4-trifluoromethoxycinnamyl)amino)piperidin-1-yl)phenoxymethyl)-6-nitro-2,3-dihydroimidazo[2,1-b]oxazole 2.76 g of (R)-2-methyl-2-(4-(4-(N-methyl-N-tert-butoxycarbonylamino)piperidin-1-yl)phenoxymethyl)-6-nitro-2,3- dihydroimidazo[2,1-b]oxazole was dissolved in 5 ml of trifluoroacetic acid and 10 ml of dichloromethane, followed by stirring at room temperature for 0.5 hours. Thereafter, the reaction solution was concentrated under a reduced pressure, and then, 10 ml of dichloromethane and 10 ml of N,N-dimethylethylamine were added thereto. The mixture was stirred at room temperature for 10 minutes, and it was then concentrated under a reduced pressure. The residue was dissolved in 30 ml of dichloroethane, and 1.43 g of 4-trifluoromethoxycinnamylaldehyde and 1.78 g of triacetoxy sodium borohydride were then added thereto while cooled by ice. The mixture was warmed to room temperature, followed by stirring overnight. Thereafter, an aqueous solution of potassium carbonate and dichloromethane were added to the reaction solution. The mixture was stirred, and then extracted with dichloromethane. The organic layer was dried over magnesium sulfate, and then filtered. The obtained filtrate was concentrated under a reduced pressure. The residue was purified by silica gel column chromatography (dichloromethane:acetone from 5:1 to 1:1). The resultant product was then recrystallized from an aqueous acetone to obtain 1.976 g (yield: 58.9%) of light yellow powders, (R)-2-methyl-2-(4-(4-(N-methyl-N-(4-trifluoromethoxycinnamyl)amino)piperidin-1-yl)phenoxymethyl)-6-nitro-2,3-dihydroimidazo[2,1-b]oxazole.

Melting point: 213.0° C.-214.9° C.

Example 1485

(R)-2-(4-(4-(3,4-dichlorocinnamyl)piperazin-1-yl)phenoxymethyl)-2-methyl-6-nitro-2,3-dihydroimidazo[2,1-b]oxazole 2.76 g of (R)-2-methyl-2-(4-(4-tert-butoxycarbonylpiperazin-1-yl)phenoxymethyl)-6-nitro-2,3-dihydroimidazo[2,1-b]oxazole was dissolved in 5 ml of trifluoroacetic acid and 10 ml of dichloromethane, followed by stirring at room temperature for 0.5 hours. Thereafter, the reaction solution was concentrated under a reduced pressure, and then, 10 ml of dichloromethane and 10 ml of N,N-dimethylethylamine were added thereto. The mixture was stirred at room temperature for 5 minutes, and it was then concentrated under a reduced pressure. The residue was dissolved in 30 ml of dichloroethane, and 1.33 g of 3,4-dichlorocinnamylaldehyde and 1.78 g of triacetoxy sodium borohydride were then added thereto. The mixture was stirred at room temperature overnight. Thereafter, an aqueous solution of potassium carbonate and dichloromethane were added to the reaction solution. The mixture was stirred, and then extracted with dichloromethane. The organic layer was dried over magnesium sulfate, and then filtered. The obtained filtrate was concentrated under a reduced pressure. The residue was purified by silica gel column chromatography (dichloromethane:acetone from 5:1 to 1:1). The resultant product was then crystallized from a mixed solvent consisting of dichloromethane and ethyl acetate to obtain 2.243 g (yield: 68.7%) of light yellow powders, (R)-2-(4-(4-(3,4-dichlorocinnamyl)piperazin-1-yl)phenoxymethyl)-2-methyl-6-nitro-2,3-dihydroimidazo[2,1-b]oxazole.

Melting point: 204.7° C.-206.4° C.

Example 1486

(R)-2-methyl-2-(4-(N-methyl-N-(1-(4-trifluoromethoxyphenyl)piperidin-4-ylmethyl)amino)phenoxymethyl)-6-nitro-2,3-dihydroimidazo[2,1-b]oxazole 0.408 g of (R)-2-chloro-1-(2-methyl-2-oxyranylmethyl)-4-nitro-1H-imidazole and 0.57 g of 4-(N-methyl-N-(1-(4-trifluoromethoxyphenyl)piperidin-4-ylmethyl)amino)phenol were dissolved in 6 ml of DMF, and 72 mg of sodium hydride was then added thereto, followed by stirring at 50° C. to 60° C. for 2 hours. Thereafter, the reaction solution was cooled to room temperature. Water was added to the reaction solution, and the mixture was then extracted repeatedly with ethyl acetate. The combined organic layer was washed with water and then with a saturated aqueous solution of sodium chloride, and then dried over magnesium sulfate. The magnesium sulfate was filtered off, and the filtrate was concentrated under a reduced pressure. The residue was purified by silica gel column chromatography (from hexane:ethyl acetate=1:3 to dichloromethane:ethyl acetate=1:1). The resultant product was recrystallized from an aqueous acetone to obtain 0.130 g (yield: 15.4%) of orange powdery crystals, (R)-2-methyl-2-(4-(N-methyl-N-(1-(4-trifluoromethoxyphenyl)piperidin-4-ylmethyl)amino)phenoxymethyl)-6-nitro-2,3-dihydroimidazo[2,1-b]oxazole.

Melting point: 172.5° C.-175.2° C.

Example 1487

(R)-2-methyl-2-(4-(N-methyl-N-(1-(4-trifluoromethoxyphenyl)piperidin-4-ylmethyl)amino)phenoxymethyl)-6-nitro-2,3-dihydroimidazo[2,1-b]oxazole 0.131 g of (R)-2-chloro-1-(2-methyl-2-oxyranylmethyl)-4-nitro-1H-imidazole and 0.177 g of 4-(N-methyl-N-(1-(4-trifluoromethoxyphenyl)piperidin-4-yl)amino)phenol were dissolved in 4 ml of DMF, and 23 mg of sodium hydride was then added thereto, followed by stirring at 50° C. to 60° C. for 2 hours. Thereafter, the reaction solution was cooled to room temperature. Water was added to the reaction solution, and the mixture was then extracted repeatedly with ethyl acetate. The combined organic layer was washed with water and then with a saturated aqueous solution of sodium chloride, and then dried over magnesium sulfate. The magnesium sulfate was filtered off, and the filtrate was concentrated under a reduced pressure. The residue was purified by silica gel column chromatography (from hexane:ethyl acetate=1:3 to dichloromethane:ethyl acetate=1:1). The resultant product was recrystallized from an aqueous acetone to obtain 93 mg (yield: 35%) of light yellow powdery crystals, (R)-2-methyl-2-(4-(N-methyl-N-(1-(4-trifluoromethoxyphenyl)piperidin-4-yl)amino)phenoxymethyl)-6-nitro-2,3-dihydroimidazo[2,1-b]oxazole.

Melting point: 137.9° C.-139.2° C.

Example 1488

(R)-2-methyl-6-nitro-2-(4-(1-(2-(4-trifluoromethylphenyl)thiazol-4-ylmethyl)piperidin-4-yl)phenoxymethyl)-2,3-dihydroimidazo[2,1-b]oxazole 0.300 g of (R)-2-methyl-6-nitro-2-(4-(1-tert-butoxycarbonylpiperidin-4-yl)phenoxymethyl)-2,3-dihydroimidazo[2,1-b]oxazole was added to 1 ml of trifluoroacetic acid and 1 ml of dichloromethane, followed by stirring at room temperature for 1 hour. Thereafter, the reaction solution was concentrated under a reduced pressure, the residue was then dissolved in 1 ml of dichloromethane, and 1 ml of triethylamine was then added thereto. The mixture was stirred at room temperature for 5 minutes, and it was then concentrated under a reduced pressure. The residue was dissolved in 5 ml of methanol, and then, 0.219 g of 2-(4-trifluoromethylphenyl)thiazol-4-carbaldehyde, 82 mg of sodium cyanotrihydroborate, and 0.5 ml of acetic acid were added thereto while cooled by ice. The obtained mixture was stirred at room temperature for 3 days. Thereafter, an aqueous saturated solution of sodium bicarbonate was added thereto. The mixture was stirred, extracted with ethyl acetate, and then washed with a saturated aqueous solution of sodium chloride. The organic layer was dried over magnesium sulfate, and then concentrated under a reduced pressure. The residue was purified by silica gel column chromatography (from dichloromethane:acetone=3:1 to dichloromethane methanol=20:1). The resultant product was then recrystallized from an aqueous acetone to obtain 65 mg (yield: 16.6%) of white powders, (R)-2-methyl-6-nitro-2-(4-(1-(2-(4-trifluoromethylphenyl)thiazol-4-ylmethyl)piperidin-4-yl)phenoxymethyl)-2,3-dihydroimidazo[2,1-b]oxazole.

Melting point: 194.6° C.-196.4° C.

Example 1489

OPC-77094

(R)-2-methyl-6-nitro-2-(4-(1-(4-trifluoromethylcinnamyl)piperidin-4-yl)phenoxymethyl)-2,3-dihydroimidazo[2,1-b]oxazole 0.300 g of (R)-2-methyl-6-nitro-2-(4-(1-tert-butoxycarbonylpiperidin-4-yl)phenoxymethyl)-2,3-dihydroimidazo[2,1-b]oxazole was added to 1 ml of trifluoroacetic acid and 1 ml of dichloromethane, followed by stirring at room temperature for 1 hour. Thereafter, the reaction solution was concentrated under a reduced pressure, the residue was then dissolved in 1 ml of dichloromethane, and 1 ml of triethylamine was then added thereto. The mixture was stirred at room temperature for 5 minutes, and it was then concentrated under a reduced pressure. The residue was dissolved in 5 ml of methanol, and then, 0.170 g of 4-trifluoromethylcinnamylaldehyde, 82 mg of sodium cyanotrihydroborate, and 0.5 ml of acetic acid were added thereto while cooled by ice. Thereafter, the obtained mixture was stirred at room temperature for 3 days. An aqueous saturated solution of sodium bicarbonate was added thereto. The mixture was stirred, extracted with ethyl acetate, and then washed with a saturated aqueous solution of sodium chloride. The organic layer was dried over magnesium sulfate, and then concentrated under a reduced pressure. The residue was purified by silica gel column chromatography (from dichloromethane:acetone=3:1 to dichloromethane: methanol=20:1). The resultant product was then recrystallized from an aqueous acetone to obtain 66 mg (yield: 18.6%) of white powders, (R)-2-methyl-6-nitro-2-(4-(1-(4-trifluoromethylcinnamyl)piperidin-4-yl)phenoxymethyl)-2,3-dihydroimidazo[2,1-b]oxazole.

Melting point: 185.9° C.-187.1° C.

Example 1490

(R)-2-methyl-6-nitro-2-(4-(4-(2-(4-trifluoromethoxyphenoxy)ethyl)piperazin-1-yl)phenoxymethyl)-2,3-dihydroimidazo[2,1-b]oxazole 0.300 g of (R)-2-methyl-6-nitro-2-(4-(4-tert-butoxycarbonylpiperazin-1-yl)phenoxymethyl)-2,3-dihydroimidazo[2,1-b]oxazole was added to 3 ml of trifluoroacetic acid and 3 ml of dichloromethane, followed by stirring at room temperature for 2 hours. Thereafter, the reaction solution was concentrated under a reduced pressure, the residue was then dissolved in 3 ml of dichloromethane, and 3 ml of triethylamine was then added thereto. The mixture was stirred at room temperature for 10 minutes, and it was then concentrated under a reduced pressure. The residue was dissolved in 5 ml of methanol, and then, 0.170 g of 4-trifluoromethoxyphenoxyacetaldehyde, 82 mg of sodium cyanotrihydroborate, and 0.1 ml of acetic acid were added thereto while cooled by ice. Thereafter, the obtained mixture was stirred at room temperature overnight. An aqueous saturated solution of sodium bicarbonate was added thereto. The mixture was stirred, extracted with ethyl acetate, and then washed with a saturated aqueous solution of sodium chloride. The organic layer was dried over magnesium sulfate, and then concentrated under a reduced pressure. The residue was purified by silica gel column chromatography (from dichloromethane: acetone 3:1 to dichloromethane:methanol=20:1). The resultant product was then recrystallized from an aqueous acetone to obtain 157 mg (yield: 42.7%) of white powders, (R)-2-methyl-6-nitro-2-(4-(4-(2-(4-trifluoromethoxyphenoxy)ethyl)piperazin-1-yl)phenoxymethyl)-2,3-dihydroimidazo[2,1-b]oxazole.

Melting point: 194.8° C.-195.6° C.

Example 1491

(R)-2-methyl-6-nitro-2-(4-(4-(4-trifluoromethylcinnamyl)piperazin-1-yl)phenoxymethyl)-2,3-dihydroimidazo[2,1-b]oxazole 0.300 g of (R)-2-methyl-6-nitro-2-(4-(4-tert-butoxycarbonylpiperazin-1-yl)phenoxymethyl)-2,3-dihydroimidazo[2,1-b]oxazole was added to 3 ml of trifluoroacetic acid and 3 ml of dichloromethane, followed by stirring at room temperature for 1 hour. Thereafter, the reaction solution was concentrated under a reduced pressure, the residue was then dissolved in 3 ml of dichloromethane, and 3 ml of triethylamine was then added thereto. The mixture was stirred at room temperature for 5 minutes, and it was then concentrated under a reduced pressure. The residue was dissolved in 5 ml of methanol, and then, 0.170 g of 4-trifluoromethylcinnnamylaldehyde, 82 mg of sodium cyanotrihydroborate, and 0.1 ml of acetic acid were added thereto while cooled by ice. The obtained mixture was stirred at room temperature for 3 days. Thereafter, an aqueous saturated solution of sodium bicarbonate was added thereto. The mixture was stirred, extracted with ethyl acetate, and then washed with a saturated aqueous solution of sodium chloride. The organic layer was dried over magnesium sulfate, and then concentrated under a reduced pressure. The residue was purified by silica gel column chromatography (from dichloromethane:acetone=3:1 to dichloromethane:methanol=20:1). The resultant product was then recrystallized from an aqueous acetone to obtain 66 mg (yield: 18.6%) of light yellow powders, (R)-2-methyl-6-nitro-2-(4-(4-(4-trifluoromethylcinnamyl)piperazin-1-yl)phenoxymethyl)-2,3-dihydroimidazo[2,1-b]oxazole.

Melting point: 199.7° C.-202.0° C.

Example 1492

(R)-2-methyl-6-nitro-2-(4-(4-(2-(4-trifluoromethylphenyl)thiazol-4-ylmethyl)piperazin-1-yl)phenoxymethyl)-2,3-dihydroimidazo[2,1-b]oxazole 0.300 g of (R)-2-methyl-6-nitro-2-(4-(4-tert-butoxycarbonylpiperazin-1-yl)phenoxymethyl)-2,3-dihydroimidazo[2,1-b]oxazole was added to 3 ml of trifluoroacetic acid and 3 ml of dichloromethane, followed by stirring at room temperature for 2 hours. Thereafter, the reaction solution was concentrated under a reduced pressure. The residue was dissolved in 3 ml of dichloromethane, and 3 ml of triethylamine was then added thereto. The mixture was stirred at room temperature for 10 minutes, and then concentrated under a reduced pressure. The residue was dissolved in 5 ml of methanol, and then, 0.218 g of 2-(4-trifluoromethylphenyl)thiazol-4-carbaldehyde, 82 mg of sodium cyanotrihydroborate, and 0.5 ml of acetic acid were added thereto while cooled by ice. The mixture was stirred at room temperature overnight. Thereafter, an aqueous saturated solution of sodium bicarbonate was added thereto. The mixture was stirred, then extracted with ethyl acetate, and then washed with a saturated aqueous solution of sodium chloride. The organic layer was dried over magnesium sulfate, and then concentrated under a reduced pressure. The residue was purified by silica gel column chromatography (from dichloromethane:acetone=3:1 to dichloromethane methanol=20:1). The resultant product was then crystallized from an aqueous acetone to obtain 0.167 g (yield: 42.6%) of white powders, (R)-2-methyl-6-nitro-2-(4-(4-(2-(4-trifluoromethylphenyl)thiazol-4-ylmethyl)piperazin-1-yl)phenoxymethyl)-2,3-dihydroimidazo[2,1-b]oxazole.

Melting point: 210.0° C.-212.1° C.

Example 1493

(R)-2-(4-(4-(N-(4-chlorophenyl)-N-methylamino)piperidin-1-yl)phenoxymethyl)-2-methyl-6-nitro-2,3-dihydroimidazo[2,1-b]oxazole 776 mg of 4-(4-(N-(4-chlorophenyl)-N-methylamino)piperidin-1-yl)phenol was dissolved in 10 ml of DMF, and 108 mg of sodium hydride was then added thereto, followed by stirring at 70° C. to 80° C. for 10 minutes. Thereafter, the reaction solution was cooled by ice, and 746 mg of (R)-2-chloro-1-(2-methyl-2-oxyranylmethyl)-4-nitro-1H-imidazole was then added thereto, followed by stirring at 70° C. to 80° C. for 20 minutes. Thereafter, the reaction solution was cooled to room temperature. Ice water was added to the reaction solution, the mixture was then stirred, and the insoluble precipitate was then removed by filtration. The filtrate was dissolved in dichloromethane, washed with a saturated aqueous solution of sodium chloride, and then dried over magnesium sulfate. The magnesium sulfate was filtered off, and the filtrate was concentrated under a reduced pressure. The residue was purified by silica gel column chromatography (dichloromethane:ethyl acetate=10:1). The resultant product was then recrystallized from a mixed solvent consisting of dichloromethane and ethyl acetate to obtain 485 mg (yield: 39.8%) of white powdery crystals, (R)-2-(4-(4-(N-(4-chlorophenyl)-N-methylamino)piperidin-1-yl)phenoxymethyl)-2-methyl-6-nitro-2,3-dihydroimidazo[2,1-b]oxazole.

Melting point: 173.7° C.-175.1° C.

Example 1494

(R)-2-methyl-6-nitro-2-(4-(4-(4-trifluoromethylphenoxymethyl)piperidin-1-yl)phenoxymethyl)-2,3-dihydroimidazo[2,1-b]oxazole 574 mg of (R)-2-chloro-1-(2-methyl-2-oxyranylmethyl)-4-nitro-1H-imidazole and 844 mg of 4-(4-(4-trifluoromethylphenoxymethyl)piperidin-1-yl)phenol were heated to 140° C., followed by stirring for 4 hours. Thereafter, the mixture was cooled to room temperature, and the mixture was then purified by silica gel column chromatography (hexane:ethyl acetate=1:3). After completion of the concentration, the residue was dissolved in 10 ml of DMF. 174 mg of sodium tert-butoxide was added thereto while cooled by ice, and the mixture was then stirred at room temperature for 2 hours. Thereafter, the solvent was removed under a reduced pressure, and then, 100 ml of acetone and 10 ml of silica gel were added to the residue, followed by concentration. The residue was purified by silica gel column chromatography (dichloromethane:ethyl acetate from 10:1 to 1:1). The resultant product was then recrystallized from a mixed solvent consisting of dichloromethane and ethyl acetate to obtain 1.15 g (yield: 38%) of white powders, (R)-2-methyl-6-nitro-2-(4-(4-(4-trifluoromethylphenoxymethyl)piperidin-1-yl)phenoxymethyl)-2,3-dihydroimidazo[2,1-b]oxazole.

Melting point: 223.2° C.-225.2° C. (decomposition)

Example 1495

(R)-2-methyl-6-nitro-2-(4-(4-(4-trifluoromethylbenzyloxymethyl)piperidin-1-yl)phenoxymethyl)-2,3-dihydroimidazo[2,1-b]oxazole 2.48 g of 4-(4-(4-trifluoromethylbenzyloxymethyl)piperidin-1-yl)phenol was dissolved in 30 ml of DMF, and 312 mg of sodium hydride was then added thereto, followed by stirring at 70° C. to 80° C. for 10 minutes. Thereafter, the reaction solution was cooled by ice, and 2.07 g of (R)-2-chloro-1-(2-methyl-2-oxyranylmethyl)-4-nitro-1H-imidazole was then added thereto, followed by stirring at 70° C. to 80° C. for 20 minutes. Thereafter, the reaction solution was cooled to room temperature. Ice water was added to the reaction solution, the mixture was then stirred, and the insoluble precipitate was then removed by filtration. The filtrate was dissolved in dichloromethane, washed with a saturated aqueous solution of sodium chloride, and then dried over magnesium sulfate. The magnesium sulfate was filtered off, and the filtrate was concentrated under a reduced pressure. The residue was purified by silica gel column chromatography (dichloromethane:ethyl acetate=10:1). The resultant product was then recrystallized from ethyl acetate to obtain 1.66 g (yield: 44.7%) of white powdery crystals, (R)-2-methyl-6-nitro-2-(4-(4-(4-trifluoromethylbenzyloxymethyl)piperidin-1-yl)phenoxymethyl)-2,3-dihydroimidazo[2,1-b]oxazole.

Melting point: 172.3° C.-172.9° C.

Example 1496

(R)-2-methyl-6-nitro-2-(4-(4-(4-chloromethylphenoxymethyl)piperidin-1-yl)phenoxymethyl)-2,3-dihydroimidazo[2,1-b]oxazole 1.09 g of 4-(4-(4-chloromethylphenoxymethyl)piperidin-1-yl)phenol was dissolved in 20 ml of DMF, and 158 mg of sodium hydride was then added thereto, followed by stirring at 70° C. to 80° C. for 20 minutes. Thereafter, the reaction solution was cooled by ice, and 1.04 g of (R)-2-chloro-1-(2-methyl-2-oxyranylmethyl)-4-nitro-1H-imidazole was then added thereto, followed by stirring at 60° C. for 30 minutes. Thereafter, the reaction solution was cooled to room temperature. Ice water was added to the reaction solution, the mixture was then stirred, and the insoluble precipitate was then removed by filtration. The filtrate was dissolved in dichloromethane, washed with a saturated aqueous solution of sodium chloride, and then dried over magnesium sulfate. The magnesium sulfate was filtered off, and the filtrate was concentrated under a reduced pressure. The residue was purified by silica gel column chromatography (dichloromethane:methanol=20:1). The resultant product was then recrystallized from ethyl acetate to obtain 744 mg (yield: 43.5%) of light yellow powdery crystals, (R)-2-methyl-6-nitro-2-(4-(4-

(4-chloromethylphenoxymethyl)piperidin-1-yl)phenoxymethyl)-2,3-dihydroimidazo[2,1-b]oxazole.

Melting point: 140.4° C.-141.7° C.

Example 1497

(R)-6-nitro-2-(4-(4-(4-trifluoromethylphenoxymethyl)piperidin-1-yl)phenoxymethyl)-2,3-dihydroimidazo[2,1-b]oxazole 1.22 g of 4-(4-(4-trifluoromethylphenoxymethyl)piperidin-1-yl)phenol was dissolved in 15 ml of DMF, and 196 mg of sodium hydride was then added thereto, followed by stirring at 70° C. to 80° C. for 30 minutes. Thereafter, the reaction solution was cooled by ice, and 1.57 g of (R)-2-chloro-1-oxyranylmethyl-4-nitro-1H-imidazole was then added thereto, followed by stirring at 80° C. for 20 minutes. Thereafter, the reaction solution was cooled to room temperature. Ice water was added to the reaction solution, the mixture was then stirred, and the insoluble precipitate was then removed by filtration. The filtrate was dissolved in dichloromethane, washed with a saturated aqueous solution of sodium chloride, and then dried over magnesium sulfate. The magnesium sulfate was filtered, and the filtrate was concentrated under a reduced pressure. The residue was purified by silica gel column chromatography (dichloromethane methanol=20:1). The resultant product was then recrystallized from ethyl acetate to obtain 505 mg (yield: 22.1%) of white powdery crystals, (R)-6-nitro-2-(4-(4-(4-trifluoromethylphenoxymethyl)piperidin-1-yl)phenoxymethyl)-2,3-dihydroimidazo[2,1-b]oxazole.

Melting point: 175.0° C.-180° C.

Example 1498

(R)-2-(4'-(4-(4-chlorobenzyl)piperazin-1-yl)biphenyl-4-yloxymethyl)-2-methyl-6-nitro-2,3-dihydroimidazo[2,1-b]oxazole 850 mg of (R)-2-methyl-2-(4'-(4-tert-butoxycarbonylpiperazin-1-yl)biphenyl-4-yloxymethyl)-6-nitro-2,3-dihydroimidazo[2,1-b]oxazole was dissolved in 10 ml of trifluoroacetic acid and 5 ml of dichloromethane, followed by stirring at room temperature overnight. Thereafter, the reaction solution was concentrated under a reduced pressure, and then, 6 ml of dichloromethane and 6 ml of triethylamine were added thereto. The mixture was stirred at room temperature for 5 minutes, and it was then concentrated under a reduced pressure. The residue was dissolved in 10 ml of DMF, and then, 444.2 mg of 4-chlorobenzaldehyde and 672 mg of triacetoxy sodium borohydride were added thereto while cooled by ice, followed by stirring at room temperature overnight. Thereafter, an aqueous sodium bicarbonate solution and ethyl acetate were added to the reaction solution, the mixture was stirred, and the insoluble precipitate was removed by filtration. The filtrate was washed with water and ethyl acetate, and was then dried to obtain 730 mg (yield: 51.8%) of light yellow powders, (R)-2-(4'-(4-(4-chlorobenzyl)piperazin-1-yl)biphenyl-4-yloxymethyl)-2-methyl-6-nitro-2,3-dihydroimidazo[2,1-b]oxazole.

Melting point: 247.8° C.-248.5° C. (decomposition)

Example 1499

(R)-2-methyl-6-nitro-2-(4'-(4-(4-trifluoromethylbenzyl)piperazin-1-yl)biphenyl-4-yloxymethyl)-2,3-dihydroimidazo[2,1-b]oxazole 790 mg of (R)-2-methyl-2-(4'-(4-tert-butoxycarbonylpiperazin-1-yl)biphenyl-4-yloxymethyl)-6-nitro-2,3-dihydroimidazo[2,1-b]oxazole was dissolved in 10 ml of trifluoroacetic acid and 5 ml of dichloromethane, followed by stirring at room temperature overnight. Thereafter, the reaction solution was concentrated under a reduced pressure, and then, 6 ml of dichloromethane and 6 ml of triethylamine were added thereto. The mixture was stirred at room temperature for 5 minutes, and it was then concentrated under a reduced pressure. The residue was dissolved in 15 ml of DMF, and then, 0.4 ml of 4-trifluoromethylbenzaldehyde and 625 mg of triacetoxy sodium borohydride were added thereto while cooled by ice, followed by stirring at room temperature overnight. Thereafter, water was added to the reaction solution, the mixture was stirred, and the insoluble precipitate was removed by filtration. The filtrate was washed with water and then dissolved in dichloromethane. The obtained solution was washed with a saturated aqueous solution of sodium chloride, and then dried over sodium sulfate. The sodium sulfate was filtered, and the filtrate was concentrated under a reduced pressure. The residue was purified by silica gel column chromatography (dichloromethane:methanol=20:1). The resultant product was then recrystallized from a mixed solvent consisting of dichloromethane and ethyl acetate to obtain 585 mg (yield: 60.5%) of light yellow powders, (R)-2-methyl-6-nitro-2-(4'-(4-(4-trifluoromethylbenzyl)piperazin-1-yl)biphenyl-4-yloxymethyl)-2,3-dihydroimidazo[2,1-b]oxazole.

Melting point: 247.7° C.-248.4° C. (decomposition)

Example 1500

(R)-2-methyl-6-nitro-2-(4-(4-(2-(4-trifluoromethoxybenzyloxy)ethyl)piperidin-1-yl)phenoxymethyl)-2,3-dihydroimidazo[2,1-b]oxazole 959 mg of (R)-2-chloro-1-(2-methyl-2-oxyranylmethyl)-4-nitro-1H-imidazole and 1.24 g of 4-(4-(2-(4-trifluoromethoxybenzyloxy)ethyl)piperidin-1-yl)phenol were dissolved in 20 ml of DMF, and 176 mg of sodium hydride was then added thereto, followed by stirring at 55° C. for 1 hour. Thereafter, the temperature of the reaction solution was cooled to room temperature. Ice water was added to the reaction solution, the mixture was then stirred, and the insoluble precipitate was then removed by filtration. The filtrate was dissolved in dichloromethane, washed with a saturated aqueous solution of sodium chloride, and then dried over magnesium sulfate. The magnesium sulfate was filtered off, and the filtrate was concentrated under a reduced pressure. The residue was purified by silica gel column chromatography (dichloromethane:ethyl acetate=10:1). The resultant product was then recrystallized from a mixed solvent consisting of dichloromethane and ethyl acetate to obtain 562 mg (yield: 28.8%) of white powdery crystals, (R)-2-methyl-6-nitro-2-(4-(4-(2-(4-trifluoromethoxybenzyloxy)ethyl)piperidin-1-yl)phenoxymethyl)-2,3-dihydroimidazo[2,1-b]oxazole.

Melting point: 204.8° C.-206.7° C.

Example 1501

(R)-2-methyl-6-nitro-2-(4-(4-(2-(4-trifluoromethylbenzyloxy)ethyl)piperidin-1-yl)phenoxymethyl)-2,3-dihydroimidazo[2,1-b]oxazole 741 mg of (R)-2-chloro-1-(2-methyl-2-oxyranylmethyl)-4-nitro-1H-imidazole and 1.00 g of 4-(4-(2-(4-trifluoromethylbenzyloxy)ethyl)piperidin-1-yl)phenol were dissolved in 10 ml of DMF, and 136 mg of sodium hydride was then added thereto, followed by stirring at 55° C. for 1 hour. Thereafter, the reaction solution was cooled to room temperature. Ice water was added to the reaction solution, the mixture was then stirred, and the insoluble precipitate was then removed by filtration. The filtrate was dissolved in dichloromethane, washed with a saturated aqueous solution of sodium chloride, and then dried over magnesium sulfate. The magnesium sulfate was filtered, and the filtrate was concentrated under a reduced pressure. The residue was purified by silica gel column chromatography (dichloromethane:ethyl acetate=10:1). The resultant product was then recrystallized from a mixed solvent consisting of dichloromethane and ethyl acetate to obtain 548 mg (yield: 37.3%) of white powdery crystals, (R)-2-methyl-6-nitro-2-(4-(4-(2-(4-trifluoromethylbenzyloxy)ethyl)piperidin-1-yl)phenoxymethyl)-2,3-dihydroimidazo[2,1-b]oxazole.

Melting point: 198.0° C.-199.2° C.

Example 1502

(R)-2-(4-(4-(2-(4-chlorobenzyloxy)ethyl)piperidin-1-yl)phenoxymethyl)-2-methyl-6-nitro-2,3-dihydroimidazo[2,1-b]oxazole 900 mg of (R)-2-chloro-1-(2-methyl-2-oxyranylmethyl)-4-nitro-1H-imidazole and 1.10 g of 4-(4-(2-(4-chlorobenzyloxy)ethyl)piperidin-1-yl)phenol were dissolved in 10 ml of DMF, and 165 mg of sodium hydride was then added thereto, followed by stirring at 55° C. for 1 hour. Thereafter, the reaction solution was cooled to room temperature. Ice water was added to the reaction solution, the mixture was then stirred, and the insoluble precipitate was then removed by filtration. The filtrate was dissolved in dichloromethane, washed with a saturated aqueous solution of sodium chloride, and then dried over magnesium sulfate. The magnesium sulfate was filtered off, and the filtrate was concentrated under a reduced pressure. The residue was purified by silica gel column chromatography (dichloromethane:ethyl acetate=10:1). The resultant product was then recrystallized from a mixed solvent consisting of dichloromethane and ethyl acetate to obtain 548 mg (yield: 37.3%) of white powdery crystals, (R)-2-(4-(4-(2-(4-chlorobenzyloxy)ethyl)piperidin-1-yl)phenoxymethyl)-2-methyl-6-nitro-2,3-dihydroimidazo[2,1-b]oxazole.

Melting point: 197.6° C.-198.2° C.

Example 1503

(R)-2-methyl-6-nitro-2-(4-(4-(4-(4-(4-trifluoromethoxyphenoxy)piperidin-1-yl)benzyl)piperazin-1-yl)phenoxymethyl)-2,3-dihydroimidazo[2,1-b]oxazole 350 mg of (R)-2-methyl-2-(4-(4-tert-butoxycarbonylpiperazin-1-yl)phenoxymethyl)-6-nitro-2,3-dihydroimidazo[2,1-b]oxazole was dissolved in 10 ml of trifluoroacetic acid, followed by stirring at room temperature for 5 hours. Thereafter, the reaction solution was concentrated under a reduced pressure, and then, 2 ml of dichloromethane and 2 ml of triethylamine were added thereto. The mixture was stirred at room temperature for 5 minutes, and it was then concentrated under a reduced pressure. The residue was dissolved in 10 ml of dichloroethane, and then, 278 mg of 4-(4-(4-trifluoromethoxyphenoxy)piperidin-1-yl)benzaldehyde and 242 mg of triacetoxy sodium borohydride were added thereto while cooled by ice, followed by stirring at room temperature overnight. Thereafter, an aqueous sodium bicarbonate solution was added to the reaction solution, and then extracted with dichloromethane. The extract was washed with a saturated aqueous solution of sodium chloride, and then dried over magnesium sulfate. The magnesium sulfate was filtered off, and the filtrate was concentrated under a reduced pressure. The residue was purified by silica gel column chromatography (dichloromethane:ethyl acetate=10:1). The resultant product was then recrystallized from a mixed solvent consisting of dichloromethane and diisopropyl ether to obtain 295 mg (yield: 55%) of light yellow powders, (R)-2-methyl-6-nitro-2-(4-(4-(4-(4-(4-trifluoromethoxyphenoxy)piperidin-1-yl)benzyl)piperazin-1-yl)phenoxymethyl)-2,3-dihydroimidazo[2,1-b]oxazole.

Melting point: 198.2° C.-201.4° C.

Example 1504

(R)-2-(4'-(4-(3,4-dichlorobenzyl)piperazin-1-yl)biphenyl-4-yloxymethyl)-2-methyl-6-nitro-2,3-dihydroimidazo[2,1-b]oxazole 350 mg of (R)-2-methyl-2-(4'-(4-tert-butoxycarbonylpiperazin-1-yl)biphenyl-4-yloxymethyl)-6-nitro-2,3-dihydroimidazo[2,1-b]oxazole was dissolved in 10 ml of trifluoroacetic acid, followed by stirring at room temperature for 5 hours. Thereafter, the reaction solution was concentrated under a reduced pressure, and then, 2 ml of dichloromethane and 2 ml of triethylamine were added thereto. The mixture was stirred at room temperature for 5 minutes, and it was then concentrated under a reduced pressure. The residue was dissolved in 10 ml of dichloroethane, and then, 278 mg of 3,4-dichlorobenzaldehyde and 242 mg of triacetoxy sodium borohydride were added thereto while cooled by ice, followed by stirring at room temperature overnight. Thereafter, water was added to the reaction solution, the mixture was stirred, and the insoluble precipitate was removed by filtration. The filtrate was dissolved in dichloromethane. The solution was washed with a saturated aqueous solution of sodium chloride, and then dried over magnesium sulfate. The magnesium sulfate was filtered off, and the filtrate was concentrated under a reduced pressure. The residue was purified by silica gel column chromatography (dichloromethane methanol=20:1) to obtain 252 mg (yield: 41.1%) of light yellow powders, (R)-2-(4'-(4-(3,4-dichlorobenzyl)piperazin-1-yl)biphenyl-4-yloxymethyl)-2-methyl-6-nitro-2,3-dihydroimidazo[2,1-b]oxazole.

Melting point: 222.6° C.-225.1° C. (decomposition)

Example 1505

(R)-2-methyl-6-nitro-2-(4-(4-(4-(4-trifluoromethoxyphenoxy)phenylamino)piperidin-1-yl)phenoxymethyl)-2,3-dihydroimidazo[2,1-b]oxazole 376 mg of 4-(4-trifluoromethoxyphenoxy)aniline and 453 mg of triacetoxy sodium borohydride were added to a dichloroethane solution (10 ml) containing 400 mg of (R)-2-methyl-6-nitro-2-(4-(4-oxopiperidin-1-yl)phenoxymethyl)-2,3-dihydroimidazo[2,1-b]oxazole. The mixture was stirred at room temperature overnight. Thereafter, an aqueous saturated solution of sodium bicarbonate was added to the reaction solution, followed by repeated extraction with dichloromethane. The organic layer was dried over magnesium sulfate, and it was then filtered. The filtrate was concentrated under a reduced pressure, and the residue was purified by silica gel column chromatography (dichloromethane methanol=20:1). The resultant product was recrystallized from a mixed solvent consisting of dichloromethane and diisopropyl ether to obtain 650 mg (yield: 83.2%) of white powders, (R)-2-methyl-6-nitro-2-(4-(4-(4-(4-trifluoromethoxyphenoxy)phenylamino)piperidin-1-yl)phenoxymethyl)-2,3-dihydroimidazo[2,1-b]oxazole.

Melting point: 198.6° C.-201.1° C. (decomposition)

Example 1506

(R)-2-methyl-6-nitro-2-(4-(4-(N-methyl-N-(3-(4-trifluoromethoxyphenoxy)propyl)amino)piperidin-1-yl)phenoxymethyl)-2,3-dihydroimidazo[2,1-b]oxazole 237 mg of (R)-2-methyl-6-nitro-2-(4-(4-(3-(4-trifluoromethoxyphenoxy)propylamino)piperidin-1-yl)phenoxymethyl)-2,3-dihydroimidazo[2,1-b]oxazole was dissolved in a mixed solvent consisting of 10 ml of dichloromethane and 10 ml of methanol. Thereafter, 0.15 ml of a 30% formaldehyde aqueous solution, 71.4 mg of sodium cyanotrihydroborate, and 0.01 ml of acetic acid were added to the mixture, followed by stirring at room temperature overnight. Thereafter, an aqueous saturated solution of sodium bicarbonate was added to the reaction solution, followed by repeated extraction with dichloromethane. The organic layer was dried over magnesium sulfate, and it was then filtered. The filtrate was concentrated under a reduced pressure, and the residue was purified by silica gel column chromatography (dichloromethane: methanol=20:1). The resultant product was recrystallized from a mixed solvent consisting of dichloromethane and diisopropyl ether to obtain 215 mg (yield: 88.7%) of fine yellow powders, (R)-2-methyl-6-nitro-2-(4-(4-(N-methyl-N-(3-(4-trifluoromethoxyphenoxy)propyl)amino)piperidin-1-yl)phenoxymethyl)-2,3-dihydroimidazo[2,1-b]oxazole.

Melting point: 167.4° C.-170.2° C.

Example 1507

(R)-2-(4-(4-(3,4-dichlorophenylamino)piperidin-1-yl)phenoxymethyl)-2-methyl-6-nitro-2,3-dihydroimidazo[2,1-b]oxazole 628 mg of (R)-2-chloro-1-(2-methyl-2-oxyranylmethyl)-4-nitro-1H-imidazole and 750 mg of 4-(4-(3,4-dichlorophenylamino)piperidin-1-yl)phenol were dissolved in 10 ml of DMF, and then, 117 mg of sodium hydride was then added thereto, followed by stirring at 60° C. for 20 minutes. Thereafter, the reaction solution was cooled to room temperature. Water was added to the reaction solution, and the insoluble precipitate was then removed by filtration. The filtrate was dissolved in dichloromethane, washed with a saturated aqueous solution of sodium chloride, and then dried over magnesium sulfate. The magnesium sulfate was filtered off, and the filtrate was concentrated under a reduced pressure. The residue was purified by silica gel column chromatography (from dichloromethane:ethyl acetate=9:1 to 8:2). The resultant product was then recrystallized from a mixed solvent consisting of dichloromethane and diisopropyl ether to obtain 441 mg (yield: 39%) of light yellow powdery crystals, (R)-2-(4-(4-(3,4-dichlorophenylamino)piperidin-1-yl)phenoxymethyl)-2-methyl-6-nitro-2,3-dihydroimidazo[2,1-b]oxazole.

Melting point: 146° C.-147.4° C.

Example 1508

(R)-2-methyl-6-nitro-2-(4-(4-(N-methyl-N-(2-(4-trifluoromethoxyphenoxy)ethyl)amino)piperidin-1-yl)phenoxymethyl)-2,3-dihydroimidazo[2,1-b]oxazole 200 mg of (R)-2-methyl-6-nitro-2-(4-(4-(2-(4-trifluoromethoxyphenoxy)ethylamino)piperidin-1-yl)phenoxymethyl)-2,3-dihydroimidazo[2,1-b]oxazole was dissolved in a mixed solvent consisting of 2 ml of dichloromethane and 2 ml of methanol. Thereafter, 0.13 ml of a 30% formaldehyde aqueous solution, 65 mg of sodium cyanotrihydroborate, and 0.07 ml of acetic acid were added to the mixture, followed by stirring at room temperature overnight. Thereafter, an aqueous saturated solution of sodium bicarbonate was added to the reaction solution, followed by repeated extraction with dichloromethane. The organic layer was dried over magnesium sulfate, and it was then filtered. The filtrate was concentrated under a reduced pressure, and the residue was purified by silica gel column chromatography (dichloromethane: methanol=20:1). The resultant product was recrystallized from a mixed solvent consisting of dichloromethane and diisopropyl ether to obtain 155 mg (yield: 75.7%) of white powders, (R)-2-methyl-6-nitro-2-(4-(4-(N-methyl-N-(2-(4-trifluoromethoxyphenoxy)ethyl)amino)piperidin-1-yl)phenoxymethyl)-2,3-dihydroimidazo[2,1-b]oxazole.

Melting point: 185.7° C.-187.7° C.

Example 1509

(R)-2-methyl-6-nitro-2-(4-(4-(4-(4-trifluoromethoxyphenyl)piperazin-1-yl)piperidin-1-yl)phenoxymethyl)-2,3-dihydroimidazo[2,1-b]oxazole 145 mg of 1-trifluoromethoxyphenylpiperazine, 273 mg of triacetoxy sodium borohydride, and 0.061 ml of acetic acid were added to an acetonitrile solution (15 ml) containing 200 mg of (R)-2-methyl-6-nitro-2-(4-(4-oxopiperidin-1-yl)phenoxymethyl)-2,3-dihydroimidazo[2,1-b]oxazole, followed by stirring at room temperature for 11 days. Thereafter, an aqueous saturated solution of sodium bicarbonate was added to the reaction solution, followed by repeated extraction with dichloromethane. The organic layer was dried over magnesium sulfate, and it was then filtered. The filtrate was concentrated under a reduced pressure, and the residue was purified by silica gel column chromatography (dichloromethane: methanol=20:1). The resultant product was recrystallized from isopropyl alcohol to obtain 143 mg (yield: 44.2%) of white powders, (R)-2-methyl-6-nitro-2-(4-(4-(4-(4-trifluoromethoxyphenyl)piperazin-1-yl)piperidin-1-yl)phenoxymethyl)-2,3-dihydroimidazo[2,1-b]oxazole.

Melting point: 279° C.-281° C.

Example 1510

(R)-2-(4-(4-(3,5-dichlorophenylamino)piperidin-1-yl)phenoxymethyl)-2-methyl-6-nitro-2,3-dihydroimidazo[2,1-b]oxazole 1.82 g of (R)-2-chloro-1-(2-methyl-2-oxyranylmethyl)-4-nitro-1H-imidazole and 2.02 g of 4-(4-(3,5-dichlorophenylamino)piperidin-1-yl)phenol were dissolved in 20 ml of DMF, and then, 264 mg of sodium hydride was added thereto, followed by stirring at 60° C. for 20 minutes. Thereafter, the reaction solution was cooled to room temperature. Water and ethyl acetate were added to the reaction solution, the mixture was stirred, and the insoluble precipitate was then removed by filtration. The filtrate was dissolved in dichloromethane, washed with a saturated aqueous solution of sodium chloride, and then dried over magnesium sulfate. The magnesium sulfate was filtered off, and the filtrate was concentrated under a reduced pressure. The residue was purified by silica gel column chromatography (from dichloromethane:ethyl acetate=9:1 to dichloromethane:methanol=20:1). The resultant product was then recrystallized from a mixed solvent consisting of ethyl acetate and diethyl ether to obtain 1.19 g (yield: 38%) of light yellow powdery crystals, (R)-2-(4-(4-(3,5-dichlorophenylamino)piperidin-1-yl)phenoxymethyl)-2-methyl-6-nitro-2,3-dihydroimidazo[2,1-b]oxazole.

Melting point: 122° C.-124° C.

Example 1511

(R)-2-(4-(4-(4-(4-chlorophenyl)piperazin-1-yl)piperidin-1-yl)phenoxymethyl)-2-methyl-6-nitro-2,3-dihydroimidazo[2,1-b]oxazole 10 ml of an aqueous 20% sodium carbonate solution was added to an aqueous solution (10 ml) containing 290 mg of 1-(4-chlorophenyl)piperazine dihydrochloride, and thereafter, ultrasonic wave was applied to the mixture. The resultant product was extracted with dichloromethane, and dried over sodium sulfate. Thereafter, the solvent was removed under a reduced pressure. The residue was dissolved in 15 ml of dichloroethane. Thereafter, 200 mg of (R)-2-methyl-6-nitro-2-(4-(4-oxopiperidin-1-yl)phenoxymethyl)-2,3-dihydroimidazo[2,1-b]oxazole, 341 ml of triacetoxy sodium borohydride, and 0.092 ml of acetic acid were added to the mixture, followed by stirring at room temperature for 24 hours. Thereafter, an aqueous 20% sodium carbonate solution was added to the reaction solution, and the mixture was then concentrated under a reduced pressure. Water was added to the residue, and the insoluble precipitate was collected by filtration. The precipitate was washed with water and then dried. The resultant product was then recrystallized from isopropyl alcohol to obtain 232 mg (yield: 78.1%) of light yellow powders, (R)-2-(4-(4-(4-(4-chlorophenyl)piperazin-1-yl)piperidin-1-yl)phenoxymethyl)-2-methyl-6-nitro-2,3-dihydroimidazo[2,1-b]oxazole.

Melting point: 247° C.-249° C.

Example 1512

(R)-2-methyl-2-(4-(4-(4-(N-methyl-N-(4-chlorophenyl)amino)piperidin-1-yl)piperidin-1-yl)phenoxymethyl)-6-nitro-2,3-dihydroimidazo[2,1-b]oxazole 241 mg of 4-(N-methyl-N-(4-chlorophenyl)amino)piperidine, 341 mg of triacetoxy sodium borohydride, and 0.092 ml of acetic acid were added to a dichloroethane solution (15 ml) containing 200 mg of (R)-2-methyl-6-nitro-2-(4-(4-oxopiperidin-1-yl)phenoxymethyl)-2,3-dihydroimidazo[2,1-b]oxazole. The mixture was stirred at room temperature for 20 hours. Thereafter, an aqueous 20% sodium carbonate solution was added to the reaction solution, followed by repeated extraction with dichloromethane. The organic layer was dried over sodium sulfate, and it was then filtered. The filtrate was concentrated under a reduced pressure, and the residue was purified by silica gel column chromatography (dichloromethane methanol=20:1). The resultant product was then recrystallized from a mixed solvent consisting of dichloromethane and diethyl ether to obtain 105 mg (yield: 33.6%) of white powders, (R)-2-methyl-2-(4-(4-(4-(N-methyl-N-(4-chlorophenyl)amino)piperidin-1-yl)piperidin-1-yl)phenoxymethyl)-6-nitro-2,3-dihydroimidazo[2,1-b]oxazole.

Melting point: 230.8° C.-232° C.

Example 1513

(R)-2-methyl-2-(4-(4-(4-(N-methyl-N-(4-trifluoromethoxyphenyl)amino)piperidin-1-yl)piperidin-1-yl)phenoxymethyl)-6-nitro-2,3-dihydroimidazo[2,1-b]oxazole 283 mg of 4-(N-methyl-N-(4-trifluoromethoxyphenyl)amino)piperidine, 328 mg of triacetoxy sodium borohydride, and 0.089 ml of acetic acid were added to a dichloroethane solution (15 ml) containing 192 mg of (R)-2-methyl-6-nitro-2-(4-(4-oxopiperidin-1-yl)phenoxymethyl)-2,3-dihydroimidazo[2,1-b]oxazole, followed by stirring at room temperature for 14 hours. Thereafter, an aqueous 20% sodium carbonate solution was added to the reaction solution, followed by repeated extraction with dichloromethane. The organic layer was dried over sodium sulfate, and it was then filtered. The filtrate was concentrated under a reduced pressure, and the residue was purified by silica gel column chromatography (dichloromethane:methanol=20:1). The resultant product was recrystallized from a mixed solvent consisting of dichloromethane and diethyl ether to obtain 153 mg (yield: 47.1%) of yellow powders, (R)-2-methyl-2-(4-(4-(4-(N-methyl-N-(4-trifluoromethoxyphenyl)amino)piperidin-1-yl)piperidin-1-yl)phenoxymethyl)-6-nitro-2,3-dihydroimidazo[2,1-b]oxazole.

Melting point: 196° C.-197° C.

Example 1514

(R)-2-(4-(4-(4-propylphenylamino)piperidin-1-yl)phenoxymethyl)-2-methyl-6-nitro-2,3-dihydroimidazo[2,1-b]oxazole 1.86 g of (R)-2-chloro-1-(2-methyl-2-oxyranylmethyl)-4-nitro-1H-imidazole and 1.9 g of 4-(4-(4-propylphenylamino)piperidin-1-yl)phenol were dissolved in 20 ml of DMF, and then, 269 mg of sodium hydride was then added thereto, followed by stirring at 50° C. for 2 hours. Thereafter, the reaction solution was cooled to room temperature. Water and ethyl acetate were added thereto, the mixture was stirred, and the insoluble precipitate was then removed by filtration. The filtrate was dissolved in dichloromethane, washed with a saturated aqueous solution of sodium chloride, and then dried over magnesium sulfate. The magnesium sulfate was filtered off, and the filtrate was concentrated under a reduced pressure. The residue was purified by silica gel column chromatography (from dichloromethane:ethyl acetate 9:1 to dichloromethane:methanol=20:1). The resultant product was then recrystallized from a mixed solvent consisting of ethyl acetate and diisopropyl ether to obtain 660 mg (yield: 21.9%) of light yellow powdery crystals, (R)-2-(4-(4-(4-propylphenylamino)piperidin-1-yl)phenoxymethyl)-2-methyl-6-nitro-2,3-dihydroimidazo[2,1-b]oxazole.

Melting point: 222° C.-223° C.

Example 1515

(R)-2-(4-(4-(N-methyl-N-(4-propylphenyl)amino)piperidin-1-yl)phenoxymethyl)-2-methyl-6-nitro-2,3-dihydroimidazo[2,1-b]oxazole 300 mg of (R)-2-(4-(4-(4-propylphenylamino)piperidin-1-yl)phenoxymethyl)-2-methyl-6-nitro-2,3-dihydroimidazo[2,1-b]oxazole was dissolved in a mixed solvent consisting of 4 ml of dichloromethane and 4 ml of methanol. Thereafter, 0.14 ml of a 30% formaldehyde aqueous solution, 115 mg of sodium cyanotrihydroborate, and 0.1 ml of acetic acid were added to the mixture, followed by stirring at room temperature overnight. Thereafter, an aqueous 20% sodium carbonate solution was added to the reaction solution, followed by repeated extraction with dichloromethane. The organic layer was dried over magnesium sulfate, and it was then filtered. The filtrate was concentrated under a reduced pressure, and the residue was purified by silica gel column chromatography (dichloromethane:methanol=40:1). The resultant product was recrystallized from a mixed solvent consisting of ethyl acetate and diisopropyl ether to obtain 258 mg (yield: 83.6%) of fine yellow powders, (R)-2-(4-(4-(N-methyl-N-(4-propylphenyl)amino)piperidin-1-yl)phenoxymethyl)-2-methyl-6-nitro-2,3-dihydroimidazo[2,1-b]oxazole.

Melting point: 198° C.-199° C.

Test Example 1

Antibacterial Test

Agar-Plate Dilution Method

The minimum inhibitory concentration of 2,3-dihydro-6-nitroimidazo[2,1-b]oxazole obtained in Sample 129 against *M. tuberculosis* H37Rv in 7H11 medium (BBL Co.) was determined. A bacterial suspension of the strain used was prepared beforehand by culturing the bacteria in 7H9 medium (BBL Co.) followed by calculation of the viable cell count and cryopreservation at −80° C. The final viable cell count of the preparation was approximately $10^6$ CFU/ml. A 5-μL portion of the bacterial suspension was added to 7H11 agar medium containing the test compound, cultured at 37° C. for 14 days, and then tested to measure the minimum inhibitory concentration.

The minimal inhibitory concentration against *M. tuberculosis* H37Rv was 0.0015 μg/mL.

Test Example 2

Antibacterial Test

Agar-Plate Dilution Method

For test compounds shown in the following table, the minimum inhibitory concentration against *M. tuberculosis* Kurono in 7H11 medium (BBL Co.) was determined. A bacterial suspension of the strain used was prepared beforehand by culturing the bacteria in 7H9 medium (BBL Co.) followed by calculation of the viable cell count and cryopreservation at −80° C. The final viable cell count of the preparation was approximately $10^6$ CFU/mL. A 5-μL portion of the bacterial suspension was added to 7H11 agar medium containing a test compound, cultured at 37° C. for 14 days, and then tested to measure the minimum inhibitory concentration.

The results are shown in the Table 183 below.

TABLE 183

| Test Compound | Minimum Inhibitory Concentration (μg/ml) |
| --- | --- |
| Compound of Example 1 | 0.2 |
| Compound of Example 8 | 0.006 |
| Compound of Example 9 | 0.012 |
| Compound of Example 30 | 0.003 |
| Compound of Example 31 | 0.003 |
| Compound of Example 34 | 0.024 |
| Compound of Example 86 | 0.006 |
| Compound of Example 88 | 0.024 |
| Compound of Example 99 | 0.0015 |
| Compound of Example 102 | 0.0015 |
| Compound of Example 105 | 0.012 |
| Compound of Example 107 | 0.024 |
| Compound of Example 108 | 0.0015 |
| Compound of Example 109 | 0.024 |
| Compound of Example 115 | 0.003 |
| Compound of Example 132 | 0.003 |
| Compound of Example 134 | 0.006 |

TABLE 183-continued

| Test Compound | Minimum Inhibitory Concentration (μg/ml) |
| --- | --- |
| Compound of Example 145 | 0.024 |
| Compound of Example 178 | 0.024 |
| Compound of Example 185 | 0.024 |
| Compound of Example 211 | 0.024 |
| Compound of Example 214 | 0.024 |
| Compound of Example 222 | 0.024 |
| Compound of Example 225 | 0.024 |
| Compound of Example 230 | 0.012 |
| Compound of Example 240 | 0.024 |
| Compound of Example 324 | 0.024 |
| Compound of Example 325 | 0.012 |
| Compound of Example 326 | <0.012 |
| Compound of Example 327 | 0.012 |
| Compound of Example 330 | 0.012 |
| Compound of Example 331 | 0.024 |
| Compound of Example 335 | 0.012 |
| Compound of Example 336 | 0.024 |
| Compound of Example 337 | <0.12 |
| Compound of Example 338 | 0.024 |
| Compound of Example 339 | 0.006 |
| Compound of Example 340 | 0.024 |
| Compound of Example 341 | 0.006 |
| Compound of Example 344 | 0.006 |
| Compound of Example 345 | 0.012 |
| Compound of Example 346 | 0.024 |
| Compound of Example 349 | <0.012 |
| Compound of Example 349 | 0.012 |
| Compound of Example 359 | 0.012 |
| Compound of Example 362 | 0.012 |
| Compound of Example 368 | 0.024 |
| Compound of Example 369 | 0.006 |
| Compound of Example 370 | 0.012 |
| Compound of Example 371 | 0.006 |
| Compound of Example 373 | 0.012 |
| Compound of Example 377 | 0.024 |
| Compound of Example 382 | 0.024 |
| Compound of Example 384 | 0.024 |
| Compound of Example 385 | 0.024 |
| Compound of Example 388 | 0.012 |
| Compound of Example 389 | 0.012 |
| Compound of Example 390 | 0.012 |
| Compound of Example 392 | <0.008 |
| Compound of Example 393 | 0.024 |
| Compound of Example 396 | 0.012 |
| Compound of Example 408 | 0.024 |
| Compound of Example 422 | 0.024 |
| Compound of Example 426 | 0.024 |
| Compound of Example 439 | 0.39 |
| Compound of Example 440 | 0.05 |
| Compound of Example 471 | 0.024 |
| Compound of Example 473 | 0.024 |
| Compound of Example 480 | 0.024 |
| Compound of Example 483 | 0.024 |
| Compound of Example 487 | 0.024 |
| Compound of Example 488 | 0.024 |
| Compound of Example 508 | 0.05 |
| Compound of Example 519 | 0.024 |
| Compound of Example 530 | 0.012 |
| Compound of Example 602 | 0.024 |
| Compound of Example 612 | 0.024 |
| Compound of Example 614 | 0.024 |
| Compound of Example 646 | 0.012 |
| Compound of Example 647 | 0.024 |
| Compound of Example 648 | 0.024 |
| Compound of Example 660 | 0.024 |
| Compound of Example 663 | 0.05 |
| Compound of Example 664 | 0.024 |
| Compound of Example 665 | 0.024 |
| Compound of Example 679 | 0.024 |
| Compound of Example 694 | 0.1 |
| Compound of Example 695 | 0.024 |
| Compound of Example 698 | 0.012 |
| Compound of Example 721 | 0.024 |
| Compound of Example 738 | 0.003 |
| Compound of Example 739 | 0.012 |
| Compound of Example 756 | 0.05 |

TABLE 183-continued

| Test Compound | Minimum Inhibitory Concentration (μg/ml) |
|---|---|
| Compound of Example 761 | 0.78 |
| Compound of Example 768 | 0.012 |
| Compound of Example 753 | 0.024 |
| Compound of Example 780 | 0.006 |

The invention claimed is:

1. A 2,3-dihydro-6-nitroimidazo[2,1-b]oxazole compound represented by the following general formula (1), an optically active form thereof, or a pharmacologically acceptable salt thereof:

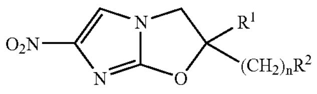

(1)

wherein $R^1$ represents a hydrogen atom, or a C1-C6 alkyl group, n represents an integer between 0 and 6, $R^1$ and $—(CH_2)_nR^2$ may bind to each other together with carbon atoms adjacent thereto, so as to form a spiro ring represented by the following general formula (30):

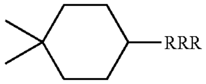

(30)

wherein RRR represents a piperidyl group [wherein, on the piperidine ring, at least one phenoxy group may be substituted (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted)], and $R^2$ represents a group described in any one of the following (a) to (y):

(a) a phenyl group (wherein, on a phenyl ring of the phenyl group, at least one piperidyl group may be substituted [(wherein, on the piperidine ring, at least one phenoxy group may be substituted (wherein, on a phenyl ring of the phenoxy group, at least one selected from the group consisting of a halogen atom, a halogen substituted or unsubstituted $C_1$-$C_6$ alkyl group, and a halogen substituted or unsubstituted C1-C6 alkoxy group, may be substituted)]);

(b) a benzothiazolyloxy group (wherein, on the benzothiazole ring, at least one selected from the group consisting of the following (b-1) to (b-5) may be substituted:

(b-1) a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted], (b-2) a piperazinyl group [wherein, on the piperazine ring, at least one selected from the group consisting of a phenyl C1-C6 alkyl group (wherein, on a phenyl group of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), a phenyl $C_2$-$C_6$ alkenyl group (wherein, on a phenyl group of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted), and a phenyl group (wherein, on a phenyl group of the phenyl group, at least one selected from the group consisting of a halogen atom, a halogen substituted or unsubstituted C1-C6 alkyl group, and a halogen substituted or unsubstituted C1-C6 alkoxy group, may be substituted), may be substituted], (b-3) a piperidyl group [wherein, on the piperidine ring, at least one selected from the group consisting of an amino group (wherein, on the amino group, at least one selected from the group consisting of a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted] and a C1-C6 alkyl group may be substituted), a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted), and a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), may be substituted], (b-4) a pyrrolyl group [wherein, on the pyrrole ring, at least one selected from the group consisting of a C1-C6 alkyl group and a phenyl C1-C6 alkyl group (wherein, on a phenyl ring of the phenyl C1-C6 alkyl group, at least one selected from the group consisting of a halogen atom, a halogen substituted or unsubstituted C1-C6alkyl group, and a halogen substituted or unsubstituted C1-C6 alkoxy group, may be substituted) may be substituted], and (b-5) a phenylthio group (wherein, on a phenyl ring, of the phenylthio group at least one selected from the group consisting of a halogen atom, a halogen substituted or unsubstituted C1-C6 alkyl group, and a halogen substituted or unsubstituted C1-C6 alkoxy group, may be substituted));

(c) a quinolyloxy group (wherein, on the quinoline ring, at least one selected from the group consisting of the following (c-1) to (c-4) may be substituted:

(c-1) a halogen atom, (c-2) a phenoxy group [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted], (c-3) a piperazinyl group [wherein, on the piperazine ring, at least one selected from the group consisting of a phenyl C1-C6 alkyl group (wherein, on a phenyl ring, of the phenyl C1-C6 alkyl group at least one selected from the group consisting of a halogen atom, a halogen substituted or unsubstituted C1-C6 alkyl group, and a halogen substituted or unsubstituted C1-C6 alkoxy group, may be substituted), a phenyl group [wherein, on a phenyl ring of the phenyl group, at least one group selected from the group consisting of a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted), a halogen atom, a halogen substituted or unsubstituted C1-C6 alkyl group, and a halogen substituted or unsubstituted C1-C6 alkoxy group, may be substituted], and a phenyl C2-C6 alkenyl group [wherein, on a phenyl ring of the phenyl C1-C6 alkenyl group, at least one selected from the group consisting of a halogen atom, a halogen substituted or unsubstituted C1-C6 alkyl group, and a halogen substituted or unsubstituted C1-C6 alkoxy group, may be substituted], may be substituted], and (c-4) a piperidyl group [wherein, on the piperidine ring, at least one selected from the following group may be substituted: an amino group (wherein, on the amino group, at least one selected from the group consisting of a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted] and a C1-C6 alkyl group may be substituted); a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted); a phenyl C1-C6 alkyl group (wherein, on a phenyl ring of the phenyl C1-C6 alkyl group, at least one selected from the group consisting of a C1-C4 alkylenedioxy group, a halogen atom, a halogen substituted or unsubstituted C1-C6 alkyl group, and a halogen substituted or unsubstituted C1-C6 alkoxy group, may be substituted); a phenyl C1-C6 alkoxy group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted); a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted); a naphthyl C1-C6 alkyl group; and a phenyl C1-C6 alkylidene group (wherein, on a phenyl ring of the phenyl C1-C6 alkylidene group, at least one selected from the group consisting of a halogen atom, a halogen substituted or unsubstituted C1-C6 alkyl group, and a halogen substituted or unsubstituted C1-C6 alkoxy group, may be substituted)]);

(d) a pyridyloxy group (wherein, on the pyridine ring, at least one selected from the group consisting of the following (d-1) and (d-2) may be substituted:

(d-1) a piperidyl group [wherein, on the piperidine ring, at least one selected from the group consisting of a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted), a phenyl C1-C6 alkoxy substituted C1-C6 alkyl group (wherein, on a phenyl ring of the phenyl C1-C6 alkoxy substituted C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), a phenoxy C1-C6 alkyl group (wherein, on a phenyl ring of the phenoxy C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), and a phenyl C1-C6 alkyl group (wherein, on a phenyl ring of the phenyl C1-C6 alkyl group, at least one selected from the group consisting of a halogen atom, a halogen substituted or unsubstituted $C_1$-C6 alkyl group, and a halogen substituted or unsubstituted C1-C6 alkoxy group, may be substituted), may be substituted]; and (d-2) a piperazinyl group [wherein, on the piperazine ring, at least one selected from the group consisting of a C1-C6 alkoxycarbonyl group, a furyl C1-C6 alkyl group [wherein, on the furan ring, at least one phenyl group may be substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)], a pyridyl C1-C6 alkyl group [wherein, on the pyridine ring, at least one selected from the group consisting of a furyl group and a phenyl group may be substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)], a benzothienyl C1-C6 alkyl group (wherein, on the benzothiophene ring, at least one selected from the group consisting of a halogen atom, a halogen substituted or unsubstituted C1-C6 alkyl group, and a halogen substituted or unsubstituted C1-C6 alkoxy group, may be substituted), a phenyl C2-C6 alkenyl group (wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted), a benzofuryl C1-C6 alkyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted], a benzofuryl C2-C6 alkenyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted], a thiazolyl C1-C6 alkyl group [wherein, on the thiazole ring, at least one phenyl group may be substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)], a phenoxy C1-C6 alkyl group (wherein on a phenyl ring of the phenoxy C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), an indolyl C1-C6 alkyl group (wherein, on the indole ring, at least one selected from the group consisting of a halogen atom, a halogen substituted or unsubstituted C1-C6 alkyl group, and a halogen substituted or unsubstituted C1-C6 alkoxy group, may be substituted), and a phenyl C1-C6 alkyl group (wherein, on a phenyl ring of the phenyl C1-C6 alkyl group, at least one selected from the group consisting of a benzofuryl group, a halogen atom, a halogen substituted or unsubstituted C1-C6 alkyl group, and a halogen substituted or unsubstituted C1-C6 alkoxy group, may be substituted) may be substituted]);

(e) a 1,2,3,4-tetrahydroquinolyloxy group (wherein, on the 1,2,3,4-tetrahydroquinoline ring, at least one selected from the group consisting of an oxo group, a phenyl group [wherein, on a phenyl ring of the phenyl group at least one selected from the group consisting of a halogen atom, a halogen substituted or unsubstituted C1-C6 alkyl group, and a halogen substituted or unsubstituted C1-C6 alkoxy group, may be substituted], and a phenyl C1-C6 alkyl group [wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted], may be substituted);

(f) a 1,2,3,4-tetrahydronaphthyloxy group (wherein, on the 1,2,3,4-tetrahydronaphthalene ring, at least one oxo group may be substituted);

(g) a 2H-chromenyoxyl group (wherein, on the 2H-chromene ring, at least one oxo group may be substituted);

(h) a naphthyloxy group (wherein, on the naphthalene ring, at least one piperidyl group may be substituted [wherein, on the piperidine ring, at least one phenoxy group may be substituted (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted)]);

(i) a 1,2,3,4-tetrahydroisoquinolyloxy group (wherein, on the 1,2,3,4-tetrahydroisoquinoline ring, at least one selected from the group consisting of a C1-C6 alkoxycarbonyl group, a phenyl C1-C6 alkyl group [wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted], and a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted], may be substituted);

(j) a group —$NR^{22}R^{23}$ (wherein $R^{22}$ represents a hydrogen atom or C1-C6 alkyl group, and $R^{23}$ represents at least one selected from the following (j-1) to (j-5):

(j-1) a phenyl group [wherein, on a phenyl ring of the phenyl group, at least one piperidyl group is substituted (wherein, on the piperidine ring, at least one phenoxy group may be substituted [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted])], (j-2) a phenyl C1-C6 alkyl group [wherein, on a phenyl ring of the phenyl C1-C6 alkyl group, at least one group selected from the group consisting of a piperidyl group (wherein, on the piperidine ring, a phenoxy group is substituted [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted]) and a group —$NR^{24}R^{25}$ (wherein $R^{24}$ represents a hydrogen atom or C1-C6 alkyl group, and $R^{25}$ represents a phenyl C2-C6 alkenyl group [wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted]), is substituted], (j-3) a piperidyl C1-C6 alkyl group [wherein, on the piperidine ring, at least one phenyl group is substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)], (j-4) a thiazolyl group [wherein, on the thiazole ring, at least one group selected from the group consisting of a phenyl group (wherein, on a phenyl ring, of the phenyl group at least one selected from the group consisting of a halogen atom, a halogen substituted or unsubstituted C1-C6 alkyl group, and a halogen substituted or unsubstituted C1-C6 alkoxy group, may be substituted), a piperazinyl C1-C6 alkyl group (wherein, on the piperazine ring, at least one phenyl group may be substituted [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted]), and a piperidyl C1-C6 alkyl group (wherein, on the piperidine ring, at least one phenoxy group may be substituted [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted]), may be substituted], and (j-5) a phenyl C2-C6 alkenyl group (wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted));

(k) a benzoxazolyloxy group (wherein, on the benzoxazole ring at least one selected from the group consisting of a piperazinyl group [wherein, on the piperazine ring, at least one selected from the group consisting of a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), and a phenyl C2-C6 alkenyl group (wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted), may be substituted], a piperidyl group (wherein, on the piperidine ring, at least one selected from the group consisting of a phenyl C1-C6 alkyl group [wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted] and an amino group [wherein, on the amino group, at least one selected from the group consisting of a C1-C6 alkyl group and a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) may be substituted] may be substituted), and a phenyl group, [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted], may be substituted);

(l) a benzoimidazolyloxy group (wherein, on the benzoimidazole ring, at least one selected from the group consisting of a C1-C6 alkyl group, a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted], a piperidyl group [wherein, on the piperidine ring, at least one phenoxy group (wherein, on a phenyl ring of the phenoxy group, at least one selected from the group consisting of a halogen atom, a halogen substituted or unsubstituted C1-C6 alkyl group and a halogen substituted or unsubstituted C1-C6 alkoxy group may be substituted) may be substituted], a piperazinyl group [wherein, on the piperazine ring, at least one phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group and a halogen substituted or unsubstituted C1-C6 alkoxy group may be substituted) may be substituted] and a phenyl C1-C6 alkyl group [wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted], may be substituted);

(m) a 1,2,3,4-tetrahydroisoquinolyl group (wherein, on the 1,2,3,4-tetrahydroisoquinoline ring, at least one selected from the group consisting of the following (m-1) and (m-2) may be substituted:

(m-1) an amino group [wherein, on the amino group, at least one selected from the group consisting of a C1-C6 alkyl group, a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted), and a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), may be substituted] and (m-2) a phenoxy group [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted]);

(n) a piperidyl group (wherein, on the piperidine ring, at least one selected from the group consisting of the following (n-1) to (n-4) may be substituted:

(n-1) a phenyl group [wherein, on a phenyl ring of the phenyl group, at least one group $—NR^{26}R^{27}$ is substituted (wherein $R^{26}$ represents a hydrogen atom or C1-C6 alkyl group, and $R^{27}$ represents a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted])], (n-2) a group $—W_1NR^{28}R^{29}$ [wherein W, represents a C1-C6 alkylene group, $R^{28}$ represents a hydrogen atom or C1-C6 alkyl group, and $R^{29}$ represents a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)], (n-3) a C1-C6 alkoxy group wherein two phenyl groups are substituted [wherein, on a phenyl ring of the two phenyl groups, at least one selected from the group consisting of a halogen atom, a halogen substituted or unsubstituted C1-C6 alkyl group, and a halogen substituted or unsubstituted C1-C6 alkoxy group, may be substituted], and (n-4) a phenyl C1-C6 alkyl group [wherein, on a phenyl group ring of the phenyl C1-C6 alkyl group, at least one phenyl group is substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)]);

(o) a piperazinyl group (wherein, on the piperazine ring, at least one selected from the following group is substituted: a C1-C6 alkyl group wherein two phenyl groups are substituted [wherein, on a phenyl ring of the two phenyl groups, at least one selected from the group consisting of a halogen atom, a halogen substituted or unsubstituted C1-C6 alkyl group, and a halogen substituted or unsubstituted C1-C6 alkoxy group, may be substituted], a phenyl C1-C6 alkyl group [wherein, on a phenyl ring of the phenyl C1-C6 alkyl group, at least one phenoxy group is substituted (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, is substituted)], a thiazolyl group (wherein, on the thiazole ring, at least one phenyl group may be substituted), a phenoxy C1-C6 alkyl group (wherein, on a phenyl ring of the phenoxy C1-C6 alkyl group, at least one selected from the group consisting of a phenyl group (wherein, on a phenyl ring of the phenyl group, halogen atom, a halogen substituted or unsubstituted C1-C6 alkyl group, and a halogen substituted or unsubstituted C1-C6 alkoxy group, may be substituted), a halogen atom, a halogen substituted or unsubstituted C1-C6 alkyl group, and a halogen substituted or unsubstituted C1-C6 alkoxy group, may be substituted), a phenyl C2-C6 alkenyl group [wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, is substituted], and an imidazolyl group [wherein, on the imidazole ring, at least one phenyl group may be substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)]);

(p) a thiazolyl C1-C6 alkoxy group (wherein, on the thiazole ring, at least one type selected from the group consisting of the following (p-1) to (p-5) may be substituted:

(p-1) a phenoxy C1-C6 alkyl group [wherein, on a phenyl ring of the phenoxy C1-C6 alkyl group, at least one-selected from the group consisting of a halogen atom, a halogen substituted or unsubstituted C1-C6 alkyl group, and a halogen substituted or unsubstituted C1-C6 alkoxy group, may be substituted], (p-2) an anilino C1-C6 alkyl group [wherein, on a phenyl ring of the anilino C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted], (p-3) a phenyl C1-C6 alkyl group [wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted], (p-4) a piperazinyl C1-C6 alkyl group [wherein, on the piperazine ring, at least one phenyl group may be substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)], and (p-5) a piperidyl C1-C6 alkyl group [wherein, on the piperidine ring, at least one phenoxy group may be substituted (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted)]);

(q) an 8-azabicyclo[3.2.1]octyl group (wherein, on the 8-azabicyclo[3,2,1]octane ring, at least one phenoxy group may be substituted [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted]);

(r) a group represented by the following chemical formula (31):

(31)

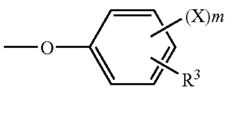

[wherein X represents a halogen atom, or an amino substituted C1-C6 alkyl group which may have a C1-C6 alkyl group as a substituent, m represents an integer between 0 and 3, and $R^3$ represents a group described in any one of the following (i) to (xxii):

(i) a group —(W) o-$NR^4R^5$ (wherein W represents a group —CO— or a C1-C6 alkylene group, o represents 0 or 1, $R^4$ represents a hydrogen atom, C1-C6 alkyl group, or phenylcarbamoyl group [wherein, on a phenyl ring of the phenylcarbamoyl group, at least one selected from the group consisting of a halogen atom, a halogen substituted or unsubstituted C1-C6 alkyl group, and a halogen-substituted or unsubstituted C1-C6 alkoxy group, may be substituted], and $R^5$ represents: a phenyl C1-C6 alkoxycarbonyl group [wherein, on a phenyl ring of the phenyl C1-C6 alkoxycarbonyl group, at least one selected from the group consisting of a halogen atom, a halogen substituted or unsubstituted C1-C6 alkyl group, and a halogen substituted or unsubstituted C1-C6 alkoxy group, may be substituted]; a phenyl C2-C6 alkenylcarbonyl group [wherein, on a phenyl ring of the phenyl C2-C6 alkenylcarbonyl group at least one selected from the group consisting of a halogen atom, a halogen substituted or unsubstituted C1-C6 alkyl group, and a halogen substituted or unsubstituted C1-C6 alkoxy group, may be substituted]; a phenyl C2-C6 alkenyl group [wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted]; a piperidyl C1-C6 alkyl group [wherein, on the piperidine ring, at least one phenyl group may be substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)]; a phenyl C1-C6 alkyl group (wherein, on a phenyl ring of the phenyl C1-C6 alkyl group, at least one phenyl group is substituted (wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted)); a benzofuryl C1-C6 alkyl group (wherein, on the benzofuran ring, at least one halogen substituted or unsubstituted C1-C6 alkyl group may be substituted); a piperidinylcarbonyl C1-C6 alkyl group [wherein, on the piperidine ring, at least one phenoxy group may be substituted (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted); or a group represented by the following chemical formula (32):

(32)

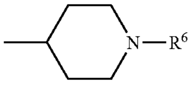

wherein $R^6$ represents: a C1-C6 alkyl group; a phenyl group (wherein, on a phenyl ring of the phenyl group, at least one selected from the following group may be substituted: a C1-C4 alkylenedioxy group, a cyano group, a nitro group, an amino group that may have a C1-C6 alkyl group as a substituent, an amino substituted sulfonyl group that may have a C1-C6 alkyl group as a substituent, a C1-C6 alkoxycarbonyl group, a C1-C6 alkylthio group, a phenoxy group, a phenyl C1-C6 alkoxy group, a pyrrolidinyl group [wherein, on the pyrrolidine ring, at least one oxo group may be substituted], an imidazolyl group, an isoxazolyl group, an oxazolyl group, a phenyl C1-C6 alkyl group, a phenyl group, an amino C1-C6 alkyl group that may have a C1-C6 alkyl group as a substituent, a pyrrolidinyl C1-C6 alkoxy group, a halogen atom, a halogen substituted or unsubstituted C1-C6 alkyl group, and a halogen substituted or unsubstituted C1-C6 alkoxy group); a phenyl C1-C6 alkoxycarbonyl group (wherein, on a phenyl ring of the phenyl C1-C6 alkoxycarbonyl group, at least one selected from the group consisting of a halogen atom, a halogen substituted or unsubstituted C1-C6 alkyl group, and a halogen substituted or unsubstituted C1-C6 alkoxy group, may be substituted); a benzofuryl C1-C6 alkyl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted); a benzofuryl C2-C6 alkenyl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted); a phenoxy C1-C6 alkyl group (wherein, on a phenyl ring of the phenoxy C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted); a thiazolyl C1-C6 alkyl group (wherein, on the thiazole ring, at least one phenyl group may be substituted [wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted]); a phenyl C1-C6 alkyl group [wherein, on a phenyl ring of the phenyl C1-C6 alkyl group, at least one selected from the group consisting of a phenyl group (wherein, on a phenyl ring of the phenyl group, a halogen atom, a halogen substituted or unsubstituted C1-C6 alkyl group, and a halogen substituted or unsubstituted C1-C6 alkoxy group, may be substituted), a halogen atom, a halogen substituted or unsubstituted C1-C6 alkyl group, and a halogen substituted or unsubstituted C1-C6 alkoxy group, may be substituted]; a pyridyl C1-C6 alkyl group [wherein, on the pyridine ring, at least one phenyl group may be substituted (wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted)]; a C1-C6 alkoxycarbonyl group; a benzoyl group (wherein, on a phenyl ring of the benzoyl group, at least one selected from the group consisting of a halogen atom, a halogen substituted or unsubstituted C1-C6 alkyl group, and a halogen substituted or unsubstituted C1-C6 alkoxy group, may be substituted); a phenylcarbamoyl group (wherein, on a phenyl ring of the phenylcarbamoyl group, at least one selected from the group consisting of a halogen atom, a halogen substituted or unsubstituted C1-C6 alkyl group, and a halogen substituted or unsubstituted C1-C6 alkoxy group, may be substituted); a phenylcarbamoyl group (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted); a benzothienyl C1-C6 alkyl group (wherein, on the benzothiophene ring, at least one halogen atom may be substituted); an indolyl C1-C6 alkyl group (wherein, on the indole ring, at least one selected from the group consisting of a halogen atom, a halogen substituted or unsubstituted C1-C6 alkyl group, and a halogen substituted or unsubstituted C1-C6 alkoxy group, may be substituted); a 4H-1,3-benzodioxinyl group (wherein, on the 4H-1,3-benzodioxine ring, at least one halogen atom may be substituted); benzothienyl group; a naphthyl group; a quinolyl group; a benzothiazolyl group (wherein, on the benzothiazole ring, at least one C1-C6 alkyl group may be substituted); a 2,3-dihydro-1 H-indenyl group (wherein, on the 2,3-dihydro-1 H-indan ring, at least one oxo group may be substituted); or a 9H-fluorenyl group or phenyl C2-C6 alkenyl group (wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted));

(ii) a group represented by the following chemical formula (33):

(33)

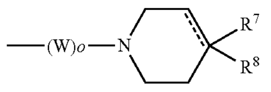

(wherein W and o are the same as above, a dotted line represents that the bond may be a double bond, and when the dotted line represents a double bond, it means that only $R^8$ is substituted; $R^7$ represents a hydrogen atom, hydroxyl group, C1-C6 alkoxy group, or phenyl group [wherein, on a phenyl ring of the phenyl group, halogen may be substituted]; and $R^8$ represents a group described in any one of the following (1) to (63):

(1) a phenyl C1-C6 alkoxy substituted C1-C6 alkyl group (wherein, on a phenyl ring of the phenyl C1-C6 alkoxyl substituted C1-C6 alkyl group, at least one selected from the group consisting of a C1-C4 alkylenedioxy group, a halogen atom, a cyano group, a phenyl group, a phenyl C1-C6 alkoxy group, a phenyl C2-C6 alkenyl group, a phenoxy group, a C1-C6 alkylthio group, a halogen substituted or unsubstituted C1-C6 alkyl group, and a halogen substituted or unsubstituted C1-C6 alkoxy group, may be substituted);

(2) a phenyl C1-C6 alkoxy group (wherein, on a phenyl ring of the phenyl C1-C6 alkoxy group, at least one selected from the group consisting of a cyano group, a phenyl group, a C1-C6 alkoxycarbonyl group, a phenoxy group, a C1-C6 alkylthio group, a halogen atom, a halogen substituted or unsubstituted C1-C6 alkyl group, and a halogen substituted or unsubstituted C1-C6 alkoxy group, may be substituted);

(3) a phenyl C2-C6 alkenyloxy group (wherein, on a phenyl ring of the phenyl C2-C6 alkenyloxy group, at least one selected from the group consisting of a halogen atom, a halogen substituted or unsubstituted C1-C6 alkyl group, and a halogen substituted or unsubstituted C1-C6 alkoxy group, may be substituted);

(4) a group —(W) o-$NR^9R^{10}$ (wherein W and o are the same as above, and $R^9$ and $R^{10}$ each identically or differently represent: a hydrogen atom; a C1-C6 alkyl group that may have a hydroxyl group as a substituent;

a C1-C6 alkanoyl group; a C1-C6 alkoxycarbonyl group; a phenyl C1-C6 alkoxycarbonyl group [wherein, on a phenyl ring of the phenyl C1-C6 alkoxycarbonyl group, at least one selected from the group consisting of a halogen atom, a halogen substituted or unsubstituted C1-C6 alkyl group, and a halogen substituted or unsubstituted C1-C6 alkoxy group, may be substituted]; a phenyl group wherein on a phenyl ring of the phenyl group, at least one selected from the following group may be substituted as a substituent: a halogen atom, a halogen substituted or unsubstituted C1-C6 alkyl group, a halogen substituted or unsubstituted C1-C6 alkoxy group, an amino group that may have, as a substituent, a group selected from the group consisting of a C1-C6 alkanoyl group and a C1-C6 alkyl group, a C1-C6 alkoxycarbonyl group, a phenyl group, a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted), an aminosulfonyl group, a 1,2,3,4-tetrahydroquinolyl group (wherein, on the 1,2,3,4-tetrahydroquinoline ring, at least one oxo group may be substituted as a substituent), a C1-C6 alkylsulfonyl group, a C3-C8 cycloalkyl group, a nitro group, a cyano group, a C1-C6 alkylthio group, a phenylsulfonyl group (wherein, on a phenyl ring of the phenylsulfonyl group, at least one selected from the group consisting of a halogen atom, a halogen substituted or unsubstituted C1-C6 alkyl group, and a halogen substituted or unsubstituted C1-C6 alkoxy group, may be substituted), a hydroxyl group substituted C1-C6 alkyl group, and a group represented by the following chemical formula (34):

(34)

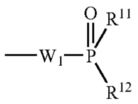

(wherein $W_1$ represents a C1-C6 alkylene group, and $R^{11}$ and $R^{12}$ each identically or differently represent a C1-C6 alkoxy group)]; a phenyl C1-C6 alkyl group [wherein, on a phenyl ring of the phenyl C1-C6 alkyl group, at least one selected from the group consisting of a C1-C4 alkylenedioxy group, a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted), a group —$N(R^{11A})R^{12A}$ (wherein $R^{11A}$ and $R^{12A}$ each identically or differently represent a hydrogen atom, C1-C6 alkyl group, or phenyl group, and $R^{11A}$ and $R^{12A}$ may bind to each other together with nitrogen atoms adjacent thereto directly or through nitrogen, oxygen or sulfur atoms, so as to form a 5-7 membered saturated heterocyclic ring), a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted), a phenyl C1-C6 alkoxy group, an amino group substituted C1-C6 alkoxy group that may have a C1-C6 alkyl group as a substituent, a halogen atom, a halogen substituted or unsubstituted C1-C6 alkyl group, and a halogen substituted or unsubstituted C1-C10 alkoxy group, may be substituted as a substituent]; a benzofuryl C1-C6 alkyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted]; a phenylsulfonyl group [wherein, on a phenyl ring of the phenylsulfonyl group, at least one selected from the group consisting of a halogen atom, a halogen substituted or unsubstituted C1-C6 alkyl group, and a halogen substituted or unsubstituted C1-C6 alkoxy group, and a C1-C4 alkylenedioxy may be substituted]; a phenoxycarbonyl group [wherein, on a phenyl ring of the phenoxycarbonyl group, at least one selected from the group consisting of a halogen atom, a halogen substituted or unsubstituted C1-C6 alkyl group, and a halogen substituted or unsubstituted C1-C6 alkoxy group, may be substituted]; a phenyl C2-C6 alkenyl group [wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted]; a C1-C6 alkoxy substituted C1-C6 alkyl group; a C2-C6 alkenyl group; a C1-C6 alkoxy substituted C2-C6 alkanoyl group; a C3-C8 cycloalkyl substituted C1-C6 alkyl group; a phenoxy C1-C6 alkyl group [wherein, on a phenyl ring of the phenoxy C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted]; a benzoyl group [wherein, on a phenyl ring of the benzoyl group, at least one selected from the group consisting of a halogen atom, a halogen substituted or unsubstituted C1-C6 alkyl group, and a halogen substituted or unsubstituted C1-C6 alkoxy group, may be substituted]; a phenylcarbamoyl group [wherein, on a phenyl ring of the phenylcarbamoyl group, at least one selected from the group consisting of a halogen atom, a halogen substituted or unsubstituted C1-C6 alkyl group, and a halogen substituted or unsubstituted C1-C6 alkoxy group, may be substituted]; a pyridyl group; a pyridyl C1-C6 alkyl group; an imdazolyl C1-C6 alkyl group; a 1,2,3,4-tetrahydroquinolyl group [wherein, on the 1,2,3,4-tetrahydroquinoline ring, at least one selected from the group consisting of an oxo group and a C1-C6 alkyl group may be substituted as a substituent]; a quinolyl group; an indolyl group; an amino group that may have a C1-C6 alkyl group as a substituent; an indazolyl group; a naphthyl group; a C3-C8 cycloalkyl group; an amino substituted C1-C6 alkyl group that may have a C1-C6 alkyl group as a substituent; a cyano substituted C1-C6 alkyl group; a furyl substituted C1-C6 alkyl group; a group of the formula (35)

(35)

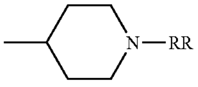

(wherein RR represents a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)); or a piperazinyl substituted C1-C6 alkyl group [wherein, on a piperazine ring, at least one phenyl group may be substituted as a substituent (wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted)], further, $R^9$ and $R^{10}$ may bind to each other together with nitrogen atoms adjacent thereto directly or through nitrogen, oxygen or sulfur atoms, so as to form a 1,2,3,4-tetrahydroisoquinolyl group, isoindolyl group, or 5-7 membered saturated heterocyclic ring, wherein, on the heterocyclic ring, at least one selected from the following group may be substituted: a halogen atom, a halogen substituted or unsubstituted C1-C6 alkyl group, a halogen substituted or unsubstituted C1-C6 alkoxy group, a phenyl group [wherein, on a phenyl ring of the phenyl group, at least one selected from the group consisting of a phenyl group, a halogen atom, a halogen substituted or unsubstituted C1-C6 alkyl group, and a halogen substituted or unsubstituted C1-C6 alkoxy group, may be substituted], a benzoyl group [wherein, on a phenyl ring of the benzoyl group, at least one selected from the group consisting of a halogen atom, a halogen substituted or unsubstituted C1-C6 alkyl group, and a halogen substituted or unsubstituted C1-C6 alkoxy group, may be substituted], a pyridyl C1-C6 alkyl group, a C3-C8 cycloalkyl group, a phenyl C1-C6 alkyl group [wherein, on a phenyl ring of the phenyl C1-C6 alkyl group, at least one selected from the group consisting of a C1-C4 alkylenedioxy group, a halogen atom, a halogen substituted or unsubstituted C1-C6 alkyl group, and a halogen substituted or unsubstituted C1-C6 alkoxy group, may be substituted], a piperidyl C1-C6 alkyl group, a piperidyl group, a phenyl C1-C6 alkoxy group [wherein, on a phenyl ring of the phenyl C1-C6 alkoxy group, at least one selected from the group consisting of a halogen atom, a halogen substituted or unsubstituted C1-C6 alkyl group, and a halogen substituted or unsubstituted C1-C6 alkoxy group, may be substituted], a phenoxy group [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted], an amino group wherein at least one selected from the group consisting of a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted], a C1-C6 alkyl group, and a phenyl C1-C6 alkyl group [wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted], may be substituted as a substituent, a benzoxazolyl group, a phenyl C2-C6 alkenyl group (wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted), and a benzoimidazolyl group);

(5) a phenyl C1-C6 alkyl group (wherein, on a phenyl ring of the phenyl C1-C6 alkyl group, at least one selected from the group consisting of a halogen atom, a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted), a halogen substituted or unsubstituted C1-C6 alkyl group, and a halogen substituted or unsubstituted C1-C6 alkoxy group, may be substituted);

(6) a carbamoyloxy group (wherein, on the amino group, at least one selected from the group consisting of a C1-C6 alkyl group and a phenyl group [wherein, on a phenyl ring of the phenyl group, at least one selected from the group consisting, of a halogen atom, a halogen substituted or unsubstituted C1-C6 alkyl group, and a halogen substituted or unsubstituted C1-C6 alkoxy group, may be substituted] may be substituted);

(7) a carbamoyloxy substituted C1-C6 alkyl group (wherein, on the amino group, at least one selected from the group consisting of a C1-C6 alkyl group, a phenyl C1-C6 alkyl group, a C3-C8 cycloalkyl group, a naphthyl group, a 2,3-dihydro-1H-indenyl group, a 2,3-dihydrobenzofuryl group, and a phenyl group [wherein, on a phenyl ring of the phenyl group, at least one selected from the group consisting of a C1-C4 alkylenedioxy group, a cyano group, a phenoxy group, a C1-C6 alkylthio group, a C1-C6 alkanoyl group, a phenyl group, a phenyl C1-C6 alkyl group, a halogen atom, a halogen substituted or unsubstituted C1-C10 alkyl group, and a halogen substituted or unsubstituted C1-C10 alkoxy group, may be substituted], may be substituted);

(8) a phenoxy C1-C6 alkyl group (wherein, on a phenyl ring of the phenoxy C1-C6 alkyl group, at least one selected from the following group may be substituted: a halogen atom; a C1-C4 alkylenedioxy group; a C1-C6 alkoxycarbonyl group; a phenyl group; a phenoxy group; a pyrrolyl group; a benzothiazolyl group; a 1,2,4-triazolyl group; an imidazolyl group; an isoxazolyl group; a benzoxazolyl group; a benzotriazolyl group; a cyano group; a nitro group; a C2-C6 alkenyl group; a C1-C6 alkanoyl group; a C1-C6 alkoxycarbonyl substituted C1-C6 alkyl group; a C1-C6 alkanoyl substituted C1-C6 differently represent a hydrogen atom, C1-C6 alkyl group, C1-C6 alkanoyl group, or phenyl group, and $R^{11B}$ and $R^{12B}$ may bind to each other together with nitrogen atoms adjacent thereto directly or through nitrogen, oxygen or sulfur atoms, so as to form a 5-7 membered saturated heterocyclic ring, wherein, on the heterocyclic ring, at least one selected from the group consisting of a C1-C6 alkoxycarbonyl group and an amino group [wherein, on the amino group, at least one selected from a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted] may be substituted); a phenyl C1-C6 alkoxy group; a phenyl C1-C6 alkyl group; a C1-C6 alkylthio group; a C3-C8 cycloalkyl group; a halogen substituted or unsubstituted C1-C6 alkyl group; and a halogen substituted or unsubstituted C1-C10 alkoxy group);

(9) a tetrahydropyranyloxy C1-C6 alkyl group;

(10) a hydroxyl substituted C1-C6 alkyl group;

(11) a furyl C1-C6 alkoxy substituted C1-C6 alkyl group (wherein, on the furan ring, at least one C1-C6 alkoxycarbonyl group may be substituted);

(12) a tetrazolyl C1-C6 alkoxy substituted C1-C6 alkyl group (wherein, on the tetrazole ring, at least one selected from the group consisting of a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted), a phenyl C1-C6 alkyl group, and a C3-C8 cycloalkyl C1-C6 alkyl group, may be substituted);

(13) an isoxazolyl C1-C6 alkoxy substituted C1-C6 alkyl group (wherein, on the isoxazole ring, at least one C1-C6 alkyl group may be substituted);

(14) a benzothienyl C1-C6 alkoxy substituted C1-C6 alkyl group (wherein, on the benzothiophene ring, at least one selected from the group consisting of a halogen atom, a halogen substituted or unsubstituted C1-C6 alkyl group, and a halogen substituted or unsubstituted C1-C6 alkoxy group, may be substituted);

(15) a 1,3,4-oxadiazolylC1-C6 alkoxy substituted C1-C6 alkyl group (wherein, on the 1,3,4-oxadiazole ring, a phenyl group may be substituted [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted]);

(16) a C2-C6 alkynyloxy substituted C1-C6 alkyl group;

(17) a naphthyl C1-C6 alkoxy substituted C1-C6 alkyl group;

(18) a 1,2,4-oxadiazolylC1-C6 alkoxy substituted C1-C6 alkyl group [wherein, on the 1,2,4-oxadiazole ring, a phenyl group may be substituted];

(19) a pyridyl C1-C6 alkoxy substituted C1-C6 alkyl group [wherein, on the pyridine ring, at least one selected from the group consisting of a halogen atom, a halogen substituted or unsubstituted C1-C6 alkyl group, and a halogen substituted or unsubstituted C1-C6 alkoxy group, may be substituted];

(20) a thiazolyl C1-C6 alkoxy substituted C1-C6 alkyl group [wherein, on the thiazole ring, at least one selected from the group consisting of a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted];

(21) a 1,2,3,4-tetrahydronaphthyl C1-C6 alkoxy substituted C1-C6 alkyl group [wherein, on the 1,2,3,4-tetrahydronaphthalene ring, at least one C1-C6 alkyl group may be substituted];

(22) a carbamoyl C1-C6 alkoxy substituted C1-C6 alkyl group [wherein, on the amino group, at least one selected from the group consisting of a C3-C8 cycloalkyl group and a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) may be substituted];

(23) a benzofuryl C1-C6 alkoxy substituted C1-C6 alkyl group [wherein, on the benzofuran ring, at least one cyano group may be substituted];

(24) a benzofuryl C1-C6 alkyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted];

(25) a phenoxy group [wherein, on a phenyl ring of the phenoxy group, at least one selected from the group consisting of a phenyl C1-C6 alkoxy group, a C3-C8 cycloalkyl group, a C7-C10 alkoxy group, and a phenoxy group, is substituted];

(26) a naphthyloxy group;

(27) a 2,3-dihydrobenzofuryloxy group [wherein, on the 2,3-dihydrobenzofuran ring, at least one oxo group may be substituted];

(28) a benzothiazolyloxy group [wherein, on the benzothiazole ring, at least one C1-C6 alkyl group may be substituted];

(29) a 1,2,3,4-tetrahydronaphthyloxy group [wherein, on the 1,2,3,4-tetrahydronaphthalene ring, at least one oxo group may be substituted];

(30) a dibenzofuryloxy group;

(31) a quinolyloxy group;

(32) a furyl C1-C6 alkoxy group [wherein, on the furan ring, at least one C1-C6 alkoxycarbonyl group may be substituted];

(33) a tetrazolyl C1-C6 alkoxy group [wherein, on the tetrazole ring, at least one selected from the group consisting of a phenyl C1-C6 alkyl group and a C3-C8 cycloalkyl C1-C6 alkyl group may be substituted];

(34) a 1,2,4-oxadiazolylC1-C6 alkoxy group [wherein, on the 1,2,4-oxadiazole ring, a phenyl group may be substituted (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted)];

(35) a benzothienyl C1-C6 alkoxy group [wherein, on the benzothiophene ring, at least one halogen atom may be substituted];

(36) an isoxazolyl C1-C6 alkoxy group [wherein, on the isoxazole ring, at least one C1-C6 alkyl group may be substituted];

(37) a 1,3,4-oxadiazolyl C1-C6 alkoxy group [wherein, on the 1,3,4-oxadiazole ring, at least one phenyl group may be substituted (wherein, on a phenyl ring of the phenyl group, at least one C1-C6 alkyl group may be substituted)];

(38) a naphthyl C1-C6 alkoxy group;

(39) a pyridyl C1-C6 alkoxy group (wherein, on the pyridine ring, at least one halogen substituted or unsubstituted C1-C6 alkyl group may be substituted);

(40) a thiazolyl C1-C6 alkoxy group [wherein, on the thiazole ring, at least one phenyl group may be substituted (wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted)];

(41) a 1,2,3,4-tetrahydronaphthyl C1-C6 alkoxy group (wherein, on the 1,2,3,4-tetrahydronaphthalene ring, at least one C1-C6 alkyl group may be substituted);

(42) a phenoxy C1-C6 alkoxy group (wherein, on a phenyl ring of the phenoxy C1-C6 alkoxy group, at least one selected from the group consisting of a halogen atom, a halogen substituted or unsubstituted C1-C6 alkyl group, and a halogen substituted or unsubstituted C1-C6 alkoxy group, may be substituted);

(43) a carbamoyl C1-C6 alkoxy group [wherein, on the amino group, at least one selected from the group consisting of a C3-C8 cycloalkyl group and a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) may be substituted];

(44) a benzofuryl C1-C6 alkoxy group (wherein, on the benzofuran ring, at least one cyano group may be substituted);

(45) a naphthyloxy C1-C6 alkyl group (wherein, on the naphthalene ring, at least one C1-C6 alkoxy group may be substituted);

(46) a benzothiazolyloxy C1-C6 alkyl group (wherein, on the benzothiazole ring, at least one C1-C6 alkyl group may be substituted);

(47) a quinolyloxy C1-C6 alkyl group (wherein, on the quinoline ring, at least one C1-C6 alkyl group may be substituted);

(48) a 2,3-dihydrobenzofuryloxy C1-C6 alkyl group (wherein, on the 2,3-dihydrobenzofuran ring, at least one selected from the group consisting of a C1-C6 alkyl group and an oxo group may be substituted);

(49) a 1,2,3,4-tetrahydronaphthyloxy C1-C6 alkyl group (wherein, on the 1,2,3,4-tetrahydronaphthalene ring, at least one oxo group may be substituted);

(50) a 2,3-dihydro-1H-indenyloxy C1-C6 alkyl group (wherein, on the 2,3-dihydro-1H-indene ring, at least one oxo group may be substituted);

(51) a benzoxathiolanyloxy C1-C6 alkyl group (wherein, on the benzoxathiolane ring, at least one oxo group may be substituted);

(52) an isoquinolyloxy C1-C6 alkyl group;

(53) a pyridyloxy C1-C6 alkyl group;

(54) a dibenzofuryloxy C1-C6 alkyl group;

(55) a 2H-1-benzopyranyloxy C1-C6 alkyl group (wherein, on the 2H-1-benzopyran ring, at least one oxo group may be substituted);

(56) a benzoisoxazolyloxy C1-C6 alkyl group;

(57) a benzofurazanyloxy C1-C6 alkyl group;

(58) a quinoxalyloxy C1-C6 alkyl group;

(59) a C1-C6 alkoxy C1-C6 alkoxy substituted C1-C6 alkyl group;

(60) a thienyl C1-C6 alkoxy substituted C1-C6 alkyl group (wherein, on the thiophene ring, at least one halogen atom may be substituted);

(61) a phenyl C2-C6 alkenyloxy substituted C1-C6 alkyl group (wherein, on a phenyl ring of the phenyl C2-C6 alkenyloxy substituted C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted);

(62) a quinolyl C1-C6 alkoxy substituted C1-C6 alkyl group; and

(63) a piperidylcarbonyl C1-C6 alkoxy substituted C1-C6 alkyl group, and further, $R^7$ and $R^8$ together may form a group $=C(R^{29})(R^{30})$ wherein $R^{29}$ and $R^{30}$ each identically or differently represent a hydrogen atom, C1-C6 alkyl group, or phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted]); (iii) a group represented by the following chemical formula (36):

(36)

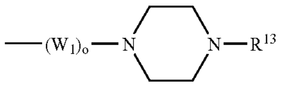

(wherein $W_1$ and o are the same as above, and $R^{13}$ represents: a 2,3-dihydro-1H-indenyl group; a benzothienyl group; a phenyl C2-C10 alkenyl group [wherein, on a phenyl ring of the phenyl C2-C10 alkenyl group, at least one selected from the group consisting of a halogen atom, a C1-C4 alkylenedioxy group, a C1-C6 alkylthio group, a benzoyl group, a cyano group, a nitro group, a C2-C6 alkanoyloxy group, an amino group that may have a C1-C6 alkyl group as a substituent, a hydroxyl group, a phenyl C1-C6 alkoxy group, a phenoxy group, a halogen substituted or unsubstituted C1-C6 alkyl group, and a halogen substituted or unsubstituted C1-C6 alkoxy group, may be substituted]; a naphthyl C2-C6 alkenyl group; a benzofuryl C1-C6 alkyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted]; a benzothienyl C2-C6 alkenyl group; a benzothiazolyl C2-C6 alkenyl group [wherein, on the benzothiazole ring, at least one C1-C6 alkyl group may be substituted]; a phenyl C1-C6 alkyl group [wherein, on a phenyl ring of the phenyl C1-C6 alkyl group, at least one selected from the following group is substituted: a piperidinyl group (on the piperidine ring, at least one phenoxy group may be substituted [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted]), a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, is substituted), and a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted)]; a diphenyl C1-C6 alkyl group [wherein, on a phenyl ring of the diphenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted]; a benzoyl C1-C6 alkyl group [wherein, on a phenyl ring of the benzoyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted]; an amino group wherein at least one selected from the following group may be substituted: a C1-C6 alkyl group, a C1-C6 alkoxycarbonyl group, and a phenyl C1-C6 alkyl group [wherein, on a phenyl ring of the phenyl C1-C6 alkyl group, at least one selected from the group consisting of a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted), a halogen atom, a halogen substituted or unsubstituted C1-C6 alkyl group, and a halogen substituted or unsubstituted C1-C6 alkoxy group, may be substituted]; an amino C1-C6 alkyl group wherein at least one selected from the group consisting of a C1-C6 alkyl group and a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) may be substituted; a benzofuryl C2-C6 alkenyl group [wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted]; a piperidyl group [wherein, on the piperidine ring, at least one phenyl C2-C6 alkenyl group may be substituted (wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted)]; a ferrocene substituted C1-C6 alkyl group; an indolyl C1-C6 alkyl group (wherein, on the indole ring, at least one halogen atom may be substituted); a phenyl C2-C6 alkynyl group; a phenyl group [wherein, on a phenyl ring of the phenyl C2-C6 alkynyl group, at least one selected from the group consisting of a C1-C4 alkylenedioxy group, a phenyl group, a C1-C6 alkoxycarbonyl group, a hydroxyl group, and a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted), is substituted]; a benzofuryl group [wherein, on the benzofuran ring, at least one selected from the group consisting of a halogen atom and a C1-C6 alkyl group may be substituted]; a benzohthiazolinyl group [wherein, on the benzothiazoline ring, at least one oxo group may be substituted]; a benzothienyl group [wherein, on the benzothiophene ring, at least one halogen atom may be substituted]; a naphthyl group; a 1,2,3,4-tetrahydroquinolyl group [wherein, on the 1,2,3,4-tetrahydroquinoline ring, at least one selected from the group consisting of an oxo group and a C1-C6 alkyl group may be substituted]; a benzoisoxazolyl group; a 2,3-dihydrobenzofuryl group; a 1,2-dihydroquinolyl group [wherein, on the 1,2-dihydroquinoline ring, at least one oxo group may be substituted]; a 1,2,3,4-tetrahydroquinazolinyl group [wherein, on the 1,2,3,4-tetrahydroquinazoline ring, at least one selected from the group consisting of an oxo group and a C1-C6 alkyl group may be substituted]; a benzocycloheptyl group; a phenoxy C1-C6 alkyl group [wherein, on a phenyl ring of the phenoxy C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted]; a benzothienyl substituted C1-C6 alkyl group [wherein, on the benzothiophene ring, at least one halogen atom may be substituted]; a naphthyl substituted C1-C6 alkyl group (wherein, on the naphthalene ring, at least one C1-C6 alkoxy group may be substituted); a pyridyl substituted C1-C6 alkyl group [wherein, on the pyridine ring, at least one halogen atom may be substituted]; a furyl substituted C1-C6 alkyl group [wherein, on the furan ring, at least one nitro group may be substituted]; a thienyl substituted C1-C6 alkyl group [wherein, on the thiophene ring, at least one halogen atom may be substituted]; a thiazolyl substituted C1-C6 alkyl group [wherein, on the thiazole ring, at least one selected from the group consisting of a C1-C6 alkyl group and a phenyl group (wherein, on a phenyl ring of the phenyl group, at least one selected from the group consisting of a halogen atom and a halogen substituted or unsubstituted C1-C6 alkyl group may be substituted) may be substituted]; a tetrazolyl substituted C1-C6 alkyl group [wherein, on the tetrazole ring, at least one C1-C6 alkyl group may be substituted]; an isoxazolyl substituted C1-C6 alkyl group [wherein, on the isoxazole ring, at least one C1-C6 alkyl group may be substituted]; a 1,2,4-oxadiazolyl substituted C1-C6 alkyl group [wherein, on the 1,2,4-oxadiazole ring, at least one phenyl group may be substituted (wherein, on the phenyl ring, a C1-C6 alkyl group may be substituted)]; or a benzofurazanyl substituted C1-C6 alkyl group);

(iv) a group represented by the following chemical formula (37):

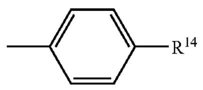

(37)

(wherein $R^{14}$ represents: a phenylamino group [wherein, at the N-position of the phenylamino group, a C1-C6 alkyl group may be substituted, and on the phenyl ring of the phenylamino group, at least one halogen substituted or unsubstituted C1-C6 alkoxy group may be substituted]; a piperidyl group [wherein, on the piperidine ring, at least one selected from the group consisting of a phenoxy group (wherein, on a phenyl ring of the phenoxy group, a halogen substituted or unsubstituted C1-C6 alkoxy group may be substituted) and an amino group (wherein, on the amino group, at least one selected from the group consisting of a C1-C6 alkyl group and a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted] may be substituted as a substituent) may be substituted]; a piperazinyl group [wherein, on the piperazine ring, at least one selected from the following group may be substituted: a C1-C6 alkoxycarbonyl group, a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), a phenyl C2-C6 alkenyl group (wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted), and a benzoyl group (wherein, on a phenyl ring of the benzoyl group, at least one selected from the group consisting of a halogen atom, a halogen substituted or unsubstituted C1-C6 alkyl group, and a halogen substituted or unsubstituted C1-C6 alkoxy group, may be substituted)]; a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted); a homopiperazinyl group [wherein, on the homopiperazine ring, at least one selected from the group consisting of a C1-C6 alkoxycarbonyl group and a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted) may be substituted]; or a phenoxy group [wherein, on a phenyl ring of the phenoxy group, at least one selected from the group consisting of a halogen substituted or unsubstituted C1-C6 alkoxy group and a phenoxy substituted phenyl group (wherein, on a phenyl ring of the phenoxy substituted phenyl group, at least one halogen substituted or unsubstituted C1-C6 alkoxy group may be substituted), may be substituted]);

(v) a group represented by the following chemical formula (38):

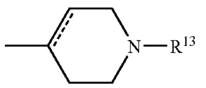

(38)

(wherein $R^{13}$ is the same as above, and a dotted line represents that the bond may be a double bond);

(vi) a homopiperazinyl group (wherein, on the homopiperazine ring, at least one selected from the following group may be substituted: a C1-C6 alkoxycarbonyl group; a phenyl C1-C6 alkyl group [wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted]; a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkoxycarbonyl group [wherein, on a phenyl ring of the phenyl C1-C6 alkoxycarbonyl group, at least one selected from the group consisting of a halogen atom, a halogen substituted or unsubstituted C1-C6 alkyl group, and a halogen substituted or unsubstituted C1-C6 alkoxy group, may be substituted]; a phenylcarbamoyl group [wherein, on a phenyl ring of the phenylcarbamoyl group, at least one selected from the group consisting of a halogen atom, a halogen substituted or unsubstituted C1-C6 alkyl group, and a halogen substituted or unsubstituted C1-C6 alkoxy group, may be substituted]; a phenyl C2-C6 alkenyl group [wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted]; and a benzoyl group [wherein, on a phenyl ring of the benzoyl group, at least one selected from the group consisting of a halogen atom, a halogen substituted or unsubstituted C1-C6 alkyl group, and a halogen substituted or unsubstituted C1-C6 alkoxy group, may be substituted]);

(vii) a group represented by the following chemical formula (39):

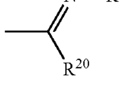

(39)

(wherein $R^{19}$ represents a C1-C6 alkoxy group, and $R^{20}$ represents a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted]);

(viii) a group —$CHR^{20}R^{21}$ (wherein $R^{20}$ is the same as above, and $R^{21}$ represents an amino group that may have a C1-C6 alkyl group as a substituent);

(ix) a 1,2,3,4-tetrahydroisoquinolyl group (wherein, on the 1,2,3,4-tetrahydroisoquinoline ring, at least one amino group may be substituted [wherein, on the amino group, at least one selected from the group consisting of a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted) and a C1-C6 alkyl group may be substituted]);

(x) an oxazolyl group (wherein, on the oxazole ring, at least one selected from the following group may be substituted: a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted], a C1-C6 alkyl group, and a piperidyl group [wherein, on the piperidine ring, at least one phenoxy group may be substituted (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted)]);

(xi) an isoindolinyl group (wherein, on the isoindoline ring, at least one selected from the group consisting of a halogen atom, a halogen substituted or unsubstituted C1-C6 alkyl group, and a halogen substituted or unsubstituted C1-C6 alkoxy group, may be substituted);

(xii) a thiazolyl group (wherein, on the thiazole ring, at least one selected from the following group may be substituted: a phenoxy C1-C6 alkyl group [wherein, on a phenyl ring of the phenoxy C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted]; a phenyl group [wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted]; a phenyl C1-C6 alkyl group [wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted]; a group —$(W_1)oNR^{31}R^{32}$ [wherein $W_1$ and o are the same as above, and $R^{31}$ and $R^{32}$ each identically or differently represent a hydrogen atom, C1-C6 alkyl group, phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted), or phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted)]; a piperazinyl group [wherein, on the piperazine ring, at least one phenyl group may be substituted (wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted)]; a piperidyl group [wherein, on the piperidine ring, at least one selected from the group consisting of a phenoxy group (wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted) and a phenyl C1-C6 alkyl group may be substituted]; and a phenoxy group [wherein, on a phenyl ring of the phenoxy group, at least one selected from the group consisting of a halogen atom, a halogen substituted or unsubstituted C1-C6 alkyl group, and a halogen substituted or unsubstituted C1-C6 alkoxy group, may be substituted]);

(xiii) a hydroxyl group substituted C1-C6 alkyl group;

(xiv) an oxazolyl C1-C6 alkyl group [wherein, on the oxazole ring, at least one phenyl group may be substituted (wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted)];

(xv) an isoxazolyl group [wherein, on the isoxazoline ring, at least one phenyl ring may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)];

(xvi) a benzoxazolyl group (wherein, on the benzoxazole ring, at least one halogen atom may be substituted);

(xvii) a phenylthio group (wherein, on a phenyl ring of the phenylthio group, at least one selected from the group consisting of a halogen atom, a halogen substituted or unsubstituted C1-C6 alkyl group, and a halogen substituted or unsubstituted C1-C6 alkoxy group, may be substituted);

(xviii) a benzoimidazolyl group [wherein, on the benzoimidazole ring, at least one selected from the group consisting of a halogen atom and a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted) may be substituted];

(xiv) a pyrrolidinyl group [wherein, on the pyrrolidine ring, at least one amino group is substituted (wherein, on the amino group, at least one selected from the group consisting of a C1-C6 alkyl group and a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) may be substituted)];

(xx) a phenylsulfonyl group (wherein, on a phenyl ring of the phenylsulfonyl group, at least one selected from the group consisting of a halogen atom, a halogen substituted or unsubstituted C1-C6 alkyl group, and a halogen substituted or unsubstituted C1-C6 alkoxy group, may be substituted);

(xxi) an imidazolyl group [wherein, on the imidazole ring, at least one phenyl group is substituted (wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted)]; and (xxii) a phenylsulfinyl group (wherein, on a phenyl ring of the phenylsulfinyl group, at least one selected from the group consisting of a halogen atom, a halogen substituted or unsubstituted C1-C6 alkyl group, and a halogen substituted or unsubstituted C1-C6 alkoxy group, may be substituted)];

(s) an imidazolyl group (wherein, on the imidazole ring, at least one selected from the group consisting of a halogen atom and a nitro group may be substituted);

(t) an isoindolinyloxy group [wherein, on the isoindoline ring, at least one selected from the following group may be substituted: a C1-C6 alkoxycarbonyl group, a phenyl C1-C6 alkyl group (wherein, on a phenyl ring of the phenyl C1-C6 alkyl group, at least one selected from the group consisting of a benzofuryl group, a halogen atom, a halogen substituted or unsubstituted C1-C6 alkyl group, and a halogen substituted or unsubstituted C1-C6 alkoxy group, may be substituted), a phenyl C2-C6 alkenyl group (wherein, on a phenyl ring of the phenyl C2-C6 alkenyl group, at least one selected from the group consisting of a halogen atom, a halogen substituted or unsubstituted C1-C6 alkyl group, and a halogen substituted or unsubstituted C1-C6 alkoxy group, may be substituted), a furyl C1-C6 alkyl group [wherein, on the furan ring, at least one phenyl group may be substituted (wherein, on a phenyl ring of the at least one phenyl group, at least one selected from the group consisting of a halogen atom, a halogen substituted or unsubstituted C1-C6 alkyl group, and a halogen substituted or unsubstituted C1-C6 alkoxy group, may be substituted)], a pyridyl C1-C6 alkyl group [wherein, on the pyridine ring, at least one selected from the group consisting of a furyl group and a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) may be substituted], a benzofuryl C1-C6 alkyl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted), a benzothienyl C1-C6 alkyl group (wherein, on the benzothiophene ring, at least one halogen atom may be substituted), a benzofuryl C2-C6 alkenyl group (wherein, on the benzofuran ring, at least one selected from the group consisting of a halogen atom, a halogen substituted or unsubstituted C1-C6 alkyl group, and a halogen substituted or unsubstituted C1-C6 alkoxy group, may be substituted), a thiazolyl group [wherein, on the thiazole ring, at least one phenyl group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)], and a phenoxy C1-C6 alkyl group (wherein, on a phenyl ring of the phenoxy C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted)];

(u) a benzothiazolidinyloxy group [wherein, on the benzothiazolidine ring, at least one selected from the group consisting of an oxo group and a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted), may be substituted];

(v) an indolyloxy group [wherein, on the indole ring, at least one phenyl C1-C6 alkyl group may be substituted (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted)];

(w) a pyrrolidinyl group [wherein, on the pyrrolidine ring, at least one amino group is substituted (wherein, on the amino group, at least one selected from the group consisting of a C1-C6 alkyl group and a phenyl group (wherein, on a phenyl ring of the phenyl group, at least one selected from the group consisting of a halogen atom, a halogen substituted or unsubstituted C1-C6 alkyl group, and a halogen substituted or unsubstituted C1-C6 alkoxy group, may be substituted) may be substituted)];

(x) an indolinyl group (wherein, on the indoline ring, at least one halogen atom may be substituted); and (y) an indolinyloxy group [wherein, on the indoline ring, at least one selected from the group consisting of a phenyl C1-C6 alkyl group (wherein, on a phenyl ring of the phenyl C1-C6 alkyl group, at least one selected from the group consisting of a halogen atom, a halogen substituted or unsubstituted C1-C6 alkyl group, and a halogen substituted or unsubstituted C1-C6 alkoxy group, may be substituted) and an oxo group may be substituted].

2. The 2,3-dihydro-6-nitroimidazo[2,1-b]oxazole compound, an optically active form thereof, or a pharmacologically acceptable salt thereof according to claim 1, wherein $R^2$ represents a group described in any one of (a) to (c), (e) to (h), (j) to (q), and (s) to (y).

3. The 2,3-dihydro-6-nitroimidazo[2,1-b]oxazole compound, an optically active form thereof, or a pharmacologically acceptable salt thereof according to claim 1, wherein $R^2$ represents the group described in (d).

4. The 2,3-dihydro-6-nitroimidazo[2,1-b]oxazole compound, an optically active form thereof, or a pharmacologically acceptable salt thereof according to claim 1, wherein $R^2$ represents the group described in (i).

5. The 2,3-dihydro-6-nitroimidazo[2,1-b]oxazole compound, an optically active form thereof, or a pharmacologically acceptable salt thereof according to claim 1, wherein $R^2$ represents the group described in (r).

6. The 2,3-dihydro-6-nitroimidazo[2,1-b]oxazole compound, an optically active form thereof, or a pharmacologically acceptable salt thereof according to claim 1, wherein $R^1$ represents a hydrogen atom.

7. The 2,3-dihydro-6-nitroimidazo[2,1-b]oxazole compound, an optically active form thereof, or a pharmacologically acceptable salt thereof according to claim 1, wherein $R^1$ represents a C1-C6 alkyl group.

8. The 2,3-dihydro-6-nitroimidazo[2,1-b]oxazole compound, an optically active form thereof, or a pharmacologically acceptable salt thereof according to claim 1, wherein $R^1$ and $-(CH_2)_nR^2$ may bind to each other to form a spiro ring together with the carbon atom adjacent thereto, represented by the following formula (30):

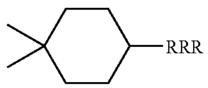

(30)

wherein RRR represents a piperidyl group [wherein, on the piperidine ring, at least one phenoxy group may be substituted (wherein, on the phenyl ring, at least one selected from the group consisting of a halogen atom, a halogen substituted or unsubstituted C1-C6 alkyl group, and a halogen substituted or unsubstituted C1-C6 alkoxy group, may be substituted)].

9. The 2,3-dihydro-6-nitroimidazo[2,1-b]oxazole compound, an optically active form thereof, or a pharmacologically acceptable salt thereof according to claim 6 or 7, wherein $R^3$ represents the group described in (i).

10. The 2,3-dihydro-6-nitroimidazo[2,1-b]oxazole compound, an optically active form thereof, or a pharmacologically acceptable salt thereof according to claim 6 or 7, wherein $R^3$ represents the group described in (ii).

11. The 2,3-dihydro-6-nitroimidazo[2,1-b]oxazole compound, an optically active form thereof, or a pharmacologically acceptable salt thereof according to claim 6 or 7, wherein $R^3$ represents the group described in (iii).

12. The 2,3-dihydro-6-nitroimidazo[2,1-b]oxazole compound, an optically active form thereof, or a pharmacologically acceptable salt thereof according to claim 6 or 7, wherein $R^3$ represents the group described in (iv).

13. The 2,3-dihydro-6-nitroimidazo[2,1-b]oxazole compound, an optically active form thereof, or a pharmacologically acceptable salt thereof according to claim 6 or 7, wherein $R^3$ represents the group described in (v).

14. The 2,3-dihydro-6-nitroimidazo[2,1-b]oxazole compound, an optically active form thereof, or a pharmacologically acceptable salt thereof according to claim 6 or 7, wherein $R^3$ represents the group described in (vi).

15. The 2,3-dihydro-6-nitroimidazo[2,1-b]oxazole compound, an optically active form thereof, or a pharmacologically acceptable salt thereof according to claim 6 or 7, wherein $R^3$ represents the group described in (vii).

16. The 2,3-dihydro-6-nitroimidazo[2,1-b]oxazole compound, an optically active form thereof, or a pharmacologically acceptable salt thereof according to claim 6 or 7, wherein $R^3$ represents the group described in (viii).

17. The 2,3-dihydro-6-nitroimidazo[2,1-b]oxazole compound, an optically active form thereof, or a pharmacologically acceptable salt thereof according to claim 6 or 7, wherein $R^3$ represents the group described in (ix).

18. The 2,3-dihydro-6-nitroimidazo[2,1-b]oxazole compound, an optically active form thereof, or a pharmacologically acceptable salt thereof according to claim 6 or 7, wherein $R^3$ represents the group described in (x).

19. The 2,3-dihydro-6-nitroimidazo[2,1-b]oxazole compound, an optically active form thereof, or a pharmacologically acceptable salt thereof according to claim 6 or 7, wherein $R^3$ represents the group described in (xi).

20. The 2,3-dihydro-6-nitroimidazo[2,1-b]oxazole compound, an optically active form thereof, or a pharmacologically acceptable salt thereof according to claim 6 or 7, wherein $R^3$ represents the group described in (xii).

21. The 2,3-dihydro-6-nitroimidazo[2,1-b]oxazole compound, an optically active form thereof, or a pharmacologically acceptable salt thereof according to claim 6 or 7, wherein $R^3$ represents the group described in (xiii).

22. The 2,3-dihydro-6-nitroimidazo[2,1-b]oxazole compound, an optically active form thereof, or a pharmacologically acceptable salt thereof according to claim 6 or 7, wherein $R^3$ represents the group described in (xiv).

23. The 2,3-dihydro-6-nitroimidazo[2,1-b]oxazole compound, an optically active form thereof, or a pharmacologically acceptable salt thereof according to claim 6 or 7, wherein $R^3$ represents the group described in (xv).

24. The 2,3-dihydro-6-nitroimidazo[2,1-b]oxazole compound, an optically active form thereof, or a pharmacologically acceptable salt thereof according to claim 6 or 7, wherein $R^3$ represents the group described in (xvi).

25. The 2,3-dihydro-6-nitroimidazo[2,1-b]oxazole compound, an optically active form thereof, or a pharmacologically acceptable salt thereof according to claim 6 or 7, wherein $R^3$ represents the group described in (xvii).

26. The 2,3-dihydro-6-nitroimidazo[2,1-b]oxazole compound, an optically active form thereof, or a pharmacologically acceptable salt thereof according to claim 6 or 7, wherein $R^3$ represents the group described in (xviii).

27. The 2,3-dihydro-6-nitroimidazo[2,1-b]oxazole compound, an optically active form thereof, or a pharmacologically acceptable salt thereof according to claim 6 or 7, wherein $R^3$ represents the group described in (xix).

28. The 2,3-dihydro-6-nitroimidazo[2,1-b]oxazole compound, an optically active form thereof, or a pharmacologically acceptable salt thereof according to claim 6 or 7, wherein $R^3$ represents the group described in (xx).

29. The 2,3-dihydro-6-nitroimidazo[2,1-b]oxazole compound, an optically active form thereof, or a pharmacologically acceptable salt thereof according to claim 6 or 7, wherein $R^3$ represents the group described in (xxi).

30. The 2,3-dihydro-6-nitroimidazo[2,1-b]oxazole compound, an optically active form thereof, or a pharmacologically acceptable salt thereof according to claim 6 or 7, wherein $R^3$ represents the group described in (xxii).

31. The 2,3-dihydro-6-nitroimidazo[2,1-b]oxazole compound, or a pharmacologically acceptable salt thereof according to claim 1, which is selected from the group consisting of:

2-methyl-6-nitro-2-{4-[4-(4-trifluoromethylbenzyloxymethyl)piperidin-1-yl]phenoxymethyl}-2,3-dihydroimidazo[2,1-b]oxazole, (R)-2-methyl-6-nitro-2-{4-[4-(4-trifluoromethylbenzyloxymethyl)piperidin-1-yl]phenoxymethy}-2,3-dihydroimidazo[2,1-b]oxazole, (S)-2-methyl-6-nitro-2-{4-[4-(4-trifluoromethylbenzyloxymethyl)piperidin-1-yl]phenoxymethyl}-2,3-dihydroimidazo[2,1-b]oxazole, 2-methyl-6-nitro-2-{-4-[4-(4-chlorophenoxymethyl)piperidin-1-yl]phenoxymethyl}-2,3-dihydroimidazo[2,1-b]oxazole, (R)-2-methyl-6-nitro-2-{4-[4-(4-chlorophenoxymethyl)piperidin-1-yl]phenoxymethyl}-2,3-dihydroimidazo[2,1-b]oxazole, (S)-2-methyl-6-nitro-2-{4-[4-(4-chlorophenoxymethyl)piperidin-1-yl]phenoxymethyl}-2,3-dihydroimidazo[2,1-b]oxazole, 2-methyl-6-nitro-2-{4-[4-(4-trifluoromethylcinnamyl)piperazin-1-yl]phenoxymethyl}-2,3-dihydroimidazo[2,1-b]oxazole, (R)-2-methyl-6-nitro-2-{4-[4-(4-trifluoromethylcinnamyl)piperazin-1-yl]phenoxymethyl}-2,3-dihydroimidazo[2,1-b]oxazole, (S)-2-methyl-6-nitro-2-{4-[4-(4-trifluoromethylcinnamyl)piperazin-1-yl]phenoxymethyl}-2,3-dihydroimidazo[2,1-b]oxazole, 2-methyl-6-nitro-2-{4-[4-(4-trifluoromethoxycinnamyl)piperazin-1-yl]phenoxymethyl}-2,3-dihydroimidazo[2,1-b]oxazole, (R)-2-methyl-6-nitro-2-{4-[4-(4-trifluoromethoxycinnamyl)piperazin-1-yl]phenoxymethyl}-2,3-dihydroimidazo[2,1-Noxazole, (S)-2-methyl-6-nitro-2-{4-[4-(4-trifluoromethoxycinnamyl)piperazin-1-yl]phenoxymethyl}-2,3-dihydroimidazo[2,1-b]oxazole, 2-methyl-6-nitro-2-{4-[4-(4-trifluoromethylphenoxymethyl)piperidin-1-yl]phenoxymethyl}-2,3-dihydroimidazo[2,1-b]oxazole, (R)-2-methyl-6-nitro-2-{4-[4-(4-trifluoromethylphenoxymethyl)piperidin-1-yl]phenoxymethyl}-2,3-dihydroimidazo[2,1-b]oxazole, (S)-2-methyl-6-nitro-2-{4-[4-(4-trifluoromethylphenoxymethyl)piperidin-1-yl]phenoxymethyl}-2,3-dihydroimidazo[2,1-b]oxazole, 6-nitro-2-{4-[4-(4-trifluoromethoxybenzyloxy)piperidin-1-yl]phenoxymethyl}-2,3-dihydroimidazo[2,1-b]oxazole, (R)-6-nitro-2-{4-[4-(4-trifluoromethoxybenzyloxy)piperidin-1-yl]phenoxymethyl}-2,3-dihydroimidazo[2,1-b]oxazole, (S)-6-nitro-2-{4-[4-(4-trifluoromethoxybenzyloxy)piperidin-1-yl]phenoxymethyl}-2,3-dihydroimidazo[2,1-b]oxazole, 6-nitro-2-{4-[4-(4-trifluoromethoxyphenoxymethyl)piperidin-1-yl]phenoxymethyl}-2,3-dihydroimidazo[2,1-b]oxazole, (R)-6-nitro-2-{4-[4-(4-trifluoromethoxyphenoxymethyl)piperidin-1-yl]phenoxymethyl}-2,3-dihydroimidazo[2,1-b]oxazole, (S)-6-nitro-2-{4-[4-(4-trifluoromethoxyphenoxymethyl)piperidin-1-yl]phenoxymethyl}-2,3-dihydroimidazo[2,1-b]oxazole, 6-nitro-2-{4-[4-(4-trifluoromethoxybenzyl)piperidin-1-yl]phenoxymethyl}-2,3-dihydroimidazo[2,1-Noxazole, (R)-6-nitro-2-{4-[4-(4-trifluoromethoxybenzyl)piperidin-1-yl]phenoxymethyl}-2,3-dihydroimidazo[2,1-Noxazole, (S)-6-nitro-2-{4-[4-(4-trifluoromethoxybenzyl)piperidin-1-yl]-phenoxymethyl}-2,3-dihydroimidazo[2,1-b]oxazole, 2-methyl-6-nitro-2-[4-{4-[4-(4-trifluoromethoxybenzyl)piperidln-1-yl]phenoxymethyl}-2,3-dihydroimidazo[2,1-b]oxazole, (R)-2-methyl-6-nitro-2-[4-{4-[4-(4-trifluoromethoxybenzyl)piperidin-1-yl]phenoxymethyl}-2,3-dihydroimidazo[2,1-b]oxazole, (S)-2-methyl-6-nitro-2-[4-{4-[4-(4-trifluoromethoxybenzyl)piperidin-1-yl]phenoxymethyl}-2,3-dihydroimidazo[2,1-b]oxazole, 2-methyl-6-nitro-2-[4-{4-[4-(4-trifluoromethylphenyl)piperazin-1-yl]piperidin-1-yl}phenoxymethyl]-2,3-dihydroimidazo[2,1-b]oxazole, (R)-2-methyl-6-nitro-2-[4-{4-[4-(4-trifluoromethylphenyl)piperazin-1-yl]piperidin-1-yl}phenoxymethyl}-2,3-dihydroimidazo[2,1-b]oxazole, (S)-2-methyl-6-nitro-2-[4-{4-[4-(4-trifluoromethylphenyl)piperazin-1-yl]piperidin-1-yl]phenoxymethyl}-2,3-dihydroimidazo[2,1-b]oxazole, 2-methyl-6-nitro-2-[4-{4-[4-(4-trifluoromethoxyphenoxy)benzyl]piperazin-1-yl}phenoxymethyl]-2,3-dihydroimidazo[2,1-b]oxazole, (R)-2-methyl-6-nitro-2-[4-{4-[4-(4-trifluoromethoxyphenoxy)benzyl)piperazin-1-yl]phenoxymethyl}-2,3-dihydroimidazo[2,1-b]oxazole, (S)-2-methyl-6-nitro-2-[4-{4-[4-(4-trifluoromethoxyphenoxy)benzyl]piperazin-1-yl}phenoxymethyl]-2,3-dihydroimidazo[2,1-b]oxazole, 6-nitro-2-[4-{4-[3-(4-trifluoromethoxyphenyl)propyl]piperidin-1-yl]phenoxymethyl}-2,3-dihydroimidazo[2,1-b]oxazole, (R)-6-nitro-2-{4-[3-(4-trifluoromethoxyphenyl)propyl] piperidin-1-yl}phenoxymethyl]-2,3-dihydroimidazo[2,1-b]oxazole, (S)-6-nitro-2-[4-{4-[3-(4-trifluoromethoxyphenyl)propyl]piperidin-1-yl]phenoxymethyl}-2,3-dihydroimidazo[2,1-b]oxazole, 2-methyl-6-nitro-2-{4-[2-(4-trifluoromethoxyphenyl)oxazol-4-yl]phenoxymethyl}-2,3-dihydroimidazo[2,1-b] oxazole, (R)-2-methyl-6-nitro-2-{4-[2-(4-trifluoromethoxyphenyl)oxazol-4-yl]phenoxymethyl}-2,3-dihydroimidazo [2,1-Noxazole, (S)-2-methyl-6-nitro-2-{4-[2-(4-trifluoromethoxyphenyl) oxazol-4-yl]phenoxymethyl}-2,3-dihydroimidazo[2,1-b]oxazole, 6-nitro-2-{4-[4-(4-chlorophenoxymethyl)piperidin-1-yl] phenoxymethyl}-2,3-dihydroimidazo[2,1-b]oxazole, (R)-6-nitro-2-{4-[4-(4-chlorophenoxymethyl)piperidin-1-yl]phenoxymethyl}-2,3-dihydroimidazo[2,1-b]oxazole, (S)-6-nitro-2-{4-[4-(4-chlorophenoxymethyl)piperidin-1-yl]phenoxymethyl}-2,3-dihydroimidazo[2,1-b]oxazole, 2-methyl-6-nitro-2-{4-[4-(5-trifluoromethylbenzofuran-2-yl)methylpiperidin-1-yl]phenoxymethyl}-2,3-dihydroimidazo[2,1-b]oxazole, (R)-2-methyl-6-nitro-2-{4-[4-(5-trifluoromethylbenzofuran-2-yl) methylpiperidin-1-yl]phenoxymethyl}-2,3-dihydroimidazo[2,1-b]oxazole, (S)-2-methyl-6-nitro-2-{4-[4-(5-trifluoromethylbenzofuran-2-yl)methylpiperidin-1-yl]phenoxymethyl}-2,3-dihydroimidazo[2,1-b]oxazole, 2-methyl-6-nitro-2-{4-[2-(4-chlorophenyl)oxazol-4-yl] phenoxymethyl}-2,3-dihydroimidazo[2,1-b]oxazole, (R)-2-methyl-6-nitro-2-{4-[2-(4-chlorophenyl)oxazol-4-yl]phenoxymethyl}-2,3-dihydroimidazo[2,1-b]oxazole, (S)-2-methyl-6-nitro-2-{4-[2-(4-chlorophenyl)oxazol-4-yl]phenoxymethyl}-2,3-dihydroimidazo[2,1-b]oxazole, 6-nitro-2-{4-[4-(4-trifluoromethylphenoxymethyl)piperidin-1-yl]phenoxymethyl}-2,3-dihydroimidazo[2,1-b] oxazole, (R)-6-nitro-2-{4-[4-(4-trifluoromethylphenoxymethyl)piperidin-1-yl]phenoxymethyl}-2,3-dihydroimidazo[2,1-b]oxazole, (S)-6-nitro-2-{4-[4-(4-trifluoromethylphenoxymethyl)piperidin-1-yl]phenoxymethyl}-2,3-dihydroimidazo[2,1-b]oxazole, 2-methyl-6-nitro-2-{4-[4-(4-bromocinnamyl)piperazin-1-yl]phenoxymethyl}-2,3-dihydroimidazo[2,1-b]oxazole, (R)-2-methyl-6-nitro-2-{4-[4-(4-bromocinnamyl)piperazin-1-yl]phenoxymethyl}-2,3-dihydroimidazo[2,1-b] oxazole, (S)-2-methyl-6-nitro-2-{4-[4-(4-bromocinnamyl)piperazin-1-yl]phenoxymethyl}-2,3-dihydroimidazo[2,1-b] oxazole, 2-methyl-6-nitro-2-[2-(4-trifluoromethoxyphenyl)-1,2,3,4-tetrahydroisoquinolin-6-yloxymethyl]-2,3-dihydroimidazo[2,1-b]oxazole, (R)-2-methyl-6-nitro-2-[2-(4-trifluoromethoxyphenyl)-1,2,3,4-tetrahydroisoquinolin-6-yloxymethyl]-2,3-dihydroimidazo[2,1-b]oxazole, and (S)-2-methyl-6-nitro-2-[2-(4-trifluoromethoxyphenyl)-1,2,3,4-tetrahydroisoquinolin-6-yloxymethyl]-2,3-dihydroimidazo[2,1-b]oxazole.

32. An antituberculous agent, characterized in that said agent comprises the 2,3-dihydro-6-nitroimidazo[2,1-b]oxazole compound, an optically active form thereof, or a pharmacologically acceptable salt thereof according to claim 1.

* * * * *

UNITED STATES PATENT AND TRADEMARK OFFICE
CERTIFICATE OF CORRECTION

PATENT NO. : 8,163,753 B2
APPLICATION NO. : 10/574597
DATED : April 24, 2012
INVENTOR(S) : Hidetsugu Tsubouchi et al.

It is certified that error appears in the above-identified patent and that said Letters Patent is hereby corrected as shown below:

In the Claims

In claim 1, column 479, line 52, "$C_1$-$C_6$ alkyl group" should read --C1-C6 alkyl group--.

In claim 1, column 480, line 4, "$C_2$-$C_6$ alkenyl" should read --C2-C6 alkenyl--.

In claim 1, column 480, line 42, "C1-C6alkyl group" should read --C1-C6 alkyl group--.

In claim 1, column 486, line 19, "{wherein W, represents" should read --{wherein $W_1$ represents--.

In claim 1, column 495, line 7, "oxadiazolylC1-C6" should read --oxadiazolyl C1-C6--.

In claim 1, column 495, line 19, "oxadiazolylC1-C6" should read --oxadiazolyl C1-C6--.

In claim 31, column 508, line 9, "[2,1-Noxazole" should read --[2,1-b] oxazole--.

In claim 31, column 508, line 42, "[2,1-Noxazole" should read --[2,1-b] oxazole--.

In claim 31, column 508, line 45, "[2,1-Noxazole" should read --[2,1-b] oxazole--.

In claim 31, column 509, line 25, "[2,1-Noxazole" should read --[2,1-b] oxazole--.

Signed and Sealed this
First Day of October, 2013

Teresa Stanek Rea
*Deputy Director of the United States Patent and Trademark Office*